(12) United States Patent
Jachmann et al.

(10) Patent No.: US 8,247,431 B2
(45) Date of Patent: Aug. 21, 2012

(54) HETEROCYCLIC HYDRAZIDE COMPOUND AND PESTICIDAL USE OF THE SAME

(75) Inventors: Markus Jachmann, Kobe (JP); Yoshihiko Nokura, Toyonaka (JP); Hiroshi Ikegami, Ikeda (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 390 days.

(21) Appl. No.: 12/594,452

(22) PCT Filed: Apr. 11, 2008

(86) PCT No.: PCT/JP2008/057560
§ 371 (c)(1),
(2), (4) Date: Oct. 2, 2009

(87) PCT Pub. No.: WO2008/130021
PCT Pub. Date: Oct. 30, 2008

(65) Prior Publication Data
US 2010/0137362 A1 Jun. 3, 2010

(30) Foreign Application Priority Data
Apr. 12, 2007 (JP) .................. 2007-104468

(51) Int. Cl.
*C07D 401/14* (2006.01)
*A01N 43/40* (2006.01)

(52) U.S. Cl. ........ 514/314; 514/256; 514/340; 514/341; 546/169; 546/256; 546/268.1; 546/268.4

(58) Field of Classification Search .................. None
See application file for complete search history.

(56) References Cited

FOREIGN PATENT DOCUMENTS

| WO | WO-02/070483 A | 9/2002 |
|---|---|---|
| WO | WO-2007/043677 A | 6/2007 |

OTHER PUBLICATIONS

International Preliminary Search Report on Patentability and Written Opinion of the International Searching Authority, issued Oct. 13, 2009, in PCTJP2008/057560.

*Primary Examiner* — Zinna Northington Davis
(74) *Attorney, Agent, or Firm* — Birch, Stewart, Kolasch & Birch, LLP

(57) ABSTRACT

A hydrazide compound represented by the formula (I), an N-oxide thereof or suitable salt thereof: has excellent pesticidal activity.

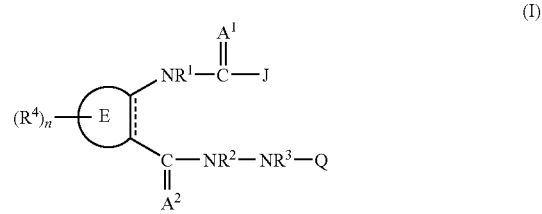

21 Claims, No Drawings

HETEROCYCLIC HYDRAZIDE COMPOUND AND PESTICIDAL USE OF THE SAME

CONTINUING DATA

This application is a 371 of PCT/JP2008/057560 filed Apr. 11, 2008.

TECHNICAL FIELD

The present invention relates to a hydrazide compound and pesticidal use of the same.

BACKGROUND ART

WO 2002/070483 discloses several 5- and 6-membered heteroaromatic diamide compounds activity. Furthermore, in WO 2007/020050 is heterobicylic diamide compounds described and their use of for controlling harmful pests in agriculture.

DISCLOSURE OF THE INVENTION

The present invention is intended to provide a compound having excellent efficacy of controlling pests.

The present inventors have intensively studied in order to find out a compound having excellent efficacy of controlling pests and, as a result, found out that a hydrazide compound represented by the following formula (1) has excellent controlling efficacy. Thus, the present invention has been completed.

According to the present invention, there is provided:

A hydrazide compound represented by the formula (1) (hereinafter referred to as the present compound), an N-oxide thereof or suitable salt thereof:

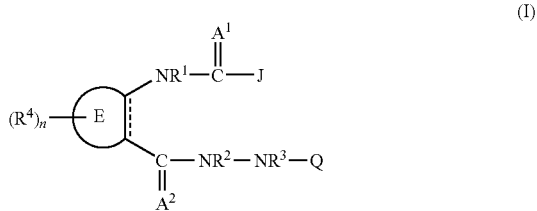

(I)

wherein $A^1$ and $A^2$ independently represent an oxygen atom or a sulfur atom;

E represents, together with the two contiguous linking carbon atoms, a 5- or 6-membered heteroaromatic ring system or a 8-, 9- or 10-membered fused heterobicyclic ring system;

$R^1$ represents a hydrogen atom, C1-C6 alkyl optionally substituted with one or more halogen atoms, C2-C6 cyanoalkyl, C1-C6 hydroxyalkyl, C2-C6 alkoxyalkyl optionally substituted with one or more halogen atoms, C2-C6 alkenyl optionally substituted with one or more halogen atoms, C2-C6 alkynyl optionally substituted with one or more halogen atoms, C3-C6 cycloalkyl optionally substituted with one or more halogen atoms, C1-C6 alkylthio optionally substituted with one or more halogen atoms, C1-C6 alkylsulfinyl optionally substituted with one or more halogen atoms, C1-C6 alkylsulfonyl optionally substituted with one or more halogen atoms, C2-C6 alkylcarbonyl optionally substituted with one or more halogen atoms, C2-C6 alkoxycarbonyl, C2-C6 alkylaminocarbonyl, C3-C8 dialkylaminocarbonyl, C4-C6 cycloalkylaminocarbonyl, or C3-C6 trialkylsilyl;

or represents phenyl, C7-C9 phenylalkyl or phenylcarbonyl: each said phenyl ring optionally substituted with one or more independent substituents selected from the group consisting of (1) a halogen atom, (2) cyano, (3) nitro, (4) hydroxyl, (5) carboxyl, (6) C1-C6 alkyl optionally substituted with one or more halogen atoms, (7) C1-C6 hydroxyalkyl, (8) C1-C6 alkoxy optionally substituted with one or more halogen atoms, (9) C2-C6 cyanoalkyl, (10) C2-C6 alkoxyalkyl optionally substituted with one or more halogen atoms, (11) C2-C6 alkenyl optionally substituted with one or more halogen atoms, (12) C2-C6 alkynyl optionally substituted with one or more halogen atoms, (13) C3-C6 cycloalkyl optionally substituted with one or more halogen atoms, (14) C1-C6 alkylthio optionally substituted with one or more halogen atoms, (15) C1-C6 alkylsulfinyl optionally substituted with one or more halogen atoms, (16) C1-C6 alkylsulfonyl optionally substituted with one or more halogen atoms, (17) C1-C6 alkylamino, (18) C2-C8 dialkylamino, (19) C3-C6 cycloalkylamino, (20) C2-C6 alkylcarbonyl, (21) C2-C6 alkoxycarbonyl, (22) C2-C6 alkylaminocarbonyl, (23) C3-C8 dialkylaminocarbonyl, (24) C4-C6 cycloalkylaminocarbonyl and (25) C3-C6 trialkylsilyl;

$R^2$ and $R^3$ independently represent a hydrogen atom, C1-C6 alkyl optionally substituted with one or more halogen atoms, C2-C6 cyanoalkyl, C1-C6 hydroxyalkyl, C2-C6 alkoxyalkyl optionally substituted with one or more halogen atoms, C2-C6 alkenyl optionally substituted with one or more halogen atoms, C2-C6 alkynyl optionally substituted with one or more halogen atoms, C3-C6 cycloalkyl optionally substituted with one or more halogen atoms, C1-C6 alkylthio optionally substituted with one or more halogen atoms, C1-C6 alkylsulfinyl optionally substituted with one or more halogen atoms, C1-C6 alkylsulfonyl optionally substituted with one or more halogen atoms, C2-C6 alkylcarbonyl optionally substituted with one or more halogen atoms, C2-C6 alkoxycarbonyl, C2-C6 alkylaminocarbonyl, C3-C8 dialkylaminocarbonyl, C4-C6 cycloalkylaminocarbonyl, or C3-C6 trialkylsilyl;

or represents phenyl, C7-C9 phenylalkyl or phenylcarbonyl: each said phenyl ring optionally substituted with one or more independent substituents selected from the group consisting of (1) a halogen atom, (2) cyano, (3) nitro, (4) hydroxyl, (5) carboxyl, (6) C1-C6 alkyl optionally substituted with one or more halogen atoms, (7) C1-C6 hydroxyalkyl, (8) C1-C6 alkoxy optionally substituted with one or more halogen atoms, (9) C2-C6 cyanoalkyl, (10) C2-C6 alkoxyalkyl optionally substituted with one or more halogen atoms, (11) C2-C6 alkenyl optionally substituted with one or more halogen atoms, (12) C2-C6 alkynyl optionally substituted with one or more halogen atoms, (13) C3-C6 cycloalkyl optionally substituted with one or more halogen atoms, (14) C1-C6 alkylthio optionally substituted with one or more halogen atoms, (15) C1-C6 alkylsulfinyl optionally substituted with one or more halogen atoms, (16) C1-C6 alkylsulfonyl optionally substituted with one or more halogen atoms, (17) C1-C6 alkylamino, (18) C2-C8 dialkylamino, (19) C3-C6 cycloalkylamino, (20) C2-C6 alkylcarbonyl, (21) C2-C6 alkoxycarbonyl, (22) C2-C6 alkylaminocarbonyl, (23) C3-C8 dialkylaminocarbonyl, (24) C4-C6 cycloalkylaminocarbonyl and (25) C3-C6 trialkylsilyl; or $R^2$ and $R^3$ are taken together with the two nitrogen atoms to which they are attached to form a 5- to 8-membered ring containing two nitrogen atoms, one or more $CH_2$ or $C(=O)$, and optionally one or two ring members selected from the group consisting of (1) an oxygen atom, (2) a sulfur atom, (3) $S(=O)$, (4) $S(=O)_2$ and (4) $NR^a$ (wherein $R^a$ represents C1-C6 alkyl optionally substituted with one or more halogen atoms, C2-C6 alkoxycarbonyl optionally substituted with one or more halogen atoms, or a phenyl optionally substituted with one or more independent substituents from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms);

and wherein the ring at the carbon atoms is optionally substituted with one or more independent substituents selected from the group consisting of (1) a halogen atom, (2) C1-C6 alkyl optionally substituted with one or more halogen atoms, and (3) C2-C6 alkoxycarbonyl optionally substituted with one or more halogen atoms;

$R^4$ represents a halogen atom, cyano, nitro, hydroxyl, carboxyl, C1-C6 alkyl optionally substituted with one or more halogen atoms, C1-C6 alkoxy optionally substituted with one or more halogen atoms, C2-C6 cyanoalkyl, C2-C6 alkoxyalkyl optionally substituted with one or more halogen atoms, C2-C6 alkenyl optionally substituted with one or more halogen atoms, C2-C6 alkynyl optionally substituted with one or more halogen atoms, C3-C6 cycloalkyl optionally substituted with one or more halogen atoms, C1-C6 alkylthio optionally substituted with one or more halogen atoms, C1-C6 alkylsulfinyl optionally substituted with one or more halogen atoms, C1-C6 alkylsulfonyl optionally substituted with one or more halogen atoms, C1-C6 alkylamino, C2-C8 dialkylamino, C3-C6 cycloalkylamino, C2-C6 alkylcarbonyl optionally substituted with one or more halogen atoms, C2-C6 alkoxycarbonyl, C2-C6 alkylaminocarbonyl, C3-C8 dialkylaminocarbonyl, or C3-C6 trialkylsilyl;

or represents a phenyl, benzyl, phenoxy, or a 5- or 6-membered heteroaromatic ring, each ring optionally substituted with one or more substituents selected from the group consisting of (1) a halogen atom, (2) cyano, (3) nitro, (4) hydroxyl, (5) carboxyl, (6) C1-C6 alkyl optionally substituted with one or more halogen atoms, (7) C1-C6 hydroxyalkyl, (8) C1-C6 alkoxy optionally substituted with one or more halogen atoms, (9) C2-C6 cyanoalkyl, (10) C2-C6 alkoxyalkyl optionally substituted with one or more halogen atoms, (11) C2-C6 alkenyl optionally substituted with one or more halogen atoms, (12) C2-C6 alkynyl optionally substituted with one or more halogen atoms, (13) C3-C6 cycloalkyl optionally substituted with one or more halogen atoms, (14) C1-C6 alkylthio optionally substituted with one or more halogen atoms, (15) C1-C6 alkylsulfinyl optionally substituted with one or more halogen atoms, (16) C1-C6 alkylsulfonyl optionally substituted with one or more halogen atoms, (17) C1-C6 alkylamino, (18) C2-C8 dialkylamino, (19) C3-C6 cycloalkylamino, (20) C2-C6 alkylcarbonyl, (21) C2-C6 alkoxycarbonyl, (22) C2-C6 alkylaminocarbonyl, (23) C3-C8 dialkylaminocarbonyl, (24) C4-C6 cycloalkylaminocarbonyl and (25) C3-C6 trialkylsilyl;

n represents an integer of 0 to 3 (provided that, when n is an integer of 2 or more, $R^4$'s may be the same or different);

Q represents Q1, Q2, Q3, Q4, Q5 or Q6:

Q1:

—$C(=A^{31})-R^6$

Q2:

—$C(=A^{32})-OR^7$

Q3:

—$C(=A^{33})-SR^8$

Q4:

—$C(=A^{34})-NR^9R^{10}$

Q5:

—$S(O)_m-R^{11}$

Q6:

—$S(O)_m-NR^{12}R^{13}$, $A^{31}$, $A^{32}$, $A^{33}$ and $A^{34}$ represent an oxygen atom, or a sulfur atom;

m represents an integer of 0 to 2;

$R^6$ represents a hydrogen atom; C2-C6 alkenyl optionally substituted with one or more halogen atoms; C2-C6 alkynyl optionally substituted with one or more halogen atoms; C1-C6 alkyl optionally substituted with one or more independent substituents selected from the group consisting of (1) a halogen atom, (2) C1-C6 alkoxy optionally substituted with one or more halogen atoms, (3) C1-C6 alkylthio optionally substituted with one or more halogen atoms, (4) C1-C6 alkylsulfinyl optionally substituted with one or more halogen atoms, (5) C1-C6 alkylsulfonyl optionally substituted with one or more halogen atoms, (6) C2-C6 dialkylamino optionally substituted with one or more halogen atoms, and (7) C3-C6 cycloalkyl optionally substituted with one or more halogen atoms; C3-C6 cycloalkyl optionally substituted with one or more independent substituents selected from the group consisting of (1) a halogen atom, and (2) C1-C6 alkyl optionally substituted with one or more halogen atoms; phenyl optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms; naphthyl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms; 5- to 6-membered heteroaryl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms; 3- to 8-membered non-aromatic heterocyclic ring optionally substituted with one or more independent substituents selected from the group consisting of (1) a halogen atom, and (2) C1-C6 alkyl optionally substituted with one or more halogen atoms; C7-C9 phenylalkyl or C7-C9 phenoxyalkyl: each said phenyl ring optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms;

$R^7$ and $R^8$ represent C1-C6 alkyl optionally substituted with one or more halogen atoms; C2-C6 alkoxyalkyl optionally substituted with one or more halogen atoms; C2-C6 alkenyl optionally substituted with one or more halogen atoms; C2-C6 alkynyl optionally substituted with one or more halogen atoms; C3-C6 cycloalkyl optionally substituted with one or more independent substituents selected from the group consisting of (1) a halogen atom, and (2) C1-C6 alkyl optionally substituted with one or more halogen atoms; phenyl optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms; 5- to 6-membered heteroaryl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms; or C7-C9 phenylalkyl whose phenyl ring moiety optionally is substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms;

$R^9$ and $R^{10}$ independently represent a hydrogen atom; C1-C6 alkyl optionally substituted with one or more halogen atoms; C2-C6 alkoxyalkyl optionally substituted with one or more halogen atoms; C2-C6 alkenyl optionally substituted with one or more halogen atoms; C2-C6 alkynyl optionally substituted with one or more halogen atoms; C3-C6 cycloalkyl optionally substituted with one or more independent substituents selected from the group consisting of (1) a halogen atom, and (2) C1-C6 alkyl optionally substituted with one or more halogen atoms; phenyl optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms; 5- to 6-membered heteroaryl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms; or C7-C9 phenylalkyl whose phenyl ring moiety optionally is substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms; $R^{11}$ represents C1-C6 alkyl optionally substituted with one or more halogen atoms; C3-C6 cycloalkyl optionally substituted with one or more independent substituents selected from the group consisting of (1) a halogen atom, and (2) C1-C6 alkyl optionally substituted with one or more halogen atoms; or a phenyl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms; 5- to 6-membered heteroaryl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms; or 3- to 8-membered non-aromatic heterocyclic ring optionally substituted with one or more independent substituents selected from the group consisting of (1) a halogen atom, and (2) C1-C6 alkyl optionally substituted with one or more halogen atoms;

$R^{12}$ and $R^{13}$ independently represent C1-C6 alkyl optionally substituted with one or more halogen atoms; C3-C6 cycloalkyl optionally substituted with one or more independent substituents selected from the group consisting of (1) a halogen atom, and (2) C1-C6 alkyl optionally substituted with one or more halogen atoms; or phenyl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms;

J represents J1 or J2:

J1:

J2:

$X^a$, $Y^a$, $Z^a$, $X^b$, $Y^b$ and $Z^b$ independently represent CH or a nitrogen atom;

$R^{19a}$ and $R^{19b}$ represent a hydrogen atom; C1-C6 alkyl optionally substituted with one or more halogen atoms; C2-C6 cyanoalkyl, C2-C6 alkoxyalkyl optionally substituted with one or more halogen atoms; C2-C6 alkenyl optionally substituted with one or more halogen atoms; C2-C6 alkynyl optionally substituted with one or more halogen atoms; C3-C6 cycloalkyl optionally substituted with one or more independent substituents selected from the group consisting of (1) a halogen atom, and (2) C1-C6 alkyl optionally substituted with one or more halogen atoms; phenyl optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms; 5- to 6-membered heteroaryl optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms; C7-C9 phenylalkyl whose phenyl ring is optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms; or C7-C9 pyridinylalkyl whose pyridine ring is optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms;

$R^{20a}$ and $R^{20b}$ represent a halogen atom; cyano; nitro; thiocyanato; C1-C6 alkyl optionally substituted with one or more halogen atoms; C1-C6 alkoxy optionally substituted with one or more halogen atoms; C2-C6 cyanoalkyloxy; C2-C6 alkoxyalkyloxy optionally substituted with one or more halogen atoms; C2-C6 alkenyloxy optionally substituted with one or more halogen atoms; C2-C6 alkynyloxy optionally substituted with one or more halogen atoms; C1-C6 alkylthio optionally substituted with one or more halogen atoms; C1-C6 alkylsulfinyl optionally substituted with one or more halogen atoms; C1-C6 alkylsulfonyl optionally substituted with one or more halogen atoms; phenyl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms; 5- to 6-membered heteroaryl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms; or phenoxy optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms;

p represents an integer of 0 to 3 (provided that, when p is an integer of 2 or 3, two or more $R^{20a}$s may be the same or different); and q represents an integer of 0 to 3 (provided that, when q is an integer of 2 or 3, two or more $R^{20b}$s may be the same or different).

Furthermore this invention also contains a method of controlling an invertebrate pest applying the present compound, an N-oxide thereof or an agricultural suitable salt thereof by contacting directly to a pest, or to a place where a pest inhabits. With includes the use of the present compound, an N-oxide thereof or an agricultural suitable salt thereof as active ingredient in a pesticidal composition.

A composition comprising of the present compound, an N-oxide thereof or an agricultural suitable salt thereof and at least one additional component selected from the group of surfactants, solid diluents and liquid diluents. This invention also includes a method for controlling an invertebrate pest by using the present compound, an N-oxide thereof or an agricultural suitable salt thereof as active ingredient in a pesticidal composition and a biological active amount of at least one additional compound or agent. The invention also pertains to the use of the present compound, an N-oxide thereof or an agricultural suitable salt thereof for manufacturing a pesticidal preparation.

BEST MODE FOR CARRYING OUT THE INVENTION

The compounds of this invention include every possible sterioisomer in terms of enantiomers and diastereomers that can be formed from different configuration at centers of asymmetry and different double bond configuration according to well-accepted definition of configuration isomers (Eliel, Ernest L., Wilien, Samuel H., *Stereochemistry of Organic Compounds*, John Wiley & Son, 1994). The compounds of the invention can be present as a mixture of the above-mentioned isomers, as a single diastereomer or in an optically enriched form as active ingredients. Furthermore, the compounds of formula I of this invention can be present as an N-oxide thereof or an agricultural suitable salt thereof. All available nitrogen atoms whose lone pairs are not part of an aromatic molecular H-orbital according to Hückel's rule can be oxidized at their lone pairs to form N-oxides by using commonly known methods. Agricultural suitable salts of the compounds of this invention can be formed by addition of an inorganic or organic acid to the compound like for example hydrochloric, hydrobromic, sulfuric, nitric and phosphoric acid as well as acetic, propionic, butyric, oxalic, malonic, tartaric, lactic, maleic, fumaric, citric, p-toluenesulfonic and salicylic acid. In case where compounds contain acidic moieties like carboxyl, sulfonyl or phenol, salts can be formed by addition of an inorganic or organic base like e.g. the hydroxides and carbonates of lithium, sodium, potassium, magnesium, calcium and barium or amines like ammonia, pyridine or triethylamine. The term 'aromatic' and 'heteroaromatic' indicates that the carbocyclic or heterocyclic ring system is fully unsaturated with a planar ring system allowing the ring systems p-orbitals and optionally lone pair orbitals of heteroatoms, which are perpendicular to the ring plane to overlap to form a Π-molecular orbital with (4n+2) Π-electrons according to Hückel's rule (n is 0 or a positive integer). The term 'non-aromatic' or 'non-aromatic heterocyclic ring system' refers to a ring system, which is fully or partial saturated or which is fully unsaturated but does not fulfill the requirements of Hückel's rule as mentioned above. The term 'hetero' in 'heteroaromatic', 'heterobicyclic' and 'non-aromatic heterocyclic ring' denotes a ring system that contains at least one or more atom different from carbon, selected from the group of oxygen, nitrogen and sulfur. The heterocyclic ring system can be attached at any available carbon or nitrogen atom by replacement of hydrogen.

Hereinafter, the examples of the "substituents" are illustrated.

Examples of the 5- or 6-membered heteroaromatic ring system substituted with ($R^4$), include E-1 to E-39 shown below. The heteroaromatic ring systems E-1 to E-39 are attached with their upper right bond of an available carbon atom to the nitrogen atom of the —$NR^1(C=A^1)$J moiety. The hydrazide moiety —$(C=A^2)_N R^2 NR^3 Q$ is attached with the —$(C=A^2)$ carbon atom to an available carbon atom at the lower right bond of the exemplified ring systems E-1 to E-39.

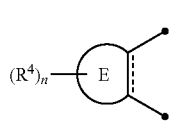 = 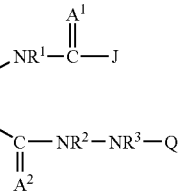

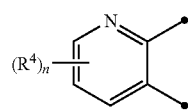 E-1

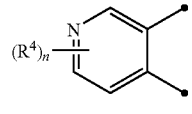 E-2

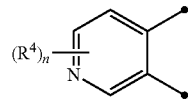 E-3

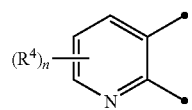 E-4

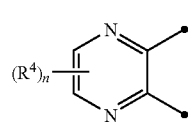 E-5

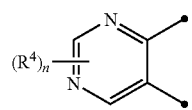 E-6

-continued

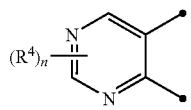 E-7

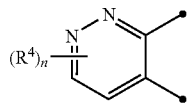 E-8

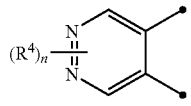 E-9

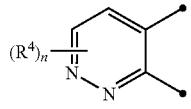 E-10

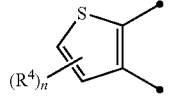 E-11

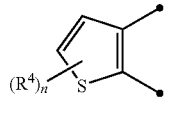 E-12

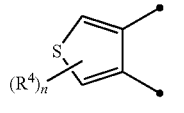 E-13

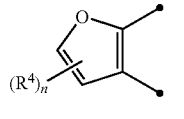 E-14

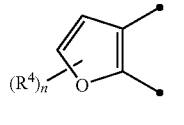 E-15

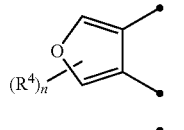 E-16

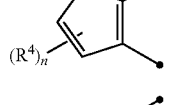 E-17

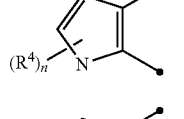 E-18

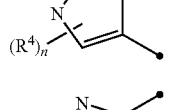 E-19

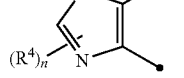 E-20

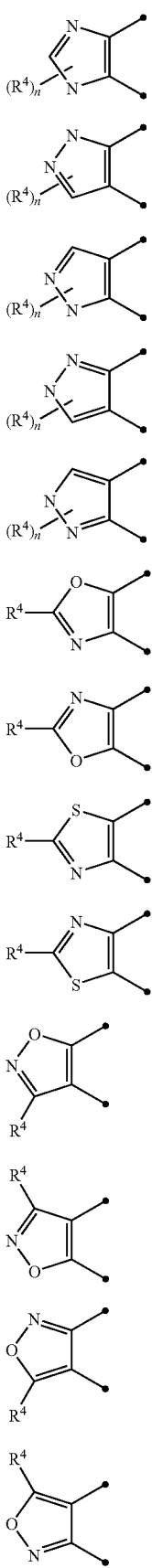
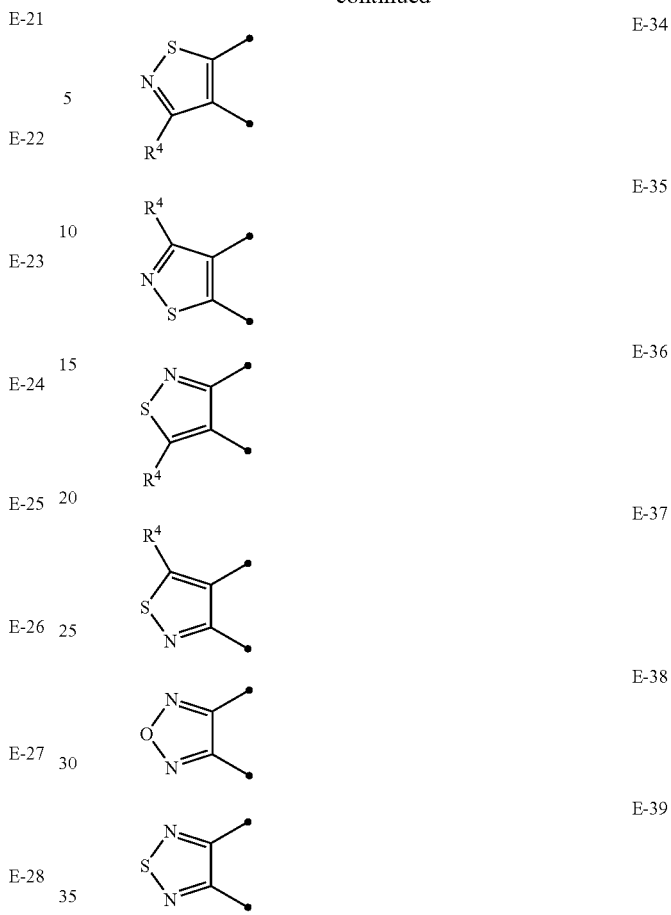

Examples of the 8-, 9- or 10-membered fused heterobicyclic ring system substituted with (R⁴), include E-40 to E-109 shown below. Substitution of said heterobicyclic ring systems with substituents R⁴ is possible by substitution of carbon and nitrogen H-atoms on the aromatic ring systems as well as on non-aromatic linking moieties (E-97-101, E-103, E-105, E-107-109). The heteroaromatic ring systems E-40 to E-109 are attached with their upper right bond of an available carbon atom to the nitrogen atom of the —NR¹(C=A¹)J moiety. The hydrazide moiety —(C=A²)$_N$R²NR³Q is attached with the —(C=A²) carbon atom to an available carbon atom at the lower right bond of the exemplified ring systems E-40 to E-109.

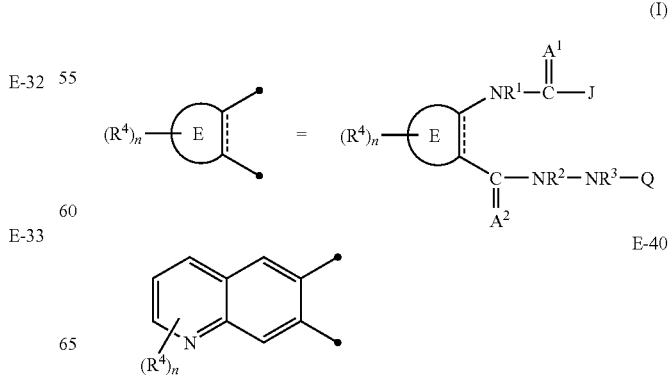

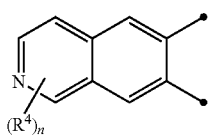 E-41
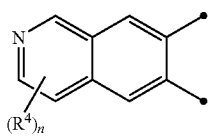 E-42
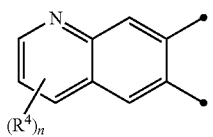 E-43
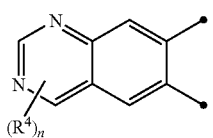 E-44
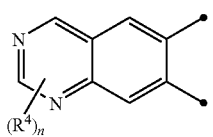 E-45
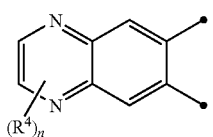 E-46
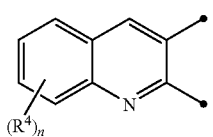 E-47
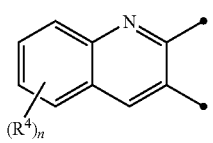 E-48
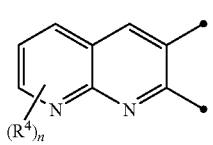 E-49
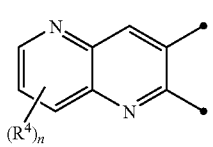 E-50
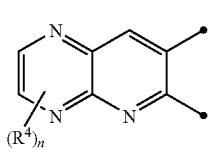 E-51
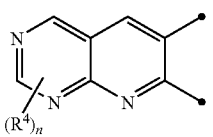 E-52
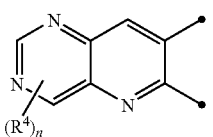 E-53
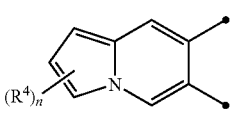 E-54
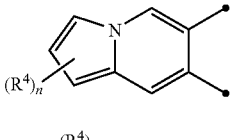 E-55
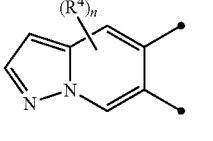 E-56
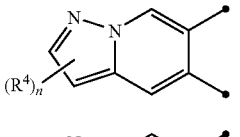 E-57
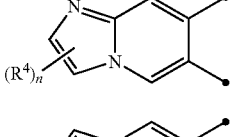 E-58
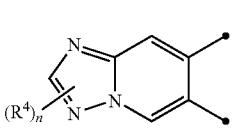 E-59
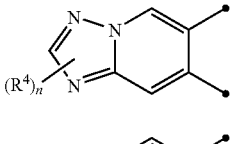 E-60
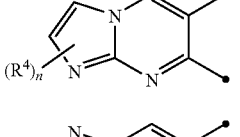 E-61
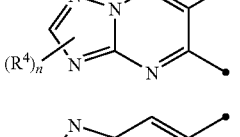 E-62
E-63
E-64

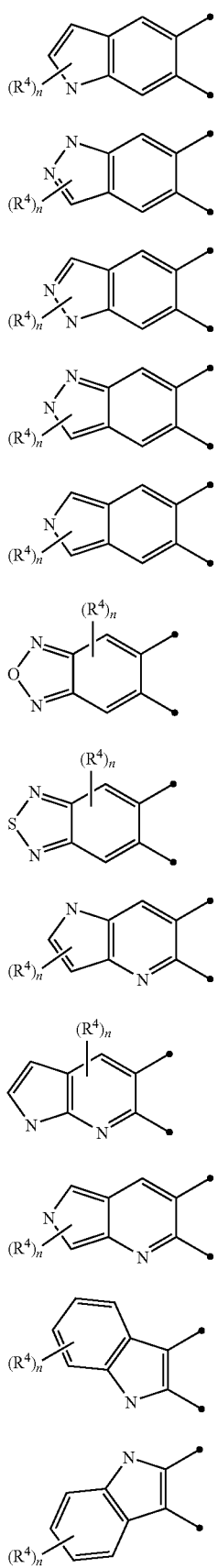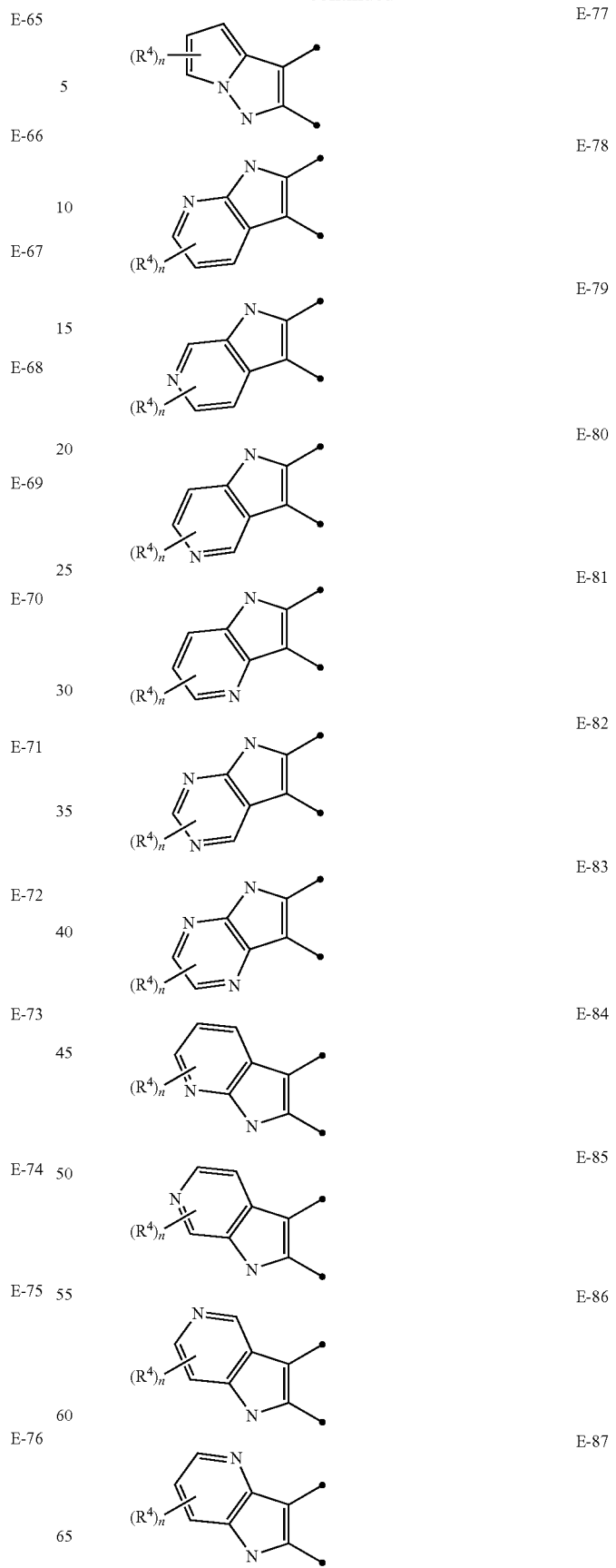

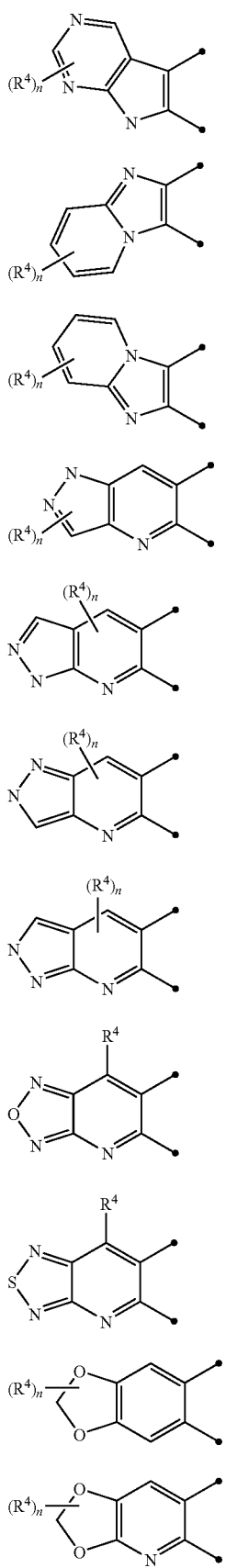
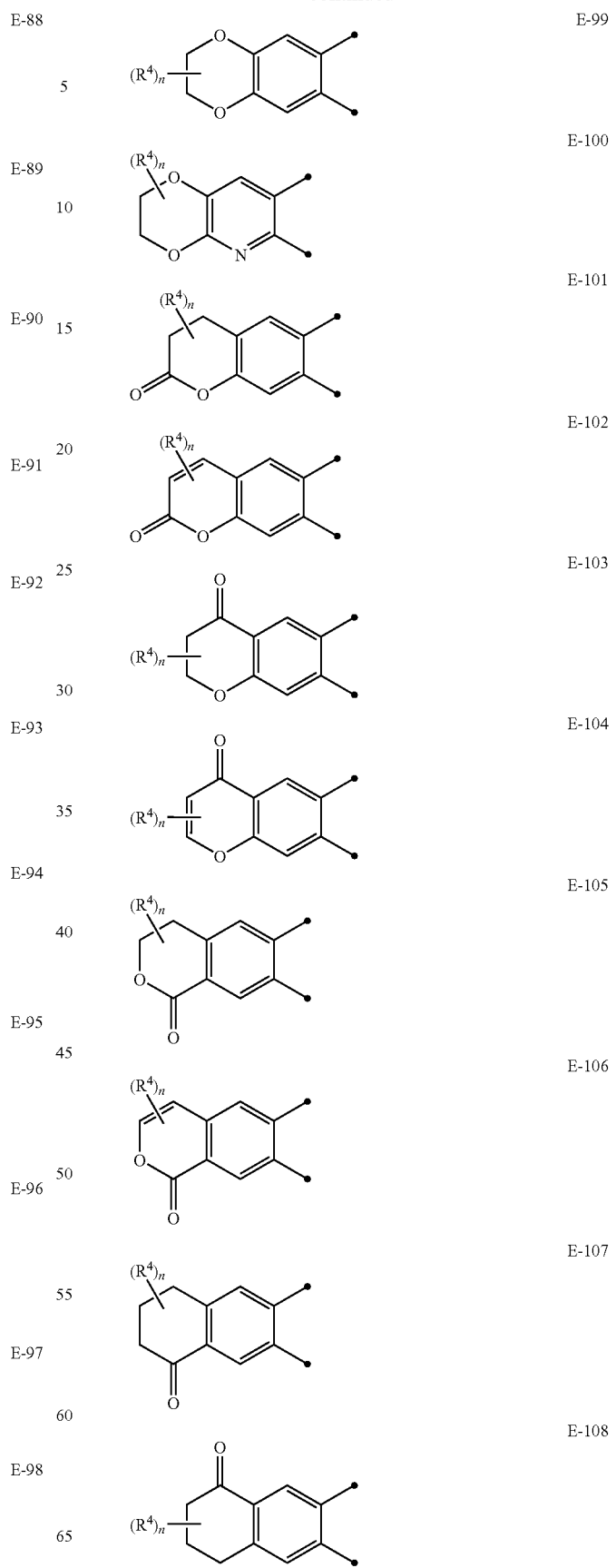

E-109

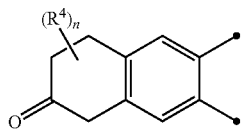

Preferred ring systems include E-2, E-4, E-7, E-12, E-13, E-22, E-40 and E47; most preferred E-2 and E-4.

Examples of a halogen atom include a fluorine atom, a chlorine atom, a bromine atom and an iodine atom.

Examples of C1-C6 alkyl optionally substituted with one or more halogen atoms include methyl, ethyl, propyl, isopropyl, butyl, isobutyl, sec-butyl, tert-butyl, pentyl and hexyl as well as fluoromethyl, difluoromethyl, trifluoromethyl, chloromethyl, dichloromethyl, trichloromethyl, 2,2,2-trifluoroethyl, 1,1,2,2-tetrafluoroethyl and pentafluoroethyl.

Examples of C1-C6 alkyl optionally substituted with one or more independent substituents selected from the group consisting of (1) a halogen atom, (2) C1-C6 alkoxy optionally substituted with one or more halogen atoms, (3) C1-C6 alkylthio optionally substituted with one or more halogen atoms, (4) C1-C6 alkylsulfinyl optionally substituted with one or more halogen atoms, (5) C1-C6 alkylsulfonyl optionally substituted with one or more halogen atoms, (6) C2-C6 dialkylamino optionally substituted with one or more halogen atoms, and (7) C3-C6 cycloalkyl optionally substituted with one or more halogen atoms include methyl, trifluoromethyl, trichloromethyl, chloromethyl, dichloromethyl, fluoromethyl, difluoromethyl, methoxymethyl, ethoxymethyl, methylthiomethyl, ethylthiomethyl, methylsulfinylmethyl, methylsulfonylmethyl, dimethylaminomethyl, cyclopropylmethyl, cyclopentylmethyl, cyclohexylmethyl, ethyl, pentafluoroethyl, propyl, isopropyl, butyl, isobutyl, sec-butyl, tert-butyl, pentyl and hexyl.

Examples of C2-C6 cyanoalkyl include cyanomethyl and 2-cyanoethyl.

Examples of C2-C6 cyanoalkoxy include cyanomethoxy and 2-cyanoethoxy.

Examples of C1-C6 hydroxyalky include hydroxymethyl, 1-hydroxyethyl, 2-hydroxyethyl, 1-hydroxypropyl, 2-hydroxypropyl, 3-hydroxypropyl and 2-hydroxy-isopropyl.

Examples of C1-C6 alkoxy optionally substituted with one or more halogen atoms include methoxy, trifluoromethoxy, ethoxy, 2,2,2-trifluoroethoxy, propyloxy, isopropyloxy, butoxy, isobutyloxy, sec-butoxy, tert-butoxy, pentyloxy and hexyloxy.

Examples of C2-C6 alkoxyalkyl optionally substituted with one or more halogen atoms include methoxymethyl, ethoxymethyl, 2-methoxyethyl, 2-ethoxyethyl and 2-isopropyloxyethyl.

Examples of C2-C6 alkoxyalkyloxy optionally substituted with one or more halogen atoms include 2-(methoxy)ethoxy.

Examples of C2-C6 alkenyl optionally substituted with one or more halogen atoms include 2-propenyl, 3-chloro-2-propenyl, 2-chloro-2-propenyl, 3,3-dichloro-2-propenyl, 2-butenyl, 3-butenyl, 2-methyl-2-propenyl, 3-methyl-2-butenyl, 2-pentenyl and 2-hexenyl as well as polyenes like 1,3-pentadienyl and 2,4-hexadienyl and all possible diastereomers.

Examples of C2-C6 alkenyloxy optionally substituted with one or more halogen atoms include 2-propenyloxy, 3,3-dichloro-2-propenoxy and 2-methyl-2-propenyloxy.

Examples of C2-C6 alkynyl optionally substituted with one or more halogen atoms include 2-propynyl, 3-chloro-2-propynyl, 3-bromo-2-propynyl, 2-butynyl and 3-butynyl as well as polyynes like 2,5-hexadiynyl.

Examples of C2-C6 alkynyloxy optionally substituted with one or more halogen atoms include 2-propynyloxy, 3-chloro-2-propynyloxy and 2-butynyloxy.

Examples of C1-C6 alkylthio optionally substituted with one or more halogen atoms include methylthio, trifluoromethylthio, ethylthio, propylthio, isopropylthio, butylthio, isobutylthio, sec-butylthio, tert-butylthio, pentylthio and hexylthio.

Examples of C1-C6 alkylsulfinyl optionally substituted with one or more halogen atoms include methylsulfinyl, trifluoromethylsulfinyl, ethylsulfinyl, propylsulfinyl, isopropylsulfinyl, butylsulfinyl, isobutylsulfinyl, sec-butylsulfinyl, tert-butylsulfinyl, pentylsulfinyl and hexylsulfinyl. The definition includes both sulfoxide enantiomers.

Examples of C1-C6 alkylsulfonyl optionally substituted with one or more halogen atoms include methylsulfonyl, trifluoromethylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl and hexylsulfonyl.

Examples of C1-C6 alkylamino include methylamino, ethylamino, n-propylamino, isopropylamino, n-butylamino, sec-butylamino, isobutylamino and tert-butylamino.

Examples of C1-C6 alkylamino optionally substituted with one or more halogen atoms alkylamino include methylamino, ethylamino, n-propylamino, isopropylamino, n-butylamino, sec-butylamino, isobutylamino, tert-butylamino, 2-fluoroethyl amino, 2,2,2-trifluoroethyl amino, 2,2,3,3,3-pentafluoropropyl amino and 2,2,3,3,4,4,4-heptafluoroamino.

Examples of C2-C8 dialkylamino include dimethylamino, diethylamino, ethylmethylamino, di-n-propylamino, diisopropylamino and di-n-butylamino.

Examples of C2-C8 dialkylamino optionally substituted with one or more halogen atoms include dimethylamino, diethylamino, ethylmethylamino, bis(2,2,2-trifluoroethyl)amino, di-n-propylamino, diisopropylamino and di-n-butylamino.

Examples of C3-C6 cycloalkylamino include cyclopropyl amino, cyclobutylamino, cyclopentylamino and cyclohexylamino.

Examples of C2-C6 alkylcarbonyl include acetyl, propionyl, isobutyryl and trimethylacetyl.

Examples of C2-C6 alkylcarbonyl optionally substituted with one or more halogen atoms include acetyl, trifluoroacetyl, trichloroacetyl, propionyl, pentafluoropropionyl, isobutyryl and trimethylacetyl.

Examples of C2-C6 alkoxycarbonyl include methoxycarbonyl, ethoxycarbonyl, isopropoxycarbonyl and tert-butoxycarbonyl.

Examples of C2-C6 alkoxycarbonyl optionally substituted with one or more halogen atoms include methoxycarbonyl, ethoxycarbonyl, 2-fluoroethoxycarbonyl, 2,2,2-trifluoroethoxycarbonyl, 2,2,2-trichloroethoxycarbonyl, isopropoxycarbonyl and tert-butoxycarbonyl.

Examples of C2-C6 alkylaminocarbonyl include methylaminocarbonyl, ethylaminocarbonyl, n-propylaminocarbonylcarbonyl, isopropylaminocarbonyl, n-butylaminocarbonyl, sec-butylaminocarbonyl, isobutylaminocarbonyl and tert-butylaminocarbonyl.

Examples of C2-C6 alkylaminocarbonyl optionally substituted with one or more halogen atoms include methylaminocarbonyl, ethylaminocarbonyl, n-propylaminocarbonyl, isopropylaminocarbonyl, n-butylaminocarbonyl, sec-butylaminocarbonyl, isobutylaminocarbonyl, tert-butylaminocarbonyl, 2-fluoroethylaminocarbonyl, 2,2,2-trifluoroethylaminocarbonyl, 2,2,3,3,3-pentafluoropropylcarbonylaminocarbonyl and 2,2,3,3,4,4,4-heptafluorobutylaminocarbonyl.

Examples of C3-C8 dialkylaminocarbonyl include dimethylaminocarbonyl and diethylaminocarbonyl.

Examples of C4-C6 cycloalkylaminocarbonyl include cyclopropylaminocarbonyl, cyclobutylaminocarbonyl, cyclopentylaminocarbonyl and cyclohexylaminocarbonyl.

Examples of C3-C6 trialkylsilyl include trimthylsilyl, triethylsilyl and tertbutyldimethylsilyl.

Examples of C3-C6 cycloalkyl optionally substituted with one or more independent substituents selected from the group consisting of (1) a halogen atom, and (2) C1-C6 alkyl optionally substituted with one or more halogen atoms include cyclopropyl, 2-methylcyclopropyl, cyclobutyl, cyclopentyl and cyclohexyl.

Examples of phenyl optionally substituted with one or more independent substituents selected from the group consisting of (1) a halogen atom, (2) cyano, (3) nitro, (4) hydroxyl, (5) carboxyl, (6) C1-C6 alkyl optionally substituted with one or more halogen atoms, (7) C1-C6 hydroxyalkyl, (8) C1-C6 alkoxy optionally substituted with one or more halogen atoms, (9) C2-C6 cyanoalkyl optionally substituted with one or more halogen atoms, (10) C2-C6 alkoxyalkyl optionally substituted with one or more halogen atoms, (11) C2-C6 alkenyl optionally substituted with one or more halogen atoms, (12) C2-C6 alkynyl optionally substituted with one or more halogen atoms, (13) C3-C6 cycloalkyl optionally substituted with one or more halogen atoms, (14) C1-C6 alkylthio optionally substituted with one or more halogen atoms, (15) C1-C6 alkylsulfinyl optionally substituted with one or more halogen atoms, (16) C1-C6 alkylsulfonyl optionally substituted with one or more halogen atoms, (17) C1-C6 alkylamino, (18) C2-C8 dialkylamino, (19) C3-C6 cycloalkylamino, (20) C2-C6 alkylcarbonyl, (21) C2-C6 alkoxycarbonyl, (22) C2-C6 alkylaminocarbonyl, (23) C3-C8 dialkylaminocarbonyl, (24) C4-C6 cycloalkylaminocarbonyl and (25) C3-C6 trialkylsilyl include phenyl, 2-fluorophenyl, 3-fluorophenyl, 4-fluorophenyl, 2-chlorophenyl, 3-chlorophenyl, 4-chlorophenyl, 2-bromophenyl, 2-iodophenyl, 2,6-difluorophenyl, 2,6-dichlorophenyl, 2-chloro-6-fluorophenyl, 2-chloro-4-fluorophenyl, 2-cyanophenyl, 3-cyanophenyl, 4-cyanophenyl, 2-nitrophenyl, 3-nitrophenyl, 4-nitrophenyl, 2-methylphenyl, 3-methylphenyl, 4-methylphenyl, 2-ethylphenyl, 2-isopropylphenyl, 2-tert-butylphenyl, 2-(trifluoromethyl)phenyl, 3-(trifluoromethyl)phenyl, 4-(trifluoromethyl)phenyl, 2-methoxyphenyl, 3-methoxyphenyl, 4-methoxyphenyl, 2-ethoxyphenyl, 2-(trifluoromethoxy)phenyl, 2-(methylthio)phenyl, 2-(methylsulfinyl)phenyl and 2-(methylsulfonyl)phenyl.

Examples of benzyl optionally substituted with one or more substituents selected from the group consisting of (1) a halogen atom, (2) cyano, (3) nitro, (4) hydroxyl, (5) carboxyl, (6) C1-C6 alkyl optionally substituted with one or more halogen atoms, (7) C1-C6 hydroxyalkyl, (8) C1-C6 alkoxy optionally substituted with one or more halogen atoms, (9) C2-C6 cyanoalkyl optionally substituted with one or more halogen atoms, (10) C2-C6 alkoxyalkyl optionally substituted with one or more halogen atoms, (11) C2-C6 alkenyl optionally substituted with one or more halogen atoms, (12) C2-C6 alkynyl optionally substituted with one or more halogen atoms, (13) C3-C6 cycloalkyl optionally substituted with one or more halogen atoms, (14) C1-C6 alkylthio optionally substituted with one or more halogen atoms, (15) C1-C6 alkylsulfinyl optionally substituted with one or more halogen atoms, (16) C1-C6 alkylsulfonyl optionally substituted with one or more halogen atoms, (17) C1-C6 alkylamino, (18) C2-C8 dialkylamino, (19) C3-C6 cycloalkylamino, (20) C2-C6 alkylcarbonyl, (21) C2-C6 alkoxycarbonyl, (22) C2-C6 alkylaminocarbonyl, (23) C3-C8 dialkylaminocarbonyl, (24) C4-C6 cycloalkylaminocarbonyl and (25) C3-C6 trialkylsilyl include benzyl, 2-fluorobenzyl, 3-fluorobenzyl, 4-fluorobenzyl, 2-chlorobenzyl, 3-chlorobenzyl, 4-chlorobenzyl, 2-bromobenzyl, 2-iodobenzyl, 2,6-difluorobenzyl, 2,6-dichlorobenzyl, 2-chloro-6-fluorobenzyl, 2-chloro-4-fluorobenzyl, 2-cyanobenzyl, 3-cyanobenzyl, 4-cyanobenzyl, 2-nitrobenzyl, 3-nitrobenzyl, 4-nitrobenzyl, 2-methylbenzyl, 3-methylbenzyl, 4-methylbenzyl, 2-ethylbenzyl, 2-isopropylbenzyl, 2-tert-butylbenzyl, 2-(trifluoromethyl)benzyl, 3-(trifluoromethyl)benzyl, 4-(trifluoromethyl)benzyl, 2-methoxybenzyl, 3-methoxybenzyl, 4-methoxybenzyl, 2-ethoxybenzyl, 2-(trifluoromethoxy)benzyl, 2-(methylthio)benzyl, 2-(methylsulfinyl)benzyl and 2-(methylsulfonyl)benzyl.

Examples of C7-C9 phenylalkyl optionally substituted with one or more independent substituents selected from the group consisting of (1) a halogen atom, (2) cyano, (3) nitro, (4) hydroxyl, (5) carboxyl, (6) C1-C6 alkyl optionally substituted with one or more halogen atoms, (7) C1-C6 hydroxyalkyl, (8) C1-C6 alkoxy optionally substituted with one or more halogen atoms, (9) C2-C6 cyanoalkyl optionally substituted with one or more halogen atoms, (10) C2-C6 alkoxyalkyl optionally substituted with one or more halogen atoms, (11) C2-C6 alkenyl optionally substituted with one or more halogen atoms, (12) C2-C6 alkynyl optionally substituted with one or more halogen atoms, (13) C3-C6 cycloalkyl optionally substituted with one or more halogen atoms, (14) C1-C6 alkylthio optionally substituted with one or more halogen atoms, (15) C1-C6 alkylsulfinyl optionally substituted with one or more halogen atoms, (16) C1-C6 alkylsulfonyl optionally substituted with one or more halogen atoms, (17) C1-C6 alkylamino, (18) C2-C8 dialkylamino, (19) C3-C6 cycloalkylamino, (20) C2-C6 alkylcarbonyl, (21) C2-C6 alkoxycarbonyl, (22) C2-C6 alkylaminocarbonyl, (23) C3-C8 dialkylaminocarbonyl, (24) C4-C6 cycloalkylaminocarbonyl and (25) C3-C6 trialkylsilyl include benzyl, 1-phenylethyl, 2-phenylethyl, 2-chlorobenzyl, 3-chlorobenzyl, 4-chlorobenzyl, 2-cyanobenzyl, 3-cyanobenzyl, 4-cyanobenzyl, 2-nitrobenzyl, 3-nitrobenzyl, 4-nitrobenzyl, 2-methylbenzyl, 3-methylbenzyl, 4-methylbenzyl, 2-(trifluoromethyl)benzyl, 3-(trifluoromethyl)benzyl, 4-(trifluoromethyl)benzyl, 2-methoxybenzyl, 3-methoxybenzyl and 4-methoxybenzyl.

Examples of phenoxy optionally substituted with one or more substituents selected from the group consisting of (1) a halogen atom, (2) cyano, (3) nitro, (4) hydroxyl, (5) carboxyl, (6) C1-C6 alkyl optionally substituted with one or more halogen atoms, (7) C1-C6 hydroxyalkyl, (8) C1-C6 alkoxy optionally substituted with one or more halogen atoms, (9) C2-C6 cyanoalkyl optionally substituted with one or more halogen atoms, (10) C2-C6 alkoxyalkyl optionally substituted with one or more halogen atoms, (11) C2-C6 alkenyl optionally substituted with one or more halogen atoms, (12) C2-C6 alkynyl optionally substituted with one or more halogen atoms, (13) C3-C6 cycloalkyl optionally substituted with one or more halogen atoms, (14) C1-C6 alkylthio optionally substituted with one or more halogen atoms, (15) C1-C6 alkylsulfinyl optionally substituted with one or more halogen atoms, (16) C1-C6 alkylsulfonyl optionally substituted with one or more halogen atoms, (17) C1-C6 alkylamino, (18) C2-C8 dialkylamino, (19) C3-C6 cycloalkylamino, (20) C2-C6 alkylcarbonyl, (21) C2-C6 alkoxycarbonyl, (22) C2-C6 alkylaminocarbonyl, (23) C3-C8 dialkylaminocarbonyl, (24) C4-C6 cycloalkylaminocarbonyl and (25) C3-C6 trialkylsilyl include phenoxy, 2-chlorophenoxy, 3-chlorophenoxy, 4-chlorophenoxy, 2-cyanophenoxy, 3-cyanophenoxy, 4-cyanophenoxy, 2-nitrophenoxy, 3-nitrophenoxy, 4-nitrophenoxy, 2-methylphenoxy, 3-methylphenoxy, 4-methylphenoxy, 2-(trifluoromethyl)phenoxy, 3-(trifluoromethyl)phenoxy, 4-(trifluoromethyl)phenoxy, 2-methoxyphenoxy, 3-methoxyphenoxy, 4-methoxyphenoxy and 4-(trifluoromethoxy)phenoxy.

Examples of C7-C9 phenoxyalkyl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms include phenoxymethyl, phenoxyethyl, 2-chlorophenoxymethyl, 2-chlorophenoxyethyl, 3-chlorophenoxymethyl, 3-chlorophenoxyethyl, 4-chlorophenoxymethyl, 4-chlorophenoxyethyl, 2-cyanophenoxymethyl, 2-cyanophenoxyethyl, 3-cyanophenoxymethyl, 3-cyanophenoxyethyl, 4-cyanophenoxymethyl, 4-cyanophenoxyethyl, 2-nitrophenoxymethyl, 2-nitrophenoxyethyl, 3-nitrophenoxymethyl, 3-nitrophenoxyethyl, 4-nitrophenoxymethyl, 4-nitrophenoxyethyl, 2-methylphenoxymethyl, 2-methylphenoxyethyl, 3-methylphenoxymethyl, 3-methylphenoxyethyl, 4-methylphenoxymethyl, 4-methylphenoxyethyl, 2-(trifluoromethyl)phenoxymethyl, 2-(trifluoromethyl)phenoxyethyl, 3-(trifluoromethyl)phenoxymethyl, 3-(trifluoromethyl)phenoxyethyl, 4-(trifluoromethyl)phenoxymethyl, 4-(trifluoromethyl)phenoxyethyl, 2-methoxyphenoxymethyl, 2-methoxyphenoxyethyl, 3-methoxyphenoxymethyl, 3-methoxyphenoxyethyl, 4-methoxyphenoxymethyl, 4-methoxyphenoxyethyl, 4-(trifluoromethoxy)phenoxymethyl and 4-(trifluoromethoxy)phenoxyethyl.

Examples of phenylcarbonyl optionally substituted with one or more independent substituents selected from the group consisting of (1) a halogen atom, (2) cyano, (3) nitro, (4) hydroxyl, (5) carboxyl, (6) C1-C6 alkyl optionally substituted with one or more halogen atoms, (7) C1-C6 hydroxyalkyl, (8) C1-C6 alkoxy optionally substituted with one or more halogen atoms, (9) C2-C6 cyanoalkyl optionally substituted with one or more halogen atoms, (10) C2-C6 alkoxyalkyl optionally substituted with one or more halogen atoms, (11) C2-C6 alkenyl optionally substituted with one or more halogen atoms, (12) C2-C6 alkynyl optionally substituted with one or more halogen atoms, (13) C3-C6 cycloalkyl optionally substituted with one or more halogen atoms, (14) C1-C6 alkylthio optionally substituted with one or more halogen atoms, (15) C1-C6 alkylsulfinyl optionally substituted with one or more halogen atoms, (16) C1-C6 alkylsulfonyl optionally substituted with one or more halogen atoms, (17) C1-C6 alkylamino, (18) C2-C8 dialkylamino, (19) C3-C6 cycloalkylamino, (20) C2-C6 alkylcarbonyl, (21) C2-C6 alkoxycarbonyl, (22) C2-C6 alkylaminocarbonyl, (23) C3-C8 dialkylaminocarbonyl, (24) C4-C6 cycloalkylaminocarbonyl and (25) C3-C6 trialkylsilyl include benzoyl, 2-fluorobenzoyl, 3-fluorobenzoyl, 4-fluorobenzoyl, 2-chlorobenzoyl, 3-chlorobenzoyl, 4-chlorobenzoyl, 2-bromobenzoyl, 2-iodobenzoyl, 2,6-difluorobenzoyl, 2,6-dichlorobenzoyl, 2-chloro-6-fluorobenzoyl, 2-chloro-4-fluorobenzoyl, 2-cyanobenzoyl, 3-cyanobenzoyl, 4-cyanobenzoyl, 2-nitrobenzoyl, 3-nitrobenzoyl, 4-nitrobenzoyl, 2-methylbenzoyl, 3-methylbenzoyl, 4-methylbenzoyl, 2-ethylbenzoyl, 2-isopropylbenzoyl, 2-tert-butylbenzoyl, 2-(trifluoromethyl)benzoyl, 3-(trifluoromethyl)benzoyl, 4-(trifluoromethyl)benzoyl, 2-methoxybenzoyl, 3-methoxybenzoyl, 4-methoxybenzoyl, 2-ethoxybenzoyl, 2-(trifluoromethoxy)benzoyl, 2-(methylthio)benzoyl, 2-(methylsulfinyl)benzoyl and 2-(methylsulfonyl)benzoyl.

Examples of naphthyl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms include 1-naphthyl and 2-naphthyl.

Examples of 5- or 6-membered heteroaromatic ring optionally substituted with one or more substituents selected from the group consisting of (1) a halogen atom, (2) cyano, (3) nitro, (4) hydroxyl, (5) carboxyl, (6) C1-C6 alkyl optionally substituted with one or more halogen atoms, (7) C1-C6 hydroxyalkyl, (8) C1-C6 alkoxy optionally substituted with one or more halogen atoms, (9) C2-C6 cyanoalkyl optionally substituted with one or more halogen atoms, (10) C2-C6 alkoxyalkyl optionally substituted with one or more halogen atoms, (11) C2-C6 alkenyl optionally substituted with one or more halogen atoms, (12) C2-C6 alkynyl optionally substituted with one or more halogen atoms, (13) C3-C6 cycloalkyl optionally substituted with one or more halogen atoms, (14) C1-C6 alkylthio optionally substituted with one or more halogen atoms, (15) C1-C6 alkylsulfinyl optionally substituted with one or more halogen atoms, (16) C1-C6 alkylsulfonyl optionally substituted with one or more halogen atoms, (17) C1-C6 alkylamino, (18) C2-C8 dialkylamino, (19) C3-C6 cycloalkylamino, (20) C2-C6 alkylcarbonyl, (21) C2-C6 alkoxycarbonyl, (22) C2-C6 alkylaminocarbonyl, (23) C3-C8 dialkylaminocarbonyl, (24) C4-C6 cycloalkylaminocarbonyl and (25) C3-C6 trialkylsilyl include 2-pyridinyl, 3-fluoro-2-pyridinyl, 3-chloro-2-pyridinyl, 3-bromo-2-pyridinyl, 3-iodo-2-pyridinyl, 3-methyl-2-pyridinyl, 3-trifluoromethyl-2-pyridinyl, 3-methoxy-2-pyridinyl, 3-cyano-2-pyridinyl, 3-nitro-2-pyridinyl, 3-pyridinyl, 2-chloro-3-pyridinyl, 4-chloro-3-pyridinyl, 4-pyridinyl, 3-chloro-4-pyridinyl, 3,5-dichloro-4-pyridinyl, 2-pyrimidinyl, 4-methyl-2-pyrimidinyl, 4,6-dimethyl-2-pyrimidinyl, 4-pyrimidinyl, 5-chloro-4-pyrimidinyl, pyrazinyl, 3-methyl-2-pyrazinyl, 2-thiazolyl, 1-methyl-5-pyrazolyl, 4-chloro-1-methyl-5-pyrazolyl, 4-chloro-1,3-dimethyl-5-pyrazolyl and 4-chloro-5-methyl-3-isooxazolyl.

Examples of 3- to 8-membered non-aromatic heterocyclic ring optionally substituted with one or more independent substituents selected from the group consisting of (1) a halogen atom, and (2) C1-C6 alkyl optionally substituted with one or more halogen atoms include pyrrolidin-1-yl, piperidino, 3,5-dimethylpiperidino, hexamethyleneimin-1-yl, heptamethyleneimin-1-yl, morpholino, 2,6-dimethylmorpholino, thiomorpholin-4-yl, 4-methylpiperazin-1-yl, 4-(ethoxycarbonyl)piperazin-1-yl and 4-phenylpiperazin-1-yl.

Examples of C7-C9 pyridinylalkyl whose pyridine ring is optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms include 2-pyridinylmethyl, 3-pyridinylmethyl, 4-pyridinylmethyl, 3-chloro-2-pyridinylmethyl and 2-chloro-3-pyridinylmethyl.

Examples of $R^2$ and $R^3$ are taken together with the two nitrogen atoms to which they are attached to form a 5- to 8-membered ring containing two nitrogen atoms, one or more $CH_2$ or C(=O), and optionally one or two ring members selected from the group consisting of (1) an oxygen atom, (2) a sulfur atom, (3) S(=O), (4) S(=O)$_2$ and (4) NR$^a$ are shown below as ring T. Said ring at the carbon atoms is substituted by one or more independent $G^6$, which represents a halogen atom, C1-C6 alkyl optionally substituted with one or more halogen atoms, and C2-C6 alkoxycarbonyl optionally substituted with one or more halogen atoms. Further ring members from nitrogen —NR$^a$— (not included the two contiguous linking nitrogen atoms) with free valences can be substituted by R$^a$ which is selected from the group consisting of C1-C6 alkyl optionally substituted with one or more halogen atoms, C2-C6 alkoxycarbonyl optionally substituted with one or more halogen atoms, or a phenyl optionally substituted with one or more independent substituents selected from the group consisting of a halogen atom, cyano, nitro, C1-C6 alkyl optionally substituted with one or more halogen atoms, C1-C6 alkoxy optionally substituted with one or more halogen atoms, C1-C6 alkylthio optionally substituted with one or more halogen atoms, C1-C6 alkylsulfinyl optionally substituted with one or more halogen atoms, C1-C6 alkylsulfonyl optionally substituted with one or more halogen atoms, C1-C6 alkylamino optionally substituted with one or more halogen atoms, C2-C6 dialkylamino optionally substituted with one or more halogen atoms, C2-C6 alkylcarbonyl optionally substituted with one or more halogen atoms, C2-C6 alkoxycarbonyl optionally substituted with one or more halogen atoms, C2-C6 alkylaminocarbonyl optionally substituted with one or more halogen atoms and C3-C6 dialkylaminocarbonyl optionally substituted with one or more halogen atoms.

T-1
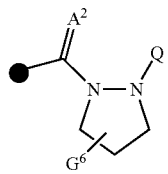

T-2
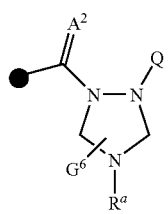

T-3
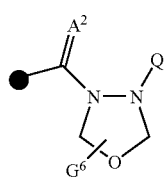

T-4
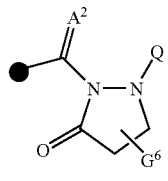

T-5
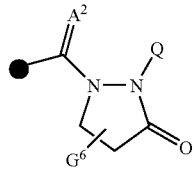

T-6
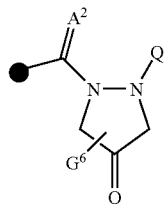

T-7
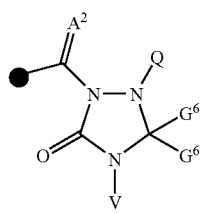

-continued

T-8
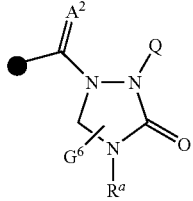

T-9
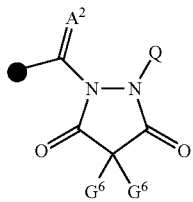

T-10
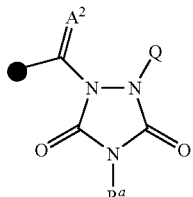

T-11
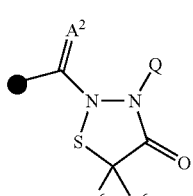

T-12
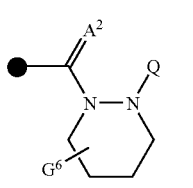

T-13
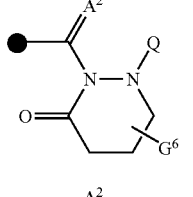

T-14
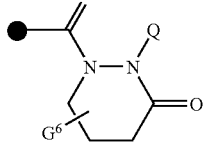

T-15
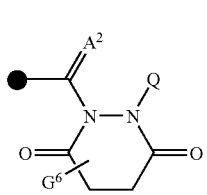

T-16 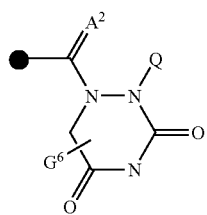
T-17 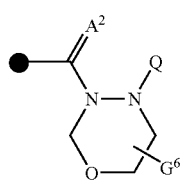
T-18 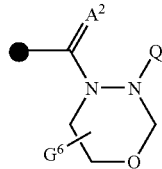
T-19 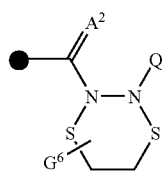
T-20 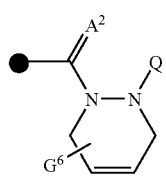
T-21 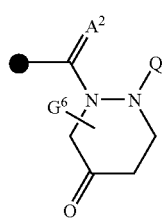
T-22 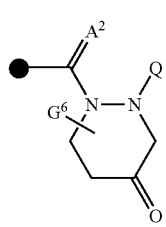
T-23 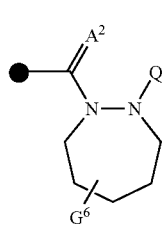
T-24 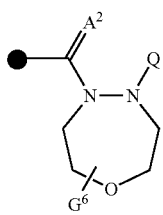
T-25 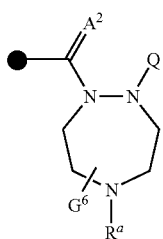
T-26 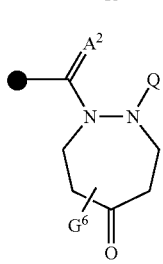
T-27 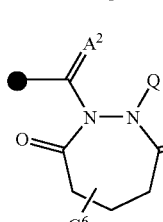
T-28 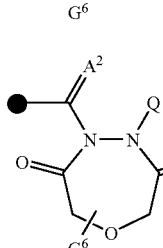
T-29 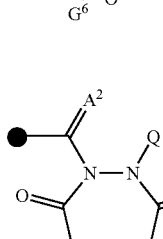
T-30 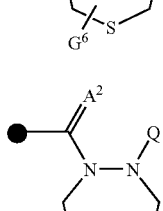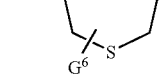

-continued

T-31
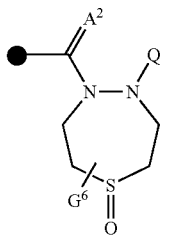

T-32
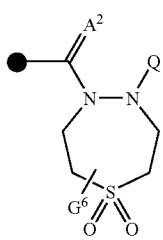

T-33
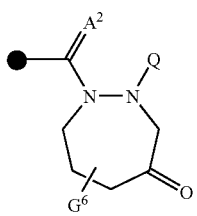

T-34
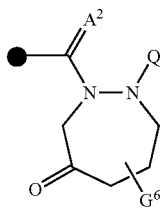

T-35
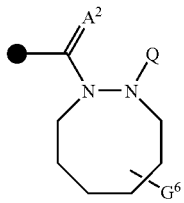

Said ring systems T are connected with the left upper nitrogen atom from the two contiguous linking nitrogen atoms via —(C=A$^2$)- moiety with the ring system E, which represents, a 5- or 6-membered heteroaromatic ring system or a 8-, 9- or 10-membered fused heterobicyclic ring system.

The substituent Q represents Q1, Q2, Q3, Q4, Q5 or Q6:

Q1:
—C(=A$^{31}$)—R$^6$

Q2:
—C(=A$^{32}$)—OR$^7$

Q3:
—C(=A$^{33}$)—SR$^8$

Q4:
—C(=A$^{34}$)—NR$^9$R$^{10}$

-continued

Q5:
—S(O)$_m$—R$^{11}$

Q6:
—S(O)$_m$—NR$^{12}$R$^{13}$,

A$^{31}$, A$^{32}$, A$^{33}$ and A$^{34}$ represent an oxygen atom, or a sulfur atom; m represents an integer of 0 to 2. Substituents R$^6$ to R$^{13}$ are selected as explained above in the summary of the invention.

J represents J1 or J2. Examples for said ring J1 and J2 are shown below as J-1.1 to J-1.8 and J-2.1 to J-2.8. The ring systems J-1.1 to J-1.8 and J-2.1 to J-2.8 are connected with their very left carbon atom via the —(C=A$^1$)- group of the —NR$^1$(C=A$^1$)J moiety with the ring system E, which represents, a 5- or 6-membered heteroaromatic ring system or a 8-, 9- or 10-membered fused heterobicyclic ring system. One nitrogen atom is substituted by R$^{19a}$ (J1) or R$^{19b}$ (J2) Ring carbon atoms are optionally substituted by 1 to 3 substituents R$^{20a}$ (J1) or R$^{20b}$ (J2) provided that, when 2 or 3 substituents R$^{20a}$ (J1) or R$^{20b}$ (J2) are present, two or more R$^{20a}$'s and R$^{20b}$'s may be the same or different. Substituents R$^{19a}$(J1), R$^{19b}$(J2), R$^{20a}$ (J1) and R$^{20b}$(J2) are selected as explained above in the summary of the invention.

Preferred ring systems include J-1.1, J-1.2, J-2.1 and J-2.2; most preferred J-1.1 and J-1.2.

J1:
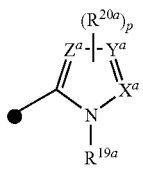

J2:
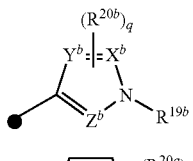

J-1.1
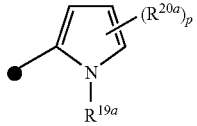

J-1.2
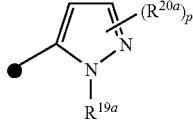

J-1.3
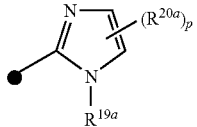

J-1.4
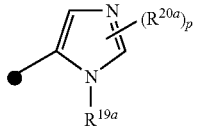

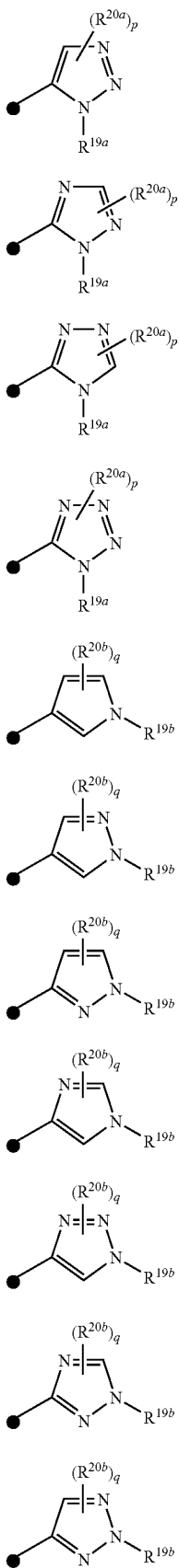
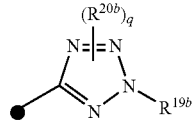

Detailed examples of the group represented by J1 include 1-phenylpyrazol-5-yl, 1-(2-chlorophenyl)pyrazol-5-yl, 1-(2-pyridinyl)pyrazol-5-yl, 1-(3-chloro-2-pyridinyl)pyrazol-5-yl, a 3-fluoro-1-phenylpyrazol-5-yl, 1-(2-chlorophenyl)-3-fluoropyrazol-5-yl, 3-fluoro-1-(2-pyridinyl)pyrazol-5-yl, 3-fluoro-1-(3-chloro-2-pyridinyl)pyrazol-5-yl, 3-chloro-1-phenylpyrazol-5-yl, 3-chloro-1-(2-chlorophenyl)pyrazol-5-yl, 3-chloro-1-(2-pyridinyl)pyrazol-5-yl, 3-chloro-1-(3-chloro-2-pyridinyl)pyrazol-5-yl, 3-bromo-1-phenylpyrazol-5-yl, 3-bromo-1-(2-chlorophenyl)pyrazol-5-yl, 3-bromo-1-(2-pyridinyl)pyrazol-5-yl, 3-bromo-1-(3-chloro-2-pyridinyl)pyrazol-5-yl, 3-iodo-1-phenylpyrazol-5-yl, 3-iodo-1-(2-chlorophenyl)pyrazol-5-yl, 3-iodo-1-(2-pyridinyl)pyrazol-5-yl, 3-iodo-1-(3-chloro-2-pyridinyl)pyrazol-5-yl, 3-methyl-1-phenylpyrazol-5-yl, 1-(2-chlorophenyl)-3-methylpyrazol-5-yl, 3-methyl-1-(2-pyridinyl)pyrazol-5-yl, 1-(3-chloro-2-pyridinyl)-3-methylpyrazol-5-yl, 1-phenyl-3-(trifluoromethyl)pyrazol-5-yl, 1-(2-chlorophenyl)-3-(trifluoromethyl)pyrazol-5-yl, 1-(2-pyridinyl)-3-(trifluoromethyl)pyrazol-5-yl, 1-(3-chloro-2-pyridinyl)-3-(trifluoromethyl)pyrazol-5-yl, 3-chloro-1-methylpyrazol-5-yl, 3-chloro-1-ethylpyrazol-5-yl, 3-chloro-1-isopropylpyrazol-5-yl, 1-tert-butyl-3-chloropyrazol-5-yl, 3-chloro-1-(3-fluoro-2-pyridinyl)pyrazol-5-yl, 1-(3-bromo-2-pyridinyl)-3-chloropyrazol-5-yl, 3-chloro-1-(3-iodo-2-pyridinyl)pyrazol-5-yl, 3-chloro-1-(3-methyl-2-pyridinyl)pyrazol-5-yl, 3-chloro-1-(3-trifluoromethyl-2-pyridinyl)pyrazol-5-yl, 3-chloro-1-(3-methoxy-2-pyridinyl)pyrazol-5-yl, 3-chloro-1-(3-cyano-2-pyridinyl)pyrazol-5-yl, 3-chloro-1-(3-nitro-2-pyridinyl)pyrazol-5-yl, 3-bromo-1-methylpyrazol-5-yl, 3-bromo-1-ethylpyrazol-5-yl, 3-bromo-1-isopropylpyrazol-5-yl, 3-bromo-1-tert-butylpyrazol-5-yl, 3-bromo-1-(3-fluoro-2-pyridinyl)pyrazol-5-yl, 3-bromo-1-(3-bromo-2-pyridinyl)pyrazol-5-yl, 3-bromo-1-(3-iodo-2-pyridinyl)pyrazol-5-yl, 3-bromo-1-(3-methyl-2-pyridinyl)pyrazol-5-yl, 3-bromo-1-(3-trifluoromethyl-2-pyridinyl)pyrazol-5-yl, 3-bromo-1-(3-methoxy-2-pyridinyl)pyrazol-5-yl, 3-bromo-1-(3-cyano-2-pyridinyl)pyrazol-5-yl, 3-bromo-1-(3-nitro-2-pyridinyl)pyrazol-5-yl, 1-methyl-3-(trifluoromethyl)pyrazol-5-yl, 1-ethyl-3-(trifluoromethyl)pyrazol-5-yl, 1-isopropyl-3-(trifluoromethyl)pyrazol-5-yl, 1-tert-butyl-3-(trifluoromethyl)pyrazol-5-yl, 1-(3-fluoro-2-pyridinyl)-3-(trifluoromethyl)pyrazol-5-yl, 1-(3-bromo-2-pyridinyl)-3-(trifluoromethyl)pyrazol-5-yl, 1-(3-iodo-2-pyridinyl)-3-(trifluoromethyl)pyrazol-5-yl, 1-(3-methyl-2-pyridinyl)-3-(trifluoromethyl)pyrazol-5-yl, 1-(3-trifluoromethyl-2-pyridinyl)-3-(trifluoromethyl)pyrazol-5-yl, 1-(3-methoxy-2-pyridinyl)-3-(trifluoromethyl)pyrazol-5-yl, 1-(3-cyano-2-pyridinyl)-3-(trifluoromethyl)pyrazol-5-yl, 1-(3-nitro-2-pyridinyl)-3-(trifluoromethyl)pyrazol-5-yl, 1-(3-chloro-2-pyridinyl)-3-ethylpyrazol-5-yl, 1-(3-chloro-2-pyridinyl)-3-isopropylpyrazol-5-yl, 3-tert-butyl-1-(3-chloro-2-pyridinyl)pyrazol-5-yl, 1-(3-chloro-2-pyridinyl)-3-(methylthio)pyrazol-5-yl, 1-(3-chloro-2-pyridinyl)-3-(ethylthio)pyrazol-5-yl, 1-(3-chloro-2-pyridinyl)-3-(isopropylthio)pyrazol-5-yl, 3-tert-butylthio-1-(3-chloro-2-pyridinyl)pyrazol-5-yl, 1-(3-chloro-2-pyridinyl)-3-(methylsulfinyl)pyrazol-5-yl, 1-(3-chloro-2-pyridinyl)-3-(ethylsulfinyl)pyrazol-5-yl, 1-(3-chloro-2-pyridinyl)-3-(isopropylsulfinyl)pyrazol-5-yl, 3-tert-butylsulfinyl-1-(3-chloro-2-pyridinyl)pyrazol-5-yl, 1-(3-chloro-2-pyridinyl)-3-(methylsulfonyl)pyrazol-5-yl, 1-(3-chloro-2-pyridinyl)-3-(ethylsulfonyl)pyrazol-5-yl, 1-(3-chloro-2-pyridinyl)-3-(isopropylsulfonyl)pyrazol-5-yl, 3-tert-butylsulfonyl-1-(3-chloro-2-pyridinyl)

pyrazol-5-yl, 1-(3-chloro-2-pyridinyl)-3-(2,2,2-trifluoroethoxy)pyrazol-5-yl, 1-(3-chloro-2-pyridinyl)-3-cyanopyrazol-5-yl, 1-(2-chlorophenyl)pyrrol-2-yl, 1-(3-chloro-2-pyridinyl)pyrrol-2-yl, 4-chloro-1-(2-chlorophenyl)pyrrol-2-yl, 4-chloro-1-(3-chloro-2-pyridinyl)pyrrol-2-yl, 5-chloro-1-(2-chlorophenyl)pyrrol-2-yl, 5-chloro-1-(3-chloro-2-pyridinyl)pyrrol-2-yl, 1-(2-chlorophenyl)-4,5-dichloropyrrol-2-yl, 1-(3-chloro-2-pyridinyl)-4,5-dichloropyrrol-2-yl, 4-bromo-1-(2-chlorophenyl)pyrrol-2-yl, 4-bromo-1-(3-chloro-2-pyridinyl)pyrrol-2-yl, 5-bromo-1-(2-chlorophenyl)pyrrol-2-yl, 5-bromo-1-(3-chloro-2-pyridinyl)pyrrol-2-yl, 1-(2-chlorophenyl)-4,5-dibromopyrrol-2-yl, 1-(3-chloro-2-pyridinyl)-4,5-dibromopyrrol-2-yl, 1-(2-chlorophenyl)-4-iodopyrrol-2-yl, 1-(3-chloro-2-pyridinyl)-4-iodopyrrol-2-yl, 1-(2-chlorophenyl)-5-iodopyrrol-2-yl, 1-(3-chloro-2-pyridinyl)-5-iodopyrrol-2-yl, 1-(2-chlorophenyl)-4,5-diiodopyrrol-2-yl, 1-(3-chloro-2-pyridinyl)-4,5-diiodopyrrol-2-yl, 1-(2-chlorophenyl)-4-(trifluoromethyl)pyrrol-2-yl, 1-(3-chloro-2-pyridinyl)-4-(trifluoromethyl)pyrrol-2-yl, 1-(2-chlorophenyl)-5-(trifluoromethyl)pyrrol-2-yl, 1-(3-chloro-2-pyridinyl)-5-(trifluoromethyl)pyrrol-2-yl, 1-(2-chlorophenyl)imidazol-2-yl, 1-(3-chloro-2-pyridinyl)imidazol-2-yl, 4-chloro-1-(2-chlorophenyl)imidazol-2-yl, 4-chloro-1-(3-chloro-2-pyridinyl)imidazol-2-yl, 4-bromo-1-(2-chlorophenyl)imidazol-2-yl, 4-bromo-1-(3-chloro-2-pyridinyl)imidazol-2-yl, 1-(2-chlorophenyl)-4-(trifluoromethyl)imdazol-2-yl, 1-(3-chloro-2-pyridinyl)-4-(trifluoromethyl)imidazol-2-yl, 1-(2-chlorophenyl)-1,2,4-triazol-5-yl, 1-(3-chloro-2-pyridinyl)-1,2,4-triazol-5-yl, 3-chloro-1-(2-chlorophenyl)-1,2,4-triazol-5-yl, 3-chloro-1-(3-chloro-2-pyridinyl)-1,2,4-triazol-5-yl, 3-bromo-1-(2-chlorophenyl)-1,2,4-triazol-5-yl, 3-bromo-1-(3-chloro-2-pyridinyl)-1,2,4-triazol-5-yl, 1-(2-chlorophenyl)-3-(trifluoromethyl)-1,2,4-triazol-5-yl and 1-(3-chloro-2-pyridinyl)-3-(trifluoromethyl)-1,2,4-triazol-5-yl.

Examples of the group represented by J2 include 1-methyl-3-phenylpyrazol-4-yl, 3-(2-chlorophenyl)-1-methylpyrazol-4-yl, 1-methyl-3-(2-pyridinyl)pyrazol-4-yl, 3-(3-chloro-2-pyridinyl)-1-methylpyrazol-4-yl, 1-methyl-5-phenylpyrazol-4-yl, 5-(2-chlorophenyl)-1-methylpyrazol-4-yl, 1-methyl-5-(2-pyridinyl)pyrazol-4-yl, 5-(3-chloro-2-pyridinyl)-1-methylpyrazol-4-yl, 3-phenyl-1-(2,2,2-trifluoroethyl)pyrazol-4-yl, 3-(2-chlorophenyl)-1-(2,2,2-trifluoroethyl)pyrazol-4-yl, 3-(2-pyridinyl)-1-(2,2,2-trifluoroethyl)pyrazol-4-yl, 3-(3-chloro-2-pyridinyl)-1-(2,2,2-trifluoroethyl)pyrazol-4-yl, 5-phenyl-1-(2,2,2-trifluoroethyl)pyrazol-4-yl, 5-(2-chlorophenyl)-1-(2,2,2-trifluoroethyl)pyrazol-4-yl, 5-(2-pyridinyl)-1-(2,2,2-trifluoroethyl)pyrazol-4-yl, 5-(3-chloro-2-pyridinyl)-1-(2,2,2-trifluoroethyl)pyrazol-4-yl, 1-(difluoromethyl)-3-phenylpyrazol-4-yl, 3-(2-chlorophenyl)-1-(difluoromethyl)pyrazol-4-yl, 1-(difluoromethyl)-3-(2-pyridinyl)pyrazol-4-yl, 3-(3-chloro-2-pyridinyl)-1-(difluoromethyl)pyrazol-4-yl, 1-(difluoromethyl)-5-phenylpyrazol-4-yl, 5-(2-chlorophenyl)-1-(difluoromethyl)pyrazol-4-yl, 1-(difluoromethyl)-5-(2-pyridinyl)pyrazol-4-yl, 5-(3-chloro-2-pyridinyl)-1-(difluoromethyl)pyrazol-4-yl, 3-(2-chlorophenyl)-1-ethylpyrazol-4-yl, 3-(3-chloro-2-pyridinyl)-1-ethylpyrazol-4-yl, 5-(2-chlorophenyl)-1-ethylpyrazol-4-yl, 5-(3-chloro-2-pyridinyl)-1-ethylpyrazol-4-yl, 3-(2-chlorophenyl)-1-isopropylpyrazol-4-yl, 3-(3-chloro-2-pyridinyl)-1-isopropylpyrazol-4-yl, 5-(2-chlorophenyl)-1-isopropylpyrazol-4-yl, 5-(3-chloro-2-pyridinyl)-1-isopropylpyrazol-4-yl, 3-(2-chlorophenyl)-1-tert-butylpyrazol-4-yl, 3-(3-chloro-2-pyridinyl)-1-tert-butylpyrazol-4-yl, 5-(2-chlorophenyl)-1-tert-butylpyrazol-4-yl and 5-(3-chloro-2-pyridinyl)-1-tert-butylpyrazol-4-yl.

Hereinafter, preferred embodiments of the present invention are illustrated.

Preferred compounds are:

Preferred Compound 1: The compound according to the present compound, an N-oxide thereof or suitable salt thereof, wherein E is a 5- or 6-membered heteroaromatic ring.

Preferred Compound 2: The compound according to the Preferred Compound 1, wherein
$A^1$ and $A^2$ are oxygen atoms; and
$R^1$ is a hydrogen atom or alkyl optionally substituted with one or more halogen atoms.

Preferred Compound 3: The compound according to the Preferred Compound 2, wherein J is J-1.1, J-1.2, J-2.1, J-2.2 or J-2.3:

J-1.1:

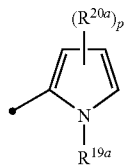

J-1.2:

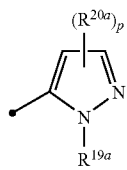

J-2.1:

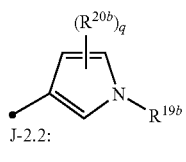

J-2.2:

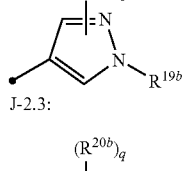

J-2.3:

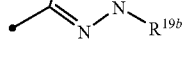

wherein
$R^{19a}$ and $R^{19b}$ represent a hydrogen atom; C1-C6 alkyl optionally substituted with one or more halogen atoms; C3-C6 cycloalkyl optionally substituted with one or more independent substituents selected from the group consisting of (1) a halogen atom and (2) C1-C6 alkyl optionally substituted with one or more halogen atoms;

phenyl optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms;

5- to 6-membered heteroaryl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms;

$R^{20a}$ and $R^{20b}$ represent a halogen atom, cyano, C1-C6 alkyl optionally substituted with one or more halogen atoms, C1-C6 alkoxy optionally substituted with one or more halogen atoms, C2-C6 cyanoalkyloxy, C2-C6 alkoxyalkyloxy optionally substituted with one or more halogen atoms, C2-C6 alkenyloxy optionally substituted with one or more halogen atoms, C1-C6 alkylthio optionally substituted with one or more halogen atoms, C1-C6 alkylsulfinyl optionally substituted with one or more halogen atoms, C1-C6 alkylsulfonyl optionally substituted with one or more halogen atoms;

or phenyl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms;

5- to 6-membered heteroaryl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms;

or phenoxy optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms;

p represents an integer of 0 to 3; and q represents an integer of 0 to 3 (provided that, when p is an integer of 2 or 3, two or more $R^{20a}$'s may be the same or different and, when q is an integer of 2 or 3, two or more $R^{20b}$'s may be the same or different).

Preferred Compound 4: The compound according to the present compound, an N-oxide thereof or suitable salt thereof, wherein Q is Q1;

$A^{31}$ is oxygen; and $R^6$ represents a hydrogen atom; C1-C6 alkyl optionally substituted with one or more independent substituents selected from the group consisting of (1) a halogen atom, (2) C1-C6 alkoxy optionally substituted with one or more halogen atoms, (3) C1-C6 alkylthio optionally substituted with one or more halogen atoms, (4) C1-C6 alkylsulfinyl optionally substituted with one or more halogen atoms, (5) C1-C6 alkylsulfonyl optionally substituted with one or more halogen atoms, (6) C2-C6 dialkylamino optionally substituted with one or more halogen atoms, and (7) C3-C6 cycloalkyl optionally substituted with one or more halogen atoms;

C3-C6 cycloalkyl optionally substituted with one or more independent substituents selected from the group consisting of (1) a halogen atom, and (2) C1-C6 alkyl optionally substituted with one or more halogen atoms;

phenyl optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms;

5- to 6-membered heteroaryl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms;

3- to 8-membered non-aromatic heterocyclic optionally substituted with one or more independent substituents selected from the group consisting of (1) a halogen atom, and (2) C1-C6 alkyl optionally substituted with one or more halogen atoms;

or C7-C9 phenylalkyl or C7-C9 phenoxyalkyl: each said phenyl ring optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms.

Preferred Compound 5: The compound according to the Preferred Compound 4, wherein $A^1$ and $A^2$ are oxygen atoms.

Preferred Compound 6: The compound according to the present compound, an N-oxide thereof or suitable salt thereof, wherein Q is Q2;

$A^{32}$ is oxygen; and $R^7$ is C1-C6 alkyl optionally substituted with one or more halogen atoms; C2-C6 alkenyl optionally substituted with one or more halogen atoms; C3-C6 cycloalkyl optionally substituted with one or more independent substituents selected from the group consisting of (1) a halogen atom, and (2) C1-C6 alkyl optionally substituted with one or more halogen atoms;

phenyl optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms;

5- to 6-membered heteroaryl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms;

or C7-C9 phenylalkyl whose ring moiety is optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms.

Preferred Compound 7: The compound according to the Preferred Compound 6, wherein $A^1$ and $A^2$ are oxygen atoms.

Preferred Compound 8: The compound according to the present compound, an N-oxide thereof or suitable salt thereof, wherein Q is Q4;

$A^{34}$ is oxygen; and $R^9$ and $R^{10}$ independently represent a hydrogen atom; C1-C6 alkyl optionally substituted with one or more halogen atoms; C3-C6 cycloalkyl optionally substituted with one or more independent substituents selected from the group consisting of (1) a halogen atom, and (2) C1-C6 alkyl optionally substituted with one or more halogen atoms;

phenyl optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl (13) C2-C6 alkylaminocarbonyl optionally substituted with one or more halogen atoms and (14) C3-C6 dialkylaminocarbonyl optionally substituted with one or more halogen atoms;

5- to 6-membered heteroaryl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms;

or C7-C9 phenylalkyl whose ring moiety is optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms.

Preferred Compound 9: The compound according to the Preferred Compound 8, wherein $A^1$ and $A^2$ are oxygen atoms.

Preferred Compound 10: A hydrazide compound represented by the formula (II-1) or (II-2),

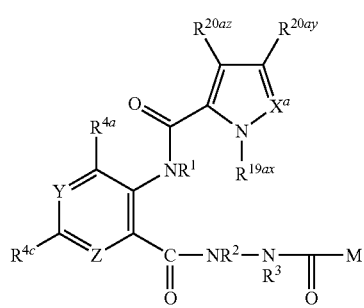

(II-1)

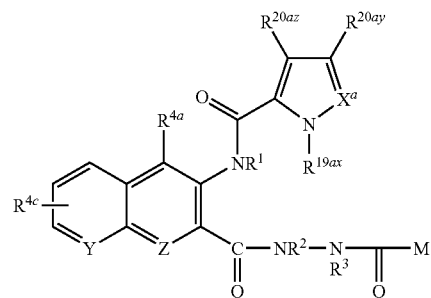

(II-2)

wherein $X^a$ represents a nitrogen atom or $CR^{20aax}$;

Y and Z represent independently a nitrogen atom or $CR^{4b}$, but not Y and Z are $CR^{4b}$ at the same time;

$R^1$ represets a hydrogen atom or C1-C6 alkyl optionally substituted with one or more halogen atoms;

$R^2$ and $R^3$ independently represent a hydrogen atom, C1-C6 alkyl optionally substituted with one or more halogen atoms, C2-C6 cyanoalkyl, C1-C6 hydroxyalkyl, C2-C6 alkoxyalkyl optionally substituted with one or more halogen atoms, C2-C6 alkenyl optionally substituted with one or more halogen atoms, C2-C6 alkynyl optionally substituted with one or more halogen atoms, C3-C6 cycloalkyl optionally substituted with one or more halogen atoms, C1-C6 alkylthio optionally substituted with one or more halogen atoms, C1-C6 alkylsulfinyl optionally substituted with one or more halogen atoms, C1-C6 alkylsulfonyl optionally substituted with one or more halogen atoms, C2-C6 alkylcarbonyl optionally substituted with one or more halogen atoms, C2-C6 alkoxycarbonyl, C2-C6 alkylaminocarbonyl, C3-C8 dialkylaminocarbonyl, C4-C6 cycloalkylaminocarbonyl, or C3-C6 trialkylsilyl;

or represents phenyl, C7-C9 phenylalkyl or phenylcarbonyl: each said phenyl ring optionally substituted with one or more independent substituents selected from the group consisting of (1) a halogen atom, (2) cyano, (3) nitro, (4) hydroxyl, (5) carboxyl, (6) C1-C6 alkyl optionally substituted with one or more halogen atoms, (7) C1-C6 hydroxyalkyl, (8) C1-C6 alkoxy optionally substituted with one or more halogen atoms, (9) C2-C6 cyanoalkyl, (10) C2-C6 alkoxyalkyl optionally substituted with one or more halogen atoms, (11) C2-C6 alkenyl optionally substituted with one or more halogen atoms, (12) C2-C6 alkynyl optionally substituted with one or more halogen atoms, (13) C3-C6 cycloalkyl optionally substituted with one or more halogen atoms, (14) C1-C6 alkylthio optionally substituted with one or more halogen atoms, (15) C1-C6 alkylsulfinyl optionally substituted with one or more halogen atoms, (16) C1-C6 alkylsulfonyl optionally substituted with one or more halogen atoms, (17) C1-C6 alkylamino, (18) C2-C8 dialkylamino, (19) C3-C6 cycloalkylamino, (20) C2-C6 alkylcarbonyl, (21) C2-C6 alkoxycarbonyl, (22) C2-C6 alkylaminocarbonyl, (23) C3-C8 dialkylaminocarbonyl, (24) C4-C6 cycloalkylaminocarbonyl and (25) C3-C6 trialkylsilyl; or $R^2$ and $R^3$ are taken together with the two nitrogen atoms to which they are attached to form a 5- to 8-membered ring containing two nitrogen atoms, one or more $CH_2$ or C(=O), and optionally one or two ring members selected from the group consisting of (1) an oxygen atom, (2) a sulfur atom, (3) S(=O), (4) S(=O)$_2$ and (4) $NR^a$ (wherein $R^a$ represents C1-C6 alkyl optionally substituted with one or more halogen atoms, C2-C6 alkoxycarbonyl optionally substituted with one or more halogen atoms, or a phenyl optionally substituted with one or more independent substituents from (1) a halogen atom, (2) cyano, (3) nitro, (4) C1-C6 alkyl optionally substituted with one or more halogen atoms, (5) C1-C6 alkoxy optionally substituted with one or more halogen atoms, (6)

C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms;

and wherein the ring at the carbon atoms is optionally substituted with one or more independent substituents selected from the group consisting of (1) a halogen atom, (2) C1-C6 alkyl optionally substituted with one or more halogen atoms, and (3) C2-C6 alkoxycarbonyl optionally substituted with one or more halogen atoms;

$R^{4a}$, $R^{4b}$ and $R^{4c}$ independently represent a halogen atom, cyano, nitro, hydroxyl, carboxyl, C1-C6 alkyl optionally substituted with one or more halogen atoms, C2-C6 alkoxy optionally substituted with one or more halogen atoms, C2-C6 cyanoalkyl, C2-C6 alkoxyalkyl optionally substituted with one or more halogen atoms, C2-C6 alkenyl optionally substituted with one or more halogen atoms, C2-C6 alkynyl optionally substituted with one or more halogen atoms, C3-C6 cycloalkyl optionally substituted with one or more halogen atoms, C1-C6 alkylthio optionally substituted with one or more halogen atoms, C1-C6 alkylsulfinyl optionally substituted with one or more halogen atoms, C1-C6 alkylsulfonyl optionally substituted with one or more halogen atoms, C1-C6 alkylamino, C2-C8 dialkylamino, C3-C6 cycloalkylamino, C2-C6 alkylcarbonyl optionally substituted with one or more halogen atoms, C2-C6 alkoxycarbonyl, C2-C6 alkylaminocarbonyl, C3-C8 dialkylaminocarbonyl, C3-C6 trialkylsilyl;

or represents independently phenyl, benzyl, phenoxy, or 5- or 6-membered heteroaromatic ring, each ring optionally substituted with one or more substituents selected from the group consisting of (1) a halogen atom, (2) cyano, (3) nitro, (4) hydroxyl, (5) carboxyl, (6) C1-C6 alkyl optionally substituted with one or more halogen atoms, (7) C1-C6 hydroxyalkyl, (8) C1-C6 alkoxy optionally substituted with one or more halogen atoms, (9) C2-C6 cyanoalkyl, (10) C2-C6 alkoxyalkyl optionally substituted with one or more halogen atoms, (11) C2-C6 alkenyl optionally substituted with one or more halogen atoms, (12) C2-C6 alkynyl optionally substituted with one or more halogen atoms, (13) C3-C6 cycloalkyl optionally substituted with one or more halogen atoms, (14) C1-C6 alkylthio optionally substituted with one or more halogen atoms, (15) C1-C6 alkylsulfinyl optionally substituted with one or more halogen atoms, (16) C1-C6 alkylsulfonyl optionally substituted with one or more halogen atoms, (17) C1-C6 alkylamino, (18) C2-C8 dialkylamino, (19) C3-C6 cycloalkylamino, (20) C2-C6 alkylcarbonyl, (21) C2-C6 alkoxycarbonyl, (22) C2-C6 alkylaminocarbonyl, (23) C3-C8 dialkylaminocarbonyl, (24) C4-C6 cycloalkylaminocarbonyl and (25) C3-C6 trialkylsilyl;

M is a hydrogen atom; C1-C6 alkyl optionally substituted with one or more independent substituents selected from the group consisting of (1) a halogen atom, (2) C1-C6 alkoxy optionally substituted with one or more halogen atoms, (3) C1-C6 alkylthio optionally substituted with one or more halogen atoms, (4) C1-C6 alkylsulfinyl optionally substituted with one or more halogen atoms, (5) C1-C6 alkylsulfonyl optionally substituted with one or more halogen atoms, (6) C2-C6 dialkylamino optionally substituted with one or more halogen atoms, and (7) C3-C6 cycloalkyl optionally substituted with one or more halogen atoms; C1-C6 alkoxy optionally substituted with one or more halogen atoms; C1-C6 alkylthio optionally substituted with one or more halogen atoms; C1-C6 alkylamino; C2-C8 dialkylamino;

phenyl, C7-C9 phenylalkyl or C7-C9 phenoxyalkyl: each said phenyl ring optionally substituted with one or more independent substituents selected from the group consisting of (1) a halogen atom, (2) cyano, (3) nitro, (4) C1-C6 alkyl optionally substituted with one or more halogen atoms, and (5) C1-C6 alkoxy optionally substituted with one or more halogen atoms;

5- to 6-membered heteroaryl optionally substituted with one or more independent substituents selected from the group consisting of (1) a halogen atom, (2) cyano, (3) nitro, (4) C1-C6 alkyl optionally substituted with one or more halogen atoms, and (5) C1-C6 alkoxy optionally substituted with one or more halogen atoms;

or 3- to 8-membered non-aromatic heterocyclic ring optionally substituted with one or more independent substituents selected from the group consisting of (1) a halogen atom, and (2) C1-C6 alkyl optionally substituted with one or more halogen atoms;

$R^{19ax}$ represents a hydrogen atom; C1-C6 alkyl optionally substituted with one or more halogen atoms; C2-C6 cyanoalkyl; C2-C6 alkoxyalkyl optionally substituted with one or more halogen atoms; C2-C6 alkenyl optionally substituted with one or more halogen atoms; C2-C6 alkynyl optionally substituted with one or more halogen atoms; C3-C6 cycloalkyl optionally substituted with one or more independent substituents selected from the group consisting of (1) a halogen atom, and (2) C1-C6 alkyl optionally substituted with one or more halogen atoms;

phenyl optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms;

5- to 6-membered heteroaryl optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms;

C7-C9 phenylalkyl whose phenyl ring is optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms;

or C7-C9 pyridinylalkyl whose pyridine ring is optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms; and $R^{20ax}$, $R^{20ay}$ and $R^{20az}$ represent a halogen atom; cyano; nitro; thiocyanato; C1-C6 alkyl optionally substituted with one or more halogen atoms; C1-C6 alkoxy optionally substituted with one or more halogen atoms; C2-C6 cyanoalkyloxy; C2-C6 alkoxyalkyloxy optionally substituted with one or more halogen atoms; C2-C6 alkenyloxy optionally substituted with one or more halogen atoms; C2-C6 alkynyloxy optionally substituted with one or more halogen atoms; C1-C6 alkylthio optionally substituted with one or more halogen atoms; C1-C6 alkylsulfinyl optionally substituted with one or more halogen atoms; C1-C6 alkylsulfonyl optionally substituted with one or more halogen atoms; phenyl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms;

5- to 6-membered heteroaryl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms;

or phenoxy optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms.

Preferred Compound 11: The compound according to the Preferred Compound 10, wherein
$R^1$ is a hydrogen atom;
$R^2$ is a hydrogen atom or C1-C6 alkyl optionally substituted with one or more halogen atoms;
$R^3$ is a hydrogen atom, C1-C6 alkyl optionally substituted with one or more halogen atoms or C2-C6 alkoxycarbonyl;
$R^{4a}$ is a halogen atom or C1-C6 alkyl optionally substituted with one or more halogen atoms;

$R^{4c}$ is a hydrogen atom, a halogen atom, cyano or C1-C6 alkyl optionally substituted with one or more halogen atoms;
$R^{19a}$ is

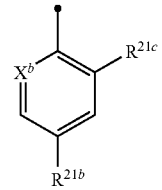

wherein
$X^b$ is a nitrogen atom or $CR^{21a}$;
$R^{20ax}$ and $R^{23ay}$ are independently a hydrogen atom, a halogen atom, C1-C6 alkyl optionally substituted with one or more halogen atoms, C1-C6 alkoxy optionally substituted with one or more halogen atoms or C1-C6 alkylthio optionally substituted with one or more halogen atoms;
$R^{20az}$ is a hydrogen atom; and
$R^{21a}$, $R^{21b}$ and $R^{21c}$ are independently selected from the group consisting of a hydrogen atom, a halogen atom or C1-C6 alkyl optionally substituted with one or more halogen atoms.

Preferred Compound 12: The compound according to the Preferred Compound 11, wherein
$X^a$ and $X^b$ are nitrogen atoms;
Y is CH; and
Z is a nitrogen atom.

Preferred Compound 13: The compound according to the Preferred Compound 11, wherein
$X^a$ and $X^b$ are nitrogen atoms;
Y is a nitrogen atom; and
Z is CH.

Preferred Compound 14: The compound according to the Preferred Compound 11, wherein $R^{4b}$ is a hydrogen atom.

Preferred Compound 15: The compound according to the Preferred Compound 14, wherein M is a hydrogen atom, C1-C6 alkyl, C1-C6 alkoxy, amino, C1-C6 alkylamino or C2-C8 dialkylamino.

Preferred Compound 16: The compound according to the Preferred Compound 15, wherein
$R^2$ is a hydrogen atom, methyl or ethyl;
$R^3$ is a hydrogen atom, methyl, ethyl or methoxycarbonyl;
$R^{4a}$ is methyl, chloro, bromo or iodo;
$R^{4c}$ is hydrogen, fluoro, chloro, bromo, iodo or cyano;
$R^{20ay}$ is chloro, bromo, iodo, trifluoromethyl or pentafluoroethoxy;
$R^{22b}$ is a hydrogen atom;
$R^{22c}$ is chloro or bromo; and
M is hydrogen, methoxy, ethoxy, methylamino or dimethylamino.

Preferred Compound 17: The compound of the Preferred Compound 16, wherein
$R^2$ is a hydrogen atom;
$R^3$ is methyl or ethyl; and
M is a hydrogen atom.

Preferred Compound 18: The compound of the Preferred Compound 17, wherein
$R^2$ and $R^3$ are independently hydrogen, methyl or ethyl; and
M is methoxy or ethoxy.

Preferred Compound 19: A hydrazide compound represented by the formula (II-1),
$X^a$, Y, Z, $R^1$, $R^2$, $R^3$, $R^{4a}$, $R^{4b}$, $R^{4c}$, M, $R^{19ax}$, $R^{20ax}$, $R^{20ay}$, and $R^{20az}$ are described above.

Preferred Compound 20: The compound according to the Preferred Compound 19, wherein
$R^1$ is a hydrogen atom;
$R^2$ is a hydrogen atom or C1-C6 alkyl optionally substituted with one or more halogen atoms;
$R^3$ is a hydrogen atom, C1-C6 alkyl optionally substituted with one or more halogen atoms or C2-C6 alkoxycarbonyl;

$R^{4a}$ is a halogen atom or C1-C6 alkyl optionally substituted with one or more halogen atoms;

$R^{4c}$ is a hydrogen atom, a halogen atom, cyano or 1-C6 alkyl optionally substituted with one or more halogen atoms;

$R^{19a}$ is

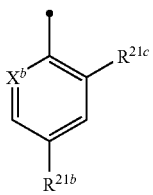

wherein $X^b$ is a nitrogen atom or $CR^{21a}$;

$R^{20ax}$ and $R^{23ay}$ are independently a hydrogen atom, a halogen atom, C1-C6 alkyl optionally substituted with one or more halogen atoms, C1-C6 alkoxy optionally substituted with one or more halogen atoms or C1-C6 alkylthio optionally substituted with one or more halogen atoms;

$R^{20\ az}$ is a hydrogen atom; and $R^{21a}$, $R^{21b}$ and $R^{21c}$ are independently selected from the group consisting of a hydrogen atom, a halogen atom or C1-C6 alkyl optionally substituted with one or more halogen atoms.

Preferred Compound 21: The compound according to the Preferred Compound 20, wherein $X^a$ and $X^b$ are nitrogen atoms;
Y is CH; and
Z is a nitrogen atom.

Preferred Compound 22: The compound according to the Preferred Compound 20, wherein $X^a$ and $X^b$ are nitrogen atoms;
Y is a nitrogen atom; and
Z is CH.

Preferred Compound 23: The compound according to the Preferred Compound 20, wherein $R^{4b}$ is a hydrogen atom.

Preferred Compound 24: The compound according to the Preferred Compound 23, wherein M is a hydrogen atom, C1-C6 alkyl, C1-C6 alkoxy, amino, C1-C6 alkylamino or C2-C8 dialkylamino.

Preferred Compound 25: The compound according to the Preferred Compound 24, wherein $R^2$ is a hydrogen atom, methyl or ethyl;
$R^3$ is a hydrogen atom, methyl, ethyl or methoxycarbonyl;
$R^{4a}$ is methyl, chloro, bromo or iodo;
$R^{4c}$ is hydrogen, fluoro, chloro, bromo, iodo or cyano;
$R^{20ay}$ is chloro, bromo, iodo, trifluoromethyl or pentafluoroethoxy;
$R^{22b}$ is a hydrogen atom;
$R^{22c}$ is chloro or bromo; and
M is hydrogen, methoxy, ethoxy, methylamino or dimethylamino.

Preferred Compound 26: The compound of the Preferred Compound 25, wherein $R^2$ is a hydrogen atom;
$R^3$ is methyl or ethyl; and
M is a hydrogen atom.

Preferred Compound 27: The compound of the Preferred Compound 26, wherein $R^2$ and $R^3$ are independently hydrogen, methyl or ethyl; and
M is methoxy or ethoxy.

This invention further pertains to:

A pesticide comprising the present compound or an N-oxide thereof or suitable salt thereof as an active ingredient.

A method of controlling a pest which comprises applying the present compound, an N-oxide thereof or suitable salt thereof directly to a pest, or to a place where a pest inhabits.

Use of the present compound, an N-oxide thereof or suitable salt thereof for controlling a pest.

Use of the present compound, an N-oxide thereof or suitable salt thereof for manufacturing a pesticidal preparation.

Hereinafter, a process for producing the present compound will be explained.

The present compound can be produced, for example, by the following Process A-1 to Process C-1.

Process A-1

Among the present compounds, a compound represented by the formula (1):

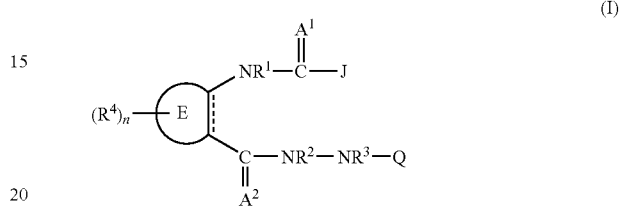

(1)

wherein $R^1$, $R^2$, $R^3$, $R^4$, $A^1$, $A^2$, J and n are as defined above;

E represents, together with the two contiguous linking carbon atoms, a 5- or 6-membered heteroaromatic ring system or a 8-, 9- or 10-membered fused heterobicyclic ring system;

Q' represents a group selected from the group consisting of Q1 to Q6 (provided that the compound wherein Q' is Q4, and $R^8$ and $R^9$ are a hydrogen atom is excluded) (hereinafter, referred to as the compound (I)) can be produced by reacting a compound represented by the formula (2):

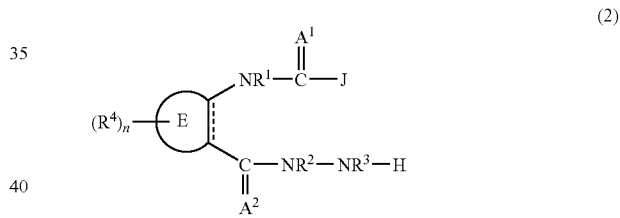

(2)

wherein $R^1$, $R^2$, $R^3$, $R^4$, $A^1$, $A^2$, J and n are as defined above (hereinafter, referred to as the compound (2)), and a compound represented by the formula (3):

$$L^1\text{-}Q' \qquad (3)$$

wherein Q' is as defined above; and $L^1$ represents a halogen atom or a Q'-O— (provided that the case where Q' is Q4, and $R^8$ and $R^9$ are a hydrogen atom is excluded) (hereinafter, referred to as the compound (3)).

The reaction is performed in the presence or the absence of a solvent. Examples of the solvent to be used in the reaction include ethers such as 1,4-dioxane, diethyl ether, tetrahydrofuran, methyl tert-butyl ether, and the like, halogenated hydrocarbons such as dichloromethane, chloroform, carbon tetrachloride, 1,2-dichloroethane, chlorobenzene, and the like, hydrocarbons such as toluene, benzene, xylene, and the like, nitriles such as acetonitrile and the like, aprotic polar solvents such as N,N-dimethylformamide, N-methlpyrrolidone, 1,3-dimethyl-2-imidadzolidinone, dimethyl sulfoxide, and the like, and a mixture thereof.

The amount of the compound (3) to be used in the reaction is usually 1 to 2 mols per 1 mol of the compound (2).

The reaction is performed in the presence of a base, if necessary. Examples of the base include nitrogen-containing heterocyclic compounds such as pyridine, picoline, 2,6-lutidine, 1,8-diazabicyclo[5,4,0]7-undecene (DBU), 1,5-diazabicyclo[4,3,0]5-nonene (DBN), and the like, tertiary amines such as triethylamine, N,N-diisopropylethylamine, and the like, and inorganic bases such as potassium carbonate, sodium hydride, and the like. The amount of the base when the reaction is performed in the presence of the base is usually 1 to 2 mols per 1 mol of the compound (2), while the base may be used in an excess amount in case that the base used is liquid under the reaction conditions such as pyridine, and the like.

The reaction temperature is usually in a range of 0 to 100° C., and the reaction time is usually in a range of 0.1 to 24 hours.

After completion of the reaction, the compound (1-i) can be isolated by pouring the reaction mixture into water and extracting the mixture with an organic solvent, or collecting a deposited precipitate by filtration. The isolated compound (1-i) may be further purified by recrystallization, chromatography, or the like.

Process A-2

Among the present compounds, a compound represented by the formula (I-ii):

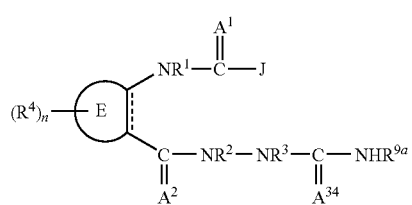

(1-ii)

wherein $R^1$, $R^2$, $R^3$, $R^4$, $A^1$, $A^2$, $A^{34}$, J and n are as defined above, and $R^{9a}$ represents C1-C6 alkyl optionally substituted with at least one halogen atom; C2-C6 alkoxyalkyl optionally substituted with at least one halogen atom; C2-C6 alkenyl optionally substituted with at least one halogen atom; 3-C6 alkynyl optionally substituted with at least one halogen atom; C3-C6 cycloalkyl optionally substituted with one or more independent substituents selected from the group consisting of (1) a halogen atom and (2) C1-C6 alkyl group; a phenyl optionally substituted with one or more independent substituents selected from the group consisting of (1) a halogen atom (2) cyano group, (3) nitro group, (4) C1-C6 alkyl optionally substituted with at least one halogen atom, (5) C1-C6 alkoxy optionally substituted with at least one halogen atom, (6) C1-C6 alkylthio optionally substituted with at least one halogen atom, (7) C1-C6 alkylsulfinyl optionally substituted with at least one halogen atom, (8) C1-C6 alkylsulfonyl optionally substituted with at least one halogen atom, (9) C2-C6 dialkylamino optionally substituted with at least one halogen atom and (10) C2-C6 alkoxycarbonyl optionally substituted with at least one halogen atom; 5- to 6-membered heteroaryl optionally substituted with one or more independent substituents selected from the group consisting of (1) halogen atom, (2) cyano group, (3) nitro group, (4) C1-C6 alkyl optionally substituted with at least one halogen atom and (5) C1-C6 alkoxy optionally substituted with at least one halogen atom; or C7-C9 phenylalkyl whose benzene ring moiety may be substituted with one or more independent substituents selected from the group consisting of (1) a halogen atom, (2) cyano group, (3) nitro group, (4) C1-C6 alkyl optionally substituted with at least one halogen atom and (5) C1-C6 alkoxy optionally substituted with at least one halogen atom (hereinafter, referred to as the compound (1-ii)) can be produced by reacting the compound (2) with a compound represented by the formula (4):

$$A^{34}=C=N-R^{9a} \quad (4)$$

wherein $A^{34}$ and $R^{9a}$ are as defined above (hereinafter, referred to as the compound (4)).

The reaction is performed in the presence or the absence of a solvent. Examples of the solvent to be used in the reaction include ethers such as 1,4-dioxane, diethyl ether, tetrahydrofuran, methyl tert-butyl ether, and the like, halogenated hydrocarbons such as dichloromethane, chloroform, carbon tetrachloride, 1,2-dichloroethane, chlorobenzene, and the like, hydrocarbons such as toluene, benzene, xylene, and the like, nitriles such as acetonitrile, and the like, aprotic polar solvents such as N,N-dimethylformamide, N-methylpyrrolidone, 1,3-dimethyl-2-imidazolidinone, dimethyl sulfoxide, and the like, and a mixture thereof.

The amount of the compound (4) used in the reaction is usually 1 to 2 mols per 1 mol of the compound (2).

The reaction temperature is usually in a range of 0 to 100° C., and the reaction time is a usually a range of 0.1 to 24 hours.

After completion of the reaction, the compound (1-ii) can be isolated by pouring the reaction mixture into water, and extracting the mixture with an organic solvent, or collecting a deposited precipitate by filtration. The isolated compound (1-ii) may be further purified by recrystallization, chromatography, or the like.

Process A-3

Among the present compounds, a compound represented by the formula (1-iii):

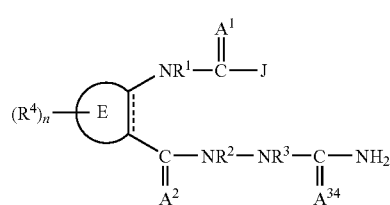

(1-iii)

wherein $R^1$, $R^2$, $R^3$, $R^4$, A" $A^2$, $A^{34}$, J and n are as defined above (hereinafter, referred to as the compound (I-iii)) can be produced by reacting the compound (2) and a cyanate or a thiocyanate.

The reaction is performed in the presence of a solvent. Examples of the solvent used in the reaction include acids such as organic acids such as acetic acids, and the like and mineral acids such as hydrochloric acid, and the like, as well as a mixture of these acids and water, chloroform, or the like.

The amount of the cyanate or the thiocyanate used in the reaction is usually 1 to 2 mols per 1 mol of the compound (2).

The reaction temperature is usually in a range of 0 to 100° C., and the reaction time is usually in a range of 0.1 to 24 hours.

Examples of the cyanate or the thiocyanate include potassium cyanate, sodium cyanate, ammonium cyanate, potassium thiocyanate, sodium thiocyanate and ammonium thiocyanate.

After completion of the reaction, the compound (I-iii) can be isolated by pouring the reaction mixture into water and extracting the mixture with an organic solvent, or collecting a deposited precipitate by filtration. The isolated Compound (I-iii) may be further purified by recrystallization, chromatography, or the like.

Process B-1

The present compound can be produced by reacting a compound represented by the formula (6):

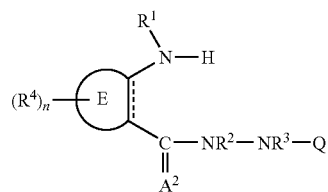

(6)

wherein $R^1$, $R^2$, $R^3$, $R^4$, $A^2$, Q and n are as defined above (hereinafter, referred to as Compound (6)) and a compound represented by the formula (7):

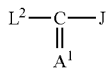  (7)

wherein $A^1$ and J are as define above, and $L^2$ represents a halogen atom (hereinafter, referred to as the compound (7)).

The reaction is performed in the presence or the absence of a solvent. Examples of the solvent used in the reaction include ethers such as 1,4-dioxane, diethyl ether, tetrahydrofuran, methyl tert-butyl ether, and the like, halogenated hydrocarbons such as dichloromethane, chloroform, carbon tetrachloride, 1,2-dichloroethane, chlorobenzene, and the like, hydrocarbons such as toluene, benzene, xylene, and the like, nitriles such as acetonitrile, and the like, aprotic polar solvents such as N,N-dimethylformamide, N-methylpyrrolidone, 1,3-dimethyl-2-imidazolidinone, dimethyl sulfoxide, and the like, and a mixture thereof.

The amount of the compound (7) used in the reaction is usually 1 to 2 mols per 1 mol of the compound (6).

The reaction is performed in the presence of a base, if necessary. Examples of the base include nitrogen-containing heterocyclic compounds such as pyridine, picoline, 2,6-lutidine, 1,8-diazabicyclo[5,4,0]7-undecene (DBU), 1,5-diazadicyclo[4,3,0]5-nonene (DBN), and the like, tertiary amines such as triethylamine, N,N-diisopropylethylamine, and the like, and inorganic bases such as potassium carbonate, sodium hydride, and the like. The amount of the base when the reaction is performed in the presence of the base is usually 1 to 2 mole per 1 mol of the compound (6), while the base may be used in an excess amount in case that the base used is liquid under the reaction conditions such as pyridine, and the like.

The reaction temperature is usually in a range of 0 to 100° C., and the reaction time is usually in a range of 0.1 to 24 hours.

After completion of the reaction, the present compound can be isolated by pouring the reaction mixture into water, and extracting the mixture with an organic solvent, or collecting a deposited precipitation by filtration. The isolated present compound may be further purified by recrystallization, chromatography, or the like.

Process B-2

Among the present compounds, a compound represented by the formula (I-iv):

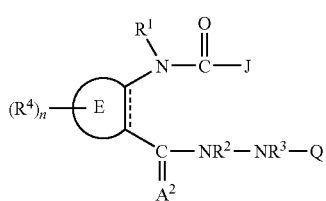  (1-iv)

wherein $R^1$, $R^2$, $R^3$, $R^4$, $A^2$, J, Q and n are as defined above (hereinafter referred to as the compound (I-iv)) can be produced by reacting the compound (6) and a compound represented by the formula (8):

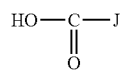  (8)

wherein J is as defined above (hereinafter, referred to as the compound (8)) in the presence of a dehydrating agent.

The reaction is performed in the presence or the absence of a solvent. Examples of the solvent to be used in the reaction include ethers such as 1,4-dioxane, diethyl ether, tetrahydrofuran, methyl tert-butyl ether, and the like, halogenated hydrocarbons such as dichloromethane, chloroform, carbon tetrachloride, 1,2-dichloroethane, chlorobenzene, and the like, hydrocarbons such as toluene, benzene, xylene, and the like, nitriles such as acetonitrile, and the like, aprotic polar solvents such as N,N-dimethylformamide, N-methylpyrrolidone, 1,3-dimethyl-2-imidazolidinone, dimethyl sulfoxide, and the like, and a mixture thereof.

The amount of the compound (8) used in the reaction is usually 1 to 2 mols per 1 mol of the compound (6).

Examples of the dehydrating agent to be used in the reaction include carbodiimides such as dicyclohexylcarbodiimide (DCC), 1-ethyl-3-(3-dimethylaminopropyl)carbodiimide hydrochloride (WSC), and the like. The amount of the dehydrating agent to be used is usually 1 to 2 mols per 1 mol of the compound (6).

The reaction temperature is usually in a range of 0 to 100° C., and the reaction time is usually in a range of 0.1 to 24 hours.

After completion of the reaction, the compound (I-iv) can be isolated by pouring the reaction mixture into water, and extracting the mixture with an organic solvent, or collecting a deposited precipitate by filtration. The isolated compound (1-iv) may be further purified by recrystallization, chromatography, or the like.

Process C-1

Among the present compounds, a compound represented by the formula (I-v):

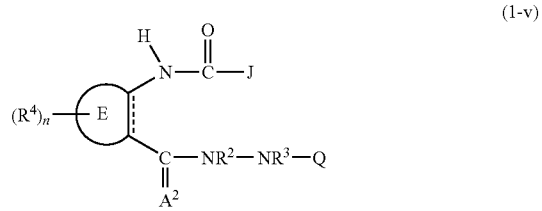  (1-v)

wherein $R^2$, $R^3$, $R^4$, J, Q and n are as defined above (hereinafter, referred to as the compound (1-v)) can be produced by reacting a compound represented by the formula (9):

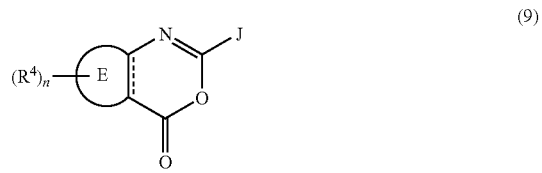  (9)

wherein $R^4$, J and n are as defined above (hereinafter, referred to as the compound (9)) and a compound represented by the formula (10):

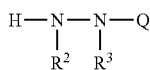

(10)

wherein $R^2$, $R^3$ and Q are as defined above (hereinafter, referred to as the compound (10)).

The reaction is performed in the presence or the absence of a solvent. Examples of the solvent used in the reaction include ethers such as 1,4-dioxane, diethyl ether, tetrahydrofuran, methyl tert-butyl ether, and the like, halogenated hydrocarbons such as dichloromethane, chloroform, carbon tetrachloride, 1,2-dichloroethane, chlorobenzene, and the like, hydrocarbons such as toluene, benzene, xylene, and the like, nitriles such as acetonitrile, and the like, aprotic polar solvents such as N,N-dimethylformamide, N-methylpyrrolidone, 1,3-dimethyl-2-imidaozolidinone, dimethyl sulfoxide, and the like, and a mixture thereof.

The amount of the compound (10) to be used in the reaction is usually 1 to 20 mols per 1 mol of the compound (9).

The reaction temperature is usually in a range of 0 to 100° C., and the reaction time is usually in a range of 0.1 to 48 hours.

After completion of the reaction, the compound (1-v) can be isolated by pouring the reaction mixture into water, and extracting the mixture with an organic solvent, or collecting a deposited precipitate by filtration. The isolated compound (1-v) may be further purified by recrystallization, chromatography, or the like.

Process C-2

Among the present compounds, a compound represented by the formula (I-yl):

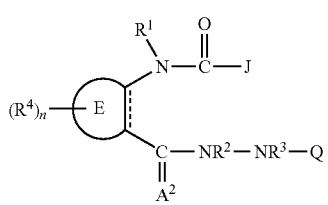

(1-iv)

wherein $R^2$, $R^3$, $R^4$, $A^1$, J, Q and n are as defined above, $R^{1-a}$ represents C1-C6 alkyl optionally substituted with at least one halogen atom; C2-C6 cyanoalkyl group; C2-C6 alkoxyalkyl optionally substituted with at least one halogen atom; C2-C6 alkenyl optionally substituted with at least one halogen atom; C3-C6 alkynyl optionally substituted with at least one halogen atom; or C7-C9 phenylalkyl in which a benzene ring part may be substituted with one or more independent substituents selected from the group consisting of (1) a halogen atom, (2) cyano group, (3) nitro group, (4) C1-C6 alkyl optionally substituted with at least one halogen atom and (5) C1-C6 alkoxy optionally substituted with at least one halogen atom (hereinafter, referred to as the compound (1-yl)) can be produced by reacting a compound represented by the formula (11):

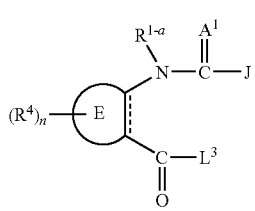

(11)

wherein $R^{1-a}$, $R^4$, $A^1$, J and n are as defined above, and $L^3$ represents a halogen atom (hereinafter, referred to as the compound (11)) and the compound (10).

The reaction is performed in the presence or the absence of a solvent. Examples of the solvent to be used in the reaction include ethers such as 1,4-dioxane, diethyl ether, tetrahydrofuran, methyl tert-butyl ether, and the like, halogenated hydrocarbons such as dichloromethane, chloroform, carbon tetrachloride, 1,2-dichlorethane, chlorobenzene, and the like, hydrocarbons such as toluene, benzene, xylene, and the like, nitriles such as acetonitrile, and the like, aprotic polar solvents such as N,N-diethylformamide, N-methylpyrrolidone, 1,3-dimethyl-2-imidazolidinone, dimethyl sulfoxide, and the like, and a mixture thereof.

The amount of the compound (10) to be used in the reaction is usually 1 to 2 mols per 1 mol of the compound (11).

The reaction is performed in the presence of a base, if necessary. Examples of the base include nitrogen-containing heterocyclic compounds such as pyridine, picoline, 2,6-lutidine, 1,8-diazabicyclo[5,4,0]7-undecene (DBU), 1,5-diazabicyclo[4,3,0]5-nonene (DBN), and the like, tertiary amines such as triethylamine, N,N-diisopropylethylamine, and the like, and inorganic bases such as potassium carbonate, sodium hydride, and the like. The amount of the base to be used when the reaction is performed in the presence of a base is usually 1 to 2 mols per 1 mol of the compound (11), while the base may be used in an excess amount in the case that the base used is liquid under the reaction conditions such as pyridine and the like.

The reaction temperature is usually in a range of 0 to 100° C., and the reaction time is usually in a range of 0.1 to 24 hours.

After completion of the reaction, the compound (1-yl) can be isolated after pouring the reaction mixture into water, and extracting the mixture with an organic solvent, or collecting a deposited precipitate by filtration. The isolated compound (1-yl) may be further purified by recrystallization, chromatography or the like.

Process C-3

The compound (1-yl) can also be produced by reacting a compound represented by the formula (12):

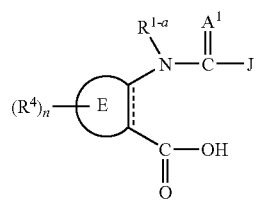

(12)

wherein $R^4$, $R^{1-a}$, $A^1$, J and n are as defined above (hereinafter, referred to as Compound (12)) and the compound (10) in the presence of a dehydrating agent.

The reaction is performed in the presence or the absence of a solvent. Examples of the solvent to be used in the reaction include ethers such as 1,4-dioxane, diethyl ether, tetrahydrofuran, methyl tert-butyl ether, and the like, halogenated hydrocarbons such as dichloromethane, chloroform, carbon tetrachloride, 1,2-dichlroethane, chlorobenzene, and the like, hydrocarbons such as toluene, benzene, xylene, and the like, nitriles such as acetonitrile, and the like, aprotic polar solvents such as N,N-dimethylformamide, N-methylpyrrolidone, 1,3-dimethyl-2-imidazolidinone, dimethyl sulfoxide, and the like, and a mixture thereof.

The amount of the compound (10) used in the reaction is usually 1 to 2 mols per 1 mol of the compound (12).

Examples of the dehydrating agent used in the reaction include carbodiimides such as dicyclohexylcarbodiimide (DCC), 1-ethyl-3-(3-dimethylaminopropyl)carbodiimide hydrochloride (WSC), and the like. The amount of the dehydrating agent to be used is usually 1 to 2 mols per 1 mol of the compound (12).

The reaction temperature is usually in a range of 0 to 100° C., and the reaction time is usually in a range of 0.1 to 24 hours.

After completion of the reaction, the compound (1-yl) can be isolated by pouring the reaction mixture into water and extracting the mixture with an organic solvent, or collecting a deposited precipitate by filtration. The isolated compound (1-yl) may be further purified by recrystallization, chromatography, or the like.

Then, a process for producing intermediates for producing the present compound will be explained.

Reference Process 1

Among the compound (2), a compound represented by the formula (2-i):

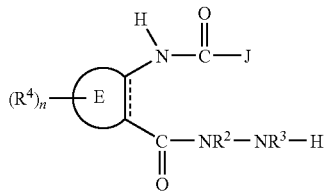

(2-i)

wherein $R^2$, $R^3$, $R^4$, J and n are as defined above (hereinafter, referred to as the compound (2-i)) can be produced by reacting the compound (9) and a compound represented by the formula (13):

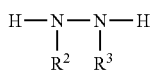

(13)

wherein $R^2$ and $R^3$ are as defined above (hereinafter, referred to as the compound (13)).

The reaction is performed in the presence or the absence of a solvent. Examples of the solvent used in the reaction include ethers such as 1,4-dioxane, diethyl ether, tetrahydrofuran, methyl tert-butyl ether, and the like, halogenated hydrocarbons such as dichloromethane, chloroform, carbon tetrachloride, 1,2-dichloroethane, chlorobenzene and the like, hydrocarbons such as toluene, benzene, xylene and the like, nitriles such as acetonitrile, and the like, aprotic polar solvents such as N,N-dimethylformamide, N-methylpyrrolidone, 1,3-dimethyl-2-imidazolidinone, dimethyl sulfoxide, and the like, alcohols such as methanol, ethanol, 2-propanol, and the like, and a mixture thereof.

The amount of the compound (13) to be used in the reaction is usually 1 to 5 mols per 1 mol of the compound (9).

The reaction temperature is usually in a range of −50 to 100° C., and the reaction time is usually in a range of 0.1 to 24 hours.

After completion of the reaction, the compound (2-i) can be isolated by pouring the reaction mixture into water, and extracting the mixture with an organic solvent, or collecting a deposited precipitate by filtration. The isolated compound (2-i) may be further purified by recrystallization, chromatography, or the like.

Reference Process 2

Among the compound (2), a compound represented by the formula (2-ii):

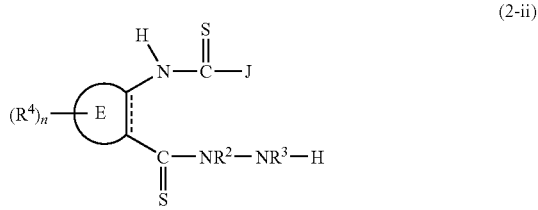

(2-ii)

wherein $R^2$, $R^3$, $R^4$, J and n are as defined above (hereinafter, referred to as Compound (2-ii)) can be produced by reacting a compound represented by the formula (14):

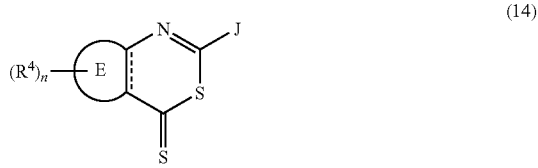

(14)

wherein $R^4$, J and n are as defined above (hereinafter, referred to as the compound (14)) and the compound (13).

The reaction is performed in the presence or the absence of a solvent. Examples of the solvent to be used in the reaction include ethers such as 1,4-dioxane, diethyl ether, tetrahydrofuran, methyl tert-butyl ether, and the like, halogenated hydrocarbons such as dichloromethane, chloroform, carbon tetrachloride, 1,2-dichloroethane, chlorobenzene and the like, hydrocarbons such as toluene, benzene, xylene, and the like, nitriles such as acetonitrile, and the like, aprotic polar solvents such as N,N-dimethylformamide, N-methylpyrrolidone, 1,3-dimethyl-2-imidazolidinone, dimethyl sulfoxide, and the like, alcohols such as methanol, ethanol, 2-propanol, and the like, and a mixture thereof.

The amount of the compound (13) to be used in the reaction is usually 1 to 5 mols per 1 mol of the compound (14).

The reaction temperature is usually in a range of −50 to 100° C., and the reaction time is usually in a range of 0.1 to 24 hours.

After completion of the reaction, the compound (2-ii) can be isolated by pouring the reaction mixture into water, and extracting the mixture with an organic solvent, or collecting a deposited precipitate by filtration. The isolated compound (2-ii) may be further purified by recrystallization, chromatography, or the like.

Reference Process 3

Among the compound (2), a compound represented by the formula (2-iii):

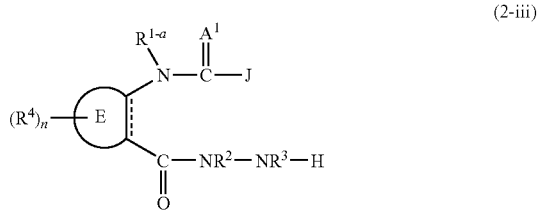

(2-iii)

wherein $R^{1-n}$, $R^2$, $R^3$, $R^4$, $A^1$, J and n are as defined above (hereinafter, referred to as the compound (2-iii)) can be produced by reacting the compound (11) and the compound (13).

The reaction is performed in the presence or the absence of a solvent. Examples of the solvent used in the reaction include ethers such as 1,4-dioxane, diethyl ether, tetrahydrofuran, methyl tert-butyl ether, and the like, halogenated hydrocarbons such as dichloromethane, chloroform, carbon tetrachloride, 1,2-dichloroethane, chlorobenzene, and the like, hydrocarbons such as toluene, benzene, xylene, and the like, nitriles such as acetonitrile, and the like, aprotic polar solvents such as N,N-dimethylformamide, N-methylpyrrolidone, 1,3-dimethyl-2-imidazolidinone, dimethyl sulfoxide, and the like, and a mixture thereof.

The amount of Compound (13) used in the reaction is usually 2 to 10 mols per 1 mol of the compound (11).

The reaction temperature is usually in a range of −50 to 100° C., and the reaction time is in a range of 0.1 to 24 hours.

After completion of the reaction, the compound (2-iii) can be isolated by pouring the reaction mixture into water, and extracting the mixture with an organic solvent, or collecting a deposited precipitate by filtration. The isolated compound (2-iii) may be further purified by recrystallization, chromatography, or the like.

Reference Process 4

The compound (9) can be produced by reacting a compound represented by the formula (16).

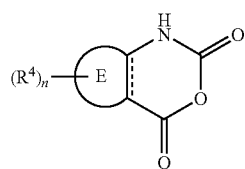

(16)

wherein $R^4$ and n are as defined above (hereinafter, referred to as the compound (16)) and a compound represented by the formula (7'):

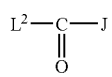

(7')

wherein J and $L^2$ are as defined above (hereinafter, referred to as Compound (7')).

The reaction is performed in the presence or the absence of a solvent in the presence of a base. Examples of the solvent to be used in the reaction include ethers such as 1,4-dioxane, diethyl ether, tetrahydrofuran, methyl tert-butyl ether, and the like, halogenated hydrocarbons such as dichloromethane, chloroform, carbon tetrachloride, 1,2-dichloroethane, chlorobenzene, and the like, hydrocarbons such as toluene, benzene, xylene, and the like, nitriles such as acetonitrile, and the like, aprotic polar solvents such as N,N-dimethylformamide, N-methylpyrrolidone, 1,3-dimethyl-2-imidazolidinone, dimethyl sulfoxide, and the like, and a mixture thereof.

The amount of the compound (7') used in the reaction is usually 0.5 to 2 mols per 1 mol of the compound (16).

Examples of the base to be used in the reaction include nitrogen-containing heterocyclic compounds such as pyridine, picoline, 2,6-lutidine, 1,8-diazabicyclo[5,4,0]7-undecene (DBU), 1,5-diazabicyclo[4,3,0]5-nonene (DBN), and the like, tertiary amines such as triethylamine, N,N-diisopropylethylamine, and the like, and inorganic bases such as potassium carbonate, sodium hydride, and the like. The amount of the base to be used is usually 1 to 2 mols per 1 mol of the compound (16), while the base may be used in an excess amount in case that the base is liquid under the reaction conditions such as pyridine, and the like.

The reaction temperature is usually in a range of 50 to 150° C., and the reaction time is usually in a range of 1 to 24 hours.

After completion of the reaction, the compound (9) can be isolated by pouring the reaction mixture into water, and extracting the mixture with an organic solvent, or collecting a deposited precipitates by filtration. The isolated compound (9) may be further purified by recrystallization, chromatography, or the like.

Reference Process 5

The compound (9) can be produced by reacting a compound represented by the formula (17):

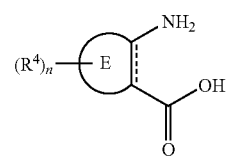

(17)

wherein $R^4$ and n are as defined above (hereinafter, referred to as Compound (17)) and the compound (7').

The reaction is performed in the presence or the absence of a solvent. Examples of the solvent to be used in the reaction include ethers such as 1,4-dioxane, diethyl ether, tetrahydrofuran, methyl tert-butyl ether, and the like, halogenated hydrocarbons such as dichloromethane, chloroform, carbon tetrachloride, 1,2-dichloroethane, chlorobenzene, and the like, hydrocarbons such as toluene, benzene, xylene, and the like, nitriles such as acetonitrile, and the like, aprotic polar solvents such as N,N-dimethylformamide, N-methylpyrrolidone, 1,3-dimethyl-2-imidazolidinone, dimethyl sulfoxide, and the like, and a mixture thereof.

The process comprises the following step 5-1 and step 5-2.

Step 5-1

This step is performed by reacting the compound (17) and the compound (7') in the presence of a base.

The amount of the compound (7') to be used in this step is usually 1 to 2 mols per 1 mol of the compound (17). Examples of the base include nitrogen-containing heterocyclic compounds such as pyridine, picoline, 2,6-lutidine, 1,8-diazabicyclo[5,4,0]7-undecene (DBU), 1,5-diazabicyclo[4,3,0]5-nonene (DBN), and the like, tertiary amines such as triethylamine, N,N-diisopropylethylamine, and the like, and inorganic bases such as potassium carbonate, sodium hydride, and the like. The amount of the base to be used is usually 1 to 2 mols per 1 mol of the compound (17).

The reaction temperature of this step is usually in a range of 0 to 50° C., and the reaction time is usually in a range of 0.1 to 24 hours.

After completion of this step, usually, the reaction mixture is used as it is in the next step 5-2.

Step 5-2

This step is performed by reacting the reaction mixture in the step 5-1 and a sulfonyl halide in the presence of a base.

Examples of the sulfonyl halide used in this step include methanesulfonyl chloride, p-toluenesulfonyl chloride, and trifluoromethanesulfonyl chloride. The amount of the sulfonyl halide to be used in this step is usually 1 to 2 mols per 1 mol of the compound (17) used in the step 5-1.

Examples of the base include the same bases as those described with respect to the step 5-1. The amount of the base is usually 2 to 4 mols per 1 mol of the compound (17) used in the step 5-1.

The reaction temperature of this step is usually in a range of 0 to 50° C., and the reaction time is usually in a range of 0.1 to 24 hours.

After completion of this step, the compound (9) can be isolated by pouring the reaction mixture into water, followed by conventional extraction with an organic solvent. The isolated compound (9) may be further purified by recrystallization, chromatography, or the like.

Reference Process 6

The compound (14) can be produced by reacting the compound (9) with a thiocarbonylation agent.

The reaction is performed in the presence or the absence of a solvent. Examples of the solvent to be used in the reaction include ethers such as 1,4-dioxane, diethyl ether, tetrahydrofuran, methyl tert-butyl ether, diglyme, and the like, halogenated hydrocarbons such as dichloromethane, chloroform, carbon tetrachloride, 1,2-dichloroethane, chlorobenzene, and the like, hydrocarbons such as toluene, benzene, xylene, and the like, nitriles such as acetonitrile, and the like, pyridines such as pyridine, picoline, lutidine, and the like, and a mixture thereof.

Examples of the thiocarbonylation agent to be used in the reaction include diphosphorus pentasulfide, a Lawesson's reagent (2,4-bis-(4-methoxyphenyl)-1,3-dithia-2,4-diphosphetane 2,4-disulfide), and the like.

The amount of the thiocarbonylation agent to be used in the reaction is usually 1 to 3 mols per 1 mol of the compound (9).

The reaction temperature is usually in a range of 0° C. to 200° C., and the reaction time is usually in a range of 1 to 24 hours.

After completion of the reaction, the compound (14) can be isolated by collecting a precipitate deposited in the reaction mixture by filtration, or extracting the reaction mixture with an organic solvent. The isolated compound (14) may be further purified by recrystallization, chromatography, or the like.

Reference Process 7

The compound (11) can be produced by reacting the compound (12) with a halogenating agent.

The reaction is performed in the presence or the absence of a solvent. Examples of the solvent to be used in the reaction include ethers such as 1,4-dioxane, diethyl ether, tetrahydrofuran, methyl tert-butyl ether, and the like, halogenated hydrocarbons such as dichloromethane, chloroform, carbon tetrachloride, 1,2-dichloroethane, chlorobenzene, and the like, hydrocarbons such as toluene, benzene, xylene, and the like, nitriles such as acetonitrile, and the like, aprotic polar solvents such as N,N-dimethylformamide, N-methylpyrrolidone, 1,3-dimethyl-2-imidazolidinone, dimethyl sulfoxide, and the like, and a mixture thereof.

Examples of the halogenating agent to be used in the reaction include thionyl chloride, thionyl bromide, phosphorus oxychloride, phosphorus oxybromide, phosphorus pentachloride, oxalyl chloride, and phosgene.

The amount of the halogenating agent to be used in the reaction is usually 1 to 2 mols per 1 mol of the compound (12) and, in some cases, the halogenating agent may be used in an excess amount.

The reaction temperature is usually in a range of 0° C. to 150° C., and the reaction time is usually in a range of 0.1 to 24 hours.

After completion of the reaction, the compound (11) can be isolated by collecting a precipitate deposited in the reaction mixture, or concentrating the reaction mixture. The isolated compound (11) is usually used as it is in the next step and, if necessary, may be further purified by recrystallization, or the like.

Reference Process 8

The compound (12) can be produced by reacting a compound represented by the formula (18'):

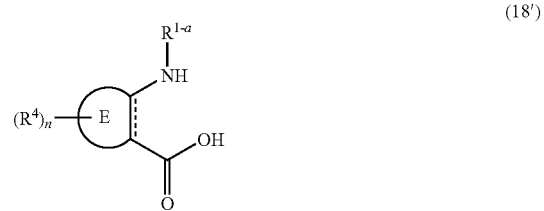

wherein $R^{1-a}$, $R^4$ and n are as defined above (hereinafter, referred to as the compound (18')) and the compound (7).

The reaction is performed in the presence or the absence of a solvent. Examples of the solvent used in the reaction include ethers such as 1,4-dioxane, diethyl ether, tetrahydrofuran, methyl tert-butyl ether, and the like, halogenated hydrocarbons such as dichloromethane, chloroform, carbon tetrachloride, 1,2-dichloroethane, chlorobenzene, and the like, hydrocarbons such as toluene, benzene, xylene, and the like, nitriles such as acetonitrile, and the like, aprotic polar solvents such as N,N-dimethylformamide, N-methylpyrrolidone, 1,3-dimethyl-2-imidazolidinone, dimethyl sulfoxide, and the like, and a mixture thereof.

The amount of the compound (7) to be used in the reaction is usually 1 to 2 mols per 1 mol of the compound (18').

The reaction is performed in the presence of a base. Examples of the base to be used include nitrogen-containing heterocyclic compounds such as pyridine, picoline, 2,6-lutidine, 1,8-diazabicyclo[5,4,0]7-undecene (DBU), 1,5-diazabicyclo[4,3,0]5-nonene (DBN), and the like, tertiary amines such as triethylamine, N,N-diisopropylethylamine, and the like, inorganic bases such as potassium carbonate, sodium hydride, and the like. The amount of the base to be used is usually 1 to 2 mols per 1 mol of the compound (18').

The reaction temperature is usually in a range of 0 to 50° C., and the reaction time is usually in range of 0.1 to 24 hours.

After completion of the reaction, the compound (12) can be isolated by pouring the reaction mixture into water, followed by conventional extraction with an organic solvent, or collecting a deposited precipitate by filtration. The isolated compound (12) may be further purified by recrystallization, chromatography, or the like.

Reference Process 9

The compound (6) can be produced by reacting a compound represented by the formula (20):

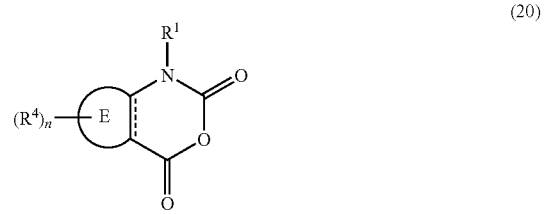

wherein R', $R^4$ and n are as defined above (hereinafter, referred to as the compound (20)) and the compound (10).

The reaction is performed in the presence or the absence of a solvent. Examples of the solvent used in the reaction include ethers such as 1,4-dioxane, diethyl ether, tetrahydrofuran, methyl tert-butyl ether, and the like, halogenated hydrocarbons such as dichloromethane, chloroform, carbon tetrachloride, 1,2-dichloroethane, chlorobenzene, and the like, hydrocarbons such as toluene, benzene, xylene, and the like, nitriles such as acetonitrile, and the like, aprotic polar solvents such as N,N-dimethylformamide, N-methylpyrrolidone, 1,3-dimethyl-2-imidazolidinone, dimethyl sulfoxide, and the like, alcohols such as methanol, ethanol, isopropyl alcohol, and the like, and a mixture thereof.

The amount of the compound (10) to be used in the reaction is usually 1 to 2 mols per 1 mol of the compound (20).

The reaction temperature is usually in a range of −20 to 150° C., and the reaction time is usually in a range of 0.1 to 24 hours.

After completion of the reaction, the compound (20) can be isolated by pouring the reaction mixture into water, and extracting the mixture with an organic solvent, or collecting a deposited precipitate by filtration. The isolated Compound (20) may be further purified by recrystallization, chromatography, or the like.

The compounds (3), (4) and (13) are known compounds, or can be produced from known compounds according to known processes (e.g. see Organic Functional Group Preparations, 2nd edition, Vol. 1, chapter 12, pp. 359-376 (Stanley R. Sandler, Wolf Karo.) or Organic Functional Group Preparations, 2nd edition, Vol. 1, chapter 14, pp. 434-465 (Stanley R. Sandler, Wolf Karo.)).

As an aspect of the compound (2), the following compound is mentioned:

A hydrazide compound of the formula (II):

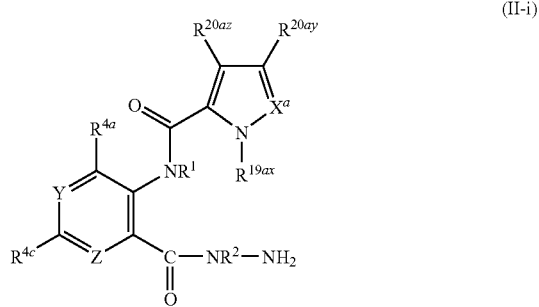

(II-i)

wherein $X^a$ represents a nitrogen atom or $CR^{20ax}$;

Y and Z represent independently a nitrogen atom or $CR^{4b}$, but not Y and Z are $CR^{4b}$ at the same time;

$R^1$ is a hydrogen atom or C1-C6 alkyl optionally substituted with one or more halogen atoms;

$R^2$ represent a hydrogen atom, C1-C6 alkyl optionally substituted with one or more halogen atoms, C2-C6 cyanoalkyl, C1-C6 hydroxyalkyl, C2-C6 alkoxyalkyl optionally substituted with one or more halogen atoms, C2-C6 alkenyl optionally substituted with one or more halogen atoms, C2-C6 alkynyl optionally substituted with one or more halogen atoms, C3-C6 cycloalkyl optionally substituted with one or more halogen atoms, C1-C6 alkylthio optionally substituted with one or more halogen atoms, C1-C6 alkylsulfinyl optionally substituted with one or more halogen atoms, C1-C6 alkylsulfonyl optionally substituted with one or more halogen atoms, C2-C6 alkylcarbonyl optionally substituted with one or more halogen atoms, C2-C6 alkoxycarbonyl, C2-C6 alkylaminocarbonyl, C3-C8 dialkylaminocarbonyl, C4-C6 cycloalkylaminocarbonyl, or C3-C6 trialkylsilyl;

or represents phenyl, C7-C9 phenylalkyl or phenylcarbonyl: each said phenyl ring optionally substituted with one or more independent substituents selected from the group consisting of (1) a halogen atom, (2) cyano, (3) nitro, (4) hydroxyl, (5) carboxyl, (6) C1-C6 alkyl optionally substituted with one or more halogen atoms, (7) C1-C6 hydroxyalkyl, (8) C1-C6 alkoxy optionally substituted with one or more halogen atoms, (9) C2-C6 cyanoalkyl, (10) C2-C6 alkoxyalkyl optionally substituted with one or more halogen atoms, (11) C2-C6 alkenyl optionally substituted with one or more halogen atoms, (12) C2-C6 alkynyl optionally substituted with one or more halogen atoms, (13) C3-C6 cycloalkyl optionally substituted with one or more halogen atoms, (14) C1-C6 alkylthio optionally substituted with one or more halogen atoms, (15) C1-C6 alkylsulfinyl optionally substituted with one or more halogen atoms, (16) C1-C6 alkylsulfonyl optionally substituted with one or more halogen atoms, (17) C1-C6 alkylamino, (18) C2-C8 dialkylamino, (19) C3-C6 cycloalkylamino, (20) C2-C6 alkylcarbonyl, (21) C2-C6 alkoxycarbonyl, (22) C2-C6 alkylaminocarbonyl, (23) C3-C8 dialkylaminocarbonyl, (24) C4-C6 cycloalkylaminocarbonyl and (25) C3-C6 trialkylsilyl;

$R^{4a}$, $R^{4b}$ and $R^{4c}$ are independently a halogen atom, cyano, nitro, hydroxyl, carboxyl, C1-C6 alkyl optionally substituted with one or more halogen atoms, C1-C6 alkoxy optionally substituted with one or more halogen atoms, C2-C6 cyanoalkyl, C2-C6 alkoxyalkyl optionally substituted with one or more halogen atoms, C2-C6 alkenyl optionally substituted with one or more halogen atoms, C2-C6 alkynyl optionally substituted with one or more halogen atoms, C3-C6 cycloalkyl optionally substituted with one or more halogen atoms, C1-C6 alkylthio optionally substituted with one or more halogen atoms, C1-C6 alkylsulfinyl optionally substituted with one or more halogen atoms, C1-C6 alkylsulfonyl optionally substituted with one or more halogen atoms, C1-C6 alkylamino, C2-C8 dialkylamino, C3-C6 cycloalkylamino, C2-C6 alkylcarbonyl optionally substituted with one or more halogen atoms, C2-C6 alkoxycarbonyl, C2-C6 alkylaminocarbonyl, C3-C8 dialkylaminocarbonyl, C3-C6 trialkylsilyl;

or represents independently phenyl, benzyl or phenoxy, each ring optionally substituted with one or more substituents selected from the group consisting of (1) a halogen atom, (2) cyano, (3) nitro, (4) hydroxyl, (5) carboxyl, (6) C1-C6 alkyl optionally substituted with one or more halogen atoms, (7) C1-C6 hydroxyalkyl, (8) C1-C6 alkoxy optionally substituted with one or more halogen atoms, (9) C2-C6 cyanoalkyl, (10) C2-C6 alkoxyalkyl optionally substituted with one or more halogen atoms, (11) C2-C6 alkenyl optionally substituted with one or more halogen atoms, (12) C2-C6 alkynyl optionally substituted with one or more halogen atoms, (13) C3-C6 cycloalkyl optionally substituted with one or more halogen atoms, (14) C1-C6 alkylthio optionally substituted with one or more halogen atoms, (15) C1-C6 alkylsulfinyl optionally substituted with one or more halogen atoms, (16) C1-C6 alkylsulfonyl optionally substituted with one or more halogen atoms, (17) C1-C6 alkylamino, (18) C2-C8 dialkylamino, (19) C3-C6 cycloalkylamino, (20) C2-C6 alkylcarbonyl, (21) C2-C6 alkoxycarbonyl, (22) C2-C6 alkylaminocarbonyl, (23) C3-C8 dialkylaminocarbonyl, (24) C4-C6 cycloalkylaminocarbonyl and (25) C3-C6 trialkylsilyl;

or 5- or 6-membered heteroaromatic optionally substituted with one or more substituents selected from the group consisting of (1) a halogen atom, (2) cyano, (3) nitro, (4) hydroxyl, (5) carboxyl, (6) C1-C6 alkyl optionally substituted with one or more halogen atoms, (7) C1-C6 hydroxyalkyl, (8) C1-C6 alkoxy optionally substituted with one or more halogen atoms, (9) C2-C6 cyanoalkyl, (10) C2-C6 alkoxyalkyl optionally substituted with one or more halogen atoms, (11) C2-C6 alkenyl optionally substituted with one or more halogen atoms, (12) C2-C6 alkynyl optionally substituted with one or more halogen atoms, (13) C3-C6 cycloalkyl optionally substituted with one or more halogen atoms, (14) C1-C6 alkylthio optionally substituted with one or more halogen atoms, (15) C1-C6 alkylsulfinyl optionally substituted with one or more halogen atoms, (16) C1-C6 alkylsulfonyl optionally substituted with one or more halogen atoms, (17) C1-C6 alkylamino, (18) C2-C8 dialkylamino, (19) C3-C6 cycloalkylamino, (20) C2-C6 alkylcarbonyl, (21) C2-C6 alkoxycarbonyl, (22) C2-C6 alkylaminocarbonyl, (23)

C3-C8 dialkylaminocarbonyl, (24) C4-C6 cycloalkylaminocarbonyl and (25) C3-C6 trialkylsilyl;

$R^{19ax}$ represent a hydrogen atom; C1-C6 alkyl optionally substituted with one or more halogen atoms; C2-C6 cyanoalkyl; C2-C6 alkoxyalkyl optionally substituted with one or more halogen atoms; C2-C6 alkenyl optionally substituted with one or more halogen atoms; C2-C6 alkynyl optionally substituted with one or more halogen atoms; C3-C6 cycloalkyl optionally substituted with one or more independent substituents selected from the group consisting of (1) a halogen atom, and (2) C1-C6 alkyl optionally substituted with one or more halogen atoms;

phenyl optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms;

5- to 6-membered heteroaryl optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms;

C7-C9 phenylalkyl whose phenyl ring is optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms;

or C7-C9 pyridinylalkyl whose pyridine ring is optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms; and $R^{20ax}$, $R^{20ay}$ and $R^{20az}$ represent a halogen atom; cyano; nitro; thiocyanato; C1-C6 alkyl optionally substituted with one or more halogen atoms; C1-C6 alkoxy optionally substituted with one or more halogen atoms; C2-C6 cyanoalkyloxy; C2-C6 alkoxyalkyloxy optionally substituted with one or more halogen atoms; C2-C6 alkenyloxy optionally substituted with one or more halogen atoms; C2-C6 alkynyloxy optionally substituted with one or more halogen atoms; C1-C6 alkylthio optionally substituted with one or more halogen atoms; C1-C6 alkylsulfinyl optionally substituted with one or more halogen atoms; C1-C6 alkylsulfonyl optionally substituted with one or more halogen atoms; phenyl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms;

5- to 6-membered heteroaryl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms;

or phenoxy optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms.

The compound (10) can be produced, for example, according to the following scheme (1).

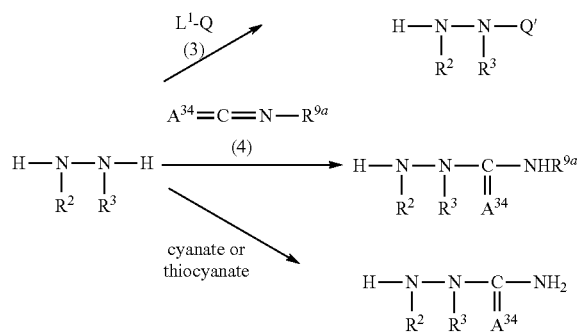

In Scheme (I), $A^{34}$, $L^1$, Q', $R^2$, $R^3$ and $R^{9a}$ are as defined above.

Among the compound (10), a compound represented by the formula (10-i):

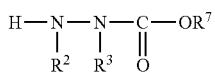
(10-i)

wherein $R^2$, $R^3$ and $R^7$ are as defined above, can be produced, for example, according to the following scheme (2).

Scheme (2)

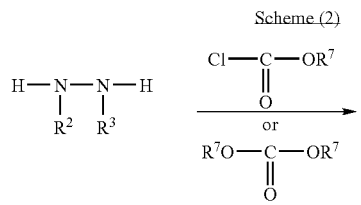

In Scheme (2), $R^2$, $R^3$ and $R^7$ are as defined above.
The compound (17) can be produced, for example, according to the following Scheme (3).

Scheme (3)

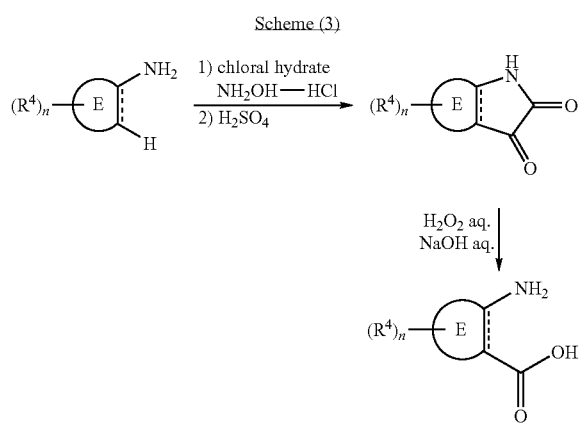

In Scheme (3), $R^4$ and n are as defined above.
The compounds (16), (18') and (20) can be produced, for example, according to the following Scheme (4).

Scheme (4)

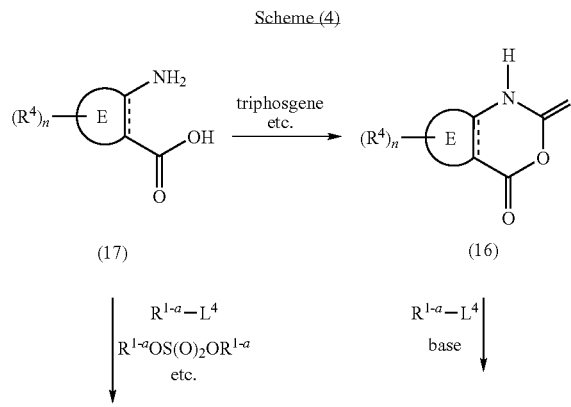

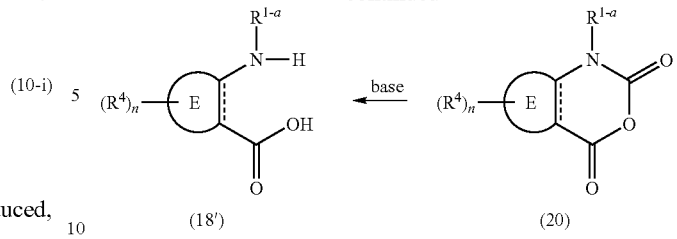

In Scheme (4), $R^{1-a}$, $R^4$ and n are as defined above, and $L^4$ represents a leaving group (e.g. a halogen atom, a methanesulfonyloxy group, a p-toluenesulfonyloxy etc.).
The compound (8) can be produced, for example, according to the process shown in the following Scheme (7).

Scheme (7)

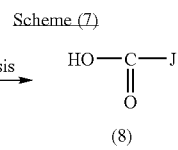
(8)

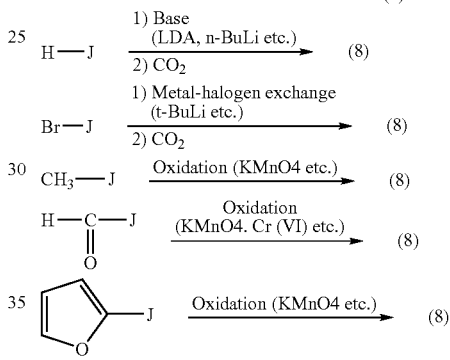

In Scheme (7), J is as defined above, $R'^7$ represents a methyl or an ethyl group, LDA represents lithium diisopropylamide, n-BuLi represents normal butyl lithium, and t-BuLi represents tertiary butyl lithium.

Among the compound (8), a compound represented by the

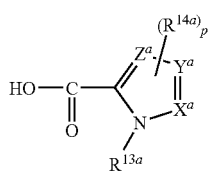
(8-i)

wherein $R^{13a}$, $R^{14a}$, $X^a$, $Y^a$, $Z^a$ and p are as defined above, can be produced, for example, according to the process shown in the following Scheme (8).

Scheme (8)

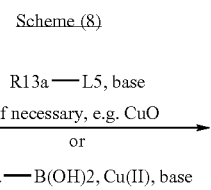

-continued

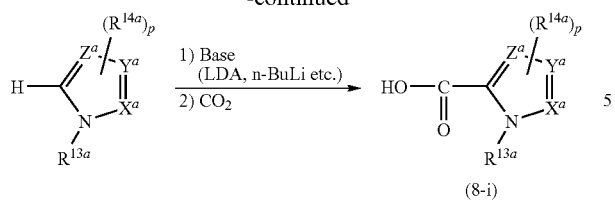

(8-i)

In Scheme (8), $R^{13a}$, $R^{14a}$, $X^a$, $Y^a$, $Z^a$, p, LDA and n-BuLi are as defined above, and $L^5$ represents a leaving group (e.g. a halogen atom, a methanesulfonyloxy group, a p-toluenesulfonyloxy group, a methylsulfonyl etc.).

Among the compound (8), a compound represented by the formula (8-ii):

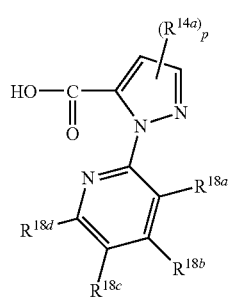

(8-ii)

wherein $R^{14a}$ and p are as defined above, $R^{18a}$, $R^{18b}$, $R^{18c}$ and $R^{18d}$ each, independently, represent a hydrogen atom, a halogen atom, cyano group, nitro group, C1-C6 alkyl optionally substituted with at least one halogen atom, C1-C6 alkoxy optionally substituted with at least one halogen atom, C1-C6 alkylthio optionally substituted with at least one halogen atom, C1-C6 alkylsulfinyl optionally substituted with at least one halogen atom, or C1-C6 alkylsulfonyl optionally substituted with at least one halogen atom, can be produced, for example, according to the process shown in the following Scheme (9).

-continued

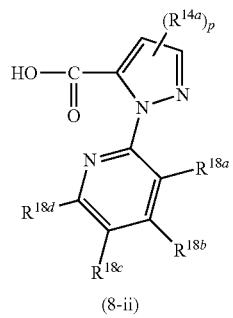

(8-ii)

In Scheme (9), $R^{14a}$, $R^{18a}$, $R^{18b}$, $R^{18c}$, $R^{18d}$, LDA and p are as defined above, and $L^6$ represents a leaving group (e.g. a halogen atom, a methylsulfonyl etc.).

Among the compound (8), a compound represented by the formula (8-iii):

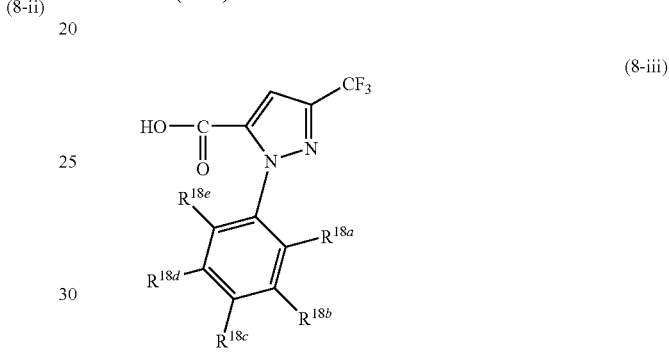

(8-iii)

wherein $R^{18a}$, $R^{18b}$, $R_{18c}$, $R^{18d}$ and $R^{18e}$ independently represent a hydrogen atom, a halogen atom, cyano group, nitro group, C1-C6 alkyl optionally substituted with at least one halogen atom, C1-C6 alkoxy optionally substituted with at least one halogen atom, C1-C6 alkylthio optionally substituted with at least one halogen atom, C1-C6 alkylsulfinyl optionally substituted with at least one halogen atom, or C1-C6 alkylsulfonyl optionally substituted with at least one halogen atom, can be produced, for example, according to the process shown in the following Scheme (10).

Scheme (9)

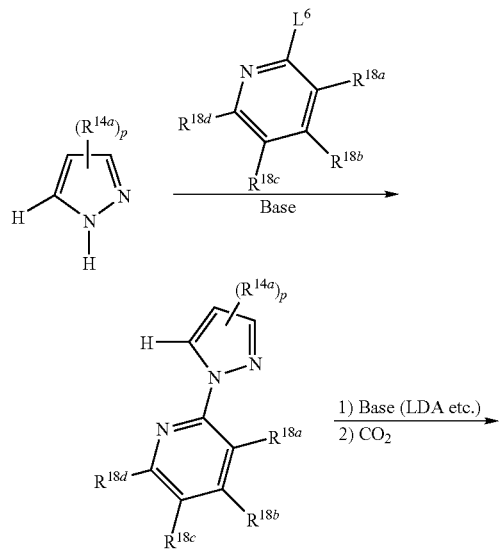

Scheme (10)

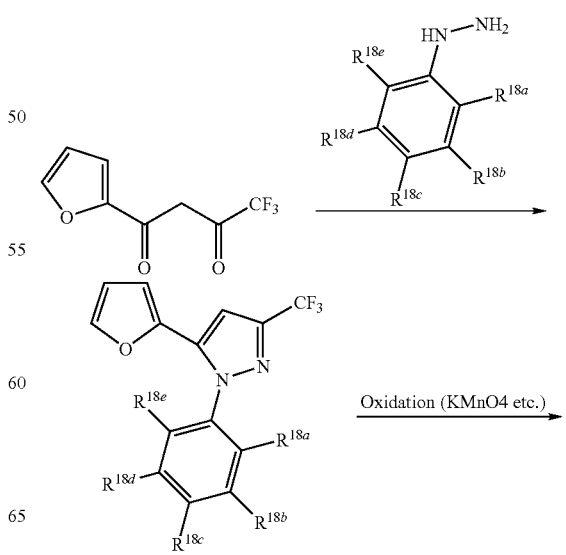

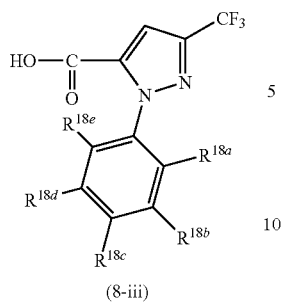

(8-iii)

In Scheme (10), $R^{18a}$, $R^{18b}$, $R^{18c}$, $R^{18d}$ and $R^{18e}$ are as defined above.

Among the compound (8), a compound represented by the formula (8-iv):

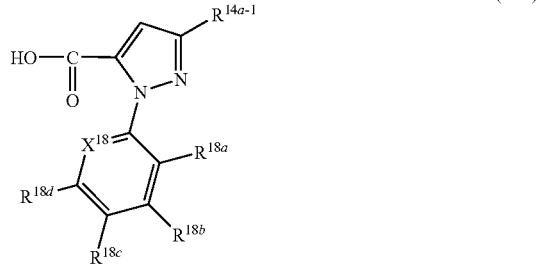

(8-iv)

wherein $X^{18}$ represents —N=, or —$CR^{18e}$=; $R^{18a}$, $R^{18b}$, $R^{18c}$, $R^{18d}$ and $R^{18e}$ are as defined above, and $R^{14a-1}$ represents C1-C6 alkyl optionally substituted with at least one halogen atom, can be produced, for example, according to the process shown in the following Scheme (11).

Scheme (11)

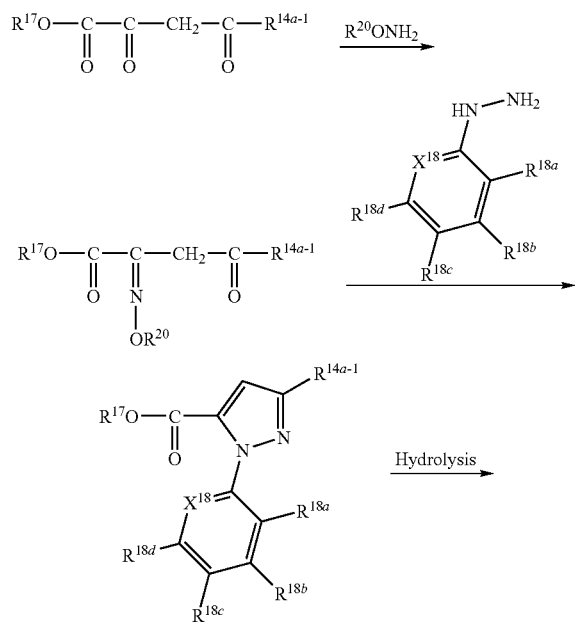

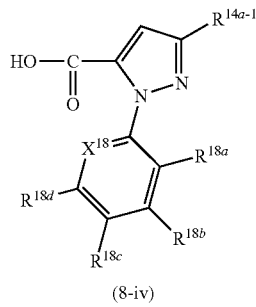

(8-iv)

In Scheme (11), $R^{14a-1}$, $R^{17}$, $R^{18a}$, $R^{18b}$, $R^{18c}$, $R^{18d}$ and $X^{18}$ are as defined above, and $R^{20}$ represents a methyl or an ethyl group.

Among the compound (8), a compound represented by the formula (8-vii):

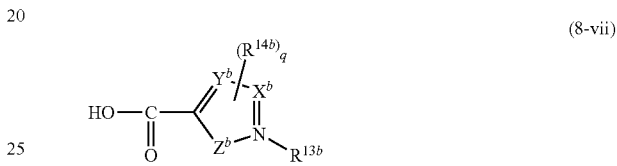

(8-vii)

wherein $R^{13b}$, $R^{14b}$, $X^b$, $Y^b$, $Z^b$ and q are as defined above, can be produced, for example, according to the process shown in the following Scheme (14).

Scheme (14)

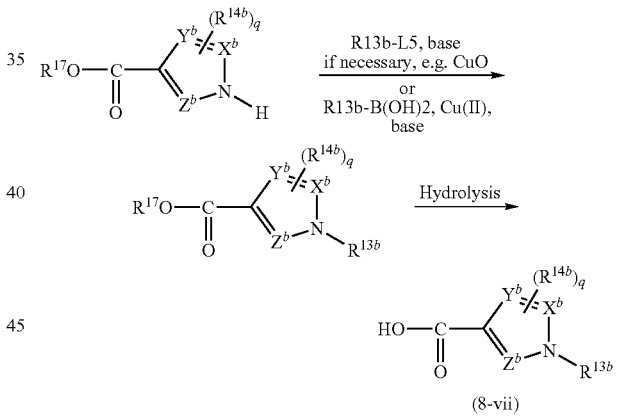

(8-vii)

In Scheme (14), $R^{13b}$, $R^{14b}$, $R^{17}$, $X^b$, $Y^b$, $Z^b$, $L^5$ and q are as defined above.

Among the compound (8), a compound represented by the formula (8-viii) and the formula (8-ix):

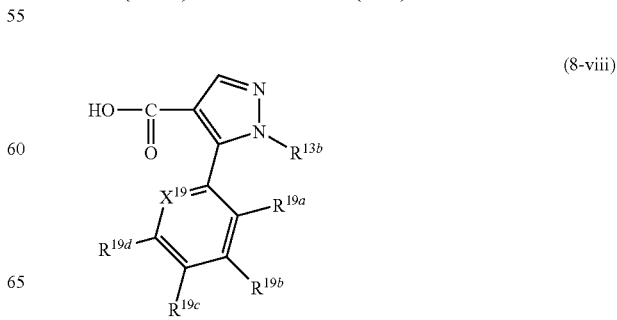

(8-viii)

-continued

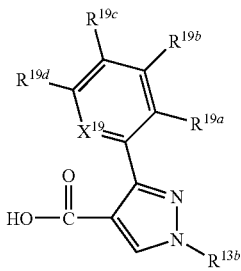
(8-ix)

[wherein
R$^{13b}$, is as defined above;
X$^{19}$ represents —N═, or —CR$^{19e}$═; and
R$^{19a}$, R$^{19b}$, R$^{19c}$, R$^{19d}$ and R$^{19e}$, each, independently, represent a hydrogen atom, a halogen atom, cyano group, a nitro group, C1-C6 alkyl optionally substituted with at least one halogen atom, C1-C6 alkoxy optionally substituted with at least one halogen atom, C1-C6 alkylthio optionally substituted with at least one halogen atom, C1-C6 alkylsulfinyl optionally substituted with at least one halogen atom, or C1-C6 alkylsulfonyl optionally substituted with at least one halogen atom]
can be produced, for example, according to the process shown in the following Scheme (15).

Scheme (15)

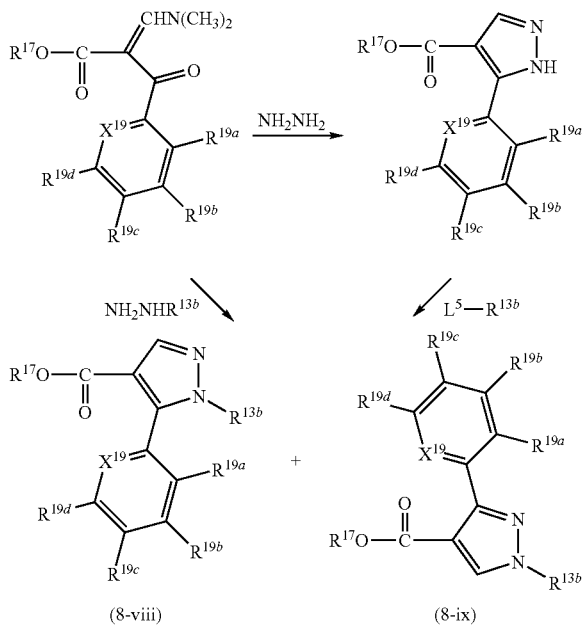

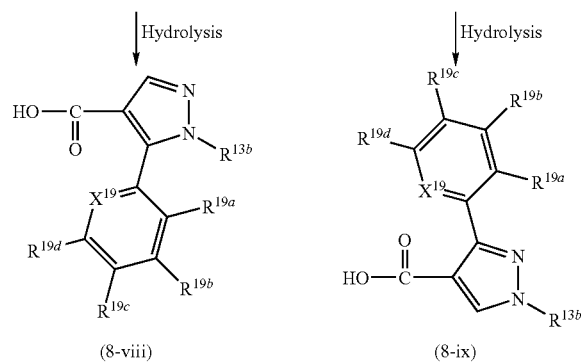

In Scheme (15), R$^{13b}$, R$^{17}$, R$^{19a}$, R$^{19b}$, R$^{19c}$, R$^{19d}$, L$^5$ and X$^{19}$ are as defined above.

Among the compound (7), a compound represented by the formula (7-i):

(7-i)

wherein L$^2$ and J are as defined above, can be produced, for example, according to the process shown in the following Scheme (16).

Scheme (16)

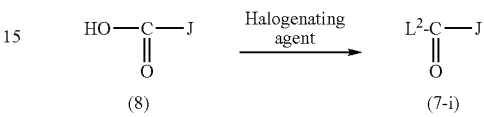

In Scheme (16), L$^2$ and J are as defined above.

Among the compound (7), a compound represented by the formula (7-ii):

(7-ii)

wherein L$^2$ and J are as defined above, can be produced, for example, according to the process shown in the following scheme (17).

Scheme (17)

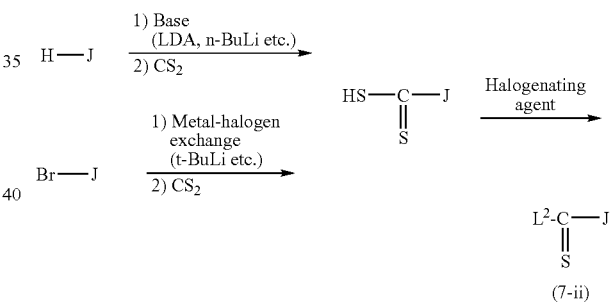

In Scheme (17), L$^2$ and J are as defined above, LDA represents lithium diisopropylamide, n-BuLi represents normal butyl lithium, and t-BuLi represents tertiary butyl lithium.

Among the compound (8), a compound represented by the formula (8-v):

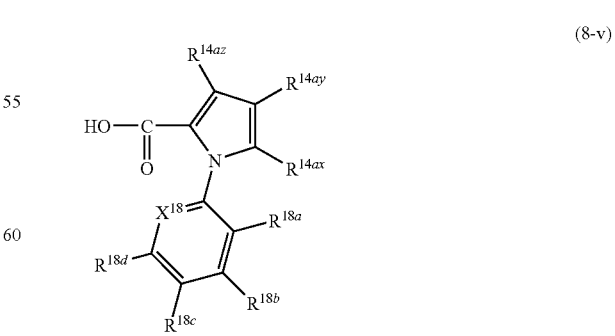
(8-v)

wherein R$^{18a}$, R$^{18b}$, R$_{18c}$, R$^{18d}$ and X$^{18}$ are as defined above, and R$^{14ax}$, R$^{14ay}$, X$^{14az}$ and X independently represent a hydrogen atom, a halogen atom, cyano group, C1-C6 alkyl optionally substituted with at least one halogen atom, C1-C6 alkoxy optionally substituted with at least one halogen atom, C1-C6 alkylthio optionally substituted with at least one halogen atom, C1-C6 alkylsulfinyl optionally substituted with at least one halogen atom, or C1-C6 alkylsulfonyl optionally substituted with at least one halogen atom, can be produced, for example, according to the process shown in the following Scheme (18).

Scheme (18)

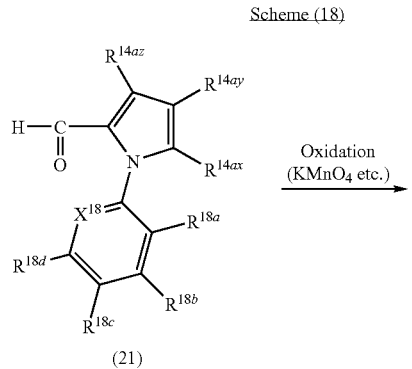

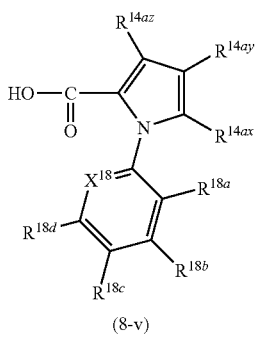

(8-v)

In Scheme (18) $R^{18a}$, $R^{18b}$, $R^{18c}$, $R^{18d}$, $X^{18}$, $R^{14ax}$, $R^{14ay}$, and $X^{14az}$ are as defined above.

The compounds (21) in scheme (18) can be produced, for example, according to the process shown in the following Scheme (19).

Scheme (19)

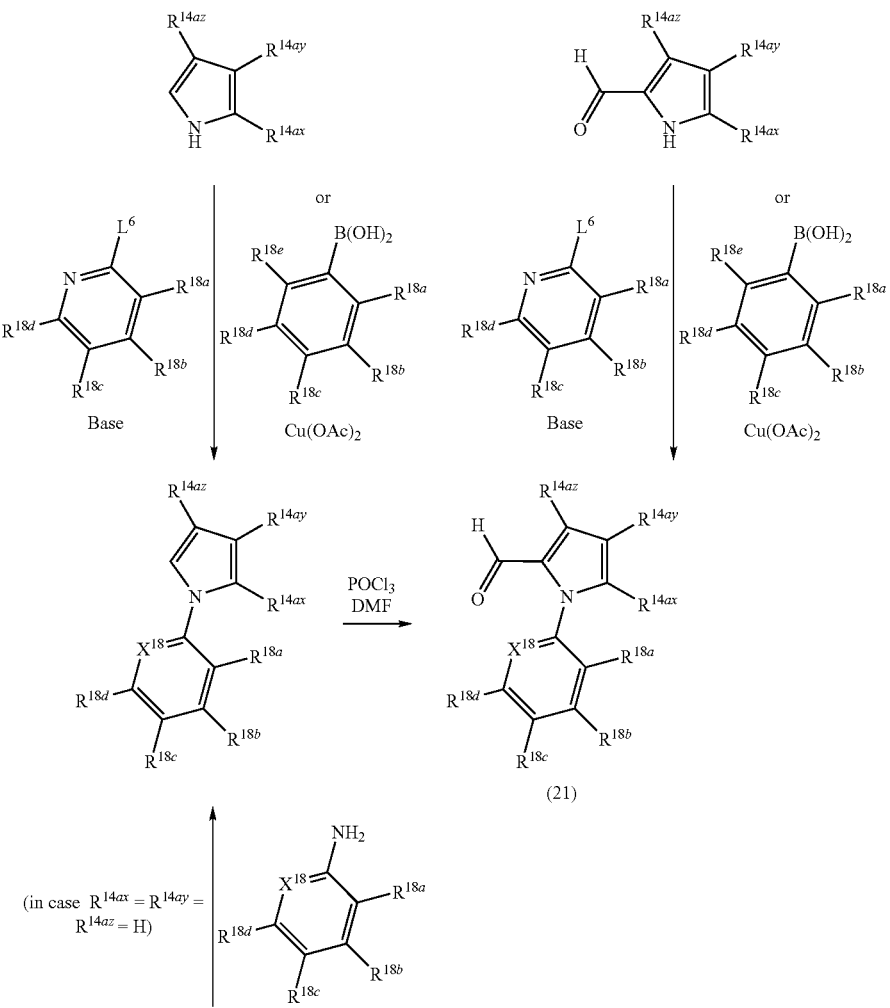

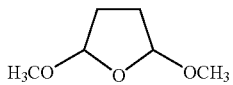

In Scheme (19), $R^{18a}$, $R^{18b}$, $R^{18c}$, $R^{18d}$, $R^{18e}$, $X^{18}$, $R^{14ax}$, $R^{14ay}$, $X^{14az}$ and $L^6$ are as defined above Among the compounds (21) in scheme (18), a compound represented by the formula (21-i), the formula (21-ii), and the formula (21-iii):

(21-i)

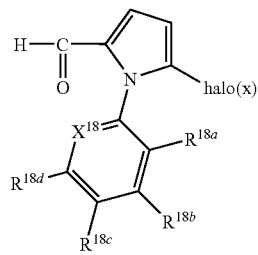

(21-ii)

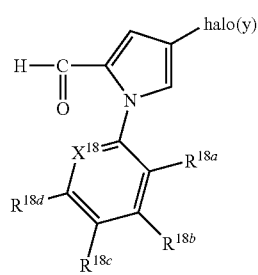

(21-iii)

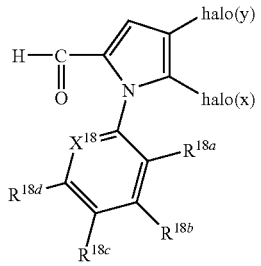

wherein $R^{18a}$, $R^{18b}$, $R^{18c}$, $R^{18d}$ and $X^{18}$ are as defined above, and halo(x) and halo(y) independently represent a halogen atom, can be produced, for example, according to the process shown in the following Scheme (20).

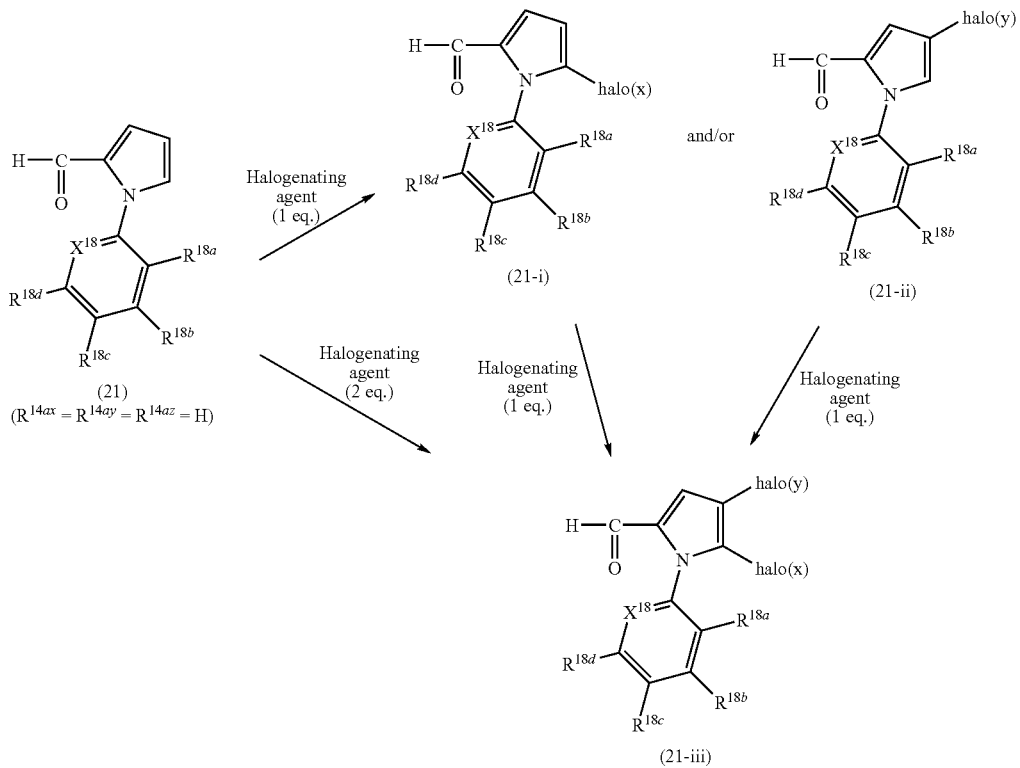

In Scheme (20), $R^{18a}$, $R^{18b}$, $R^{18c}$, $R^{18d}$, $X^{18}$, halo(x) and halo(y) are as defined above.

Among the compound (8), a compound represented by the formula (8-yl):

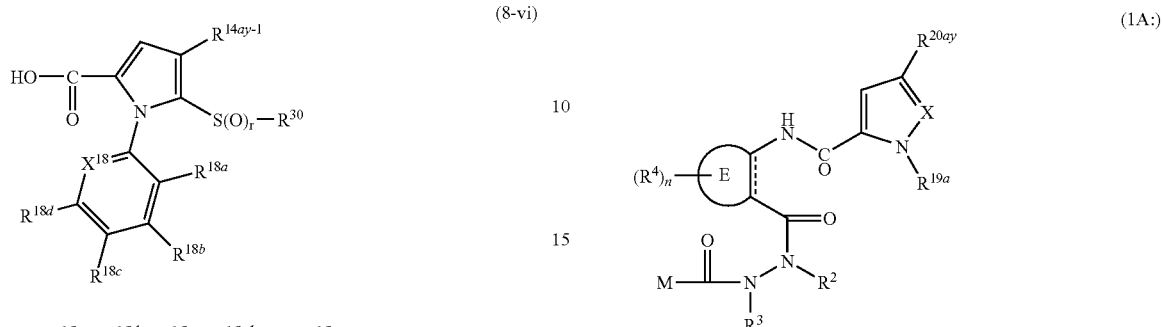

(8-vi)

wherein $R^{18a}$, $R^{18b}$, $R^{18c}$, $R^{18d}$ and $X^{18}$ are as defined above, $R^{14ay-1}$ represents a hydrogen atom or a halogen atom, $R^{30}$ represents C1-C6 alkyl optionally substituted with at least one halogen atom, and r represents an integer of 0 to 2, can be produced, for example, according to the process shown in the following Scheme (21).

In Scheme (21), $R^{18a}$, $R^{18b}$, $R^{18c}$, $R^{18d}$, $X^{18}$, $R^{14ay-1}$, $R^{30}$, r and $L^4$ are as defined above.

The specific examples of the present compound are summarized in the following compounds 1 to 277.

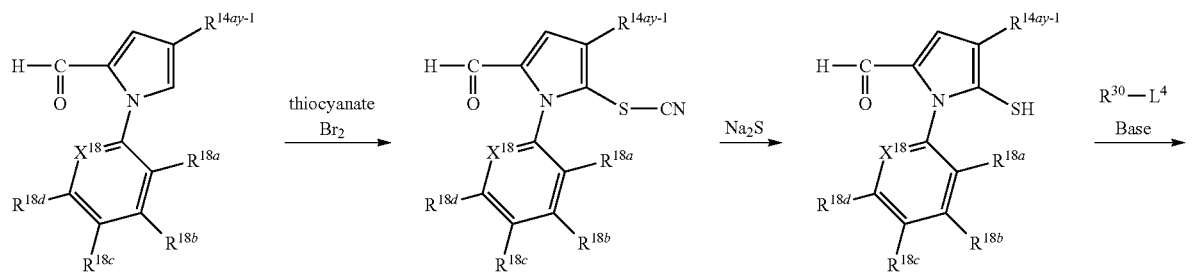

(1A:)

Compound 1:
Compounds of formula 1A wherein $R^2$, $R^3$, M, $R^{19a}$, $R^{20ay}$ and X corresponds to a row in Table A, and E substituted with $(R^4)_n$ is:

Scheme (21)

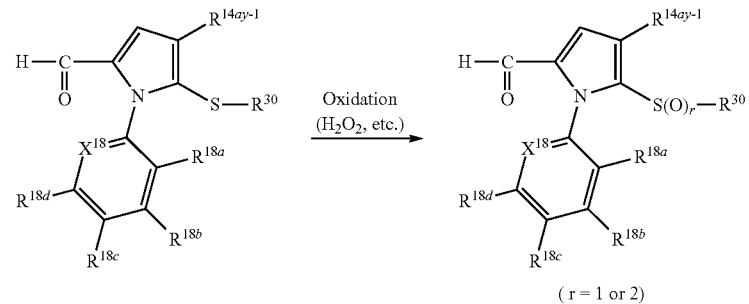

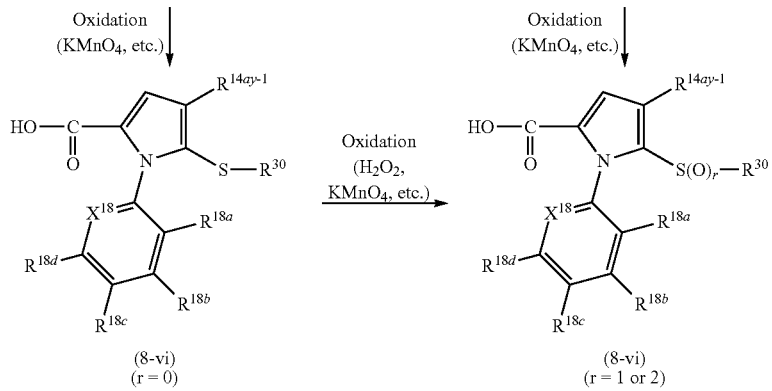

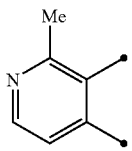

Compound 2:

Compounds of formula 1A wherein $R^2$, $R^3$, M, $R^{19a}$, $R^{20ay}$ and X corresponds to a row in Table A, and E substituted with $(R^4)_n$ is:

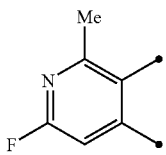

Compound 3:

Compounds of formula 1A wherein $R^2$, $R^3$, M, $R^{19a}$, $R^{20ay}$ and X corresponds to a row in Table A, and E substituted with $(R^4)_n$ is:

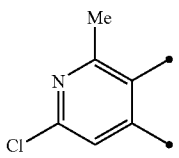

Compound 4:

Compounds of formula 1A wherein $R^2$, $R^3$, M, $R^{19a}$, $R^{20ay}$ and X corresponds to a row in Table A, and E substituted with $(R^4)_n$ is:

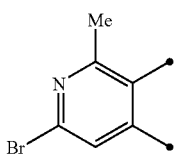

Compound 5:

Compounds of formula 1A wherein $R^2$, $R^3$, M, $R^{19a}$, $R^{20ay}$ and X corresponds to a row in Table A, and E substituted with $(R^4)_n$ is:

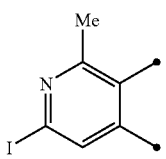

Compound 6:

Compounds of formula 1A wherein $R^2$, $R^3$, M, $R^{19a}$, $R^{20ay}$ and X corresponds to a row in Table A, and E substituted with $(R^4)_n$ is:

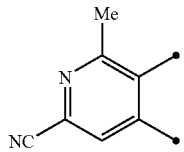

Compound 7:

Compounds of formula 1A wherein $R^2$, $R^3$, M, $R^{19a}$, $R^{20ay}$ and X corresponds to a row in Table A, and E substituted with $(R^4)_n$ is:

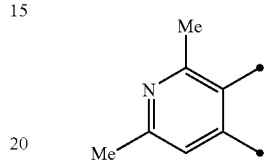

Compound 8:

Compounds of formula 1A wherein $R^2$, $R^3$, M, $R^{19a}$, $R^{20ay}$ and X corresponds to a row in Table A, and E substituted with $(R^4)_n$ is:

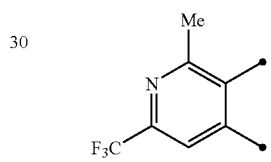

Compound 9:

Compounds of formula 1A wherein $R^2$, $R^3$, M, $R^{19a}$, $R^{20ay}$ and X corresponds to a row in Table A, and E substituted with $(R^4)_n$ is:

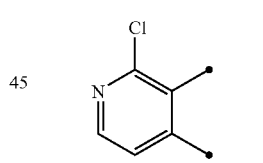

Compound 10:

Compounds of formula 1A wherein $R^2$, $R^3$, M, $R^{19a}$, $R^{20ay}$ and X corresponds to a row in Table A, and E substituted with $(R^4)_n$ is:

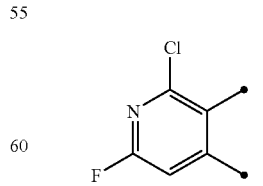

Compound 11:

Compounds of formula 1A wherein $R^2$, $R^3$, M, $R^{19a}$, $R^{20ay}$ and X corresponds to a row in Table A, and E substituted with $(R^4)_n$ is:

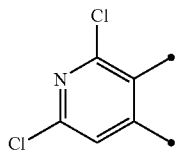

Compound 12:
Compounds of formula 1A wherein $R^2$, $R^3$, M, $R^{19a}$, $R^{20ay}$ and X corresponds to a row in Table A, and E substituted with $(R^4)_n$ is:

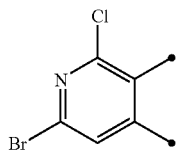

Compound 13:
Compounds of formula 1A wherein $R^2$, $R^3$, M, $R^{19a}$, $R^{20ay}$ and X corresponds to a row in Table A, and E substituted with $(R^4)_n$ is:

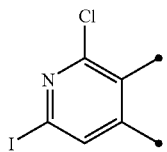

Compound 14:
Compounds of formula 1A wherein $R^2$, $R^3$, M, $R^{19a}$, $R^{20ay}$ and X corresponds to a row in Table A, and E substituted with $(R^4)_n$ is:

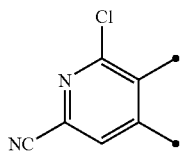

Compound 15:
Compounds of formula 1A wherein $R^2$, $R^3$, M, $R^{19a}$, $R^{20ay}$ and X corresponds to a row in Table A, and E substituted with $(R^4)_n$ is:

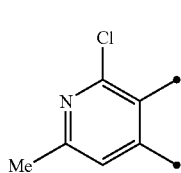

Compound 16:
Compounds of formula 1A wherein $R^2$, $R^3$, M, $R^{19a}$, $R^{20ay}$ and X corresponds to a row in Table A, and E substituted with $(R^4)_n$ is:

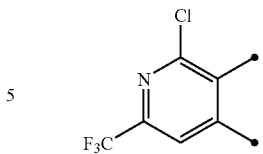

Compound 17:
Compounds of formula 1A wherein $R^2$, $R^3$, M, $R^{19a}$, $R^{20ay}$ and X corresponds to a row in Table A, and E substituted with $(R^4)_n$ is:

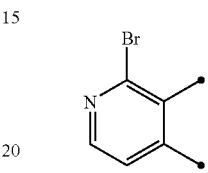

Compound 18:
Compounds of formula 1A wherein $R^2$, $R^3$, M, $R^{19a}$, $R^{20ay}$ and X corresponds to a row in Table A, and E substituted with $(R^4)_n$ is:

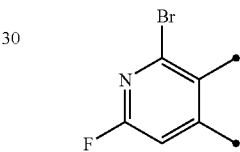

Compound 19:
Compounds of formula 1A wherein $R^2$, $R^3$, M, $R^{19a}$, $R^{20ay}$ and X corresponds to a row in Table A, and E substituted with $(R^4)_n$ is:

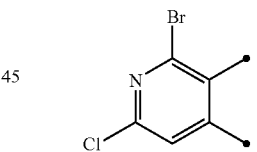

Compound 20:
Compounds of formula 1A wherein $R^2$, $R^3$, M, $R^{19a}$, $R^{20ay}$ and X corresponds to a row in Table A, and E substituted with $(R^4)_n$ is:

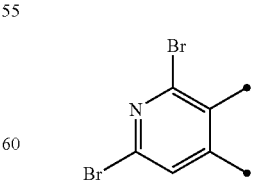

Compound 21:
Compounds of formula 1A wherein $R^2$, $R^3$, M, $R^{19a}$, $R^{20ay}$ and X corresponds to a row in Table A, and E substituted with $(R^4)_n$ is:

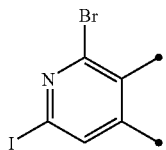

Compound 22:

Compounds of formula 1A wherein $R^2$, $R^3$, M, $R^{19a}$, $R^{20ay}$ and X corresponds to a row in Table A, and E substituted with $(R^4)_n$ is:

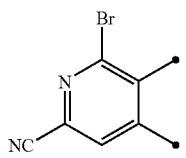

Compound 23:

Compounds of formula 1A wherein $R^2$, $R^3$, M, $R^{19a}$, $R^{20ay}$ and X corresponds to a row in Table A, and E substituted with $(R^4)_n$ is:

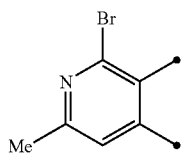

Compound 24:

Compounds of formula 1A wherein $R^2$, $R^3$, M, $R^{19a}$, $R^{20ay}$ and X corresponds to a row in Table A, and E substituted with $(R^4)_n$ is:

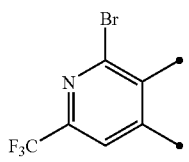

Compound 25:

Compounds of formula 1A wherein $R^2$, $R^3$, M, $R^{19a}$, $R^{20ay}$ and X corresponds to a row in Table A, and E substituted with $(R^4)_n$ is:

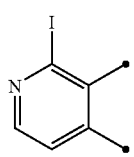

Compound 26:

Compounds of formula 1A wherein $R^2$, $R^3$, M, $R^{19a}$, $R^{20ay}$ and X corresponds to a row in Table A, and E substituted with $(R^4)_n$ is:

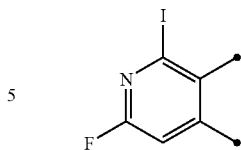

Compound 27:

Compounds of formula 1A wherein $R^2$, $R^3$, M, $R^{19a}$, $R^{20ay}$ and X corresponds to a row in Table A, and E substituted with $(R^4)_n$ is:


Compound 28:

Compounds of formula 1A wherein $R^2$, $R^3$, M, $R^{19a}$, $R^{20ay}$ and X corresponds to a row in Table A, and E substituted with $(R^4)_n$ is:


Compound 29:

Compounds of formula 1A wherein $R^2$, $R^3$, M, $R^{19a}$, $R^{20ay}$ and X corresponds to a row in Table A, and E substituted with $(R^4)_n$ is:

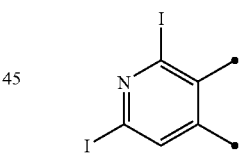

Compound 30:

Compounds of formula 1A wherein $R^2$, $R^3$, M, $R^{19a}$, $R^{20ay}$ and X corresponds to a row in Table A, and E substituted with $(R^4)_n$ is:

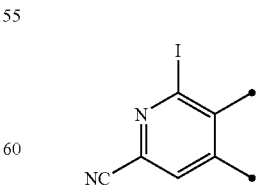

Compound 31:

Compounds of formula 1A wherein $R^2$, $R^3$, M, $R^{19a}$, $R^{20ay}$ and X corresponds to a row in Table A, and E substituted with $(R^4)_n$ is:

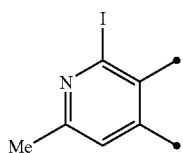

Compound 32:

Compounds of formula 1A wherein $R^2$, $R^3$, M, $R^{19a}$, $R^{20ay}$ and X corresponds to a row in Table A, and E substituted with $(R^4)_n$ is:

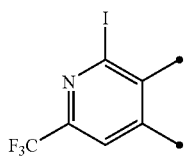

Compound 33:

Compounds of formula 1A wherein $R^2$, $R^3$, M, $R^{19a}$, $R^{20ay}$ and X corresponds to a row in Table A, and E substituted with $(R^4)_n$ is:

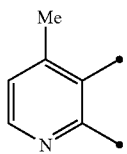

Compound 34:

Compounds of formula 1A wherein $R^2$, $R^3$, M, $R^{19a}$, $R^{20ay}$ and X corresponds to a row in Table A, and E substituted with $(R^4)_n$ is:

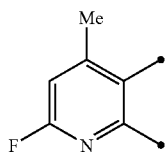

Compound 35:

Compounds of formula 1A wherein $R^2$, $R^3$, M, $R^{19a}$, $R^{20ay}$ and X corresponds to a row in Table A, and E substituted with $(R^4)_n$ is:

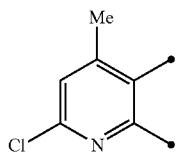

Compound 36:

Compounds of formula 1A wherein $R^2$, $R^3$, M, $R^{19a}$, $R^{20ay}$ and X corresponds to a row in Table A, and E substituted with $(R^4)_n$ is:

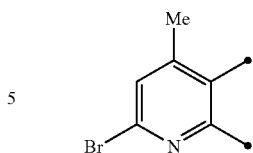

Compound 37:

Compounds of formula 1A wherein $R^2$, $R^3$, M, $R^{19a}$, $R^{20ay}$ and X corresponds to a row in Table A, and E substituted with $(R^4)_n$ is:

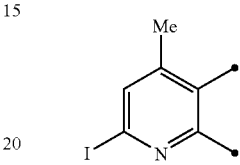

Compound 38:

Compounds of formula 1A wherein $R^2$, $R^3$, M, $R^{19a}$, $R^{20ay}$ and X corresponds to a row in Table A, and E substituted with $(R^4)_n$ is:

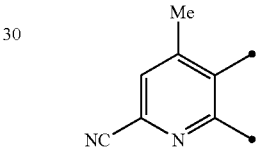

Compound 39:

Compounds of formula 1A wherein $R^2$, $R^3$, M, $R^{19a}$, $R^{20ay}$ and X corresponds to a row in Table A, and E substituted with $(R^4)_n$ is:

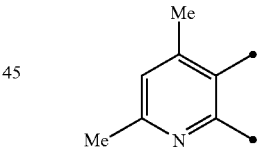

Compound 40:

Compounds of formula 1A wherein $R^2$, $R^3$, M, $R^{19a}$, $R^{20ay}$ and X corresponds to a row in Table A, and E substituted with $(R^4)_n$ is:

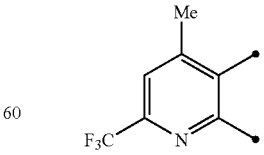

Compound 41:

Compounds of formula 1A wherein $R^2$, $R^3$, M, $R^{19a}$, $R^{20ay}$ and X corresponds to a row in Table A, and E substituted with $(R^4)_n$ is:

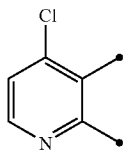

Compound 42:

Compounds of formula 1A wherein $R^2$, $R^3$, M, $R^{19a}$, $R^{20ay}$ and X corresponds to a row in Table A, and E substituted with $(R^4)_n$ is:

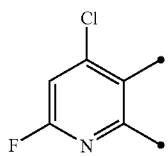

Compound 43:

Compounds of formula 1A wherein $R^2$, $R^3$, M, $R^{19a}$, $R^{20ay}$ and X corresponds to a row in Table A, and E substituted with $(R^4)_n$ is:

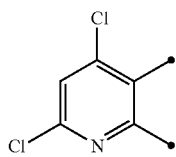

Compound 44:

Compounds of formula 1A wherein $R^2$, $R^3$, M, $R^{19a}$, $R^{20ay}$ and X corresponds to a row in Table A, and E substituted with $(R^4)_n$ is:

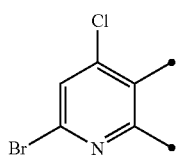

Compound 45:

Compounds of formula 1A wherein $R^2$, $R^3$, M, $R^{19a}$, $R^{20ay}$ and X corresponds to a row in Table A, and E substituted with $(R^4)_n$ is:

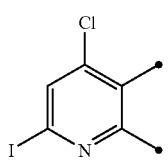

Compound 46:

Compounds of formula 1A wherein $R^2$, $R^3$, M, $R^{19a}$, $R^{20ay}$ and X corresponds to a row in Table A, and E substituted with $(R^4)_n$ is:

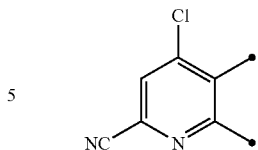

Compound 47:

Compounds of formula 1A wherein $R^2$, $R^3$, M, $R^{19a}$, $R^{20ay}$ and X corresponds to a row in Table A, and E substituted with $(R^4)_n$ is:

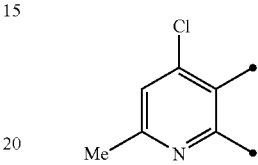

Compound 48:

Compounds of formula 1A wherein $R^2$, $R^3$, M, $R^{19a}$, $R^{20ay}$ and X corresponds to a row in Table A, and E substituted with $(R^4)_n$ is:

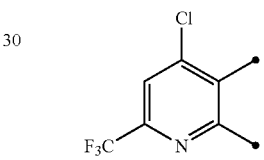

Compound 49:

Compounds of formula 1A wherein $R^2$, $R^3$, M, $R^{19a}$, $R^{20ay}$ and X corresponds to a row in Table A, and E substituted with $(R^4)_n$ is:

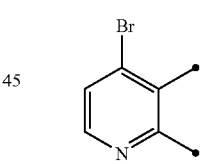

Compound 50:

Compounds of formula 1A wherein $R^2$, $R^3$, M, $R^{19a}$, $R^{20ay}$ and X corresponds to a row in Table A, and E substituted with $(R^4)_n$ is:

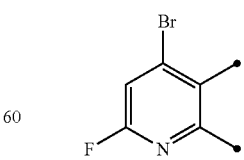

Compound 51:

Compounds of formula 1A wherein $R^2$, $R^3$, M, $R^{19a}$, $R^{20ay}$ and X corresponds to a row in Table A, and E substituted with $(R^4)_n$ is:

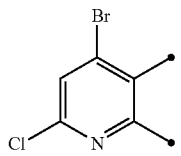

Compound 52:

Compounds of formula 1A wherein $R^2$, $R^3$, M, $R^{19a}$, $R^{20ay}$ and X corresponds to a row in Table A, and E substituted with $(R^4)_n$ is:

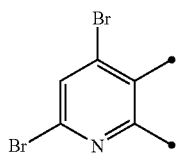

Compound 53:

Compounds of formula 1A wherein $R^2$, $R^3$, M, $R^{19a}$, $R^{20ay}$ and X corresponds to a row in Table A, and E substituted with $(R^4)_n$ is:

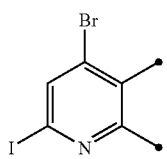

Compound 54:

Compounds of formula 1A wherein $R^2$, $R^3$, M, $R^{19a}$, $R^{20ay}$ and X corresponds to a row in Table A, and E substituted with $(R^4)_n$ is:

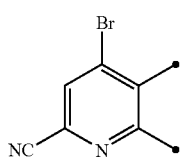

Compound 55:

Compounds of formula 1A wherein $R^2$, $R^3$, M, $R^{19a}$, $R^{20ay}$ and X corresponds to a row in Table A, and E substituted with $(R^4)_n$ is:

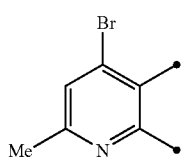

Compound 56:

Compounds of formula 1A wherein $R^2$, $R^3$, M, $R^{19a}$, $R^{20ay}$ and X corresponds to a row in Table A, and E substituted with $(R^4)_n$ is:

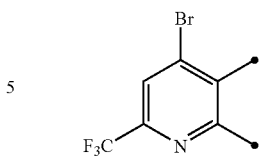

Compound 57:

Compounds of formula 1A wherein $R^2$, $R^3$, M, $R^{19a}$, $R^{20ay}$ and X corresponds to a row in Table A, and E substituted with $(R^4)_n$ is:

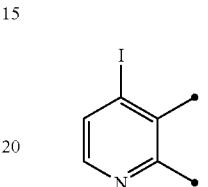

Compound 58:

Compounds of formula 1A wherein $R^2$, $R^3$, M, $R^{19a}$, $R^{20ay}$ and X corresponds to a row in Table A, and E substituted with $(R^4)_n$ is:

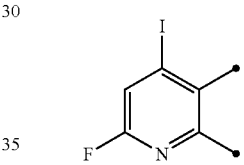

Compound 59:

Compounds of formula 1A wherein $R^2$, $R^3$, M, $R^{19a}$, $R^{20ay}$ and X corresponds to a row in Table A, and E substituted with $(R^4)_n$ is:


Compound 60:

Compounds of formula 1A wherein $R^2$, $R^3$, M, $R^{19a}$, $R^{20ay}$ and X corresponds to a row in Table A, and E substituted with $(R^4)_n$ is:


Compound 61:
Compounds of formula 1A wherein $R^2$, $R^3$, M, $R^{19a}$, $R^{20ay}$ and X corresponds to a row in Table A, and E substituted with $(R^4)_n$ is:

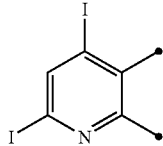

Compound 62:
Compounds of formula 1A wherein $R^2$, $R^3$, M, $R^{19a}$, $R^{20ay}$ and X corresponds to a row in Table A, and E substituted with $(R^4)_n$ is:

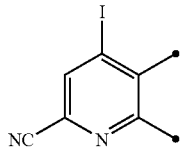

Compound 63:
Compounds of formula 1A wherein $R^2$, $R^3$, M, $R^{19a}$, $R^{20ay}$ and X corresponds to a row in Table A, and E substituted with $(R^4)_n$ is:

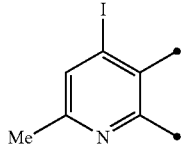

Compound 64:
Compounds of formula 1A wherein $R^2$, $R^3$, M, $R^{19a}$, $R^{20ay}$ and X corresponds to a row in Table A, and E substituted with $(R^4)_n$ is:

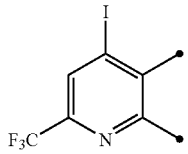

TABLE A

| No. | $R^2$ | $R^3$ | M | $R^{19a}$ | X | $R^{20ay}$ |
|---|---|---|---|---|---|---|
| | H | H | H | 3-chloro-2-pyridinyl | N | Cl |
| | Me | H | H | 3-chloro-2-pyridinyl | N | Cl |
| | H | Me | H | 3-chloro-2-pyridinyl | N | Cl |
| | Me | Me | H | 3-chloro-2-pyridinyl | N | Cl |
| | Et | H | H | 3-chloro-2-pyridinyl | N | Cl |
| | H | Et | H | 3-chloro-2-pyridinyl | N | Cl |
| | Et | Et | H | 3-chloro-2-pyridinyl | N | Cl |
| | n-Pr | H | H | 3-chloro-2-pyridinyl | N | Cl |
| | H | n-Pr | H | 3-chloro-2-pyridinyl | N | Cl |
| | iso-Pr | H | H | 3-chloro-2-pyridinyl | N | Cl |
| | H | iso-Pr | H | 3-chloro-2-pyridinyl | N | Cl |
| | iso-Bu | H | H | 3-chloro-2-pyridinyl | N | Cl |
| | H | iso-Bu | H | 3-chloro-2-pyridinyl | N | Cl |
| | tert-Bu | H | H | 3-chloro-2-pyridinyl | N | Cl |
| | H | tert-Bu | H | 3-chloro-2-pyridinyl | N | Cl |
| | $CH_2CF_3$ | H | H | 3-chloro-2-pyridinyl | N | Cl |
| | H | $CH_2CF_3$ | H | 3-chloro-2-pyridinyl | N | Cl |
| | $CH_2CN$ | H | H | 3-chloro-2-pyridinyl | N | Cl |
| | H | $CH_2CN$ | H | 3-chloro-2-pyridinyl | N | Cl |
| | $CH_2OMe$ | H | H | 3-chloro-2-pyridinyl | N | Cl |
| | H | $CH_2OMe$ | H | 3-chloro-2-pyridinyl | N | Cl |
| | $CH_2CH=CH_2$ | H | H | 3-chloro-2-pyridinyl | N | Cl |
| | H | $CH_2CH=CH_2$ | H | 3-chloro-2-pyridinyl | N | Cl |

TABLE A-continued

| No. | $R^2$ | $R^3$ | M | $R^{19a}$ | X | $R^{20ay}$ |
|---|---|---|---|---|---|---|
| | $CH_2CCH$ | H | H | 3-chloro-2-pyridinyl | N | Cl |
| | H | $CH_2CCH$ | H | 3-chloro-2-pyridinyl | N | Cl |
| | H | $CO_2Me$ | H | 3-chloro-2-pyridinyl | N | Cl |
| | Me | Et | H | 3-chloro-2-pyridinyl | N | Cl |
| | Et | Me | H | 3-chloro-2-pyridinyl | N | Cl |
| | $CH_2CH=CH_2$ | Me | H | 3-chloro-2-pyridinyl | N | Cl |
| | $CH_2CH=CH_2$ | Et | H | 3-chloro-2-pyridinyl | N | Cl |
| | Me | $CH_2CH=CH_2$ | H | 3-chloro-2-pyridinyl | N | Cl |
| | Et | $CH_2CH=CH_2$ | H | 3-chloro-2-pyridinyl | N | Cl |
| | $CH_2CH=CH_2$ | $CH_2CH=CH_2$ | H | 3-chloro-2-pyridinyl | N | Cl |
| | $CH_2CCH$ | Me | H | 3-chloro-2-pyridinyl | N | Cl |
| | $CH_2CCH$ | Et | H | 3-chloro-2-pyridinyl | N | Cl |
| | Me | $CH_2CCH$ | H | 3-chloro-2-pyridinyl | N | Cl |
| | Et | $CH_2CCH$ | H | 3-chloro-2-pyridinyl | N | Cl |
| | $CH_2CCH$ | $CH_2CCH$ | H | 3-chloro-2-pyridinyl | N | Cl |
| | cyc-Pr | H | H | 3-chloro-2-pyridinyl | N | Cl |
| | H | cyc-Pr | H | 3-chloro-2-pyridinyl | N | Cl |
| | iso-Bu | iso-Bu | H | 3-chloro-2-pyridinyl | N | Cl |
| | sec-Bu | H | H | 3-chloro-2-pyridinyl | N | Cl |
| | H | sec-Bu | H | 3-chloro-2-pyridinyl | N | Cl |
| | cyc-Bu | H | H | 3-chloro-2-pyridinyl | N | Cl |
| | H | cyc-Bu | H | 3-chloro-2-pyridinyl | N | Cl |
| | $CH_2$-cyc-Pr | H | H | 3-chloro-2-pyridinyl | N | Cl |
| | H | $CH_2$-cyc-Pr | H | 3-chloro-2-pyridinyl | N | Cl |
| | $CH_2$-cyc-Bu | H | H | 3-chloro-2-pyridinyl | N | Cl |
| | H | $CH_2$-cyc-Bu | H | 3-chloro-2-pyridinyl | N | Cl |
| | $CH_2CF_3$ | Me | H | 3-chloro-2-pyridinyl | N | Cl |
| | $CH_2CF_3$ | Et | H | 3-chloro-2-pyridinyl | N | Cl |
| | Me | $CH_2CF_3$ | H | 3-chloro-2-pyridinyl | N | Cl |
| | Et | $CH_2CF_3$ | H | 3-chloro-2-pyridinyl | N | Cl |
| | $CH_2CF_3$ | $CH_2CF_3$ | H | 3-chloro-2-pyridinyl | N | Cl |
| | $CH_2CN$ | Me | H | 3-chloro-2-pyridinyl | N | Cl |
| | $CH_2CN$ | Et | H | 3-chloro-2-pyridinyl | N | Cl |
| | Me | $CH_2CN$ | H | 3-chloro-2-pyridinyl | N | Cl |
| | Et | $CH_2CN$ | H | 3-chloro-2-pyridinyl | N | Cl |
| | $CH_2CN$ | $CH_2CN$ | H | 3-chloro-2-pyridinyl | N | Cl |
| | $CH_2CH_2OMe$ | H | H | 3-chloro-2-pyridinyl | N | Cl |
| | H | $CH_2CH_2OMe$ | H | 3-chloro-2-pyridinyl | N | Cl |
| | $CH_2CH_2OMe$ | $CH_2CH_2OMe$ | H | 3-chloro-2-pyridinyl | N | Cl |

TABLE A-continued

| No. | R² | R³ | M | R¹⁹ᵃ | X | R²⁰ᵃʸ |
|---|---|---|---|---|---|---|
| | CH₂CH₂SMe | H | H | 3-chloro-2-pyridinyl | N | Cl |
| | H | CH₂CH₂SMe | H | 3-chloro-2-pyridinyl | N | Cl |
| | Me | CO₂Me | H | 3-chloro-2-pyridinyl | N | Cl |
| | Et | CO₂Me | H | 3-chloro-2-pyridinyl | N | Cl |
| | H | 2-pyridinyl | H | 3-chloro-2-pyridinyl | N | Cl |
| | H | 3-pyridinyl | H | 3-chloro-2-pyridinyl | N | Cl |
| | H | 4-pyridinyl | H | 3-chloro-2-pyridinyl | N | Cl |
| | —(CH₂)₃— | | H | 3-chloro-2-pyridinyl | N | Cl |
| | —(CH₂)₄— | | H | 3-chloro-2-pyridinyl | N | Cl |
| | —CH₂NHCH₂— | | H | 3-chloro-2-pyridinyl | N | Cl |
| | —CH₂NMeCH₂— | | H | 3-chloro-2-pyridinyl | N | Cl |
| | —CH₂N(iso-Pr)CH₂— | | H | 3-chloro-2-pyridinyl | N | Cl |
| | —CH₂N(CHO)CH₂— | | H | 3-chloro-2-pyridinyl | N | Cl |
| | —CH₂N(Ac)CH₂— | | H | 3-chloro-2-pyridinyl | N | Cl |
| | —CH₂N(CO₂Me)CH₂— | | H | 3-chloro-2-pyridinyl | N | Cl |
| | —CH₂N(CO₂Et)CH₂— | | H | 3-chloro-2-pyridinyl | N | Cl |
| | H | H | H | 3-chloro-2-pyridinyl | N | Br |
| | Me | H | H | 3-chloro-2-pyridinyl | N | Br |
| | H | Me | H | 3-chloro-2-pyridinyl | N | Br |
| | Me | Me | H | 3-chloro-2-pyridinyl | N | Br |
| | Et | H | H | 3-chloro-2-pyridinyl | N | Br |
| | H | Et | H | 3-chloro-2-pyridinyl | N | Br |
| | Et | Et | H | 3-chloro-2-pyridinyl | N | Br |
| | n-Pr | H | H | 3-chloro-2-pyridinyl | N | Br |
| | H | n-Pr | H | 3-chloro-2-pyridinyl | N | Br |
| | iso-Pr | H | H | 3-chloro-2-pyridinyl | N | Br |
| | H | iso-Pr | H | 3-chloro-2-pyridinyl | N | Br |
| | iso-Bu | H | H | 3-chloro-2-pyridinyl | N | Br |
| | H | iso-Bu | H | 3-chloro-2-pyridinyl | N | Br |
| | tert-Bu | H | H | 3-chloro-2-pyridinyl | N | Br |
| | H | tert-Bu | H | 3-chloro-2-pyridinyl | N | Br |
| | CH₂CF₃ | H | H | 3-chloro-2-pyridinyl | N | Br |
| | H | CH₂CF₃ | H | 3-chloro-2-pyridinyl | N | Br |
| | CH₂CN | H | H | 3-chloro-2-pyridinyl | N | Br |
| | H | CH₂CN | H | 3-chloro-2-pyridinyl | N | Br |
| | CH₂OMe | H | H | 3-chloro-2-pyridinyl | N | Br |
| | H | CH₂OMe | H | 3-chloro-2-pyridinyl | N | Br |
| | CH₂CH=CH₂ | H | H | 3-chloro-2-pyridinyl | N | Br |
| | H | CH₂CH=CH₂ | H | 3-chloro-2-pyridinyl | N | Br |

TABLE A-continued

| No. | $R^2$ | $R^3$ | M | $R^{19a}$ | X | $R^{20ay}$ |
|---|---|---|---|---|---|---|
| | $CH_2CCH$ | H | H | 3-chloro-2-pyridinyl | N | Br |
| | H | $CH_2CCH$ | H | 3-chloro-2-pyridinyl | N | Br |
| | H | $CO_2Me$ | H | 3-chloro-2-pyridinyl | N | Br |
| | Me | Et | H | 3-chloro-2-pyridinyl | N | Br |
| | Et | Me | H | 3-chloro-2-pyridinyl | N | Br |
| | $CH_2CH=CH_2$ | Me | H | 3-chloro-2-pyridinyl | N | Br |
| | $CH_2CH=CH_2$ | Et | H | 3-chloro-2-pyridinyl | N | Br |
| | Me | $CH_2CH=CH_2$ | H | 3-chloro-2-pyridinyl | N | Br |
| | Et | $CH_2CH=CH_2$ | H | 3-chloro-2-pyridinyl | N | Br |
| | $CH_2CH=CH_2$ | $CH_2CH=CH_2$ | H | 3-chloro-2-pyridinyl | N | Br |
| | $CH_2CCH$ | Me | H | 3-chloro-2-pyridinyl | N | Br |
| | $CH_2CCH$ | Et | H | 3-chloro-2-pyridinyl | N | Br |
| | Me | $CH_2CCH$ | H | 3-chloro-2-pyridinyl | N | Br |
| | Et | $CH_2CCH$ | H | 3-chloro-2-pyridinyl | N | Br |
| | $CH_2CCH$ | $CH_2CCH$ | H | 3-chloro-2-pyridinyl | N | Br |
| | cyc-Pr | H | H | 3-chloro-2-pyridinyl | N | Br |
| | H | cyc-Pr | H | 3-chloro-2-pyridinyl | N | Br |
| | iso-Bu | iso-Bu | H | 3-chloro-2-pyridinyl | N | Br |
| | sec-Bu | H | H | 3-chloro-2-pyridinyl | N | Br |
| | H | sec-Bu | H | 3-chloro-2-pyridinyl | N | Br |
| | cyc-Bu | H | H | 3-chloro-2-pyridinyl | N | Br |
| | H | cyc-Bu | H | 3-chloro-2-pyridinyl | N | Br |
| | $CH_2$-cyc-Pr | H | H | 3-chloro-2-pyridinyl | N | Br |
| | H | $CH_2$-cyc-Pr | H | 3-chloro-2-pyridinyl | N | Br |
| | $CH_2$-cyc-Bu | H | H | 3-chloro-2-pyridinyl | N | Br |
| | H | $CH_2$-cyc-Bu | H | 3-chloro-2-pyridinyl | N | Br |
| | $CH_2CF_3$ | Me | H | 3-chloro-2-pyridinyl | N | Br |
| | $CH_2CF_3$ | Et | H | 3-chloro-2-pyridinyl | N | Br |
| | Me | $CH_2CF_3$ | H | 3-chloro-2-pyridinyl | N | Br |
| | Et | $CH_2CF_3$ | H | 3-chloro-2-pyridinyl | N | Br |
| | $CH_2CF_3$ | $CH_2CF_3$ | H | 3-chloro-2-pyridinyl | N | Br |
| | $CH_2CN$ | Me | H | 3-chloro-2-pyridinyl | N | Br |
| | $CH_2CN$ | Et | H | 3-chloro-2-pyridinyl | N | Br |
| | Me | $CH_2CN$ | H | 3-chloro-2-pyridinyl | N | Br |
| | Et | $CH_2CN$ | H | 3-chloro-2-pyridinyl | N | Br |
| | $CH_2CN$ | $CH_2CN$ | H | 3-chloro-2-pyridinyl | N | Br |
| | $CH_2CH_2OMe$ | H | H | 3-chloro-2-pyridinyl | N | Br |
| | H | $CH_2CH_2OMe$ | H | 3-chloro-2-pyridinyl | N | Br |
| | $CH_2CH_2OMe$ | $CH_2CH_2OMe$ | H | 3-chloro-2-pyridinyl | N | Br |

TABLE A-continued

| No. | R² | R³ | M | R^19a | X | R^20ay |
|---|---|---|---|---|---|---|
| | CH₂CH₂SMe | H | H | 3-chloro-2-pyridinyl | N | Br |
| | H | CH₂CH₂SMe | H | 3-chloro-2-pyridinyl | N | Br |
| | Me | CO₂Me | H | 3-chloro-2-pyridinyl | N | Br |
| | Et | CO₂Me | H | 3-chloro-2-pyridinyl | N | Br |
| | H | 2-pyridinyl | H | 3-chloro-2-pyridinyl | N | Br |
| | H | 3-pyridinyl | H | 3-chloro-2-pyridinyl | N | Br |
| | H | 4-pyridinyl | H | 3-chloro-2-pyridinyl | N | Br |
| | —(CH₂)₃— | | H | 3-chloro-2-pyridinyl | N | Br |
| | —(CH₂)₄— | | H | 3-chloro-2-pyridinyl | N | Br |
| | —CH₂NHCH₂— | | H | 3-chloro-2-pyridinyl | N | Br |
| | —CH₂NMeCH₂— | | H | 3-chloro-2-pyridinyl | N | Br |
| | —CH₂N(iso-Pr)CH₂— | | H | 3-chloro-2-pyridinyl | N | Br |
| | —CH₂N(CHO)CH₂— | | H | 3-chloro-2-pyridinyl | N | Br |
| | —CH₂N(Ac)CH₂— | | H | 3-chloro-2-pyridinyl | N | Br |
| | —CH₂N(CO₂Me)CH₂— | | H | 3-chloro-2-pyridinyl | N | Br |
| | —CH₂N(CO₂Et)CH₂— | | H | 3-chloro-2-pyridinyl | N | Br |
| | H | H | H | 3-chloro-2-pyridinyl | N | CF₃ |
| | Me | H | H | 3-chloro-2-pyridinyl | N | CF₃ |
| | H | Me | H | 3-chloro-2-pyridinyl | N | CF₃ |
| | Me | Me | H | 3-chloro-2-pyridinyl | N | CF₃ |
| | Et | H | H | 3-chloro-2-pyridinyl | N | CF₃ |
| | H | Et | H | 3-chloro-2-pyridinyl | N | CF₃ |
| | Et | Et | H | 3-chloro-2-pyridinyl | N | CF₃ |
| | n-Pr | H | H | 3-chloro-2-pyridinyl | N | CF₃ |
| | H | n-Pr | H | 3-chloro-2-pyridinyl | N | CF₃ |
| | iso-Pr | H | H | 3-chloro-2-pyridinyl | N | CF₃ |
| | H | iso-Pr | H | 3-chloro-2-pyridinyl | N | CF₃ |
| | iso-Bu | H | H | 3-chloro-2-pyridinyl | N | CF₃ |
| | H | iso-Bu | H | 3-chloro-2-pyridinyl | N | CF₃ |
| | tert-Bu | H | H | 3-chloro-2-pyridinyl | N | CF₃ |
| | H | tert-Bu | H | 3-chloro-2-pyridinyl | N | CF₃ |
| | CH₂CF₃ | H | H | 3-chloro-2-pyridinyl | N | CF₃ |
| | H | CH₂CF₃ | H | 3-chloro-2-pyridinyl | N | CF₃ |
| | CH₂CCH | CH₂CCH | Me | 3-chloro-2-pyridinyl | N | CF₃ |
| | cyc-Pr | H | Me | 3-chloro-2-pyridinyl | N | CF₃ |
| | H | cyc-Pr | Me | 3-chloro-2-pyridinyl | N | CF₃ |
| | iso-Bu | iso-Bu | Me | 3-chloro-2-pyridinyl | N | CF₃ |
| | sec-Bu | H | Me | 3-chloro-2-pyridinyl | N | CF₃ |
| | H | sec-Bu | Me | 3-chloro-2-pyridinyl | N | CF₃ |

TABLE A-continued

| No. | R² | R³ | M | R¹⁹ᵃ | X | R²⁰ᵃʸ |
|---|---|---|---|---|---|---|
| | cyc-Bu | H | Me | 3-chloro-2-pyridinyl | N | CF₃ |
| | H | cyc-Bu | Me | 3-chloro-2-pyridinyl | N | CF₃ |
| | CH₂cyc-Pr | H | Me | 3-chloro-2-pyridinyl | N | CF₃ |
| | H | CH₂cyc-Pr | Me | 3-chloro-2-pyridinyl | N | CF₃ |
| | CH₂cyc-Bu | H | Me | 3-chloro-2-pyridinyl | N | CF₃ |
| | H | CH₂cyc-Bu | Me | 3-chloro-2-pyridinyl | N | CF₃ |
| | CH₂CF₃ | Me | Me | 3-chloro-2-pyridinyl | N | CF₃ |
| | CH₂CF₃ | Et | Me | 3-chloro-2-pyridinyl | N | CF₃ |
| | Me | CH₂CF₃ | Me | 3-chloro-2-pyridinyl | N | CF₃ |
| | Et | CH₂CF₃ | Me | 3-chloro-2-pyridinyl | N | CF₃ |
| | CH₂CF₃ | CH₂CF₃ | Me | 3-chloro-2-pyridinyl | N | CF₃ |
| | CH₂CN | Me | Me | 3-chloro-2-pyridinyl | N | CF₃ |
| | CH₂CN | Et | Me | 3-chloro-2-pyridinyl | N | CF₃ |
| | Me | CH₂CN | Me | 3-chloro-2-pyridinyl | N | CF₃ |
| | Et | CH₂CN | Me | 3-chloro-2-pyridinyl | N | CF₃ |
| | CH₂CN | CH₂CN | Me | 3-chloro-2-pyridinyl | N | CF₃ |
| | CH₂CH₂OMe | H | Me | 3-chloro-2-pyridinyl | N | CF₃ |
| | H | CH₂CH₂OMe | Me | 3-chloro-2-pyridinyl | N | CF₃ |
| | CH₂CH₂OMe | CH₂CH₂OMe | Me | 3-chloro-2-pyridinyl | N | CF₃ |
| | CH₂CH₂SMe | H | Me | 3-chloro-2-pyridinyl | N | CF₃ |
| | H | CH₂CH₂SMe | Me | 3-chloro-2-pyridinyl | N | CF₃ |
| | Me | CO₂Me | Me | 3-chloro-2-pyridinyl | N | CF₃ |
| | Et | CO₂Me | Me | 3-chloro-2-pyridinyl | N | CF₃ |
| | H | 2-pyridinyl | Me | 3-chloro-2-pyridinyl | N | CF₃ |
| | H | 3-pyridinyl | Me | 3-chloro-2-pyridinyl | N | CF₃ |
| | H | 4-pyridinyl | Me | 3-chloro-2-pyridinyl | N | CF₃ |
| | —(CH₂)₃— | | Me | 3-chloro-2-pyridinyl | N | CF₃ |
| | —(CH₂)₄— | | Me | 3-chloro-2-pyridinyl | N | CF₃ |
| | —CH₂NHCH₂— | | Me | 3-chloro-2-pyridinyl | N | CF₃ |
| | —CH₂NMeCH₂— | | Me | 3-chloro-2-pyridinyl | N | CF₃ |
| | —CH₂N(iso-Pr)CH₂— | | Me | 3-chloro-2-pyridinyl | N | CF₃ |
| | —CH₂N(CHO)CH₂— | | Me | 3-chloro-2-pyridinyl | N | CF₃ |
| | —CH₂N(Ac)CH₂— | | Me | 3-chloro-2-pyridinyl | N | CF₃ |
| | —CH₂N(CO₂Me)CH₂— | | Me | 3-chloro-2-pyridinyl | N | CF₃ |
| | —CH₂N(CO₂Et)CH₂— | | Me | 3-chloro-2-pyridinyl | N | CF₃ |
| | H | H | OMe | 3-chloro-2-pyridinyl | N | Cl |
| | Me | H | OMe | 3-chloro-2-pyridinyl | N | Cl |
| | H | Me | OMe | 3-chloro-2-pyridinyl | N | Cl |
| | Me | Me | OMe | 3-chloro-2-pyridinyl | N | Cl |

TABLE A-continued

| No. | $R^2$ | $R^3$ | M | $R^{19a}$ | X | $R^{20ay}$ |
|---|---|---|---|---|---|---|
| | Et | H | OMe | 3-chloro-2-pyridinyl | N | Cl |
| | H | Et | OMe | 3-chloro-2-pyridinyl | N | Cl |
| | Et | Et | OMe | 3-chloro-2-pyridinyl | N | Cl |
| | n-Pr | H | OMe | 3-chloro-2-pyridinyl | N | Cl |
| | H | n-Pr | OMe | 3-chloro-2-pyridinyl | N | Cl |
| | iso-Pr | H | OMe | 3-chloro-2-pyridinyl | N | Cl |
| | H | iso-Pr | OMe | 3-chloro-2-pyridinyl | N | Cl |
| | iso-Bu | H | OMe | 3-chloro-2-pyridinyl | N | Cl |
| | H | iso-Bu | OMe | 3-chloro-2-pyridinyl | N | Cl |
| | tert-Bu | H | OMe | 3-chloro-2-pyridinyl | N | Cl |
| | H | tert-Bu | OMe | 3-chloro-2-pyridinyl | N | Cl |
| | $CH_2CF_3$ | H | OMe | 3-chloro-2-pyridinyl | N | Cl |
| | H | $CH_2CF_3$ | OMe | 3-chloro-2-pyridinyl | N | Cl |
| | $CH_2CN$ | H | OMe | 3-chloro-2-pyridinyl | N | Cl |
| | H | $CH_2CN$ | OMe | 3-chloro-2-pyridinyl | N | Cl |
| | $CH_2OMe$ | H | OMe | 3-chloro-2-pyridinyl | N | Cl |
| | H | $CH_2OMe$ | OMe | 3-chloro-2-pyridinyl | N | Cl |
| | $CH_2CH=CH_2$ | H | OMe | 3-chloro-2-pyridinyl | N | Cl |
| | H | $CH_2CH=CH_2$ | OMe | 3-chloro-2-pyridinyl | N | Cl |
| | $CH_2CCH$ | H | OMe | 3-chloro-2-pyridinyl | N | Cl |
| | H | $CH_2CCH$ | OMe | 3-chloro-2-pyridinyl | N | Cl |
| | H | $CO_2Me$ | OMe | 3-chloro-2-pyridinyl | N | Cl |
| | Me | Et | OMe | 3-chloro-2-pyridinyl | N | Cl |
| | Et | Me | OMe | 3-chloro-2-pyridinyl | N | Cl |
| | $CH_2CH=CH_2$ | Me | OMe | 3-chloro-2-pyridinyl | N | Cl |
| | $CH_2CH=CH_2$ | Et | OMe | 3-chloro-2-pyridinyl | N | Cl |
| | Me | $CH_2CH=CH_2$ | OMe | 3-chloro-2-pyridinyl | N | Cl |
| | Et | $CH_2CH=CH_2$ | OMe | 3-chloro-2-pyridinyl | N | Cl |
| | $CH_2CH=CH_2$ | $CH_2CH=CH_2$ | OMe | 3-chloro-2-pyridinyl | N | Cl |
| | $CH_2CCH$ | Me | OMe | 3-chloro-2-pyridinyl | N | Cl |
| | $CH_2CCH$ | Et | OMe | 3-chloro-2-pyridinyl | N | Cl |
| | Me | $CH_2CCH$ | OMe | 3-chloro-2-pyridinyl | N | Cl |
| | Et | $CH_2CCH$ | OMe | 3-chloro-2-pyridinyl | N | Cl |
| | $CH_2CCH$ | $CH_2CCH$ | OMe | 3-chloro-2-pyridinyl | N | Cl |
| | cyc-Pr | H | OMe | 3-chloro-2-pyridinyl | N | Cl |
| | H | cyc-Pr | OMe | 3-chloro-2-pyridinyl | N | Cl |
| | iso-Bu | iso-Bu | OMe | 3-chloro-2-pyridinyl | N | Cl |
| | sec-Bu | H | OMe | 3-chloro-2-pyridinyl | N | Cl |
| | H | sec-Bu | OMe | 3-chloro-2-pyridinyl | N | Cl |

TABLE A-continued

| No. | R² | R³ | M | R¹⁹ᵃ | X | R²⁰ᵃʸ |
|-----|-----|-----|-----|------|---|------|
| | cyc-Bu | H | OMe | 3-chloro-2-pyridinyl | N | Cl |
| | H | cyc-Bu | OMe | 3-chloro-2-pyridinyl | N | Cl |
| | CH₂cyc-Pr | H | OMe | 3-chloro-2-pyridinyl | N | Cl |
| | H | CH₂cyc-Pr | OMe | 3-chloro-2-pyridinyl | N | Cl |
| | CH₂cyc-Bu | H | OMe | 3-chloro-2-pyridinyl | N | Cl |
| | H | CH₂cyc-Bu | OMe | 3-chloro-2-pyridinyl | N | Cl |
| | CH₂CF₃ | Me | OMe | 3-chloro-2-pyridinyl | N | Cl |
| | CH₂CF₃ | Et | OMe | 3-chloro-2-pyridinyl | N | Cl |
| | Me | CH₂CF₃ | OMe | 3-chloro-2-pyridinyl | N | Cl |
| | Et | CH₂CF₃ | OMe | 3-chloro-2-pyridinyl | N | Cl |
| | CH₂CF₃ | CH₂CF₃ | OMe | 3-chloro-2-pyridinyl | N | Cl |
| | CH₂CN | Me | OMe | 3-chloro-2-pyridinyl | N | Cl |
| | CH₂CN | Et | OMe | 3-chloro-2-pyridinyl | N | Cl |
| | Me | CH₂CN | OMe | 3-chloro-2-pyridinyl | N | Cl |
| | Et | CH₂CN | OMe | 3-chloro-2-pyridinyl | N | Cl |
| | CH₂CN | CH₂CN | OMe | 3-chloro-2-pyridinyl | N | Cl |
| | CH₂CH₂OMe | H | OMe | 3-chloro-2-pyridinyl | N | Cl |
| | H | CH₂CH₂OMe | OMe | 3-chloro-2-pyridinyl | N | Cl |
| | CH₂CH₂OMe | CH₂CH₂OMe | OMe | 3-chloro-2-pyridinyl | N | Cl |
| | CH₂CH₂SMe | H | OMe | 3-chloro-2-pyridinyl | N | Cl |
| | H | CH₂CH₂SMe | OMe | 3-chloro-2-pyridinyl | N | Cl |
| | Me | CO₂Me | OMe | 3-chloro-2-pyridinyl | N | Cl |
| | Et | CO₂Me | OMe | 3-chloro-2-pyridinyl | N | Cl |
| | H | 2-pyridinyl | OMe | 3-chloro-2-pyridinyl | N | Cl |
| | H | 3-pyridinyl | OMe | 3-chloro-2-pyridinyl | N | Cl |
| | H | 4-pyridinyl | OMe | 3-chloro-2-pyridinyl | N | Cl |
| | —(CH₂)₃— | | OMe | 3-chloro-2-pyridinyl | N | Cl |
| | —(CH₂)₄— | | OMe | 3-chloro-2-pyridinyl | N | Cl |
| | —CH₂NHCH₂— | | OMe | 3-chloro-2-pyridinyl | N | Cl |
| | —CH₂NMeCH₂— | | OMe | 3-chloro-2-pyridinyl | N | Cl |
| | —CH₂N(iso-Pr)CH₂— | | OMe | 3-chloro-2-pyridinyl | N | Cl |
| | —CH₂N(CHO)CH₂— | | OMe | 3-chloro-2-pyridinyl | N | Cl |
| | —CH₂N(Ac)CH₂— | | OMe | 3-chloro-2-pyridinyl | N | Cl |
| | —CH₂N(CO₂Me)CH₂— | | OMe | 3-chloro-2-pyridinyl | N | Cl |
| | —CH₂N(CO₂Et)CH₂— | | OMe | 3-chloro-2-pyridinyl | N | Cl |
| | H | H | OMe | 3-chloro-2-pyridinyl | N | Br |
| | Me | H | OMe | 3-chloro-2-pyridinyl | N | Br |
| | H | Me | OMe | 3-chloro-2-pyridinyl | N | Br |
| | Me | Me | OMe | 3-chloro-2-pyridinyl | N | Br |

TABLE A-continued

| No. | $R^2$ | $R^3$ | M | $R^{19a}$ | X | $R^{20ay}$ |
|---|---|---|---|---|---|---|
| | Et | H | OMe | 3-chloro-2-pyridinyl | N | Br |
| | H | Et | OMe | 3-chloro-2-pyridinyl | N | Br |
| | Et | Et | OMe | 3-chloro-2-pyridinyl | N | Br |
| | n-Pr | H | OMe | 3-chloro-2-pyridinyl | N | Br |
| | H | n-Pr | OMe | 3-chloro-2-pyridinyl | N | Br |
| | iso-Pr | H | OMe | 3-chloro-2-pyridinyl | N | Br |
| | H | iso-Pr | OMe | 3-chloro-2-pyridinyl | N | Br |
| | iso-Bu | H | OMe | 3-chloro-2-pyridinyl | N | Br |
| | H | iso-Bu | OMe | 3-chloro-2-pyridinyl | N | Br |
| | tert-Bu | H | OMe | 3-chloro-2-pyridinyl | N | Br |
| | H | tert-Bu | OMe | 3-chloro-2-pyridinyl | N | Br |
| | $CH_2CF_3$ | H | OMe | 3-chloro-2-pyridinyl | N | Br |
| | H | $CH_2CF_3$ | OMe | 3-chloro-2-pyridinyl | N | Br |
| | $CH_2CN$ | H | OMe | 3-chloro-2-pyridinyl | N | Br |
| | H | $CH_2CN$ | OMe | 3-chloro-2-pyridinyl | N | Br |
| | $CH_2OMe$ | H | OMe | 3-chloro-2-pyridinyl | N | Br |
| | H | $CH_2OMe$ | OMe | 3-chloro-2-pyridinyl | N | Br |
| | $CH_2CH=CH_2$ | H | OMe | 3-chloro-2-pyridinyl | N | Br |
| | H | $CH_2CH=CH_2$ | OMe | 3-chloro-2-pyridinyl | N | Br |
| | $CH_2CCH$ | H | OMe | 3-chloro-2-pyridinyl | N | Br |
| | H | $CH_2CCH$ | OMe | 3-chloro-2-pyridinyl | N | Br |
| | H | $CO_2Me$ | OMe | 3-chloro-2-pyridinyl | N | Br |
| | Me | Et | OMe | 3-chloro-2-pyridinyl | N | Br |
| | Et | Me | OMe | 3-chloro-2-pyridinyl | N | Br |
| | $CH_2CH=CH_2$ | Me | OMe | 3-chloro-2-pyridinyl | N | Br |
| | $CH_2CH=CH_2$ | Et | OMe | 3-chloro-2-pyridinyl | N | Br |
| | Me | $CH_2CH=CH_2$ | OMe | 3-chloro-2-pyridinyl | N | Br |
| | Et | $CH_2CH=CH_2$ | OMe | 3-chloro-2-pyridinyl | N | Br |
| | $CH_2CH=CH_2$ | $CH_2CH=CH_2$ | OMe | 3-chloro-2-pyridinyl | N | Br |
| | $CH_2CCH$ | Me | OMe | 3-chloro-2-pyridinyl | N | Br |
| | $CH_2CCH$ | Et | OMe | 3-chloro-2-pyridinyl | N | Br |
| | Me | $CH_2CCH$ | OMe | 3-chloro-2-pyridinyl | N | Br |
| | Et | $CH_2CCH$ | OMe | 3-chloro-2-pyridinyl | N | Br |
| | $CH_2CCH$ | $CH_2CCH$ | OMe | 3-chloro-2-pyridinyl | N | Br |
| | cyc-Pr | H | OMe | 3-chloro-2-pyridinyl | N | Br |
| | H | cyc-Pr | OMe | 3-chloro-2-pyridinyl | N | Br |
| | iso-Bu | iso-Bu | OMe | 3-chloro-2-pyridinyl | N | Br |
| | sec-Bu | H | OMe | 3-chloro-2-pyridinyl | N | Br |
| | H | sec-Bu | OMe | 3-chloro-2-pyridinyl | N | Br |

TABLE A-continued

| No. | R² | R³ | M | R¹⁹ᵃ | X | R²⁰ᵃʸ |
|---|---|---|---|---|---|---|
| | cyc-Bu | H | OMe | 3-chloro-2-pyridinyl | N | Br |
| | H | cyc-Bu | OMe | 3-chloro-2-pyridinyl | N | Br |
| | CH₂cyc-Pr | H | OMe | 3-chloro-2-pyridinyl | N | Br |
| | H | CH₂cyc-Pr | OMe | 3-chloro-2-pyridinyl | N | Br |
| | CH₂cyc-Bu | H | OMe | 3-chloro-2-pyridinyl | N | Br |
| | H | CH₂cyc-Bu | OMe | 3-chloro-2-pyridinyl | N | Br |
| | CH₂CF₃ | Me | OMe | 3-chloro-2-pyridinyl | N | Br |
| | CH₂CF₃ | Et | OMe | 3-chloro-2-pyridinyl | N | Br |
| | Me | CH₂CF₃ | OMe | 3-chloro-2-pyridinyl | N | Br |
| | Et | CH₂CF₃ | OMe | 3-chloro-2-pyridinyl | N | Br |
| | CH₂CF₃ | CH₂CF₃ | OMe | 3-chloro-2-pyridinyl | N | Br |
| | CH₂CN | Me | OMe | 3-chloro-2-pyridinyl | N | Br |
| | CH₂CN | Et | OMe | 3-chloro-2-pyridinyl | N | Br |
| | Me | CH₂CN | OMe | 3-chloro-2-pyridinyl | N | Br |
| | Et | CH₂CN | OMe | 3-chloro-2-pyridinyl | N | Br |
| | CH₂CN | CH₂CN | OMe | 3-chloro-2-pyridinyl | N | Br |
| | CH₂CH₂OMe | H | OMe | 3-chloro-2-pyridinyl | N | Br |
| | H | CH₂CH₂OMe | OMe | 3-chloro-2-pyridinyl | N | Br |
| | CH₂CH₂OMe | CH₂CH₂OMe | OMe | 3-chloro-2-pyridinyl | N | Br |
| | CH₂CH₂SMe | H | OMe | 3-chloro-2-pyridinyl | N | Br |
| | H | CH₂CH₂SMe | OMe | 3-chloro-2-pyridinyl | N | Br |
| | Me | CO₂Me | OMe | 3-chloro-2-pyridinyl | N | Br |
| | Et | CO₂Me | OMe | 3-chloro-2-pyridinyl | N | Br |
| | H | 2-pyridinyl | OMe | 3-chloro-2-pyridinyl | N | Br |
| | H | 3-pyridinyl | OMe | 3-chloro-2-pyridinyl | N | Br |
| | H | 4-pyridinyl | OMe | 3-chloro-2-pyridinyl | N | Br |
| | —(CH₂)₃— | | OMe | 3-chloro-2-pyridinyl | N | Br |
| | —(CH₂)₄— | | OMe | 3-chloro-2-pyridinyl | N | Br |
| | —CH₂NHCH₂— | | OMe | 3-chloro-2-pyridinyl | N | Br |
| | —CH₂NMeCH₂— | | OMe | 3-chloro-2-pyridinyl | N | Br |
| | —CH₂N(iso-Pr)CH₂— | | OMe | 3-chloro-2-pyridinyl | N | Br |
| | —CH₂N(CHO)CH₂— | | OMe | 3-chloro-2-pyridinyl | N | Br |
| | —CH₂N(Ac)CH₂— | | OMe | 3-chloro-2-pyridinyl | N | Br |
| | —CH₂N(CO₂Me)CH₂— | | OMe | 3-chloro-2-pyridinyl | N | Br |
| | —CH₂N(CO₂Et)CH₂— | | OMe | 3-chloro-2-pyridinyl | N | Br |
| | H | H | OMe | 3-chloro-2-pyridinyl | N | CF₃ |
| | Me | H | OMe | 3-chloro-2-pyridinyl | N | CF₃ |
| | H | Me | OMe | 3-chloro-2-pyridinyl | N | CF₃ |
| | Me | Me | OMe | 3-chloro-2-pyridinyl | N | CF₃ |

TABLE A-continued

| No. | $R^2$ | $R^3$ | M | $R^{19a}$ | X | $R^{20ay}$ |
|---|---|---|---|---|---|---|
| | Et | H | OMe | 3-chloro-2-pyridinyl | N | $CF_3$ |
| | H | Et | OMe | 3-chloro-2-pyridinyl | N | $CF_3$ |
| | Et | Et | OMe | 3-chloro-2-pyridinyl | N | $CF_3$ |
| | n-Pr | H | OMe | 3-chloro-2-pyridinyl | N | $CF_3$ |
| | H | n-Pr | OMe | 3-chloro-2-pyridinyl | N | $CF_3$ |
| | iso-Pr | H | OMe | 3-chloro-2-pyridinyl | N | $CF_3$ |
| | H | iso-Pr | OMe | 3-chloro-2-pyridinyl | N | $CF_3$ |
| | iso-Bu | H | OMe | 3-chloro-2-pyridinyl | N | $CF_3$ |
| | H | iso-Bu | OMe | 3-chloro-2-pyridinyl | N | $CF_3$ |
| | tert-Bu | H | OMe | 3-chloro-2-pyridinyl | N | $CF_3$ |
| | H | tert-Bu | OMe | 3-chloro-2-pyridinyl | N | $CF_3$ |
| | $CH_2CF_3$ | H | OMe | 3-chloro-2-pyridinyl | N | $CF_3$ |
| | H | $CH_2CF_3$ | OMe | 3-chloro-2-pyridinyl | N | $CF_3$ |
| | $CH_2CN$ | H | OMe | 3-chloro-2-pyridinyl | N | $CF_3$ |
| | H | $CH_2CN$ | OMe | 3-chloro-2-pyridinyl | N | $CF_3$ |
| | $CH_2OMe$ | H | OMe | 3-chloro-2-pyridinyl | N | $CF_3$ |
| | H | $CH_2OMe$ | OMe | 3-chloro-2-pyridinyl | N | $CF_3$ |
| | $CH_2CH=CH_2$ | H | OMe | 3-chloro-2-pyridinyl | N | $CF_3$ |
| | H | $CH_2CH=CH_2$ | OMe | 3-chloro-2-pyridinyl | N | $CF_3$ |
| | $CH_2CCH$ | H | OMe | 3-chloro-2-pyridinyl | N | $CF_3$ |
| | H | $CH_2CCH$ | OMe | 3-chloro-2-pyridinyl | N | $CF_3$ |
| | H | $CO_2Me$ | OMe | 3-chloro-2-pyridinyl | N | $CF_3$ |
| | Me | Et | OMe | 3-chloro-2-pyridinyl | N | $CF_3$ |
| | Et | Me | OMe | 3-chloro-2-pyridinyl | N | $CF_3$ |
| | $CH_2CH=CH_2$ | Me | OMe | 3-chloro-2-pyridinyl | N | $CF_3$ |
| | $CH_2CH=CH_2$ | Et | OMe | 3-chloro-2-pyridinyl | N | $CF_3$ |
| | Me | $CH_2CH=CH_2$ | OMe | 3-chloro-2-pyridinyl | N | $CF_3$ |
| | Et | $CH_2CH=CH_2$ | OMe | 3-chloro-2-pyridinyl | N | $CF_3$ |
| | $CH_2CH=CH_2$ | $CH_2CH=CH_2$ | OMe | 3-chloro-2-pyridinyl | N | $CF_3$ |
| | $CH_2CCH$ | Me | OMe | 3-chloro-2-pyridinyl | N | $CF_3$ |
| | $CH_2CCH$ | Et | OMe | 3-chloro-2-pyridinyl | N | $CF_3$ |
| | Me | $CH_2CCH$ | OMe | 3-chloro-2-pyridinyl | N | $CF_3$ |
| | Et | $CH_2CCH$ | OMe | 3-chloro-2-pyridinyl | N | $CF_3$ |
| | $CH_2CCH$ | $CH_2CCH$ | OMe | 3-chloro-2-pyridinyl | N | $CF_3$ |
| | cyc-Pr | H | OMe | 3-chloro-2-pyridinyl | N | $CF_3$ |
| | H | cyc-Pr | OMe | 3-chloro-2-pyridinyl | N | $CF_3$ |
| | iso-Bu | iso-Bu | OMe | 3-chloro-2-pyridinyl | N | $CF_3$ |
| | sec-Bu | H | OMe | 3-chloro-2-pyridinyl | N | $CF_3$ |
| | H | sec-Bu | OMe | 3-chloro-2-pyridinyl | N | $CF_3$ |

TABLE A-continued

| No. | $R^2$ | $R^3$ | M | $R^{19a}$ | X | $R^{20ay}$ |
|---|---|---|---|---|---|---|
| | cyc-Bu | H | OMe | 3-chloro-2-pyridinyl | N | $CF_3$ |
| | H | cyc-Bu | OMe | 3-chloro-2-pyridinyl | N | $CF_3$ |
| | $CH_2$cyc-Pr | H | OMe | 3-chloro-2-pyridinyl | N | $CF_3$ |
| | H | $CH_2$cyc-Pr | OMe | 3-chloro-2-pyridinyl | N | $CF_3$ |
| | $CH_2$cyc-Bu | H | OMe | 3-chloro-2-pyridinyl | N | $CF_3$ |
| | H | $CH_2$cyc-Bu | OMe | 3-chloro-2-pyridinyl | N | $CF_3$ |
| | $CH_2CF_3$ | Me | OMe | 3-chloro-2-pyridinyl | N | $CF_3$ |
| | $CH_2CF_3$ | Et | OMe | 3-chloro-2-pyridinyl | N | $CF_3$ |
| | Me | $CH_2CF_3$ | OMe | 3-chloro-2-pyridinyl | N | $CF_3$ |
| | Et | $CH_2CF_3$ | OMe | 3-chloro-2-pyridinyl | N | $CF_3$ |
| | $CH_2CF_3$ | $CH_2CF_3$ | OMe | 3-chloro-2-pyridinyl | N | $CF_3$ |
| | $CH_2CN$ | Me | OMe | 3-chloro-2-pyridinyl | N | $CF_3$ |
| | $CH_2CN$ | Et | OMe | 3-chloro-2-pyridinyl | N | $CF_3$ |
| | Me | $CH_2CN$ | OMe | 3-chloro-2-pyridinyl | N | $CF_3$ |
| | Et | $CH_2CN$ | OMe | 3-chloro-2-pyridinyl | N | $CF_3$ |
| | $CH_2CN$ | $CH_2CN$ | OMe | 3-chloro-2-pyridinyl | N | $CF_3$ |
| | $CH_2CH_2OMe$ | H | OMe | 3-chloro-2-pyridinyl | N | $CF_3$ |
| | H | $CH_2CH_2OMe$ | OMe | 3-chloro-2-pyridinyl | N | $CF_3$ |
| | $CH_2CH_2OMe$ | $CH_2CH_2OMe$ | OMe | 3-chloro-2-pyridinyl | N | $CF_3$ |
| | $CH_2CH_2SMe$ | H | OMe | 3-chloro-2-pyridinyl | N | $CF_3$ |
| | H | $CH_2CH_2SMe$ | OMe | 3-chloro-2-pyridinyl | N | $CF_3$ |
| | Me | $CO_2Me$ | OMe | 3-chloro-2-pyridinyl | N | $CF_3$ |
| | Et | $CO_2Me$ | OMe | 3-chloro-2-pyridinyl | N | $CF_3$ |
| | H | 2-pyridinyl | OMe | 3-chloro-2-pyridinyl | N | $CF_3$ |
| | H | 3-pyridinyl | OMe | 3-chloro-2-pyridinyl | N | $CF_3$ |
| | H | 4-pyridinyl | OMe | 3-chloro-2-pyridinyl | N | $CF_3$ |
| | —$(CH_2)_3$— | | OMe | 3-chloro-2-pyridinyl | N | $CF_3$ |
| | —$(CH_2)_4$— | | OMe | 3-chloro-2-pyridinyl | N | $CF_3$ |
| | —$CH_2NHCH_2$— | | OMe | 3-chloro-2-pyridinyl | N | $CF_3$ |
| | —$CH_2NMeCH_2$— | | OMe | 3-chloro-2-pyridinyl | N | $CF_3$ |
| | —$CH_2N(iso$-$Pr)CH_2$— | | OMe | 3-chloro-2-pyridinyl | N | $CF_3$ |
| | —$CH_2N(CHO)CH_2$— | | OMe | 3-chloro-2-pyridinyl | N | $CF_3$ |
| | —$CH_2N(Ac)CH_2$— | | OMe | 3-chloro-2-pyridinyl | N | $CF_3$ |
| | —$CH_2N(CO_2Me)CH_2$— | | OMe | 3-chloro-2-pyridinyl | N | $CF_3$ |
| | —$CH_2N(CO_2Et)CH_2$— | | OMe | 3-chloro-2-pyridinyl | N | $CF_3$ |
| | H | H | OEt | 3-chloro-2-pyridinyl | N | Cl |
| | Me | H | OEt | 3-chloro-2-pyridinyl | N | Cl |
| | H | Me | OEt | 3-chloro-2-pyridinyl | N | Cl |
| | Me | Me | OEt | 3-chloro-2-pyridinyl | N | Cl |

TABLE A-continued

| No. | $R^2$ | $R^3$ | M | $R^{19a}$ | X | $R^{20ay}$ |
|---|---|---|---|---|---|---|
| | Et | H | OEt | 3-chloro-2-pyridinyl | N | Cl |
| | H | Et | OEt | 3-chloro-2-pyridinyl | N | Cl |
| | Et | Et | OEt | 3-chloro-2-pyridinyl | N | Cl |
| | n-Pr | H | OEt | 3-chloro-2-pyridinyl | N | Cl |
| | H | n-Pr | OEt | 3-chloro-2-pyridinyl | N | Cl |
| | iso-Pr | H | OEt | 3-chloro-2-pyridinyl | N | Cl |
| | H | iso-Pr | OEt | 3-chloro-2-pyridinyl | N | Cl |
| | iso-Bu | H | OEt | 3-chloro-2-pyridinyl | N | Cl |
| | H | iso-Bu | OEt | 3-chloro-2-pyridinyl | N | Cl |
| | tert-Bu | H | OEt | 3-chloro-2-pyridinyl | N | Cl |
| | H | tert-Bu | OEt | 3-chloro-2-pyridinyl | N | Cl |
| | $CH_2CF_3$ | H | OEt | 3-chloro-2-pyridinyl | N | Cl |
| | H | $CH_2CF_3$ | OEt | 3-chloro-2-pyridinyl | N | Cl |
| | $CH_2CN$ | H | OEt | 3-chloro-2-pyridinyl | N | Cl |
| | H | $CH_2CN$ | OEt | 3-chloro-2-pyridinyl | N | Cl |
| | $CH_2OMe$ | H | OEt | 3-chloro-2-pyridinyl | N | Cl |
| | H | $CH_2OMe$ | OEt | 3-chloro-2-pyridinyl | N | Cl |
| | $CH_2CH=CH_2$ | H | OEt | 3-chloro-2-pyridinyl | N | Cl |
| | H | $CH_2CH=CH_2$ | OEt | 3-chloro-2-pyridinyl | N | Cl |
| | $CH_2CCH$ | H | OEt | 3-chloro-2-pyridinyl | N | Cl |
| | H | $CH_2CCH$ | OEt | 3-chloro-2-pyridinyl | N | Cl |
| | H | $CO_2Me$ | OEt | 3-chloro-2-pyridinyl | N | Cl |
| | Me | Et | OEt | 3-chloro-2-pyridinyl | N | Cl |
| | Et | Me | OEt | 3-chloro-2-pyridinyl | N | Cl |
| | $CH_2CH=CH_2$ | Me | OEt | 3-chloro-2-pyridinyl | N | Cl |
| | $CH_2CH=CH_2$ | Et | OEt | 3-chloro-2-pyridinyl | N | Cl |
| | Me | $CH_2CH=CH_2$ | OEt | 3-chloro-2-pyridinyl | N | Cl |
| | Et | $CH_2CH=CH_2$ | OEt | 3-chloro-2-pyridinyl | N | Cl |
| | $CH_2CH=CH_2$ | $CH_2CH=CH_2$ | OEt | 3-chloro-2-pyridinyl | N | Cl |
| | $CH_2CCH$ | Me | OEt | 3-chloro-2-pyridinyl | N | Cl |
| | $CH_2CCH$ | Et | OEt | 3-chloro-2-pyridinyl | N | Cl |
| | Me | $CH_2CCH$ | OEt | 3-chloro-2-pyridinyl | N | Cl |
| | Et | $CH_2CCH$ | OEt | 3-chloro-2-pyridinyl | N | Cl |
| | $CH_2CCH$ | $CH_2CCH$ | OEt | 3-chloro-2-pyridinyl | N | Cl |
| | cyc-Pr | H | OEt | 3-chloro-2-pyridinyl | N | Cl |
| | H | cyc-Pr | OEt | 3-chloro-2-pyridinyl | N | Cl |
| | iso-Bu | iso-Bu | OEt | 3-chloro-2-pyridinyl | N | Cl |
| | sec-Bu | H | OEt | 3-chloro-2-pyridinyl | N | Cl |
| | H | sec-Bu | OEt | 3-chloro-2-pyridinyl | N | Cl |

TABLE A-continued

| No. | R² | R³ | M | R¹⁹ᵃ | X | R²⁰ᵃʸ |
|---|---|---|---|---|---|---|
| | cyc-Bu | H | OEt | 3-chloro-2-pyridinyl | N | Cl |
| | H | cyc-Bu | OEt | 3-chloro-2-pyridinyl | N | Cl |
| | CH₂cyc-Pr | H | OEt | 3-chloro-2-pyridinyl | N | Cl |
| | H | CH₂cyc-Pr | OEt | 3-chloro-2-pyridinyl | N | Cl |
| | CH₂cyc-Bu | H | OEt | 3-chloro-2-pyridinyl | N | Cl |
| | H | CH₂cyc-Bu | OEt | 3-chloro-2-pyridinyl | N | Cl |
| | CH₂CF₃ | Me | OEt | 3-chloro-2-pyridinyl | N | Cl |
| | CH₂CF₃ | Et | OEt | 3-chloro-2-pyridinyl | N | Cl |
| | Me | CH₂CF₃ | OEt | 3-chloro-2-pyridinyl | N | Cl |
| | Et | CH₂CF₃ | OEt | 3-chloro-2-pyridinyl | N | Cl |
| | CH₂CF₃ | CH₂CF₃ | OEt | 3-chloro-2-pyridinyl | N | Cl |
| | CH₂CN | Me | OEt | 3-chloro-2-pyridinyl | N | Cl |
| | CH₂CN | Et | OEt | 3-chloro-2-pyridinyl | N | Cl |
| | Me | CH₂CN | OEt | 3-chloro-2-pyridinyl | N | Cl |
| | Et | CH₂CN | OEt | 3-chloro-2-pyridinyl | N | Cl |
| | CH₂CN | CH₂CN | OEt | 3-chloro-2-pyridinyl | N | Cl |
| | CH₂CH₂OMe | H | OEt | 3-chloro-2-pyridinyl | N | Cl |
| | H | CH₂CH₂OMe | OEt | 3-chloro-2-pyridinyl | N | Cl |
| | CH₂CH₂OMe | CH₂CH₂OMe | OEt | 3-chloro-2-pyridinyl | N | Cl |
| | CH₂CH₂SMe | H | OEt | 3-chloro-2-pyridinyl | N | Cl |
| | H | CH₂CH₂SMe | OEt | 3-chloro-2-pyridinyl | N | Cl |
| | Me | CO₂Me | OEt | 3-chloro-2-pyridinyl | N | Cl |
| | Et | CO₂Me | OEt | 3-chloro-2-pyridinyl | N | Cl |
| | H | 2-pyridinyl | OEt | 3-chloro-2-pyridinyl | N | Cl |
| | H | 3-pyridinyl | OEt | 3-chloro-2-pyridinyl | N | Cl |
| | H | 4-pyridinyl | OEt | 3-chloro-2-pyridinyl | N | Cl |
| | —(CH₂)₃— | | OEt | 3-chloro-2-pyridinyl | N | Cl |
| | —(CH₂)₄— | | OEt | 3-chloro-2-pyridinyl | N | Cl |
| | —CH₂NHCH₂— | | OEt | 3-chloro-2-pyridinyl | N | Cl |
| | —CH₂NMeCH₂— | | OEt | 3-chloro-2-pyridinyl | N | Cl |
| | —CH₂N(iso-Pr)CH₂— | | OEt | 3-chloro-2-pyridinyl | N | Cl |
| | —CH₂N(CHO)CH₂— | | OEt | 3-chloro-2-pyridinyl | N | Cl |
| | —CH₂N(Ac)CH₂— | | OEt | 3-chloro-2-pyridinyl | N | Cl |
| | —CH₂N(CO₂Me)CH₂— | | OEt | 3-chloro-2-pyridinyl | N | Cl |
| | —CH₂N(CO₂Et)CH₂— | | OEt | 3-chloro-2-pyridinyl | N | Cl |
| | H | H | OEt | 3-chloro-2-pyridinyl | N | Br |
| | Me | H | OEt | 3-chloro-2-pyridinyl | N | Br |
| | H | Me | OEt | 3-chloro-2-pyridinyl | N | Br |
| | Me | Me | OEt | 3-chloro-2-pyridinyl | N | Br |

TABLE A-continued

| No. | $R^2$ | $R^3$ | M | $R^{19a}$ | X | $R^{20ay}$ |
|---|---|---|---|---|---|---|
| | Et | H | OEt | 3-chloro-2-pyridinyl | N | Br |
| | H | Et | OEt | 3-chloro-2-pyridinyl | N | Br |
| | Et | Et | OEt | 3-chloro-2-pyridinyl | N | Br |
| | n-Pr | H | OEt | 3-chloro-2-pyridinyl | N | Br |
| | H | n-Pr | OEt | 3-chloro-2-pyridinyl | N | Br |
| | iso-Pr | H | OEt | 3-chloro-2-pyridinyl | N | Br |
| | H | iso-Pr | OEt | 3-chloro-2-pyridinyl | N | Br |
| | iso-Bu | H | OEt | 3-chloro-2-pyridinyl | N | Br |
| | H | iso-Bu | OEt | 3-chloro-2-pyridinyl | N | Br |
| | tert-Bu | H | OEt | 3-chloro-2-pyridinyl | N | Br |
| | H | tert-Bu | OEt | 3-chloro-2-pyridinyl | N | Br |
| | $CH_2CF_3$ | H | OEt | 3-chloro-2-pyridinyl | N | Br |
| | H | $CH_2CF_3$ | OEt | 3-chloro-2-pyridinyl | N | Br |
| | $CH_2CN$ | H | OEt | 3-chloro-2-pyridinyl | N | Br |
| | H | $CH_2CN$ | OEt | 3-chloro-2-pyridinyl | N | Br |
| | $CH_2OMe$ | H | OEt | 3-chloro-2-pyridinyl | N | Br |
| | H | $CH_2OMe$ | OEt | 3-chloro-2-pyridinyl | N | Br |
| | $CH_2CH=CH_2$ | H | OEt | 3-chloro-2-pyridinyl | N | Br |
| | H | $CH_2CH=CH_2$ | OEt | 3-chloro-2-pyridinyl | N | Br |
| | $CH_2CCH$ | H | OEt | 3-chloro-2-pyridinyl | N | Br |
| | H | $CH_2CCH$ | OEt | 3-chloro-2-pyridinyl | N | Br |
| | H | $CO_2Me$ | OEt | 3-chloro-2-pyridinyl | N | Br |
| | Me | Et | OEt | 3-chloro-2-pyridinyl | N | Br |
| | Et | Me | OEt | 3-chloro-2-pyridinyl | N | Br |
| | $CH_2CH=CH_2$ | Me | OEt | 3-chloro-2-pyridinyl | N | Br |
| | $CH_2CH=CH_2$ | Et | OEt | 3-chloro-2-pyridinyl | N | Br |
| | Me | $CH_2CH=CH_2$ | OEt | 3-chloro-2-pyridinyl | N | Br |
| | Et | $CH_2CH=CH_2$ | OEt | 3-chloro-2-pyridinyl | N | Br |
| | $CH_2CH=CH_2$ | $CH_2CH=CH_2$ | OEt | 3-chloro-2-pyridinyl | N | Br |
| | $CH_2CCH$ | Me | OEt | 3-chloro-2-pyridinyl | N | Br |
| | $CH_2CCH$ | Et | OEt | 3-chloro-2-pyridinyl | N | Br |
| | Me | $CH_2CCH$ | OEt | 3-chloro-2-pyridinyl | N | Br |
| | Et | $CH_2CCH$ | OEt | 3-chloro-2-pyridinyl | N | Br |
| | $CH_2CCH$ | $CH_2CCH$ | OEt | 3-chloro-2-pyridinyl | N | Br |
| | cyc-Pr | H | OEt | 3-chloro-2-pyridinyl | N | Br |
| | H | cyc-Pr | OEt | 3-chloro-2-pyridinyl | N | Br |
| | iso-Bu | iso-Bu | OEt | 3-chloro-2-pyridinyl | N | Br |
| | sec-Bu | H | OEt | 3-chloro-2-pyridinyl | N | Br |
| | H | sec-Bu | OEt | 3-chloro-2-pyridinyl | N | Br |

TABLE A-continued

| No. | $R^2$ | $R^3$ | M | $R^{19a}$ | X | $R^{20ay}$ |
|---|---|---|---|---|---|---|
| | cyc-Bu | H | OEt | 3-chloro-2-pyridinyl | N | Br |
| | H | cyc-Bu | OEt | 3-chloro-2-pyridinyl | N | Br |
| | $CH_2$cyc-Pr | H | OEt | 3-chloro-2-pyridinyl | N | Br |
| | H | $CH_2$cyc-Pr | OEt | 3-chloro-2-pyridinyl | N | Br |
| | $CH_2$cyc-Bu | H | OEt | 3-chloro-2-pyridinyl | N | Br |
| | H | $CH_2$cyc-Bu | OEt | 3-chloro-2-pyridinyl | N | Br |
| | $CH_2CF_3$ | Me | OEt | 3-chloro-2-pyridinyl | N | Br |
| | $CH_2CF_3$ | Et | OEt | 3-chloro-2-pyridinyl | N | Br |
| | Me | $CH_2CF_3$ | OEt | 3-chloro-2-pyridinyl | N | Br |
| | Et | $CH_2CF_3$ | OEt | 3-chloro-2-pyridinyl | N | Br |
| | $CH_2CF_3$ | $CH_2CF_3$ | OEt | 3-chloro-2-pyridinyl | N | Br |
| | $CH_2CN$ | Me | OEt | 3-chloro-2-pyridinyl | N | Br |
| | $CH_2CN$ | Et | OEt | 3-chloro-2-pyridinyl | N | Br |
| | Me | $CH_2CN$ | OEt | 3-chloro-2-pyridinyl | N | Br |
| | Et | $CH_2CN$ | OEt | 3-chloro-2-pyridinyl | N | Br |
| | $CH_2CN$ | $CH_2CN$ | OEt | 3-chloro-2-pyridinyl | N | Br |
| | $CH_2CH_2OMe$ | H | OEt | 3-chloro-2-pyridinyl | N | Br |
| | H | $CH_2CH_2OMe$ | OEt | 3-chloro-2-pyridinyl | N | Br |
| | $CH_2CH_2OMe$ | $CH_2CH_2OMe$ | OEt | 3-chloro-2-pyridinyl | N | Br |
| | $CH_2CH_2SMe$ | H | OEt | 3-chloro-2-pyridinyl | N | Br |
| | H | $CH_2CH_2SMe$ | OEt | 3-chloro-2-pyridinyl | N | Br |
| | Me | $CO_2Me$ | OEt | 3-chloro-2-pyridinyl | N | Br |
| | Et | $CO_2Me$ | OEt | 3-chloro-2-pyridinyl | N | Br |
| | H | 2-pyridinyl | OEt | 3-chloro-2-pyridinyl | N | Br |
| | H | 3-pyridinyl | OEt | 3-chloro-2-pyridinyl | N | Br |
| | H | 4-pyridinyl | OEt | 3-chloro-2-pyridinyl | N | Br |
| | —$(CH_2)_3$— | | OEt | 3-chloro-2-pyridinyl | N | Br |
| | —$(CH_2)_4$— | | OEt | 3-chloro-2-pyridinyl | N | Br |
| | —$CH_2NHCH_2$— | | OEt | 3-chloro-2-pyridinyl | N | Br |
| | —$CH_2NMeCH_2$— | | OEt | 3-chloro-2-pyridinyl | N | Br |
| | —$CH_2N(iso\text{-}Pr)CH_2$— | | OEt | 3-chloro-2-pyridinyl | N | Br |
| | —$CH_2N(CHO)CH_2$— | | OEt | 3-chloro-2-pyridinyl | N | Br |
| | —$CH_2N(Ac)CH_2$— | | OEt | 3-chloro-2-pyridinyl | N | Br |
| | —$CH_2N(CO_2Me)CH_2$— | | OEt | 3-chloro-2-pyridinyl | N | Br |
| | —$CH_2N(CO_2Et)CH_2$— | | OEt | 3-chloro-2-pyridinyl | N | Br |
| | H | H | OEt | 3-chloro-2-pyridinyl | N | $CF_3$ |
| | Me | H | OEt | 3-chloro-2-pyridinyl | N | $CF_3$ |
| | H | Me | OEt | 3-chloro-2-pyridinyl | N | $CF_3$ |
| | Me | Me | OEt | 3-chloro-2-pyridinyl | N | $CF_3$ |

TABLE A-continued

| No. | $R^2$ | $R^3$ | M | $R^{19a}$ | X | $R^{20ay}$ |
|---|---|---|---|---|---|---|
| | Et | H | OEt | 3-chloro-2-pyridinyl | N | $CF_3$ |
| | H | Et | OEt | 3-chloro-2-pyridinyl | N | $CF_3$ |
| | Et | Et | OEt | 3-chloro-2-pyridinyl | N | $CF_3$ |
| | n-Pr | H | OEt | 3-chloro-2-pyridinyl | N | $CF_3$ |
| | H | n-Pr | OEt | 3-chloro-2-pyridinyl | N | $CF_3$ |
| | iso-Pr | H | OEt | 3-chloro-2-pyridinyl | N | $CF_3$ |
| | H | iso-Pr | OEt | 3-chloro-2-pyridinyl | N | $CF_3$ |
| | iso-Bu | H | OEt | 3-chloro-2-pyridinyl | N | $CF_3$ |
| | H | iso-Bu | OEt | 3-chloro-2-pyridinyl | N | $CF_3$ |
| | tert-Bu | H | OEt | 3-chloro-2-pyridinyl | N | $CF_3$ |
| | H | tert-Bu | OEt | 3-chloro-2-pyridinyl | N | $CF_3$ |
| | $CH_2CF_3$ | H | OEt | 3-chloro-2-pyridinyl | N | $CF_3$ |
| | H | $CH_2CF_3$ | OEt | 3-chloro-2-pyridinyl | N | $CF_3$ |
| | $CH_2CN$ | H | OEt | 3-chloro-2-pyridinyl | N | $CF_3$ |
| | H | $CH_2CN$ | OEt | 3-chloro-2-pyridinyl | N | $CF_3$ |
| | $CH_2OMe$ | H | OEt | 3-chloro-2-pyridinyl | N | $CF_3$ |
| | H | $CH_2OMe$ | OEt | 3-chloro-2-pyridinyl | N | $CF_3$ |
| | $CH_2CH=CH_2$ | H | OEt | 3-chloro-2-pyridinyl | N | $CF_3$ |
| | H | $CH_2CH=CH_2$ | OEt | 3-chloro-2-pyridinyl | N | $CF_3$ |
| | $CH_2CCH$ | H | OEt | 3-chloro-2-pyridinyl | N | $CF_3$ |
| | H | $CH_2CCH$ | OEt | 3-chloro-2-pyridinyl | N | $CF_3$ |
| | H | $CO_2Me$ | OEt | 3-chloro-2-pyridinyl | N | $CF_3$ |
| | Me | Et | OEt | 3-chloro-2-pyridinyl | N | $CF_3$ |
| | Et | Me | OEt | 3-chloro-2-pyridinyl | N | $CF_3$ |
| | $CH_2CH=CH_2$ | Me | OEt | 3-chloro-2-pyridinyl | N | $CF_3$ |
| | $CH_2CH=CH_2$ | Et | OEt | 3-chloro-2-pyridinyl | N | $CF_3$ |
| | Me | $CH_2CH=CH_2$ | OEt | 3-chloro-2-pyridinyl | N | $CF_3$ |
| | Et | $CH_2CH=CH_2$ | OEt | 3-chloro-2-pyridinyl | N | $CF_3$ |
| | $CH_2CH=CH_2$ | $CH_2CH=CH_2$ | OEt | 3-chloro-2-pyridinyl | N | $CF_3$ |
| | $CH_2CCH$ | Me | OEt | 3-chloro-2-pyridinyl | N | $CF_3$ |
| | $CH_2CCH$ | Et | OEt | 3-chloro-2-pyridinyl | N | $CF_3$ |
| | Me | $CH_2CCH$ | OEt | 3-chloro-2-pyridinyl | N | $CF_3$ |
| | Et | $CH_2CCH$ | OEt | 3-chloro-2-pyridinyl | N | $CF_3$ |
| | $CH_2CCH$ | $CH_2CCH$ | OEt | 3-chloro-2-pyridinyl | N | $CF_3$ |
| | cyc-Pr | H | OEt | 3-chloro-2-pyridinyl | N | $CF_3$ |
| | H | cyc-Pr | OEt | 3-chloro-2-pyridinyl | N | $CF_3$ |
| | iso-Bu | iso-Bu | OEt | 3-chloro-2-pyridinyl | N | $CF_3$ |
| | sec-Bu | H | OEt | 3-chloro-2-pyridinyl | N | $CF_3$ |
| | H | sec-Bu | OEt | 3-chloro-2-pyridinyl | N | $CF_3$ |

TABLE A-continued

| No. | $R^2$ | $R^3$ | M | $R^{19a}$ | X | $R^{20ay}$ |
|---|---|---|---|---|---|---|
| | cyc-Bu | H | OEt | 3-chloro-2-pyridinyl | N | $CF_3$ |
| | H | cyc-Bu | OEt | 3-chloro-2-pyridinyl | N | $CF_3$ |
| | $CH_2$cyc-Pr | H | OEt | 3-chloro-2-pyridinyl | N | $CF_3$ |
| | H | $CH_2$cyc-Pr | OEt | 3-chloro-2-pyridinyl | N | $CF_3$ |
| | $CH_2$cyc-Bu | H | OEt | 3-chloro-2-pyridinyl | N | $CF_3$ |
| | H | $CH_2$cyc-Bu | OEt | 3-chloro-2-pyridinyl | N | $CF_3$ |
| | $CH_2CF_3$ | Me | OEt | 3-chloro-2-pyridinyl | N | $CF_3$ |
| | $CH_2CF_3$ | Et | OEt | 3-chloro-2-pyridinyl | N | $CF_3$ |
| | Me | $CH_2CF_3$ | OEt | 3-chloro-2-pyridinyl | N | $CF_3$ |
| | Et | $CH_2CF_3$ | OEt | 3-chloro-2-pyridinyl | N | $CF_3$ |
| | $CH_2CF_3$ | $CH_2CF_3$ | OEt | 3-chloro-2-pyridinyl | N | $CF_3$ |
| | $CH_2CN$ | Me | OEt | 3-chloro-2-pyridinyl | N | $CF_3$ |
| | $CH_2CN$ | Et | OEt | 3-chloro-2-pyridinyl | N | $CF_3$ |
| | Me | $CH_2CN$ | OEt | 3-chloro-2-pyridinyl | N | $CF_3$ |
| | Et | $CH_2CN$ | OEt | 3-chloro-2-pyridinyl | N | $CF_3$ |
| | $CH_2CN$ | $CH_2CN$ | OEt | 3-chloro-2-pyridinyl | N | $CF_3$ |
| | $CH_2CH_2OMe$ | H | OEt | 3-chloro-2-pyridinyl | N | $CF_3$ |
| | H | $CH_2CH_2OMe$ | OEt | 3-chloro-2-pyridinyl | N | $CF_3$ |
| | $CH_2CH_2OMe$ | $CH_2CH_2OMe$ | OEt | 3-chloro-2-pyridinyl | N | $CF_3$ |
| | $CH_2CH_2SMe$ | H | OEt | 3-chloro-2-pyridinyl | N | $CF_3$ |
| | H | $CH_2CH_2SMe$ | OEt | 3-chloro-2-pyridinyl | N | $CF_3$ |
| | Me | $CO_2Me$ | OEt | 3-chloro-2-pyridinyl | N | $CF_3$ |
| | Et | $CO_2Me$ | OEt | 3-chloro-2-pyridinyl | N | $CF_3$ |
| | H | 2-pyridinyl | OEt | 3-chloro-2-pyridinyl | N | $CF_3$ |
| | H | 3-pyridinyl | OEt | 3-chloro-2-pyridinyl | N | $CF_3$ |
| | H | 4-pyridinyl | OEt | 3-chloro-2-pyridinyl | N | $CF_3$ |
| | —$(CH_2)_3$— | | OEt | 3-chloro-2-pyridinyl | N | $CF_3$ |
| | —$(CH_2)_4$— | | OEt | 3-chloro-2-pyridinyl | N | $CF_3$ |
| | —$CH_2NHCH_2$— | | OEt | 3-chloro-2-pyridinyl | N | $CF_3$ |
| | —$CH_2NMeCH_2$— | | OEt | 3-chloro-2-pyridinyl | N | $CF_3$ |
| | —$CH_2N(iso-Pr)CH_2$— | | OEt | 3-chloro-2-pyridinyl | N | $CF_3$ |
| | —$CH_2N(CHO)CH_2$— | | OEt | 3-chloro-2-pyridinyl | N | $CF_3$ |
| | —$CH_2N(Ac)CH_2$— | | OEt | 3-chloro-2-pyridinyl | N | $CF_3$ |
| | —$CH_2N(CO_2Me)CH_2$— | | OEt | 3-chloro-2-pyridinyl | N | $CF_3$ |
| | —$CH_2N(CO_2Et)CH_2$— | | OEt | 3-chloro-2-pyridinyl | N | $CF_3$ |
| | H | H | $NH_2$ | 3-chloro-2-pyridinyl | N | Cl |
| | Me | H | $NH_2$ | 3-chloro-2-pyridinyl | N | Cl |
| | H | Me | $NH_2$ | 3-chloro-2-pyridinyl | N | Cl |
| | Me | Me | $NH_2$ | 3-chloro-2-pyridinyl | N | Cl |

TABLE A-continued

| No. | $R^2$ | $R^3$ | M | $R^{19a}$ | X | $R^{20ay}$ |
|---|---|---|---|---|---|---|
| | Et | H | $NH_2$ | 3-chloro-2-pyridinyl | N | Cl |
| | H | Et | $NH_2$ | 3-chloro-2-pyridinyl | N | Cl |
| | Et | Et | $NH_2$ | 3-chloro-2-pyridinyl | N | Cl |
| | n-Pr | H | $NH_2$ | 3-chloro-2-pyridinyl | N | Cl |
| | H | n-Pr | $NH_2$ | 3-chloro-2-pyridinyl | N | Cl |
| | iso-Pr | H | $NH_2$ | 3-chloro-2-pyridinyl | N | Cl |
| | H | iso-Pr | $NH_2$ | 3-chloro-2-pyridinyl | N | Cl |
| | iso-Bu | H | $NH_2$ | 3-chloro-2-pyridinyl | N | Cl |
| | H | iso-Bu | $NH_2$ | 3-chloro-2-pyridinyl | N | Cl |
| | tert-Bu | H | $NH_2$ | 3-chloro-2-pyridinyl | N | Cl |
| | H | tert-Bu | $NH_2$ | 3-chloro-2-pyridinyl | N | Cl |
| | $CH_2CF_3$ | H | $NH_2$ | 3-chloro-2-pyridinyl | N | Cl |
| | H | $CH_2CF_3$ | $NH_2$ | 3-chloro-2-pyridinyl | N | Cl |
| | $CH_2CN$ | H | $NH_2$ | 3-chloro-2-pyridinyl | N | Cl |
| | H | $CH_2CN$ | $NH_2$ | 3-chloro-2-pyridinyl | N | Cl |
| | $CH_2OMe$ | H | $NH_2$ | 3-chloro-2-pyridinyl | N | Cl |
| | H | $CH_2OMe$ | $NH_2$ | 3-chloro-2-pyridinyl | N | Cl |
| | $CH_2CH=CH_2$ | H | $NH_2$ | 3-chloro-2-pyridinyl | N | Cl |
| | H | $CH_2CH=CH_2$ | $NH_2$ | 3-chloro-2-pyridinyl | N | Cl |
| | $CH_2CCH$ | H | $NH_2$ | 3-chloro-2-pyridinyl | N | Cl |
| | H | $CH_2CCH$ | $NH_2$ | 3-chloro-2-pyridinyl | N | Cl |
| | H | $CO_2Me$ | $NH_2$ | 3-chloro-2-pyridinyl | N | Cl |
| | Me | Et | $NH_2$ | 3-chloro-2-pyridinyl | N | Cl |
| | Et | Me | $NH_2$ | 3-chloro-2-pyridinyl | N | Cl |
| | $CH_2CH=CH_2$ | Me | $NH_2$ | 3-chloro-2-pyridinyl | N | Cl |
| | $CH_2CH=CH_2$ | Et | $NH_2$ | 3-chloro-2-pyridinyl | N | Cl |
| | Me | $CH_2CH=CH_2$ | $NH_2$ | 3-chloro-2-pyridinyl | N | Cl |
| | Et | $CH_2CH=CH_2$ | $NH_2$ | 3-chloro-2-pyridinyl | N | Cl |
| | $CH_2CH=CH_2$ | $CH_2CH=CH_2$ | $NH_2$ | 3-chloro-2-pyridinyl | N | Cl |
| | $CH_2CCH$ | Me | $NH_2$ | 3-chloro-2-pyridinyl | N | Cl |
| | $CH_2CCH$ | Et | $NH_2$ | 3-chloro-2-pyridinyl | N | Cl |
| | Me | $CH_2CCH$ | $NH_2$ | 3-chloro-2-pyridinyl | N | Cl |
| | Et | $CH_2CCH$ | $NH_2$ | 3-chloro-2-pyridinyl | N | Cl |
| | $CH_2CCH$ | $CH_2CCH$ | $NH_2$ | 3-chloro-2-pyridinyl | N | Cl |
| | cyc-Pr | H | $NH_2$ | 3-chloro-2-pyridinyl | N | Cl |
| | H | cyc-Pr | $NH_2$ | 3-chloro-2-pyridinyl | N | Cl |
| | iso-Bu | iso-Bu | $NH_2$ | 3-chloro-2-pyridinyl | N | Cl |
| | sec-Bu | H | $NH_2$ | 3-chloro-2-pyridinyl | N | Cl |
| | H | sec-Bu | $NH_2$ | 3-chloro-2-pyridinyl | N | Cl |

TABLE A-continued

| No. | R² | R³ | M | R¹⁹ᵃ | X | R²⁰ᵃʸ |
|---|---|---|---|---|---|---|
| | cyc-Bu | H | $NH_2$ | 3-chloro-2-pyridinyl | N | Cl |
| | H | cyc-Bu | $NH_2$ | 3-chloro-2-pyridinyl | N | Cl |
| | $CH_2$_cyc-Pr | H | $NH_2$ | 3-chloro-2-pyridinyl | N | Cl |
| | H | $CH_2$_cyc-Pr | $NH_2$ | 3-chloro-2-pyridinyl | N | Cl |
| | $CH_2$_cyc-Bu | H | $NH_2$ | 3-chloro-2-pyridinyl | N | Cl |
| | H | $CH_2$_cyc-Bu | $NH_2$ | 3-chloro-2-pyridinyl | N | Cl |
| | $CH_2CF_3$ | Me | $NH_2$ | 3-chloro-2-pyridinyl | N | Cl |
| | $CH_2CF_3$ | Et | $NH_2$ | 3-chloro-2-pyridinyl | N | Cl |
| | Me | $CH_2CF_3$ | $NH_2$ | 3-chloro-2-pyridinyl | N | Cl |
| | Et | $CH_2CF_3$ | $NH_2$ | 3-chloro-2-pyridinyl | N | Cl |
| | $CH_2CF_3$ | $CH_2CF_3$ | $NH_2$ | 3-chloro-2-pyridinyl | N | Cl |
| | $CH_2CN$ | Me | $NH_2$ | 3-chloro-2-pyridinyl | N | Cl |
| | $CH_2CN$ | Et | $NH_2$ | 3-chloro-2-pyridinyl | N | Cl |
| | Me | $CH_2CN$ | $NH_2$ | 3-chloro-2-pyridinyl | N | Cl |
| | Et | $CH_2CN$ | $NH_2$ | 3-chloro-2-pyridinyl | N | Cl |
| | $CH_2CN$ | $CH_2CN$ | $NH_2$ | 3-chloro-2-pyridinyl | N | Cl |
| | $CH_2CH_2OMe$ | H | $NH_2$ | 3-chloro-2-pyridinyl | N | Cl |
| | H | $CH_2CH_2OMe$ | $NH_2$ | 3-chloro-2-pyridinyl | N | Cl |
| | $CH_2CH_2OMe$ | $CH_2CH_2OMe$ | $NH_2$ | 3-chloro-2-pyridinyl | N | Cl |
| | $CH_2CH_2SMe$ | H | $NH_2$ | 3-chloro-2-pyridinyl | N | Cl |
| | H | $CH_2CH_2SMe$ | $NH_2$ | 3-chloro-2-pyridinyl | N | Cl |
| | Me | $CO_2Me$ | $NH_2$ | 3-chloro-2-pyridinyl | N | Cl |
| | Et | $CO_2Me$ | $NH_2$ | 3-chloro-2-pyridinyl | N | Cl |
| | H | 2-pyridinyl | $NH_2$ | 3-chloro-2-pyridinyl | N | Cl |
| | H | 3-pyridinyl | $NH_2$ | 3-chloro-2-pyridinyl | N | Cl |
| | H | 4-pyridinyl | $NH_2$ | 3-chloro-2-pyridinyl | N | Cl |
| | —$(CH_2)_3$— | | $NH_2$ | 3-chloro-2-pyridinyl | N | Cl |
| | —$(CH_2)_4$— | | $NH_2$ | 3-chloro-2-pyridinyl | N | Cl |
| | —$CH_2NHCH_2$— | | $NH_2$ | 3-chloro-2-pyridinyl | N | Cl |
| | —$CH_2NMeCH_2$— | | $NH_2$ | 3-chloro-2-pyridinyl | N | Cl |
| | —$CH_2N(iso\text{-}Pr)CH_2$— | | $NH_2$ | 3-chloro-2-pyridinyl | N | Cl |
| | —$CH_2N(CHO)CH_2$— | | $NH_2$ | 3-chloro-2-pyridinyl | N | Cl |
| | —$CH_2N(Ac)CH_2$— | | $NH_2$ | 3-chloro-2-pyridinyl | N | Cl |
| | —$CH_2N(CO_2Me)CH_2$— | | $NH_2$ | 3-chloro-2-pyridinyl | N | Cl |
| | —$CH_2N(CO_2Et)CH_2$— | | $NH_2$ | 3-chloro-2-pyridinyl | N | Cl |
| | H | H | $NH_2$ | 3-chloro-2-pyridinyl | N | Br |
| | Me | H | $NH_2$ | 3-chloro-2-pyridinyl | N | Br |
| | H | Me | $NH_2$ | 3-chloro-2-pyridinyl | N | Br |
| | Me | Me | $NH_2$ | 3-chloro-2-pyridinyl | N | Br |

TABLE A-continued

| No. | $R^2$ | $R^3$ | M | $R^{19a}$ | X | $R^{20ay}$ |
|---|---|---|---|---|---|---|
| | Et | H | $NH_2$ | 3-chloro-2-pyridinyl | N | Br |
| | H | Et | $NH_2$ | 3-chloro-2-pyridinyl | N | Br |
| | Et | Et | $NH_2$ | 3-chloro-2-pyridinyl | N | Br |
| | n-Pr | H | $NH_2$ | 3-chloro-2-pyridinyl | N | Br |
| | H | n-Pr | $NH_2$ | 3-chloro-2-pyridinyl | N | Br |
| | iso-Pr | H | $NH_2$ | 3-chloro-2-pyridinyl | N | Br |
| | H | iso-Pr | $NH_2$ | 3-chloro-2-pyridinyl | N | Br |
| | iso-Bu | H | $NH_2$ | 3-chloro-2-pyridinyl | N | Br |
| | H | iso-Bu | $NH_2$ | 3-chloro-2-pyridinyl | N | Br |
| | tert-Bu | H | $NH_2$ | 3-chloro-2-pyridinyl | N | Br |
| | H | tert-Bu | $NH_2$ | 3-chloro-2-pyridinyl | N | Br |
| | $CH_2CF_3$ | H | $NH_2$ | 3-chloro-2-pyridinyl | N | Br |
| | H | $CH_2CF_3$ | $NH_2$ | 3-chloro-2-pyridinyl | N | Br |
| | $CH_2CN$ | H | $NH_2$ | 3-chloro-2-pyridinyl | N | Br |
| | H | $CH_2CN$ | $NH_2$ | 3-chloro-2-pyridinyl | N | Br |
| | $CH_2OMe$ | H | $NH_2$ | 3-chloro-2-pyridinyl | N | Br |
| | H | $CH_2OMe$ | $NH_2$ | 3-chloro-2-pyridinyl | N | Br |
| | $CH_2CH=CH_2$ | H | $NH_2$ | 3-chloro-2-pyridinyl | N | Br |
| | H | $CH_2CH=CH_2$ | $NH_2$ | 3-chloro-2-pyridinyl | N | Br |
| | $CH_2CCH$ | H | $NH_2$ | 3-chloro-2-pyridinyl | N | Br |
| | H | $CH_2CCH$ | $NH_2$ | 3-chloro-2-pyridinyl | N | Br |
| | H | $CO_2Me$ | $NH_2$ | 3-chloro-2-pyridinyl | N | Br |
| | Me | Et | $NH_2$ | 3-chloro-2-pyridinyl | N | Br |
| | Et | Me | $NH_2$ | 3-chloro-2-pyridinyl | N | Br |
| | $CH_2CH=CH_2$ | Me | $NH_2$ | 3-chloro-2-pyridinyl | N | Br |
| | $CH_2CH=CH_2$ | Et | $NH_2$ | 3-chloro-2-pyridinyl | N | Br |
| | Me | $CH_2CH=CH_2$ | $NH_2$ | 3-chloro-2-pyridinyl | N | Br |
| | Et | $CH_2CH=CH_2$ | $NH_2$ | 3-chloro-2-pyridinyl | N | Br |
| | $CH_2CH=CH_2$ | $CH_2CH=CH_2$ | $NH_2$ | 3-chloro-2-pyridinyl | N | Br |
| | $CH_2CCH$ | Me | $NH_2$ | 3-chloro-2-pyridinyl | N | Br |
| | $CH_2CCH$ | Et | $NH_2$ | 3-chloro-2-pyridinyl | N | Br |
| | Me | $CH_2CCH$ | $NH_2$ | 3-chloro-2-pyridinyl | N | Br |
| | Et | $CH_2CCH$ | $NH_2$ | 3-chloro-2-pyridinyl | N | Br |
| | $CH_2CCH$ | $CH_2CCH$ | $NH_2$ | 3-chloro-2-pyridinyl | N | Br |
| | cyc-Pr | H | $NH_2$ | 3-chloro-2-pyridinyl | N | Br |
| | H | cyc-Pr | $NH_2$ | 3-chloro-2-pyridinyl | N | Br |
| | iso-Bu | iso-Bu | $NH_2$ | 3-chloro-2-pyridinyl | N | Br |
| | sec-Bu | H | $NH_2$ | 3-chloro-2-pyridinyl | N | Br |
| | H | sec-Bu | $NH_2$ | 3-chloro-2-pyridinyl | N | Br |

TABLE A-continued

| No. | $R^2$ | $R^3$ | M | $R^{19a}$ | X | $R^{20ay}$ |
|---|---|---|---|---|---|---|
| | cyc-Bu | H | $NH_2$ | 3-chloro-2-pyridinyl | N | Br |
| | H | cyc-Bu | $NH_2$ | 3-chloro-2-pyridinyl | N | Br |
| | $CH_2$cyc-Pr | H | $NH_2$ | 3-chloro-2-pyridinyl | N | Br |
| | H | $CH_2$cyc-Pr | $NH_2$ | 3-chloro-2-pyridinyl | N | Br |
| | $CH_2$cyc-Bu | H | $NH_2$ | 3-chloro-2-pyridinyl | N | Br |
| | H | $CH_2$cyc-Bu | $NH_2$ | 3-chloro-2-pyridinyl | N | Br |
| | $CH_2CF_3$ | Me | $NH_2$ | 3-chloro-2-pyridinyl | N | Br |
| | $CH_2CF_3$ | Et | $NH_2$ | 3-chloro-2-pyridinyl | N | Br |
| | Me | $CH_2CF_3$ | $NH_2$ | 3-chloro-2-pyridinyl | N | Br |
| | Et | $CH_2CF_3$ | $NH_2$ | 3-chloro-2-pyridinyl | N | Br |
| | $CH_2CF_3$ | $CH_2CF_3$ | $NH_2$ | 3-chloro-2-pyridinyl | N | Br |
| | $CH_2CN$ | Me | $NH_2$ | 3-chloro-2-pyridinyl | N | Br |
| | $CH_2CN$ | Et | $NH_2$ | 3-chloro-2-pyridinyl | N | Br |
| | Me | $CH_2CN$ | $NH_2$ | 3-chloro-2-pyridinyl | N | Br |
| | Et | $CH_2CN$ | $NH_2$ | 3-chloro-2-pyridinyl | N | Br |
| | $CH_2CN$ | $CH_2CN$ | $NH_2$ | 3-chloro-2-pyridinyl | N | Br |
| | $CH_2CH_2OMe$ | H | $NH_2$ | 3-chloro-2-pyridinyl | N | Br |
| | H | $CH_2CH_2OMe$ | $NH_2$ | 3-chloro-2-pyridinyl | N | Br |
| | $CH_2CH_2OMe$ | $CH_2CH_2OMe$ | $NH_2$ | 3-chloro-2-pyridinyl | N | Br |
| | $CH_2CH_2SMe$ | H | $NH_2$ | 3-chloro-2-pyridinyl | N | Br |
| | H | $CH_2CH_2SMe$ | $NH_2$ | 3-chloro-2-pyridinyl | N | Br |
| | Me | $CO_2Me$ | $NH_2$ | 3-chloro-2-pyridinyl | N | Br |
| | Et | $CO_2Me$ | $NH_2$ | 3-chloro-2-pyridinyl | N | Br |
| | H | 2-pyridinyl | $NH_2$ | 3-chloro-2-pyridinyl | N | Br |
| | H | 3-pyridinyl | $NH_2$ | 3-chloro-2-pyridinyl | N | Br |
| | H | 4-pyridinyl | $NH_2$ | 3-chloro-2-pyridinyl | N | Br |
| | —$(CH_2)_3$— | | $NH_2$ | 3-chloro-2-pyridinyl | N | Br |
| | —$(CH_2)_4$— | | $NH_2$ | 3-chloro-2-pyridinyl | N | Br |
| | —$CH_2NHCH_2$— | | $NH_2$ | 3-chloro-2-pyridinyl | N | Br |
| | —$CH_2NMeCH_2$— | | $NH_2$ | 3-chloro-2-pyridinyl | N | Br |
| | —$CH_2N(iso\text{-}Pr)CH_2$— | | $NH_2$ | 3-chloro-2-pyridinyl | N | Br |
| | —$CH_2N(CHO)CH_2$— | | $NH_2$ | 3-chloro-2-pyridinyl | N | Br |
| | —$CH_2N(Ac)CH_2$— | | $NH_2$ | 3-chloro-2-pyridinyl | N | Br |
| | —$CH_2N(CO_2Me)CH_2$— | | $NH_2$ | 3-chloro-2-pyridinyl | N | Br |
| | —$CH_2N(CO_2Et)CH_2$— | | $NH_2$ | 3-chloro-2-pyridinyl | N | Br |
| | H | H | $NH_2$ | 3-chloro-2-pyridinyl | N | $CF_3$ |
| | Me | H | $NH_2$ | 3-chloro-2-pyridinyl | N | $CF_3$ |
| | H | Me | $NH_2$ | 3-chloro-2-pyridinyl | N | $CF_3$ |
| | Me | Me | $NH_2$ | 3-chloro-2-pyridinyl | N | $CF_3$ |

TABLE A-continued

| No. | R² | R³ | M | R¹⁹ᵃ | X | R²⁰ᵃʸ |
|---|---|---|---|---|---|---|
| | Et | H | NH₂ | 3-chloro-2-pyridinyl | N | CF₃ |
| | H | Et | NH₂ | 3-chloro-2-pyridinyl | N | CF₃ |
| | Et | Et | NH₂ | 3-chloro-2-pyridinyl | N | CF₃ |
| | n-Pr | H | NH₂ | 3-chloro-2-pyridinyl | N | CF₃ |
| | H | n-Pr | NH₂ | 3-chloro-2-pyridinyl | N | CF₃ |
| | iso-Pr | H | NH₂ | 3-chloro-2-pyridinyl | N | CF₃ |
| | H | iso-Pr | NH₂ | 3-chloro-2-pyridinyl | N | CF₃ |
| | iso-Bu | H | NH₂ | 3-chloro-2-pyridinyl | N | CF₃ |
| | H | iso-Bu | NH₂ | 3-chloro-2-pyridinyl | N | CF₃ |
| | tert-Bu | H | NH₂ | 3-chloro-2-pyridinyl | N | CF₃ |
| | H | tert-Bu | NH₂ | 3-chloro-2-pyridinyl | N | CF₃ |
| | CH₂CF₃ | H | NH₂ | 3-chloro-2-pyridinyl | N | CF₃ |
| | H | CH₂CF₃ | NH₂ | 3-chloro-2-pyridinyl | N | CF₃ |
| | CH₂CN | H | NH₂ | 3-chloro-2-pyridinyl | N | CF₃ |
| | H | CH₂CN | NH₂ | 3-chloro-2-pyridinyl | N | CF₃ |
| | CH₂OMe | H | NH₂ | 3-chloro-2-pyridinyl | N | CF₃ |
| | H | CH₂OMe | NH₂ | 3-chloro-2-pyridinyl | N | CF₃ |
| | CH₂CH=CH₂ | H | NH₂ | 3-chloro-2-pyridinyl | N | CF₃ |
| | H | CH₂CH=CH₂ | NH₂ | 3-chloro-2-pyridinyl | N | CF₃ |
| | CH₂CCH | H | NH₂ | 3-chloro-2-pyridinyl | N | CF₃ |
| | H | CH₂CCH | NH₂ | 3-chloro-2-pyridinyl | N | CF₃ |
| | H | CO₂Me | NH₂ | 3-chloro-2-pyridinyl | N | CF₃ |
| | Me | Et | NH₂ | 3-chloro-2-pyridinyl | N | CF₃ |
| | Et | Me | NH₂ | 3-chloro-2-pyridinyl | N | CF₃ |
| | CH₂CH=CH₂ | Me | NH₂ | 3-chloro-2-pyridinyl | N | CF₃ |
| | CH₂CH=CH₂ | Et | NH₂ | 3-chloro-2-pyridinyl | N | CF₃ |
| | Me | CH₂CH=CH₂ | NH₂ | 3-chloro-2-pyridinyl | N | CF₃ |
| | Et | CH₂CH=CH₂ | NH₂ | 3-chloro-2-pyridinyl | N | CF₃ |
| | CH₂CH=CH₂ | CH₂CH=CH₂ | NH₂ | 3-chloro-2-pyridinyl | N | CF₃ |
| | CH₂CCH | Me | NH₂ | 3-chloro-2-pyridinyl | N | CF₃ |
| | CH₂CCH | Et | NH₂ | 3-chloro-2-pyridinyl | N | CF₃ |
| | Me | CH₂CCH | NH₂ | 3-chloro-2-pyridinyl | N | CF₃ |
| | Et | CH₂CCH | NH₂ | 3-chloro-2-pyridinyl | N | CF₃ |
| | CH₂CCH | CH₂CCH | NH₂ | 3-chloro-2-pyridinyl | N | CF₃ |
| | cyc-Pr | H | NH₂ | 3-chloro-2-pyridinyl | N | CF₃ |
| | H | cyc-Pr | NH₂ | 3-chloro-2-pyridinyl | N | CF₃ |
| | iso-Bu | iso-Bu | NH₂ | 3-chloro-2-pyridinyl | N | CF₃ |
| | sec-Bu | H | NH₂ | 3-chloro-2-pyridinyl | N | CF₃ |
| | H | sec-Bu | NH₂ | 3-chloro-2-pyridinyl | N | CF₃ |

TABLE A-continued

| No. | $R^2$ | $R^3$ | M | $R^{19a}$ | X | $R^{20ay}$ |
|---|---|---|---|---|---|---|
| | cyc-Bu | H | $NH_2$ | 3-chloro-2-pyridinyl | N | $CF_3$ |
| | H | cyc-Bu | $NH_2$ | 3-chloro-2-pyridinyl | N | $CF_3$ |
| | $CH_2$cyc-Pr | H | $NH_2$ | 3-chloro-2-pyridinyl | N | $CF_3$ |
| | H | $CH_2$cyc-Pr | $NH_2$ | 3-chloro-2-pyridinyl | N | $CF_3$ |
| | $CH_2$cyc-Bu | H | $NH_2$ | 3-chloro-2-pyridinyl | N | $CF_3$ |
| | H | $CH_2$cyc-Bu | $NH_2$ | 3-chloro-2-pyridinyl | N | $CF_3$ |
| | $CH_2CF_3$ | Me | $NH_2$ | 3-chloro-2-pyridinyl | N | $CF_3$ |
| | $CH_2CF_3$ | Et | $NH_2$ | 3-chloro-2-pyridinyl | N | $CF_3$ |
| | Me | $CH_2CF_3$ | $NH_2$ | 3-chloro-2-pyridinyl | N | $CF_3$ |
| | Et | $CH_2CF_3$ | $NH_2$ | 3-chloro-2-pyridinyl | N | $CF_3$ |
| | $CH_2CF_3$ | $CH_2CF_3$ | $NH_2$ | 3-chloro-2-pyridinyl | N | $CF_3$ |
| | $CH_2CN$ | Me | $NH_2$ | 3-chloro-2-pyridinyl | N | $CF_3$ |
| | $CH_2CN$ | Et | $NH_2$ | 3-chloro-2-pyridinyl | N | $CF_3$ |
| | Me | $CH_2CN$ | $NH_2$ | 3-chloro-2-pyridinyl | N | $CF_3$ |
| | Et | $CH_2CN$ | $NH_2$ | 3-chloro-2-pyridinyl | N | $CF_3$ |
| | $CH_2CN$ | $CH_2CN$ | $NH_2$ | 3-chloro-2-pyridinyl | N | $CF_3$ |
| | $CH_2CH_2OMe$ | H | $NH_2$ | 3-chloro-2-pyridinyl | N | $CF_3$ |
| | H | $CH_2CH_2OMe$ | $NH_2$ | 3-chloro-2-pyridinyl | N | $CF_3$ |
| | $CH_2CH_2OMe$ | $CH_2CH_2OMe$ | $NH_2$ | 3-chloro-2-pyridinyl | N | $CF_3$ |
| | $CH_2CH_2SMe$ | H | $NH_2$ | 3-chloro-2-pyridinyl | N | $CF_3$ |
| | H | $CH_2CH_2SMe$ | $NH_2$ | 3-chloro-2-pyridinyl | N | $CF_3$ |
| | Me | $CO_2Me$ | $NH_2$ | 3-chloro-2-pyridinyl | N | $CF_3$ |
| | Et | $CO_2Me$ | $NH_2$ | 3-chloro-2-pyridinyl | N | $CF_3$ |
| | H | 2-pyridinyl | $NH_2$ | 3-chloro-2-pyridinyl | N | $CF_3$ |
| | H | 3-pyridinyl | $NH_2$ | 3-chloro-2-pyridinyl | N | $CF_3$ |
| | H | 4-pyridinyl | $NH_2$ | 3-chloro-2-pyridinyl | N | $CF_3$ |
| | —$(CH_2)_3$— | | $NH_2$ | 3-chloro-2-pyridinyl | N | $CF_3$ |
| | —$(CH_2)_4$— | | $NH_2$ | 3-chloro-2-pyridinyl | N | $CF_3$ |
| | —$CH_2NHCH_2$— | | $NH_2$ | 3-chloro-2-pyridinyl | N | $CF_3$ |
| | —$CH_2NMeCH_2$— | | $NH_2$ | 3-chloro-2-pyridinyl | N | $CF_3$ |
| | —$CH_2N$(iso-Pr)$CH_2$— | | $NH_2$ | 3-chloro-2-pyridinyl | N | $CF_3$ |
| | —$CH_2N$(CHO)$CH_2$— | | $NH_2$ | 3-chloro-2-pyridinyl | N | $CF_3$ |
| | —$CH_2N$(Ac)$CH_2$— | | $NH_2$ | 3-chloro-2-pyridinyl | N | $CF_3$ |
| | —$CH_2N$($CO_2Me$)$CH_2$— | | $NH_2$ | 3-chloro-2-pyridinyl | N | $CF_3$ |
| | —$CH_2N$($CO_2Et$)$CH_2$— | | $NH_2$ | 3-chloro-2-pyridinyl | N | $CF_3$ |
| | H | H | NHMe | 3-chloro-2-pyridinyl | N | Cl |
| | Me | H | NHMe | 3-chloro-2-pyridinyl | N | Cl |
| | H | Me | NHMe | 3-chloro-2-pyridinyl | N | Cl |
| | Me | Me | NHMe | 3-chloro-2-pyridinyl | N | Cl |

TABLE A-continued

| No. | $R^2$ | $R^3$ | M | $R^{19a}$ | X | $R^{20ay}$ |
|---|---|---|---|---|---|---|
| | Et | H | NHMe | 3-chloro-2-pyridinyl | N | Cl |
| | H | Et | NHMe | 3-chloro-2-pyridinyl | N | Cl |
| | Et | Et | NHMe | 3-chloro-2-pyridinyl | N | Cl |
| | n-Pr | H | NHMe | 3-chloro-2-pyridinyl | N | Cl |
| | H | n-Pr | NHMe | 3-chloro-2-pyridinyl | N | Cl |
| | iso-Pr | H | NHMe | 3-chloro-2-pyridinyl | N | Cl |
| | H | iso-Pr | NHMe | 3-chloro-2-pyridinyl | N | Cl |
| | iso-Bu | H | NHMe | 3-chloro-2-pyridinyl | N | Cl |
| | H | iso-Bu | NHMe | 3-chloro-2-pyridinyl | N | Cl |
| | tert-Bu | H | NHMe | 3-chloro-2-pyridinyl | N | Cl |
| | H | tert-Bu | NHMe | 3-chloro-2-pyridinyl | N | Cl |
| | $CH_2CF_3$ | H | NHMe | 3-chloro-2-pyridinyl | N | Cl |
| | H | $CH_2CF_3$ | NHMe | 3-chloro-2-pyridinyl | N | Cl |
| | $CH_2CN$ | H | NHMe | 3-chloro-2-pyridinyl | N | Cl |
| | H | $CH_2CN$ | NHMe | 3-chloro-2-pyridinyl | N | Cl |
| | $CH_2OMe$ | H | NHMe | 3-chloro-2-pyridinyl | N | Cl |
| | H | $CH_2OMe$ | NHMe | 3-chloro-2-pyridinyl | N | Cl |
| | $CH_2CH=CH_2$ | H | NHMe | 3-chloro-2-pyridinyl | N | Cl |
| | H | $CH_2CH=CH_2$ | NHMe | 3-chloro-2-pyridinyl | N | Cl |
| | $CH_2CCH$ | H | NHMe | 3-chloro-2-pyridinyl | N | Cl |
| | H | $CH_2CCH$ | NHMe | 3-chloro-2-pyridinyl | N | Cl |
| | H | $CO_2Me$ | NHMe | 3-chloro-2-pyridinyl | N | Cl |
| | Me | Et | NHMe | 3-chloro-2-pyridinyl | N | Cl |
| | Et | Me | NHMe | 3-chloro-2-pyridinyl | N | Cl |
| | $CH_2CH=CH_2$ | Me | NHMe | 3-chloro-2-pyridinyl | N | Cl |
| | $CH_2CH=CH_2$ | Et | NHMe | 3-chloro-2-pyridinyl | N | Cl |
| | Me | $CH_2CH=CH_2$ | NHMe | 3-chloro-2-pyridinyl | N | Cl |
| | Et | $CH_2CH=CH_2$ | NHMe | 3-chloro-2-pyridinyl | N | Cl |
| | $CH_2CH=CH_2$ | $CH_2CH=CH_2$ | NHMe | 3-chloro-2-pyridinyl | N | Cl |
| | $CH_2CCH$ | Me | NHMe | 3-chloro-2-pyridinyl | N | Cl |
| | $CH_2CCH$ | Et | NHMe | 3-chloro-2-pyridinyl | N | Cl |
| | Me | $CH_2CCH$ | NHMe | 3-chloro-2-pyridinyl | N | Cl |
| | Et | $CH_2CCH$ | NHMe | 3-chloro-2-pyridinyl | N | Cl |
| | $CH_2CCH$ | $CH_2CCH$ | NHMe | 3-chloro-2-pyridinyl | N | Cl |
| | cyc-Pr | H | NHMe | 3-chloro-2-pyridinyl | N | Cl |
| | H | cyc-Pr | NHMe | 3-chloro-2-pyridinyl | N | Cl |
| | iso-Bu | iso-Bu | NHMe | 3-chloro-2-pyridinyl | N | Cl |
| | sec-Bu | H | NHMe | 3-chloro-2-pyridinyl | N | Cl |

TABLE A-continued

| No. | R² | R³ | M | R¹⁹ᵃ | X | R²⁰ᵃʸ |
|---|---|---|---|---|---|---|
| | H | sec-Bu | NHMe | 3-chloro-2-pyridinyl | N | Cl |
| | cyc-Bu | H | NHMe | 3-chloro-2-pyridinyl | N | Cl |
| | H | cyc-Bu | NHMe | 3-chloro-2-pyridinyl | N | Cl |
| | CH₂cyc-Pr | H | NHMe | 3-chloro-2-pyridinyl | N | Cl |
| | H | CH₂cyc-Pr | NHMe | 3-chloro-2-pyridinyl | N | Cl |
| | CH₂cyc-Bu | H | NHMe | 3-chloro-2-pyridinyl | N | Cl |
| | H | CH₂cyc-Bu | NHMe | 3-chloro-2-pyridinyl | N | Cl |
| | CH₂CF₃ | Me | NHMe | 3-chloro-2-pyridinyl | N | Cl |
| | CH₂CF₃ | Et | NHMe | 3-chloro-2-pyridinyl | N | Cl |
| | Me | CH₂CF₃ | NHMe | 3-chloro-2-pyridinyl | N | Cl |
| | Et | CH₂CF₃ | NHMe | 3-chloro-2-pyridinyl | N | Cl |
| | CH₂CF₃ | CH₂CF₃ | NHMe | 3-chloro-2-pyridinyl | N | Cl |
| | CH₂CN | Me | NHMe | 3-chloro-2-pyridinyl | N | Cl |
| | CH₂CN | Et | NHMe | 3-chloro-2-pyridinyl | N | Cl |
| | Me | CH₂CN | NHMe | 3-chloro-2-pyridinyl | N | Cl |
| | Et | CH₂CN | NHMe | 3-chloro-2-pyridinyl | N | Cl |
| | CH₂CN | CH₂CN | NHMe | 3-chloro-2-pyridinyl | N | Cl |
| | CH₂CH₂OMe | H | NHMe | 3-chloro-2-pyridinyl | N | Cl |
| | H | CH₂CH₂OMe | NHMe | 3-chloro-2-pyridinyl | N | Cl |
| | CH₂CH₂OMe | CH₂CH₂OMe | NHMe | 3-chloro-2-pyridinyl | N | Cl |
| | CH₂CH₂SMe | H | NHMe | 3-chloro-2-pyridinyl | N | Cl |
| | H | CH₂CH₂SMe | NHMe | 3-chloro-2-pyridinyl | N | Cl |
| | Me | CO₂Me | NHMe | 3-chloro-2-pyridinyl | N | Cl |
| | Et | CO₂Me | NHMe | 3-chloro-2-pyridinyl | N | Cl |
| | H | 2-pyridinyl | NHMe | 3-chloro-2-pyridinyl | N | Cl |
| | H | 3-pyridinyl | NHMe | 3-chloro-2-pyridinyl | N | Cl |
| | H | 4-pyridinyl | NHMe | 3-chloro-2-pyridinyl | N | Cl |
| | —(CH₂)₃— | | NHMe | 3-chloro-2-pyridinyl | N | Cl |
| | —(CH₂)₄— | | NHMe | 3-chloro-2-pyridinyl | N | Cl |
| | —CH₂NHCH₂— | | NHMe | 3-chloro-2-pyridinyl | N | Cl |
| | —CH₂NMeCH₂— | | NHMe | 3-chloro-2-pyridinyl | N | Cl |
| | —CH₂N(iso-Pr)CH₂— | | NHMe | 3-chloro-2-pyridinyl | N | Cl |
| | —CH₂N(CHO)CH₂— | | NHMe | 3-chloro-2-pyridinyl | N | Cl |
| | —CH₂N(Ac)CH₂— | | NHMe | 3-chloro-2-pyridinyl | N | Cl |
| | —CH₂N(CO₂Me)CH₂— | | NHMe | 3-chloro-2-pyridinyl | N | Cl |
| | —CH₂N(CO₂Et)CH₂— | | NHMe | 3-chloro-2-pyridinyl | N | Cl |
| | H | H | NHMe | 3-chloro-2-pyridinyl | N | Br |
| | Me | H | NHMe | 3-chloro-2-pyridinyl | N | Br |
| | H | Me | NHMe | 3-chloro-2-pyridinyl | N | Br |

TABLE A-continued

| No. | $R^2$ | $R^3$ | M | $R^{19a}$ | X | $R^{20ay}$ |
|-----|-------|-------|---|-----------|---|------------|
|  | Me | Me | NHMe | 3-chloro-2-pyridinyl | N | Br |
|  | Et | H | NHMe | 3-chloro-2-pyridinyl | N | Br |
|  | H | Et | NHMe | 3-chloro-2-pyridinyl | N | Br |
|  | Et | Et | NHMe | 3-chloro-2-pyridinyl | N | Br |
|  | n-Pr | H | NHMe | 3-chloro-2-pyridinyl | N | Br |
|  | H | n-Pr | NHMe | 3-chloro-2-pyridinyl | N | Br |
|  | iso-Pr | H | NHMe | 3-chloro-2-pyridinyl | N | Br |
|  | H | iso-Pr | NHMe | 3-chloro-2-pyridinyl | N | Br |
|  | iso-Bu | H | NHMe | 3-chloro-2-pyridinyl | N | Br |
|  | H | iso-Bu | NHMe | 3-chloro-2-pyridinyl | N | Br |
|  | tert-Bu | H | NHMe | 3-chloro-2-pyridinyl | N | Br |
|  | H | tert-Bu | NHMe | 3-chloro-2-pyridinyl | N | Br |
|  | $CH_2CF_3$ | H | NHMe | 3-chloro-2-pyridinyl | N | Br |
|  | H | $CH_2CF_3$ | NHMe | 3-chloro-2-pyridinyl | N | Br |
|  | $CH_2CN$ | H | NHMe | 3-chloro-2-pyridinyl | N | Br |
|  | H | $CH_2CN$ | NHMe | 3-chloro-2-pyridinyl | N | Br |
|  | $CH_2OMe$ | H | NHMe | 3-chloro-2-pyridinyl | N | Br |
|  | H | $CH_2OMe$ | NHMe | 3-chloro-2-pyridinyl | N | Br |
|  | $CH_2CH=CH_2$ | H | NHMe | 3-chloro-2-pyridinyl | N | Br |
|  | H | $CH_2CH=CH_2$ | NHMe | 3-chloro-2-pyridinyl | N | Br |
|  | $CH_2CCH$ | H | NHMe | 3-chloro-2-pyridinyl | N | Br |
|  | H | $CH_2CCH$ | NHMe | 3-chloro-2-pyridinyl | N | Br |
|  | H | $CO_2Me$ | NHMe | 3-chloro-2-pyridinyl | N | Br |
|  | Me | Et | NHMe | 3-chloro-2-pyridinyl | N | Br |
|  | Et | Me | NHMe | 3-chloro-2-pyridinyl | N | Br |
|  | $CH_2CH=CH_2$ | Me | NHMe | 3-chloro-2-pyridinyl | N | Br |
|  | $CH_2CH=CH_2$ | Et | NHMe | 3-chloro-2-pyridinyl | N | Br |
|  | Me | $CH_2CH=CH_2$ | NHMe | 3-chloro-2-pyridinyl | N | Br |
|  | Et | $CH_2CH=CH_2$ | NHMe | 3-chloro-2-pyridinyl | N | Br |
|  | $CH_2CH=CH_2$ | $CH_2CH=CH_2$ | NHMe | 3-chloro-2-pyridinyl | N | Br |
|  | $CH_2CCH$ | Me | NHMe | 3-chloro-2-pyridinyl | N | Br |
|  | $CH_2CCH$ | Et | NHMe | 3-chloro-2-pyridinyl | N | Br |
|  | Me | $CH_2CCH$ | NHMe | 3-chloro-2-pyridinyl | N | Br |
|  | Et | $CH_2CCH$ | NHMe | 3-chloro-2-pyridinyl | N | Br |
|  | $CH_2CCH$ | $CH_2CCH$ | NHMe | 3-chloro-2-pyridinyl | N | Br |
|  | cyc-Pr | H | NHMe | 3-chloro-2-pyridinyl | N | Br |
|  | H | cyc-Pr | NHMe | 3-chloro-2-pyridinyl | N | Br |
|  | iso-Bu | iso-Bu | NHMe | 3-chloro-2-pyridinyl | N | Br |
|  | sec-Bu | H | NHMe | 3-chloro-2-pyridinyl | N | Br |

TABLE A-continued

| No. | $R^2$ | $R^3$ | M | $R^{19a}$ | X | $R^{20ay}$ |
|---|---|---|---|---|---|---|
| | H | sec-Bu | NHMe | 3-chloro-2-pyridinyl | N | Br |
| | cyc-Bu | H | NHMe | 3-chloro-2-pyridinyl | N | Br |
| | H | cyc-Bu | NHMe | 3-chloro-2-pyridinyl | N | Br |
| | $CH_2$cyc-Pr | H | NHMe | 3-chloro-2-pyridinyl | N | Br |
| | H | $CH_2$cyc-Pr | NHMe | 3-chloro-2-pyridinyl | N | Br |
| | $CH_2$cyc-Bu | H | NHMe | 3-chloro-2-pyridinyl | N | Br |
| | H | $CH_2$cyc-Bu | NHMe | 3-chloro-2-pyridinyl | N | Br |
| | $CH_2CF_3$ | Me | NHMe | 3-chloro-2-pyridinyl | N | Br |
| | $CH_2CF_3$ | Et | NHMe | 3-chloro-2-pyridinyl | N | Br |
| | Me | $CH_2CF_3$ | NHMe | 3-chloro-2-pyridinyl | N | Br |
| | Et | $CH_2CF_3$ | NHMe | 3-chloro-2-pyridinyl | N | Br |
| | $CH_2CF_3$ | $CH_2CF_3$ | NHMe | 3-chloro-2-pyridinyl | N | Br |
| | $CH_2CN$ | Me | NHMe | 3-chloro-2-pyridinyl | N | Br |
| | $CH_2CN$ | Et | NHMe | 3-chloro-2-pyridinyl | N | Br |
| | Me | $CH_2CN$ | NHMe | 3-chloro-2-pyridinyl | N | Br |
| | Et | $CH_2CN$ | NHMe | 3-chloro-2-pyridinyl | N | Br |
| | $CH_2CN$ | $CH_2CN$ | NHMe | 3-chloro-2-pyridinyl | N | Br |
| | $CH_2CH_2OMe$ | H | NHMe | 3-chloro-2-pyridinyl | N | Br |
| | H | $CH_2CH_2OMe$ | NHMe | 3-chloro-2-pyridinyl | N | Br |
| | $CH_2CH_2OMe$ | $CH_2CH_2OMe$ | NHMe | 3-chloro-2-pyridinyl | N | Br |
| | $CH_2CH_2SMe$ | H | NHMe | 3-chloro-2-pyridinyl | N | Br |
| | H | $CH_2CH_2SMe$ | NHMe | 3-chloro-2-pyridinyl | N | Br |
| | Me | $CO_2Me$ | NHMe | 3-chloro-2-pyridinyl | N | Br |
| | Et | $CO_2Me$ | NHMe | 3-chloro-2-pyridinyl | N | Br |
| | H | 2-pyridinyl | NHMe | 3-chloro-2-pyridinyl | N | Br |
| | H | 3-pyridinyl | NHMe | 3-chloro-2-pyridinyl | N | Br |
| | H | 4-pyridinyl | NHMe | 3-chloro-2-pyridinyl | N | Br |
| | —$(CH_2)_3$— | | NHMe | 3-chloro-2-pyridinyl | N | Br |
| | —$(CH_2)_4$— | | NHMe | 3-chloro-2-pyridinyl | N | Br |
| | —$CH_2NHCH_2$— | | NHMe | 3-chloro-2-pyridinyl | N | Br |
| | —$CH_2NMeCH_2$— | | NHMe | 3-chloro-2-pyridinyl | N | Br |
| | —$CH_2N$(iso-Pr)$CH_2$— | | NHMe | 3-chloro-2-pyridinyl | N | Br |
| | —$CH_2N$(CHO)$CH_2$— | | NHMe | 3-chloro-2-pyridinyl | N | Br |
| | —$CH_2N$(Ac)$CH_2$— | | NHMe | 3-chloro-2-pyridinyl | N | Br |
| | —$CH_2N$($CO_2Me$)$CH_2$— | | NHMe | 3-chloro-2-pyridinyl | N | Br |
| | —$CH_2N$($CO_2Et$)$CH_2$— | | NHMe | 3-chloro-2-pyridinyl | N | Br |
| | H | H | NHMe | 3-chloro-2-pyridinyl | N | $CF_3$ |
| | Me | H | NHMe | 3-chloro-2-pyridinyl | N | $CF_3$ |
| | H | Me | NHMe | 3-chloro-2-pyridinyl | N | $CF_3$ |

TABLE A-continued

| No. | R² | R³ | M | R¹⁹ᵃ | X | R²⁰ᵃʸ |
|---|---|---|---|---|---|---|
| | Me | Me | NHMe | 3-chloro-2-pyridinyl | N | CF₃ |
| | Et | H | NHMe | 3-chloro-2-pyridinyl | N | CF₃ |
| | H | Et | NHMe | 3-chloro-2-pyridinyl | N | CF₃ |
| | Et | Et | NHMe | 3-chloro-2-pyridinyl | N | CF₃ |
| | n-Pr | H | NHMe | 3-chloro-2-pyridinyl | N | CF₃ |
| | H | n-Pr | NHMe | 3-chloro-2-pyridinyl | N | CF₃ |
| | iso-Pr | H | NHMe | 3-chloro-2-pyridinyl | N | CF₃ |
| | H | iso-Pr | NHMe | 3-chloro-2-pyridinyl | N | CF₃ |
| | iso-Bu | H | NHMe | 3-chloro-2-pyridinyl | N | CF₃ |
| | H | iso-Bu | NHMe | 3-chloro-2-pyridinyl | N | CF₃ |
| | tert-Bu | H | NHMe | 3-chloro-2-pyridinyl | N | CF₃ |
| | H | tert-Bu | NHMe | 3-chloro-2-pyridinyl | N | CF₃ |
| | CH₂CF₃ | H | NHMe | 3-chloro-2-pyridinyl | N | CF₃ |
| | H | CH₂CF₃ | NHMe | 3-chloro-2-pyridinyl | N | CF₃ |
| | CH₂CN | H | NHMe | 3-chloro-2-pyridinyl | N | CF₃ |
| | H | CH₂CN | NHMe | 3-chloro-2-pyridinyl | N | CF₃ |
| | CH₂OMe | H | NHMe | 3-chloro-2-pyridinyl | N | CF₃ |
| | H | CH₂OMe | NHMe | 3-chloro-2-pyridinyl | N | CF₃ |
| | CH₂CH=CH₂ | H | NHMe | 3-chloro-2-pyridinyl | N | CF₃ |
| | H | CH₂CH=CH₂ | NHMe | 3-chloro-2-pyridinyl | N | CF₃ |
| | CH₂CCH | H | NHMe | 3-chloro-2-pyridinyl | N | CF₃ |
| | H | CH₂CCH | NHMe | 3-chloro-2-pyridinyl | N | CF₃ |
| | H | CO₂Me | NHMe | 3-chloro-2-pyridinyl | N | CF₃ |
| | Me | Et | NHMe | 3-chloro-2-pyridinyl | N | CF₃ |
| | Et | Me | NHMe | 3-chloro-2-pyridinyl | N | CF₃ |
| | CH₂CH=CH₂ | Me | NHMe | 3-chloro-2-pyridinyl | N | CF₃ |
| | CH₂CH=CH₂ | Et | NHMe | 3-chloro-2-pyridinyl | N | CF₃ |
| | Me | CH₂CH=CH₂ | NHMe | 3-chloro-2-pyridinyl | N | CF₃ |
| | Et | CH₂CH=CH₂ | NHMe | 3-chloro-2-pyridinyl | N | CF₃ |
| | CH₂CH=CH₂ | CH₂CH=CH₂ | NHMe | 3-chloro-2-pyridinyl | N | CF₃ |
| | CH₂CCH | Me | NHMe | 3-chloro-2-pyridinyl | N | CF₃ |
| | CH₂CCH | Et | NHMe | 3-chloro-2-pyridinyl | N | CF₃ |
| | Me | CH₂CCH | NHMe | 3-chloro-2-pyridinyl | N | CF₃ |
| | Et | CH₂CCH | NHMe | 3-chloro-2-pyridinyl | N | CF₃ |
| | CH₂CCH | CH₂CCH | NHMe | 3-chloro-2-pyridinyl | N | CF₃ |
| | cyc-Pr | H | NHMe | 3-chloro-2-pyridinyl | N | CF₃ |
| | H | cyc-Pr | NHMe | 3-chloro-2-pyridinyl | N | CF₃ |
| | iso-Bu | iso-Bu | NHMe | 3-chloro-2-pyridinyl | N | CF₃ |
| | sec-Bu | H | NHMe | 3-chloro-2-pyridinyl | N | CF₃ |

TABLE A-continued

| No. | R² | R³ | M | R¹⁹ᵃ | X | R²⁰ᵃʸ |
|---|---|---|---|---|---|---|
| | H | sec-Bu | NHMe | 3-chloro-2-pyridinyl | N | CF₃ |
| | cyc-Bu | H | NHMe | 3-chloro-2-pyridinyl | N | CF₃ |
| | H | cyc-Bu | NHMe | 3-chloro-2-pyridinyl | N | CF₃ |
| | CH₂cyc-Pr | H | NHMe | 3-chloro-2-pyridinyl | N | CF₃ |
| | H | CH₂cyc-Pr | NHMe | 3-chloro-2-pyridinyl | N | CF₃ |
| | CH₂cyc-Bu | H | NHMe | 3-chloro-2-pyridinyl | N | CF₃ |
| | H | CH₂cyc-Bu | NHMe | 3-chloro-2-pyridinyl | N | CF₃ |
| | CH₂CF₃ | Me | NHMe | 3-chloro-2-pyridinyl | N | CF₃ |
| | CH₂CF₃ | Et | NHMe | 3-chloro-2-pyridinyl | N | CF₃ |
| | Me | CH₂CF₃ | NHMe | 3-chloro-2-pyridinyl | N | CF₃ |
| | Et | CH₂CF₃ | NHMe | 3-chloro-2-pyridinyl | N | CF₃ |
| | CH₂CF₃ | CH₂CF₃ | NHMe | 3-chloro-2-pyridinyl | N | CF₃ |
| | CH₂CN | Me | NHMe | 3-chloro-2-pyridinyl | N | CF₃ |
| | CH₂CN | Et | NHMe | 3-chloro-2-pyridinyl | N | CF₃ |
| | Me | CH₂CN | NHMe | 3-chloro-2-pyridinyl | N | CF₃ |
| | Et | CH₂CN | NHMe | 3-chloro-2-pyridinyl | N | CF₃ |
| | CH₂CN | CH₂CN | NHMe | 3-chloro-2-pyridinyl | N | CF₃ |
| | CH₂CH₂OMe | H | NHMe | 3-chloro-2-pyridinyl | N | CF₃ |
| | H | CH₂CH₂OMe | NHMe | 3-chloro-2-pyridinyl | N | CF₃ |
| | CH₂CH₂OMe | CH₂CH₂OMe | NHMe | 3-chloro-2-pyridinyl | N | CF₃ |
| | CH₂CH₂SMe | H | NHMe | 3-chloro-2-pyridinyl | N | CF₃ |
| | H | CH₂CH₂SMe | NHMe | 3-chloro-2-pyridinyl | N | CF₃ |
| | Me | CO₂Me | NHMe | 3-chloro-2-pyridinyl | N | CF₃ |
| | Et | CO₂Me | NHMe | 3-chloro-2-pyridinyl | N | CF₃ |
| | H | 2-pyridinyl | NHMe | 3-chloro-2-pyridinyl | N | CF₃ |
| | H | 3-pyridinyl | NHMe | 3-chloro-2-pyridinyl | N | CF₃ |
| | H | 4-pyridinyl | NHMe | 3-chloro-2-pyridinyl | N | CF₃ |
| | —(CH₂)₃— | | NHMe | 3-chloro-2-pyridinyl | N | CF₃ |
| | —(CH₂)₄— | | NHMe | 3-chloro-2-pyridinyl | N | CF₃ |
| | —CH₂NHCH₂— | | NHMe | 3-chloro-2-pyridinyl | N | CF₃ |
| | —CH₂NMeCH₂— | | NHMe | 3-chloro-2-pyridinyl | N | CF₃ |
| | —CH₂N(iso-Pr)CH₂— | | NHMe | 3-chloro-2-pyridinyl | N | CF₃ |
| | —CH₂N(CHO)CH₂— | | NHMe | 3-chloro-2-pyridinyl | N | CF₃ |
| | —CH₂N(Ac)CH₂— | | NHMe | 3-chloro-2-pyridinyl | N | CF₃ |
| | —CH₂N(CO₂Me)CH₂— | | NHMe | 3-chloro-2-pyridinyl | N | CF₃ |
| | —CH₂N(CO₂Et)CH₂— | | NHMe | 3-chloro-2-pyridinyl | N | CF₃ |
| | H | H | NMe₂ | 3-chloro-2-pyridinyl | N | Cl |
| | Me | H | NMe₂ | 3-chloro-2-pyridinyl | N | Cl |
| | H | Me | NMe₂ | 3-chloro-2-pyridinyl | N | Cl |

TABLE A-continued

| No. | $R^2$ | $R^3$ | M | $R^{19a}$ | X | $R^{20ay}$ |
|---|---|---|---|---|---|---|
| | Me | Me | $NMe_2$ | 3-chloro-2-pyridinyl | N | Cl |
| | Et | H | $NMe_2$ | 3-chloro-2-pyridinyl | N | Cl |
| | H | Et | $NMe_2$ | 3-chloro-2-pyridinyl | N | Cl |
| | Et | Et | $NMe_2$ | 3-chloro-2-pyridinyl | N | Cl |
| | n-Pr | H | $NMe_2$ | 3-chloro-2-pyridinyl | N | Cl |
| | H | n-Pr | $NMe_2$ | 3-chloro-2-pyridinyl | N | Cl |
| | iso-Pr | H | $NMe_2$ | 3-chloro-2-pyridinyl | N | Cl |
| | H | iso-Pr | $NMe_2$ | 3-chloro-2-pyridinyl | N | Cl |
| | iso-Bu | H | $NMe_2$ | 3-chloro-2-pyridinyl | N | Cl |
| | H | iso-Bu | $NMe_2$ | 3-chloro-2-pyridinyl | N | Cl |
| | tert-Bu | H | $NMe_2$ | 3-chloro-2-pyridinyl | N | Cl |
| | H | tert-Bu | $NMe_2$ | 3-chloro-2-pyridinyl | N | Cl |
| | $CH_2CF_3$ | H | $NMe_2$ | 3-chloro-2-pyridinyl | N | Cl |
| | H | $CH_2CF_3$ | $NMe_2$ | 3-chloro-2-pyridinyl | N | Cl |
| | $CH_2CN$ | H | $NMe_2$ | 3-chloro-2-pyridinyl | N | Cl |
| | H | $CH_2CN$ | $NMe_2$ | 3-chloro-2-pyridinyl | N | Cl |
| | $CH_2OMe$ | H | $NMe_2$ | 3-chloro-2-pyridinyl | N | Cl |
| | H | $CH_2OMe$ | $NMe_2$ | 3-chloro-2-pyridinyl | N | Cl |
| | $CH_2CH=CH_2$ | H | $NMe_2$ | 3-chloro-2-pyridinyl | N | Cl |
| | H | $CH_2CH=CH_2$ | $NMe_2$ | 3-chloro-2-pyridinyl | N | Cl |
| | $CH_2CCH$ | H | $NMe_2$ | 3-chloro-2-pyridinyl | N | Cl |
| | H | $CH_2CCH$ | $NMe_2$ | 3-chloro-2-pyridinyl | N | Cl |
| | H | $CO_2Me$ | $NMe_2$ | 3-chloro-2-pyridinyl | N | Cl |
| | Me | Et | $NMe_2$ | 3-chloro-2-pyridinyl | N | Cl |
| | Et | Me | $NMe_2$ | 3-chloro-2-pyridinyl | N | Cl |
| | $CH_2CH=CH_2$ | Me | $NMe_2$ | 3-chloro-2-pyridinyl | N | Cl |
| | $CH_2CH=CH_2$ | Et | $NMe_2$ | 3-chloro-2-pyridinyl | N | Cl |
| | Me | $CH_2CH=CH_2$ | $NMe_2$ | 3-chloro-2-pyridinyl | N | Cl |
| | Et | $CH_2CH=CH_2$ | $NMe_2$ | 3-chloro-2-pyridinyl | N | Cl |
| | $CH_2CH=CH_2$ | $CH_2CH=CH_2$ | $NMe_2$ | 3-chloro-2-pyridinyl | N | Cl |
| | $CH_2CCH$ | Me | $NMe_2$ | 3-chloro-2-pyridinyl | N | Cl |
| | $CH_2CCH$ | Et | $NMe_2$ | 3-chloro-2-pyridinyl | N | Cl |
| | Me | $CH_2CCH$ | $NMe_2$ | 3-chloro-2-pyridinyl | N | Cl |
| | Et | $CH_2CCH$ | $NMe_2$ | 3-chloro-2-pyridinyl | N | Cl |
| | $CH_2CCH$ | $CH_2CCH$ | $NMe_2$ | 3-chloro-2-pyridinyl | N | Cl |
| | cyc-Pr | H | $NMe_2$ | 3-chloro-2-pyridinyl | N | Cl |
| | H | cyc-Pr | $NMe_2$ | 3-chloro-2-pyridinyl | N | Cl |
| | iso-Bu | iso-Bu | $NMe_2$ | 3-chloro-2-pyridinyl | N | Cl |
| | sec-Bu | H | $NMe_2$ | 3-chloro-2-pyridinyl | N | Cl |

TABLE A-continued

| No. | R² | R³ | M | R¹⁹ᵃ | X | R²⁰ᵃʸ |
|---|---|---|---|---|---|---|
| | H | sec-Bu | NMe₂ | 3-chloro-2-pyridinyl | N | Cl |
| | cyc-Bu | H | NMe₂ | 3-chloro-2-pyridinyl | N | Cl |
| | H | cyc-Bu | NMe₂ | 3-chloro-2-pyridinyl | N | Cl |
| | CH₂ cyc-Pr | H | NMe₂ | 3-chloro-2-pyridinyl | N | Cl |
| | H | CH₂ cyc-Pr | NMe₂ | 3-chloro-2-pyridinyl | N | Cl |
| | CH₂ cyc-Bu | H | NMe₂ | 3-chloro-2-pyridinyl | N | Cl |
| | H | CH₂ cyc-Bu | NMe₂ | 3-chloro-2-pyridinyl | N | Cl |
| | CH₂CF₃ | Me | NMe₂ | 3-chloro-2-pyridinyl | N | Cl |
| | CH₂CF₃ | Et | NMe₂ | 3-chloro-2-pyridinyl | N | Cl |
| | Me | CH₂CF₃ | NMe₂ | 3-chloro-2-pyridinyl | N | Cl |
| | Et | CH₂CF₃ | NMe₂ | 3-chloro-2-pyridinyl | N | Cl |
| | CH₂CF₃ | CH₂CF₃ | NMe₂ | 3-chloro-2-pyridinyl | N | Cl |
| | CH₂CN | Me | NMe₂ | 3-chloro-2-pyridinyl | N | Cl |
| | CH₂CN | Et | NMe₂ | 3-chloro-2-pyridinyl | N | Cl |
| | Me | CH₂CN | NMe₂ | 3-chloro-2-pyridinyl | N | Cl |
| | Et | CH₂CN | NMe₂ | 3-chloro-2-pyridinyl | N | Cl |
| | CH₂CN | CH₂CN | NMe₂ | 3-chloro-2-pyridinyl | N | Cl |
| | CH₂CH₂OMe | H | NMe₂ | 3-chloro-2-pyridinyl | N | Cl |
| | H | CH₂CH₂OMe | NMe₂ | 3-chloro-2-pyridinyl | N | Cl |
| | CH₂CH₂OMe | CH₂CH₂OMe | NMe₂ | 3-chloro-2-pyridinyl | N | Cl |
| | CH₂CH₂SMe | H | NMe₂ | 3-chloro-2-pyridinyl | N | Cl |
| | H | CH₂CH₂SMe | NMe₂ | 3-chloro-2-pyridinyl | N | Cl |
| | Me | CO₂Me | NMe₂ | 3-chloro-2-pyridinyl | N | Cl |
| | Et | CO₂Me | NMe₂ | 3-chloro-2-pyridinyl | N | Cl |
| | H | 2-pyridinyl | NMe₂ | 3-chloro-2-pyridinyl | N | Cl |
| | H | 3-pyridinyl | NMe₂ | 3-chloro-2-pyridinyl | N | Cl |
| | H | 4-pyridinyl | NMe₂ | 3-chloro-2-pyridinyl | N | Cl |
| | —(CH₂)₃— | | NMe₂ | 3-chloro-2-pyridinyl | N | Cl |
| | —(CH₂)₄— | | NMe₂ | 3-chloro-2-pyridinyl | N | Cl |
| | —CH₂NHCH₂— | | NMe₂ | 3-chloro-2-pyridinyl | N | Cl |
| | —CH₂NMeCH₂— | | NMe₂ | 3-chloro-2-pyridinyl | N | Cl |
| | —CH₂N(iso-Pr)CH₂— | | NMe₂ | 3-chloro-2-pyridinyl | N | Cl |
| | —CH₂N(CHO)CH₂— | | NMe₂ | 3-chloro-2-pyridinyl | N | Cl |
| | —CH₂N(Ac)CH₂— | | NMe₂ | 3-chloro-2-pyridinyl | N | Cl |
| | —CH₂N(CO₂Me)CH₂— | | NMe₂ | 3-chloro-2-pyridinyl | N | Cl |
| | —CH₂N(CO₂Et)CH₂— | | NMe₂ | 3-chloro-2-pyridinyl | N | Cl |
| | H | H | NMe₂ | 3-chloro-2-pyridinyl | N | Br |
| | Me | H | NMe₂ | 3-chloro-2-pyridinyl | N | Br |
| | H | Me | NMe₂ | 3-chloro-2-pyridinyl | N | Br |

TABLE A-continued

| No. | $R^2$ | $R^3$ | M | $R^{19a}$ | X | $R^{20ay}$ |
|---|---|---|---|---|---|---|
| | Me | Me | $NMe_2$ | 3-chloro-2-pyridinyl | N | Br |
| | Et | H | $NMe_2$ | 3-chloro-2-pyridinyl | N | Br |
| | H | Et | $NMe_2$ | 3-chloro-2-pyridinyl | N | Br |
| | Et | Et | $NMe_2$ | 3-chloro-2-pyridinyl | N | Br |
| | n-Pr | H | $NMe_2$ | 3-chloro-2-pyridinyl | N | Br |
| | H | n-Pr | $NMe_2$ | 3-chloro-2-pyridinyl | N | Br |
| | iso-Pr | H | $NMe_2$ | 3-chloro-2-pyridinyl | N | Br |
| | H | iso-Pr | $NMe_2$ | 3-chloro-2-pyridinyl | N | Br |
| | iso-Bu | H | $NMe_2$ | 3-chloro-2-pyridinyl | N | Br |
| | H | iso-Bu | $NMe_2$ | 3-chloro-2-pyridinyl | N | Br |
| | tert-Bu | H | $NMe_2$ | 3-chloro-2-pyridinyl | N | Br |
| | H | tert-Bu | $NMe_2$ | 3-chloro-2-pyridinyl | N | Br |
| | $CH_2CF_3$ | H | $NMe_2$ | 3-chloro-2-pyridinyl | N | Br |
| | H | $CH_2CF_3$ | $NMe_2$ | 3-chloro-2-pyridinyl | N | Br |
| | $CH_2CN$ | H | $NMe_2$ | 3-chloro-2-pyridinyl | N | Br |
| | H | $CH_2CN$ | $NMe_2$ | 3-chloro-2-pyridinyl | N | Br |
| | $CH_2OMe$ | H | $NMe_2$ | 3-chloro-2-pyridinyl | N | Br |
| | H | $CH_2OMe$ | $NMe_2$ | 3-chloro-2-pyridinyl | N | Br |
| | $CH_2CH=CH_2$ | H | $NMe_2$ | 3-chloro-2-pyridinyl | N | Br |
| | H | $CH_2CH=CH_2$ | $NMe_2$ | 3-chloro-2-pyridinyl | N | Br |
| | $CH_2CCH$ | H | $NMe_2$ | 3-chloro-2-pyridinyl | N | Br |
| | H | $CH_2CCH$ | $NMe_2$ | 3-chloro-2-pyridinyl | N | Br |
| | H | $CO_2Me$ | $NMe_2$ | 3-chloro-2-pyridinyl | N | Br |
| | Me | Et | $NMe_2$ | 3-chloro-2-pyridinyl | N | Br |
| | Et | Me | $NMe_2$ | 3-chloro-2-pyridinyl | N | Br |
| | $CH_2CH=CH_2$ | Me | $NMe_2$ | 3-chloro-2-pyridinyl | N | Br |
| | $CH_2CH=CH_2$ | Et | $NMe_2$ | 3-chloro-2-pyridinyl | N | Br |
| | Me | $CH_2CH=CH_2$ | $NMe_2$ | 3-chloro-2-pyridinyl | N | Br |
| | Et | $CH_2CH=CH_2$ | $NMe_2$ | 3-chloro-2-pyridinyl | N | Br |
| | $CH_2CH=CH_2$ | $CH_2CH=CH_2$ | $NMe_2$ | 3-chloro-2-pyridinyl | N | Br |
| | $CH_2CCH$ | Me | $NMe_2$ | 3-chloro-2-pyridinyl | N | Br |
| | $CH_2CCH$ | Et | $NMe_2$ | 3-chloro-2-pyridinyl | N | Br |
| | Me | $CH_2CCH$ | $NMe_2$ | 3-chloro-2-pyridinyl | N | Br |
| | Et | $CH_2CCH$ | $NMe_2$ | 3-chloro-2-pyridinyl | N | Br |
| | $CH_2CCH$ | $CH_2CCH$ | $NMe_2$ | 3-chloro-2-pyridinyl | N | Br |
| | cyc-Pr | H | $NMe_2$ | 3-chloro-2-pyridinyl | N | Br |
| | H | cyc-Pr | $NMe_2$ | 3-chloro-2-pyridinyl | N | Br |
| | iso-Bu | iso-Bu | $NMe_2$ | 3-chloro-2-pyridinyl | N | Br |
| | sec-Bu | H | $NMe_2$ | 3-chloro-2-pyridinyl | N | Br |

TABLE A-continued

| No. | R² | R³ | M | R¹⁹ᵃ | X | R²⁰ᵃʸ |
|---|---|---|---|---|---|---|
| | H | sec-Bu | NMe₂ | 3-chloro-2-pyridinyl | N | Br |
| | cyc-Bu | H | NMe₂ | 3-chloro-2-pyridinyl | N | Br |
| | H | cyc-Bu | NMe₂ | 3-chloro-2-pyridinyl | N | Br |
| | CH₂cyc-Pr | H | NMe₂ | 3-chloro-2-pyridinyl | N | Br |
| | H | CH₂cyc-Pr | NMe₂ | 3-chloro-2-pyridinyl | N | Br |
| | CH₂cyc-Bu | H | NMe₂ | 3-chloro-2-pyridinyl | N | Br |
| | H | CH₂cyc-Bu | NMe₂ | 3-chloro-2-pyridinyl | N | Br |
| | CH₂CF₃ | Me | NMe₂ | 3-chloro-2-pyridinyl | N | Br |
| | CH₂CF₃ | Et | NMe₂ | 3-chloro-2-pyridinyl | N | Br |
| | Me | CH₂CF₃ | NMe₂ | 3-chloro-2-pyridinyl | N | Br |
| | Et | CH₂CF₃ | NMe₂ | 3-chloro-2-pyridinyl | N | Br |
| | CH₂CF₃ | CH₂CF₃ | NMe₂ | 3-chloro-2-pyridinyl | N | Br |
| | CH₂CN | Me | NMe₂ | 3-chloro-2-pyridinyl | N | Br |
| | CH₂CN | Et | NMe₂ | 3-chloro-2-pyridinyl | N | Br |
| | Me | CH₂CN | NMe₂ | 3-chloro-2-pyridinyl | N | Br |
| | Et | CH₂CN | NMe₂ | 3-chloro-2-pyridinyl | N | Br |
| | CH₂CN | CH₂CN | NMe₂ | 3-chloro-2-pyridinyl | N | Br |
| | CH₂CH₂OMe | H | NMe₂ | 3-chloro-2-pyridinyl | N | Br |
| | H | CH₂CH₂OMe | NMe₂ | 3-chloro-2-pyridinyl | N | Br |
| | CH₂CH₂OMe | CH₂CH₂OMe | NMe₂ | 3-chloro-2-pyridinyl | N | Br |
| | CH₂CH₂SMe | H | NMe₂ | 3-chloro-2-pyridinyl | N | Br |
| | H | CH₂CH₂SMe | NMe₂ | 3-chloro-2-pyridinyl | N | Br |
| | Me | CO₂Me | NMe₂ | 3-chloro-2-pyridinyl | N | Br |
| | Et | CO₂Me | NMe₂ | 3-chloro-2-pyridinyl | N | Br |
| | H | 2-pyridinyl | NMe₂ | 3-chloro-2-pyridinyl | N | Br |
| | H | 3-pyridinyl | NMe₂ | 3-chloro-2-pyridinyl | N | Br |
| | H | 4-pyridinyl | NMe₂ | 3-chloro-2-pyridinyl | N | Br |
| | —(CH₂)₃— | | NMe₂ | 3-chloro-2-pyridinyl | N | Br |
| | —(CH₂)₄— | | NMe₂ | 3-chloro-2-pyridinyl | N | Br |
| | —CH₂NHCH₂— | | NMe₂ | 3-chloro-2-pyridinyl | N | Br |
| | —CH₂NMeCH₂— | | NMe₂ | 3-chloro-2-pyridinyl | N | Br |
| | —CH₂N(iso-Pr)CH₂— | | NMe₂ | 3-chloro-2-pyridinyl | N | Br |
| | —CH₂N(CHO)CH₂— | | NMe₂ | 3-chloro-2-pyridinyl | N | Br |
| | —CH₂N(Ac)CH₂— | | NMe₂ | 3-chloro-2-pyridinyl | N | Br |
| | —CH₂N(CO₂Me)CH₂— | | NMe₂ | 3-chloro-2-pyridinyl | N | Br |
| | —CH₂N(CO₂Et)CH₂— | | NMe₂ | 3-chloro-2-pyridinyl | N | Br |
| | H | H | NMe₂ | 3-chloro-2-pyridinyl | N | CF₃ |
| | Me | H | NMe₂ | 3-chloro-2-pyridinyl | N | CF₃ |
| | H | Me | NMe₂ | 3-chloro-2-pyridinyl | N | CF₃ |

TABLE A-continued

| No. | $R^2$ | $R^3$ | M | $R^{19a}$ | X | $R^{20ay}$ |
|---|---|---|---|---|---|---|
| | Me | Me | $NMe_2$ | 3-chloro-2-pyridinyl | N | $CF_3$ |
| | Et | H | $NMe_2$ | 3-chloro-2-pyridinyl | N | $CF_3$ |
| | H | Et | $NMe_2$ | 3-chloro-2-pyridinyl | N | $CF_3$ |
| | Et | Et | $NMe_2$ | 3-chloro-2-pyridinyl | N | $CF_3$ |
| | n-Pr | H | $NMe_2$ | 3-chloro-2-pyridinyl | N | $CF_3$ |
| | H | n-Pr | $NMe_2$ | 3-chloro-2-pyridinyl | N | $CF_3$ |
| | iso-Pr | H | $NMe_2$ | 3-chloro-2-pyridinyl | N | $CF_3$ |
| | H | iso-Pr | $NMe_2$ | 3-chloro-2-pyridinyl | N | $CF_3$ |
| | iso-Bu | H | $NMe_2$ | 3-chloro-2-pyridinyl | N | $CF_3$ |
| | H | iso-Bu | $NMe_2$ | 3-chloro-2-pyridinyl | N | $CF_3$ |
| | tert-Bu | H | $NMe_2$ | 3-chloro-2-pyridinyl | N | $CF_3$ |
| | H | tert-Bu | $NMe_2$ | 3-chloro-2-pyridinyl | N | $CF_3$ |
| | $CH_2CF_3$ | H | $NMe_2$ | 3-chloro-2-pyridinyl | N | $CF_3$ |
| | H | $CH_2CF_3$ | $NMe_2$ | 3-chloro-2-pyridinyl | N | $CF_3$ |
| | $CH_2CN$ | H | $NMe_2$ | 3-chloro-2-pyridinyl | N | $CF_3$ |
| | H | $CH_2CN$ | $NMe_2$ | 3-chloro-2-pyridinyl | N | $CF_3$ |
| | $CH_2OMe$ | H | $NMe_2$ | 3-chloro-2-pyridinyl | N | $CF_3$ |
| | H | $CH_2OMe$ | $NMe_2$ | 3-chloro-2-pyridinyl | N | $CF_3$ |
| | $CH_2CH=CH_2$ | H | $NMe_2$ | 3-chloro-2-pyridinyl | N | $CF_3$ |
| | H | $CH_2CH=CH_2$ | $NMe_2$ | 3-chloro-2-pyridinyl | N | $CF_3$ |
| | $CH_2CCH$ | H | $NMe_2$ | 3-chloro-2-pyridinyl | N | $CF_3$ |
| | H | $CH_2CCH$ | $NMe_2$ | 3-chloro-2-pyridinyl | N | $CF_3$ |
| | H | $CO_2Me$ | $NMe_2$ | 3-chloro-2-pyridinyl | N | $CF_3$ |
| | Me | Et | $NMe_2$ | 3-chloro-2-pyridinyl | N | $CF_3$ |
| | Et | Me | $NMe_2$ | 3-chloro-2-pyridinyl | N | $CF_3$ |
| | $CH_2CH=CH_2$ | Me | $NMe_2$ | 3-chloro-2-pyridinyl | N | $CF_3$ |
| | $CH_2CH=CH_2$ | Et | $NMe_2$ | 3-chloro-2-pyridinyl | N | $CF_3$ |
| | Me | $CH_2CH=CH_2$ | $NMe_2$ | 3-chloro-2-pyridinyl | N | $CF_3$ |
| | Et | $CH_2CH=CH_2$ | $NMe_2$ | 3-chloro-2-pyridinyl | N | $CF_3$ |
| | $CH_2CH=CH_2$ | $CH_2CH=CH_2$ | $NMe_2$ | 3-chloro-2-pyridinyl | N | $CF_3$ |
| | $CH_2CCH$ | Me | $NMe_2$ | 3-chloro-2-pyridinyl | N | $CF_3$ |
| | $CH_2CCH$ | Et | $NMe_2$ | 3-chloro-2-pyridinyl | N | $CF_3$ |
| | Me | $CH_2CCH$ | $NMe_2$ | 3-chloro-2-pyridinyl | N | $CF_3$ |
| | Et | $CH_2CCH$ | $NMe_2$ | 3-chloro-2-pyridinyl | N | $CF_3$ |
| | $CH_2CCH$ | $CH_2CCH$ | $NMe_2$ | 3-chloro-2-pyridinyl | N | $CF_3$ |
| | cyc-Pr | H | $NMe_2$ | 3-chloro-2-pyridinyl | N | $CF_3$ |
| | H | cyc-Pr | $NMe_2$ | 3-chloro-2-pyridinyl | N | $CF_3$ |
| | iso-Bu | iso-Bu | $NMe_2$ | 3-chloro-2-pyridinyl | N | $CF_3$ |
| | sec-Bu | H | $NMe_2$ | 3-chloro-2-pyridinyl | N | $CF_3$ |

TABLE A-continued

| No. | R² | R³ | M | R¹⁹ᵃ | X | R²⁰ᵃʸ |
|---|---|---|---|---|---|---|
| | H | sec-Bu | NMe₂ | 3-chloro-2-pyridinyl | N | CF₃ |
| | cyc-Bu | H | NMe₂ | 3-chloro-2-pyridinyl | N | CF₃ |
| | H | cyc-Bu | NMe₂ | 3-chloro-2-pyridinyl | N | CF₃ |
| | CH₂cyc-Pr | H | NMe₂ | 3-chloro-2-pyridinyl | N | CF₃ |
| | H | CH₂cyc-Pr | NMe₂ | 3-chloro-2-pyridinyl | N | CF₃ |
| | CH₂cyc-Bu | H | NMe₂ | 3-chloro-2-pyridinyl | N | CF₃ |
| | H | CH₂cyc-Bu | NMe₂ | 3-chloro-2-pyridinyl | N | CF₃ |
| | CH₂CF3 | Me | NMe₂ | 3-chloro-2-pyridinyl | N | CF₃ |
| | CH₂CF₃ | Et | NMe₂ | 3-chloro-2-pyridinyl | N | CF₃ |
| | Me | CH₂CF₃ | NMe₂ | 3-chloro-2-pyridinyl | N | CF₃ |
| | Et | CH₂CF₃ | NMe₂ | 3-chloro-2-pyridinyl | N | CF₃ |
| | CH₂CF₃ | CH₂CF₃ | NMe₂ | 3-chloro-2-pyridinyl | N | CF₃ |
| | CH₂CN | Me | NMe₂ | 3-chloro-2-pyridinyl | N | CF₃ |
| | CH₂CN | Et | NMe₂ | 3-chloro-2-pyridinyl | N | CF₃ |
| | Me | CH₂CN | NMe₂ | 3-chloro-2-pyridinyl | N | CF₃ |
| | Et | CH₂CN | NMe₂ | 3-chloro-2-pyridinyl | N | CF₃ |
| | CH₂CN | CH₂CN | NMe₂ | 3-chloro-2-pyridinyl | N | CF₃ |
| | CH₂CH₂OMe | H | NMe₂ | 3-chloro-2-pyridinyl | N | CF₃ |
| | H | CH₂CH₂OMe | NMe₂ | 3-chloro-2-pyridinyl | N | CF₃ |
| | CH₂CH₂OMe | CH₂CH₂OMe | NMe₂ | 3-chloro-2-pyridinyl | N | CF₃ |
| | CH₂CH₂SMe | H | NMe₂ | 3-chloro-2-pyridinyl | N | CF₃ |
| | H | CH₂CH₂SMe | NMe₂ | 3-chloro-2-pyridinyl | N | CF₃ |
| | Me | CO₂Me | NMe₂ | 3-chloro-2-pyridinyl | N | CF₃ |
| | Et | CO₂Me | NMe₂ | 3-chloro-2-pyridinyl | N | CF₃ |
| | H | 2-pyridinyl | NMe₂ | 3-chloro-2-pyridinyl | N | CF₃ |
| | H | 3-pyridinyl | NMe₂ | 3-chloro-2-pyridinyl | N | CF₃ |
| | H | 4-pyridinyl | NMe₂ | 3-chloro-2-pyridinyl | N | CF₃ |
| | —(CH₂)₃— | | NMe₂ | 3-chloro-2-pyridinyl | N | CF₃ |
| | —(CH₂)₄— | | NMe₂ | 3-chloro-2-pyridinyl | N | CF₃ |
| | —CH₂NHCH₂— | | NMe₂ | 3-chloro-2-pyridinyl | N | CF₃ |
| | —CH₂NMeCH₂— | | NMe₂ | 3-chloro-2-pyridinyl | N | CF₃ |
| | —CH₂N(iso-Pr)CH₂— | | NMe₂ | 3-chloro-2-pyridinyl | N | CF₃ |
| | —CH₂N(CHO)CH₂— | | NMe₂ | 3-chloro-2-pyridinyl | N | CF₃ |
| | —CH₂N(Ac)CH₂— | | NMe₂ | 3-chloro-2-pyridinyl | N | CF₃ |
| | —CH₂N(CO₂Me)CH₂— | | NMe₂ | 3-chloro-2-pyridinyl | N | CF₃ |
| | —CH₂N(CO₂Et)CH₂— | | NMe₂ | 3-chloro-2-pyridinyl | N | CF₃ |
| | H | H | SMe | 3-chloro-2-pyridinyl | N | Cl |
| | Me | H | SMe | 3-chloro-2-pyridinyl | N | Cl |
| | H | Me | SMe | 3-chloro-2-pyridinyl | N | Cl |

TABLE A-continued

| No. | R² | R³ | M | R¹⁹ᵃ | X | R²⁰ᵃʸ |
|---|---|---|---|---|---|---|
| | Me | Me | SMe | 3-chloro-2-pyridinyl | N | Cl |
| | Et | H | SMe | 3-chloro-2-pyridinyl | N | Cl |
| | H | Et | SMe | 3-chloro-2-pyridinyl | N | Cl |
| | Et | Et | SMe | 3-chloro-2-pyridinyl | N | Cl |
| | H | CO₂Me | SMe | 3-chloro-2-pyridinyl | N | Cl |
| | Me | Et | SMe | 3-chloro-2-pyridinyl | N | Cl |
| | Et | Me | SMe | 3-chloro-2-pyridinyl | N | Cl |
| | CH₂CH=CH₂ | H | SMe | 3-chloro-2-pyridinyl | N | Cl |
| | H | CH₂CH=CH₂ | SMe | 3-chloro-2-pyridinyl | N | Cl |
| | CH₂CCH | H | SMe | 3-chloro-2-pyridinyl | N | Cl |
| | H | CH₂CCH | SMe | 3-chloro-2-pyridinyl | N | Cl |
| | iso-Pr | H | SMe | 3-chloro-2-pyridinyl | N | Cl |
| | H | iso-Pr | SMe | 3-chloro-2-pyridinyl | N | Cl |
| | H | 2-pyridinyl | SMe | 3-chloro-2-pyridinyl | N | Cl |
| | H | 3-pyridinyl | SMe | 3-chloro-2-pyridinyl | N | Cl |
| | H | 4-pyridinyl | SMe | 3-chloro-2-pyridinyl | N | Cl |
| | —(CH₂)₃— | | SMe | 3-chloro-2-pyridinyl | N | Cl |
| | —(CH₂)₄— | | SMe | 3-chloro-2-pyridinyl | N | Cl |
| | H | H | SMe | 3-chloro-2-pyridinyl | N | Br |
| | Me | H | SMe | 3-chloro-2-pyridinyl | N | Br |
| | H | Me | SMe | 3-chloro-2-pyridinyl | N | Br |
| | Me | Me | SMe | 3-chloro-2-pyridinyl | N | Br |
| | Et | H | SMe | 3-chloro-2-pyridinyl | N | Br |
| | H | Et | SMe | 3-chloro-2-pyridinyl | N | Br |
| | Et | Et | SMe | 3-chloro-2-pyridinyl | N | Br |
| | H | CO₂Me | SMe | 3-chloro-2-pyridinyl | N | Br |
| | Me | Et | SMe | 3-chloro-2-pyridinyl | N | Br |
| | Et | Me | SMe | 3-chloro-2-pyridinyl | N | Br |
| | CH₂CH=CH₂ | H | SMe | 3-chloro-2-pyridinyl | N | Br |
| | H | CH₂CH=CH₂ | SMe | 3-chloro-2-pyridinyl | N | Br |
| | CH₂CCH | H | SMe | 3-chloro-2-pyridinyl | N | Br |
| | H | CH₂CCH | SMe | 3-chloro-2-pyridinyl | N | Br |
| | iso-Pr | H | SMe | 3-chloro-2-pyridinyl | N | Br |
| | H | iso-Pr | SMe | 3-chloro-2-pyridinyl | N | Br |
| | H | 2-pyridinyl | SMe | 3-chloro-2-pyridinyl | N | Br |
| | H | 3-pyridinyl | SMe | 3-chloro-2-pyridinyl | N | Br |
| | H | 4-pyridinyl | SMe | 3-chloro-2-pyridinyl | N | Br |
| | —(CH₂)₃— | | SMe | 3-chloro-2-pyridinyl | N | Br |
| | —(CH₂)₄— | | SMe | 3-chloro-2-pyridinyl | N | Br |

TABLE A-continued

| No. | R² | R³ | M | R¹⁹ᵃ | X | R²⁰ᵃʸ |
|---|---|---|---|---|---|---|
| | H | H | SMe | 3-chloro-2-pyridinyl | N | CF₃ |
| | Me | H | SMe | 3-chloro-2-pyridinyl | N | CF₃ |
| | H | Me | SMe | 3-chloro-2-pyridinyl | N | CF₃ |
| | Me | Me | SMe | 3-chloro-2-pyridinyl | N | CF₃ |
| | Et | H | SMe | 3-chloro-2-pyridinyl | N | CF₃ |
| | H | Et | SMe | 3-chloro-2-pyridinyl | N | CF₃ |
| | Et | Et | SMe | 3-chloro-2-pyridinyl | N | CF₃ |
| | H | CO₂Me | SMe | 3-chloro-2-pyridinyl | N | CF₃ |
| | Me | Et | SMe | 3-chloro-2-pyridinyl | N | CF₃ |
| | Et | Me | SMe | 3-chloro-2-pyridinyl | N | CF₃ |
| | CH₂CH=CH₂ | H | SMe | 3-chloro-2-pyridinyl | N | CF₃ |
| | H | CH₂CH=CH₂ | SMe | 3-chloro-2-pyridinyl | N | CF₃ |
| | CH₂CCH | H | SMe | 3-chloro-2-pyridinyl | N | CF₃ |
| | H | CH₂CCH | SMe | 3-chloro-2-pyridinyl | N | CF₃ |
| | iso-Pr | H | SMe | 3-chloro-2-pyridinyl | N | CF₃ |
| | H | iso-Pr | SMe | 3-chloro-2-pyridinyl | N | CF₃ |
| | H | 2-pyridinyl | SMe | 3-chloro-2-pyridinyl | N | CF₃ |
| | H | 3-pyridinyl | SMe | 3-chloro-2-pyridinyl | N | CF₃ |
| | H | 4-pyridinyl | SMe | 3-chloro-2-pyridinyl | N | CF₃ |
| | —(CH₂)₃— | | SMe | 3-chloro-2-pyridinyl | N | CF₃ |
| | —(CH₂)₄— | | SMe | 3-chloro-2-pyridinyl | N | CF₃ |
| | H | H | H | 3-chloro-2-pyridinyl | CH | Cl |
| | Me | H | H | 3-chloro-2-pyridinyl | CH | Cl |
| | H | Me | H | 3-chloro-2-pyridinyl | CH | Cl |
| | Me | Me | H | 3-chloro-2-pyridinyl | CH | Cl |
| | Et | H | H | 3-chloro-2-pyridinyl | CH | Cl |
| | H | Et | H | 3-chloro-2-pyridinyl | CH | Cl |
| | Et | Et | H | 3-chloro-2-pyridinyl | CH | Cl |
| | H | CO₂Me | H | 3-chloro-2-pyridinyl | CH | Cl |
| | Me | Et | H | 3-chloro-2-pyridinyl | CH | Cl |
| | Et | Me | H | 3-chloro-2-pyridinyl | CH | Cl |
| | CH₂CH=CH₂ | H | H | 3-chloro-2-pyridinyl | CH | Cl |
| | H | CH₂CH=CH₂ | H | 3-chloro-2-pyridinyl | CH | Cl |
| | CH₂CCH | H | H | 3-chloro-2-pyridinyl | CH | Cl |
| | H | CH₂CCH | H | 3-chloro-2-pyridinyl | CH | Cl |
| | iso-Pr | H | H | 3-chloro-2-pyridinyl | CH | Cl |
| | H | iso-Pr | H | 3-chloro-2-pyridinyl | CH | Cl |
| | H | 2-pyridinyl | H | 3-chloro-2-pyridinyl | CH | Cl |
| | H | 3-pyridinyl | H | 3-chloro-2-pyridinyl | CH | Cl |

TABLE A-continued

| No. | $R^2$ | $R^3$ | M | $R^{19a}$ | X | $R^{20ay}$ |
|---|---|---|---|---|---|---|
| | H | 4-pyridinyl | H | 3-chloro-2-pyridinyl | CH | Cl |
| | | —(CH$_2$)$_3$— | H | 3-chloro-2-pyridinyl | CH | Cl |
| | | —(CH$_2$)$_4$— | H | 3-chloro-2-pyridinyl | CH | Cl |
| | H | H | OMe | 3-chloro-2-pyridinyl | CH | Cl |
| | Me | H | OMe | 3-chloro-2-pyridinyl | CH | Cl |
| | H | Me | OMe | 3-chloro-2-pyridinyl | CH | Cl |
| | Me | Me | OMe | 3-chloro-2-pyridinyl | CH | Cl |
| | Et | H | OMe | 3-chloro-2-pyridinyl | CH | Cl |
| | H | Et | OMe | 3-chloro-2-pyridinyl | CH | Cl |
| | Et | Et | OMe | 3-chloro-2-pyridinyl | CH | Cl |
| | H | CO$_2$Me | OMe | 3-chloro-2-pyridinyl | CH | Cl |
| | Me | Et | OMe | 3-chloro-2-pyridinyl | CH | Cl |
| | Et | Me | OMe | 3-chloro-2-pyridinyl | CH | Cl |
| | CH$_2$CH=CH$_2$ | H | OMe | 3-chloro-2-pyridinyl | CH | Cl |
| | H | CH$_2$CH=CH$_2$ | OMe | 3-chloro-2-pyridinyl | CH | Cl |
| | CH$_2$CCH | H | OMe | 3-chloro-2-pyridinyl | CH | Cl |
| | H | CH$_2$CCH | OMe | 3-chloro-2-pyridinyl | CH | Cl |
| | iso-Pr | H | OMe | 3-chloro-2-pyridinyl | CH | Cl |
| | H | iso-Pr | OMe | 3-chloro-2-pyridinyl | CH | Cl |
| | H | 2-pyridinyl | OMe | 3-chloro-2-pyridinyl | CH | Cl |
| | H | 3-pyridinyl | OMe | 3-chloro-2-pyridinyl | CH | Cl |
| | H | 4-pyridinyl | OMe | 3-chloro-2-pyridinyl | CH | Cl |
| | | —(CH$_2$)$_3$— | OMe | 3-chloro-2-pyridinyl | CH | Cl |
| | | —(CH$_2$)$_4$— | OMe | 3-chloro-2-pyridinyl | CH | Cl |
| | H | H | NMe$_2$ | 3-chloro-2-pyridinyl | CH | Cl |
| | Me | H | NMe$_2$ | 3-chloro-2-pyridinyl | CH | Cl |
| | H | Me | NMe$_2$ | 3-chloro-2-pyridinyl | CH | Cl |
| | Me | Me | NMe$_2$ | 3-chloro-2-pyridinyl | CH | Cl |
| | Et | H | NMe$_2$ | 3-chloro-2-pyridinyl | CH | Cl |
| | H | Et | NMe$_2$ | 3-chloro-2-pyridinyl | CH | Cl |
| | Et | Et | NMe$_2$ | 3-chloro-2-pyridinyl | CH | Cl |
| | H | CO$_2$Me | NMe$_2$ | 3-chloro-2-pyridinyl | CH | Cl |
| | Me | Et | NMe$_2$ | 3-chloro-2-pyridinyl | CH | Cl |
| | Et | Me | NMe$_2$ | 3-chloro-2-pyridinyl | CH | Cl |
| | CH$_2$CH=CH$_2$ | H | NMe$_2$ | 3-chloro-2-pyridinyl | CH | Cl |
| | H | CH$_2$CH=CH$_2$ | NMe$_2$ | 3-chloro-2-pyridinyl | CH | Cl |
| | CH$_2$CCH | H | NMe$_2$ | 3-chloro-2-pyridinyl | CH | Cl |
| | H | CH$_2$CCH | NMe$_2$ | 3-chloro-2-pyridinyl | CH | Cl |
| | iso-Pr | H | NMe$_2$ | 3-chloro-2-pyridinyl | CH | Cl |

TABLE A-continued

| No. | $R^2$ | $R^3$ | M | $R^{19a}$ | X | $R^{20ay}$ |
|-----|-------|-------|---|-----------|---|------------|
|  | H | iso-Pr | $NMe_2$ | 3-chloro-2-pyridinyl | CH | Cl |
|  | H | 2-pyridinyl | $NMe_2$ | 3-chloro-2-pyridinyl | CH | Cl |
|  | H | 3-pyridinyl | $NMe_2$ | 3-chloro-2-pyridinyl | CH | Cl |
|  | H | 4-pyridinyl | $NMe_2$ | 3-chloro-2-pyridinyl | CH | Cl |
|  | —$(CH_2)_3$— | | $NMe_2$ | 3-chloro-2-pyridinyl | CH | Cl |
|  | —$(CH_2)_4$— | | $NMe_2$ | 3-chloro-2-pyridinyl | CH | Cl |
|  | H | H | NHMe | 3-chloro-2-pyridinyl | CH | Cl |
|  | Me | H | NHMe | 3-chloro-2-pyridinyl | CH | Cl |
|  | H | Me | NHMe | 3-chloro-2-pyridinyl | CH | Cl |
|  | Me | Me | NHMe | 3-chloro-2-pyridinyl | CH | Cl |
|  | Et | H | NHMe | 3-chloro-2-pyridinyl | CH | Cl |
|  | H | Et | NHMe | 3-chloro-2-pyridinyl | CH | Cl |
|  | Et | Et | NHMe | 3-chloro-2-pyridinyl | CH | Cl |
|  | H | $CO_2Me$ | NHMe | 3-chloro-2-pyridinyl | CH | Cl |
|  | Me | Et | NHMe | 3-chloro-2-pyridinyl | CH | Cl |
|  | Et | Me | NHMe | 3-chloro-2-pyridinyl | CH | Cl |
|  | $CH_2CH=CH_2$ | H | NHMe | 3-chloro-2-pyridinyl | CH | Cl |
|  | H | $CH_2CH=CH_2$ | NHMe | 3-chloro-2-pyridinyl | CH | Cl |
|  | $CH_2CCH$ | H | NHMe | 3-chloro-2-pyridinyl | CH | Cl |
|  | H | $CH_2CCH$ | NHMe | 3-chloro-2-pyridinyl | CH | Cl |
|  | iso-Pr | H | NHMe | 3-chloro-2-pyridinyl | CH | Cl |
|  | H | iso-Pr | NHMe | 3-chloro-2-pyridinyl | CH | Cl |
|  | H | 2-pyridinyl | NHMe | 3-chloro-2-pyridinyl | CH | Cl |
|  | H | 3-pyridinyl | NHMe | 3-chloro-2-pyridinyl | CH | Cl |
|  | H | 4-pyridinyl | NHMe | 3-chloro-2-pyridinyl | CH | Cl |
|  | —$(CH_2)_3$— | | NHMe | 3-chloro-2-pyridinyl | CH | Cl |
|  | —$(CH_2)_4$— | | NHMe | 3-chloro-2-pyridinyl | CH | Cl |
|  | H | H | H | 3-chloro-2-pyridinyl | CCl | H |
|  | Me | H | H | 3-chloro-2-pyridinyl | CCl | H |
|  | H | Me | H | 3-chloro-2-pyridinyl | CCl | H |
|  | Me | Me | H | 3-chloro-2-pyridinyl | CCl | H |
|  | Et | H | H | 3-chloro-2-pyridinyl | CCl | H |
|  | H | Et | H | 3-chloro-2-pyridinyl | CCl | H |
|  | Et | Et | H | 3-chloro-2-pyridinyl | CCl | H |
|  | H | $CO_2Me$ | H | 3-chloro-2-pyridinyl | CCl | H |
|  | Me | Et | H | 3-chloro-2-pyridinyl | CCl | H |
|  | Et | Me | H | 3-chloro-2-pyridinyl | CCl | H |
|  | $CH_2CH=CH_2$ | H | H | 3-chloro-2-pyridinyl | CCl | H |
|  | H | $CH_2CH=CH_2$ | H | 3-chloro-2-pyridinyl | CCl | H |

TABLE A-continued

| No. | R² | R³ | M | R¹⁹ᵃ | X | R²⁰ᵃʸ |
|---|---|---|---|---|---|---|
| | CH₂CCH | H | H | 3-chloro-2-pyridinyl | CCl | H |
| | H | CH₂CCH | H | 3-chloro-2-pyridinyl | CCl | H |
| | iso-Pr | H | H | 3-chloro-2-pyridinyl | CCl | H |
| | H | iso-Pr | H | 3-chloro-2-pyridinyl | CCl | H |
| | H | 2-pyridinyl | H | 3-chloro-2-pyridinyl | CCl | H |
| | H | 3-pyridinyl | H | 3-chloro-2-pyridinyl | CCl | H |
| | H | 4-pyridinyl | H | 3-chloro-2-pyridinyl | CCl | H |
| | —(CH₂)₃— | | H | 3-chloro-2-pyridinyl | CCl | H |
| | —(CH₂)₄— | | H | 3-chloro-2-pyridinyl | CCl | H |
| | H | H | OMe | 3-chloro-2-pyridinyl | CCl | H |
| | Me | H | OMe | 3-chloro-2-pyridinyl | CCl | H |
| | H | Me | OMe | 3-chloro-2-pyridinyl | CCl | H |
| | Me | Me | OMe | 3-chloro-2-pyridinyl | CCl | H |
| | Et | H | OMe | 3-chloro-2-pyridinyl | CCl | H |
| | H | Et | OMe | 3-chloro-2-pyridinyl | CCl | H |
| | Et | Et | OMe | 3-chloro-2-pyridinyl | CCl | H |
| | H | CO₂Me | OMe | 3-chloro-2-pyridinyl | CCl | H |
| | Me | Et | OMe | 3-chloro-2-pyridinyl | CCl | H |
| | Et | Me | OMe | 3-chloro-2-pyridinyl | CCl | H |
| | CH₂CH=CH₂ | H | OMe | 3-chloro-2-pyridinyl | CCl | H |
| | H | CH₂CH=CH₂ | OMe | 3-chloro-2-pyridinyl | CCl | H |
| | CH₂CCH | H | OMe | 3-chloro-2-pyridinyl | CCl | H |
| | H | CH₂CCH | OMe | 3-chloro-2-pyridinyl | CCl | H |
| | iso-Pr | H | OMe | 3-chloro-2-pyridinyl | CCl | H |
| | H | iso-Pr | OMe | 3-chloro-2-pyridinyl | CCl | H |
| | H | 2-pyridinyl | OMe | 3-chloro-2-pyridinyl | CCl | H |
| | H | 3-pyridinyl | OMe | 3-chloro-2-pyridinyl | CCl | H |
| | H | 4-pyridinyl | OMe | 3-chloro-2-pyridinyl | CCl | H |
| | —(CH₂)₃— | | OMe | 3-chloro-2-pyridinyl | CCl | H |
| | —(CH₂)₄— | | OMe | 3-chloro-2-pyridinyl | CCl | H |
| | H | H | NMe₂ | 3-chloro-2-pyridinyl | CCl | H |
| | Me | H | NMe₂ | 3-chloro-2-pyridinyl | CCl | H |
| | H | Me | NMe₂ | 3-chloro-2-pyridinyl | CCl | H |
| | Me | Me | NMe₂ | 3-chloro-2-pyridinyl | CCl | H |
| | Et | H | NMe₂ | 3-chloro-2-pyridinyl | CCl | H |
| | H | Et | NMe₂ | 3-chloro-2-pyridinyl | CCl | H |
| | Et | Et | NMe₂ | 3-chloro-2-pyridinyl | CCl | H |
| | H | CO₂Me | NMe₂ | 3-chloro-2-pyridinyl | CCl | H |
| | Me | Et | NMe₂ | 3-chloro-2-pyridinyl | CCl | H |

TABLE A-continued

| No. | R² | R³ | M | R¹⁹ᵃ | X | R²⁰ᵃʸ |
|---|---|---|---|---|---|---|
| | Et | Me | NMe₂ | 3-chloro-2-pyridinyl | CCl | H |
| | CH₂CH=CH₂ | H | NMe₂ | 3-chloro-2-pyridinyl | CCl | H |
| | H | CH₂CH=CH₂ | NMe₂ | 3-chloro-2-pyridinyl | CCl | H |
| | CH₂CCH | H | NMe₂ | 3-chloro-2-pyridinyl | CCl | H |
| | H | CH₂CCH | NMe₂ | 3-chloro-2-pyridinyl | CCl | H |
| | iso-Pr | H | NMe₂ | 3-chloro-2-pyridinyl | CCl | H |
| | H | iso-Pr | NMe₂ | 3-chloro-2-pyridinyl | CCl | H |
| | H | 2-pyridinyl | NMe₂ | 3-chloro-2-pyridinyl | CCl | H |
| | H | 3-pyridinyl | NMe₂ | 3-chloro-2-pyridinyl | CCl | H |
| | H | 4-pyridinyl | NMe₂ | 3-chloro-2-pyridinyl | CCl | H |
| | —(CH₂)₃— | | NMe₂ | 3-chloro-2-pyridinyl | CCl | H |
| | —(CH₂)₄— | | NMe₂ | 3-chloro-2-pyridinyl | CCl | H |
| | H | H | NHMe | 3-chloro-2-pyridinyl | CCl | H |
| | Me | H | NHMe | 3-chloro-2-pyridinyl | CC | H |
| | H | Me | NHMe | 3-chloro-2-pyridinyl | CCl | H |
| | Me | Me | NHMe | 3-chloro-2-pyridinyl | CCl | H |
| | Et | H | NHMe | 3-chloro-2-pyridinyl | CCl | H |
| | H | Et | NHMe | 3-chloro-2-pyridinyl | CCl | H |
| | Et | Et | NHMe | 3-chloro-2-pyridinyl | CCl | H |
| | H | CO₂Me | NHMe | 3-chloro-2-pyridinyl | CCl | H |
| | Me | Et | NHMe | 3-chloro-2-pyridinyl | CCl | H |
| | Et | Me | NHMe | 3-chloro-2-pyridinyl | CCl | H |
| | CH₂CH=CH₂ | H | NHMe | 3-chloro-2-pyridinyl | CCl | H |
| | H | CH₂CH=CH₂ | NHMe | 3-chloro-2-pyridinyl | CCl | H |
| | CH₂CCH | H | NHMe | 3-chloro-2-pyridinyl | CCl | H |
| | H | CH₂CCH | NHMe | 3-chloro-2-pyridinyl | CCl | H |
| | iso-Pr | H | NHMe | 3-chloro-2-pyridinyl | CCl | H |
| | H | iso-Pr | NHMe | 3-chloro-2-pyridinyl | CCl | H |
| | H | 2-pyridinyl | NHMe | 3-chloro-2-pyridinyl | CCl | H |
| | H | 3-pyridinyl | NHMe | 3-chloro-2-pyridinyl | CCl | H |
| | H | 4-pyridinyl | NHMe | 3-chloro-2-pyridinyl | CCl | H |
| | —(CH₂)₃— | | NHMe | 3-chloro-2-pyridinyl | CCl | H |
| | —(CH₂)₄— | | NHMe | 3-chloro-2-pyridinyl | CCl | H |
| | H | H | H | 3-chloro-2-pyridinyl | CCl | Cl |
| | Me | H | H | 3-chloro-2-pyridinyl | CCl | Cl |
| | H | Me | H | 3-chloro-2-pyridinyl | CCl | Cl |
| | Me | Me | H | 3-chloro-2-pyridinyl | CCl | Cl |
| | Et | H | H | 3-chloro-2-pyridinyl | CCl | Cl |
| | H | Et | H | 3-chloro-2-pyridinyl | CCl | Cl |

TABLE A-continued

| No. | R² | R³ | M | R¹⁹ᵃ | X | R²⁰ᵃʸ |
|---|---|---|---|---|---|---|
| | Et | Et | H | 3-chloro-2-pyridinyl | CCl | Cl |
| | H | CO₂Me | H | 3-chloro-2-pyridinyl | CCl | Cl |
| | Me | Et | H | 3-chloro-2-pyridinyl | CCl | Cl |
| | Et | Me | H | 3-chloro-2-pyridinyl | CCl | Cl |
| | CH₂CH=CH₂ | H | H | 3-chloro-2-pyridinyl | CCl | Cl |
| | H | CH₂CH=CH₂ | H | 3-chloro-2-pyridinyl | CCl | Cl |
| | CH₂CCH | H | H | 3-chloro-2-pyridinyl | CCl | Cl |
| | H | CH₂CCH | H | 3-chloro-2-pyridinyl | CCl | Cl |
| | iso-Pr | H | H | 3-chloro-2-pyridinyl | CCl | Cl |
| | H | iso-Pr | H | 3-chloro-2-pyridinyl | CCl | Cl |
| | H | 2-pyridinyl | H | 3-chloro-2-pyridinyl | CCl | Cl |
| | H | 3-pyridinyl | H | 3-chloro-2-pyridinyl | CCl | Cl |
| | H | 4-pyridinyl | H | 3-chloro-2-pyridinyl | CCl | Cl |
| | —(CH₂)₃— | | H | 3-chloro-2-pyridinyl | CCl | Cl |
| | —(CH₂)₄— | | H | 3-chloro-2-pyridinyl | CCl | Cl |
| | H | H | OMe | 3-chloro-2-pyridinyl | CCl | Cl |
| | Me | H | OMe | 3-chloro-2-pyridinyl | CCl | Cl |
| | H | Me | OMe | 3-chloro-2-pyridinyl | CCl | Cl |
| | Me | Me | OMe | 3-chloro-2-pyridinyl | CCl | Cl |
| | Et | H | OMe | 3-chloro-2-pyridinyl | CCl | Cl |
| | H | Et | OMe | 3-chloro-2-pyridinyl | CCl | Cl |
| | Et | Et | OMe | 3-chloro-2-pyridinyl | CCl | Cl |
| | H | CO₂Me | OMe | 3-chloro-2-pyridinyl | CCl | Cl |
| | Me | Et | OMe | 3-chloro-2-pyridinyl | CCl | Cl |
| | Et | Me | OMe | 3-chloro-2-pyridinyl | CCl | Cl |
| | CH₂CH=CH₂ | H | OMe | 3-chloro-2-pyridinyl | CCl | Cl |
| | H | CH₂CH=CH₂ | OMe | 3-chloro-2-pyridinyl | CCl | Cl |
| | CH₂CCH | H | OMe | 3-chloro-2-pyridinyl | CCl | Cl |
| | H | CH₂CCH | OMe | 3-chloro-2-pyridinyl | CCl | Cl |
| | iso-Pr | H | OMe | 3-chloro-2-pyridinyl | CCl | Cl |
| | H | iso-Pr | OMe | 3-chloro-2-pyridinyl | CCl | Cl |
| | H | 2-pyridinyl | OMe | 3-chloro-2-pyridinyl | CCl | Cl |
| | H | 3-pyridinyl | OMe | 3-chloro-2-pyridinyl | CCl | Cl |
| | H | 4-pyridinyl | OMe | 3-chloro-2-pyridinyl | CCl | Cl |
| | —(CH₂)₃— | | OMe | 3-chloro-2-pyridinyl | CCl | Cl |
| | —(CH₂)₄— | | OMe | 3-chloro-2-pyridinyl | CCl | Cl |
| | H | H | NMe₂ | 3-chloro-2-pyridinyl | CCl | Cl |
| | Me | H | NMe₂ | 3-chloro-2-pyridinyl | CCl | Cl |
| | H | Me | NMe₂ | 3-chloro-2-pyridinyl | CCl | Cl |

TABLE A-continued

| No. | R² | R³ | M | R¹⁹ᵃ | X | R²⁰ᵃʸ |
|---|---|---|---|---|---|---|
| | Me | Me | NMe₂ | 3-chloro-2-pyridinyl | CCl | Cl |
| | Et | H | NMe₂ | 3-chloro-2-pyridinyl | CCl | Cl |
| | H | Et | NMe₂ | 3-chloro-2-pyridinyl | CCl | Cl |
| | Et | Et | NMe₂ | 3-chloro-2-pyridinyl | CCl | Cl |
| | H | CO₂Me | NMe₂ | 3-chloro-2-pyridinyl | CCl | Cl |
| | Me | Et | NMe₂ | 3-chloro-2-pyridinyl | CCl | Cl |
| | Et | Me | NMe₂ | 3-chloro-2-pyridinyl | CCl | Cl |
| | CH₂CH=CH₂ | H | NMe₂ | 3-chloro-2-pyridinyl | CCl | Cl |
| | H | CH₂CH=CH₂ | NMe₂ | 3-chloro-2-pyridinyl | CCl | Cl |
| | CH₂CCH | H | NMe₂ | 3-chloro-2-pyridinyl | CCl | Cl |
| | H | CH₂CCH | NMe₂ | 3-chloro-2-pyridinyl | CCl | Cl |
| | iso-Pr | H | NMe₂ | 3-chloro-2-pyridinyl | CCl | Cl |
| | H | iso-Pr | NMe₂ | 3-chloro-2-pyridinyl | CCl | Cl |
| | H | 2-pyridinyl | NMe₂ | 3-chloro-2-pyridinyl | CCl | Cl |
| | H | 3-pyridinyl | NMe₂ | 3-chloro-2-pyridinyl | CCl | Cl |
| | H | 4-pyridinyl | NMe₂ | 3-chloro-2-pyridinyl | CCl | Cl |
| | —(CH₂)₃— | | NMe₂ | 3-chloro-2-pyridinyl | CCl | Cl |
| | —(CH₂)₄— | | NMe₂ | 3-chloro-2-pyridinyl | CCl | Cl |
| | H | H | NHMe | 3-chloro-2-pyridinyl | CCl | Cl |
| | Me | H | NHMe | 3-chloro-2-pyridinyl | CCl | Cl |
| | H | Me | NHMe | 3-chloro-2-pyridinyl | CCl | Cl |
| | Me | Me | NHMe | 3-chloro-2-pyridinyl | CCl | Cl |
| | Et | H | NHMe | 3-chloro-2-pyridinyl | CCl | Cl |
| | H | Et | NHMe | 3-chloro-2-pyridinyl | CCl | Cl |
| | Et | Et | NHMe | 3-chloro-2-pyridinyl | CCl | Cl |
| | H | CO₂Me | NHMe | 3-chloro-2-pyridinyl | CCl | Cl |
| | Me | Et | NHMe | 3-chloro-2-pyridinyl | CCl | Cl |
| | Et | Me | NHMe | 3-chloro-2-pyridinyl | CCl | Cl |
| | CH₂CH=CH₂ | H | NHMe | 3-chloro-2-pyridinyl | CCl | Cl |
| | H | CH₂CH=CH₂ | NHMe | 3-chloro-2-pyridinyl | CCl | Cl |
| | CH₂CCH | H | NHMe | 3-chloro-2-pyridinyl | CCl | Cl |
| | H | CH₂CCH | NHMe | 3-chloro-2-pyridinyl | CCl | Cl |
| | iso-Pr | H | NHMe | 3-chloro-2-pyridinyl | CCl | Cl |
| | H | iso-Pr | NHMe | 3-chloro-2-pyridinyl | CCl | Cl |
| | H | 2-pyridinyl | NHMe | 3-chloro-2-pyridinyl | CCl | Cl |
| | H | 3-pyridinyl | NHMe | 3-chloro-2-pyridinyl | CCl | Cl |
| | H | 4-pyridinyl | NHMe | 3-chloro-2-pyridinyl | CCl | Cl |
| | —(CH₂)₃— | | NHMe | 3-chloro-2-pyridinyl | CCl | Cl |
| | —(CH₂)₄— | | NHMe | 3-chloro-2-pyridinyl | CCl | Cl |

TABLE A-continued

| No. | $R^2$ | $R^3$ | M | $R^{19a}$ | X | $R^{20ay}$ |
|---|---|---|---|---|---|---|
| | H | H | H | 3-chloro-2-pyridinyl | CH | Br |
| | Me | H | H | 3-chloro-2-pyridinyl | CH | Br |
| | H | Me | H | 3-chloro-2-pyridinyl | CH | Br |
| | Me | Me | H | 3-chloro-2-pyridinyl | CH | Br |
| | Et | H | H | 3-chloro-2-pyridinyl | CH | Br |
| | H | Et | H | 3-chloro-2-pyridinyl | CH | Br |
| | Et | Et | H | 3-chloro-2-pyridinyl | CH | Br |
| | H | $CO_2Me$ | H | 3-chloro-2-pyridinyl | CH | Br |
| | Me | Et | H | 3-chloro-2-pyridinyl | CH | Br |
| | Et | Me | H | 3-chloro-2-pyridinyl | CH | Br |
| | $CH_2CH{=}CH_2$ | H | H | 3-chloro-2-pyridinyl | CH | Br |
| | H | $CH_2CH{=}CH_2$ | H | 3-chloro-2-pyridinyl | CH | Br |
| | $CH_2CCH$ | H | H | 3-chloro-2-pyridinyl | CH | Br |
| | H | $CH_2CCH$ | H | 3-chloro-2-pyridinyl | CH | Br |
| | iso-Pr | H | H | 3-chloro-2-pyridinyl | CH | Br |
| | H | iso-Pr | H | 3-chloro-2-pyridinyl | CH | Br |
| | H | 2-pyridinyl | H | 3-chloro-2-pyridinyl | CH | Br |
| | H | 3-pyridinyl | H | 3-chloro-2-pyridinyl | CH | Br |
| | H | 4-pyridinyl | H | 3-chloro-2-pyridinyl | CH | Br |
| | —$(CH_2)_3$— | | H | 3-chloro-2-pyridinyl | CH | Br |
| | —$(CH_2)_4$— | | H | 3-chloro-2-pyridinyl | CH | Br |
| | H | H | OMe | 3-chloro-2-pyridinyl | CH | Br |
| | Me | H | OMe | 3-chloro-2-pyridinyl | CH | Br |
| | H | Me | OMe | 3-chloro-2-pyridinyl | CH | Br |
| | Me | Me | OMe | 3-chloro-2-pyridinyl | CH | Br |
| | Et | H | OMe | 3-chloro-2-pyridinyl | CH | Br |
| | H | Et | OMe | 3-chloro-2-pyridinyl | CH | Br |
| | Et | Et | OMe | 3-chloro-2-pyridinyl | CH | Br |
| | H | $CO_2Me$ | OMe | 3-chloro-2-pyridinyl | CH | Br |
| | Me | Et | OMe | 3-chloro-2-pyridinyl | CH | Br |
| | Et | Me | OMe | 3-chloro-2-pyridinyl | CH | Br |
| | $CH_2CH{=}CH_2$ | H | OMe | 3-chloro-2-pyridinyl | CH | Br |
| | H | $CH_2CH{=}CH_2$ | OMe | 3-chloro-2-pyridinyl | CH | Br |
| | $CH_2CCH$ | H | OMe | 3-chloro-2-pyridinyl | CH | Br |
| | H | $CH_2CCH$ | OMe | 3-chloro-2-pyridinyl | CH | Br |
| | iso-Pr | H | OMe | 3-chloro-2-pyridinyl | CH | Br |
| | H | iso-Pr | OMe | 3-chloro-2-pyridinyl | CH | Br |
| | H | 2-pyridinyl | OMe | 3-chloro-2-pyridinyl | CH | Br |
| | H | 3-pyridinyl | OMe | 3-chloro-2-pyridinyl | CH | Br |

TABLE A-continued

| No. | $R^2$ | $R^3$ | M | $R^{19a}$ | X | $R^{20ay}$ |
|---|---|---|---|---|---|---|
| | H | 4-pyridinyl | OMe | 3-chloro-2-pyridinyl | CH | Br |
| | | —(CH$_2$)$_3$— | OMe | 3-chloro-2-pyridinyl | CH | Br |
| | | —(CH$_2$)$_4$— | OMe | 3-chloro-2-pyridinyl | CH | Br |
| | H | H | NMe$_2$ | 3-chloro-2-pyridinyl | CH | Br |
| | Me | H | NMe$_2$ | 3-chloro-2-pyridinyl | CH | Br |
| | H | Me | NMe$_2$ | 3-chloro-2-pyridinyl | CH | Br |
| | Me | Me | NMe$_2$ | 3-chloro-2-pyridinyl | CH | Br |
| | Et | H | NMe$_2$ | 3-chloro-2-pyridinyl | CH | Br |
| | H | Et | NMe$_2$ | 3-chloro-2-pyridinyl | CH | Br |
| | Et | Et | NMe$_2$ | 3-chloro-2-pyridinyl | CH | Br |
| | H | CO$_2$Me | NMe$_2$ | 3-chloro-2-pyridinyl | CH | Br |
| | Me | Et | NMe$_2$ | 3-chloro-2-pyridinyl | CH | Br |
| | Et | Me | NMe$_2$ | 3-chloro-2-pyridinyl | CH | Br |
| | CH$_2$CH=CH$_2$ | H | NMe$_2$ | 3-chloro-2-pyridinyl | CH | Br |
| | H | CH$_2$CH=CH$_2$ | NMe$_2$ | 3-chloro-2-pyridinyl | CH | Br |
| | CH$_2$CCH | H | NMe$_2$ | 3-chloro-2-pyridinyl | CH | Br |
| | H | CH$_2$CCH | NMe$_2$ | 3-chloro-2-pyridinyl | CH | Br |
| | iso-Pr | H | NMe$_2$ | 3-chloro-2-pyridinyl | CH | Br |
| | H | iso-Pr | NMe$_2$ | 3-chloro-2-pyridinyl | CH | Br |
| | H | 2-pyridinyl | NMe$_2$ | 3-chloro-2-pyridinyl | CH | Br |
| | H | 3-pyridinyl | NMe$_2$ | 3-chloro-2-pyridinyl | CH | Br |
| | H | 4-pyridinyl | NMe$_2$ | 3-chloro-2-pyridinyl | CH | Br |
| | | —(CH$_2$)$_3$— | NMe$_2$ | 3-chloro-2-pyridinyl | CH | Br |
| | | —(CH$_2$)$_4$— | NMe$_2$ | 3-chloro-2-pyridinyl | CH | Br |
| | H | H | NHMe | 3-chloro-2-pyridinyl | CH | Br |
| | Me | H | NHMe | 3-chloro-2-pyridinyl | CH | Br |
| | H | Me | NHMe | 3-chloro-2-pyridinyl | CH | Br |
| | Me | Me | NHMe | 3-chloro-2-pyridinyl | CH | Br |
| | Et | H | NHMe | 3-chloro-2-pyridinyl | CH | Br |
| | H | Et | NHMe | 3-chloro-2-pyridinyl | CH | Br |
| | Et | Et | NHMe | 3-chloro-2-pyridinyl | CH | Br |
| | H | CO$_2$Me | NHMe | 3-chloro-2-pyridinyl | CH | Br |
| | Me | Et | NHMe | 3-chloro-2-pyridinyl | CH | Br |
| | Et | Me | NHMe | 3-chloro-2-pyridinyl | CH | Br |
| | CH$_2$CH=CH$_2$ | H | NHMe | 3-chloro-2-pyridinyl | CH | Br |
| | H | CH$_2$CH=CH$_2$ | NHMe | 3-chloro-2-pyridinyl | CH | Br |
| | CH$_2$CCH | H | NHMe | 3-chloro-2-pyridinyl | CH | Br |
| | H | CH$_2$CCH | NHMe | 3-chloro-2-pyridinyl | CH | Br |
| | iso-Pr | H | NHMe | 3-chloro-2-pyridinyl | CH | Br |

TABLE A-continued

| No. | $R^2$ | $R^3$ | M | $R^{19a}$ | X | $R^{20ay}$ |
|---|---|---|---|---|---|---|
| | H | iso-Pr | NHMe | 3-chloro-2-pyridinyl | CH | Br |
| | H | 2-pyridinyl | NHMe | 3-chloro-2-pyridinyl | CH | Br |
| | H | 3-pyridinyl | NHMe | 3-chloro-2-pyridinyl | CH | Br |
| | H | 4-pyridinyl | NHMe | 3-chloro-2-pyridinyl | CH | Br |
| | —(CH$_2$)$_3$— | | NHMe | 3-chloro-2-pyridinyl | CH | Br |
| | —(CH$_2$)$_4$— | | NHMe | 3-chloro-2-pyridinyl | CH | Br |
| | H | H | H | 3-chloro-2-pyridinyl | CBr | H |
| | Me | H | H | 3-chloro-2-pyridinyl | CBr | H |
| | H | Me | H | 3-chloro-2-pyridinyl | CBr | H |
| | Me | Me | H | 3-chloro-2-pyridinyl | CBr | H |
| | Et | H | H | 3-chloro-2-pyridinyl | CBr | H |
| | H | Et | H | 3-chloro-2-pyridinyl | CBr | H |
| | Et | Et | H | 3-chloro-2-pyridinyl | CBr | H |
| | H | CO$_2$Me | H | 3-chloro-2-pyridinyl | CBr | H |
| | Me | Et | H | 3-chloro-2-pyridinyl | CBr | H |
| | Et | Me | H | 3-chloro-2-pyridinyl | CBr | H |
| | CH$_2$CH=CH$_2$ | H | H | 3-chloro-2-pyridinyl | CBr | H |
| | H | CH$_2$CH=CH$_2$ | H | 3-chloro-2-pyridinyl | CBr | H |
| | CH$_2$CCH | H | H | 3-chloro-2-pyridinyl | CBr | H |
| | H | CH$_2$CCH | H | 3-chloro-2-pyridinyl | CBr | H |
| | iso-Pr | H | H | 3-chloro-2-pyridinyl | CBr | H |
| | H | iso-Pr | H | 3-chloro-2-pyridinyl | CBr | H |
| | H | 2-pyridinyl | H | 3-chloro-2-pyridinyl | CBr | H |
| | H | 3-pyridinyl | H | 3-chloro-2-pyridinyl | CBr | H |
| | H | 4-pyridinyl | H | 3-chloro-2-pyridinyl | CBr | H |
| | —(CH$_2$)$_3$— | | H | 3-chloro-2-pyridinyl | CBr | H |
| | —(CH$_2$)$_4$— | | H | 3-chloro-2-pyridinyl | CBr | H |
| | H | H | OMe | 3-chloro-2-pyridinyl | CBr | H |
| | Me | H | OMe | 3-chloro-2-pyridinyl | CBr | H |
| | H | Me | OMe | 3-chloro-2-pyridinyl | CBr | H |
| | Me | Me | OMe | 3-chloro-2-pyridinyl | CBr | H |
| | Et | H | OMe | 3-chloro-2-pyridinyl | CBr | H |
| | H | Et | OMe | 3-chloro-2-pyridinyl | CBr | H |
| | Et | Et | OMe | 3-chloro-2-pyridinyl | CBr | H |
| | H | CO$_2$Me | OMe | 3-chloro-2-pyridinyl | CBr | H |
| | Me | Et | OMe | 3-chloro-2-pyridinyl | CBr | H |
| | Et | Me | OMe | 3-chloro-2-pyridinyl | CBr | H |
| | CH$_2$CH=CH$_2$ | H | OMe | 3-chloro-2-pyridinyl | CBr | H |
| | H | CH$_2$CH=CH$_2$ | OMe | 3-chloro-2-pyridinyl | CBr | H |

TABLE A-continued

| No. | R² | R³ | M | R¹⁹ᵃ | X | R²⁰ᵃʸ |
|---|---|---|---|---|---|---|
| | CH₂CCH | H | OMe | 3-chloro-2-pyridinyl | CBr | H |
| | H | CH₂CCH | OMe | 3-chloro-2-pyridinyl | CBr | H |
| | iso-Pr | H | OMe | 3-chloro-2-pyridinyl | CBr | H |
| | H | iso-Pr | OMe | 3-chloro-2-pyridinyl | CBr | H |
| | H | 2-pyridinyl | OMe | 3-chloro-2-pyridinyl | CBr | H |
| | H | 3-pyridinyl | OMe | 3-chloro-2-pyridinyl | CBr | H |
| | H | 4-pyridinyl | OMe | 3-chloro-2-pyridinyl | CBr | H |
| | —(CH₂)₃— | | OMe | 3-chloro-2-pyridinyl | CBr | H |
| | —(CH₂)₄— | | OMe | 3-chloro-2-pyridinyl | CBr | H |
| | H | H | NMe₂ | 3-chloro-2-pyridinyl | CBr | H |
| | Me | H | NMe₂ | 3-chloro-2-pyridinyl | CBr | H |
| | H | Me | NMe₂ | 3-chloro-2-pyridinyl | CBr | H |
| | Me | Me | NMe₂ | 3-chloro-2-pyridinyl | CBr | H |
| | Et | H | NMe₂ | 3-chloro-2-pyridinyl | CBr | H |
| | H | Et | NMe₂ | 3-chloro-2-pyridinyl | CBr | H |
| | Et | Et | NMe₂ | 3-chloro-2-pyridinyl | CBr | H |
| | H | CO₂Me | NMe₂ | 3-chloro-2-pyridinyl | CBr | H |
| | Me | Et | NMe₂ | 3-chloro-2-pyridinyl | CBr | H |
| | Et | Me | NMe₂ | 3-chloro-2-pyridinyl | CBr | H |
| | CH₂CH=CH₂ | H | NMe₂ | 3-chloro-2-pyridinyl | CBr | H |
| | H | CH₂CH=CH₂ | NMe₂ | 3-chloro-2-pyridinyl | CBr | H |
| | CH₂CCH | H | NMe₂ | 3-chloro-2-pyridinyl | CBr | H |
| | H | CH₂CCH | NMe₂ | 3-chloro-2-pyridinyl | CBr | H |
| | iso-Pr | H | NMe₂ | 3-chloro-2-pyridinyl | CBr | H |
| | H | iso-Pr | NMe₂ | 3-chloro-2-pyridinyl | CBr | H |
| | H | 2-pyridinyl | NMe₂ | 3-chloro-2-pyridinyl | CBr | H |
| | H | 3-pyridinyl | NMe₂ | 3-chloro-2-pyridinyl | CBr | H |
| | H | 4-pyridinyl | NMe₂ | 3-chloro-2-pyridinyl | CBr | H |
| | —(CH₂)₃— | | NMe₂ | 3-chloro-2-pyridinyl | CBr | H |
| | —(CH₂)₄— | | NMe₂ | 3-chloro-2-pyridinyl | CBr | H |
| | H | H | NHMe | 3-chloro-2-pyridinyl | CBr | H |
| | Me | H | NHMe | 3-chloro-2-pyridinyl | CBr | H |
| | H | Me | NHMe | 3-chloro-2-pyridinyl | CBr | H |
| | Me | Me | NHMe | 3-chloro-2-pyridinyl | CBr | H |
| | Et | H | NHMe | 3-chloro-2-pyridinyl | CBr | H |
| | H | Et | NHMe | 3-chloro-2-pyridinyl | CBr | H |
| | Et | Et | NHMe | 3-chloro-2-pyridinyl | CBr | H |
| | H | CO₂Me | NHMe | 3-chloro-2-pyridinyl | CBr | H |
| | Me | Et | NHMe | 3-chloro-2-pyridinyl | CBr | H |

TABLE A-continued

| No. | R² | R³ | M | R¹⁹ᵃ | X | R²⁰ᵃʸ |
|---|---|---|---|---|---|---|
| | Et | Me | NHMe | 3-chloro-2-pyridinyl | CBr | H |
| | CH₂CH=CH₂ | H | NHMe | 3-chloro-2-pyridinyl | CBr | H |
| | H | CH₂CH=CH₂ | NHMe | 3-chloro-2-pyridinyl | CBr | H |
| | CH₂CCH | H | NHMe | 3-chloro-2-pyridinyl | CBr | H |
| | H | CH₂CCH | NHMe | 3-chloro-2-pyridinyl | CBr | H |
| | iso-Pr | H | NHMe | 3-chloro-2-pyridinyl | CBr | H |
| | H | iso-Pr | NHMe | 3-chloro-2-pyridinyl | CBr | H |
| | H | 2-pyridinyl | NHMe | 3-chloro-2-pyridinyl | CBr | H |
| | H | 3-pyridinyl | NHMe | 3-chloro-2-pyridinyl | CBr | H |
| | H | 4-pyridinyl | NHMe | 3-chloro-2-pyridinyl | CBr | H |
| | —(CH₂)₃— | | NHMe | 3-chloro-2-pyridinyl | PCBr | H |
| | —(CH₂)₄— | | NHMe | 3-chloro-2-pyridinyl | CBr | H |
| | H | H | H | 3-chloro-2-pyridinyl | CBr | Br |
| | Me | H | H | 3-chloro-2-pyridinyl | CBr | Br |
| | H | Me | H | 3-chloro-2-pyridinyl | CBr | Br |
| | Me | Me | H | 3-chloro-2-pyridinyl | CBr | Br |
| | Et | H | H | 3-chloro-2-pyridinyl | CBr | Br |
| | H | Et | H | 3-chloro-2-pyridinyl | CBr | Br |
| | Et | Et | H | 3-chloro-2-pyridinyl | CBr | Br |
| | H | CO₂Me | H | 3-chloro-2-pyridinyl | CBr | Br |
| | Me | Et | H | 3-chloro-2-pyridinyl | CBr | Br |
| | Et | Me | H | 3-chloro-2-pyridinyl | CBr | Br |
| | CH₂CH=CH₂ | H | H | 3-chloro-2-pyridinyl | CBr | Br |
| | H | CH₂CH=CH₂ | H | 3-chloro-2-pyridinyl | CBr | Br |
| | CH₂CCH | H | H | 3-chloro-2-pyridinyl | CBr | Br |
| | H | CH₂CCH | H | 3-chloro-2-pyridinyl | CBr | Br |
| | iso-Pr | H | H | 3-chloro-2-pyridinyl | CBr | Br |
| | H | iso-Pr | H | 3-chloro-2-pyridinyl | CBr | Br |
| | H | 2-pyridinyl | H | 3-chloro-2-pyridinyl | CBr | Br |
| | H | 3-pyridinyl | H | 3-chloro-2-pyridinyl | CBr | Br |
| | H | 4-pyridinyl | H | 3-chloro-2-pyridinyl | CBr | Br |
| | —(CH₂)₃— | | H | 3-chloro-2-pyridinyl | CBr | Br |
| | —(CH₂)₄— | | H | 3-chloro-2-pyridinyl | CBr | Br |
| | H | H | OMe | 3-chloro-2-pyridinyl | CBr | Br |
| | Me | H | OMe | 3-chloro-2-pyridinyl | CBr | Br |
| | H | Me | OMe | 3-chloro-2-pyridinyl | CBr | Br |
| | Me | Me | OMe | 3-chloro-2-pyridinyl | CBr | Br |
| | Et | H | OMe | 3-chloro-2-pyridinyl | CBr | Br |
| | H | Et | OMe | 3-chloro-2-pyridinyl | CBr | Br |

TABLE A-continued

| No. | R² | R³ | M | R¹⁹ᵃ | X | R²⁰ᵃʸ |
|---|---|---|---|---|---|---|
| | Et | Et | OMe | 3-chloro-2-pyridinyl | CBr | Br |
| | H | CO₂Me | OMe | 3-chloro-2-pyridinyl | CBr | Br |
| | Me | Et | OMe | 3-chloro-2-pyridinyl | CBr | Br |
| | Et | Me | OMe | 3-chloro-2-pyridinyl | CBr | Br |
| | CH₂CH=CH₂ | H | OMe | 3-chloro-2-pyridinyl | CBr | Br |
| | H | CH₂CH=CH₂ | OMe | 3-chloro-2-pyridinyl | CBr | Br |
| | CH₂CCH | H | OMe | 3-chloro-2-pyridinyl | CBr | Br |
| | H | CH₂CCH | OMe | 3-chloro-2-pyridinyl | CBr | Br |
| | iso-Pr | H | OMe | 3-chloro-2-pyridinyl | CBr | Br |
| | H | iso-Pr | OMe | 3-chloro-2-pyridinyl | CBr | Br |
| | H | 2-pyridinyl | OMe | 3-chloro-2-pyridinyl | CBr | Br |
| | H | 3-pyridinyl | OMe | 3-chloro-2-pyridinyl | CBr | Br |
| | H | 4-pyridinyl | OMe | 3-chloro-2-pyridinyl | CBr | Br |
| | —(CH₂)₃— | | OMe | 3-chloro-2-pyridinyl | CBr | Br |
| | —(CH₂)₄— | | OMe | 3-chloro-2-pyridinyl | CBr | Br |
| | H | H | NMe₂ | 3-chloro-2-pyridinyl | CBr | Br |
| | Me | H | NMe₂ | 3-chloro-2-pyridinyl | CBr | Br |
| | H | Me | NMe₂ | 3-chloro-2-pyridinyl | CBr | Br |
| | Me | Me | NMe₂ | 3-chloro-2-pyridinyl | CBr | Br |
| | Et | H | NMe₂ | 3-chloro-2-pyridinyl | CBr | Br |
| | H | Et | NMe₂ | 3-chloro-2-pyridinyl | CBr | Br |
| | Et | Et | NMe₂ | 3-chloro-2-pyridinyl | CBr | Br |
| | H | CO₂Me | NMe₂ | 3-chloro-2-pyridinyl | CBr | Br |
| | Me | Et | NMe₂ | 3-chloro-2-pyridinyl | CBr | Br |
| | Et | Me | NMe₂ | 3-chloro-2-pyridinyl | CBr | Br |
| | CH₂CH=CH₂ | H | NMe₂ | 3-chloro-2-pyridinyl | CBr | Br |
| | H | CH₂CH=CH₂ | NMe₂ | 3-chloro-2-pyridinyl | CBr | Br |
| | CH₂CCH | H | NMe₂ | 3-chloro-2-pyridinyl | CBr | Br |
| | H | CH₂CCH | NMe₂ | 3-chloro-2-pyridinyl | CBr | Br |
| | iso-Pr | H | NMe₂ | 3-chloro-2-pyridinyl | CBr | Br |
| | H | iso-Pr | NMe₂ | 3-chloro-2-pyridinyl | CBr | Br |
| | H | 2-pyridinyl | NMe₂ | 3-chloro-2-pyridinyl | CBr | Br |
| | H | 3-pyridinyl | NMe₂ | 3-chloro-2-pyridinyl | CBr | Br |
| | H | 4-pyridinyl | NMe₂ | 3-chloro-2-pyridinyl | CBr | Br |
| | —(CH₂)₃— | | NMe₂ | 3-chloro-2-pyridinyl | CBr | Br |
| | —(CH₂)₄— | | NMe₂ | 3-chloro-2-pyridinyl | CBr | Br |
| | H | H | NHMe | 3-chloro-2-pyridinyl | CBr | Br |
| | Me | H | NHMe | 3-chloro-2-pyridinyl | CBr | Br |
| | H | Me | NHMe | 3-chloro-2-pyridinyl | CBr | Br |

TABLE A-continued

| No. | R² | R³ | M | R¹⁹ᵃ | X | R²⁰ᵃʸ |
|---|---|---|---|---|---|---|
| | Me | Me | NHMe | 3-chloro-2-pyridinyl | CBr | Br |
| | Et | H | NHMe | 3-chloro-2-pyridinyl | CBr | Br |
| | H | Et | NHMe | 3-chloro-2-pyridinyl | CBr | Br |
| | Et | Et | NHMe | 3-chloro-2-pyridinyl | CBr | Br |
| | H | CO₂Me | NHMe | 3-chloro-2-pyridinyl | CBr | Br |
| | Me | Et | NHMe | 3-chloro-2-pyridinyl | CBr | Br |
| | Et | Me | NHMe | 3-chloro-2-pyridinyl | CBr | Br |
| | CH₂CH=CH₂ | H | NHMe | 3-chloro-2-pyridinyl | CBr | Br |
| | H | CH₂CH=CH₂ | NHMe | 3-chloro-2-pyridinyl | CBr | Br |
| | CH₂CCH | H | NHMe | 3-chloro-2-pyridinyl | CBr | Br |
| | H | CH₂CCH | NHMe | 3-chloro-2-pyridinyl | CBr | Br |
| | iso-Pr | H | NHMe | 3-chloro-2-pyridinyl | CBr | Br |
| | H | iso-Pr | NHMe | 3-chloro-2-pyridinyl | CBr | Br |
| | H | 2-pyridinyl | NHMe | 3-chloro-2-pyridinyl | CBr | Br |
| | H | 3-pyridinyl | NHMe | 3-chloro-2-pyridinyl | CBr | Br |
| | H | 4-pyridinyl | NHMe | 3-chloro-2-pyridinyl | CBr | Br |
| | —(CH₂)₃— | | NHMe | 3-chloro-2-pyridinyl | CBr | Br |
| | —(CH₂)₄— | | NHMe | 3-chloro-2-pyridinyl | CBr | Br |
| | H | H | H | 2-chlorophenyl | N | Cl |
| | Me | H | H | 2-chlorophenyl | N | Cl |
| | H | Me | H | 2-chlorophenyl | N | Cl |
| | Me | Me | H | 2-chlorophenyl | N | Cl |
| | Et | H | H | 2-chlorophenyl | N | Cl |
| | H | Et | H | 2-chlorophenyl | N | Cl |
| | Et | Et | H | 2-chlorophenyl | N | Cl |
| | H | CO₂Me | H | 2-chlorophenyl | N | Cl |
| | Me | Et | H | 2-chlorophenyl | N | Cl |
| | Et | Me | H | 2-chlorophenyl | N | Cl |
| | CH₂CH=CH₂ | H | H | 2-chlorophenyl | N | Cl |
| | H | CH₂CH=CH₂ | H | 2-chlorophenyl | N | Cl |
| | CH₂CCH | H | H | 2-chlorophenyl | N | Cl |
| | H | CH₂CCH | H | 2-chlorophenyl | N | Cl |
| | iso-Pr | H | H | 2-chlorophenyl | N | Cl |
| | H | iso-Pr | H | 2-chlorophenyl | N | Cl |
| | H | 2-pyridinyl | H | 2-chlorophenyl | N | Cl |
| | H | 3-pyridinyl | H | 2-chlorophenyl | N | Cl |
| | H | 4-pyridinyl | H | 2-chlorophenyl | N | Cl |
| | —(CH₂)₃— | | H | 2-chlorophenyl | N | Cl |
| | —(CH₂)₄— | | H | 2-chlorophenyl | N | Cl |
| | H | H | H | 2-chlorophenyl | N | Br |
| | Me | H | H | 2-chlorophenyl | N | Br |
| | H | Me | H | 2-chlorophenyl | N | Br |
| | Me | Me | H | 2-chlorophenyl | N | Br |
| | Et | H | H | 2-chlorophenyl | N | Br |
| | H | Et | H | 2-chlorophenyl | N | Br |
| | Et | Et | H | 2-chlorophenyl | N | Br |
| | H | CO₂Me | H | 2-chlorophenyl | N | Br |
| | Me | Et | H | 2-chlorophenyl | N | Br |
| | Et | Me | H | 2-chlorophenyl | N | Br |
| | CH₂CH=CH₂ | H | H | 2-chlorophenyl | N | Br |
| | H | CH₂CH=CH₂ | H | 2-chlorophenyl | N | Br |
| | CH₂CCH | H | H | 2-chlorophenyl | N | Br |
| | H | CH₂CCH | H | 2-chlorophenyl | N | Br |
| | iso-Pr | H | H | 2-chlorophenyl | N | Br |
| | H | iso-Pr | H | 2-chlorophenyl | N | Br |
| | H | 2-pyridinyl | H | 2-chlorophenyl | N | Br |

TABLE A-continued

| No. | R² | R³ | M | R¹⁹ᵃ | X | R²⁰ᵃʸ |
|---|---|---|---|---|---|---|
| | H | 3-pyridinyl | H | 2-chlorophenyl | N | Br |
| | H | 4-pyridinyl | H | 2-chlorophenyl | N | Br |
| | —(CH₂)₃— | | H | 2-chlorophenyl | N | Br |
| | —(CH₂)₄— | | H | 2-chlorophenyl | N | Br |
| | H | H | H | 2-chlorophenyl | N | CF₃ |
| | Me | H | H | 2-chlorophenyl | N | CF₃ |
| | H | Me | H | 2-chlorophenyl | N | CF₃ |
| | Me | Me | H | 2-chlorophenyl | N | CF₃ |
| | Et | H | H | 2-chlorophenyl | N | CF₃ |
| | H | Et | H | 2-chlorophenyl | N | CF₃ |
| | Et | Et | H | 2-chlorophenyl | N | CF₃ |
| | H | CO₂Me | H | 2-chlorophenyl | N | CF₃ |
| | Me | Et | H | 2-chlorophenyl | N | CF₃ |
| | Et | Me | H | 2-chlorophenyl | N | CF₃ |
| | CH₂CH=CH₂ | H | H | 2-chlorophenyl | N | CF₃ |
| | H | CH₂CH=CH₂ | H | 2-chlorophenyl | N | CF₃ |
| | CH₂CCH | H | H | 2-chlorophenyl | N | CF₃ |
| | H | CH₂CCH | H | 2-chlorophenyl | N | CF₃ |
| | iso-Pr | H | H | 2-chlorophenyl | N | CF₃ |
| | H | iso-Pr | H | 2-chlorophenyl | N | CF₃ |
| | H | 2-pyridinyl | H | 2-chlorophenyl | N | CF₃ |
| | H | 3-pyridinyl | H | 2-chlorophenyl | N | CF₃ |
| | H | 4-pyridinyl | H | 2-chlorophenyl | N | CF₃ |
| | —(CH₂)₃— | | H | 2-chlorophenyl | N | CF₃ |
| | —(CH₂)₄— | | H | 2-chlorophenyl | N | CF₃ |
| | H | H | OMe | 2-chlorophenyl | N | Cl |
| | Me | H | OMe | 2-chlorophenyl | N | Cl |
| | H | Me | OMe | 2-chlorophenyl | N | Cl |
| | Me | Me | OMe | 2-chlorophenyl | N | Cl |
| | Et | H | OMe | 2-chlorophenyl | N | Cl |
| | H | Et | OMe | 2-chlorophenyl | N | Cl |
| | Et | Et | OMe | 2-chlorophenyl | N | Cl |
| | H | CO₂Me | OMe | 2-chlorophenyl | N | Cl |
| | Me | Et | OMe | 2-chlorophenyl | N | Cl |
| | Et | Me | OMe | 2-chlorophenyl | N | Cl |
| | CH₂CH=CH₂ | H | OMe | 2-chlorophenyl | N | Cl |
| | H | CH₂CH=CH₂ | OMe | 2-chlorophenyl | N | Cl |
| | CH₂CCH | H | OMe | 2-chlorophenyl | N | Cl |
| | H | CH₂CCH | OMe | 2-chlorophenyl | N | Cl |
| | iso-Pr | H | OMe | 2-chlorophenyl | N | Cl |
| | H | iso-Pr | OMe | 2-chlorophenyl | N | Cl |
| | H | 2-pyridinyl | OMe | 2-chlorophenyl | N | Cl |
| | H | 3-pyridinyl | OMe | 2-chlorophenyl | N | Cl |
| | H | 4-pyridinyl | OMe | 2-chlorophenyl | N | Cl |
| | —(CH₂)₃— | | OMe | 2-chlorophenyl | N | Cl |
| | —(CH₂)₄— | | OMe | 2-chlorophenyl | N | Cl |
| | H | H | OMe | 2-chlorophenyl | N | Br |
| | Me | H | OMe | 2-chlorophenyl | N | Br |
| | H | Me | OMe | 2-chlorophenyl | N | Br |
| | Me | Me | OMe | 2-chlorophenyl | N | Br |
| | Et | H | OMe | 2-chlorophenyl | N | Br |
| | H | Et | OMe | 2-chlorophenyl | N | Br |
| | Et | Et | OMe | 2-chlorophenyl | N | Br |
| | H | CO₂Me | OMe | 2-chlorophenyl | N | Br |
| | Me | Et | OMe | 2-chlorophenyl | N | Br |
| | Et | Me | OMe | 2-chlorophenyl | N | Br |
| | CH₂CH=CH₂ | H | OMe | 2-chlorophenyl | N | Br |
| | H | CH₂CH=CH₂ | OMe | 2-chlorophenyl | N | Br |
| | CH₂CCH | H | OMe | 2-chlorophenyl | N | Br |
| | H | CH₂CCH | OMe | 2-chlorophenyl | N | Br |
| | iso-Pr | H | OMe | 2-chlorophenyl | N | Br |
| | H | iso-Pr | OMe | 2-chlorophenyl | N | Br |
| | H | 2-pyridinyl | OMe | 2-chlorophenyl | N | Br |
| | H | 3-pyridinyl | OMe | 2-chlorophenyl | N | Br |
| | H | 4-pyridinyl | OMe | 2-chlorophenyl | N | Br |
| | —(CH₂)₃— | | OMe | 2-chlorophenyl | N | Br |
| | —(CH₂)₄— | | OMe | 2-chlorophenyl | N | Br |

TABLE A-continued

| No. | $R^2$ | $R^3$ | M | $R^{19a}$ | X | $R^{20ay}$ |
|---|---|---|---|---|---|---|
| | H | H | OMe | 2-chlorophenyl | N | $CF_3$ |
| | Me | H | OMe | 2-chlorophenyl | N | $CF_3$ |
| | H | Me | OMe | 2-chlorophenyl | N | $CF_3$ |
| | Me | Me | OMe | 2-chlorophenyl | N | $CF_3$ |
| | Et | H | OMe | 2-chlorophenyl | N | $CF_3$ |
| | H | Et | OMe | 2-chlorophenyl | N | $CF_3$ |
| | Et | Et | OMe | 2-chlorophenyl | N | $CF_3$ |
| | H | $CO_2Me$ | OMe | 2-chlorophenyl | N | $CF_3$ |
| | Me | Et | OMe | 2-chlorophenyl | N | $CF_3$ |
| | Et | Me | OMe | 2-chlorophenyl | N | $CF_3$ |
| | $CH_2CH=CH_2$ | H | OMe | 2-chlorophenyl | N | $CF_3$ |
| | H | $CH_2CH=CH_2$ | OMe | 2-chlorophenyl | N | $CF_3$ |
| | $CH_2CCH$ | H | OMe | 2-chlorophenyl | N | $CF_3$ |
| | H | $CH_2CCH$ | OMe | 2-chlorophenyl | N | $CF_3$ |
| | iso-Pr | H | OMe | 2-chlorophenyl | N | $CF_3$ |
| | H | iso-Pr | OMe | 2-chlorophenyl | N | $CF_3$ |
| | H | 2-pyridinyl | OMe | 2-chlorophenyl | N | $CF_3$ |
| | H | 3-pyridinyl | OMe | 2-chlorophenyl | N | $CF_3$ |
| | H | 4-pyridinyl | OMe | 2-chlorophenyl | N | $CF_3$ |
| | —$(CH_2)_3$— | | OMe | 2-chlorophenyl | N | $CF_3$ |
| | —$(CH_2)_4$— | | OMe | 2-chlorophenyl | N | $CF_3$ |
| | H | H | NHMe | 2-chlorophenyl | N | Cl |
| | Me | H | NHMe | 2-chlorophenyl | N | Cl |
| | H | Me | NHMe | 2-chlorophenyl | N | Cl |
| | Me | Me | NHMe | 2-chlorophenyl | N | Cl |
| | Et | H | NHMe | 2-chlorophenyl | N | Cl |
| | H | Et | NHMe | 2-chlorophenyl | N | Cl |
| | Et | Et | NHMe | 2-chlorophenyl | N | Cl |
| | H | $CO_2Me$ | NHMe | 2-chlorophenyl | N | Cl |
| | Me | Et | NHMe | 2-chlorophenyl | N | Cl |
| | Et | Me | NHMe | 2-chlorophenyl | N | Cl |
| | $CH_2CH=CH_2$ | H | NHMe | 2-chlorophenyl | N | Cl |
| | H | $CH_2CH=CH_2$ | NHMe | 2-chlorophenyl | N | Cl |
| | $CH_2CCH$ | H | NHMe | 2-chlorophenyl | N | Cl |
| | H | $CH_2CCH$ | NHMe | 2-chlorophenyl | N | Cl |
| | iso-Pr | H | NHMe | 2-chlorophenyl | N | Cl |
| | H | iso-Pr | NHMe | 2-chlorophenyl | N | Cl |
| | H | 2-pyridinyl | NHMe | 2-chlorophenyl | N | Cl |
| | H | 3-pyridinyl | NHMe | 2-chlorophenyl | N | Cl |
| | H | 4-pyridinyl | NHMe | 2-chlorophenyl | N | Cl |
| | —$(CH_2)_3$— | | NHMe | 2-chlorophenyl | N | Cl |
| | —$(CH_2)_4$— | | NHMe | 2-chlorophenyl | N | Cl |
| | H | H | NHMe | 2-chlorophenyl | N | Br |
| | Me | H | NHMe | 2-chlorophenyl | N | Br |
| | H | Me | NHMe | 2-chlorophenyl | N | Br |
| | Me | Me | NHMe | 2-chlorophenyl | N | Br |
| | Et | H | NHMe | 2-chlorophenyl | N | Br |
| | H | Et | NHMe | 2-chlorophenyl | N | Br |
| | Et | Et | NHMe | 2-chlorophenyl | N | Br |
| | H | $CO_2Me$ | NHMe | 2-chlorophenyl | N | Br |
| | Me | Et | NHMe | 2-chlorophenyl | N | Br |
| | Et | Me | NHMe | 2-chlorophenyl | N | Br |
| | $CH_2CH=CH_2$ | H | NHMe | 2-chlorophenyl | N | Br |
| | H | $CH_2CH=CH_2$ | NHMe | 2-chlorophenyl | N | Br |
| | $CH_2CCH$ | H | NHMe | 2-chlorophenyl | N | Br |
| | H | $CH_2CCH$ | NHMe | 2-chlorophenyl | N | Br |
| | iso-Pr | H | NHMe | 2-chlorophenyl | N | Br |
| | H | iso-Pr | NHMe | 2-chlorophenyl | N | Br |
| | H | 2-pyridinyl | NHMe | 2-chlorophenyl | N | Br |
| | H | 3-pyridinyl | NHMe | 2-chlorophenyl | N | Br |
| | H | 4-pyridinyl | NHMe | 2-chlorophenyl | N | Br |
| | —$(CH_2)_3$— | | NHMe | 2-chlorophenyl | N | Br |
| | —$(CH_2)_4$— | | NHMe | 2-chlorophenyl | N | Br |
| | H | H | NHMe | 2-chlorophenyl | N | $CF_3$ |
| | Me | H | NHMe | 2-chlorophenyl | N | $CF_3$ |
| | H | Me | NHMe | 2-chlorophenyl | N | $CF_3$ |
| | Me | Me | NHMe | 2-chlorophenyl | N | $CF_3$ |
| | Et | H | NHMe | 2-chlorophenyl | N | $CF_3$ |
| | H | Et | NHMe | 2-chlorophenyl | N | $CF_3$ |

TABLE A-continued

| No. | $R^2$ | $R^3$ | M | $R^{19a}$ | X | $R^{20ay}$ |
|---|---|---|---|---|---|---|
| | Et | Et | NHMe | 2-chlorophenyl | N | $CF_3$ |
| | H | $CO_2Me$ | NHMe | 2-chlorophenyl | N | $CF_3$ |
| | Me | Et | NHMe | 2-chlorophenyl | N | $CF_3$ |
| | Et | Me | NHMe | 2-chlorophenyl | N | $CF_3$ |
| | $CH_2CH=CH_2$ | H | NHMe | 2-chlorophenyl | N | $CF_3$ |
| | H | $CH_2CH=CH_2$ | NHMe | 2-chlorophenyl | N | $CF_3$ |
| | $CH_2CCH$ | H | NHMe | 2-chlorophenyl | N | $CF_3$ |
| | H | $CH_2CCH$ | NHMe | 2-chlorophenyl | N | $CF_3$ |
| | iso-Pr | H | NHMe | 2-chlorophenyl | N | $CF_3$ |
| | H | iso-Pr | NHMe | 2-chlorophenyl | N | $CF_3$ |
| | H | 2-pyridinyl | NHMe | 2-chlorophenyl | N | $CF_3$ |
| | H | 3-pyridinyl | NHMe | 2-chlorophenyl | N | $CF_3$ |
| | H | 4-pyridinyl | NHMe | 2-chlorophenyl | N | $CF_3$ |
| | —$(CH_2)_3$— | | NHMe | 2-chlorophenyl | N | $CF_3$ |
| | —$(CH_2)_4$— | | NHMe | 2-chlorophenyl | N | $CF_3$ |
| | H | H | $NMe_2$ | 2-chlorophenyl | N | Cl |
| | Me | H | $NMe_2$ | 2-chlorophenyl | N | Cl |
| | H | Me | $NMe_2$ | 2-chlorophenyl | N | Cl |
| | Me | Me | $NMe_2$ | 2-chlorophenyl | N | Cl |
| | Et | H | $NMe_2$ | 2-chlorophenyl | N | Cl |
| | H | Et | $NMe_2$ | 2-chlorophenyl | N | Cl |
| | Et | Et | $NMe_2$ | 2-chlorophenyl | N | Cl |
| | H | $CO_2Me$ | $NMe_2$ | 2-chlorophenyl | N | Cl |
| | Me | Et | $NMe_2$ | 2-chlorophenyl | N | Cl |
| | Et | Me | $NMe_2$ | 2-chlorophenyl | N | Cl |
| | $CH_2CH=CH_2$ | H | $NMe_2$ | 2-chlorophenyl | N | Cl |
| | H | $CH_2CH=CH_2$ | $NMe_2$ | 2-chlorophenyl | N | Cl |
| | $CH_2CCH$ | H | $NMe_2$ | 2-chlorophenyl | N | Cl |
| | H | $CH_2CCH$ | $NMe_2$ | 2-chlorophenyl | N | Cl |
| | iso-Pr | H | $NMe_2$ | 2-chlorophenyl | N | Cl |
| | H | iso-Pr | $NMe_2$ | 2-chlorophenyl | N | Cl |
| | H | 2-pyridinyl | $NMe_2$ | 2-chlorophenyl | N | Cl |
| | H | 3-pyridinyl | $NMe_2$ | 2-chlorophenyl | N | Cl |
| | H | 4-pyridinyl | $NMe_2$ | 2-chlorophenyl | N | Cl |
| | —$(CH_2)_3$— | | $NMe_2$ | 2-chlorophenyl | N | Cl |
| | —$(CH_2)_4$— | | $NMe_2$ | 2-chlorophenyl | N | Cl |
| | H | H | $NMe_2$ | 2-chlorophenyl | N | Br |
| | Me | H | $NMe_2$ | 2-chlorophenyl | N | Br |
| | H | Me | $NMe_2$ | 2-chlorophenyl | N | Br |
| | Me | Me | $NMe_2$ | 2-chlorophenyl | N | Br |
| | Et | H | $NMe_2$ | 2-chlorophenyl | N | Br |
| | H | Et | $NMe_2$ | 2-chlorophenyl | N | Br |
| | Et | Et | $NMe_2$ | 2-chlorophenyl | N | Br |
| | H | $CO_2Me$ | $NMe_2$ | 2-chlorophenyl | N | Br |
| | Me | Et | $NMe_2$ | 2-chlorophenyl | N | Br |
| | Et | Me | $NMe_2$ | 2-chlorophenyl | N | Br |
| | $CH_2CH=CH_2$ | H | $NMe_2$ | 2-chlorophenyl | N | Br |
| | H | $CH_2CH=CH_2$ | $NMe_2$ | 2-chlorophenyl | N | Br |
| | $CH_2CCH$ | H | $NMe_2$ | 2-chlorophenyl | N | Br |
| | H | $CH_2CCH$ | $NMe_2$ | 2-chlorophenyl | N | Br |
| | iso-Pr | H | $NMe_2$ | 2-chlorophenyl | N | Br |
| | H | iso-Pr | $NMe_2$ | 2-chlorophenyl | N | Br |
| | H | 2-pyridinyl | $NMe_2$ | 2-chlorophenyl | N | Br |
| | H | 3-pyridinyl | $NMe_2$ | 2-chlorophenyl | N | Br |
| | H | 4-pyridinyl | $NMe_2$ | 2-chlorophenyl | N | Br |
| | —$(CH_2)_3$— | | $NMe_2$ | 2-chlorophenyl | N | Br |
| | —$(CH_2)_4$— | | $NMe_2$ | 2-chlorophenyl | N | Br |
| | H | H | $NMe_2$ | 2-chlorophenyl | N | $CF_3$ |
| | Me | H | $NMe_2$ | 2-chlorophenyl | N | $CF_3$ |
| | H | Me | $NMe_2$ | 2-chlorophenyl | N | $CF_3$ |
| | Me | Me | $NMe_2$ | 2-chlorophenyl | N | $CF_3$ |
| | Et | H | $NMe_2$ | 2-chlorophenyl | N | $CF_3$ |
| | H | Et | $NMe_2$ | 2-chlorophenyl | N | $CF_3$ |
| | Et | Et | $NMe_2$ | 2-chlorophenyl | N | $CF_3$ |
| | H | $CO_2Me$ | $NMe_2$ | 2-chlorophenyl | N | $CF_3$ |
| | Me | Et | $NMe_2$ | 2-chlorophenyl | N | $CF_3$ |
| | Et | Me | $NMe_2$ | 2-chlorophenyl | N | $CF_3$ |
| | $CH_2CH=CH_2$ | H | $NMe_2$ | 2-chlorophenyl | N | $CF_3$ |
| | H | $CH_2CH=CH_2$ | $NMe_2$ | 2-chlorophenyl | N | $CF_3$ |

TABLE A-continued

| No. | $R^2$ | $R^3$ | M | $R^{19a}$ | X | $R^{20ay}$ |
|---|---|---|---|---|---|---|
| | CH$_2$CCH | H | NMe$_2$ | 2-chlorophenyl | N | CF$_3$ |
| | H | CH$_2$CCH | NMe$_2$ | 2-chlorophenyl | N | CF$_3$ |
| | iso-Pr | H | NMe$_2$ | 2-chlorophenyl | N | CF$_3$ |
| | H | iso-Pr | NMe$_2$ | 2-chlorophenyl | N | CF$_3$ |
| | H | 2-pyridinyl | NMe$_2$ | 2-chlorophenyl | N | CF$_3$ |
| | H | 3-pyridinyl | NMe$_2$ | 2-chlorophenyl | N | CF$_3$ |
| | H | 4-pyridinyl | NMe$_2$ | 2-chlorophenyl | N | CF$_3$ |
| | —(CH$_2$)$_3$— | | NMe$_2$ | 2-chlorophenyl | N | CF$_3$ |
| | —(CH$_2$)$_4$— | | NMe$_2$ | 2-chlorophenyl | N | CF$_3$ |
| | H | H | H | 2,6-dichlorophenyl | N | Cl |
| | Me | H | H | 2,6-dichlorophenyl | N | Cl |
| | H | Me | H | 2,6-dichlorophenyl | N | Cl |
| | Me | Me | H | 2,6-dichlorophenyl | N | Cl |
| | Et | H | H | 2,6-dichlorophenyl | N | Cl |
| | H | Et | H | 2,6-dichlorophenyl | N | Cl |
| | Et | Et | H | 2,6-dichlorophenyl | N | Cl |
| | H | CO$_2$Me | H | 2,6-dichlorophenyl | N | Cl |
| | Me | Et | H | 2,6-dichlorophenyl | N | Cl |
| | Et | Me | H | 2,6-dichlorophenyl | N | Cl |
| | CH$_2$CH=CH$_2$ | H | H | 2,6-dichlorophenyl | N | Cl |
| | H | CH$_2$CH=CH$_2$ | H | 2,6-dichlorophenyl | N | Cl |
| | CH$_2$CCH | H | H | 2,6-dichlorophenyl | N | Cl |
| | H | CH$_2$CCH | H | 2,6-dichlorophenyl | N | Cl |
| | iso-Pr | H | H | 2,6-dichlorophenyl | N | Cl |
| | H | iso-Pr | H | 2,6-dichlorophenyl | N | Cl |
| | H | 2-pyridinyl | H | 2,6-dichlorophenyl | N | Cl |
| | H | 3-pyridinyl | H | 2,6-dichlorophenyl | N | Cl |
| | H | 4-pyridinyl | H | 2,6-dichlorophenyl | N | Cl |
| | —(CH$_2$)$_3$— | | H | 2,6-dichlorophenyl | N | Cl |
| | —(CH$_2$)$_4$— | | H | 2,6-dichlorophenyl | N | Cl |
| | H | H | H | 2,6-dichlorophenyl | N | Br |
| | Me | H | H | 2,6-dichlorophenyl | N | Br |
| | H | Me | H | 2,6-dichlorophenyl | N | Br |
| | Me | Me | H | 2,6-dichlorophenyl | N | Br |
| | Et | H | H | 2,6-dichlorophenyl | N | Br |
| | H | Et | H | 2,6-dichlorophenyl | N | Br |
| | Et | Et | H | 2,6-dichlorophenyl | N | Br |
| | H | CO$_2$Me | H | 2,6-dichlorophenyl | N | Br |
| | Me | Et | H | 2,6-dichlorophenyl | N | Br |
| | Et | Me | H | 2,6-dichlorophenyl | N | Br |
| | CH$_2$CH=CH$_2$ | H | H | 2,6-dichlorophenyl | N | Br |
| | H | CH$_2$CH=CH$_2$ | H | 2,6-dichlorophenyl | N | Br |

TABLE A-continued

| No. | $R^2$ | $R^3$ | M | $R^{19a}$ | X | $R^{20ay}$ |
|---|---|---|---|---|---|---|
| | CH$_2$CCH | H | H | 2,6-dichlorophenyl | N | Br |
| | H | CH$_2$CCH | H | 2,6-dichlorophenyl | N | Br |
| | iso-Pr | H | H | 2,6-dichlorophenyl | N | Br |
| | H | iso-Pr | H | 2,6-dichlorophenyl | N | Br |
| | H | 2-pyridinyl | H | 2,6-dichlorophenyl | N | Br |
| | H | 3-pyridinyl | H | 2,6-dichlorophenyl | N | Br |
| | H | 4-pyridinyl | H | 2,6-dichlorophenyl | N | Br |
| | —(CH$_2$)$_3$— | | H | 2,6-dichlorophenyl | N | Br |
| | —(CH$_2$)$_4$— | | H | 2,6-dichlorophenyl | N | Br |
| | H | H | H | 2,6-dichlorophenyl | N | CF$_3$ |
| | Me | H | H | 2,6-dichlorophenyl | N | CF$_3$ |
| | H | Me | H | 2,6-dichlorophenyl | N | CF$_3$ |
| | Me | Me | H | 2,6-dichlorophenyl | N | CF$_3$ |
| | Et | H | H | 2,6-dichlorophenyl | N | CF$_3$ |
| | H | Et | H | 2,6-dichlorophenyl | N | CF$_3$ |
| | Et | Et | H | 2,6-dichlorophenyl | N | CF$_3$ |
| | H | CO$_2$Me | H | 2,6-dichlorophenyl | N | CF$_3$ |
| | Me | Et | H | 2,6-dichlorophenyl | N | CF$_3$ |
| | Et | Me | H | 2,6-dichlorophenyl | N | CF$_3$ |
| | CH$_2$CH=CH$_2$ | H | H | 2,6-dichlorophenyl | N | CF$_3$ |
| | H | CH$_2$CH=CH$_2$ | H | 2,6-dichlorophenyl | N | CF$_3$ |
| | CH$_2$CCH | H | H | 2,6-dichlorophenyl | N | CF$_3$ |
| | H | CH$_2$CCH | H | 2,6-dichlorophenyl | N | CF$_3$ |
| | iso-Pr | H | H | 2,6-dichlorophenyl | N | CF$_3$ |
| | H | iso-Pr | H | 2,6-dichlorophenyl | N | CF$_3$ |
| | H | 2-pyridinyl | H | 2,6-dichlorophenyl | N | CF$_3$ |
| | H | 3-pyridinyl | H | 2,6-dichlorophenyl | N | CF$_3$ |
| | H | 4-pyridinyl | H | 2,6-dichlorophenyl | N | CF$_3$ |
| | —(CH$_2$)$_3$— | | H | 2,6-dichlorophenyl | N | CF$_3$ |
| | —(CH$_2$)$_4$— | | H | 2,6-dichlorophenyl | N | CF$_3$ |
| | H | H | OMe | 2,6-dichlorophenyl | N | Cl |
| | Me | H | OMe | 2,6-dichlorophenyl | N | Cl |
| | H | Me | OMe | 2,6-dichlorophenyl | N | Cl |
| | Me | Me | OMe | 2,6-dichlorophenyl | N | Cl |
| | Et | H | OMe | 2,6-dichlorophenyl | N | Cl |
| | H | Et | OMe | 2,6-dichlorophenyl | N | Cl |
| | Et | Et | OMe | 2,6-dichlorophenyl | N | Cl |
| | H | CO$_2$Me | OMe | 2,6-dichlorophenyl | N | Cl |
| | Me | Et | OMe | 2,6-dichlorophenyl | N | Cl |

TABLE A-continued

| No. | $R^2$ | $R^3$ | M | $R^{19a}$ | X | $R^{20ay}$ |
|---|---|---|---|---|---|---|
| | Et | Me | OMe | 2,6-dichlorophenyl | N | Cl |
| | $CH_2CH=CH_2$ | H | OMe | 2,6-dichlorophenyl | N | Cl |
| | H | $CH_2CH=CH_2$ | OMe | 2,6-dichlorophenyl | N | Cl |
| | $CH_2CCH$ | H | OMe | 2,6-dichlorophenyl | N | Cl |
| | H | $CH_2CCH$ | OMe | 2,6-dichlorophenyl | N | Cl |
| | iso-Pr | H | OMe | 2,6-dichlorophenyl | N | Cl |
| | H | iso-Pr | OMe | 2,6-dichlorophenyl | N | Cl |
| | H | 2-pyridinyl | OMe | 2,6-dichlorophenyl | N | Cl |
| | H | 3-pyridinyl | OMe | 2,6-dichlorophenyl | N | Cl |
| | H | 4-pyridinyl | OMe | 2,6-dichlorophenyl | N | Cl |
| | —$(CH_2)_3$— | | OMe | 2,6-dichlorophenyl | N | Cl |
| | —$(CH_2)_4$— | | OMe | 2,6-dichlorophenyl | N | Cl |
| | H | H | OMe | 2,6-dichlorophenyl | N | Br |
| | Me | H | OMe | 2,6-dichlorophenyl | N | Br |
| | H | Me | OMe | 2,6-dichlorophenyl | N | Br |
| | Me | Me | OMe | 2,6-dichlorophenyl | N | Br |
| | Et | H | OMe | 2,6-dichlorophenyl | N | Br |
| | H | Et | OMe | 2,6-dichlorophenyl | N | Br |
| | Et | Et | OMe | 2,6-dichlorophenyl | N | Br |
| | H | $CO_2Me$ | OMe | 2,6-dichlorophenyl | N | Br |
| | Me | Et | OMe | 2,6-dichlorophenyl | N | Br |
| | Et | Me | OMe | 2,6-dichlorophenyl | N | Br |
| | $CH_2CH=CH_2$ | H | OMe | 2,6-dichlorophenyl | N | Br |
| | H | $CH_2CH=CH_2$ | OMe | 2,6-dichlorophenyl | N | Br |
| | $CH_2CCH$ | H | OMe | 2,6-dichlorophenyl | N | Br |
| | H | $CH_2CCH$ | OMe | 2,6-dichlorophenyl | N | Br |
| | iso-Pr | H | OMe | 2,6-dichlorophenyl | N | Br |
| | H | iso-Pr | OMe | 2,6-dichlorophenyl | N | Br |
| | H | 2-pyridinyl | OMe | 2,6-dichlorophenyl | N | Br |
| | H | 3-pyridinyl | OMe | 2,6-dichlorophenyl | N | Br |
| | H | 4-pyridinyl | OMe | 2,6-dichlorophenyl | N | Br |
| | —$(CH_2)_3$— | | OMe | 2,6-dichlorophenyl | N | Br |
| | —$(CH_2)_4$— | | OMe | 2,6-dichlorophenyl | N | Br |
| | H | H | OMe | 2,6-dichlorophenyl | N | $CF_3$ |
| | Me | H | OMe | 2,6-dichlorophenyl | N | $CF_3$ |
| | H | Me | OMe | 2,6-dichlorophenyl | N | $CF_3$ |
| | Me | Me | OMe | 2,6-dichlorophenyl | N | $CF_3$ |
| | Et | H | OMe | 2,6-dichlorophenyl | N | $CF_3$ |
| | H | Et | OMe | 2,6-dichlorophenyl | N | $CF_3$ |

TABLE A-continued

| No. | $R^2$ | $R^3$ | M | $R^{19a}$ | X | $R^{20ay}$ |
|---|---|---|---|---|---|---|
| | Et | Et | OMe | 2,6-dichlorophenyl | N | $CF_3$ |
| | H | $CO_2Me$ | OMe | 2,6-dichlorophenyl | N | $CF_3$ |
| | Me | Et | OMe | 2,6-dichlorophenyl | N | $CF_3$ |
| | Et | Me | OMe | 2,6-dichlorophenyl | N | $CF_3$ |
| | $CH_2CH=CH_2$ | H | OMe | 2,6-dichlorophenyl | N | $CF_3$ |
| | H | $CH_2CH=CH_2$ | OMe | 2,6-dichlorophenyl | N | $CF_3$ |
| | $CH_2CCH$ | H | OMe | 2,6-dichlorophenyl | N | $CF_3$ |
| | H | $CH_2CCH$ | OMe | 2,6-dichlorophenyl | N | $CF_3$ |
| | iso-Pr | H | OMe | 2,6-dichlorophenyl | N | $CF_3$ |
| | H | iso-Pr | OMe | 2,6-dichlorophenyl | N | $CF_3$ |
| | H | 2-pyridinyl | OMe | 2,6-dichlorophenyl | N | $CF_3$ |
| | H | 3-pyridinyl | OMe | 2,6-dichlorophenyl | N | $CF_3$ |
| | H | 4-pyridinyl | OMe | 2,6-dichlorophenyl | N | $CF_3$ |
| | —$(CH_2)_3$— | | OMe | 2,6-dichlorophenyl | N | $CF_3$ |
| | —$(CH_2)_4$— | | OMe | 2,6-dichlorophenyl | N | $CF_3$ |
| | H | H | NHMe | 2,6-dichlorophenyl | N | Cl |
| | Me | H | NHMe | 2,6-dichlorophenyl | N | Cl |
| | H | Me | NHMe | 2,6-dichlorophenyl | N | Cl |
| | Me | Me | NHMe | 2,6-dichlorophenyl | N | Cl |
| | Et | H | NHMe | 2,6-dichlorophenyl | N | Cl |
| | H | Et | NHMe | 2,6-dichlorophenyl | N | Cl |
| | Et | Et | NHMe | 2,6-dichlorophenyl | N | Cl |
| | H | $CO_2Me$ | NHMe | 2,6-dichlorophenyl | N | Cl |
| | Me | Et | NHMe | 2,6-dichlorophenyl | N | Cl |
| | Et | Me | NHMe | 2,6-dichlorophenyl | N | Cl |
| | $CH_2CH=CH_2$ | H | NHMe | 2,6-dichlorophenyl | N | Cl |
| | H | $CH_2CH=CH_2$ | NHMe | 2,6-dichlorophenyl | N | Cl |
| | $CH_2CCH$ | H | NHMe | 2,6-dichlorophenyl | N | Cl |
| | H | $CH_2CCH$ | NHMe | 2,6-dichlorophenyl | N | Cl |
| | iso-Pr | H | NHMe | 2,6-dichlorophenyl | N | Cl |
| | H | iso-Pr | NHMe | 2,6-dichlorophenyl | N | Cl |
| | H | 2-pyridinyl | NHMe | 2,6-dichlorophenyl | N | Cl |
| | H | 3-pyridinyl | NHMe | 2,6-dichlorophenyl | N | Cl |
| | H | 4-pyridinyl | NHMe | 2,6-dichlorophenyl | N | Cl |
| | —$(CH_2)_3$— | | NHMe | 2,6-dichlorophenyl | N | Cl |
| | —$(CH_2)_4$— | | NHMe | 2,6-dichlorophenyl | N | Cl |
| | H | H | NHMe | 2,6-dichlorophenyl | N | Br |
| | Me | H | NHMe | 2,6-dichlorophenyl | N | Br |
| | H | Me | NHMe | 2,6-dichlorophenyl | N | Br |

TABLE A-continued

| No. | $R^2$ | $R^3$ | M | $R^{19a}$ | X | $R^{20ay}$ |
|---|---|---|---|---|---|---|
| | Me | Me | NHMe | 2,6-dichlorophenyl | N | Br |
| | Et | H | NHMe | 2,6-dichlorophenyl | N | Br |
| | H | Et | NHMe | 2,6-dichlorophenyl | N | Br |
| | Et | Et | NHMe | 2,6-dichlorophenyl | N | Br |
| | H | $CO_2Me$ | NHMe | 2,6-dichlorophenyl | N | Br |
| | Me | Et | NHMe | 2,6-dichlorophenyl | N | Br |
| | Et | Me | NHMe | 2,6-dichlorophenyl | N | Br |
| | $CH_2CH=CH_2$ | H | NHMe | 2,6-dichlorophenyl | N | Br |
| | H | $CH_2CH=CH_2$ | NHMe | 2,6-dichlorophenyl | N | Br |
| | $CH_2CCH$ | H | NHMe | 2,6-dichlorophenyl | N | Br |
| | H | $CH_2CCH$ | NHMe | 2,6-dichlorophenyl | N | Br |
| | iso-Pr | H | NHMe | 2,6-dichlorophenyl | N | Br |
| | H | iso-Pr | NHMe | 2,6-dichlorophenyl | N | Br |
| | H | 2-pyridinyl | NHMe | 2,6-dichlorophenyl | N | Br |
| | H | 3-pyridinyl | NHMe | 2,6-dichlorophenyl | N | Br |
| | H | 4-pyridinyl | NHMe | 2,6-dichlorophenyl | N | Br |
| | —$(CH_2)_3$— | | NHMe | 2,6-dichlorophenyl | N | Br |
| | —$(CH_2)_4$— | | NHMe | 2,6-dichlorophenyl | N | Br |
| | H | H | NHMe | 2,6-dichlorophenyl | N | $CF_3$ |
| | Me | H | NHMe | 2,6-dichlorophenyl | N | $CF_3$ |
| | H | Me | NHMe | 2,6-dichlorophenyl | N | $CF_3$ |
| | Me | Me | NHMe | 2,6-dichlorophenyl | N | $CF_3$ |
| | Et | H | NHMe | 2,6-dichlorophenyl | N | $CF_3$ |
| | H | Et | NHMe | 2,6-dichlorophenyl | N | $CF_3$ |
| | Et | Et | NHMe | 2,6-dichlorophenyl | N | $CF_3$ |
| | H | $CO_2Me$ | NHMe | 2,6-dichlorophenyl | N | $CF_3$ |
| | Me | Et | NHMe | 2,6-dichlorophenyl | N | $CF_3$ |
| | Et | Me | NHMe | 2,6-dichlorophenyl | N | $CF_3$ |
| | $CH_2CH=CH_2$ | H | NHMe | 2,6-dichlorophenyl | N | $CF_3$ |
| | H | $CH_2CH=CH_2$ | NHMe | 2,6-dichlorophenyl | N | $CF_3$ |
| | $CH_2CCH$ | H | NHMe | 2,6-dichlorophenyl | N | $CF_3$ |
| | H | $CH_2CCH$ | NHMe | 2,6-dichlorophenyl | N | $CF_3$ |
| | iso-Pr | H | NHMe | 2,6-dichlorophenyl | N | $CF_3$ |
| | H | iso-Pr | NHMe | 2,6-dichlorophenyl | N | $CF_3$ |
| | H | 2-pyridinyl | NHMe | 2,6-dichlorophenyl | N | $CF_3$ |
| | H | 3-pyridinyl | NHMe | 2,6-dichlorophenyl | N | $CF_3$ |
| | H | 4-pyridinyl | NHMe | 2,6-dichlorophenyl | N | $CF_3$ |
| | —$(CH_2)_3$— | | NHMe | 2,6-dichlorophenyl | N | $CF_3$ |
| | —$(CH_2)_4$— | | NHMe | 2,6-dichlorophenyl | N | $CF_3$ |

TABLE A-continued

| No. | $R^2$ | $R^3$ | M | $R^{19a}$ | X | $R^{20ay}$ |
|---|---|---|---|---|---|---|
| | H | H | $NMe_2$ | 2,6-dichlorophenyl | N | Cl |
| | Me | H | $NMe_2$ | 2,6-dichlorophenyl | N | Cl |
| | H | Me | $NMe_2$ | 2,6-dichlorophenyl | N | Cl |
| | Me | Me | $NMe_2$ | 2,6-dichlorophenyl | N | Cl |
| | Et | H | $NMe_2$ | 2,6-dichlorophenyl | N | Cl |
| | H | Et | $NMe_2$ | 2,6-dichlorophenyl | N | Cl |
| | Et | Et | $NMe_2$ | 2,6-dichlorophenyl | N | Cl |
| | H | $CO_2Me$ | $NMe_2$ | 2,6-dichlorophenyl | N | Cl |
| | Me | Et | $NMe_2$ | 2,6-dichlorophenyl | N | Cl |
| | Et | Me | $NMe_2$ | 2,6-dichlorophenyl | N | Cl |
| | $CH_2CH=CH_2$ | H | $NMe_2$ | 2,6-dichlorophenyl | N | Cl |
| | H | $CH_2CH=CH_2$ | $NMe_2$ | 2,6-dichlorophenyl | N | Cl |
| | $CH_2CCH$ | H | $NMe_2$ | 2,6-dichlorophenyl | N | Cl |
| | H | $CH_2CCH$ | $NMe_2$ | 2,6-dichlorophenyl | N | Cl |
| | iso-Pr | H | $NMe_2$ | 2,6-dichlorophenyl | N | Cl |
| | H | iso-Pr | $NMe_2$ | 2,6-dichlorophenyl | N | Cl |
| | H | 2-pyridinyl | $NMe_2$ | 2,6-dichlorophenyl | N | Cl |
| | H | 3-pyridinyl | $NMe_2$ | 2,6-dichlorophenyl | N | Cl |
| | H | 4-pyridinyl | $NMe_2$ | 2,6-dichlorophenyl | N | Cl |
| | —$(CH_2)_3$— | | $NMe_2$ | 2,6-dichlorophenyl | N | Cl |
| | —$(CH_2)_4$— | | $NMe_2$ | 2,6-dichlorophenyl | N | Cl |
| | H | H | $NMe_2$ | 2,6-dichlorophenyl | N | Br |
| | Me | H | $NMe_2$ | 2,6-dichlorophenyl | N | Br |
| | H | Me | $NMe_2$ | 2,6-dichlorophenyl | N | Br |
| | Me | Me | $NMe_2$ | 2,6-dichlorophenyl | N | Br |
| | Et | H | $NMe_2$ | 2,6-dichlorophenyl | N | Br |
| | H | Et | $NMe_2$ | 2,6-dichlorophenyl | N | Br |
| | Et | Et | $NMe_2$ | 2,6-dichlorophenyl | N | Br |
| | H | $CO_2Me$ | $NMe_2$ | 2,6-dichlorophenyl | N | Br |
| | Me | Et | $NMe_2$ | 2,6-dichlorophenyl | N | Br |
| | Et | Me | $NMe_2$ | 2,6-dichlorophenyl | N | Br |
| | $CH_2CH=CH_2$ | H | $NMe_2$ | 2,6-dichlorophenyl | N | Br |
| | H | $CH_2CH=CH_2$ | $NMe_2$ | 2,6-dichlorophenyl | N | Br |
| | $CH_2CCH$ | H | $NMe_2$ | 2,6-dichlorophenyl | N | Br |
| | H | $CH_2CCH$ | $NMe_2$ | 2,6-dichlorophenyl | N | Br |
| | iso-Pr | H | $NMe_2$ | 2,6-dichlorophenyl | N | Br |
| | H | iso-Pr | $NMe_2$ | 2,6-dichlorophenyl | N | Br |
| | H | 2-pyridinyl | $NMe_2$ | 2,6-dichlorophenyl | N | Br |
| | H | 3-pyridinyl | $NMe_2$ | 2,6-dichlorophenyl | N | Br |

TABLE A-continued

| No. | R² | R³ | M | R¹⁹ᵃ | X | R²⁰ᵃʸ |
|---|---|---|---|---|---|---|
| | H | 4-pyridinyl | NMe₂ | 2,6-dichlorophenyl | N | Br |
| | | —(CH₂)₃— | NMe₂ | 2,6-dichlorophenyl | N | Br |
| | | —(CH₂)₄— | NMe₂ | 2,6-dichlorophenyl | N | Br |
| | H | H | NMe₂ | 2,6-dichlorophenyl | N | CF₃ |
| | Me | H | NMe₂ | 2,6-dichlorophenyl | N | CF₃ |
| | H | Me | NMe₂ | 2,6-dichlorophenyl | N | CF₃ |
| | Me | Me | NMe₂ | 2,6-dichlorophenyl | N | CF₃ |
| | Et | H | NMe₂ | 2,6-dichlorophenyl | N | CF₃ |
| | H | Et | NMe₂ | 2,6-dichlorophenyl | N | CF₃ |
| | Et | Et | NMe₂ | 2,6-dichlorophenyl | N | CF₃ |
| | H | CO₂Me | NMe₂ | 2,6-dichlorophenyl | N | CF₃ |
| | Me | Et | NMe₂ | 2,6-dichlorophenyl | N | CF₃ |
| | Et | Me | NMe₂ | 2,6-dichlorophenyl | N | CF₃ |
| | CH₂CH=CH₂ | H | NMe₂ | 2,6-dichlorophenyl | N | CF₃ |
| | H | CH₂CH=CH₂ | NMe₂ | 2,6-dichlorophenyl | N | CF₃ |
| | CH₂CCH | H | NMe₂ | 2,6-dichlorophenyl | N | CF₃ |
| | H | CH₂CCH | NMe₂ | 2,6-dichlorophenyl | N | CF₃ |
| | iso-Pr | H | NMe₂ | 2,6-dichlorophenyl | N | CF₃ |
| | H | iso-Pr | NMe₂ | 2,6-dichlorophenyl | N | CF₃ |
| | H | 2-pyridinyl | NMe₂ | 2,6-dichlorophenyl | N | CF₃ |
| | H | 3-pyridinyl | NMe₂ | 2,6-dichlorophenyl | N | CF₃ |
| | H | 4-pyridinyl | NMe₂ | 2,6-dichlorophenyl | N | CF₃ |
| | | —(CH₂)₃— | NMe₂ | 2,6-dichlorophenyl | N | CF₃ |
| | | —(CH₂)₄— | NMe₂ | 2,6-dichlorophenyl | N | CF₃ |
| | H | H | H | Me | N | Cl |
| | Me | H | H | Me | N | Cl |
| | H | Me | H | Me | N | Cl |
| | Me | Me | H | Me | N | Cl |
| | Et | H | H | Me | N | Cl |
| | H | Et | H | Me | N | Cl |
| | Et | Et | H | Me | N | Cl |
| | H | CO₂Me | H | Me | N | Cl |
| | Me | Et | H | Me | N | Cl |
| | Et | Me | H | Me | N | Cl |
| | CH₂CH=CH₂ | H | H | Me | N | Cl |
| | H | CH₂CH=CH₂ | H | Me | N | Cl |
| | CH₂CCH | H | H | Me | N | Cl |
| | H | CH₂CCH | H | Me | N | Cl |
| | iso-Pr | H | H | Me | N | Cl |
| | H | iso-Pr | H | Me | N | Cl |
| | H | 2-pyridinyl | H | Me | N | Cl |
| | H | 3-pyridinyl | H | Me | N | Cl |
| | H | 4-pyridinyl | H | Me | N | Cl |
| | | —(CH₂)₃— | H | Me | N | Cl |
| | | —(CH₂)₄— | H | Me | N | Cl |
| | H | H | H | Me | N | Br |
| | Me | H | H | Me | N | Br |
| | H | Me | H | Me | N | Br |
| | Me | Me | H | Me | N | Br |
| | Et | H | H | Me | N | Br |
| | H | Et | H | Me | N | Br |

TABLE A-continued

| No. | $R^2$ | $R^3$ | M | $R^{19a}$ | X | $R^{20ay}$ |
|---|---|---|---|---|---|---|
| | Et | Et | H | Me | N | Br |
| | H | CO$_2$Me | H | Me | N | Br |
| | Me | Et | H | Me | N | Br |
| | Et | Me | H | Me | N | Br |
| | CH$_2$CH=CH$_2$ | H | H | Me | N | Br |
| | H | CH$_2$CH=CH$_2$ | H | Me | N | Br |
| | CH$_2$CCH | H | H | Me | N | Br |
| | H | CH$_2$CCH | H | Me | N | Br |
| | iso-Pr | H | H | Me | N | Br |
| | H | iso-Pr | H | Me | N | Br |
| | H | 2-pyridinyl | H | Me | N | Br |
| | H | 3-pyridinyl | H | Me | N | Br |
| | H | 4-pyridinyl | H | Me | N | Br |
| | —(CH$_2$)$_3$— | | H | Me | N | Br |
| | —(CH$_2$)$_4$— | | H | Me | N | Br |
| | H | H | H | Me | N | CF$_3$ |
| | Me | H | H | Me | N | CF$_3$ |
| | H | Me | H | Me | N | CF$_3$ |
| | Me | Me | H | Me | N | CF$_3$ |
| | Et | H | H | Me | N | CF$_3$ |
| | H | Et | H | Me | N | CF$_3$ |
| | Et | Et | H | Me | N | CF$_3$ |
| | H | CO$_2$Me | H | Me | N | CF$_3$ |
| | Me | Et | H | Me | N | CF$_3$ |
| | Et | Me | H | Me | N | CF$_3$ |
| | CH$_2$CH=CH$_2$ | H | H | Me | N | CF$_3$ |
| | H | CH$_2$CH=CH$_2$ | H | Me | N | CF$_3$ |
| | CH$_2$CCH | H | H | Me | N | CF$_3$ |
| | H | CH$_2$CCH | H | Me | N | CF$_3$ |
| | iso-Pr | H | H | Me | N | CF$_3$ |
| | H | iso-Pr | H | Me | N | CF$_3$ |
| | H | 2-pyridinyl | H | Me | N | CF$_3$ |
| | H | 3-pyridinyl | H | Me | N | CF$_3$ |
| | H | 4-pyridinyl | H | Me | N | CF$_3$ |
| | —(CH$_2$)$_3$— | | H | Me | N | CF$_3$ |
| | —(CH$_2$)$_4$— | | H | Me | N | CF$_3$ |
| | H | H | OMe | Me | N | Cl |
| | Me | H | OMe | Me | N | Cl |
| | H | Me | OMe | Me | N | Cl |
| | Me | Me | OMe | Me | N | Cl |
| | Et | H | OMe | Me | N | Cl |
| | H | Et | OMe | Me | N | Cl |
| | Et | Et | OMe | Me | N | Cl |
| | H | CO$_2$Me | OMe | Me | N | Cl |
| | Me | Et | OMe | Me | N | Cl |
| | Et | Me | OMe | Me | N | Cl |
| | CH$_2$CH=CH$_2$ | H | OMe | Me | N | Cl |
| | H | CH$_2$CH=CH$_2$ | OMe | Me | N | Cl |
| | CH$_2$CCH | H | OMe | Me | N | Cl |
| | H | CH$_2$CCH | OMe | Me | N | Cl |
| | iso-Pr | H | OMe | Me | N | Cl |
| | H | iso-Pr | OMe | Me | N | Cl |
| | H | 2-pyridinyl | OMe | Me | N | Cl |
| | H | 3-pyridinyl | OMe | Me | N | Cl |
| | H | 4-pyridinyl | OMe | Me | N | Cl |
| | —(CH$_2$)$_3$— | | OMe | Me | N | Cl |
| | —(CH$_2$)$_4$— | | OMe | Me | N | Cl |
| | H | H | OMe | Me | N | Br |
| | Me | H | OMe | Me | N | Br |
| | H | Me | OMe | Me | N | Br |
| | Me | Me | OMe | Me | N | Br |
| | Et | H | OMe | Me | N | Br |
| | H | Et | OMe | Me | N | Br |
| | Et | Et | OMe | Me | N | Br |
| | H | CO$_2$Me | OMe | Me | N | Br |
| | Me | Et | OMe | Me | N | Br |
| | Et | Me | OMe | Me | N | Br |
| | CH$_2$CH=CH$_2$ | H | OMe | Me | N | Br |
| | H | CH$_2$CH=CH$_2$ | OMe | Me | N | Br |

TABLE A-continued

| No. | R² | R³ | M | R¹⁹ᵃ | X | R²⁰ᵃʸ |
|---|---|---|---|---|---|---|
| | CH₂CCH | H | OMe | Me | N | Br |
| | H | CH₂CCH | OMe | Me | N | Br |
| | iso-Pr | H | OMe | Me | N | Br |
| | H | iso-Pr | OMe | Me | N | Br |
| | H | 2-pyridinyl | OMe | Me | N | Br |
| | H | 3-pyridinyl | OMe | Me | N | Br |
| | H | 4-pyridinyl | OMe | Me | N | Br |
| | —(CH₂)₃— | | OMe | Me | N | Br |
| | —(CH₂)₄— | | OMe | Me | N | Br |
| | H | H | OMe | Me | N | CF₃ |
| | Me | H | OMe | Me | N | CF₃ |
| | H | Me | OMe | Me | N | CF₃ |
| | Me | Me | OMe | Me | N | CF₃ |
| | Et | H | OMe | Me | N | CF₃ |
| | H | Et | OMe | Me | N | CF₃ |
| | Et | Et | OMe | Me | N | CF₃ |
| | H | CO₂Me | OMe | Me | N | CF₃ |
| | Me | Et | OMe | Me | N | CF₃ |
| | Et | Me | OMe | Me | N | CF₃ |
| | CH₂CH=CH₂ | H | OMe | Me | N | CF₃ |
| | H | CH₂CH=CH₂ | OMe | Me | N | CF₃ |
| | CH₂CCH | H | OMe | Me | N | CF₃ |
| | H | CH₂CCH | OMe | Me | N | CF₃ |
| | iso-Pr | H | OMe | Me | N | CF₃ |
| | H | iso-Pr | OMe | Me | N | CF₃ |
| | H | 2-pyridinyl | OMe | Me | N | CF₃ |
| | H | 3-pyridinyl | OMe | Me | N | CF₃ |
| | H | 4-pyridinyl | OMe | Me | N | CF₃ |
| | —(CH₂)₃— | | OMe | Me | N | CF₃ |
| | —(CH₂)₄— | | OMe | Me | N | CF₃ |
| | H | H | NHMe | Me | N | Cl |
| | Me | H | NHMe | Me | N | Cl |
| | H | Me | NHMe | Me | N | Cl |
| | Me | Me | NHMe | Me | N | Cl |
| | Et | H | NHMe | Me | N | Cl |
| | H | Et | NHMe | Me | N | Cl |
| | Et | Et | NHMe | Me | N | Cl |
| | H | CO₂Me | NHMe | Me | N | Cl |
| | Me | Et | NHMe | Me | N | Cl |
| | Et | Me | NHMe | Me | N | Cl |
| | CH₂CH=CH₂ | H | NHMe | Me | N | Cl |
| | H | CH₂CH=CH₂ | NHMe | Me | N | Cl |
| | CH₂CCH | H | NHMe | Me | N | Cl |
| | H | CH₂CCH | NHMe | Me | N | Cl |
| | iso-Pr | H | NHMe | Me | N | Cl |
| | H | iso-Pr | NHMe | Me | N | Cl |
| | H | 2-pyridinyl | NHMe | Me | N | Cl |
| | H | 3-pyridinyl | NHMe | Me | N | Cl |
| | H | 4-pyridinyl | NHMe | Me | N | Cl |
| | —(CH₂)₃— | | NHMe | Me | N | Cl |
| | —(CH₂)₄— | | NHMe | Me | N | Cl |
| | H | H | NHMe | Me | N | Br |
| | Me | H | NHMe | Me | N | Br |
| | H | Me | NHMe | Me | N | Br |
| | Me | Me | NHMe | Me | N | Br |
| | Et | H | NHMe | Me | N | Br |
| | H | Et | NHMe | Me | N | Br |
| | Et | Et | NHMe | Me | N | Br |
| | H | CO₂Me | NHMe | Me | N | Br |
| | Me | Et | NHMe | Me | N | Br |
| | Et | Me | NHMe | Me | N | Br |
| | CH₂CH=CH₂ | H | NHMe | Me | N | Br |
| | H | CH₂CH=CH₂ | NHMe | Me | N | Br |
| | CH₂CCH | H | NHMe | Me | N | Br |
| | H | CH₂CCH | NHMe | Me | N | Br |
| | iso-Pr | H | NHMe | Me | N | Br |
| | H | iso-Pr | NHMe | Me | N | Br |
| | H | 2-pyridinyl | NHMe | Me | N | Br |

TABLE A-continued

| No. | R² | R³ | M | R¹⁹ᵃ | X | R²⁰ᵃʸ |
|---|---|---|---|---|---|---|
| | H | 3-pyridinyl | NHMe | Me | N | Br |
| | H | 4-pyridinyl | NHMe | Me | N | Br |
| | —(CH₂)₃— | | NHMe | Me | N | Br |
| | —(CH₂)₄— | | NHMe | Me | N | Br |
| | H | H | NHMe | Me | N | CF₃ |
| | Me | H | NHMe | Me | N | CF₃ |
| | H | Me | NHMe | Me | N | CF₃ |
| | Me | Me | NHMe | Me | N | CF₃ |
| | Et | H | NHMe | Me | N | CF₃ |
| | H | Et | NHMe | Me | N | CF₃ |
| | Et | Et | NHMe | Me | N | CF₃ |
| | H | CO₂Me | NHMe | Me | N | CF₃ |
| | Me | Et | NHMe | Me | N | CF₃ |
| | Et | Me | NHMe | Me | N | CF₃ |
| | CH₂CH=CH₂ | H | NHMe | Me | N | CF₃ |
| | H | CH₂CH=CH₂ | NHMe | Me | N | CF₃ |
| | CH₂CCH | H | NHMe | Me | N | CF₃ |
| | H | CH₂CCH | NHMe | Me | N | CF₃ |
| | iso-Pr | H | NHMe | Me | N | CF₃ |
| | H | iso-Pr | NHMe | Me | N | CF₃ |
| | H | 2-pyridinyl | NHMe | Me | N | CF₃ |
| | H | 3-pyridinyl | NHMe | Me | N | CF₃ |
| | H | 4-pyridinyl | NHMe | Me | N | CF₃ |
| | —(CH₂)₃— | | NHMe | Me | N | CF₃ |
| | —(CH₂)₄— | | NHMe | Me | N | CF₃ |
| | H | H | NMe₂ | Me | N | Cl |
| | Me | H | NMe₂ | Me | N | Cl |
| | H | Me | NMe₂ | Me | N | Cl |
| | Me | Me | NMe₂ | Me | N | Cl |
| | Et | H | NMe₂ | Me | N | Cl |
| | H | Et | NMe₂ | Me | N | Cl |
| | Et | Et | NMe₂ | Me | N | Cl |
| | H | CO₂Me | NMe₂ | Me | N | Cl |
| | Me | Et | NMe₂ | Me | N | Cl |
| | Et | Me | NMe₂ | Me | N | Cl |
| | CH₂CH=CH₂ | H | NMe₂ | Me | N | Cl |
| | H | CH₂CH=CH₂ | NMe₂ | Me | N | Cl |
| | CH₂CCH | H | NMe₂ | Me | N | Cl |
| | H | CH₂CCH | NMe₂ | Me | N | Cl |
| | iso-Pr | H | NMe₂ | Me | N | Cl |
| | H | iso-Pr | NMe₂ | Me | N | Cl |
| | H | 2-pyridinyl | NMe₂ | Me | N | Cl |
| | H | 3-pyridinyl | NMe₂ | Me | N | Cl |
| | H | 4-pyridinyl | NMe₂ | Me | N | Cl |
| | —(CH₂)₃— | | NMe₂ | Me | N | Cl |
| | —(CH₂)₄— | | NMe₂ | Me | N | Cl |
| | H | H | NMe₂ | Me | N | Br |
| | Me | H | NMe₂ | Me | N | Br |
| | H | Me | NMe₂ | Me | N | Br |
| | Me | Me | NMe₂ | Me | N | Br |
| | Et | H | NMe₂ | Me | N | Br |
| | H | Et | NMe₂ | Me | N | Br |
| | Et | Et | NMe₂ | Me | N | Br |
| | H | CO₂Me | NMe₂ | Me | N | Br |
| | Me | Et | NMe₂ | Me | N | Br |
| | Et | Me | NMe₂ | Me | N | Br |
| | CH₂CH=CH₂ | H | NMe₂ | Me | N | Br |
| | H | CH₂CH=CH₂ | NMe₂ | Me | N | Br |
| | CH₂CCH | H | NMe₂ | Me | N | Br |
| | H | CH₂CCH | NMe₂ | Me | N | Br |
| | iso-Pr | H | NMe₂ | Me | N | Br |
| | H | iso-Pr | NMe₂ | Me | N | Br |
| | H | 2-pyridinyl | NMe₂ | Me | N | Br |
| | H | 3-pyridinyl | NMe₂ | Me | N | Br |
| | H | 4-pyridinyl | NMe₂ | Me | N | Br |
| | —(CH₂)₃— | | NMe₂ | Me | N | Br |
| | —(CH₂)₄— | | NMe₂ | Me | N | Br |

TABLE A-continued

| No. | $R^2$ | $R^3$ | M | $R^{19a}$ | X | $R^{20ay}$ |
|---|---|---|---|---|---|---|
| | H | H | $NMe_2$ | Me | N | $CF_3$ |
| | Me | H | $NMe_2$ | Me | N | $CF_3$ |
| | H | Me | $NMe_2$ | Me | N | $CF_3$ |
| | Me | Me | $NMe_2$ | Me | N | $CF_3$ |
| | Et | H | $NMe_2$ | Me | N | $CF_3$ |
| | H | Et | $NMe_2$ | Me | N | $CF_3$ |
| | Et | Et | $NMe_2$ | Me | N | $CF_3$ |
| | H | $CO_2Me$ | $NMe_2$ | Me | N | $CF_3$ |
| | Me | Et | $NMe_2$ | Me | N | $CF_3$ |
| | Et | Me | $NMe_2$ | Me | N | $CF_3$ |
| | $CH_2CH{=}CH_2$ | H | $NMe_2$ | Me | N | $CF_3$ |
| | H | $CH_2CH{=}CH_2$ | $NMe_2$ | Me | N | $CF_3$ |
| | $CH_2CCH$ | H | $NMe_2$ | Me | N | $CF_3$ |
| | H | $CH_2CCH$ | $NMe_2$ | Me | N | $CF_3$ |
| | iso-Pr | H | $NMe_2$ | Me | N | $CF_3$ |
| | H | iso-Pr | $NMe_2$ | Me | N | $CF_3$ |
| | H | 2-pyridinyl | $NMe_2$ | Me | N | $CF_3$ |
| | H | 3-pyridinyl | $NMe_2$ | Me | N | $CF_3$ |
| | H | 4-pyridinyl | $NMe_2$ | Me | N | $CF_3$ |
| | —$(CH_2)_3$— | | $NMe_2$ | Me | N | $CF_3$ |
| | —$(CH_2)_4$— | | $NMe_2$ | Me | N | $CF_3$ |
| | H | H | H | Et | N | Cl |
| | Me | H | H | Et | N | Cl |
| | H | Me | H | Et | N | Cl |
| | Me | Me | H | Et | N | Cl |
| | Et | H | H | Et | N | Cl |
| | H | Et | H | Et | N | Cl |
| | Et | Et | H | Et | N | Cl |
| | H | $CO_2Me$ | H | Et | N | Cl |
| | Me | Et | H | Et | N | Cl |
| | Et | Me | H | Et | N | Cl |
| | $CH_2CH{=}CH_2$ | H | H | Et | N | Cl |
| | H | $CH_2CH{=}CH_2$ | H | Et | N | Cl |
| | $CH_2CCH$ | H | H | Et | N | Cl |
| | H | $CH_2CCH$ | H | Et | N | Cl |
| | iso-Pr | H | H | Et | N | Cl |
| | H | iso-Pr | H | Et | N | Cl |
| | H | 2-pyridinyl | H | Et | N | Cl |
| | H | 3-pyridinyl | H | Et | N | Cl |
| | H | 4-pyridinyl | H | Et | N | Cl |
| | —$(CH_2)_3$— | | H | Et | N | Cl |
| | —$(CH_2)_4$— | | H | Et | N | Cl |
| | H | H | H | Et | N | Br |
| | Me | H | H | Et | N | Br |
| | H | Me | H | Et | N | Br |
| | Me | Me | H | Et | N | Br |
| | Et | H | H | Et | N | Br |
| | H | Et | H | Et | N | Br |
| | Et | Et | H | Et | N | Br |
| | H | $CO_2Me$ | H | Et | N | Br |
| | Me | Et | H | Et | N | Br |
| | Et | Me | H | Et | N | Br |
| | $CH_2CH{=}CH_2$ | H | H | Et | N | Br |
| | H | $CH_2CH{=}CH_2$ | H | Et | N | Br |
| | $CH_2CCH$ | H | H | Et | N | Br |
| | H | $CH_2CCH$ | H | Et | N | Br |
| | iso-Pr | H | H | Et | N | Br |
| | H | iso-Pr | H | Et | N | Br |
| | H | 2-pyridinyl | H | Et | N | Br |
| | H | 3-pyridinyl | H | Et | N | Br |
| | H | 4-pyridinyl | H | Et | N | Br |
| | —$(CH_2)_3$— | | H | Et | N | Br |
| | —$(CH_2)_4$— | | H | Et | N | Br |
| | H | H | H | Et | N | $CF_3$ |
| | Me | H | H | Et | N | $CF_3$ |
| | H | Me | H | Et | N | $CF_3$ |
| | Me | Me | H | Et | N | $CF_3$ |
| | Et | H | H | Et | N | $CF_3$ |
| | H | Et | H | Et | N | $CF_3$ |

TABLE A-continued

| No. | $R^2$ | $R^3$ | M | $R^{19a}$ | X | $R^{20ay}$ |
|---|---|---|---|---|---|---|
| | Et | Et | H | Et | N | $CF_3$ |
| | H | $CO_2Me$ | H | Et | N | $CF_3$ |
| | Me | Et | H | Et | N | $CF_3$ |
| | Et | Me | H | Et | N | $CF_3$ |
| | $CH_2CH{=}CH_2$ | H | H | Et | N | $CF_3$ |
| | H | $CH_2CH{=}CH_2$ | H | Et | N | $CF_3$ |
| | $CH_2CCH$ | H | H | Et | N | $CF_3$ |
| | H | $CH_2CCH$ | H | Et | N | $CF_3$ |
| | iso-Pr | H | H | Et | N | $CF_3$ |
| | H | iso-Pr | H | Et | N | $CF_3$ |
| | H | 2-pyridinyl | H | Et | N | $CF_3$ |
| | H | 3-pyridinyl | H | Et | N | $CF_3$ |
| | H | 4-pyridinyl | H | Et | N | $CF_3$ |
| | —$(CH_2)_3$— | | H | Et | N | $CF_3$ |
| | —$(CH_2)_4$— | | H | Et | N | $CF_3$ |
| | H | H | OMe | Et | N | Cl |
| | Me | H | OMe | Et | N | Cl |
| | H | Me | OMe | Et | N | Cl |
| | Me | Me | OMe | Et | N | Cl |
| | Et | H | OMe | Et | N | Cl |
| | H | Et | OMe | Et | N | Cl |
| | Et | Et | OMe | Et | N | Cl |
| | H | $CO_2Me$ | OMe | Et | N | Cl |
| | Me | Et | OMe | Et | N | Cl |
| | Et | Me | OMe | Et | N | Cl |
| | $CH_2CH{=}CH_2$ | H | OMe | Et | N | Cl |
| | H | $CH_2CH{=}CH_2$ | OMe | Et | N | Cl |
| | $CH_2CCH$ | H | OMe | Et | N | Cl |
| | H | $CH_2CCH$ | OMe | Et | N | Cl |
| | iso-Pr | H | OMe | Et | N | Cl |
| | H | iso-Pr | OMe | Et | N | Cl |
| | H | 2-pyridinyl | OMe | Et | N | Cl |
| | H | 3-pyridinyl | OMe | Et | N | Cl |
| | H | 4-pyridinyl | OMe | Et | N | Cl |
| | —$(CH_2)_3$— | | OMe | Et | N | Cl |
| | —$(CH_2)_4$— | | OMe | Et | N | Cl |
| | H | H | OMe | Et | N | Br |
| | Me | H | OMe | Et | N | Br |
| | H | Me | OMe | Et | N | Br |
| | Me | Me | OMe | Et | N | Br |
| | Et | H | OMe | Et | N | Br |
| | H | Et | OMe | Et | N | Br |
| | Et | Et | OMe | Et | N | Br |
| | H | $CO_2Me$ | OMe | Et | N | Br |
| | Me | Et | OMe | Et | N | Br |
| | Et | Me | OMe | Et | N | Br |
| | $CH_2CH{=}CH_2$ | H | OMe | Et | N | Br |
| | H | $CH_2CH{=}CH_2$ | OMe | Et | N | Br |
| | $CH_2CCH$ | H | OMe | Et | N | Br |
| | H | $CH_2CCH$ | OMe | Et | N | Br |
| | iso-Pr | H | OMe | Et | N | Br |
| | H | iso-Pr | OMe | Et | N | Br |
| | H | 2-pyridinyl | OMe | Et | N | Br |
| | H | 3-pyridinyl | OMe | Et | N | Br |
| | H | 4-pyridinyl | OMe | Et | N | Br |
| | —$(CH_2)_3$— | | OMe | Et | N | Br |
| | —$(CH_2)_4$— | | OMe | Et | N | Br |
| | H | H | OMe | Et | N | $CF_3$ |
| | Me | H | OMe | Et | N | $CF_3$ |
| | H | Me | OMe | Et | N | $CF_3$ |
| | Me | Me | OMe | Et | N | $CF_3$ |
| | Et | H | OMe | Et | N | $CF_3$ |
| | H | Et | OMe | Et | N | $CF_3$ |
| | Et | Et | OMe | Et | N | $CF_3$ |
| | H | $CO_2Me$ | OMe | Et | N | $CF_3$ |
| | Me | Et | OMe | Et | N | $CF_3$ |
| | Et | Me | OMe | Et | N | $CF_3$ |
| | $CH_2CH{=}CH_2$ | H | OMe | Et | N | $CF_3$ |
| | H | $CH_2CH{=}CH_2$ | OMe | Et | N | $CF_3$ |

TABLE A-continued

| No. | R² | R³ | M | R¹⁹ᵃ | X | R²⁰ᵃʸ |
|---|---|---|---|---|---|---|
| | CH₂CCH | H | OMe | Et | N | CF₃ |
| | H | CH₂CCH | OMe | Et | N | CF₃ |
| | iso-Pr | H | OMe | Et | N | CF₃ |
| | H | iso-Pr | OMe | Et | N | CF₃ |
| | H | 2-pyridinyl | OMe | Et | N | CF₃ |
| | H | 3-pyridinyl | OMe | Et | N | CF₃ |
| | H | 4-pyridinyl | OMe | Et | N | CF₃ |
| | —(CH₂)₃— | | OMe | Et | N | CF₃ |
| | —(CH₂)₄— | | OMe | Et | N | CF₃ |
| | H | H | NHMe | Et | N | Cl |
| | Me | H | NHMe | Et | N | Cl |
| | H | Me | NHMe | Et | N | Cl |
| | Me | Me | NHMe | Et | N | Cl |
| | Et | H | NHMe | Et | N | Cl |
| | H | Et | NHMe | Et | N | Cl |
| | Et | Et | NHMe | Et | N | Cl |
| | H | CO₂Me | NHMe | Et | N | Cl |
| | Me | Et | NHMe | Et | N | Cl |
| | Et | Me | NHMe | Et | N | Cl |
| | CH₂CH=CH₂ | H | NHMe | Et | N | Cl |
| | H | CH₂CH=CH₂ | NHMe | Et | N | Cl |
| | CH₂CCH | H | NHMe | Et | N | Cl |
| | H | CH₂CCH | NHMe | Et | N | Cl |
| | iso-Pr | H | NHMe | Et | N | Cl |
| | H | iso-Pr | NHMe | Et | N | Cl |
| | H | 2-pyridinyl | NHMe | Et | N | Cl |
| | H | 3-pyridinyl | NHMe | Et | N | Cl |
| | H | 4-pyridinyl | NHMe | Et | N | Cl |
| | —(CH₂)₃— | | NHMe | Et | N | Cl |
| | —(CH₂)₄— | | NHMe | Et | N | Cl |
| | H | H | NHMe | Et | N | Br |
| | Me | H | NHMe | Et | N | Br |
| | H | Me | NHMe | Et | N | Br |
| | Me | Me | NHMe | Et | N | Br |
| | Et | H | NHMe | Et | N | Br |
| | H | Et | NHMe | Et | N | Br |
| | Et | Et | NHMe | Et | N | Br |
| | H | CO₂Me | NHMe | Et | N | Br |
| | Me | Et | NHMe | Et | N | Br |
| | Et | Me | NHMe | Et | N | Br |
| | CH₂CH=CH₂ | H | NHMe | Et | N | Br |
| | H | CH₂CH=CH₂ | NHMe | Et | N | Br |
| | CH₂CCH | H | NHMe | Et | N | Br |
| | H | CH₂CCH | NHMe | Et | N | Br |
| | iso-Pr | H | NHMe | Et | N | Br |
| | H | iso-Pr | NHMe | Et | N | Br |
| | H | 2-pyridinyl | NHMe | Et | N | Br |
| | H | 3-pyridinyl | NHMe | Et | N | Br |
| | H | 4-pyridinyl | NHMe | Et | N | Br |
| | —(CH₂)₃— | | NHMe | Et | N | Br |
| | —(CH₂)₄— | | NHMe | Et | N | Br |
| | H | H | NHMe | Et | N | CF₃ |
| | Me | H | NHMe | Et | N | CF₃ |
| | H | Me | NHMe | Et | N | CF₃ |
| | Me | Me | NHMe | Et | N | CF₃ |
| | Et | H | NHMe | Et | N | CF₃ |
| | H | Et | NHMe | Et | N | CF₃ |
| | Et | Et | NHMe | Et | N | CF₃ |
| | H | CO₂Me | NHMe | Et | N | CF₃ |
| | Me | Et | NHMe | Et | N | CF₃ |
| | Et | Me | NHMe | Et | N | CF₃ |
| | CH₂CH=CH₂ | H | NHMe | Et | N | CF₃ |
| | H | CH₂CH=CH₂ | NHMe | Et | N | CF₃ |
| | CH₂CCH | H | NHMe | Et | N | CF₃ |
| | H | CH₂CCH | NHMe | Et | N | CF₃ |
| | iso-Pr | H | NHMe | Et | N | CF₃ |
| | H | iso-Pr | NHMe | Et | N | CF₃ |
| | H | 2-pyridinyl | NHMe | Et | N | CF₃ |

TABLE A-continued

| No. | R² | R³ | M | R¹⁹ᵃ | X | R²⁰ᵃʸ |
|---|---|---|---|---|---|---|
| | H | 3-pyridinyl | NHMe | Et | N | $CF_3$ |
| | H | 4-pyridinyl | NHMe | Et | N | $CF_3$ |
| | —(CH₂)₃— | | NHMe | Et | N | $CF_3$ |
| | —(CH₂)₄— | | NHMe | Et | N | $CF_3$ |
| | H | H | NMe₂ | Et | N | Cl |
| | Me | H | NMe₂ | Et | N | Cl |
| | H | Me | NMe₂ | Et | N | Cl |
| | Me | Me | NMe₂ | Et | N | Cl |
| | Et | H | NMe₂ | Et | N | Cl |
| | H | Et | NMe₂ | Et | N | Cl |
| | Et | Et | NMe₂ | Et | N | Cl |
| | H | CO₂Me | NMe₂ | Et | N | Cl |
| | Me | Et | NMe₂ | Et | N | Cl |
| | Et | Me | NMe₂ | Et | N | Cl |
| | CH₂CH=CH₂ | H | NMe₂ | Et | N | Cl |
| | H | CH₂CH=CH₂ | NMe₂ | Et | N | Cl |
| | CH₂CCH | H | NMe₂ | Et | N | Cl |
| | H | CH₂CCH | NMe₂ | Et | N | Cl |
| | iso-Pr | H | NMe₂ | Et | N | Cl |
| | H | iso-Pr | NMe₂ | Et | N | Cl |
| | H | 2-pyridinyl | NMe₂ | Et | N | Cl |
| | H | 3-pyridinyl | NMe₂ | Et | N | Cl |
| | H | 4-pyridinyl | NMe₂ | Et | N | Cl |
| | —(CH₂)₃— | | NMe₂ | Et | N | Cl |
| | —(CH₂)₄— | | NMe₂ | Et | N | Cl |
| | H | H | NMe₂ | Et | N | Br |
| | Me | H | NMe₂ | Et | N | Br |
| | H | Me | NMe₂ | Et | N | Br |
| | Me | Me | NMe₂ | Et | N | Br |
| | Et | H | NMe₂ | Et | N | Br |
| | H | Et | NMe₂ | Et | N | Br |
| | Et | Et | NMe₂ | Et | N | Br |
| | H | CO₂Me | NMe₂ | Et | N | Br |
| | Me | Et | NMe₂ | Et | N | Br |
| | Et | Me | NMe₂ | Et | N | Br |
| | CH₂CH=CH₂ | H | NMe₂ | Et | N | Br |
| | H | CH₂CH=CH₂ | NMe₂ | Et | N | Br |
| | CH₂CCH | H | NMe₂ | Et | N | Br |
| | H | CH₂CCH | NMe₂ | Et | N | Br |
| | iso-Pr | H | NMe₂ | Et | N | Br |
| | H | iso-Pr | NMe₂ | Et | N | Br |
| | H | 2-pyridinyl | NMe₂ | Et | N | Br |
| | H | 3-pyridinyl | NMe₂ | Et | N | Br |
| | H | 4-pyridinyl | NMe₂ | Et | N | Br |
| | —(CH₂)₃— | | NMe₂ | Et | N | Br |
| | —(CH₂)₄— | | NMe₂ | Et | N | Br |
| | H | H | NMe₂ | Et | N | $CF_3$ |
| | Me | H | NMe₂ | Et | N | $CF_3$ |
| | H | Me | NMe₂ | Et | N | $CF_3$ |
| | Me | Me | NMe₂ | Et | N | $CF_3$ |
| | Et | H | NMe₂ | Et | N | $CF_3$ |
| | H | Et | NMe₂ | Et | N | $CF_3$ |
| | Et | Et | NMe₂ | Et | N | $CF_3$ |
| | H | CO₂Me | NMe₂ | Et | N | $CF_3$ |
| | Me | Et | NMe₂ | Et | N | $CF_3$ |
| | Et | Me | NMe₂ | Et | N | $CF_3$ |
| | CH₂CH=CH₂ | H | NMe₂ | Et | N | $CF_3$ |
| | H | CH₂CH=CH₂ | NMe₂ | Et | N | $CF_3$ |
| | CH₂CCH | H | NMe₂ | Et | N | $CF_3$ |
| | H | CH₂CCH | NMe₂ | Et | N | $CF_3$ |
| | iso-Pr | H | NMe₂ | Et | N | $CF_3$ |
| | H | iso-Pr | NMe₂ | Et | N | $CF_3$ |
| | H | 2-pyridinyl | NMe₂ | Et | N | $CF_3$ |
| | H | 3-pyridinyl | NMe₂ | Et | N | $CF_3$ |
| | H | 4-pyridinyl | NMe₂ | Et | N | $CF_3$ |
| | —(CH₂)₃— | | NMe₂ | Et | N | $CF_3$ |
| | —(CH₂)₄— | | NMe₂ | Et | N | $CF_3$ |

TABLE A-continued

| No. | $R^2$ | $R^3$ | M | $R^{19a}$ | X | $R^{20ay}$ |
|---|---|---|---|---|---|---|
| | H | H | H | iso-Pr | N | Cl |
| | Me | H | H | iso-Pr | N | Cl |
| | H | Me | H | iso-Pr | N | Cl |
| | Me | Me | H | iso-Pr | N | Cl |
| | Et | H | H | iso-Pr | N | Cl |
| | H | Et | H | iso-Pr | N | Cl |
| | Et | Et | H | iso-Pr | N | Cl |
| | H | $CO_2Me$ | H | iso-Pr | N | Cl |
| | Me | Et | H | iso-Pr | N | Cl |
| | Et | Me | H | iso-Pr | N | Cl |
| | $CH_2CH{=}CH_2$ | H | H | iso-Pr | N | Cl |
| | H | $CH_2CH{=}CH_2$ | H | iso-Pr | N | Cl |
| | $CH_2CCH$ | H | H | iso-Pr | N | Cl |
| | H | $CH_2CCH$ | H | iso-Pr | N | Cl |
| | iso-Pr | H | H | iso-Pr | N | Cl |
| | H | iso-Pr | H | iso-Pr | N | Cl |
| | H | 2-pyridinyl | H | iso-Pr | N | Cl |
| | H | 3-pyridinyl | H | iso-Pr | N | Cl |
| | H | 4-pyridinyl | H | iso-Pr | N | Cl |
| | —$(CH_2)_3$— | | H | iso-Pr | N | Cl |
| | —$(CH_2)_4$— | | H | iso-Pr | N | Cl |
| | H | H | H | iso-Pr | N | Br |
| | Me | H | H | iso-Pr | N | Br |
| | H | Me | H | iso-Pr | N | Br |
| | Me | Me | H | iso-Pr | N | Br |
| | Et | H | H | iso-Pr | N | Br |
| | H | Et | H | iso-Pr | N | Br |
| | Et | Et | H | iso-Pr | N | Br |
| | H | $CO_2Me$ | H | iso-Pr | N | Br |
| | Me | Et | H | iso-Pr | N | Br |
| | Et | Me | H | iso-Pr | N | Br |
| | $CH_2CH{=}CH_2$ | H | H | iso-Pr | N | Br |
| | H | $CH_2CH{=}CH_2$ | H | iso-Pr | N | Br |
| | $CH_2CCH$ | H | H | iso-Pr | N | Br |
| | H | $CH_2CCH$ | H | iso-Pr | N | Br |
| | iso-Pr | H | H | iso-Pr | N | Br |
| | H | iso-Pr | H | iso-Pr | N | Br |
| | H | 2-pyridinyl | H | iso-Pr | N | Br |
| | H | 3-pyridinyl | H | iso-Pr | N | Br |
| | H | 4-pyridinyl | H | iso-Pr | N | Br |
| | —$(CH_2)_3$— | | H | iso-Pr | N | Br |
| | —$(CH_2)_4$— | | H | iso-Pr | N | Br |
| | H | H | H | iso-Pr | N | $CF_3$ |
| | Me | H | H | iso-Pr | N | $CF_3$ |
| | H | Me | H | iso-Pr | N | $CF_3$ |
| | Me | Me | H | iso-Pr | N | $CF_3$ |
| | Et | H | H | iso-Pr | N | $CF_3$ |
| | H | Et | H | iso-Pr | N | $CF_3$ |
| | Et | Et | H | iso-Pr | N | $CF_3$ |
| | H | $CO_2Me$ | H | iso-Pr | N | $CF_3$ |
| | Me | Et | H | iso-Pr | N | $CF_3$ |
| | Et | Me | H | iso-Pr | N | $CF_3$ |
| | $CH_2CH{=}CH_2$ | H | H | iso-Pr | N | $CF_3$ |
| | H | $CH_2CH{=}CH_2$ | H | iso-Pr | N | $CF_3$ |
| | $CH_2CCH$ | H | H | iso-Pr | N | $CF_3$ |
| | H | $CH_2CCH$ | H | iso-Pr | N | $CF_3$ |
| | iso-Pr | H | H | iso-Pr | N | $CF_3$ |
| | H | iso-Pr | H | iso-Pr | N | $CF_3$ |
| | H | 2-pyridinyl | H | iso-Pr | N | $CF_3$ |
| | H | 3-pyridinyl | H | iso-Pr | N | $CF_3$ |
| | H | 4-pyridinyl | H | iso-Pr | N | $CF_3$ |
| | —$(CH_2)_3$— | | H | iso-Pr | N | $CF_3$ |
| | —$(CH_2)_4$— | | H | iso-Pr | N | $CF_3$ |
| | H | H | OMe | iso-Pr | N | Cl |
| | Me | H | OMe | iso-Pr | N | Cl |
| | H | Me | OMe | iso-Pr | N | Cl |
| | Me | Me | OMe | iso-Pr | N | Cl |
| | Et | H | OMe | iso-Pr | N | Cl |
| | H | Et | OMe | iso-Pr | N | Cl |

TABLE A-continued

| No. | $R^2$ | $R^3$ | M | $R^{19a}$ | X | $R^{20ay}$ |
|---|---|---|---|---|---|---|
| | Et | Et | OMe | iso-Pr | N | Cl |
| | H | $CO_2Me$ | OMe | iso-Pr | N | Cl |
| | Me | Et | OMe | iso-Pr | N | Cl |
| | Et | Me | OMe | iso-Pr | N | Cl |
| | $CH_2CH=CH_2$ | H | OMe | iso-Pr | N | Cl |
| | H | $CH_2CH=CH_2$ | OMe | iso-Pr | N | Cl |
| | $CH_2CCH$ | H | OMe | iso-Pr | N | Cl |
| | H | $CH_2CCH$ | OMe | iso-Pr | N | Cl |
| | iso-Pr | H | OMe | iso-Pr | N | Cl |
| | H | iso-Pr | OMe | iso-Pr | N | Cl |
| | H | 2-pyridinyl | OMe | iso-Pr | N | Cl |
| | H | 3-pyridinyl | OMe | iso-Pr | N | Cl |
| | H | 4-pyridinyl | OMe | iso-Pr | N | Cl |
| | —$(CH_2)_3$— | | OMe | iso-Pr | N | Cl |
| | —$(CH_2)_4$— | | OMe | iso-Pr | N | Cl |
| | H | H | OMe | iso-Pr | N | Br |
| | Me | H | OMe | iso-Pr | N | Br |
| | H | Me | OMe | iso-Pr | N | Br |
| | Me | Me | OMe | iso-Pr | N | Br |
| | Et | H | OMe | iso-Pr | N | Br |
| | H | Et | OMe | iso-Pr | N | Br |
| | Et | Et | OMe | iso-Pr | N | Br |
| | H | $CO_2Me$ | OMe | iso-Pr | N | Br |
| | Me | Et | OMe | iso-Pr | N | Br |
| | Et | Me | OMe | iso-Pr | N | Br |
| | $CH_2CH=CH_2$ | H | OMe | iso-Pr | N | Br |
| | H | $CH_2CH=CH_2$ | OMe | iso-Pr | N | Br |
| | $CH_2CCH$ | H | OMe | iso-Pr | N | Br |
| | H | $CH_2CCH$ | OMe | iso-Pr | N | Br |
| | iso-Pr | H | OMe | iso-Pr | N | Br |
| | H | iso-Pr | OMe | iso-Pr | N | Br |
| | H | 2-pyridinyl | OMe | iso-Pr | N | Br |
| | H | 3-pyridinyl | OMe | iso-Pr | N | Br |
| | H | 4-pyridinyl | OMe | iso-Pr | N | Br |
| | —$(CH_2)_3$— | | OMe | iso-Pr | N | Br |
| | —$(CH_2)_4$— | | OMe | iso-Pr | N | Br |
| | H | H | OMe | iso-Pr | N | $CF_3$ |
| | Me | H | OMe | iso-Pr | N | $CF_3$ |
| | H | Me | OMe | iso-Pr | N | $CF_3$ |
| | Me | Me | OMe | iso-Pr | N | $CF_3$ |
| | Et | H | OMe | iso-Pr | N | $CF_3$ |
| | H | Et | OMe | iso-Pr | N | $CF_3$ |
| | Et | Et | OMe | iso-Pr | N | $CF_3$ |
| | H | $CO_2Me$ | OMe | iso-Pr | N | $CF_3$ |
| | Me | Et | OMe | iso-Pr | N | $CF_3$ |
| | Et | Me | OMe | iso-Pr | N | $CF_3$ |
| | $CH_2CH=CH_2$ | H | OMe | iso-Pr | N | $CF_3$ |
| | H | $CH_2CH=CH_2$ | OMe | iso-Pr | N | $CF_3$ |
| | $CH_2CCH$ | H | OMe | iso-Pr | N | $CF_3$ |
| | H | $CH_2CCH$ | OMe | iso-Pr | N | $CF_3$ |
| | iso-Pr | H | OMe | iso-Pr | N | $CF_3$ |
| | H | iso-Pr | OMe | iso-Pr | N | $CF_3$ |
| | H | 2-pyridinyl | OMe | iso-Pr | N | $CF_3$ |
| | H | 3-pyridinyl | OMe | iso-Pr | N | $CF_3$ |
| | H | 4-pyridinyl | OMe | iso-Pr | N | $CF_3$ |
| | —$(CH_2)_3$— | | OMe | iso-Pr | N | $CF_3$ |
| | —$(CH_2)_4$— | | OMe | iso-Pr | N | $CF_3$ |
| | H | H | NHMe | iso-Pr | N | Cl |
| | Me | H | NHMe | iso-Pr | N | Cl |
| | H | Me | NHMe | iso-Pr | N | Cl |
| | Me | Me | NHMe | iso-Pr | N | Cl |
| | Et | H | NHMe | iso-Pr | N | Cl |
| | H | Et | NHMe | iso-Pr | N | Cl |
| | Et | Et | NHMe | iso-Pr | N | Cl |
| | H | $CO_2Me$ | NHMe | iso-Pr | N | Cl |
| | Me | Et | NHMe | iso-Pr | N | Cl |
| | Et | Me | NHMe | iso-Pr | N | Cl |
| | $CH_2CH=CH_2$ | H | NHMe | iso-Pr | N | Cl |
| | H | $CH_2CH=CH_2$ | NHMe | iso-Pr | N | Cl |

TABLE A-continued

| No. | R² | R³ | M | R¹⁹ᵃ | X | R²⁰ᵃʸ |
|---|---|---|---|---|---|---|
| | CH₂CCH | H | NHMe | iso-Pr | N | Cl |
| | H | CH₂CCH | NHMe | iso-Pr | N | Cl |
| | iso-Pr | H | NHMe | iso-Pr | N | Cl |
| | H | iso-Pr | NHMe | iso-Pr | N | Cl |
| | H | 2-pyridinyl | NHMe | iso-Pr | N | Cl |
| | H | 3-pyridinyl | NHMe | iso-Pr | N | Cl |
| | H | 4-pyridinyl | NHMe | iso-Pr | N | Cl |
| | —(CH₂)₃— | | NHMe | iso-Pr | N | Cl |
| | —(CH₂)₄— | | NHMe | iso-Pr | N | Cl |
| | H | H | NHMe | iso-Pr | N | Br |
| | Me | H | NHMe | iso-Pr | N | Br |
| | H | Me | NHMe | iso-Pr | N | Br |
| | Me | Me | NHMe | iso-Pr | N | Br |
| | Et | H | NHMe | iso-Pr | N | Br |
| | H | Et | NHMe | iso-Pr | N | Br |
| | Et | Et | NHMe | iso-Pr | N | Br |
| | H | CO₂Me | NHMe | iso-Pr | N | Br |
| | Me | Et | NHMe | iso-Pr | N | Br |
| | Et | Me | NHMe | iso-Pr | N | Br |
| | CH₂CH=CH₂ | H | NHMe | iso-Pr | N | Br |
| | H | CH₂CH=CH₂ | NHMe | iso-Pr | N | Br |
| | CH₂CCH | H | NHMe | iso-Pr | N | Br |
| | H | CH₂CCH | NHMe | iso-Pr | N | Br |
| | iso-Pr | H | NHMe | iso-Pr | N | Br |
| | H | iso-Pr | NHMe | iso-Pr | N | Br |
| | H | 2-pyridinyl | NHMe | iso-Pr | N | Br |
| | H | 3-pyridinyl | NHMe | iso-Pr | N | Br |
| | H | 4-pyridinyl | NHMe | iso-Pr | N | Br |
| | —(CH₂)₃— | | NHMe | iso-Pr | N | Br |
| | —(CH₂)₄— | | NHMe | iso-Pr | N | Br |
| | H | H | NHMe | iso-Pr | N | CF₃ |
| | Me | H | NHMe | iso-Pr | N | CF₃ |
| | H | Me | NHMe | iso-Pr | N | CF₃ |
| | Me | Me | NHMe | iso-Pr | N | CF₃ |
| | Et | H | NHMe | iso-Pr | N | CF₃ |
| | H | Et | NHMe | iso-Pr | N | CF₃ |
| | Et | Et | NHMe | iso-Pr | N | CF₃ |
| | H | CO₂Me | NHMe | iso-Pr | N | CF₃ |
| | Me | Et | NHMe | iso-Pr | N | CF₃ |
| | Et | Me | NHMe | iso-Pr | N | CF₃ |
| | CH₂CH=CH₂ | H | NHMe | iso-Pr | N | CF₃ |
| | H | CH₂CH=CH₂ | NHMe | iso-Pr | N | CF₃ |
| | CH₂CCH | H | NHMe | iso-Pr | N | CF₃ |
| | H | CH₂CCH | NHMe | iso-Pr | N | CF₃ |
| | iso-Pr | H | NHMe | iso-Pr | N | CF₃ |
| | H | iso-Pr | NHMe | iso-Pr | N | CF₃ |
| | H | 2-pyridinyl | NHMe | iso-Pr | N | CF₃ |
| | H | 3-pyridinyl | NHMe | iso-Pr | N | CF₃ |
| | H | 4-pyridinyl | NHMe | iso-Pr | N | CF₃ |
| | —(CH₂)₃— | | NHMe | iso-Pr | N | CF₃ |
| | —(CH₂)₄— | | NHMe | iso-Pr | N | CF₃ |
| | H | H | NMe₂ | iso-Pr | N | Cl |
| | Me | H | NMe₂ | iso-Pr | N | Cl |
| | H | Me | NMe₂ | iso-Pr | N | Cl |
| | Me | Me | NMe₂ | iso-Pr | N | Cl |
| | Et | H | NMe₂ | iso-Pr | N | Cl |
| | H | Et | NMe₂ | iso-Pr | N | Cl |
| | Et | Et | NMe₂ | iso-Pr | N | Cl |
| | H | CO₂Me | NMe₂ | iso-Pr | N | Cl |
| | Me | Et | NMe₂ | iso-Pr | N | Cl |
| | Et | Me | NMe₂ | iso-Pr | N | Cl |
| | CH₂CH=CH₂ | H | NMe₂ | iso-Pr | N | Cl |
| | H | CH₂CH=CH₂ | NMe₂ | iso-Pr | N | Cl |
| | CH₂CCH | H | NMe₂ | iso-Pr | N | Cl |
| | H | CH₂CCH | NMe₂ | iso-Pr | N | Cl |
| | iso-Pr | H | NMe₂ | iso-Pr | N | Cl |

TABLE A-continued

| No. | R² | R³ | M | R¹⁹ᵃ | X | R²⁰ᵃʸ |
|---|---|---|---|---|---|---|
| | H | iso-Pr | NMe₂ | iso-Pr | N | Cl |
| | H | 2-pyridinyl | NMe₂ | iso-Pr | N | Cl |
| | H | 3-pyridinyl | NMe₂ | iso-Pr | N | Cl |
| | H | 4-pyridinyl | NMe₂ | iso-Pr | N | Cl |
| | —(CH₂)₃— | | NMe₂ | iso-Pr | N | Cl |
| | —(CH₂)₄— | | NMe₂ | iso-Pr | N | Cl |
| | H | H | NMe₂ | iso-Pr | N | Br |
| | Me | H | NMe₂ | iso-Pr | N | Br |
| | H | Me | NMe₂ | iso-Pr | N | Br |
| | Me | Me | NMe₂ | iso-Pr | N | Br |
| | Et | H | NMe₂ | iso-Pr | N | Br |
| | H | Et | NMe₂ | iso-Pr | N | Br |
| | Et | Et | NMe₂ | iso-Pr | N | Br |
| | H | CO₂Me | NMe₂ | iso-Pr | N | Br |
| | Me | Et | NMe₂ | iso-Pr | N | Br |
| | Et | Me | NMe₂ | iso-Pr | N | Br |
| | CH₂CH=CH₂ | H | NMe₂ | iso-Pr | N | Br |
| | H | CH₂CH=CH₂ | NMe₂ | iso-Pr | N | Br |
| | CH₂CCH | H | NMe₂ | iso-Pr | N | Br |
| | H | CH₂CCH | NMe₂ | iso-Pr | N | Br |
| | iso-Pr | H | NMe₂ | iso-Pr | N | Br |
| | H | iso-Pr | NMe₂ | iso-Pr | N | Br |
| | H | 2-pyridinyl | NMe₂ | iso-Pr | N | Br |
| | H | 3-pyridinyl | NMe₂ | iso-Pr | N | Br |
| | H | 4-pyridinyl | NMe₂ | iso-Pr | N | Br |
| | —(CH₂)₃— | | NMe₂ | iso-Pr | N | Br |
| | —(CH₂)₄— | | NMe₂ | iso-Pr | N | Br |
| | H | H | NMe₂ | iso-Pr | N | CF₃ |
| | Me | H | NMe₂ | iso-Pr | N | CF₃ |
| | H | Me | NMe₂ | iso-Pr | N | CF₃ |
| | Me | Me | NMe₂ | iso-Pr | N | CF₃ |
| | Et | H | NMe₂ | iso-Pr | N | CF₃ |
| | H | Et | NMe₂ | iso-Pr | N | CF₃ |
| | Et | Et | NMe₂ | iso-Pr | N | CF₃ |
| | H | CO₂Me | NMe₂ | iso-Pr | N | CF₃ |
| | Me | Et | NMe₂ | iso-Pr | N | CF₃ |
| | Et | Me | NMe₂ | iso-Pr | N | CF₃ |
| | CH₂CH=CH₂ | H | NMe₂ | iso-Pr | N | CF₃ |
| | H | CH₂CH=CH₂ | NMe₂ | iso-Pr | N | CF₃ |
| | CH₂CCH | H | NMe₂ | iso-Pr | N | CF₃ |
| | H | CH₂CCH | NMe₂ | iso-Pr | N | CF₃ |
| | iso-Pr | H | NMe₂ | iso-Pr | N | CF₃ |
| | H | iso-Pr | NMe₂ | iso-Pr | N | CF₃ |
| | H | 2-pyridinyl | NMe₂ | iso-Pr | N | CF₃ |
| | H | 3-pyridinyl | NMe₂ | iso-Pr | N | CF₃ |
| | H | 4-pyridinyl | NMe₂ | iso-Pr | N | CF₃ |
| | —(CH₂)₃— | | NMe₂ | iso-Pr | N | CF₃ |
| | —(CH₂)₄— | | NMe₂ | iso-Pr | N | CF₃ |

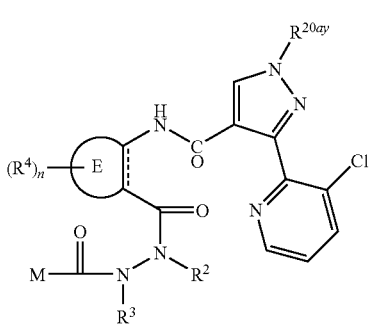

(2A)

Compound 65:

Compounds of formula 2A wherein $R^2$, $R^3$, M and $R^{20ay}$ corresponds to a row in Table B, and E substituted with $(R^4)_n$ is:

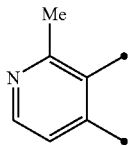

Compound 66:
Compounds of formula 2A wherein $R^2$, $R^3$, M and $R^{20ay}$ corresponds to a row in Table B, and E substituted with $(R^4)_n$ is:

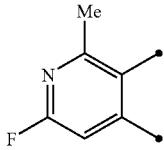

Compound 67:
Compounds of formula 2A wherein $R^2$, $R^3$, M and $R^{20ay}$ corresponds to a row in Table B, and E substituted with $(R^4)_n$ is:

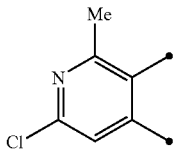

Compound 68:
Compounds of formula 2A wherein $R^2$, $R^3$, M and $R^{20ay}$ corresponds to a row in Table B, and E substituted with $(R^4)_n$ is:

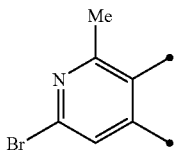

Compound 69:
Compounds of formula 2A wherein $R^2$, $R^3$, M and $R^{20ay}$ corresponds to a row in Table B, and E substituted with $(R^4)_n$ is:

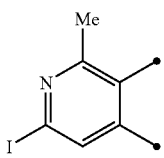

Compound 70:
Compounds of formula 2A wherein $R^2$, $R^3$, M and $R^{20ay}$ corresponds to a row in Table B, and E substituted with $(R^4)_n$ is:

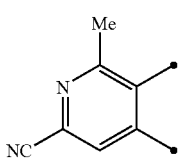

Compound 71:
Compounds of formula 2A wherein $R^2$, $R^3$, M and $R^{20ay}$ corresponds to a row in Table B, and E substituted with $(R^4)_n$ is:

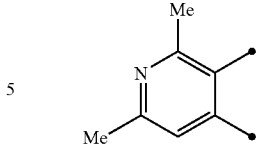

Compound 72:
Compounds of formula 2A wherein $R^2$, $R^3$, M and $R^{20ay}$ corresponds to a row in Table B, and E substituted with $(R^4)_n$ is:

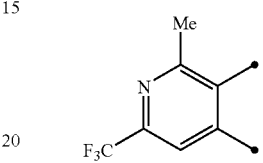

Compound 73:
Compounds of formula 2A wherein $R^2$, $R^3$, M and $R^{20ay}$ corresponds to a row in Table B, and E substituted with $(R^4)_n$ is:

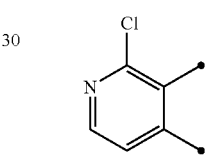

Compound 74:
Compounds of formula 2A wherein $R^2$, $R^3$, M and $R^{20ay}$ corresponds to a row in Table B, and E substituted with $(R^4)_n$ is:

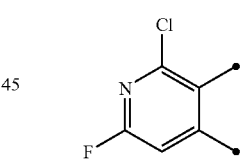

Compound 75:
Compounds of formula 2A wherein $R^2$, $R^3$, M and $R^{20ay}$ corresponds to a row in Table B, and E substituted with $(R^4)_n$ is:

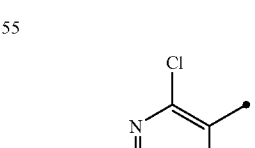

Compound 76:
Compounds of formula 2A wherein $R^2$, $R^3$, M and $R^{20ay}$ corresponds to a row in Table B, and E substituted with $(R^4)_n$ is:

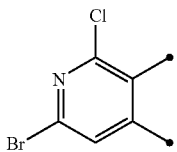

Compound 77:

Compounds of formula 2A wherein $R^2$, $R^3$, M and $R^{20ay}$ corresponds to a row in Table B, and E substituted with $(R^4)_n$ is:

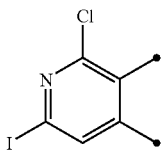

Compound 78:

Compounds of formula 2A wherein $R^2$, $R^3$, M and $R^{20ay}$ corresponds to a row in Table B, and E substituted with $(R^4)_n$ is:

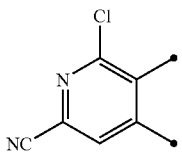

Compound 79:

Compounds of formula 2A wherein $R^2$, $R^3$, M and $R^{20ay}$ corresponds to a row in Table B, and E substituted with $(R^4)_n$ is:

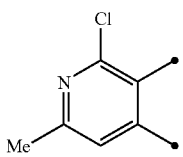

Compound 80:

Compounds of formula 2A wherein $R^2$, $R^3$, M and $R^{20ay}$ corresponds to a row in Table B, and E substituted with $(R^4)_n$ is:

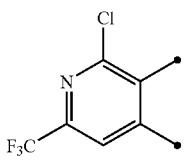

Compound 81:

Compounds of formula 2A wherein $R^2$, $R^3$, M and $R^{20ay}$ corresponds to a row in Table B, and E substituted with $(R^4)_n$ is:

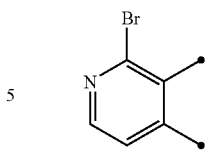

Compound 82:

Compounds of formula 2A wherein $R^2$, $R^3$, M and $R^{20ay}$ corresponds to a row in Table B, and E substituted with $(R^4)_n$ is:

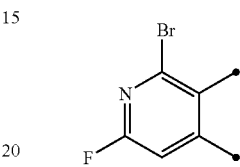

Compound 83:

Compounds of formula 2A wherein $R^2$, $R^3$, M and $R^{20ay}$ corresponds to a row in Table B, and E substituted with $(R^4)_n$ is:

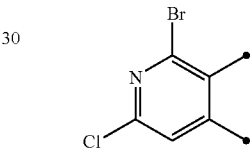

Compound 84:

Compounds of formula 2A wherein $R^2$, $R^3$, M and $R^{20ay}$ corresponds to a row in Table B, and E substituted with $(R^4)_n$ is:

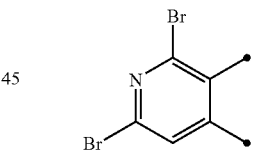

Compound 85:

Compounds of formula 2A wherein $R^2$, $R^3$, M and $R^{20ay}$ corresponds to a row in Table B, and E substituted with $(R^4)_n$ is:

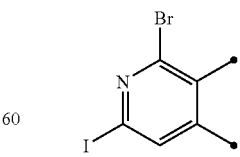

Compound 86:

Compounds of formula 2A wherein $R^2$, $R^3$, M and $R^{20ay}$ corresponds to a row in Table B, and E substituted with $(R^4)_n$ is:

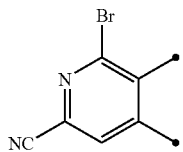

Compound 87:
Compounds of formula 2A wherein $R^2$, $R^3$, M and $R^{20ay}$ corresponds to a row in Table B, and E substituted with $(R^4)_n$ is:

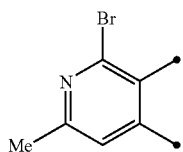

Compound 88:
Compounds of formula 2A wherein $R^2$, $R^3$, M and $R^{20ay}$ corresponds to a row in Table B, and E substituted with $(R^4)_n$ is:

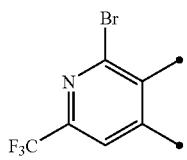

Compound 89:
Compounds of formula 2A wherein $R^2$, $R^3$, M and $R^{20ay}$ corresponds to a row in Table B, and E substituted with $(R^4)_n$ is:

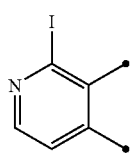

Compound 90:
Compounds of formula 2A wherein $R^2$, $R^3$, M and $R^{20ay}$ corresponds to a row in Table B, and E substituted with $(R^4)_n$ is:

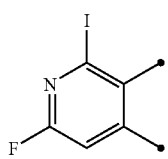

Compound 91:
Compounds of formula 2A wherein $R^2$, $R^3$, M and $R^{20ay}$ corresponds to a row in Table B, and E substituted with $(R^4)_n$ is:

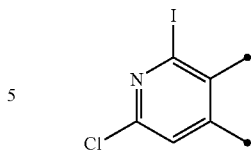

Compound 92:
Compounds of formula 2A wherein $R^2$, $R^3$, M and $R^{20ay}$ corresponds to a row in Table B, and E substituted with $(R^4)_n$ is:

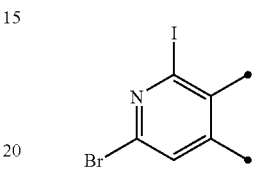

Compound 93:
Compounds of formula 2A wherein $R^2$, $R^3$, M and $R^{20ay}$ corresponds to a row in Table B, and E substituted with $(R^4)_n$ is:

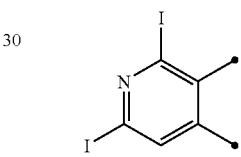

Compound 94:
Compounds of formula 2A wherein $R^2$, $R^3$, M and $R^{20ay}$ corresponds to a row in Table B, and E substituted with $(R^4)_n$ is:

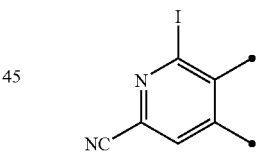

Compound 95:
Compounds of formula 2A wherein $R^2$, $R^3$, M and $R^{20ay}$ corresponds to a row in Table B, and E substituted with $(R^4)_n$ is:

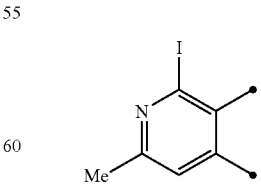

Compound 96:
Compounds of formula 2A wherein $R^2$, $R^3$, M and $R^{20ay}$ corresponds to a row in Table B, and E substituted with $(R^4)_n$ is:

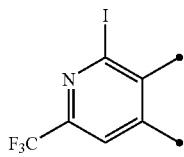

Compound 97:

Compounds of formula 2A wherein $R^2$, $R^3$, M and $R^{20ay}$ corresponds to a row in Table B, and E substituted with $(R^4)_n$ is:

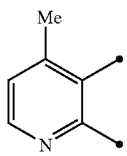

Compound 98:

Compounds of formula 2A wherein $R^2$, $R^3$, M and $R^{20ay}$ corresponds to a row in Table B, and E substituted with $(R^4)_n$ is:

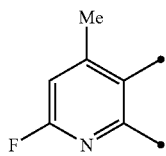

Compound 99:

Compounds of formula 2A wherein $R^2$, $R^3$, M and $R^{20ay}$ corresponds to a row in Table B, and E substituted with $(R^4)_n$ is:

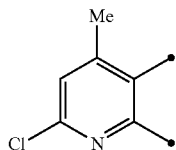

Compound 100:

Compounds of formula 2A wherein $R^2$, $R^3$, M and $R^{20ay}$ corresponds to a row in Table B, and E substituted with $(R^4)_n$ is:

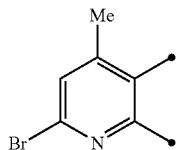

Compound 101:

Compounds of formula 2A wherein $R^2$, $R^3$, M and $R^{20ay}$ corresponds to a row in Table B, and E substituted with $(R^4)_n$ is:

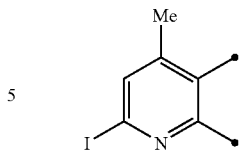

Compound 102:

Compounds of formula 2A wherein $R^2$, $R^3$, M and $R^{20ay}$ corresponds to a row in Table B, and E substituted with $(R^4)_n$ is:

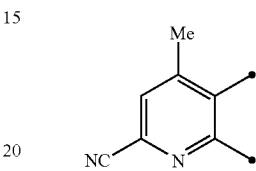

Compound 103:

Compounds of formula 2A wherein $R^2$, $R^3$, M and $R^{20ay}$ corresponds to a row in Table B, and E substituted with $(R^4)_n$ is:

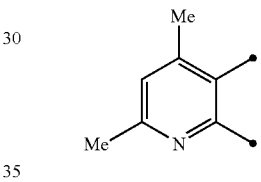

Compound 104:

Compounds of formula 2A wherein $R^2$, $R^3$, M and $R^{20ay}$ corresponds to a row in Table B, and E substituted with $(R^4)_n$ is:

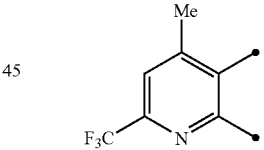

Compound 105:

Compounds of formula 2A wherein $R^2$, $R^3$, M and $R^{20ay}$ corresponds to a row in Table B, and E substituted with $(R^4)_n$ is:

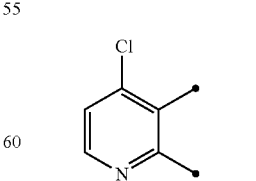

Compound 106:

Compounds of formula 2A wherein $R^2$, $R^3$, M and $R^{20ay}$ corresponds to a row in Table B, and E substituted with $(R^4)_n$ is:

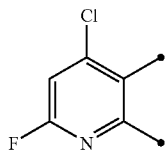

Compound 107:

Compounds of formula 2A wherein $R^2$, $R^3$, M and $R^{20ay}$ corresponds to a row in Table B, and E substituted with $(R^4)_n$ is:

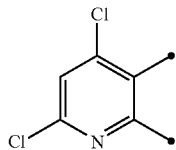

Compound 108:

Compounds of formula 2A wherein $R^2$, $R^3$, M and $R^{20ay}$ corresponds to a row in Table B, and E substituted with $(R^4)_n$ is:

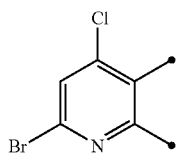

Compound 109:

Compounds of formula 2A wherein $R^2$, $R^3$, M and $R^{20ay}$ corresponds to a row in Table B, and E substituted with $(R^4)_n$ is:

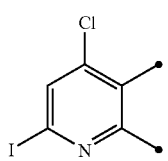

Compound 110:

Compounds of formula 2A wherein $R^2$, $R^3$, M and $R^{20ay}$ corresponds to a row in Table B, and E substituted with $(R^4)_n$ is:

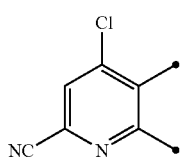

Compound 111:

Compounds of formula 2A wherein $R^2$, $R^3$, M and $R^{20ay}$ corresponds to a row in Table B, and E substituted with $(R^4)_n$ is:

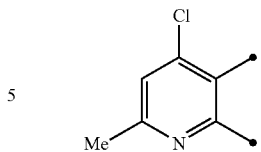

Compound 112:

Compounds of formula 2A wherein $R^2$, $R^3$, M and $R^{20ay}$ corresponds to a row in Table B, and E substituted with $(R^4)_n$ is:

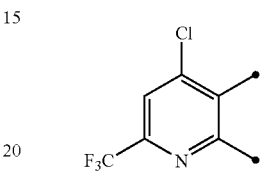

Compound 113:

Compounds of formula 2A wherein $R^2$, $R^3$, M and $R^{20ay}$ corresponds to a row in Table B, and E substituted with $(R^4)_n$ is:

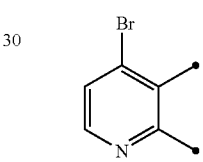

Compound 114:

Compounds of formula 2A wherein $R^2$, $R^3$, M and $R^{20ay}$ corresponds to a row in Table B, and E substituted with $(R^4)_n$ is:

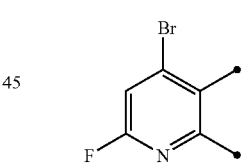

Compound 115:

Compounds of formula 2A wherein $R^2$, $R^3$, M and $R^{20ay}$ corresponds to a row in Table B, and E substituted with $(R^4)_n$ is:

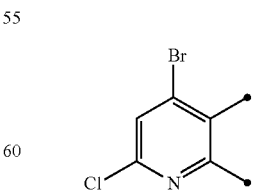

Compound 116:

Compounds of formula 2A wherein $R^2$, $R^3$, M and $R^{20ay}$ corresponds to a row in Table B, and E substituted with $(R^4)_n$ is:

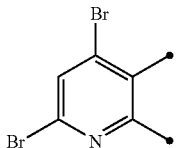

Compound 117:

Compounds of formula 2A wherein $R^2$, $R^3$, M and $R^{20ay}$ corresponds to a row in Table B, and E substituted with $(R^4)_n$ is:

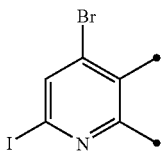

Compound 118:

Compounds of formula 2A wherein $R^2$, $R^3$, M and $R^{20ay}$ corresponds to a row in Table B, and E substituted with $(R^4)_n$ is:

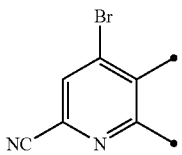

Compound 119:

Compounds of formula 2A wherein $R^2$, $R^3$, M and $R^{20ay}$ corresponds to a row in Table B, and E substituted with $(R^4)_n$ is:

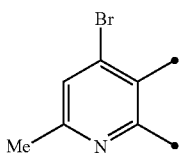

Compound 120:

Compounds of formula 2A wherein $R^2$, $R^3$, M and $R^{20ay}$ corresponds to a row in Table B, and E substituted with $(R^4)_n$ is:

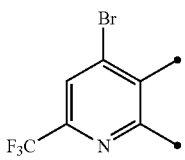

Compound 121:

Compounds of formula 2A wherein $R^2$, $R^3$, M and $R^{20ay}$ corresponds to a row in Table B, and E substituted with $(R^4)_n$ is:

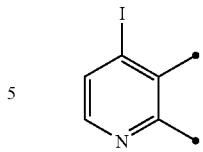

Compound 122:

Compounds of formula 2A wherein $R^2$, $R^3$, M and $R^{20ay}$ corresponds to a row in Table B, and E substituted with $(R^4)_n$ is:

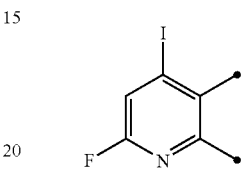

Compound 123:

Compounds of formula 2A wherein $R^2$, $R^3$, M and $R^{20ay}$ corresponds to a row in Table B, and E substituted with $(R^4)_n$ is:

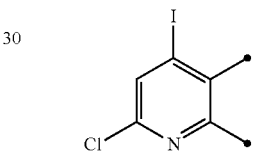

Compound 124:

Compounds of formula 2A wherein $R^2$, $R^3$, M and $R^{20ay}$ corresponds to a row in Table B, and E substituted with $(R^4)_n$ is:

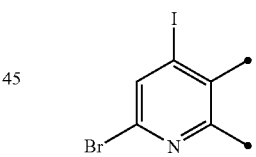

Compound 125:

Compounds of formula 2A wherein $R^2$, $R^3$, M and $R^{20ay}$ corresponds to a row in Table B, and E substituted with $(R^4)_n$ is:

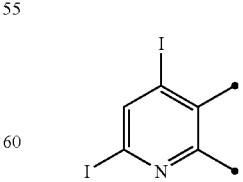

Compound 126:

Compounds of formula 2A wherein $R^2$, $R^3$, M and $R^{20ay}$ corresponds to a row in Table B, and E substituted with $(R^4)_n$ is:

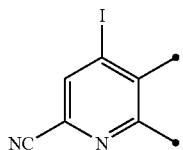

Compound 127:
Compounds of formula 2A wherein $R^2$, $R^3$, M and $R^{20ay}$ corresponds to a row in Table B, and E substituted with $(R^4)_n$ is:

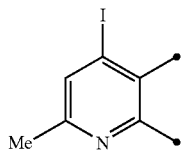

Compound 128:
Compounds of formula 2A wherein $R^2$, $R^3$, M and $R^{20ay}$ corresponds to a row in Table B, and E substituted with $(R^4)_n$ is:

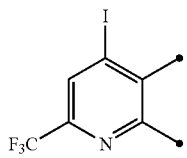

TABLE B

| No. | $R^2$ | $R^3$ | M | $R^{20ay}$ |
|---|---|---|---|---|
| | H | H | H | $CHF_2$ |
| | Me | H | H | $CHF_2$ |
| | H | Me | H | $CHF_2$ |
| | Me | Me | H | $CHF_2$ |
| | Et | H | H | $CHF_2$ |
| | H | Et | H | $CHF_2$ |
| | Et | Et | H | $CHF_2$ |
| | H | $CO_2Me$ | H | $CHF_2$ |
| | H | H | OMe | $CHF_2$ |
| | Me | H | OMe | $CHF_2$ |
| | H | Me | OMe | $CHF_2$ |
| | Me | Me | OMe | $CHF_2$ |
| | Et | H | OMe | $CHF_2$ |
| | H | Et | OMe | $CHF_2$ |
| | Et | Et | OMe | $CHF_2$ |
| | H | $CO_2Me$ | OMe | $CHF_2$ |
| | H | H | $NMe_2$ | $CHF_2$ |
| | Me | H | $NMe_2$ | $CHF_2$ |
| | H | Me | $NMe_2$ | $CHF_2$ |
| | Me | Me | $NMe_2$ | $CHF_2$ |
| | Et | H | $NMe_2$ | $CHF_2$ |
| | H | Et | $NMe_2$ | $CHF_2$ |
| | Et | Et | $NMe_2$ | $CHF_2$ |
| | H | $CO_2Me$ | $NMe_2$ | $CHF_2$ |
| | H | H | NHMe | $CHF_2$ |
| | Me | H | NHMe | $CHF_2$ |
| | H | Me | NHMe | $CHF_2$ |
| | Me | Me | NHMe | $CHF_2$ |
| | Et | H | NHMe | $CHF_2$ |
| | H | Et | NHMe | $CHF_2$ |
| | Et | Et | NHMe | $CHF_2$ |
| | H | $CO_2Me$ | NHMe | $CHF_2$ |
| | H | H | H | $CBrF_2$ |
| | Me | H | H | $CBrF_2$ |
| | H | Me | H | $CBrF_2$ |
| | Me | Me | H | $CBrF_2$ |
| | Et | H | H | $CBrF_2$ |
| | H | Et | H | $CBrF_2$ |
| | Et | Et | H | $CBrF_2$ |
| | H | $CO_2Me$ | H | $CBrF_2$ |
| | H | H | OMe | $CBrF_2$ |
| | Me | H | OMe | $CBrF_2$ |
| | H | Me | OMe | $CBrF_2$ |
| | Me | Me | OMe | $CBrF_2$ |
| | Et | H | OMe | $CBrF_2$ |
| | H | Et | OMe | $CBrF_2$ |
| | Et | Et | OMe | $CBrF_2$ |
| | H | $CO_2Me$ | OMe | $CBrF_2$ |
| | H | H | $NMe_2$ | $CBrF_2$ |
| | Me | H | $NMe_2$ | $CBrF_2$ |
| | H | Me | $NMe_2$ | $CBrF_2$ |
| | Me | Me | $NMe_2$ | $CBrF_2$ |
| | Et | H | $NMe_2$ | $CBrF_2$ |
| | H | Et | $NMe_2$ | $CBrF_2$ |
| | Et | Et | $NMe_2$ | $CBrF_2$ |
| | H | $CO_2Me$ | $NMe_2$ | $CBrF_2$ |
| | H | H | NHMe | $CBrF_2$ |
| | Me | H | NHMe | $CBrF_2$ |
| | H | Me | NHMe | $CBrF_2$ |
| | Me | Me | NHMe | $CBrF_2$ |
| | Et | H | NHMe | $CBrF_2$ |
| | H | Et | NHMe | $CBrF_2$ |
| | Et | Et | NHMe | $CBrF_2$ |
| | H | $CO_2Me$ | NHMe | $CBrF_2$ |
| | H | H | H | $CH_2CF_2$ |
| | Me | H | H | $CH_2CF_2$ |
| | H | Me | H | $CH_2CF_2$ |
| | Me | Me | H | $CH_2CF_2$ |
| | Et | H | H | $CH_2CF_2$ |
| | H | Et | H | $CH_2CF_2$ |
| | Et | Et | H | $CH_2CF_2$ |
| | H | $CO_2Me$ | H | $CH_2CF_2$ |
| | H | H | OMe | $CH_2CF_2$ |
| | Me | H | OMe | $CH_2CF_2$ |
| | H | Me | OMe | $CH_2CF_2$ |
| | Me | Me | OMe | $CH_2CF_2$ |
| | Et | H | OMe | $CH_2CF_2$ |
| | H | Et | OMe | $CH_2CF_2$ |
| | Et | Et | OMe | $CH_2CF_2$ |
| | H | $CO_2Me$ | OMe | $CH_2CF_2$ |
| | H | H | $NMe_2$ | $CH_2CF_2$ |
| | Me | H | $NMe_2$ | $CH_2CF_2$ |
| | H | Me | $NMe_2$ | $CH_2CF_2$ |
| | Me | Me | $NMe_2$ | $CH_2CF_2$ |
| | Et | H | $NMe_2$ | $CH_2CF_2$ |
| | H | Et | $NMe_2$ | $CH_2CF_2$ |
| | Et | Et | $NMe_2$ | $CH_2CF_2$ |
| | H | $CO_2Me$ | $NMe_2$ | $CH_2CF_2$ |
| | H | H | NHMe | $CH_2CF_2$ |
| | Me | H | NHMe | $CH_2CF_2$ |
| | H | Me | NHMe | $CH_2CF_2$ |
| | Me | Me | NHMe | $CH_2CF_2$ |
| | Et | H | NHMe | $CH_2CF_2$ |
| | H | Et | NHMe | $CH_2CF_2$ |
| | Et | Et | NHMe | $CH_2CF_2$ |
| | H | $CO_2Me$ | NHMe | $CH_2CF_2$ |

(3A)

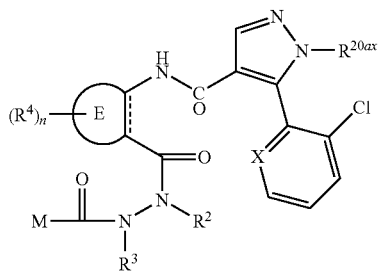

Compound 129:
Compounds of formula 3A wherein $R^2$, $R^3$, M and $R^{20ax}$ corresponds to a row in Table C, and E substituted with $(R^4)_n$ is:

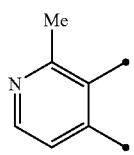

Compound 130:
Compounds of formula 3A wherein $R^2$, $R^3$, M and $R^{20ax}$ corresponds to a row in Table C, and E substituted with $(R^4)_n$ is:

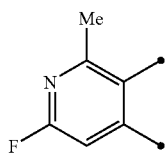

Compound 131:
Compounds of formula 3A wherein $R^2$, $R^3$, M and $R^{20ax}$ corresponds to a row in Table C, and E substituted with $(R^4)_n$ is:

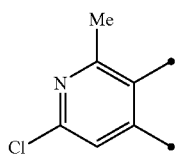

Compound 132:
Compounds of formula 3A wherein $R^2$, $R^3$, M and $R^{20ax}$ corresponds to a row in Table C, and E substituted with $(R^4)_n$ is:

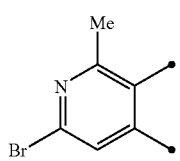

Compound 133:
Compounds of formula 3A wherein $R^2$, $R^3$, M and $R^{20ax}$ corresponds to a row in Table C, and E substituted with $(R^4)_n$ is:

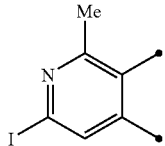

Compound 134:
Compounds of formula 3A wherein $R^2$, $R^3$, M and $R^{20ax}$ corresponds to a row in Table C, and E substituted with $(R^4)_n$ is:

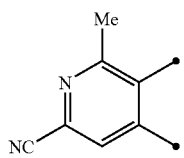

Compound 135:
Compounds of formula 3A wherein $R^2$, $R^3$, M and $R^{20ax}$ corresponds to a row in Table C, and E substituted with $(R^4)_n$ is:

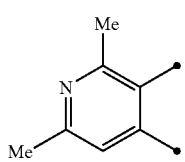

Compound 136:
Compounds of formula 3A wherein $R^2$, $R^3$, M and $R^{20ax}$ corresponds to a row in Table C, and E substituted with $(R^4)_n$ is:

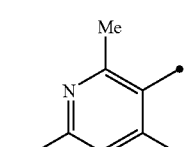

Compound 137:
Compounds of formula 3A wherein $R^2$, $R^3$, M and $R^{20ax}$ corresponds to a row in Table C, and E substituted with $(R^4)_n$ is:

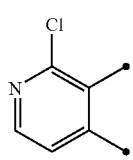

Compound 138:
Compounds of formula 3A wherein $R^2$, $R^3$, M and $R^{20ax}$ corresponds to a row in Table C, and E substituted with $(R^4)_n$ is:

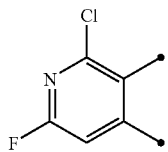

Compound 139:
Compounds of formula 3A wherein $R^2$, $R^3$, M and $R^{20ax}$ corresponds to a row in Table C, and E substituted with $(R^4)_n$ is:

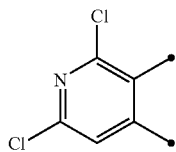

Compound 140:
Compounds of formula 3A wherein $R^2$, $R^3$, M and $R^{20ax}$ corresponds to a row in Table C, and E substituted with $(R^4)_n$ is:

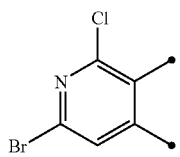

Compound 141:
Compounds of formula 3A wherein $R^2$, $R^3$, M and $R^{20ax}$ corresponds to a row in Table C, and E substituted with $(R^4)_n$ is:

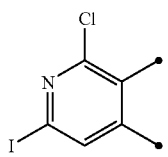

Compound 142:
Compounds of formula 3A wherein $R^2$, $R^3$, M and $R^{20ax}$ corresponds to a row in Table C, and E substituted with $(R^4)_n$ is:

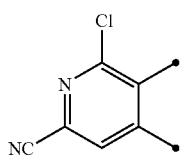

Compound 143:
Compounds of formula 3A wherein $R^2$, $R^3$, M and $R^{20ax}$ corresponds to a row in Table C, and E substituted with $(R^4)_n$ is:

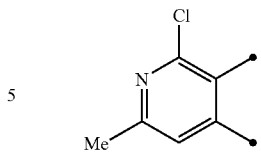

Compound 144:
Compounds of formula 3A wherein $R^2$, $R^3$, M and $R^{20ax}$ corresponds to a row in Table C, and E substituted with $(R^4)_n$ is:

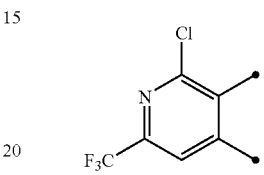

Compound 145:
Compounds of formula 3A wherein $R^2$, $R^3$, M and $R^{20ax}$ corresponds to a row in Table C, and E substituted with $(R^4)_n$ is:

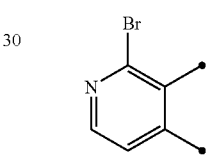

Compound 146:
Compounds of formula 3A wherein $R^2$, $R^3$, M and $R^{20ax}$ corresponds to a row in Table C, and E substituted with $(R^4)_n$ is:

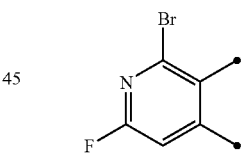

Compound 147:
Compounds of formula 3A wherein $R^2$, $R^3$, M and $R^{20ax}$ corresponds to a row in Table C, and E substituted with $(R^4)_n$ is:

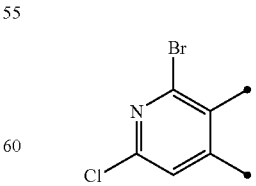

Compound 148:
Compounds of formula 3A wherein $R^2$, $R^3$, M and $R^{20ax}$ corresponds to a row in Table C, and E substituted with $(R^4)_n$ is:

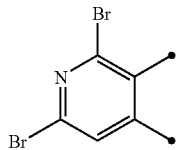

Compound 149:

Compounds of formula 3A wherein $R^2$, $R^3$, M and $R^{20ax}$ corresponds to a row in Table C, and E substituted with $(R^4)_n$ is:

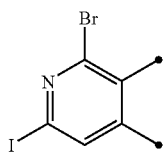

Compound 150:

Compounds of formula 3A wherein $R^2$, $R^3$, M and $R^{20ax}$ corresponds to a row in Table C, and E substituted with $(R^4)_n$ is:

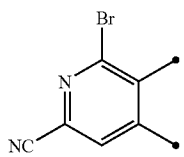

Compound 151:

Compounds of formula 3A wherein $R^2$, $R^3$, M and $R^{20ax}$ corresponds to a row in Table C, and E substituted with $(R^4)_n$ is:

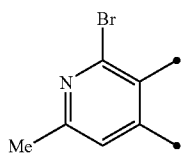

Compound 152:

Compounds of formula 3A wherein $R^2$, $R^3$, M and $R^{20ax}$ corresponds to a row in Table C, and E substituted with $(R^4)_n$ is:

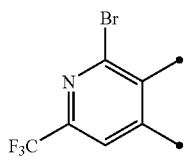

Compound 153:

Compounds of formula 3A wherein $R^2$, $R^3$, M and $R^{20ax}$ corresponds to a row in Table C, and E substituted with $(R^4)_n$ is:

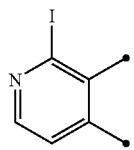

Compound 154:

Compounds of formula 3A wherein $R^2$, $R^3$, M and $R^{20ax}$ corresponds to a row in Table C, and E substituted with $(R^4)_n$ is:

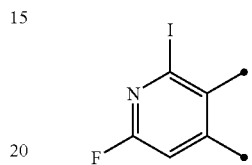

Compound 155:

Compounds of formula 3A wherein $R^2$, $R^3$, M and $R^{20ax}$ corresponds to a row in Table C, and E substituted with $(R^4)_n$ is:

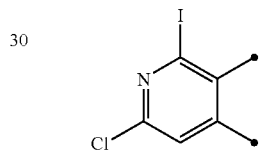

Compound 156:

Compounds of formula 3A wherein $R^2$, $R^3$, M and $R^{20ax}$ corresponds to a row in Table C, and E substituted with $(R^4)_n$ is:

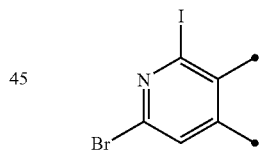

Compound 157:

Compounds of formula 3A wherein $R^2$, $R^3$, M and $R^{20ax}$ corresponds to a row in Table C, and E substituted with $(R^4)_n$ is:

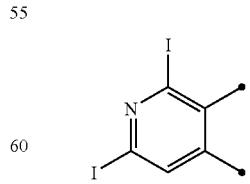

Compound 158:

Compounds of formula 3A wherein $R^2$, $R^3$, M and $R^{20ax}$ corresponds to a row in Table C, and E substituted with $(R^4)_n$ is:

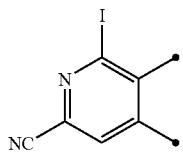

Compound 159:

Compounds of formula 3A wherein $R^2$, $R^3$, M and $R^{20ax}$ corresponds to a row in Table C, and E substituted with $(R^4)_n$ is:

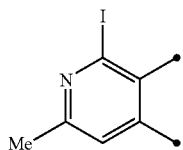

Compound 160:

Compounds of formula 3A wherein $R^2$, $R^3$, M and $R^{20ax}$ corresponds to a row in Table C, and E substituted with $(R^4)_n$ is:

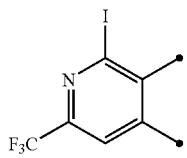

Compound 161:

Compounds of formula 3A wherein $R^2$, $R^3$, M and $R^{20ax}$ corresponds to a row in Table C, and E substituted with $(R^4)_n$ is:

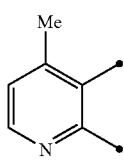

Compound 162:

Compounds of formula 3A wherein $R^2$, $R^3$, M and $R^{20ax}$ corresponds to a row in Table C, and E substituted with $(R^4)_n$ is:

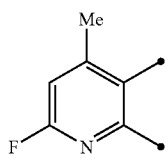

Compound 163:

Compounds of formula 3A wherein $R^2$, $R^3$, M and $R^{20ax}$ corresponds to a row in Table C, and E substituted with $(R^4)_n$ is:

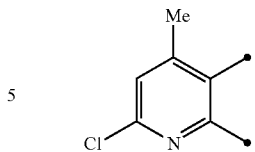

Compound 164:

Compounds of formula 3A wherein $R^2$, $R^3$, M and $R^{20ax}$ corresponds to a row in Table C, and E substituted with $(R^4)_n$ is:

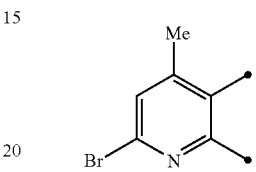

Compound 165:

Compounds of formula 3A wherein $R^2$, $R^3$, M and $R^{20ax}$ corresponds to a row in Table C, and E substituted with $(R^4)_n$ is:

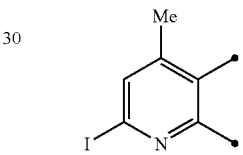

Compound 166:

Compounds of formula 3A wherein $R^2$, $R^3$, M and $R^{20ax}$ corresponds to a row in Table C, and E substituted with $(R^4)_n$ is:

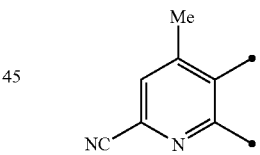

Compound 167:

Compounds of formula 3A wherein $R^2$, $R^3$, M and $R^{20ax}$ corresponds to a row in Table C, and E substituted with $(R^4)_n$ is:

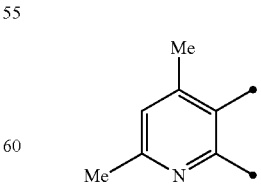

Compound 168:

Compounds of formula 3A wherein $R^2$, $R^3$, M and $R^{20ax}$ corresponds to a row in Table C, and E substituted with $(R^4)_n$ is:

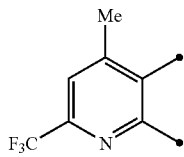

Compound 169:
Compounds of formula 3A wherein $R^2$, $R^3$, M and $R^{20ax}$ corresponds to a row in Table C, and E substituted with $(R^4)_n$ is:

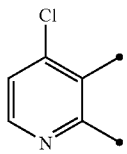

Compound 170:
Compounds of formula 3A wherein $R^2$, $R^3$, M and $R^{20ax}$ corresponds to a row in Table C, and E substituted with $(R^4)_n$ is:

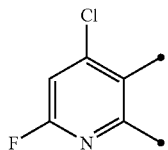

Compound 171:
Compounds of formula 3A wherein $R^2$, $R^3$, M and $R^{20ax}$ corresponds to a row in Table C, and E substituted with $(R^4)_n$ is:

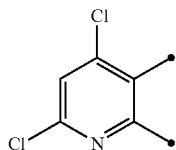

Compound 172:
Compounds of formula 3A wherein $R^2$, $R^3$, M and $R^{20ax}$ corresponds to a row in Table C, and E substituted with $(R^4)_n$ is:

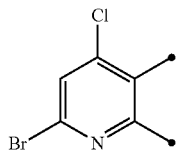

Compound 173:
Compounds of formula 3A wherein $R^2$, $R^3$, M and $R^{20ax}$ corresponds to a row in Table C, and E substituted with $(R^4)_n$ is:

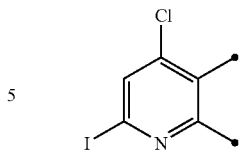

Compound 174:
Compounds of formula 3A wherein $R^2$, $R^3$, M and $R^{20ax}$ corresponds to a row in Table C, and E substituted with $(R^4)_n$ is:

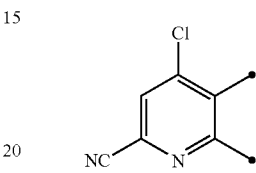

Compound 175:
Compounds of formula 3A wherein $R^2$, $R^3$, M and $R^{20ax}$ corresponds to a row in Table C, and E substituted with $(R^4)_n$ is:

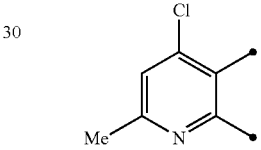

Compound 176:
Compounds of formula 3A wherein $R^2$, $R^3$, M and $R^{20ax}$ corresponds to a row in Table C, and E substituted with $(R^4)_n$ is:

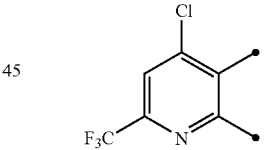

Compound 177:
Compounds of formula 3A wherein $R^2$, $R^3$, M and $R^{20ax}$ corresponds to a row in Table C, and E substituted with $(R^4)_n$ is:

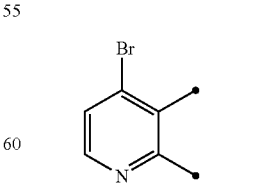

Compound 178:
Compounds of formula 3A wherein $R^2$, $R^3$, M and $R^{20ax}$ corresponds to a row in Table C, and E substituted with $(R^4)_n$ is:

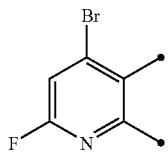

Compound 179:

Compounds of formula 3A wherein $R^2$, $R^3$, M and $R^{20ax}$ corresponds to a row in Table C, and E substituted with $(R^4)_n$ is:

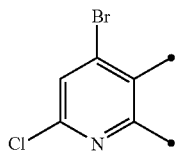

Compound 180:

Compounds of formula 3A wherein $R^2$, $R^3$, M and $R^{20ax}$ corresponds to a row in Table C, and E substituted with $(R^4)_n$ is:

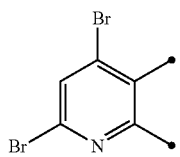

Compound 181:

Compounds of formula 3A wherein $R^2$, $R^3$, M and $R^{20ax}$ corresponds to a row in Table C, and E substituted with $(R^4)_n$ is:

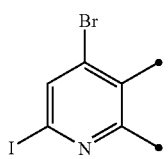

Compound 182:

Compounds of formula 3A wherein $R^2$, $R^3$, M and $R^{20ax}$ corresponds to a row in Table C, and E substituted with $(R^4)_n$ is:

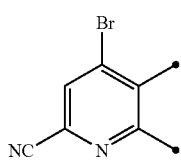

Compound 183:

Compounds of formula 3A wherein $R^2$, $R^3$, M and $R^{20ax}$ corresponds to a row in Table C, and E substituted with $(R^4)_n$ is:

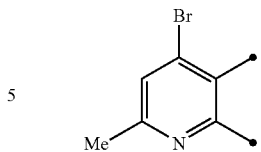

Compound 184:

Compounds of formula 3A wherein $R^2$, $R^3$, M and $R^{20ax}$ corresponds to a row in Table C, and E substituted with $(R^4)_n$ is:

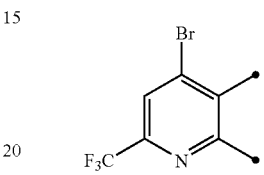

Compound 185:

Compounds of formula 3A wherein $R^2$, $R^3$, M and $R^{20ax}$ corresponds to a row in Table C, and E substituted with $(R^4)_n$ is:

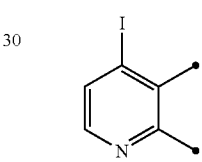

Compound 186:

Compounds of formula 3A wherein $R^2$, $R^3$, M and $R^{20ax}$ corresponds to a row in Table C, and E substituted with $(R^4)_n$ is:

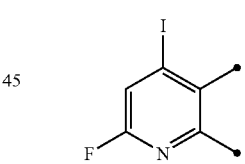

Compound 187:

Compounds of formula 3A wherein $R^2$, $R^3$, M and $R^{20ax}$ corresponds to a row in Table C, and E substituted with $(R^4)_n$ is:

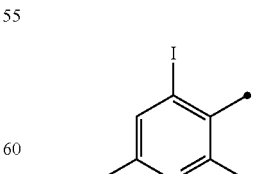

Compound 188:

Compounds of formula 3A wherein $R^2$, $R^3$, M and $R^{20ax}$ corresponds to a row in Table C, and E substituted with $(R^4)_n$ is:

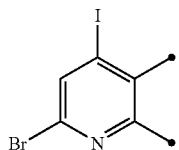

Compound 189:
Compounds of formula 3A wherein $R^2$, $R^3$, M and $R^{20ax}$ corresponds to a row in Table C, and E substituted with $(R^4)_n$ is:

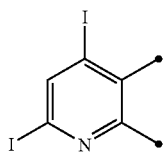

Compound 190:
Compounds of formula 3A wherein $R^2$, $R^3$, M and $R^{20ax}$ corresponds to a row in Table C, and E substituted with $(R^4)_n$ is:

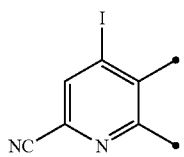

Compound 191:
Compounds of formula 3A wherein $R^2$, $R^3$, M and $R^{20ax}$ corresponds to a row in Table C, and E substituted with $(R^4)_n$ is:

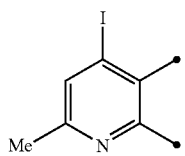

Compound 192:
Compounds of formula 3A wherein $R^2$, $R^3$, M and $R^{20ax}$ corresponds to a row in Table C, and E substituted with $(R^4)_n$ is:

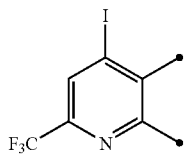

TABLE C

| No. | $R^2$ | $R^3$ | M | $R^{20ax}$ |
|---|---|---|---|---|
| | H | H | H | $CHF_2$ |
| | Me | H | H | $CHF_2$ |
| | H | Me | H | $CHF_2$ |
| | Me | Me | H | $CHF_2$ |
| | Et | H | H | $CHF_2$ |
| | H | Et | H | $CHF_2$ |
| | Et | Et | H | $CHF_2$ |
| | H | $CO_2Me$ | H | $CHF_2$ |
| | H | H | OMe | $CHF_2$ |
| | Me | H | OMe | $CHF_2$ |
| | H | Me | OMe | $CHF_2$ |
| | Me | Me | OMe | $CHF_2$ |
| | Et | H | OMe | $CHF_2$ |
| | H | Et | OMe | $CHF_2$ |
| | Et | Et | OMe | $CHF_2$ |
| | H | $CO_2Me$ | OMe | $CHF_2$ |
| | H | H | $NMe_2$ | $CHF_2$ |
| | Me | H | $NMe_2$ | $CHF_2$ |
| | H | Me | $NMe_2$ | $CHF_2$ |
| | Me | Me | $NMe_2$ | $CHF_2$ |
| | Et | H | $NMe_2$ | $CHF_2$ |
| | H | Et | $NMe_2$ | $CHF_2$ |
| | Et | Et | $NMe_2$ | $CHF_2$ |
| | H | $CO_2Me$ | $NMe_2$ | $CHF_2$ |
| | H | H | NHMe | $CHF_2$ |
| | Me | H | NHMe | $CHF_2$ |
| | H | Me | NHMe | $CHF_2$ |
| | Me | Me | NHMe | $CHF_2$ |
| | Et | H | NHMe | $CHF_2$ |
| | H | Et | NHMe | $CHF_2$ |
| | Et | Et | NHMe | $CHF_2$ |
| | H | $CO_2Me$ | NHMe | $CHF_2$ |
| | H | H | H | $CBrF_2$ |
| | Me | H | H | $CBrF_2$ |
| | H | Me | H | $CBrF_2$ |
| | Me | Me | H | $CBrF_2$ |
| | Et | H | H | $CBrF_2$ |
| | H | Et | H | $CBrF_2$ |
| | Et | Et | H | $CBrF_2$ |
| | H | $CO_2Me$ | H | $CBrF_2$ |
| | H | H | OMe | $CBrF_2$ |
| | Me | H | OMe | $CBrF_2$ |
| | H | Me | OMe | $CBrF_2$ |
| | Me | Me | OMe | $CBrF_2$ |
| | Et | H | OMe | $CBrF_2$ |
| | H | Et | OMe | $CBrF_2$ |
| | Et | Et | OMe | $CBrF_2$ |
| | H | $CO_2Me$ | OMe | $CBrF_2$ |
| | H | H | $NMe_2$ | $CBrF_2$ |
| | Me | H | $NMe_2$ | $CBrF_2$ |
| | H | Me | $NMe_2$ | $CBrF_2$ |
| | Me | Me | $NMe_2$ | $CBrF_2$ |
| | Et | H | $NMe_2$ | $CBrF_2$ |
| | H | Et | $NMe_2$ | $CBrF_2$ |
| | Et | Et | $NMe_2$ | $CBrF_2$ |
| | H | $CO_2Me$ | $NMe_2$ | $CBrF_2$ |
| | H | H | NHMe | $CBrF_2$ |
| | Me | H | NHMe | $CBrF_2$ |
| | H | Me | NHMe | $CBrF_2$ |
| | Me | Me | NHMe | $CBrF_2$ |
| | Et | H | NHMe | $CBrF_2$ |
| | H | Et | NHMe | $CBrF_2$ |
| | Et | Et | NHMe | $CBrF_2$ |
| | H | $CO_2Me$ | NHMe | $CBrF_2$ |
| | H | H | H | $CH_2CF_2$ |
| | Me | H | H | $CH_2CF_2$ |
| | H | Me | H | $CH_2CF_2$ |
| | Me | Me | H | $CH_2CF_2$ |
| | Et | H | H | $CH_2CF_2$ |
| | H | Et | H | $CH_2CF_2$ |
| | Et | Et | H | $CH_2CF_2$ |
| | H | $CO_2Me$ | H | $CH_2CF_2$ |
| | H | H | OMe | $CH_2CF_2$ |
| | Me | H | OMe | $CH_2CF_2$ |
| | H | Me | OMe | $CH_2CF_2$ |
| | Me | Me | OMe | $CH_2CF_2$ |
| | Et | H | OMe | $CH_2CF_2$ |
| | H | Et | OMe | $CH_2CF_2$ |
| | Et | Et | OMe | $CH_2CF_2$ |
| | H | $CO_2Me$ | OMe | $CH_2CF_2$ |

TABLE C-continued

| No. | $R^2$ | $R^3$ | M | $R^{20ax}$ |
|---|---|---|---|---|
| | H | H | $NMe_2$ | $CH_2CF_2$ |
| | Me | H | $NMe_2$ | $CH_2CF_2$ |
| | H | Me | $NMe_2$ | $CH_2CF_2$ |
| | Me | Me | $NMe_2$ | $CH_2CF_2$ |
| | Et | H | $NMe_2$ | $CH_2CF_2$ |
| | H | Et | $NMe_2$ | $CH_2CF_2$ |
| | Et | Et | $NMe_2$ | $CH_2CF_2$ |
| | H | $CO_2Me$ | $NMe_2$ | $CH_2CF_2$ |
| | H | H | NHMe | $CH_2CF_2$ |
| | Me | H | NHMe | $CH_2CF_2$ |
| | H | Me | NHMe | $CH_2CF_2$ |
| | Me | Me | NHMe | $CH_2CF_2$ |
| | Et | H | NHMe | $CH_2CF_2$ |
| | H | Et | NHMe | $CH_2CF_2$ |
| | Et | Et | NHMe | $CH_2CF_2$ |
| | H | $CO_2Me$ | NHMe | $CH_2CF_2$ |

(4A)

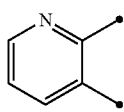

Compound 193:
Compounds of formula 4A wherein $R^2$, $R^3$, M, $R^{19a}$ and $R^{20ay}$ corresponds to a row in Table D, and E substituted with $(R^4)_n$ is:

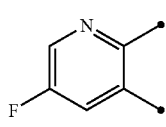

Compound 194:
Compounds of formula 4A wherein $R^2$, $R^3$, M, $R^{19a}$ and $R^{20ay}$ corresponds to a row in Table D, and E substituted with $(R^4)_n$ is:

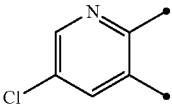

Compound 195:
Compounds of formula 4A wherein $R^2$, $R^3$, M, $R^{19a}$ and $R^{20ay}$ corresponds to a row in Table D, and E substituted with $(R^4)_n$ is:

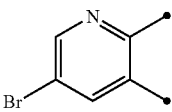

Compound 196:
Compounds of formula 4A wherein $R^2$, $R^3$, M, $R^{19a}$ and $R^{20ay}$ corresponds to a row in Table D, and E substituted with $(R^4)_n$ is:

Compound 197:
Compounds of formula 4A wherein $R^2$, $R^3$, M, $R^{19a}$ and $R^{20ay}$ corresponds to a row in Table D, and E substituted with $(R^4)_n$ is:

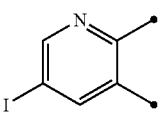

Compound 198:
Compounds of formula 4A wherein $R^2$, $R^3$, M, $R^{19a}$ and $R^{20ay}$ corresponds to a row in Table D, and E substituted with $(R^4)_n$ is:

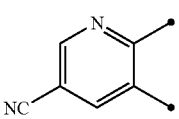

Compound 199:
Compounds of formula 4A wherein $R^2$, $R^3$, M, $R^{19a}$ and $R^{20ay}$ corresponds to a row in Table D, and E substituted with $(R^4)_n$ is:

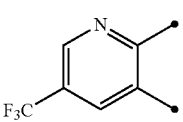

Compound 200:
Compounds of formula 4A wherein $R^2$, $R^3$, M, $R^{19a}$ and $R^{20ay}$ corresponds to a row in Table D, and E substituted with $(R^4)_n$ is:

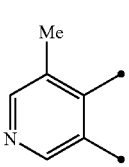

Compound 201:
Compounds of formula 4A wherein $R^2$, $R^3$, M, $R^{19a}$ and $R^{20ay}$ corresponds to a row in Table D, and E substituted with $(R^4)_n$ is:

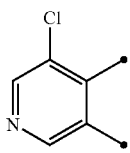

Compound 202:
Compounds of formula 4A wherein $R^2$, $R^3$, M, $R^{19a}$ and $R^{20ay}$ corresponds to a row in Table D, and E substituted with $(R^4)_n$ is:

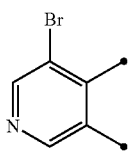

Compound 203:
Compounds of formula 4A wherein $R^2$, $R^3$, M, $R^{19a}$ and $R^{20ay}$ corresponds to a row in Table D, and E substituted with $(R^4)_n$ is:

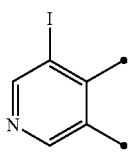

Compound 204:
Compounds of formula 4A wherein $R^2$, $R^3$, M, $R^{19a}$ and $R^{20ay}$ corresponds to a row in Table D, and E substituted with $(R^4)_n$ is:

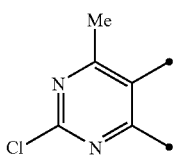

Compound 205:
Compounds of formula 4A wherein $R^2$, $R^3$, M, $R^{19a}$ and $R^{20ay}$ corresponds to a row in Table D, and E substituted with $(R^4)_n$ is:

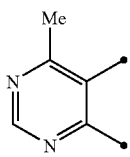

Compound 206:
Compounds of formula 4A wherein $R^2$, $R^3$, M, $R^{19a}$ and $R^{20ay}$ corresponds to a row in Table D, and E substituted with $(R^4)_n$ is:

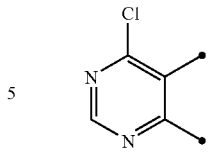

Compound 207:
Compounds of formula 4A wherein $R^2$, $R^3$, M, $R^{19a}$ and $R^{20ay}$ corresponds to a row in Table D, and E substituted with $(R^4)_n$ is:

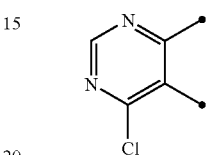

Compound 208:
Compounds of formula 4A wherein $R^2$, $R^3$, M, $R^{19a}$ and $R^{20ay}$ corresponds to a row in Table D, and E substituted with $(R^4)_n$ is:

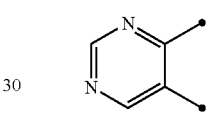

Compound 209:
Compounds of formula 4A wherein $R^2$, $R^3$, M, $R^{19a}$ and $R^{20ay}$ corresponds to a row in Table D, and E substituted with $(R^4)_n$ is:

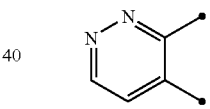

Compound 210:
Compounds of formula 4A wherein $R^2$, $R^3$, M, $R^{19a}$ and $R^{20ay}$ corresponds to a row in Table D, and E substituted with $(R^4)_n$ is:

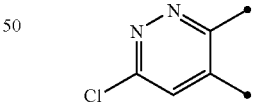

Compound 211:
Compounds of formula 4A wherein $R^2$, $R^3$, M, $R^{19a}$ and $R^{20ay}$ corresponds to a row in Table D, and E substituted with $(R^4)_n$ is:

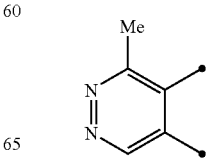

Compound 212:
Compounds of formula 4A wherein $R^2$, $R^3$, M, $R^{19a}$ and $R^{20ay}$ corresponds to a row in Table D, and E substituted with $(R^4)_n$ is:

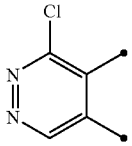

Compound 213:
Compounds of formula 4A wherein $R^2$, $R^3$, M, $R^{19a}$ and $R^{20ay}$ corresponds to a row in Table D, and E substituted with $(R^4)_n$ is:

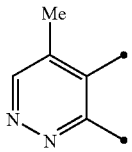

Compound 214:
Compounds of formula 4A wherein $R^2$, $R^3$, M, $R^{19a}$ and $R^{20ay}$ corresponds to a row in Table D, and E substituted with $(R^4)_n$ is:

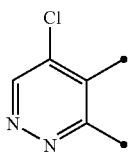

Compound 215:
Compounds of formula 4A wherein $R^2$, $R^3$, M, $R^{19a}$ and $R^{20ay}$ corresponds to a row in Table D, and E substituted with $(R^4)_n$ is:

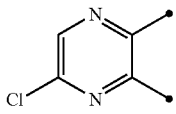

Compound 216:
Compounds of formula 4A wherein $R^2$, $R^3$, M, $R^{19a}$ and $R^{20ay}$ corresponds to a row in Table D, and E substituted with $(R^4)_n$ is:

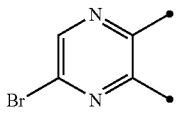

Compound 217:
Compounds of formula 4A wherein $R^2$, $R^3$, M, $R^{19a}$ and $R^{20ay}$ corresponds to a row in Table D, and E substituted with $(R^4)_n$ is:

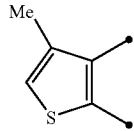

Compound 218:
Compounds of formula 4A wherein $R^2$, $R^3$, M, $R^{19a}$ and $R^{20ay}$ corresponds to a row in Table D, and E substituted with $(R^4)_n$ is:

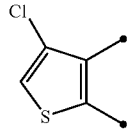

Compound 219:
Compounds of formula 4A wherein $R^2$, $R^3$, M, $R^{19a}$ and $R^{20ay}$ corresponds to a row in Table D, and E substituted with $(R^4)_n$ is:

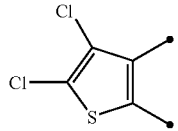

Compound 220:
Compounds of formula 4A wherein $R^2$, $R^3$, M, $R^{19a}$ and $R^{20ay}$ corresponds to a row in Table D, and E substituted with $(R^4)_n$ is:

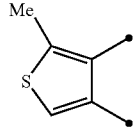

Compound 221:
Compounds of formula 4A wherein $R^2$, $R^3$, M, $R^{19a}$ and $R^{20ay}$ corresponds to a row in Table D, and E substituted with $(R^4)_n$ is:

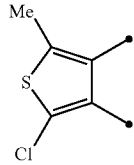

Compound 222:
Compounds of formula 4A wherein $R^2$, $R^3$, M, $R^{19a}$ and $R^{20ay}$ corresponds to a row in Table D, and E substituted with $(R^4)_n$ is:

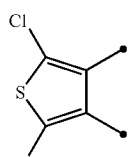

Compound 223:
Compounds of formula 4A wherein $R^2$, $R^3$, M, $R^{19a}$ and $R^{20ay}$ corresponds to a row in Table D, and E substituted with $(R^4)_n$ is:

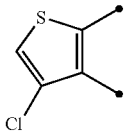

Compound 224:
Compounds of formula 4A wherein $R^2$, $R^3$, M, $R^{19a}$ and $R^{20ay}$ corresponds to a row in Table D, and E substituted with $(R^4)_n$ is:

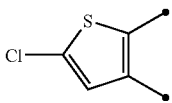

Compound 225:
Compounds of formula 4A wherein $R^2$, $R^3$, M, $R^{19a}$ and $R^{20ay}$ corresponds to a row in Table D, and E substituted with $(R^4)_n$ is:

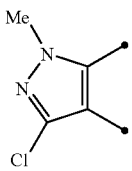

Compound 226:
Compounds of formula 4A wherein $R^2$, $R^3$, M, $R^{19a}$ and $R^{20ay}$ corresponds to a row in Table D, and E substituted with $(R^4)_n$ is:

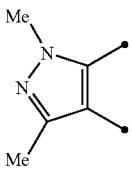

Compound 227:
Compounds of formula 4A wherein $R^2$, $R^3$, M, $R^{19a}$ and $R^{20ay}$ corresponds to a row in Table D, and E substituted with $(R^4)_n$ is:

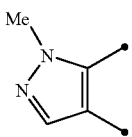

Compound 228:
Compounds of formula 4A wherein $R^2$, $R^3$, M, $R^{19a}$ and $R^{20ay}$ corresponds to a row in Table D, and E substituted with $(R^4)_n$ is:

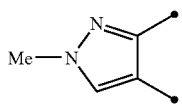

Compound 229:
Compounds of formula 4A wherein $R^2$, $R^3$, M, $R^{19a}$ and $R^{20ay}$ corresponds to a row in Table D, and E substituted with $(R^4)_n$ is:

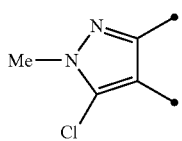

Compound 230:
Compounds of formula 4A wherein $R^2$, $R^3$, M, $R^{19a}$ and $R^{20ay}$ corresponds to a row in Table D, and E substituted with $(R^4)_n$ is:

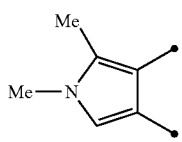

Compound 231:
Compounds of formula 4A wherein $R^2$, $R^3$, M, $R^{19a}$ and $R^{20ay}$ corresponds to a row in Table D, and E substituted with $(R^4)_n$ is:

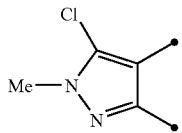

Compound 232:
Compounds of formula 4A wherein $R^2$, $R^3$, M, $R^{19a}$ and $R^{20ay}$ corresponds to a row in Table D, and E substituted with $(R^4)_n$ is:

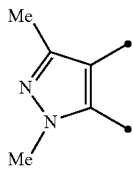

Compound 233:
Compounds of formula 4A wherein $R^2$, $R^3$, M, $R^{19a}$ and $R^{20ay}$ corresponds to a row in Table D, and E substituted with $(R^4)_n$ is:

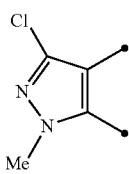

Compound 234:
Compounds of formula 4A wherein $R^2$, $R^3$, M, $R^{19a}$ and $R^{20ay}$ corresponds to a row in Table D, and E substituted with $(R^4)_n$ is:

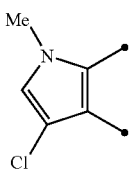

Compound 235:
Compounds of formula 4A wherein $R^2$, $R^3$, M, $R^{19a}$ and $R^{20ay}$ corresponds to a row in Table D, and E substituted with $(R^4)_n$ is:

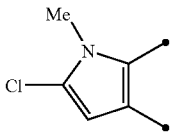

Compound 236:
Compounds of formula 4A wherein $R^2$, $R^3$, M, $R^{19a}$ and $R^{20ay}$ corresponds to a row in Table D, and E substituted with $(R^4)_n$ is:

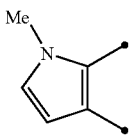

Compound 237:
Compounds of formula 4A wherein $R^2$, $R^3$, M, $R^{19a}$ and $R^{20ay}$ corresponds to a row in Table D, and E substituted with $(R^4)_n$ is:

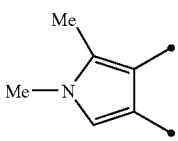

Compound 238:
Compounds of formula 4A wherein $R^2$, $R^3$, M, $R^{19a}$ and $R^{20ay}$ corresponds to a row in Table D, and E substituted with $(R^4)_n$ is:

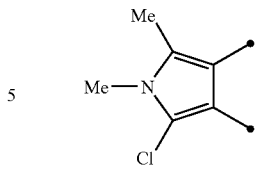

Compound 239:
Compounds of formula 4A wherein $R^2$, $R^3$, M, $R^{19a}$ and $R^{20ay}$ corresponds to a row in Table D, and E substituted with $(R^4)_n$ is:

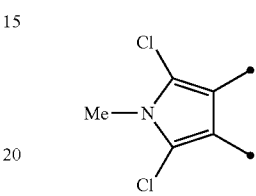

Compound 240:
Compounds of formula 4A wherein $R^2$, $R^3$, M, $R^{19a}$ and $R^{20ay}$ corresponds to a row in Table D, and E substituted with $(R^4)_n$ is:

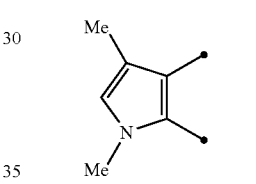

Compound 241:
Compounds of formula 4A wherein $R^2$, $R^3$, M, $R^{19a}$ and $R^{20ay}$ corresponds to a row in Table D, and E substituted with $(R^4)_n$ is:

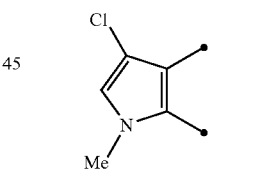

Compound 242:
Compounds of formula 4A wherein $R^2$, $R^3$, M, $R^{19a}$ and $R^{20ay}$ corresponds to a row in Table D, and E substituted with $(R^4)_n$ is:

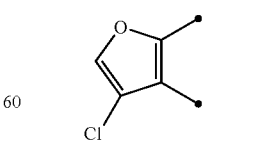

Compound 243:
Compounds of formula 4A wherein $R^2$, $R^3$, M, $R^{19a}$ and $R^{20ay}$ corresponds to a row in Table D, and E substituted with $(R^4)_n$ is:

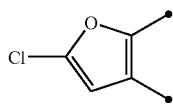

Compound 244:
Compounds of formula 4A wherein $R^2$, $R^3$, M, $R^{19a}$ and $R^{20ay}$ corresponds to a row in Table D, and E substituted with $(R^4)_n$ is:

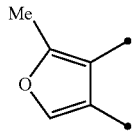

Compound 245:
Compounds of formula 4A wherein $R^2$, $R^3$, M, $R^{19a}$ and $R^{20ay}$ corresponds to a row in Table D, and E substituted with $(R^4)_n$ is:

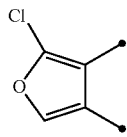

Compound 246:
Compounds of formula 4A wherein $R^2$, $R^3$, M, $R^{19a}$ and $R^{20ay}$ corresponds to a row in Table D, and E substituted with $(R^4)_n$ is:

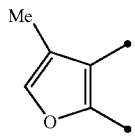

Compound 247:
Compounds of formula 4A wherein $R^2$, $R^3$, M, $R^{19a}$ and $R^{20ay}$ corresponds to a row in Table D, and E substituted with $(R^4)_n$ is:

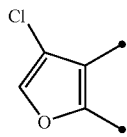

Compound 248:
Compounds of formula 4A wherein $R^2$, $R^3$, M, $R^{19a}$ and $R^{20ay}$ corresponds to a row in Table D, and E substituted with $(R^4)_n$ is:

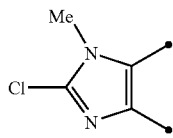

Compound 249:
Compounds of formula 4A wherein $R^2$, $R^3$, M, $R^{19a}$ and $R^{20ay}$ corresponds to a row in Table D, and E substituted with $(R^4)_n$ is:

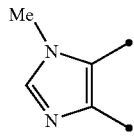

Compound 250:
Compounds of formula 4A wherein $R^2$, $R^3$, M, $R^{19a}$ and $R^{20ay}$ corresponds to a row in Table D, and E substituted with $(R^4)_n$ is:

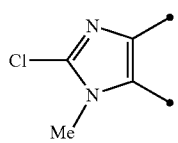

Compound 251:
Compounds of formula 4A wherein $R^2$, $R^3$, M, $R^{19a}$ and $R^{20ay}$ corresponds to a row in Table D, and E substituted with $(R^4)_n$ is:

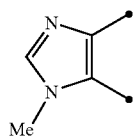

Compound 252:
Compounds of formula 4A wherein $R^2$, $R^3$, M, $R^{19a}$ and $R^{20ay}$ corresponds to a row in Table D, and E substituted with $(R^4)_n$ is:

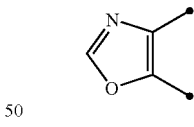

Compound 253:
Compounds of formula 4A wherein $R^2$, $R^3$, M, $R^{19a}$ and $R^{20ay}$ corresponds to a row in Table D, and E substituted with $(R^4)_n$ is:

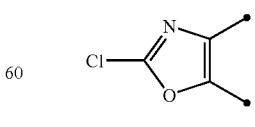

Compound 254:
Compounds of formula 4A wherein $R^2$, $R^3$, M, $R^{19a}$ and $R^{20ay}$ corresponds to a row in Table D, and E substituted with $(R^4)_n$ is:

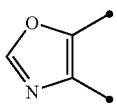

Compound 255:
Compounds of formula 4A wherein $R^2$, $R^3$, M, $R^{19a}$ and $R^{20ay}$ corresponds to a row in Table D, and E substituted with $(R^4)_n$ is:

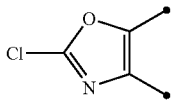

Compound 256:
Compounds of formula 4A wherein $R^2$, $R^3$, M, $R^{13a}$ and $R^{20ay}$ corresponds to a row in Table D, and E substituted with $(R^4)_n$ is:

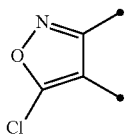

Compound 257:
Compounds of formula 4A wherein $R^2$, $R^3$, M, $R^{19a}$ and $R^{20ay}$ corresponds to a row in Table D, and E substituted with $(R^4)_n$ is:

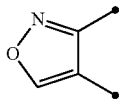

Compound 258:
Compounds of formula 4A wherein $R^2$, $R^3$, M, $R^{19a}$ and $R^{20ay}$ corresponds to a row in Table D, and E substituted with $(R^4)_n$ is:

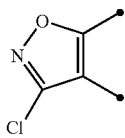

Compound 259:
Compounds of formula 4A wherein $R^2$, $R^3$, M, $R^{19a}$ and $R^{20ay}$ corresponds to a row in Table D, and E substituted with $(R^4)_n$ is:

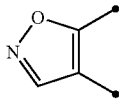

Compound 260:
Compounds of formula 4A wherein $R^2$, $R^3$, M, $R^{19a}$ and $R^{20ay}$ corresponds to a row in Table D, and E substituted with $(R^4)_n$ is:

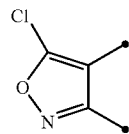

Compound 261:
Compounds of formula 4A wherein $R^2$, $R^3$, M, $R^{19a}$ and $R^{20ay}$ corresponds to a row in Table D, and E substituted with $(R^4)_n$ is:

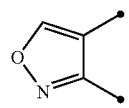

Compound 262:
Compounds of formula 4A wherein $R^2$, $R^3$, M, $R^{19a}$ and $R^{20ay}$ corresponds to a row in Table D, and E substituted with $(R^4)_n$ is:

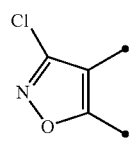

Compound 263:
Compounds of formula 4A wherein $R^2$, $R^3$, M, $R^{19a}$ and $R^{20ay}$ corresponds to a row in Table D, and E substituted with $(R^4)_n$ is:

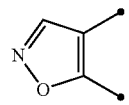

Compound 264:
Compounds of formula 4A wherein $R^2$, $R^3$, M, $R^{19a}$ and $R^{20ay}$ corresponds to a row in Table D, and E substituted with $(R^4)_n$ is:

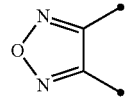

Compound 265:
Compounds of formula 4A wherein $R^2$, $R^3$, M, $R^{19a}$ and $R^{20ay}$ corresponds to a row in Table D, and E substituted with $(R^4)_n$ is:

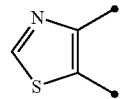

Compound 266:
Compounds of formula 4A wherein $R^2$, $R^3$, M, $R^{19a}$ and $R^{20ay}$ corresponds to a row in Table D, and E substituted with $(R^4)_n$ is:

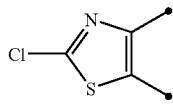

Compound 267:
Compounds of formula 4A wherein $R^2$, $R^3$, M, $R^{19a}$ and $R^{20ay}$ corresponds to a row in Table D, and E substituted with $(R^4)_n$ is:

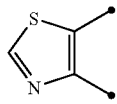

Compound 268:
Compounds of formula 4A wherein $R^2$, $R^3$, M, $R^{19a}$ and $R^{20ay}$ corresponds to a row in Table D, and E substituted with $(R^4)_n$ is:

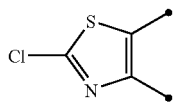

Compound 269:
Compounds of formula 4A wherein $R^2$, $R^3$, M, $R^{19a}$ and $R^{20ay}$ corresponds to a row in Table D, and E substituted with $(R^4)_n$ is:

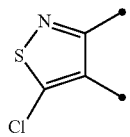

Compound 270:
Compounds of formula 4A wherein $R^2$, $R^3$, M, $R^{19a}$ and $R^{20ay}$ corresponds to a row in Table D, and E substituted with $(R^4)_n$ is:

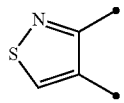

Compound 271:
Compounds of formula 4A wherein $R^2$, $R^3$, M, $R^{19a}$ and $R^{20ay}$ corresponds to a row in Table D, and E substituted with $(R^4)_n$ is:

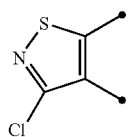

Compound 272:
Compounds of formula 4A wherein $R^2$, $R^3$, M, $R^{19a}$ and $R^{20ay}$ corresponds to a row in Table D, and E substituted with $(R^4)_n$ is:

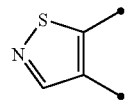

Compound 273:
Compounds of formula 4A wherein $R^2$, $R^3$, M, $R^{19a}$ and $R^{20ay}$ corresponds to a row in Table D, and E substituted with $(R^4)_n$ is:

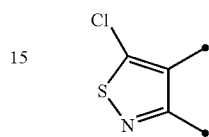

Compound 274:
Compounds of formula 4A wherein $R^2$, $R^3$, M, $R^{19a}$ and $R^{20ay}$ corresponds to a row in Table D, and E substituted with $(R^4)_n$ is:

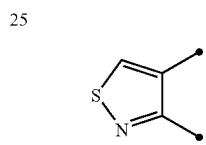

Compound 275:
Compounds of formula 4A wherein $R^2$, $R^3$, M, $R^{19a}$ and $R^{20ay}$ corresponds to a row in Table D, and E substituted with $(R^4)_n$ is:

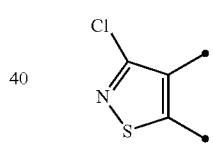

Compound 276:
Compounds of formula 4A wherein $R^2$, $R^3$, M, $R^{19a}$ and $R^{20ay}$ corresponds to a row in Table D, and E substituted with $(R^4)_n$ is:

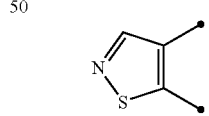

Compound 277:
Compounds of formula 4A wherein $R^2$, $R^3$, M, $R^{19a}$ and $R^{20ay}$ corresponds to a row in Table D, and E substituted with $(R^4)_n$ is:

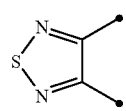

TABLE D

| R² | R³ | M | R¹⁹ᵃ | R²⁰ᵃʸ |
|---|---|---|---|---|
| H | H | H | 3-chloro-2-pyridinyl | Cl |
| Me | H | H | 3-chloro-2-pyridinyl | Cl |
| H | Me | H | 3-chloro-2-pyridinyl | Cl |
| Me | Me | H | 3-chloro-2-pyridinyl | Cl |
| Et | H | H | 3-chloro-2-pyridinyl | Cl |
| H | Et | H | 3-chloro-2-pyridinyl | Cl |
| Et | Et | H | 3-chloro-2-pyridinyl | Cl |
| H | CO₂Me | H | 3-chloro-2-pyridinyl | Cl |
| H | H | H | 3-chloro-2-pyridinyl | Br |
| Me | H | H | 3-chloro-2-pyridinyl | Br |
| H | Me | H | 3-chloro-2-pyridinyl | Br |
| Me | Me | H | 3-chloro-2-pyridinyl | Br |
| Et | H | H | 3-chloro-2-pyridinyl | Br |
| H | Et | H | 3-chloro-2-pyridinyl | Br |
| Et | Et | H | 3-chloro-2-pyridinyl | Br |
| H | CO₂Me | H | 3-chloro-2-pyridinyl | Br |
| H | H | H | 3-chloro-2-pyridinyl | CF₃ |
| Me | H | H | 3-chloro-2-pyridinyl | CF₃ |
| H | Me | H | 3-chloro-2-pyridinyl | CF₃ |
| Me | Me | H | 3-chloro-2-pyridinyl | CF₃ |
| Et | H | H | 3-chloro-2-pyridinyl | CF₃ |
| H | Et | H | 3-chloro-2-pyridinyl | CF₃ |
| Et | Et | H | 3-chloro-2-pyridinyl | CF₃ |
| H | CO₂Me | H | 3-chloro-2-pyridinyl | CF₃ |
| H | H | OMe | 3-chloro-2-pyridinyl | Cl |
| Me | H | OMe | 3-chloro-2-pyridinyl | Cl |
| H | Me | OMe | 3-chloro-2-pyridinyl | Cl |
| Me | Me | OMe | 3-chloro-2-pyridinyl | Cl |
| Et | H | OMe | 3-chloro-2-pyridinyl | Cl |
| H | Et | OMe | 3-chloro-2-pyridinyl | Cl |
| Et | Et | OMe | 3-chloro-2-pyridinyl | Cl |
| H | CO₂Me | OMe | 3-chloro-2-pyridinyl | Cl |
| H | H | OMe | 3-chloro-2-pyridinyl | Br |
| Me | H | OMe | 3-chloro-2-pyridinyl | Br |
| H | Me | OMe | 3-chloro-2-pyridinyl | Br |
| Me | Me | OMe | 3-chloro-2-pyridinyl | Br |
| Et | H | OMe | 3-chloro-2-pyridinyl | Br |
| H | Et | OMe | 3-chloro-2-pyridinyl | Br |
| Et | Et | OMe | 3-chloro-2-pyridinyl | Br |
| H | CO₂Me | OMe | 3-chloro-2-pyridinyl | Br |
| H | H | OMe | 3-chloro-2-pyridinyl | CF₃ |
| Me | H | OMe | 3-chloro-2-pyridinyl | CF₃ |
| H | Me | OMe | 3-chloro-2-pyridinyl | CF₃ |
| Me | Me | OMe | 3-chloro-2-pyridinyl | CF₃ |
| Et | H | OMe | 3-chloro-2-pyridinyl | CF₃ |
| H | Et | OMe | 3-chloro-2-pyridinyl | CF₃ |
| Et | Et | OMe | 3-chloro-2-pyridinyl | CF₃ |
| H | CO₂Me | OMe | 3-chloro-2-pyridinyl | CF₃ |

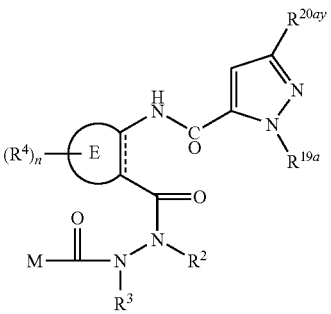

(5A)

Compound 278:

Compounds of formula 5A wherein $R^2$, $R^3$, M, $R^{19a}$ and $R^{20ay}$ corresponds to a row in Table E, and E substituted with $(R^4)_n$ is:

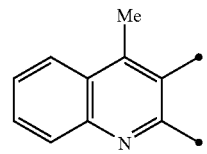

Compound 279:

Compounds of formula 5A wherein $R^2$, $R^3$, M, $R^{19a}$ and $R^{20ay}$ corresponds to a row in Table E, and E substituted with $(R^4)_n$ is:

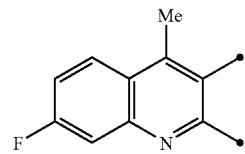

Compound 280:

Compounds of formula 5A wherein $R^2$, $R^3$, M, $R^{19a}$ and $R^{20ay}$ corresponds to a row in Table E, and E substituted with $(R^4)_n$ is:

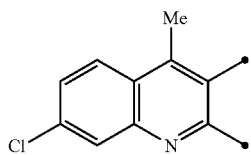

Compound 281:
Compounds of formula 5A wherein $R^2$, $R^3$, M, $R^{19a}$ and $R^{20ay}$ corresponds to a row in Table E, and E substituted with $(R^4)_n$ is:

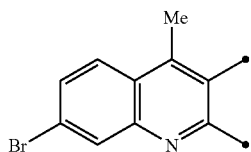

Compound 282:
Compounds of formula 5A wherein $R^2$, $R^3$, M, $R^{19a}$ and $R^{20ay}$ corresponds to a row in Table E, and E substituted with $(R^4)_n$ is:

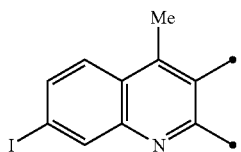

Compound 283:
Compounds of formula 5A wherein $R^2$, $R^3$, M, $R^{19a}$ and $R^{20ay}$ corresponds to a row in Table E, and E substituted with $(R^4)_n$ is:

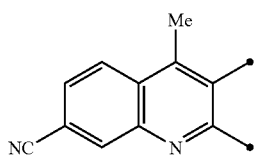

Compound 284:
Compounds of formula 5A wherein $R^2$, $R^3$, M, $R^{19a}$ and $R^{20ay}$ corresponds to a row in Table E, and E substituted with $(R^4)_n$ is:

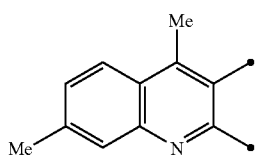

Compound 285:
Compounds of formula 5A wherein $R^2$, $R^3$, M, $R^{19a}$ and $R^{20ay}$ corresponds to a row in Table E, and E substituted with $(R^4)_n$ is:

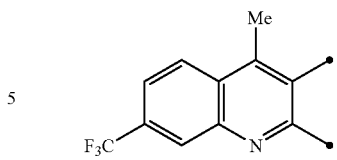

Compound 286:
Compounds of formula 5A wherein $R^2$, $R^3$, M, $R^{19a}$ and $R^{20ay}$ corresponds to a row in Table E, and E substituted with $(R^4)_n$ is:

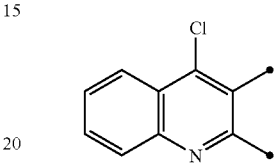

Compound 287:
Compounds of formula 5A wherein $R^2$, $R^3$, M, $R^{19a}$ and $R^{20ay}$ corresponds to a row in Table E, and E substituted with $(R^4)_n$ is:

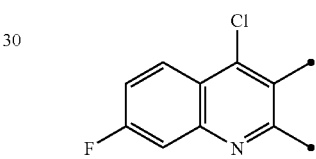

Compound 288:
Compounds of formula 5A wherein $R^2$, $R^3$, M, $R^{19a}$ and $R^{20ay}$ corresponds to a row in Table E, and E substituted with $(R^4)_n$ is:

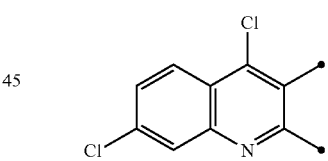

Compound 289:
Compounds of formula 5A wherein $R^2$, $R^3$, M, $R^{19a}$ and $R^{20ay}$ corresponds to a row in Table E, and E substituted with $(R^4)_n$ is:

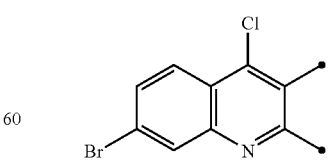

Compound 290:
Compounds of formula 5A wherein $R^2$, $R^3$, M, $R^{19a}$ and $R^{20ay}$ corresponds to a row in Table E, and E substituted with $(R^4)_n$ is:

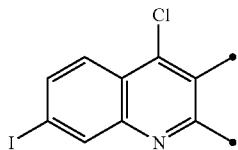

Compound 291:
Compounds of formula 5A wherein $R^2$, $R^3$, M, $R^{19a}$ and $R^{20ay}$ corresponds to a row in Table E, and E substituted with $(R^4)_n$ is:

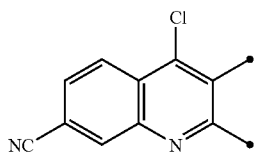

Compound 292:
Compounds of formula 5A wherein $R^2$, $R^3$, M, $R^{19a}$ and $R^{20ay}$ corresponds to a row in Table E, and E substituted with $(R^4)_n$ is:

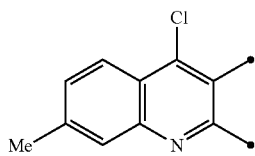

Compound 293:
Compounds of formula 5A wherein $R^2$, $R^3$, M, $R^{19a}$ and $R^{20ay}$ corresponds to a row in Table E, and E substituted with $(R^4)_n$ is:

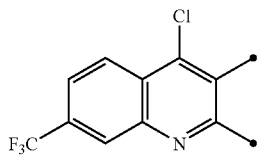

Compound 294:
Compounds of formula 5A wherein $R^2$, $R^3$, M, $R^{19a}$ and $R^{20ay}$ corresponds to a row in Table E, and E substituted with $(R^4)_n$ is:

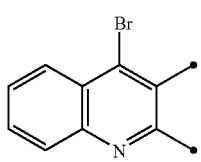

Compound 295:
Compounds of formula 5A wherein $R^2$, $R^3$, M, $R^{19a}$ and $R^{20ay}$ corresponds to a row in Table E, and E substituted with $(R^4)_n$ is:

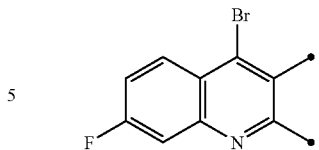

Compound 296:
Compounds of formula 5A wherein $R^2$, $R^3$, M, $R^{19a}$, $R^{20ay}$ corresponds to a row in Table E, and E substituted with $(R^4)_n$ is:

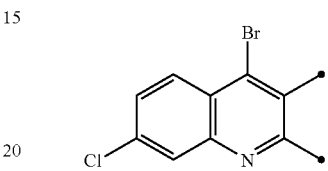

Compound 297:
Compounds of formula 5A wherein $R^2$, $R^3$, M, $R^{19a}$ and $R^{20ay}$ corresponds to a row in Table E, and E substituted with $(R^4)_n$ is:

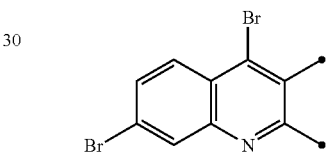

Compound 298:
Compounds of formula 5A wherein $R^2$, $R^3$, M, $R^{19a}$ and $R^{20ay}$ corresponds to a row in Table E, and E substituted with $(R^4)_n$ is:

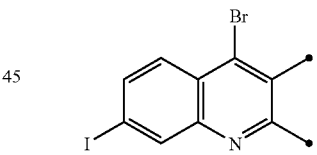

Compound 299:
Compounds of formula 5A wherein $R^2$, $R^3$, M, $R^{19a}$ and $R^{20ay}$ corresponds to a row in Table E, and E substituted with $(R^4)_n$ is:

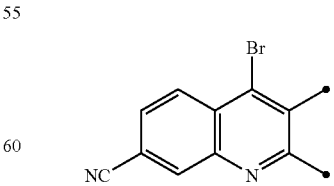

Compound 300:
Compounds of formula 5A wherein $R^2$, $R^3$, M, $R^{19a}$ and $R^{20ay}$ corresponds to a row in Table E, and E substituted with $(R^4)_n$ is:

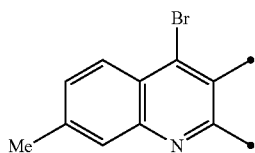

Compound 301:
Compounds of formula 5A wherein $R^2$, $R^3$, M, $R^{19a}$ and $R^{20ay}$ corresponds to a row in Table E, and E substituted with $(R^4)_n$ is:

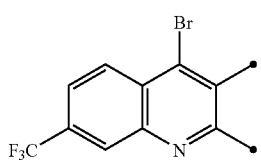

Compound 302:
Compounds of formula 5A wherein $R^2$, $R^3$, M, $R^{19a}$ and $R^{20ay}$ corresponds to a row in Table E, and E substituted with $(R^4)_n$ is:

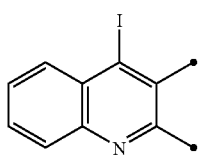

Compound 303:
Compounds of formula 5A wherein $R^2$, $R^3$, M, $R^{19a}$ and $R^{20ay}$ corresponds to a row in Table E, and E substituted with $(R^4)_n$ is:

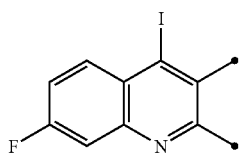

Compound 304:
Compounds of formula 5A wherein $R^2$, $R^3$, M, $R^{19a}$ and $R^{20ay}$ corresponds to a row in Table E, and E substituted with $(R^4)_n$ is:

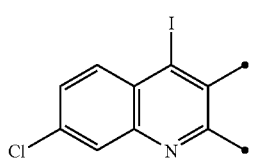

Compound 305:
Compounds of formula 5A wherein $R^2$, $R^3$, M, $R^{19a}$ and $R^{20ay}$ corresponds to a row in Table E, and E substituted with $(R^4)_n$ is:

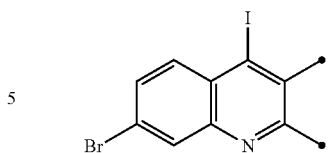

Compound 306:
Compounds of formula 5A wherein $R^2$, $R^3$, M, $R^{19a}$ and $R^{20ay}$ corresponds to a row in Table E, and E substituted with $(R^4)_n$ is:

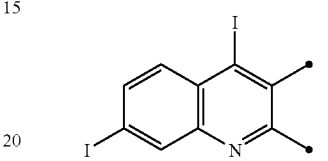

Compound 307:
Compounds of formula 5A wherein $R^2$, $R^3$, M, $R^{19a}$ and $R^{20ay}$ corresponds to a row in Table E, and E substituted with $(R^4)_n$ is:

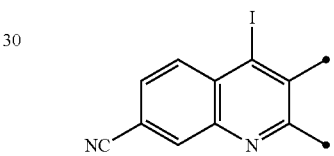

Compound 308:
Compounds of formula 5A wherein $R^2$, $R^3$, M, $R^{19a}$ and $R^{20ay}$ corresponds to a row in Table E, and E substituted with $(R^4)_n$ is:

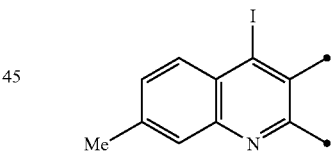

Compound 309:
Compounds of formula 5A wherein $R^2$, $R^3$, M, $R^{19a}$ and $R^{20ay}$ corresponds to a row in Table E, and E substituted with $(R^4)_n$ is:

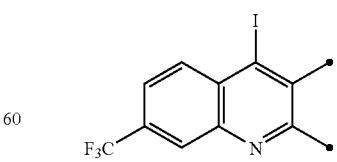

Compound 310:
Compounds of formula 5A wherein $R^2$, $R^3$, M, $R^{19a}$ and $R^{20ay}$ corresponds to a row in Table E, and E substituted with $(R^4)_n$ is:

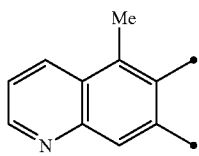

Compound 311:

Compounds of formula 5A wherein $R^2$, $R^3$, M, $R^{19a}$ and $R^{20ay}$ corresponds to a row in Table E, and E substituted with $(R^4)_n$ is:

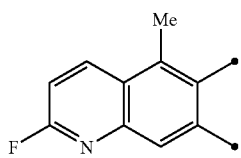

Compound 312:

Compounds of formula 5A wherein $R^2$, $R^3$, M, $R^{19a}$ and $R^{20ay}$ corresponds to a row in Table E, and E substituted with $(R^4)_n$ is:

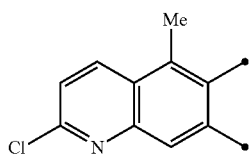

Compound 313:

Compounds of formula 5A wherein $R^2$, $R^3$, M, $R^{19a}$ and $R^{20ay}$ corresponds to a row in Table E, and E substituted with $(R^4)_n$ is:

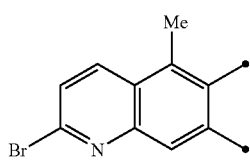

Compound 314:

Compounds of formula 5A wherein $R^2$, $R^3$, M, $R^{19a}$ and $R^{20ay}$ corresponds to a row in Table E, and E substituted with $(R^4)_n$ is:

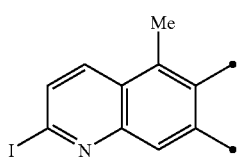

Compound 315:

Compounds of formula 5A wherein $R^2$, $R^3$, M, $R^{19a}$ and $R^{20ay}$ corresponds to a row in Table E, and E substituted with $(R^4)_n$ is:

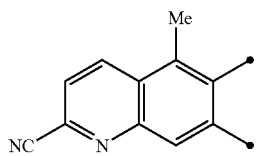

Compound 316:

Compounds of formula 5A wherein $R^2$, $R^3$, M, $R^{19a}$ and $R^{20ay}$ corresponds to a row in Table E, and E substituted with $(R^4)_n$ is:

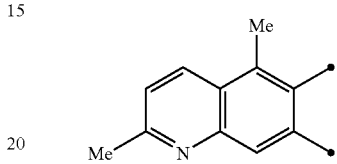

Compound 317:

Compounds of formula 5A wherein $R^2$, $R^3$, M, $R^{19a}$ and $R^{20ay}$ corresponds to a row in Table E, and E substituted with $(R^4)_n$ is:

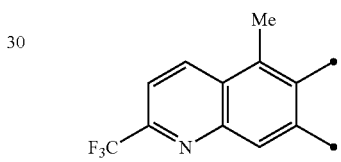

Compound 318:

Compounds of formula 5A wherein $R^2$, $R^3$, M, $R^{19a}$ and $R^{20ay}$ corresponds to a row in Table E, and E substituted with $(R^4)_n$ is:

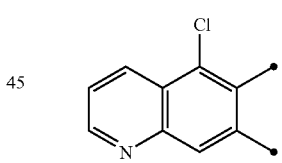

Compound 319:

Compounds of formula 5A wherein $R^2$, $R^3$, M, $R^{19a}$ and $R^{20ay}$ corresponds to a row in Table E, and E substituted with $(R^4)_n$ is:

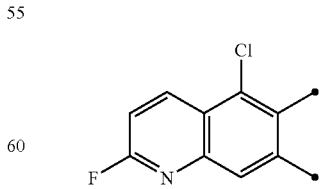

Compound 320:

Compounds of formula 5A wherein $R^2$, $R^3$, M, $R^{19a}$ and $R^{20ay}$ corresponds to a row in Table E, and E substituted with $(R^4)_n$ is:

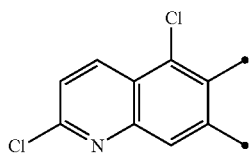

Compound 321:
Compounds of formula 5A wherein $R^2$, $R^3$, M, $R^{19a}$ and $R^{20ay}$ corresponds to a row in Table E, and E substituted with $(R^4)_n$ is:

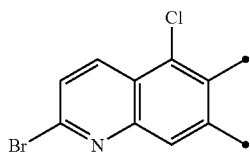

Compound 322:
Compounds of formula 5A wherein $R^2$, $R^3$, M, $R^{19a}$ and $R^{20ay}$ corresponds to a row in Table E, and E substituted with $(R^4)_n$ is:

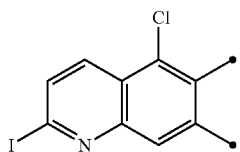

Compound 323:
Compounds of formula 5A wherein $R^2$, $R^3$, M, $R^{19a}$ and $R^{20ay}$ corresponds to a row in Table E, and E substituted with $(R^4)_n$ is:

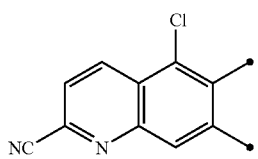

Compound 324:
Compounds of formula 5A wherein $R^2$, $R^3$, M, $R^{19a}$ and $R^{20ay}$ corresponds to a row in Table E, and E substituted with $(R^4)_n$ is:

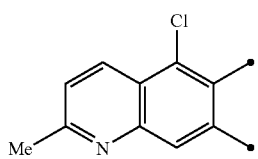

Compound 325:
Compounds of formula 5A wherein $R^2$, $R^3$, M, $R^{19a}$ and $R^{20ay}$ corresponds to a row in Table E, and E substituted with $(R^4)_n$ is:

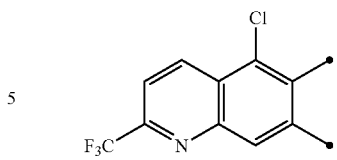

Compound 326:
Compounds of formula 5A wherein $R^2$, $R^3$, M, $R^{19a}$ and $R^{20ay}$ corresponds to a row in Table E, and E substituted with $(R^4)_n$ is:

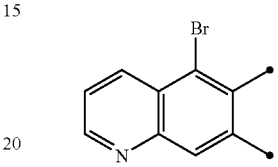

Compound 327:
Compounds of formula 5A wherein $R^2$, $R^3$, M, $R^{19a}$ and $R^{20ay}$ corresponds to a row in Table E, and E substituted with $(R^4)_n$ is:

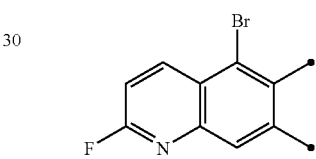

Compound 328:
Compounds of formula 5A wherein $R^2$, $R^3$, M, $R^{19a}$ and $R^{20ay}$ corresponds to a row in Table E, and E substituted with $(R^4)_n$ is:

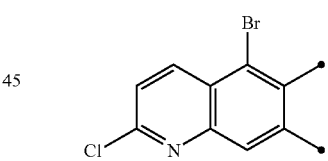

Compound 329:
Compounds of formula 5A wherein $R^2$, $R^3$, M, $R^{19a}$ and $R^{20ay}$ corresponds to a row in Table E, and E substituted with $(R^4)_n$ is:

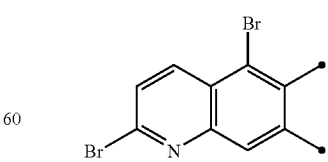

Compound 330:
Compounds of formula 5A wherein $R^2$, $R^3$, M, $R^{19a}$ and $R^{20ay}$ corresponds to a row in Table E, and E substituted with $(R^4)_n$ is:

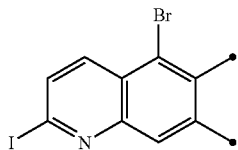

Compound 331:
Compounds of formula 5A wherein $R^2$, $R^3$, M, $R^{19a}$ and $R^{20ay}$ corresponds to a row in Table E, and E substituted with $(R^4)_n$ is:

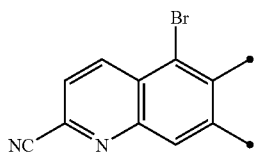

Compound 332:
Compounds of formula 5A wherein $R^2$, $R^3$, M, $R^{19a}$ and $R^{20ay}$ corresponds to a row in Table E, and E substituted with $(R^4)_n$ is:

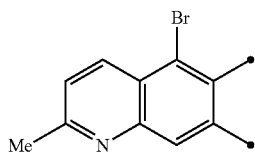

Compound 333:
Compounds of formula 5A wherein $R^2$, $R^3$, M, $R^{19a}$ and $R^{20ay}$ corresponds to a row in Table E, and E substituted with $(R^4)_n$ is:

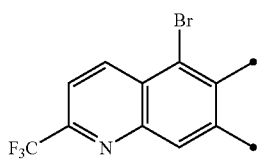

Compound 334:
Compounds of formula 5A wherein $R^2$, $R^3$, M, $R^{19a}$ and $R^{20ay}$ corresponds to a row in Table E, and E substituted with $(R^4)_n$ is:

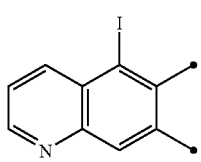

Compound 335:
Compounds of formula 5A wherein $R^2$, $R^3$, M, $R^{19a}$ and $R^{20ay}$ corresponds to a row in Table E, and E substituted with $(R^4)_n$ is:

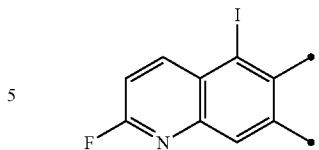

Compound 336:
Compounds of formula 5A wherein $R^2$, $R^3$, M, $R^{19a}$ and $R^{20ay}$ corresponds to a row in Table E, and E substituted with $(R^4)_n$ is:

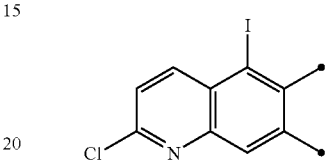

Compound 337:
Compounds of formula 5A wherein $R^2$, $R^3$, M, $R^{19a}$ and $R^{20ay}$ corresponds to a row in Table E, and E substituted with $(R^4)_n$ is:

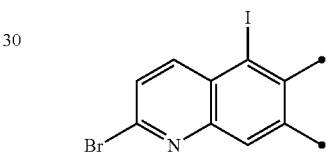

Compound 338:
Compounds of formula 5A wherein $R^2$, $R^3$, M, $R^{19a}$ and $R^{20ay}$ corresponds to a row in Table E, and E substituted with $(R^4)_n$ is:

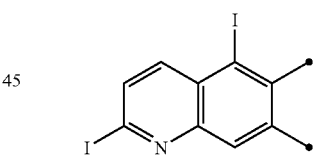

Compound 339:
Compounds of formula 5A wherein $R^2$, $R^3$, M, $R^{19a}$ and $R^{20ay}$ corresponds to a row in Table E, and E substituted with $(R^4)_n$ is:

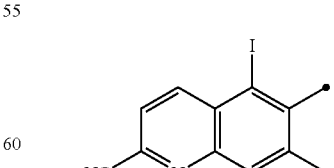

Compound 340:
Compounds of formula 5A wherein $R^2$, $R^3$, M, $R^{19a}$ and $R^{20ay}$ corresponds to a row in Table E, and E substituted with $(R^4)_n$ is:

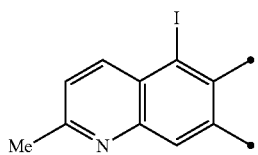

Compound 341:

Compounds of formula 5A wherein $R^2$, $R^3$, M, $R^{19a}$ and $R^{20ay}$ corresponds to a row in Table E, and E substituted with $(R^4)_n$ is:

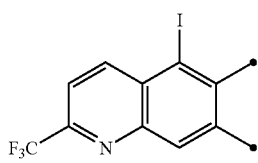

TABLE E

| $R^2$ | $R^3$ | M | $R^{19a}$ | $R^{20ay}$ |
|---|---|---|---|---|
| H | H | H | 3-chloro-2-pyridinyl | Cl |
| Me | H | H | 3-chloro-2-pyridinyl | Cl |
| H | Me | H | 3-chloro-2-pyridinyl | Cl |
| Me | Me | H | 3-chloro-2-pyridinyl | Cl |
| Et | H | H | 3-chloro-2-pyridinyl | Cl |
| H | Et | H | 3-chloro-2-pyridinyl | Cl |
| Et | Et | H | 3-chloro-2-pyridinyl | Cl |
| H | CO$_2$Me | H | 3-chloro-2-pyridinyl | Cl |
| H | H | H | 3-chloro-2-pyridinyl | Br |
| Me | H | H | 3-chloro-2-pyridinyl | Br |
| H | Me | H | 3-chloro-2-pyridinyl | Br |
| Me | Me | H | 3-chloro-2-pyridinyl | Br |
| Et | H | H | 3-chloro-2-pyridinyl | Br |
| H | Et | H | 3-chloro-2-pyridinyl | Br |
| Et | Et | H | 3-chloro-2-pyridinyl | Br |
| H | CO$_2$Me | H | 3-chloro-2-pyridinyl | Br |
| H | H | H | 3-chloro-2-pyridinyl | CF$_3$ |
| Me | H | H | 3-chloro-2-pyridinyl | CF$_3$ |
| H | Me | H | 3-chloro-2-pyridinyl | CF$_3$ |
| Me | Me | H | 3-chloro-2-pyridinyl | CF$_3$ |
| Et | H | H | 3-chloro-2-pyridinyl | CF$_3$ |
| H | Et | H | 3-chloro-2-pyridinyl | CF$_3$ |
| Et | Et | H | 3-chloro-2-pyridinyl | CF$_3$ |
| H | CO$_2$Me | H | 3-chloro-2-pyridinyl | CF$_3$ |
| H | H | Me | 3-chloro-2-pyridinyl | Cl |
| Me | H | Me | 3-chloro-2-pyridinyl | Cl |
| H | Me | Me | 3-chloro-2-pyridinyl | Cl |
| Me | Me | Me | 3-chloro-2-pyridinyl | Cl |
| Et | H | Me | 3-chloro-2-pyridinyl | Cl |
| H | Et | Me | 3-chloro-2-pyridinyl | Cl |
| Et | Et | Me | 3-chloro-2-pyridinyl | Cl |
| H | CO$_2$Me | Me | 3-chloro-2-pyridinyl | Cl |
| H | H | Me | 3-chloro-2-pyridinyl | Br |
| Me | H | Me | 3-chloro-2-pyridinyl | Br |
| H | Me | Me | 3-chloro-2-pyridinyl | Br |
| Me | Me | Me | 3-chloro-2-pyridinyl | Br |
| Et | H | Me | 3-chloro-2-pyridinyl | Br |
| H | Et | Me | 3-chloro-2-pyridinyl | Br |
| Et | Et | Me | 3-chloro-2-pyridinyl | Br |
| H | CO$_2$Me | Me | 3-chloro-2-pyridinyl | Br |
| H | H | Me | 3-chloro-2-pyridinyl | CF$_3$ |
| Me | H | Me | 3-chloro-2-pyridinyl | CF$_3$ |
| H | Me | Me | 3-chloro-2-pyridinyl | CF$_3$ |
| Me | Me | Me | 3-chloro-2-pyridinyl | CF$_3$ |
| Et | H | Me | 3-chloro-2-pyridinyl | CF$_3$ |
| H | Et | Me | 3-chloro-2-pyridinyl | CF$_3$ |
| Et | Et | Me | 3-chloro-2-pyridinyl | CF$_3$ |
| H | CO$_2$Me | Me | 3-chloro-2-pyridinyl | CF$_3$ |
| H | H | OMe | 3-chloro-2-pyridinyl | Cl |
| Me | H | OMe | 3-chloro-2-pyridinyl | Cl |
| H | Me | OMe | 3-chloro-2-pyridinyl | Cl |
| Me | Me | OMe | 3-chloro-2-pyridinyl | Cl |
| Et | H | OMe | 3-chloro-2-pyridinyl | Cl |
| H | Et | OMe | 3-chloro-2-pyridinyl | Cl |
| Et | Et | OMe | 3-chloro-2-pyridinyl | Cl |
| H | CO$_2$Me | OMe | 3-chloro-2-pyridinyl | Cl |
| H | H | OMe | 3-chloro-2-pyridinyl | Br |
| Me | H | OMe | 3-chloro-2-pyridinyl | Br |
| H | Me | OMe | 3-chloro-2-pyridinyl | Br |
| Me | Me | OMe | 3-chloro-2-pyridinyl | Br |
| Et | H | OMe | 3-chloro-2-pyridinyl | Br |
| H | Et | OMe | 3-chloro-2-pyridinyl | Br |
| Et | Et | OMe | 3-chloro-2-pyridinyl | Br |
| H | CO$_2$Me | OMe | 3-chloro-2-pyridinyl | Br |

TABLE E-continued

| $R^2$ | $R^3$ | M | $R^{19a}$ | $R^{20ay}$ |
|---|---|---|---|---|
| H | H | OMe | 3-chloro-2-pyridinyl | $CF_3$ |
| Me | H | OMe | 3-chloro-2-pyridinyl | $CF_3$ |
| H | Me | OMe | 3-chloro-2-pyridinyl | $CF_3$ |
| Me | Me | OMe | 3-chloro-2-pyridinyl | $CF_3$ |
| Et | H | OMe | 3-chloro-2-pyridinyl | $CF_3$ |
| H | Et | OMe | 3-chloro-2-pyridinyl | $CF_3$ |
| Et | Et | OMe | 3-chloro-2-pyridinyl | $CF_3$ |
| H | $CO_2Me$ | OMe | 3-chloro-2-pyridinyl | $CF_3$ |
| H | H | OEt | 3-chloro-2-pyridinyl | Cl |
| Me | H | OEt | 3-chloro-2-pyridinyl | Cl |
| H | Me | OEt | 3-chloro-2-pyridinyl | Cl |
| Me | Me | OEt | 3-chloro-2-pyridinyl | Cl |
| Et | H | OEt | 3-chloro-2-pyridinyl | Cl |
| H | Et | OEt | 3-chloro-2-pyridinyl | Cl |
| Et | Et | OEt | 3-chlorp-2-pyridinyl | Cl |
| H | $CO_2Me$ | OEt | 3-chloro-2-pyridinyl | Cl |
| H | H | OEt | 3-chloro-2-pyridinyl | Br |
| Me | H | OEt | 3-chloro-2-pyridinyl | Br |
| H | Me | OEt | 3-chloro-2-pyridinyl | Br |
| Me | Me | OEt | 3-chloro-2-pyridinyl | Br |
| Et | H | OEt | 3-chloro-2-pyridinyl | Br |
| H | Et | OEt | 3-chloro-2-pyridinyl | Br |
| Et | Et | OEt | 3-chloro-2-pyridinyl | Br |
| H | $CO_2Me$ | OEt | 3-chloro-2-pyridinyl | Br |
| H | H | OEt | 3-chloro-2-pyridinyl | $CF_3$ |
| Me | H | OEt | 3-chloro-2-pyridinyl | $CF_3$ |
| H | Me | OEt | 3-chloro-2-pyridinyl | $CF_3$ |
| Me | Me | OEt | 3-chloro-2-pyridinyl | $CF_3$ |
| Et | H | OEt | 3-chloro-2-pyridinyl | $CF_3$ |
| H | Et | OEt | 3-chloro-2-pyridinyl | $CF_3$ |
| Et | Et | OEt | 3-chloro-2-pyridinyl | $CF_3$ |
| H | $CO_2Me$ | OEt | 3-chloro-2-pyridinyl | $CF_3$ |
| H | H | $NH_2$ | 3-chloro-2-pyridinyl | Cl |
| Me | H | $NH_2$ | 3-chloro-2-pyridinyl | Cl |
| H | Me | $NH_2$ | 3-chloro-2-pyridinyl | Cl |
| Me | Me | $NH_2$ | 3-chloro-2-pyridinyl | Cl |
| Et | H | $NH_2$ | 3-chloro-2-pyridinyl | Cl |
| H | Et | $NH_2$ | 3-chloro-2-pyridinyl | Cl |
| Et | Et | $NH_2$ | 3-chloro-2-pyridinyl | Cl |
| H | $CO_2Me$ | $NH_2$ | 3-chloro-2-pyridinyl | Cl |
| H | H | $NH_2$ | 3-chloro-2-pyridinyl | Br |
| Me | H | $NH_2$ | 3-chloro-2-pyridinyl | Br |
| H | Me | $NH_2$ | 3-chloro-2-pyridinyl | Br |
| Me | Me | $NH_2$ | 3-chloro-2-pyridinyl | Br |
| Et | H | $NH_2$ | 3-chloro-2-pyridinyl | Br |
| H | Et | $NH_2$ | 3-chloro-2-pyridinyl | Br |
| Et | Et | $NH_2$ | 3-chloro-2-pyridinyl | Br |
| H | $CO_2Me$ | $NH_2$ | 3-chloro-2-pyridinyl | Br |
| H | H | $NH_2$ | 3-chloro-2-pyridinyl | $CF_3$ |
| Me | H | $NH_2$ | 3-chloro-2-pyridinyl | $CF_3$ |
| H | Me | $NH_2$ | 3-chloro-2-pyridinyl | $CF_3$ |
| Me | Me | $NH_2$ | 3-chloro-2-pyridinyl | $CF_3$ |
| Et | H | $NH_2$ | 3-chloro-2-pyridinyl | $CF_3$ |
| H | Et | $NH_2$ | 3-chloro-2-pyridinyl | $CF_3$ |
| Et | Et | $NH_2$ | 3-chloro-2-pyridinyl | $CF_3$ |
| H | $CO_2Me$ | $NH_2$ | 3-chloro-2-pyridinyl | $CF_3$ |
| H | H | NHMe | 3-chloro-2-pyridinyl | Cl |
| Me | H | NHMe | 3-chloro-2-pyridinyl | Cl |
| H | Me | NHMe | 3-chloro-2-pyridinyl | Cl |
| Me | Me | NHMe | 3-chloro-2-pyridinyl | Cl |
| Et | H | NHMe | 3-chloro-2-pyridinyl | Cl |
| H | Et | NHMe | 3-chloro-2-pyridinyl | Cl |
| Et | Et | NHMe | 3-chloro-2-pyridinyl | Cl |
| H | $CO_2Me$ | NHMe | 3-chloro-2-pyridinyl | Cl |
| H | H | NHMe | 3-chloro-2-pyridinyl | Br |
| Me | H | NHMe | 3-chloro-2-pyridinyl | Br |
| H | Me | NHMe | 3-chloro-2-pyridinyl | Br |
| Me | Me | NHMe | 3-chloro-2-pyridinyl | Br |
| Et | H | NHMe | 3-chloro-2-pyridinyl | Br |
| H | Et | NHMe | 3-chloro-2-pyridinyl | Br |
| Et | Et | NHMe | 3-chloro-2-pyridinyl | Br |
| H | $CO_2Me$ | NHMe | 3-chloro-2-pyridinyl | Br |
| H | H | NHMe | 3-chloro-2-pyridinyl | $CF_3$ |
| Me | H | NHMe | 3-chloro-2-pyridinyl | $CF_3$ |
| H | Me | NHMe | 3-chloro-2-pyridinyl | $CF_3$ |
| Me | Me | NHMe | 3-chloro-2-pyridinyl | $CF_3$ |
| Et | H | NHMe | 3-chloro-2-pyridinyl | $CF_3$ |
| H | Et | NHMe | 3-chloro-2-pyridinyl | $CF_3$ |

TABLE E-continued

| $R^2$ | $R^3$ | M | $R^{19a}$ | $R^{20ay}$ |
|---|---|---|---|---|
| Et | Et | NHMe | 3-chloro-2-pyridinyl | $CF_3$ |
| H | $CO_2Me$ | NHMe | 3-chloro-2-pyridinyl | $CF_3$ |
| H | H | $NMe_2$ | 3-chloro-2-pyridinyl | Cl |
| Me | H | $NMe_2$ | 3-chloro-2-pyridinyl | Cl |
| H | Me | $NMe_2$ | 3-chloro-2-pyridinyl | Cl |
| Me | Me | $NMe_2$ | 3-chloro-2-pyridinyl | Cl |
| Et | H | $NMe_2$ | 3-chloro-2-pyridinyl | Cl |
| H | Et | $NMe_2$ | 3-chloro-2-pyridinyl | Cl |
| Et | Et | $NMe_2$ | 3-chloro-2-pyridinyl | Cl |
| H | $CO_2Me$ | $NMe_2$ | 3-chloro-2-pyridinyl | Cl |
| H | H | $NMe_2$ | 3-chloro-2-pyridinyl | Br |
| Me | H | $NMe_2$ | 3-chloro-2-pyridinyl | Br |
| H | Me | $NMe_2$ | 3-chloro-2-pyridinyl | Br |
| Me | Me | $NMe_2$ | 3-chloro-2-pyridinyl | Br |
| Et | H | $NMe_2$ | 3-chloro-2-pyridinyl | Br |
| H | Et | $NMe_2$ | 3-chloro-2-pyridinyl | Br |
| Et | Et | $NMe_2$ | 3-chloro-2-pyridinyl | Br |
| H | $CO_2Me$ | $NMe_2$ | 3-chloro-2-pyridinyl | Br |
| H | H | $NMe_2$ | 3-chloro-2-pyridinyl | $CF_3$ |
| Me | H | $NMe_2$ | 3-chloro-2-pyridinyl | $CF_3$ |
| H | Me | $NMe_2$ | 3-chloro-2-pyridinyl | $CF_3$ |
| Me | Me | $NMe_2$ | 3-chloro-2-pyridinyl | $CF_3$ |
| Et | H | $NMe_2$ | 3-chloro-2-pyridinyl | $CF_3$ |
| H | Et | $NMe_2$ | 3-chloro-2-pyridinyl | $CF_3$ |
| Et | Et | $NMe_2$ | 3-chloro-2-pyridinyl | $CF_3$ |
| H | $CO_2Me$ | $NMe_2$ | 3-chloro-2-pyridinyl | $CF_3$ |

Examples of the pests against which the present compound has controlling efficacy include harmful arthropods such as harmful insects and harmful mites, and nemathelminths such as nematodes, and specific examples are as shown below.

Hemiptera:—

Planthoppers (Delphacidae) such as small brown planthopper (*Laodelphax striatellus*), brown rice planthopper (*Nilaparvata lugens*), and white-backed rice planthopper (*Sogatella furcifera*); leafhoppers (Deltocephalidae) such as green rice leafhopper (*Nephotettix cincticeps*), green rice leafhopper (*Nephotettix virescens*), and tea green leafhopper (*Empoasca onukii*); aphids (Aphididae) such as cotton aphid (*Aphis gossypii*), green peach aphid (*Myzus persicae*), cabbage aphid (*Brevicoryne brassicae*), spiraea aphid (*Aphis spiraecola*), potato aphid (*Macrosiphum euphorbiae*), foxglove aphid (*Aulacorthum solani*), oat bird-cherry aphid (*Rhopalosiphum padi*), tropical citrus aphid (*Toxoptera citricidus*), and mealy plum aphid (*Hyalopterus pruni*); stink bugs (Pentatomidae) such as green stink bug (*Nezara antennata*), bean bug (*Riptortus clavetus*), rice bug (*Leptocorisa chinensis*), white spotted spined bug (*Eysarcoris parvus*), and stink bug (*Halyomorpha mista*); whiteflies (Aleyrodidae) such as greenhouse whitefly (*Trialeurodes vaporariorum*), sweetpotato whitefly (*Bemisia tabaci*), silver leaf whitefly (*Bemisia argentifolii*), citrus whitefly (*Dialeurodes citri*), and citrus spiny white fly (*Aleurocanthus spiniferus*); scales (Coccidae) such as California red scale (*Aonidiella aurantii*), San Jose scale (*Comstockaspis perniciosa*), citrus north scale (*Unaspis citri*), red wax scale (*Ceroplastes rubens*), cottonycushion scale (*Icerya purchasi*), Japanese mealybug (*Planococcus kraunhiae*), Comstock mealybug (*Pseudococcus longispinis*), and white peach scale (*Pseudaulacaspis pentagona*); lace bags (Tingidae); psyllids (Psyllidae); etc.

Lepidoptera:—

Pyralid moths (Pyralidae) such as rice stem borer (*Chilo suppressalis*), yellow rice borer (*Tryporyza incertulas*), rice leafroller (*Cnaphalocrocis medinalis*), cotton leafroller (*Notarcha derogata*), Indian meal moth (*Plodia interpunctella*), oriental corn borer (*Ostrinia furnacalis*), cabbage webworm (*Hellula undalis*), and bluegrass webworm (*Pediasia teterrellus*); owlet moths (Noctuidae) such as common cutworm (*Spodoptera litura*), beet armyworm (*Spodoptera exigua*), armyworm (*Pseudaletia separata*), cabbage armyworm (*Mamestra brassicae*), black cutworm (*Agrotis ipsilon*), beet semi-looper (*Plusia nigrisigna*), *Thoricoplusia* spp., *Heliothis* spp., and *Helicoverpa* spp.; whites and sulfer butterflies (Pieridae) such as common white (*Pieris rapae*); tortricid moths (Tortricidae) such as *Adoxophyes* spp., oriental fruit moth (*Grapholita molesta*), soybean pod borer (*Leguminivora glycinivorella*), azuki bean podworm (*Matsumuraeses azukivora*), summer fruit tortrix (*Adoxophyes orana fasciata*), *Adoxophyes* sp., oriental tea tortrix (*Homona magnanima*), apple tortrix (*Archips fuscocupreanus*), and *Cydia pomonella*; leafblotch miners (Gracillariidae) such as tea leafroller (*Caloptilia theivora*), and apple leafminer (*Phyllonorycter ringoneella*); Carposimidae such as peach fruit moth (*Carposina niponensis*); lyonetiid moths (Lyonetiidae) such as *Lyonetia* spp.; tussock moths (Lymantriidae) such as *Lymantria* spp., and *Euproctis* spp.; yponomeutid moths (Yponomeutidae) such as diamondback (*Plutella xylostella*); gelechiid moths (Gelechiidae) such as pink bollworm (*Pectinophora gossypiella*), and potato tubeworm (*Phthorimaea operculella*); tiger moths and allies (Arctiidae) such as fall webworm (*Hyphantria cunea*); tineid moths (Tineidae) such as casemaking clothes moth (*Tinea translucens*), and webbing clothes moth (*Tineola bisselliella*); etc.

Thysanoptera:—

Thrips (Thripidae) such as yellow citrus thrips (*Frankliniella occidentalis*), *Thrips parmi*, yellow tea thrips (*Scirtothrips dorsalis*), onion thrip (*Thrips tabaci*), flower thrips (*Frankliniella intonsa*), etc.

Diptera:—

Housefly (*Musca domestica*), common mosquito (*Culex popiens* pallens), horsefly (*Tabanus trigonus*), onion maggot (*Hylemya antiqua*), seedcorn maggot (*Hylemya platura*), *Anopheles sinensis*, rice leafminer (*Agromyza oryzae*), rice leafminer (*Hydrellia griseola*), rice stem maggot (*Chlorops oryzae*), melon fly (*Dacus cucurbitae*), *Ceratitis capitata*, legume leafminer (*Liriomyza trifolii*), tomato leafminer (*Liriomyza sativae*), garden pea leafminer (*Chromatomyia horticola*), etc.

Coleoptera:—

Twenty-eight-spotted ladybird (*Epilachna vigintioctopunctata*), cucurbit leaf beetle (*Aulacophora femoralis*), striped flea beetle (*Phyllotreta striolata*), rice leaf beetle (*Oulema oryzae*), rice curculio (*Echinocnemus squameus*), rice water weevil (*Lissorhoptrus oryzophilus*), *Anthonomus grandis*, azuki bean weevil (*Callosobruchus chinensis*), *Sphenophorus venatus*, Japanese beetle (*Popillia japonica*), cupreous chafer (*Anomala cuprea*), corn root worm (*Diabrotica* spp.), Colorado beetle (*Leptinotarsa decemlineata*), click beetle (*Agriotes* spp.), cigarette beetle (*Lasioderma serricorne*), varied carper beetle (*Anthrenus verbasci*), red flour beetle (*Tribolium castaneum*), powder post beetle (*Lyctus*

*brunneus*), white-spotted longicorn beetle (*Anoplophora malasiaca*), pine shoot beetle (*Tomicus piniperda*), etc.

Orthoptera:—

Asiatic locust (*Locusta migratoria*), African mole cricket (*Gryllotalpa africana*), rice grasshopper (*Oxya yezoensis*), rice grasshopper (*Oxya japonica*), etc.

Hymenoptera:—

Cabbage sawfly (*Athalia rosae*), *Acromyrmex* spp., fire ant (*Solenopsis* spp.), etc.

Nematodes:—

Rice white-tip nematode (*Aphelenchoides besseyi*), strawberry bud nematode (*Nothotylenchus acris*), southern root-knot nematode (*Meloidogyne incognita*), northern root-knot nematode (*Meloidogyne hapla*), Javanese root-knot nematode (*Meloidogyne javanica*), soybean cyst nematode (*Heterodera glycines*), potato cyst nematode (*Globodera rostochiensis*), coffee root-lesion nematode (*Pratylenchus coffeae*), California root-lesion nematode (*Pratylenchus neglectus*), etc.

Dictyoptera:—

German cockroach (*Blattella germanica*), smokybrown cockroach (*Periplaneta fuliginosa*), American cockroach (*Periplaneta americana*), *Periplaneta* brunnea, oriental cockroach (*Blatta orientalis*), etc.

Acarina:—

Spider mites (Tetranychidae) such as two-spotted spider mite (*Tetranychus urticae*), Kanzawa spider mite (*Tetranychus kanzawai*), citrus red mite (*Panonychus citri*), European red mite (*Panonychus ulmi*), and *Oligonychus* spp.; eriophyid mites (Eriophyidae) such as pink citrus rust mite (*Aculops pelekassi*), pink citrus rust mite (*Phyllocoptruta citri*), tomato rust mite (*Aculops lycopersici*), purple tea mite (*Calacarus carinatus*), pink tea rust mite (*Acaphylla theavagran*), and *Eriophyes chibaensis*; tarosonemid mites (Tarsonemidae) such as broad mite (*Polyphagotarsonemus latus*); false spider mites (Tenuipalpidae) such as *Brevipalpus phoenicis*; Tuckerellidae; ticks (Ixodidae) such as *Haemaphysalis longicornis, Haemaphysalis flava, Dermacentor taiwanicus, Ixodes ovatus, Ixodes persulcatus, Boophilus microplus*, and *Rhipicephalus sanguineus*; acarid mites (Acaridae) such as mold mite (*Tyrophagus putrescentiae*), and *Tyrophagus similis*; house dust mites (Pyroglyphidae) such as *Dermatophagoides farinae*, and *Dermatophagoides ptrenyssnus*; cheyletide mites (Cheyletidae) such as *Cheyletus eruditus, Cheyletus malaccensis*, and *Cheyletus moorei*; parasitoid mites (Dermanyssidae); etc.

The pesticide of the present invention may be the present compound itself but, usually, the present compound is mixed with an inert carrier such as a solid carrier, a liquid carrier, a gaseous carrier and the like and, if necessary, a surfactant, and other preparation additives are added to formulate into a composition or a preparation such as an emulsion, oil, powder, granules, a wettable preparation, a flowable preparation, microcapsules, an aerosol, a fumigant, poison bait, a resin preparation or the like. These compositions or preparations usually contain 0.01 to 95% by weight of the present compound.

Examples of the solid carrier to be used include fine powders and granules such as clays (kaolin clay, diatomaceous earth, bentonite, fubasami clay, acid clay, etc.), synthetic hydrous silicon oxide, talc, ceramic, other inorganic minerals (sericite, quartz, sulfur, active carbon, calcium carbonate, hydrated silica, etc.), chemical fertilizers (ammonium sulfate, ammonium phosphate, ammonium nitrate, urea, ammonium chloride, etc.) and the like.

Examples of the liquid carrier include water, alcohols (methanol, ethanol, isopropyl alcohol, butanol, hexanol, benzyl alcohol, ethylene glycol, propylene glycol, phenoxyethanol, etc.), ketones (acetone, methyl ethyl ketone, cyclohexanone, etc.), aromatic hydrocarbons (toluene, xylene, ethylbenzene, dodecylbenzene, phenylxylylethane, methylnaphthalene, etc.), aliphatic hydrocarbons (hexane, cyclohexane, kerosene, gas oil, etc.), esters (ethyl acetate, butyl acetate, isopropyl myristate, ethyl oleate, diisopropyl adipate, diisobutyl adipate, propylene glycol monomethyl ether acetate, etc.), nitriles (acetonitrile, isobutyronitrile, etc.), ethers (diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, 3-methoxyl-3-methyl-1-butanol, etc.), acid amides (N,N-dimethylformamide, N,N-dimethylacetamide, etc.), halogenated hydrocarbons (dichloromethane, trichloroethane, carbon tetrachloride, etc.), sulfoxides (dimethyl sulfoxide, etc.), carbonic propylene and vegetable oils (soybean oil, cottonseed oil, etc.).

Examples of the gaseous carrier include fluorocarbon, butane gas, LPG (liquefied petroleum gas), dimethyl ether, and carbonic acid gas.

Examples of the surfactant include nonionic surfactants such as polyoxyethylene alkyl ether, polyoxyethylene alkyl aryl ether, polyethylene glycol fatty acid ester, and the like, and anionic surfactants such as alkyl sulfonate salts, alkylbenzene sulfonate salts and alkyl sulfate salts.

Examples of other preparation additives include binders, dispersing agents, coloring agents and stabilizers, specifically, casein, gelatin, sugars (starch, gum arabic, cellulose derivatives, alginic acid, etc.), lignin derivatives, bentonite, synthetic water-soluble polymers (polyvinyl alcohol, polyvinylpyrrolidone, polyacrylic acids, etc.), PAP (acidic isopropyl phosphate), BHT (2,6-di-tert-butyl-4-methylphenol), and BHA (a mixture of 2-tert-butyl-4-methoxyphenol and 3-tert-butyl-4-methoxyphenol).

The method of controlling a pest of the present invention is usually performed by applying the pesticide of the present invention directly to a pest or to a place where a pest inhabits (plant, soil, in house, animal, etc.).

When the pesticide of the present invention is used for controlling a pest in the agricultural field, an amount to be applied is usually 1 to 10,000 g per 10,000 m² in terms of the amount of the present compound. When the pesticide of the present invention is formulated into an emulsion, a wettable preparation, a flowable preparation or the like, usually, the agent is applied by diluting with water so that the active ingredient concentration becomes 0.01 to 10,000 ppm, and granules, powder or the like are usually applied as they are.

These preparations, or preparations diluted with water may be directly applied to a pest or to a plant such as a crop to be protected against a pest, or may be applied to soil of a cultivated land in order to control a pest inhabiting in the soil.

Alternatively, treatment may be performed for example, by winding a sheet-like or string-like-processed resin preparation on a crop, surrounding a crop with the resin preparation, or laying the resin preparation on soil about roots of a crop.

When the pesticide of the present invention is used for controlling a pest which inhabits in a house (e.g. fly, mosquito, cockroach, etc.), the amount to be applied is usually 0.01 to 1000 mg per 1 m² of treating area in terms of the amount of the present compound in case of surface treatment, and is usually 0.01 to 500 mg per 1 m³ of treating space in terms of the amount of the present of compound in case of spatial treatment. When the pesticide of the present invention is formulated into an emulsion, a wettable preparation, a flowable preparation or the like, usually, the agent is applied by diluting with water so that the active ingredient concentration becomes 0.1 to 1000 ppm, and oil, an aerosol, a fumigant, poison bait or the like is applied as it is.

The pesticide of the present invention may contain other harmful arthropod controlling agents, acaricides, nematicides, fungicides, herbicides, plant growth regulators, synergists, fertilizers, soil conditioners, animal feeds, and the like.

As the active ingredients of the aforementioned other harmful arthropod controlling agents, acaricides and/or nematicides, for example, the following compounds can be mentioned.

(1) Organic Phosphorus Compounds

Acephate, aluminium phosphide, butathiofos, cadusafos, chlorethoxyfos, chlorfenvinphos, chlorpyrifos, chlorpyrifos-methyl, cyanophos: CYAP, diazinon, DCIP (dichlorodiisopropyl ether), dichlofenthion: ECP, dichlorvos: DDVP, dimethoate, dimethylvinphos, disulfoton, EPN, ethion, ethoprophos, etrimfos, fenthion: MPP, fenitrothion: MEP, fosthiazate, formothion, hydrogen phosphide, isofenphos, isoxathion, malathion, mesulfenfos, methidathion: DMTP, monocrotophos, naled: BRP, oxydeprofos:ESP, parathion, phosalone, phosmet: PMP, pirimiphos-methyl, pyridafenthion, quinalphos, phenthoate: PAP, profenofos, propaphos, prothiofos, pyraclorfos, salithion, sulprofos, tebupirimfos, temephos, tetrachlorvinphos, terbufos, thiometon, trichlorphon:DEP, vamidothion, and the like.

(2) Carbamate Compounds

Alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb:MIPC, metolcarb, methomyl, methiocarb, NAC, oxamyl, pirimicarb, propoxur: PHC, XMC, thiodicarb, xylylcarb, and the like.

(3) Synthetic Pyrethroid Compounds

Acrinathrin, allethrin, benfluthrin, beta-cyfluthrin, bifenthrin, cycloprothrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, 2,3,5,6-tetrafluoro-4-(methoxymethyl)benzyl (EZ)-(1RS, 3RS;1RS,3SR)-2,2-dimethyl-3-prop-1-enylcyclopropanecarboxylate, 2,3,5,6-tetrafluoro-4-methylbenzyl (EZ)-(1RS,3RS;1RS,3SR)-2,2-dimethyl-3-prop-1-enylcyclopropanecarboxylate, 2,3,5,6-tetrafluoro-4-(methoxymethyl)benzyl (1RS,3RS;1RS,3SR)-2,2-dimethyl-3-(2-methyl-1-propenyl)cyclopropanecarboxylate, and the like.

(4) Nereistoxin Compounds

Cartap, bensultap, thiocyclam, monosultap, bisultap, and the like.

(5) Neonicotinoid Compounds

Imidacloprid, nitenpyram, acetamiprid, thiamethoxam, thiacloprid, dinotefuran, clothianidin, and the like.

(6) Benzoylurea Compounds

Chlorfluazuron, bistrifluoron, diafenthiuron, diflubenzuron, fluazuron, flucycloxuron, flufenoxuron, hexaflumuron, lufenuron, novaluron, noviflumuron, teflubenzuron, triflumuron, and the like.

(7) Phenylpyrazole Compounds

Acetoprole, ethiprole, fipronil, vaniliprole, pyriprole, pyrafluprole, and the like.

(8) Bt Toxin Insecticides

Viable endospores derived from *Bacillus thuringiensis* and crystalline toxins produced by it, as well as a mixture of thereof.

(9) Hydrazine Compounds

Chromafenozide, halofenozide, methoxyfenozide, tebufenozide, and the like.

(10) Organic Chlorine Compounds

Aldrin, dieldrin, dienochlor, endosulfan, methoxychlor, and the like.

(11) Natural Insecticides

Machine oil, nicotine-sulfate, and the like.

(12) Other Insecticides

Avermectin-B, bromopropylate, buprofezin, chlorphenapyr, cyromazine, 1,3-Dichloropropene, emamectin-benzoate, fenazaquin, flupyrazofos, hydroprene, indoxacarb, metoxadiazone, milbemycin-A, pymetrozine, pyridalyl, pyriproxyfen, spinosad, sulfluramid, tolfenpyrad, triazamate, flubendiamide, SI-0009, cyflumetofen, arsenic acid, benclothiaz, calcium cyanamide, calcium polysulfide, chlordane, DDT, DSP, flufenerim, flonicamid, flurimfen, formetanate, metam-ammonium, metam-sodium, Methyl bromide, nidinotefuran, Potassium oleate, protrifenbute, spiromesifen, sulfur, metaflumizone, spirotetramat, and the like.

Acaricides

Acequinocyl, amitraz, benzoximate, bromopropylate, chinomethionat, chlorobenzilate, CPCBS (chlorfenson), clofentezine, Kelthane(dicofol), etoxazole, fenbutatin oxide, fenothiocarb, fenpyroximate, fluacrypyrim, fluproxyfen, hexythiazox, propargite:BPPS, polynactins, pyridaben, Pyrimidifen, tebufenpyrad, tetradifon, spirodiclofen, amidoflumet, Bifenazate, Cyflumetofen, and the like.

Nematicides (Nematicidal Active Ingredients)

DCIP, fosthiazate, levamisol, methylsothiocyanate, morantel tartarate, and the like.

The present invention will be explained in more detail below by way of Preparation Examples, Formulation Examples, Test Examples, but the present invention is not limited to these Examples.

First, Preparation Examples of the present compound will be explained.

PREPARATION EXAMPLES

Example 1

Preparation of N'-(3-{[5-bromo-2-(3-chloro-pyridin-2-yl)-21'-pyrazole-3-carbonyl]-amino}-2,6-dichloro-pyridine-4-carbonyl)-hydrazinecarboxylic acid methyl ester (1)

Step 1: Preparation of pyrazole-1-sulfonic acid dimethylamide

Pyrazole (15 g) was dissolved in toluene (200 mL) and dimethylsulfamoyl chloride (23.7 mL) was slowly added. After addition of triethylamine (40 mL), the solution was stirred for 18 h at room temperature. The precipitate was filtered off, the filtrate concentrated in vacuum and the residue purified by column chromatography (silica gel 60, hexane/ethyl acetate=5:1, then 2:1, $R_f$=0.30 in hexane/ethyl acetate=2:1, KMnO$_4$-solution) to afford 17.6 g of the title compound of the formula

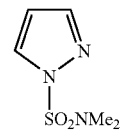

as a colorless oil.

$^1$H-NMR (CDCl$_3$, TMS) δ (ppm): 2.95 (6H, s), 6.40 (1H, dd, J=3 Hz, 2 Hz), 7.75 (1H, d, J=2 Hz), 7.95 (1H, dd, J=3 Hz, 1 Hz).

Step 2: Preparation of 3-bromo-pyrazole-1-sulfonic acid dimethylamide

Pyrazole-1-sulfonc acid dimethylamide (17.6 g) was dissolved in dry THF (200 mL) and cooled to −78° C. A solution of n-butyllithium (80 mL, 1.3 M) was added slowly over a period of 15 min and stirred for further 15 min at −78° C. A solution of 1,2-dibromo-1,1,2,2-tetrachloroethane (35.8 g) in dry THF (60 mL) was added within 10 min to this solution and stirred for further 15 min at −78° C., then the cool bath was removed and the mixture was quenched with water after stirring for 1 h. The reaction mixture was extracted 3× with ethyl acetate, the combined org. layers were washed with brine, dried over MgSO$_4$ and concentrated in vacuum. The residue was purified by column chromatography (silica gel 60, hexane/ethyl acetate=5:1, $R_f$=0.25) to afford 21.3 g of the title compound of the formula

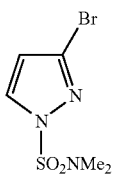

as a colorless oil.

$^1$H-NMR (CDCl$_3$, TMS) δ (ppm): 3.08 (6H, s), 6.43 (1H, m), 7.61 (1H, m).

Step 3: Preparation of 3-bromo-1H-pyrazole

To 3-bromo-pyrazole-1-sulfonic acid dimethylamide (21.3 g) was slowly added trifluoroacetic acid (30 mL) and stirred at room temperature for 2 h. Hexane was added and the formed precipitate was filtered off and washed with hexane. The filtrate was diluted with MTB-ether, washed with sat. NaHCO$_3$-solution, water and brine, dried over MgSO$_4$ and concentrated in vacuum to afford 10.7 g of a colorless oil containing 80% of the title compound of the formula

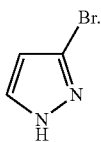

The residue was used for the next step without further purification.

$^1$H-NMR (CDCl$_3$, TMS) δ (ppm): 6.37 (1H, d, J=3 Hz), 7.55 (1H, d, J=3 Hz), 12.6 (1H, br s).

Step 4: Preparation of 2-(3-bromo-pyrazol-1-yl)-3-chloro-pyridine

The crude product of 3-bromo-1H-pyrazole (10.7 g) was dissolved in DMF (80 mL), 2,3-dichloropyridine (11.8 g) and caesium carbonate (57.3 g) were added and the mixture was stirred for 8 h at 100° C. After addition of water, the mixture was extracted 2× with MTB-ether, the combined org. layers were washed 2× with water, brine, dried over MgSO$_4$ and concentrated in vacuum. The residue was purified by column chromatography (silica gel 60, hexane/ethyl acetate=5:1, $R_f$=0.20) to afford 12.9 g of the title compound of the formula

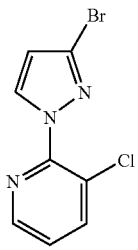

as a white solid.

$^1$H-NMR (CDCl$_3$, TMS) δ (ppm): 6.51 (1H, d, J=3 Hz), 7.31 (1H, dd, J=8 Hz, 5 Hz), 7.91 (1H, dd, J=8 Hz, 2 Hz), 8.04 (1H, d, J=3 Hz), 8.45 (1H, dd, J=5 Hz, 2 Hz).

Step 5: Preparation of 5-bromo-2-(3-chloro-pyridin-2-yl)-2H-pyrazole-3-carboxylic acid 2-(3-Bromo-pyrazol-1-yl)-3-chloro-pyridine (9.2 g) was dissolved in dry THF (80 mL) and cooled to −78° C. A solution of LDA (21.3 mL, 2.0 M) was added over a period of 10 min and stirred for further 15 min at −78° C. The solution was poured on crushed dry ice in THF (50 mL) and stirred for additional 1 h. Water and Et$_2$O were added and 2N NaOH-solution was added to adjust the pH to 10-12. The layers were separated and the aqueous layer was washed 2× with Et$_2$O and acidified with 2N HCl (pH ∼3). The resulting suspension was 3× extracted with MTB-ether, the combined org. layers were washed with brine, dried over MgSO$_4$ and concentrated to afford 7.96 g of the title compound of the formula

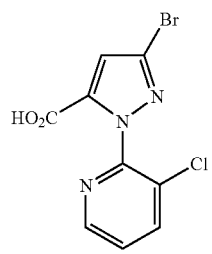

as an orange solid.

$^1$H-NMR (DMSO-d$_6$) δ (ppm): 7.23 (1H, s), 7.68 (1H, dd, J=8 Hz, 5 Hz), 8.24 (1H, dd, J=8 Hz, 2 Hz), 8.55 (1H, dd, J=5 Hz, 2 Hz).

Step 6: Preparation of 3-aminoisonicotinic acid methyl ester

3-Aminoisonicotinic acid (400 mg) was suspended in methanol (6 mL) and toluene (18 mL) was added. A solution of (trimethylsilyl)diazomethane (2.0 M in diethyl ether, 1.88 mL) was added slowly to the suspension. Within 5 to 10 minutes after addition, the suspension turned into a solution. After 2 hours stirring at room temperature, the reaction mixture was quenched with water and extracted 3× with ethyl acetate. The combined organic layer was washed with 2N hydrochloric acid, saturated bicarbonate solution and brine, dried over MgSO$_4$ and concentrated in vacuum. The residue was purified by column chromatography (silica gel 60, hexane/ethyl acetate=1:2, $R_f$=0.40) to afford 340 mg of the title compound of the formula

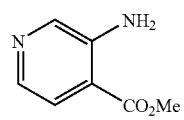

as a white solid.

$^1$H-NMR (CDCl$_3$, TMS) δ (ppm): 3.91 (3H, s), 5.65 (2H, br s), 7.59 (1H, d, J=5 Hz), 7.93 (1H, d, J=5 Hz), 8.19 (1H, s).

Step 7: Preparation of 3-amino-2,6-dichloroisonicotinic acid methyl ester

3-Aminoisonicotinic acid methyl ester (340 mg) was dissolved in DMF (3 mL), N-chlorosuccinimide (600 mg) was added and the resulting solution was stirred for 15 hours at room temperature. The product was precipitated by addition of water to the reaction mixture, filtered off and washed with water. The crude product was purified by column chromatography (silica gel 60, hexane/ethyl acetate=3:1, $R_f$=0.50) to afford 460 mg of the title compound of the formula

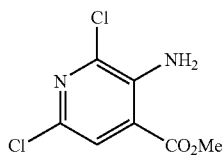

as a white solid.
$^1$H-NMR (CDCl$_3$, TMS) δ (ppm): 3.94 (3H, s), 6.17 (2H, br s), 7.66 (1H, s).

Step 8: Preparation of 3-amino-2,6-dichloroisonicotinic acid

3-Amino-2,6-dichloroisonicotinic acid methyl ester (460 mg) was dissolved in ethanol (8 mL), water (2 mL) and potassium hydroxide (234 mg) was added. The solution was stirred for 20 minutes at room temperature and for 1.5 hours under reflux. After cooling to room temperature, 2N hydrochloric acid was added to adjust the pH-value to ~3 and the so-formed yellow precipitate was extracted 3× with ethyl acetate. The combined organic layer was washed with brine, dried over MgSO$_4$ and concentrated in vacuum to afford 420 mg of the title compound of the formula

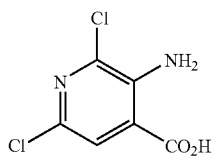

as a yellow solid. The compound was used in the following reaction step without further purification.
$^1$H-NMR (CDCl$_3$, TMS) δ (ppm): 6.21 (2H, br s), 7.69 (1H, s).

Step 9: Preparation of 2-[5-bromo-2-(3-chloro-pyridin-2-yl)-2H-pyrazol-3-yl]-6,8-dichloro-pyrido[3,4-d][1,3]oxazin-4-one A mixture of 5-bromo-2-(3-chloro-pyridin-2-yl)-2H-pyrazole-3-carboxylic acid (example 1, step 5) (745 mg) and thionyl chloride (540 μl) was stirred under reflux for 2 hours. Excess thionyl chloride was co-evaporated with dry toluene on a evaporator, the residue was re-dissolved in dry acetonitrile (10 mL) and 3-amino-2,6-dichloroisonicotinic acid (example 1, step 8) (745 mg) was added. The solution was stirred for 5 minutes at room temperature and triethylamine (490 μL) was added and stirred for 1 hour, before a second portion of triethylamine (490 μL) was added. After the mixture was stirred for further 30 minutes at room temperature, methanesulfonyl chloride (210 μL) was added. After stirring for 20 hours at room temperature, the formed precipitate was filtered off, washed carefully with water and MTB-ether and dried in vacuum to afford 731 mg of the title compound of the formula

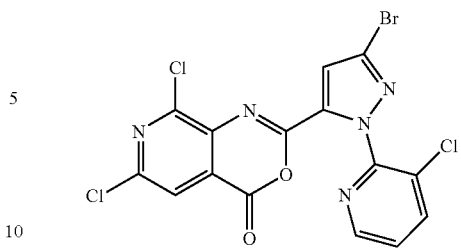

as a yellow solid.
$^1$H-NMR (CDCl$_3$, TMS) δ (ppm): 7.32 (1H, s), 7.51 (1H, dd, J=8 Hz, 5 Hz), 7.94 (1H, s), 7.99 (1H, dd, J=8 Hz, 2 Hz), 8.55 (1H, dd, J=5 Hz, 2 Hz).

Step 10: Preparation of N'-(3-{[5-bromo-2-(3-chloro-pyridin-2-yl)-2H-pyrazole-3-carbonyl]-amino}-2,6-dichloro-pyridine-4-carbonyl)-hydrazinecarboxylic acid methyl ester (1)

2-[5-Bromo-2-(3-chloro-pyridin-2-yl)-2H-pyrazol-3-yl]-6,8-dichloro-pyrido[3,4-d][1,3]oxazin-4-one (200 mg) was dissolved in DMF (8 mL) under slight warming up. Carbazaic acid methyl ester (380 mg) was added and the solution was stirred for 25 hours at room temperature. The reaction mixture was quenched with water and extracted with MTB-ether. The organic layer was washed 3× with water, brine, dried over MgSO$_4$ and concentrated in vacuum. The residue was purified by column chromatography (silica 60, hexane/ethyl acetate=1:2, $R_f$=0.20) to afford 190 mg of compound 1 of the present invention of the formula (1)

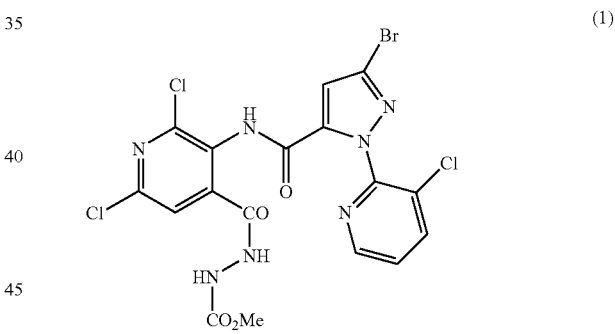

as a white solid.
$^1$H-NMR (DMSO-D$_6$) δ (ppm): 3.48-3.65 (3H, m), 7.41 (1H, s), 7.60-7.63 (2H, m), 8.18 (1H, d, J=8 Hz), 8.51 (1H, d, J=5 Hz), 9.47 (1H, br s), 10.47 (1H, br s), 10.76 (1H, br s).

Example 2

Preparation of N'-(2,6-dichloro-3-{[2-(3-chloro-pyridin-2-yl)-5-trifluoro methyl-2H-pyrazole-3-carbonyl]-amino}-pyridine-4-carbonyl)-hydrazinecarboxylic acid methyl ester (2)

Step 1: Preparation of 3-chloro-2-(3-trifluoromethyl-pyrazol-1-yl)-pyridine

3-Trifluoromethyl-1H-pyrazole (15.30 g), 2,3-dichloropyridine (16.64 g) and potassium carbonate (26.42 g) were suspended in dry DMF (100 mL) and stirred for 3 h at 130° C., overnight at rt and again for 11 h at 130° C. After complete consumption of the starting material, the reaction was cooled to room temperature and quenched with water. The mixture was extracted 2× with ethyl acetate, the combined org. layers were washed 2× with water, brine, dried over MgSO₄ and concentrated in vacuum. The residue was purified by column chromatography (silica gel 60, hexane/ethyl acetate=8:1, then 5:1, $R_f$=0.35 in hexane/ethyl acetate=3:1) to afford 22.88 g of the title compound of the formula

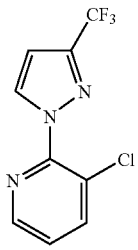

as a colorless oil.
¹H-NMR (CDCl₂, TMS) δ (ppm): 6.75 (1H, d, J=2 Hz), 7.37 (1H, dd, J=8 Hz, 5 Hz), 7.95 (1H, dd, J=8 Hz, 2 Hz), 8.14 (1H, d, J=2 Hz), 8.49 (1H, dd, J=5 Hz, 2 Hz).

Step 2: Preparation of 2-(3-chloro-pyridin-2-yl)-5-trifluoro methyl-2H-pyrazole-3-carboxylic acid 3-Chloro-2-(3-trifluoromethyl-pyrazol-1-yl)-pyridine (15 g) was dissolved in dry THF (150 mL) and cooled to −78° C. A solution of LDA (39 mL, 2.0 M) were added over a period of 15 min and stirred for further 15 min at −78° C. The flask was connected to a gas inlet and CO₂ was bubbled through the solution in a rate that the inner temperature was kept below −60° C. The solution turned to pale yellow and the cool bath was removed after further 10 min stirring at −78° C. and the CO₂-stream stopped. After the solution warmed up to room temperature, 200 ml water and 200 ml hexane were added, and 2N NaOH-solution was added to adjust the pH to 10-12. The layers were separated and the organic layer was again 2× extracted with 0.5N NaOH-solution. The combined aqueous solutions were washed 2× with Et₂O and acidified with 2N HCl (pH ~3). The resulting suspension was 3× extracted with MTB-ether, the combined org. layers were washed with brine, dried over MgSO₄ and concentrated to afford 16.08 g of the title compound of the formula

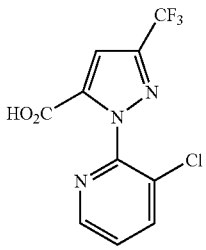

as a beige solid. The compound was used for the next step without further purification.
¹H-NMR (DMSO-d₆) δ (ppm): 7.60 (1H, s), 7.74 (1H, dd, J=8 Hz, 5 Hz), 8.30 (1H, dd, J=8 Hz, 2 Hz), 8.60 (1H, dd, J=5 Hz, 2 Hz).

Step 3: Preparation of 2-(3-chloro-pyridin-2-yl)-5-trifluoro methyl-2H-pyrazole-3-carbonyl chloride 2-(3-Chloro-pyridin-2-yl)-5-trifluoromethyl-2H-pyrazole-3-carboxylic acid (16.08 g) was mixed with thionyl chloride (12 mL) and heated under reflux for 2 h. The excess thionyl chloride was evaporated from the crude solution on a rotary evaporator under co-evaporation with dry toluene. The acid chloride was isolated by distillation of the residue under reduced pressure (125° C./3 mmHg) to afford 14.2 g of the title compound of the formula

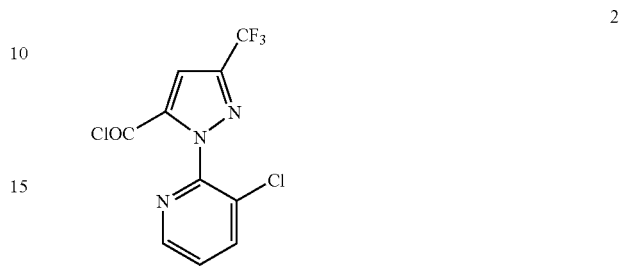

2 as a crystalline solid.
¹H-NMR (CDCl₃, TMS) δ (ppm): 7.52 (1H, s), 7.52 (1H, dd, J=8 Hz, 5 Hz), 7.97 (1H, dd, J=8 Hz, 2 Hz), 8.53 (1H, dd, J=5 Hz, 2 Hz).

Step 4: Preparation of 6,8-dichloro-2-[2-(3-chloro-pyridin-2-yl)-5-trifluoromethyl-2H-pyrazol-3-yl]-pyrido[3,4-d][1,3]oxazin-4-one 5-Trifluoromethyl-2-(3-chloro-pyridin-2-yl)-2H-pyrazole-3-carboxylic acid chloride (example 2, step 3) (242 mg) was added to a mixture of 3-amino-2,6-dichloroisonicotinic acid (example 1, step 8) (190 mg) in acetonitrile (3 mL). The mixture was stirred for 5 minutes at room temperature and triethylamine (220 µL) was added and stirred for 20 minutes, before a second portion of triethylamine (220 µL) was added. After the mixture was stirred for further 20 minutes at room temperature, methanesulfonyl chloride (70 µL) was added. After stirring for 2 hours at room temperature, the formed precipitate was filtered off, washed carefully with water and MTB-ether and dried in vacuum to afford 350 mg of the title compound of the formula

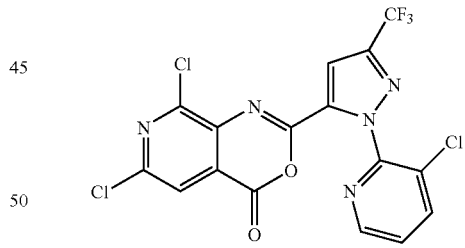

as a yellow solid.
¹H-NMR (CDCl₃, TMS) δ (ppm): 7.54-7.57 (2H, m), 7.88 (1H, s), 8.01-8.04 (1H, m), 8.56-8.58 (1H, m).

Step 5: Preparation of N'-(2,6-dichloro-3-{[2-(3-chloro-pyridin-2-yl)-5-trifluoromethyl-2H-pyrazole-3-carbonyl]-amino}-pyridine-4-carbonyl)-hydrazinecarboxylic acid methyl ester (2)

6,8-Dichloro-2-[2-(3-chloro-pyridin-2-yl)-5-trifluoromethyl-2H-pyrazol-3-yl]-pyrido[3,4-d][1,3]oxazin-4-one (200 mg) was dissolved in DMF (5 mL), carbazaic acid methyl ester (190 mg) was added and the solution was stirred for 16 hours at room temperature. The reaction mixture was quenched with water and extracted with MTB-ether. The organic layer was washed 2× with water, washed with brine, dried over MgSO₄ and concentrated in vacuum. The residue was purified by column chromatography (silica 60, hexane/ethyl acetate=1:1, then 1:2, R_f=0.20 in hexane/ethyl acetate 1:2) to afford 43 mg of compound 2 of the present invention of the formula

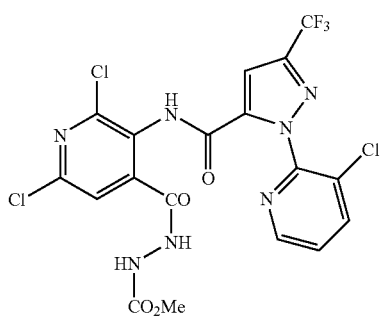

as a white solid.
¹H-NMR (DMSO-D₆) δ (ppm): 3.62 (3H, br s), 7.62 (1H, s), 7.67 (1H, dd, J=8 Hz, 5 Hz), 7.77 (1H, s), 8.23 (1H, d, J=8 Hz), 8.54 (1H, d, J=5 Hz), 9.47 (1H, s), 10.49 (1H, s), 10.92 (1H, s).

Example 3

Preparation of N'-(3-{[5-bromo-2-(3-chloro-pyridin-2-yl)-2H-pyrazole-3-carbonyl]-amino}-6-chloro-2-methyl-pyridine-4-carbonyl)-hydrazinecarboxylic acid methyl ester (3)

Step 1: preparation of (6-chloro-pyridin-3-yl)-carbamic acid tert-butyl ester

A mixture of 5-amino-2-chloropyridine (5.0 g) and di-tert-butyl dicarbonate (9.34 g) in dioxane (60 mL) was stirred for 2 hours under reflux. After cooling to room temperature, the reaction mixture was quenched with water and extracted with ethyl acetate. The organic layer was washed 5× with diluted hydrochloric acid, washed with saturated sodium bicarbonate, brine, dried over MgSO₄ and concentrated in vacuum. The residue was washed with hexane to give 5.39 g of the title compound as a white solid. The combined acidic washings were re-extracted with MTB-ether. The organic layer was washed with brine, dried over MgSO₄ and concentrated in vacuum. The residue was combined with the residue from the hexane washing and purified by column chromatography (silica 60, hexane/ethyl acetate 3:1, R_f=0.40) to afford another 650 mg of the title compound of the formula

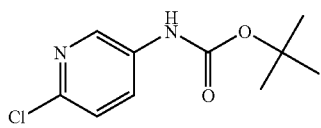

as a white solid.
¹H-NMR (CDCl₃, TMS) δ (ppm): 1.52 (9H, s), 6.60 (1H, s), 7.25 (1H, d, J=8 Hz), 7.95-7.97 (1H, br m), 8.24 (1H, d, J=3 Hz).

Step 2: Preparation of 5-tert-butoxycarbonylamino-2-chloro-isonicotinic acid

A solution of (6-chloro-pyridin-3-yl)-carbamic acid tert-butyl ester (4.19 g) in diethyl ether (150 mL) was cooled to −78° C. and N,N,N',N'-tetramethylethylendiamine (6.60 g) was added. After slow addition of n-butyl lithium solution (1.32 M in hexane, 41.6 mL) over a time period of 10 minutes, the mixture was allowed to warm up to −10° C., stirred at this temperature for 2 hours and then was re-cooled to −78° C. The mixture was poured slowly into a stirred mixture of crushed dry ice in THF and stirred for 30 minutes. The mixture was concentrated on a rotary evaporator and water was added to the residue. The aqueous layer was washed 2× with MTB-ether and acidified with 6N hydrochloric acid to pH ~3. The formed precipitate was filtered off, washed with water, ethyl acetate and dried in vacuum to afford 2.46 g of the title compound of the formula

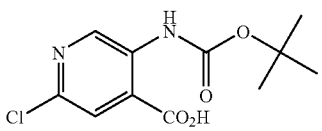

as a beige solid.
¹H-NMR (DMSO-D₆) δ (ppm): 1.48 (9H, s), 7.77 (1H, s), 9.13 (1H, s), 10.13 (1H, s).

Step 3: Preparation of 5-amino-2-chloroisonicotinic acid

A suspension of 5-tert-butoxycarbonylamino-2-chloro-isonicotinic acid (2.46 g) in aqueous 2N potassium hydroxide solution (45 mL) was stirred at 90° C. for 5 hours. After cooling to room temperature, the solution was acidified by slow addition of 6N hydrochloric acid. The formed precipitate was filtered off, washed with water, MTB-ether and hexane and dried in vacuum to afford 700 mg of the title compound of the formula

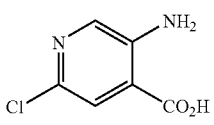

as a beige solid.
¹H-NMR (DMSO-D₆) δ (ppm): 7.47 (1H, s), 8.02 (1H, s).

Step 4: Preparation of 5-amino-3-chloroisonicotinic acid methyl ester

5-Amino-2-chloroisonicotinic acid (1.72 g) was suspended in methanol (20 mL) and toluene (60 mL) was added. A solution of (trimethylsilyl)diazomethane (2.0 M in diethyl ether, 6.5 mL) was added slowly to the suspension. Within 5 to 10 minutes after addition, the suspension turned into a solution. After 2 hours stirring at room temperature, the reaction mixture was quenched with water and extracted 3× with ethyl acetate. The combined organic layer was washed with saturated bicarbonate solution and brine, dried over MgSO₄ and concentrated in vacuum. The residue was purified by column chromatography (silica gel 60, chloroform/ethyl acetate=20:1, R_f=0.30 in chloroform/ethyl acetate=3:1) to afford 1.50 g of the title compound of the formula

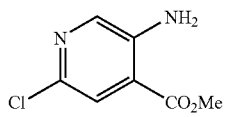

as a white solid.
$^1$H-NMR (DMSO-D$_6$) δ (ppm): 3.83 (3H, s), 6.77 (2H, s), 7.48 (1H, s), 8.05 (1H, s).

Step 5: Preparation of
3-amino-2-bromo-6-chloroisonicotinic acid methyl ester

5-Amino-3-chloroisonicotinic acid methyl ester (600 mg) was dissolved in DMF (5 mL), N-bromosuccinimide (573 mg) was added and the solution was stirred for 3 hours at 80° C. and hours at room temperature. The reaction mixture was diluted with MTB-ether and 3× washed with water, washed with brine, dried over MgSO$_4$ and concentrated in vacuum. The residue was purified by column chromatography (silica 60, hexane/ethyl acetate=10:1, R$_f$=0.20) to afford 787 mg of the title compound of the formula

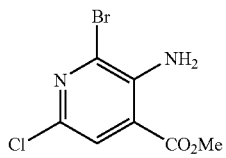

as a yellow solid.
$^1$H-NMR (CDCl$_3$, TMS) δ (ppm): 3.93 (3H, s), 6.23 (2H, br s), 7.67 (1H, s).

Step 6: Preparation of
3-amino-6-chloro-2-methylisonicotinic acid methyl ester

3-Amino-2-bromo-6-chloroisonicotinic acid methyl ester (500 mg), potassium carbonate (829 mg), tetrakis(triphenylphosphine)palladium(0) and trimethylboroxine (276 mg) were suspended in dioxane (15 mL). Water (1.5 mL) was added and the mixture was degassed using subsequent evaporation and flushing with nitrogen (5×). The reaction mixture was stirred under reflux for 7 hours. After cooling to room temperature, the mixture was quenched with water and extracted 2× with ethyl acetate. The combined organic layer was washed with brine, dried over MgSO$_4$ and concentrated in vacuum. The residue was purified by column chromatography (silica 60, hexane/ethyl acetate=3:1, R$_f$=0.25) to afford 100 mg of the title compound of the formula

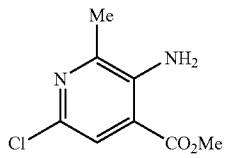

as a yellow solid.
$^1$H-NMR (CDCl$_3$, TMS) δ (ppm): 2.44 (3H, s), 3.92 (3H, s), 5.70 (2H, br s), 7.57 (1H, s).

Step 7: Preparation of
3-amino-6-chloro-2-methylisonicotinic acid

3-Amino-6-chloro-2-methylisonicotinic acid methyl ester (100 mg) was dissolved in methanol (2 mL) and 2N aqueous sodium hydroxide solution (2 mL) was added. The reaction mixture was stirred under reflux for 2.5 hours. After cooling to room temperature, water and diethyl ether were added, the layers were separated and the aqueous layer was washed with diethyl ether. The aqueous layer was acidified by addition of 2N hydrochloric acid and the formed precipitate was 3× extracted with MTB-ether. The combined organic layer was washed with brine, dried over MgSO$_4$ and concentrated in vacuum to afford 89 mg of the title compound of the formula

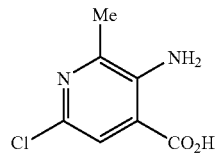

as a yellow solid. The crude product was used without further purification in the next step.
$^1$H-NMR (DMSO-D$_6$) δ (ppm): 2.33 (3H, s), 7.40 (1H, s).

Step 8: Preparation of 2-[5-bromo-2-(3-chloro-pyridin-2-yl)-2H-pyrazol-3-yl]-6-chloro-8-methyl-pyrido[3,4-d][1,3]oxazin-4-one A mixture of 5-bromo-2-(3-chloro-pyridin-2-yl)-2H-pyrazole-3-carboxylic acid (example 1, step 5) (144 mg) and thionyl chloride (105 μl) was stirred under reflux for 2 hours. Excess thionyl chloride was co-evaporated with dry toluene on a evaporator, the residue re-dissolved in dry acetonitrile (1.5 mL) and 3-amino-6-chloro-2-methylisonicotinic acid (89 mg) was added. The solution was stirred for 10 minutes at room temperature and triethylamine (65 μL) was added and stirred for 20 minutes, before a second portion of triethylamine (130 μL) was added. After the mixture was stirred for further 20 minutes at room temperature, methanesulfonyl chloride (45 μL) was added. After stirring for 48 hours at room temperature, the reaction mixture was quenched with water and extracted 3× with ethyl acetate. The combined organic layer was washed with brine, dried over MgSO$_4$ and concentrated in vacuum. The residue was purified by column chromatography (silica 60, hexane/ethyl acetate=3:1, R$_f$=0.20) to afford 67 mg of the title compound of the formula

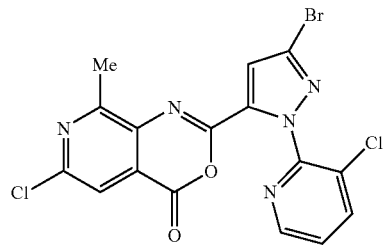

as a white solid.
$^1$H-NMR (CDCl$_3$, TMS) δ (ppm): 2.10 (3H, s), 7.28 (1H, s), 7.53 (1H, dd, J=8 Hz, 5 Hz), 7.83 (1H, s), 8.00 (1H, dd, J=8 Hz, 2 Hz), 8.56 (1H, dd, J=5 Hz, 2 Hz).

Step 9: Preparation of N'-(3-{[5-bromo-2-(3-chloro-pyridin-2-yl)-2H-pyrazole-3-carbonyl]-amino}-6-chloro-2-methyl-pyridine-4-carbonyl)-hydrazinecarboxylic acid methyl ester (3)

2-[5-Bromo-2-(3-chloro-pyridin-2-yl)-2H-pyrazol-3-yl]-6-chloro-8-methyl-pyrido[3,4-d][1,3]oxazin-4-one (67 mg) was dissolved in DMF (4 mL) and carbazaic acid methyl ester (133 mg) was added. The solution was stirred for 20 hours at room temperature. The reaction mixture was quenched with water and extracted with MTB-ether. The organic layer was washed 4× with water, washed with brine, dried over MgSO$_4$ and concentrated in vacuum. The residue was purified by column chromatography (silica 60, chloroform/ethyl acetate=1:1, R$_f$=0.20) to afford 61 mg of compound 3 of the present invention of the formula

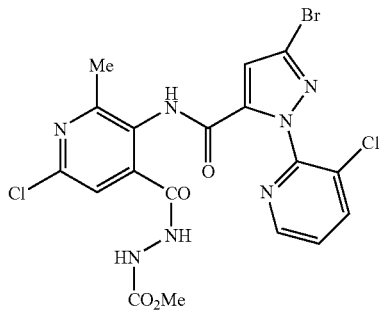

(3)

as a white solid.
$^1$H-NMR (DMSO-D$_6$) δ (ppm): 2.35 (3H, s), 3.48-3.63 (3H, br m), 7.36 (1H, s), 7.39 (1H, s), 7.62 (1H, dd, J=8 Hz, 5 Hz), 8.18 (1H, dd, J=8 Hz, 2 Hz), 8.50 (1H, dd, J=5 Hz, 2 Hz), 9.41 (1H, s), 10.38 (1H, s), 10.47 (1H, s).

Example 4

Preparation of N'-(2-bromo-3-{[5-bromo-2-(3-chloro-pyridin-2-yl)-2H-pyrazole-3-carbonyl]-amino}-6-chloro-pyridine-4-carbonyl)-hydrazinecarboxylic acid methyl ester (4)

Step 1: Preparation of 3-amino-2-bromo-6-chloroisonicotinic acid

3-Amino-2-bromo-6-chloroisonicotinic acid methyl ester (260 mg) (example 3, step 5) was dissolved in methanol (2 mL), 2N aqueous sodium hydroxide solution (2 mL) was added and the reaction mixture was stirred for 2 hours at reflux. After cooling to room temperature, diethyl ether and water were added and the layers were separated. The aqueous layer was washed with diethyl ether and acidified by addition of 2N hydrochloric acid. The formed precipitate was extracted with MTB-ether (3×), the combined organic layer was washed with brine, dried over MgSO$_4$ and concentrated in vacuum to afford 246 mg of

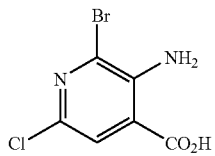

as a yellow solid.
$^1$H-NMR (DMSO-D$_6$) δ (ppm): 6.82 (2H, br s), 7.61 (1H, s).

Step 2: Preparation of 8-bromo-2-[5-bromo-2-(3-chloro-pyridin-2-yl)-2H-pyrazol-3-yl]-6-chloro-pyrido[3,4-d][1,3]oxazin-4-one A mixture of 5-bromo-2-(3-chloro-pyridin-2-yl)-2H-pyrazole-3-carboxylic acid (example 1, step 5) (1.20 g) and thionyl chloride (870 μl) was stirred under reflux for 2 hours. Excess thionyl chloride was co-evaporated with dry toluene on a evaporator, the residue re-dissolved in dry acetonitrile (12 mL) and 3-amino-2-bromo-6-chloroisonicotinic acid (750 mg) was added. The solution was stirred for 10 minutes at room temperature and triethylamine (560 μL) was added and stirred for 20 minutes, before a second portion of triethylamine (1.20 mL) was added. After the mixture was stirred for further 20 minutes at room temperature, methanesulfonyl chloride (340 μL) was added. After stirring for 20 hours at room temperature, the reaction mixture was quenched by slow addition of water. The precipitate was filtered off, washed with water/acetonitrile (1:2), acetonitrile and diethyl ether and dried in vacuum to afford 598 mg of the title compound of the formula

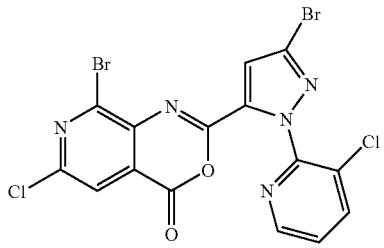

as a beige solid.
$^1$H-NMR (CDCl$_3$, TMS) δ (ppm): 7.32 (1H, s), 7.50 (1H, dd, J=8 Hz, 5 Hz), 7.94 (1H, s), 8.00 (1H, d, J=8 Hz), 8.55 (1H, d, J=5 Hz).

Step 3: Preparation of N'-(2-bromo-3-{[5-bromo-2-(3-chloro-pyridin-2-yl)-2H-pyrazole-3-carbonyl]-amino}-6-chloro-pyridine-4-carbonyl)-hydrazinecarboxylic acid methyl ester (4)

8-Bromo-2-[5-bromo-2-(3-chloro-pyridin-2-yl)-2H-pyrazol-3-yl]-6-chloro-pyrido[3,4-d][1,3]oxazin-4-one (400 mg) was dissolved in DMF (12 mL) and carbazaic acid methyl ester (696 mg) was added. The solution was stirred for 22 hours at room temperature. The reaction mixture was quenched with water and extracted with MTB-ether. The organic layer was washed 3× with water, brine, dried over MgSO$_4$ and concentrated in vacuum. The residue was purified by column chromatography (silica 60, chloroform/ethyl acetate=1:1, R$_f$=0.20) to afford 330 mg of compound 4 of the present invention of the formula (4)

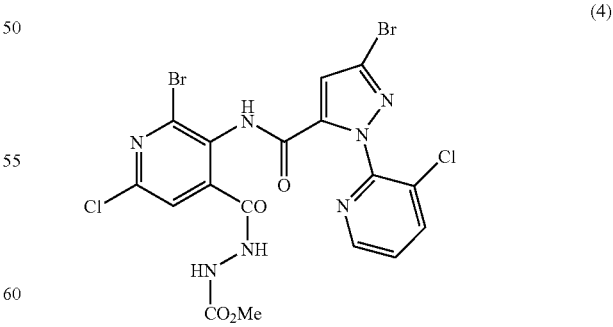

as a white solid.
$^1$H-NMR (DMSO-D$_6$) δ (ppm): 3.45-3.63 (3H, br m), 7.42 (1H, s), 7.59-7.63 (2H, m), 8.17 (1H, dd, J=8 Hz, 2 Hz), 8.51 (1H, dd, J=5 Hz, 2 Hz), 9.47 (1H, br s), 10.44 (1H, s), 10.76 (1H, s).

Example 5

Preparation of N'-(2,6-dibromo-3-{[5-bromo-2-(3-chloro-pyridin-2-yl)-2H-pyrazole-3-carbonyl]-amino}-pyridine-4-carbonyl)-hydrazinecarboxylic acid methyl ester (5)

Step 1: Preparation of pyridin-3-yl-carbamic acid tert-butyl ester

3-Aminopyridine (20.0 g) was dissolved in tert-butanol (300 mL), di-tert-butyl dicarbonate (52.0 g) was added and the solution was stirred at 50° C. for 5 hours, then for 12 hours at room temperature and another 7 hours at 50° C. The solvent was evaporated on a rotary evaporator and the residue was dissolved in ethyl acetate. The organic layer was 3× washed with water, washed with brine, dried over MgSO$_4$ and concentrated in vacuum. The residue was purified 2× by column chromatography (silica 60, hexane/ethyl acetate=1:1, then 1:2, R$_f$=0.15) to afford 6.20 g of the title compound of the formula

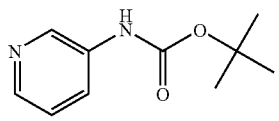

as a yellow solid.

$^1$H-NMR (CDCl$_3$, TMS) δ (ppm): 1.53 (9H, s), 6.71 (1H, s), 7.24 (1H, dd, J=8 Hz, 5 Hz), 7.99 (1H, d, J=8 Hz), 8.28 (1H, d, J=5 Hz), 8.45 (1H, d, J=2 Hz).

Step 2: Preparation of 3-tert-butoxycarbonylamino-isonicotinic acid

Pyridin-3-yl-carbamic acid tert-butyl ester (6.20 g) was dissolved in anhydrous diethyl ether (260 mL), cooled to −78° C. and N,N,N',N'-tetramethylethylendiamine (14.4 mL) was added. A solution of n-butyl lithium (1.6 M in hexane, 60 mL) was added slowly over a time period of 10 minutes. After the addition of the reagent was completed, the reaction mixture was allowed to warm to −10° C. and stirred at this temperature for 2 hours. The reaction mixture was then re-cooled to −78° C. and slowly poured on a stirred mixture of dry ice in diethyl ether. After stirring for 30 minutes, water was added to the reaction mixture and the layers were separated after complete dissolution of solid materials. The aqueous layer was washed 2× with diethyl ether and the pH-value of the aqueous layer was adjusted to 5-6. The organic layer was extracted 2× with MTB-ether. The combined organic layer was washed with a small amount of brine, dried over MgSO$_4$ and concentrated in vacuum. The residue was washed with hexane to remove oily by-products and dried in vacuum to afford 1.19 g of the title compound as beige solid. The aqueous washing was concentrated on a rotary evaporator to approx. 50 mL, inorganic salts were filtered off and MTB-ether was added to the mother liquor. 6N hydrochloric acid was slowly added into the well-stirred mixture until the pH-value was adjusted to −3. The layers were separated, the aqueous layer was washed 2× with MTB-ether and 2× with chloroform. The combined organic layer was dried over MgSO$_4$ and dried in vacuum to give another 2.03 g of beige solid. Together, the first organic extract and 3.22 g of the title compound of the formula

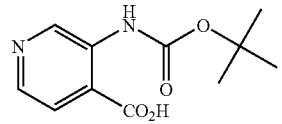

were isolated as a beige solid. The compound was used in the next step without further purification.

$^1$H-NMR (DMSO-D$_6$) δ (ppm): 1.47 (9H, s), 7.74 (1H, d, J=5 Hz), 8.34 (1H, d, J=5 Hz), 9.35 (1H, s), 10.07 (1H, s).

Step 3: Preparation of 3-aminoisonicotinic acid 3-tert-Butoxycarbonylamino-isonicotinic acid (450 mg) was dissolved in methanol (8 mL) and 6N hydrochloric acid (5 mL) was added to the solution. The resulting suspension was stirred under reflux for 2.5 hours, cooled to room temperature and washed 3× with chloroform. The aqueous layer was adjusted to pH-14 by addition of 2N sodium hydroxide solution, washed 3× with chloroform and adjusted again to pH-3 by addition of 2N hydrochloric acid. The aqueous layer was concentrated on a rotary evaporator to complete dryness and the residue was extracted with hot ethanol. The ethanol extract was filtered to remove insoluble material and concentrated in vacuum to afford 262 mg of the title compound of formula

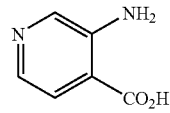

as a yellow solid. The compound was used in the next step without further purification.

$^1$H-NMR (DMSO-D$_6$) δ (ppm): 7.78 (1H, d, J=5 Hz), 7.84 (1H, d, J=5 Hz), 8.30 (1H, s).

Step 4: Preparation of 3-amino-2,6-dibromoisonicotinic acid

3-Aminoisonicotinic acid (260 mg) was dissolved in DMF (10 mL) N-bromosuccinimide (320 mg) was added and the reaction mixture was stirred at room temperature for 1 hour before another portion of N-bromosuccinimide (320 mg) was added. After stirring for 3 hours at room temperature, the reaction mixture was quenched with water. 2N Sodium hydroxide solution was added, the aqueous solution was washed 2× with diethyl ether and adjusted to pH-2 by addition of 6N hydrochloric acid. The aqueous layer was extracted 3× with MTB-ether, the combined organic layer was washed with brine, dried over MgSO$_4$ and concentrated in vacuum to afford 283 mg of the title compound of the formula

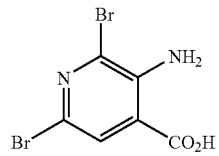

as a yellow-orange solid. The compound was contaminated with ca.10% impurities and was used without further purification in the next step.

$^1$H-NMR (CDCl$_3$, TMS) δ (ppm): 6.16 (2H, br s), 7.61 (1H, s).

Step 5: Preparation of 6,8-dibromo-2-[5-bromo-2-(3-chloro-pyridin-2-yl)-2H-pyrazol-3-yl]-pyrido[3,4-d][1,3]oxazin-4-one A mixture of 5-bromo-2-(3-chloro-pyridin-2-yl)-2H-pyrazole-3-carboxylic acid (example 1, step 5) (242 mg) and thionyl chloride (180 µL) was stirred under reflux for 2 hours. Excess thionyl chloride was co-evaporated with dry toluene on a evaporator, the residue re-dissolved in dry acetonitrile (3 mL) and 3-amino-2,6-dibromoisonicotinic acid (282 mg) was added. The solution was stirred for 10 minutes at room temperature and triethylamine (110 µL) was added and stirred for 20 minutes, before a second portion of triethylamine (220 µL) was added. After the mixture was stirred for further 20 minutes at room temperature, methanesulfonyl chloride (75 µL) was added. After stirring for 18 hours at room temperature, the reaction mixture was quenched by slow addition of water. The precipitate was filtered off, washed with water/acetonitrile (1:2), acetonitrile and diethyl ether and dried in vacuum to afford 153 mg of the title compound of the formula

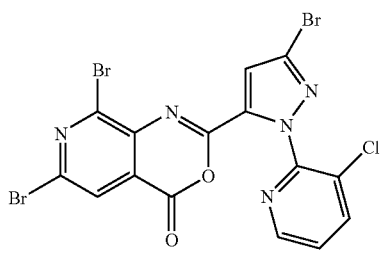

as a beige solid.
$^1$H-NMR (CDCl$_3$, TMS) δ (ppm): 7.32 (1H, s), 7.50 (1H, dd, J=8 Hz, 5 Hz), 8.00 (1H, d, J=8 Hz), 8.09 (1H, s), 8.56 (1H, d, J=5 Hz).

Step 6: Preparation of N'-(2,6-dibromo-3-{[5-bromo-2-(3-chloro-pyridin-2-yl)-2H-pyrazole-3-carbonyl]-amino}-pyridine-4-carbonyl)-hydrazinecarboxylic acid methyl ester (5)

6,8-Dibromo-2-[5-bromo-2-(3-chloro-pyridin-2-yl)-2H-pyrazol-3-yl]-pyrido[3,4-d][1,3]oxazin-4-one (153 mg) was dissolved in DMF (7 mL) and carbazic acid methyl ester (240 mg) was added. The solution was stirred for 19 hours at room temperature. The reaction mixture was quenched with water and extracted with MTB-ether. The organic layer was washed 3× with water, brine, dried over MgSO$_4$ and concentrated in vacuum. The residue was purified by column chromatography (silica 60, chloroform/ethyl acetate=1:1, R$_f$=0.20) to afford 128 mg of compound 5 of the present invention of the formula

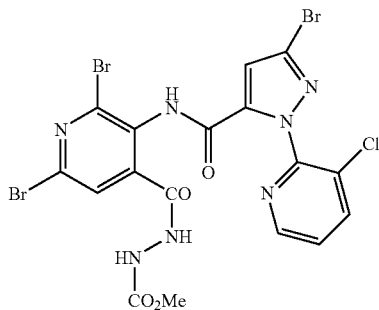

(5)

as a beige solid.

$^1$H-NMR (DMSO-D$_6$) δ (ppm): 3.49-3.62 (3H, m), 7.42 (1H, s), 7.61 (1H, dd, J=8 Hz, 5 Hz), 7.70 (1H, s), 8.17 (1H, d, J=8 Hz), 8.50 (1H, d, J=5 Hz), 9.46 (1H, br s), 10.44 (1H, s), 10.75 (1H, s).

Example 6

Preparation of N'-(4-{[5-bromo-2-(3-chloro-pyridin-2-yl)-2H-pyrazole-3-carbonyl]-amino}-5-chloro-pyridine-3-carbonyl)-hydrazinecarboxylic acid methyl ester (6)

Step 1: Preparation of (3-chloro-pyridin-4-yl)-carbamic acid tert-butyl ester 3-Chloro-isonicotinic acid (3.0 g) was dissolved in tert-butanol (80 mL), diphenyl phosphoryl azide (5.24 g) and triethylamine (2.7 mL) were added and the reaction mixture was stirred at 100° C. for 5.5 h. After cooling to room temperature, the reaction mixture was concentrated in vacuum and the residue was dissolved in ethyl acetate and water. The layers were separated and the aqueous layer was 2× extracted with ethyl acetate, the combined organic layer was washed with brine, dried over magnesium sulfate and concentrated in vacuum. The residue was purified by column chromatography (silica 60, hexane/ethyl acetate 3:1, R$_f$=0.30) to afford 2.74 g of the title compound of the formula

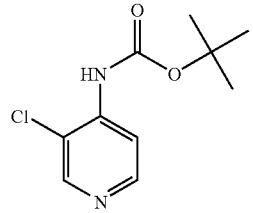

as a white solid.
$^1$H-NMR (CDCl$_3$, TMS) δ (ppm): 1.55 (9H, s), 7.18 (1H, br s), 8.15 (1H, d, J=6 Hz), 8.36 (1H, d, J=6 Hz), 8.46 (1H, s).

Step 2: Preparation of 4-tert-butoxycarbonylamino-5-chloro-nicotinic acid (3-Chloro-pyridin-4-yl)-carbamic acid tert-butyl ester (1.50 g) was dissolved in dry diethyl ether (35 mL), N,N,N',N'-tertamethylenethylendiamine (2.35 mL) was added and the reaction mixture was cooled in a dry ice/acetone cool bath to −78° C. n-Butyl lithium (9.9 mL, 1.59M in hexane) was added to the suspension, the cool bath was replaced by a sodium chloride/ice mixture and the reaction mixture was stirred at −10° C. for 1.5 h. The suspension was slowly poured on crushed dry ice (2.0 g) in dry diethyl ether (20 mL) and stirred for 1 h. Water was added and the pH was adjusted to −12 by addition of 2N sodium hydroxide solution. The aqueous layer was washed 2× with MTB-ether, 2 M hydrochloric acid was added to the aqueous layer and the pH was adjusted to −2 and the aqueous layer was 3× extracted with ethyl acetate. The combined organic layer was washed with brine, dried over magnesium sulfate and concentrated in vacuum to afford 1.03 g of the title compound of the formula

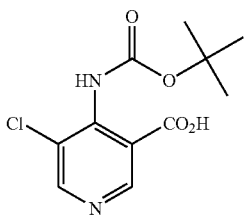

as a beige solid. The crude product contained ~30% valeric acid and was used without further purification in the next step.

¹H-NMR (DMSO-D₆) δ (ppm): 1.44 (9H, s), 8.72 (1H, s), 8.74 (1H, s), 9.49 (1H, s), 13.29 (1H, br s).

Step 3: Preparation of 4-amino-5-chloro-nicotinic acid 4-tert-Butoxycarbonylamino-5-chloro-nicotinic acid (1.03 g, crude product from step 2 in a ~3:1 mixture with valeric acid) was dissolved in methanol (10 mL), 5 M hydrochloric acid (10 mL) was added and the reaction mixture was stirred for 1.5 h under gentle reflux. After cooling to room temperature, the mixture was concentrated in vacuum, the residue was dissolved in water and the mixture was adjusted to pH ~12 by addition of 2N sodium hydroxide solution. The aqueous layer was washed 2× with a mixture of MTB-ether/hexane (1:1), then 5 M hydrochloric acid was added and the aqueous layer was adjusted to pH ~2. The aqueous layer was 2× washed with ethyl acetate and the aqueous layer was then concentrated in vacuum to dryness. The residue was 3× dissolved in methanol/toluene and co-evaporated to dryness to remove traces of water. The residue was suspended in methanol (50 mL), stirred under reflux for 30 min cooled to room temperature and insoluble salts were removed by filtration. The filtrate was concentrated and dried in vacuum to afford 1.59 g of a yellow solid containing the title compound of the formula

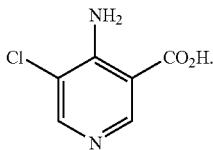

The crude product still contained inorganic salts and was used in the next step without further purification.

¹H-NMR (DMSO-D₆) δ (ppm): 8.60-9.03 (2H, br m), 8.71 (1H, s), 8.73 (1H, s).

Step 4: Preparation of 2-[5-bromo-2-(3-chloro-pyridin-2-yl)-2H-pyrazol-3-yl]-8-chloro-pyrido[4,3-d][1,3]oxazin-4-one 5-Bromo-2-(3-chloro-pyridin-2-yl)-2H-pyrazole-3-carboxylic acid (example 1, step 5) (696 mg) was suspended in dry toluene (20 mL), oxalyl chloride (580 μL) and 3 drops of dry DMF were added (gas evolution) and the reaction mixture was stirred for 1 h at room temperature. The mixture was concentrated in vacuum and excess oxalyl chloride was removed by co-evaporation with dry toluene (3×). The residue was dissolved in dry acetonitrile (20 mL) and 4-amino-5-chloro-nicotinic acid (crude mixture from the above step 3, 1.0 g) and triethylamine (320 μL) were added. The reaction mixture was stirred for 30 minutes, before a second portion of triethylamine (640 μL) was added. After the mixture was stirred for further 20 minutes at room temperature, methanesulfonyl chloride (195 μL) was added. After stirring for 4 h at room temperature, the reaction mixture was quenched by addition of water (10 mL). The precipitate was filtered off, washed with water/acetonitrile (1:2), acetonitrile and diethyl ether and dried in vacuum to afford 250 mg of the title compound of the formula

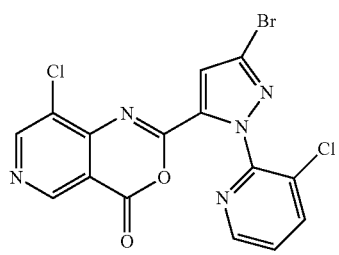

as a beige solid.

¹H-NMR (CDCl₃, TMS) δ (ppm): 7.36 (1H, s), 7.50 (1H, dd, J=8 Hz, 5 Hz), 7.99 (1H, dd, J=8 Hz, 2 Hz), 8.55 (1H, dd, J=5 Hz, 2 Hz), 8.84 (1H, s), 9.24 (1H, s).

Step 5: Preparation of N'-(4-{[5-bromo-2-(3-chloro-pyridin-2-yl)-2H-pyrazole-3-carbonyl]-amino}-5-chloro-pyridine-3-carbonyl)-hydrazinecarboxylic acid methyl ester (6)

2-[5-Bromo-2-(3-chloro-pyridin-2-yl)-2H-pyrazol-3-yl]-8-chloro-pyrido[4,3-d][1,3]oxazin-4-one (150 mg) was dissolved in DMF (10 mL) and carbazaic acid methyl ester (154 mg) was added. The solution was stirred for 2 h at room temperature before it was quenched with water. The mixture was 2× extracted with ethyl acetate, the combined organic layer was 3× washed with water, washed with brine, dried over magnesium sulfate and concentrated in vacuum. The residue was purified by column chromatography (silica 60, chloroform/methanol=10:1) to afford 99 mg of compound (6) of the present invention of the formula (6)

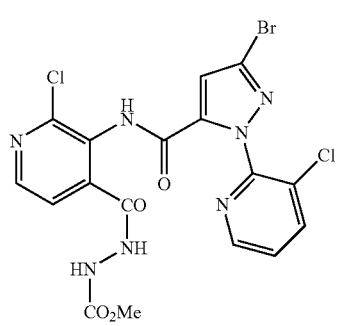

as a white solid.

¹H-NMR (DMSO-D₆) δ (ppm): 3.46-3.65 (3H, m), 7.45 (1H, s), 7.61 (1H, dd, J=8 Hz, 5 Hz), 8.17 (1H, d, J=8 Hz), 8.51 (1H, d, J=5 Hz), 8.64 (1H, s), 8.86 (1H, s), 9.40 (1H, br s), 10.44 (1H, s), 10.81 (1H, s).

Example 7

Preparation of (N'-(3-{[5-bromo-2-(3-chloro-pyridin-2-yl)-2H-pyrazole-3-carbonyl]-amino}-6-chloro-4-methyl-pyridine-2-carbonyl)-hydrazinecarboxylic acid methyl ester (7)

Step 1: Preparation of 3-amino-6-chloro-2-iodo-4-methylpyridine

5-Amino-2-chloro-4-methylpyridine (1.35 g) was dissolved in DMF (20 mL), N-iodosuccinimide (2.59 g) was added and the reaction mixture was stirred at room temperature for 12 hours. Ethyl acetate was added and the organic layer was washed 3× with water, washed with brine, dried over MgSO$_4$ and concentrated in vacuum. The residue was purified by column chromatography (silica 60, hexane/ethyl acetate=3:1, R$_f$=0.30) to afford 1.38 g of the title compound of the formula

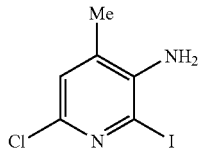

as an orange solid.
$^1$H-NMR (CDCl$_3$, TMS) δ (ppm): 2.21 (3H, s), 4.06 (2H, br s), 6.95 (1H, s).

Step 2: Preparation of 3-amino-6-chloro-2-(2-furanyl)-4-methylpyridine

3-Amino-6-chloro-2-iodo-4-methylpyridine (1.38 g), 2-furanboronic acid (861 mg), and sodium carbonate (815 mg) were suspended in a solvent mixture consistent of toluene (19 mL), THF (19 mL) and water (6 mL). The mixture was degassed using subsequent evaporation and flushing with nitrogen (5×) and tetrakis(triphenylphosphine)palladium(0) (658 mg) was added. The reaction mixture was stirred at 90° C. for 5 hours and 12 hours at room temperature. After addition of another portion of 2-furanboronic acid (430 mg) and tetrakis(triphenyl phosphine)palladium(0) (132 mg), the mixture was stirred again for 12 hours at 90° C. After 12 hours stirring at room temperature, the reaction mixture was quenched with water and extracted 2× with ethyl acetate. The combined organic layer was washed with brine, dried over MgSO$_4$ and concentrated in vacuum. The residue was purified by column chromatography (silica 60, hexane/ethyl acetate=4:1, R$_f$=0.25) to afford 929 mg of the title compound of the formula

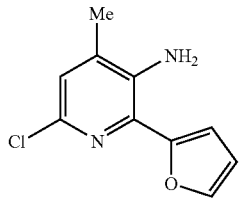

as an orange solid.
$^1$H-NMR (CDCl$_3$, TMS) δ (ppm): 2.20 (3H, s), 4.65 (2H, br s), 6.56 (1H, dd, J=4 Hz, 2 Hz), 6.94 (1H, s), 7.07 (1H, dd, J=4 Hz, 1 Hz), 7.54 (1H, dd, J=2 Hz, 1 Hz).

Step 3: Preparation of 3-amino-6-chloro-4-methyl-pyridine-2-carboxylic acid

3-Amino-6-chloro-2-(2-furanyl)-4-methylpyridine (400 mg) was dissolved in acetone (10 mL) and cooled in an ice bath to 0° C. A solution prepared of potassium permanganate (909 mg) in water (15 mL) was added drop wise to this solution. After complete addition, the reaction mixture was allowed to warm to room temperature and stirred for 2 hours. The mixture was cooled again to 0° C. and a second portion of potassium permanganate (600 mg) in water (10 mL) was added and the cool bath removed. After stirring for 2 hours, the reaction mixture was filtered through a pad of celite, the filter cake was washed carefully with water, methanol and ethyl acetate and concentrated to approx. 10 mL on a rotary evaporator. 2N Sodium hydroxide solution was added to adjust the pH-value to −12 and the aqueous layer was washed 2× with MTB-ether. The aqueous layer was then adjusted to pH ~2 by addition of 6N hydrochloric acid and extracted 3× with MTB-ether. The combined organic layer was washed with brine, dried over MgSO$_4$ and concentrated in vacuum to afford 262 mg of the title compound of the formula

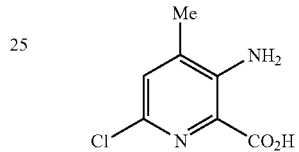

as an orange-brown solid.
$^1$H-NMR (CDCl$_3$, TMS) δ (ppm): 2.24 (3H, d, J=1 Hz), 5.94 (2H, br s), 7.21 (1H, d, J=1 Hz).

Step 4: Preparation of 2-[5-bromo-2-(3-chloro-pyridin-2-yl)-2H-pyrazol-3-yl]-6-chloro-8-methyl-pyrido[3,2-d][1,3]oxazin-4-one A mixture of 5-bromo-2-(3-chloro-pyridin-2-yl)-2H-pyrazole-3-carboxylic acid (example 1, step 5) (413 mg) and thionyl chloride (300 μl) was stirred under reflux for 2 hours. Excess thionyl chloride was co-evaporated with dry toluene on a evaporator, the residue re-dissolved in dry acetonitrile (5 mL) and 3-amino-6-chloro-4-methyl-pyridine-2-carboxylic acid (255 mg) was added. The solution was stirred for 15 minutes at room temperature and triethylamine (190 μL) was added and stirred for 30 minutes, before a second portion of triethylamine (380 μL) was added. After the mixture was stirred for further 30 minutes at room temperature, methanesulfonyl chloride (120 μL) was added. After stirring for 20 hours at room temperature, the reaction mixture was quenched by slow addition of water. The precipitate was filtered off, washed with water/acetonitrile (1:2), acetonitrile and diethyl ether and dried in vacuum to afford 112 mg of the title compound of the formula

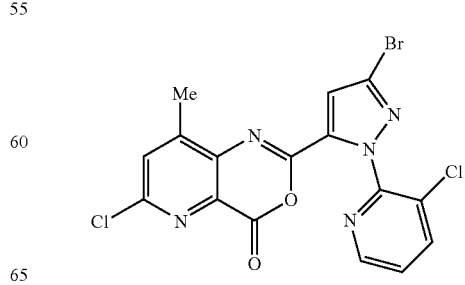

as a beige solid.

¹H-NMR (CDCl₃, TMS) δ (ppm): 1.89 (3H, d, J=1 Hz), 7.29 (1H, s), 7.47 (1H, d, J=1 Hz), 7.50 (1H, dd, J=8 Hz, 5 Hz), 7.98 (1H, dd, J=8 Hz, 2 Hz), 8.56 (1H, dd, J=5 Hz, 2 Hz).

Step 5: Preparation of (N'-(3-{[5-bromo-2-(3-chloro-pyridin-2-yl)-2H-pyrazole-3-carbonyl]-amino}-6-chloro-4-methyl-pyridine-2-carbonyl)-hydrazinecarboxylic acid methyl ester (7)

2-[5-Bromo-2-(3-chloro-pyridin-2-yl)-2H-pyrazol-3-yl]-6-chloro-8-methyl-pyrido[3,2-d][1,3]oxazin-4-one (112 mg) was dissolved in DMF (7 mL) and carbazaic acid methyl ester (223 mg) was added. The solution was stirred for 3.5 hours, dried over MgSO₄ and concentrated in vacuum. The residue was purified by column chromatography (silica 60, chloroform/ethyl acetate=3:1, R_f=0.25) to afford 113 mg of compound 7 of the present invention of the formula

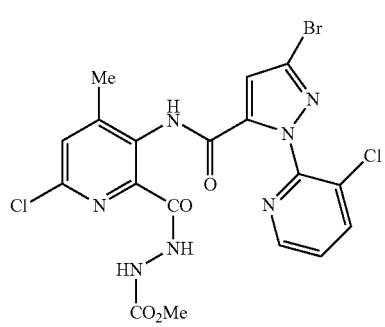

(7)

as a white solid.

¹H-NMR (DMSO-D₆) δ (ppm): 2.19 (3H, s), 3.50-3.61 (3H, br m), 7.42 (1H, s), 7.62 (1H, dd, J=8 Hz, 5 Hz), 7.73 (1H, s), 8.18 (1H, dd, J=8 Hz, 2 Hz), 8.50 (1H, dd, J=5 Hz, 2 Hz), 9.27 (1H, br s), 10.41 (1H, s), 10.56 (1H, s).

Alternative preparation of N'-(3-{[5-bromo-2-(3-chloro-pyridin-2-yl)-2H-pyrazole-3-carbonyl]-amino}-6-chloro-4-methyl-pyridine-2-carbonyl)-hydrazinecarboxylic acid methyl ester (7)

Step 1: Preparation of (6-chloro-pyridin-3-yl)-carbamic acid tert-butyl ester

6-Chloro-pyridin-3-ylamine (10.0 g) were dissolved in tert-butanol (140 mL), di-tert-butyl dicarbonate (18.7 g) were added and the solution was stirred at 50° C. for 4 h. Di-tert-butyl dicarbonate (3.40 g) was added and the reaction mixture was stirred for another 8 h at 50° C. Most of the solvent was removed in vacuum and the residue was dissolved in ethyl acetate and washed 3× with water, washed with brine, dried over magnesium sulfate and concentrated in vacuum. The residue was purified by column chromatography (silica 60, chloroform/ethyl acetate 10:1, R_f=0.30) to afford 16.5 g of the title compound of the formula

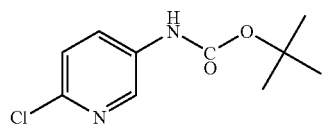

as a white solid.

¹H-NMR (CDCl₃, TMS) δ (ppm): 1.52 (9H, s), 6.54 (1H, br s), 7.27 (1H, d, J=3 Hz), 7.96 (1H, s), 8.23 (1H, d, J=3 Hz).

Step 2: Preparation of (6-chloro-4-methyl-pyridin-3-yl)-carbamic acid tert-butyl ester (6-Chloro-pyridin-3-yl)-carbamic acid tert-butyl ester (14.11 g) was dissolved in dry diethyl ether (310 mL), N,N,N',N'-tetramethyl-ethylene-1,2-diamine (23.1 mL) was added. The solution was cooled to −78° C., n-butyl lithium (97 mL, 1.59 M in hexane) was added, the cool bath replaced by an ice/sodium chloride cool bath and the suspension was stirred for 2 h at −10° C. The suspension was cooled again to −78° C. and methyl iodide (5.8 mL) was added slowly. The cool bath was removed and the reaction was quenched after 1 h by addition of water. Ethyl acetate was added and the mixture was neutralized by addition of 2 M hydrochloric acid. The layers were separated and the aqueous layer was extracted 2× with ethyl acetate, the combined organic layer was washed with brine, dried over magnesium sulfate and concentrated in vacuum. The residue was purified by column chromatography (silica 60, hexane/ethyl acetate 5:1, R_f=0.10) to afford 4.24 g of the title compound of the formula

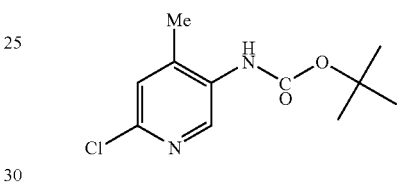

as a yellow solid.

¹H-NMR (CDCl₃, TMS) δ (ppm): 1.52 (9H, s), 2.26 (3H, s), 6.21 (1H, s), 7.13 (1H, s), 8.69 (1H, s).

Step 3: Preparation of (6-chloro-4-methyl-1-oxy-pyridin-3-yl)-carbamic acid tert-butyl ester (6-Chloro-4-methyl-pyridin-3-yl)-carbamic acid tert-butyl ester (4.24 g) was dissolved in chloroform (40 mL), 3-chloroperoxybenzoic acid (5.87 g, 77%) was added and the solution was stirred at room temperature for 21 h. A second portion of 3-chloroperoxybenzoic acid (1.17 g) was added and the reaction mixture was stirred for 5 h at room temperature. Chloroform was added until complete dissolution of the solids and the organic phase was washed with 2N sodium hydroxide solution. The aqueous washing was 1× re-extracted with chloroform and the combined organic layer was washed again with 2N sodium hydroxide solution, water, brine, dried over magnesium sulfate and concentrated in vacuum to afford 4.40 g of the title compound of the formula

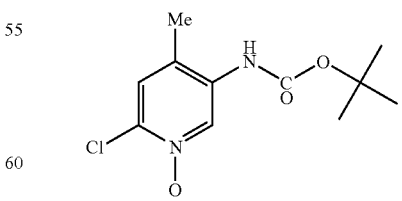

as a white solid. The crude product was used without further purification in the next step.

¹H-NMR (CDCl₃, TMS) δ (ppm): 1.52 (9H, s), 2.24 (3H, s), 6.24 (1H, s), 7.22 (1H, s), 9.13 (1H, s).

Step 4: Preparation of (6-chloro-2-cyano-4-methyl-pyridin-3-yl)-carbamic acid tert-butyl ester (6-Chloro-4-methyl-1-oxy-pyridin-3-yl)-carbamic acid tert-butyl ester (4.40 g) was suspended in dry acetonitrile (50 mL), trimethylsilyl cyanide (7.2 mL) and triethyl amine (5.37 mL) were added and the reaction mixture was stirred under reflux for 2 h. After standing for 15 h at room temperature, trimethylsilyl cyanide (4.4 mL) and triethyl amine (3.65 mL) were added and the reaction mixture was stirred for another 4 h at reflux. Water and 2N sodium hydroxide solution were added after cooling to room temperature and the mixture was 3× extracted with ethyl acetate. The combined organic layer was washed with brine, dried over magnesium sulfate and concentrated in vacuum. The residue was purified by column chromatography (silica 60, hexane/ethyl acetate=5:1, then 4:1, $R_f$=0.20 in hexane/ethyl acetate=4:1) to afford 3.72 g of the title compound of the formula

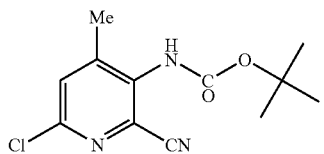

as a yellow solid.
$^1$H-NMR (CDCl$_3$, TMS) δ (ppm): 1.52 (9H, s), 2.36 (3H, s), 6.43 (1H, s), 7.42 (1H, s).

Step 5: Preparation of 3-amino-6-chloro-4-methyl-pyridine-2-carboxylic acid (6-Chloro-2-cyano-4-methyl-pyridin-3-yl)-carbamic acid tert-butyl ester (3.72 g) was dissolved in concentrated sulfuric acid (19 mL) and stirred for 1 h at 100° C. The reaction mixture was cooled to room temperature and water (19 mL) was slowly added. The reaction mixture was warmed again to 100° C. and stirred at this temperature for 2 h. Water was added after cooling to room temperature, the mixture was cooled in an ice bath and the pH was adjusted to ~14 by slow addition of solid sodium hydroxide. The aqueous solution was washed 2× with MTB-ether, the aqueous layer was then adjusted to pH ~2 by addition of 5 M hydrochloric acid and extracted 3× with ethyl acetate. The combined organic layer was washed with brine, dried over magnesium sulfate and concentrated in vacuum to afford 2.25 g of the title compound of the formula

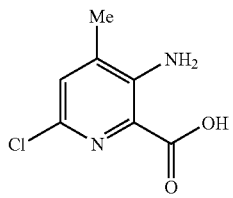

as a beige solid.
$^1$H-NMR (CDCl$_3$, TMS) δ (ppm): 2.24 (3H, s), 5.96 (2H, s), 7.20 (1H, s), 10.69 (1H, br s).

Step 6: Preparation of 2-[5-bromo-2-(3-chloro-pyridin-2-yl)-2H-pyrazol-3-yl]-6-chloro-8-methyl-pyrido[3,2-d][1,3]oxazin-4-one 5-Bromo-2-(3-chloro-pyridin-2-yl)-2H-pyrazole-3-carboxylic acid (example 1, step 5) (3.65 g) was suspended in dry toluene (50 mL), oxalyl chloride (3.10 mL) and 10 drops of dry DMF were added (gas evolution) and the reaction mixture was stirred for 1 h at room temperature. The mixture was concentrated in vacuum and excess oxalyl chloride was removed by co-evaporation with dry toluene (3×). The residue was dissolved in dry acetonitrile (20 mL) and added to a suspension of 3-amino-6-chloro-4-methyl-pyridine-2-carboxylic acid (2.25 g) in acetonitrile (30 mL). Triethylamine (1.7 mL)) was added and the reaction mixture was stirred for 20 minutes, before a second portion of triethylamine (3.4 mL) was added. After the mixture was stirred for further 50 minutes at room temperature, methanesulfonyl chloride (1.03 mL) was added. After stirring for 18 hours at room temperature, the reaction mixture was concentrated to ~25 mL and water (20 mL) was added. The precipitate was filtered off, washed with water/acetonitrile (1:2), acetonitrile and diethyl ether and dried in vacuum to afford 3.97 g of the title compound of the formula

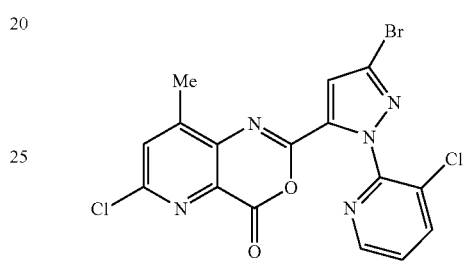

as a yellow solid.
$^1$H-NMR (CDCl$_3$, TMS) δ (ppm): 1.89 (3H, d), 7.29 (1H, s), 7.47 (1H, s), 7.50 (1H, dd, J=8 Hz, 5 Hz), 7.98 (1H, dd, J=8 Hz, 2 Hz), 8.56 (1H, dd, J=5 Hz, 2 Hz).

Step 7: Preparation of (N'-(3-{[5-bromo-2-(3-chloro-pyridin-2-yl)-2H-pyrazole-3-carbonyl]-amino}-6-chloro-4-methyl-pyridine-2-carbonyl)-hydrazinecarboxylic acid methyl ester (7)

2-[5-Bromo-2-(3-chloro-pyridin-2-yl)-2H-pyrazol-3-yl]-6-chloro-8-methyl-pyrido[3,2-d][1,3]oxazin-4-one (500 mg) was dissolved in DMF (28 mL) acarbazaic acid methyl ester (994 mg) was added. The solution was stirred for 3.5 h at room temperature before it was quenched with water. The mixture was 2× extracted with ethyl acetate, the combined organic layer was 3× washed with water, washed with brine, dried over magnesium sulfate and concentrated in vacuum. The residue was purified by column chromatography (silica 60, chloroform/ethyl acetate=3:1, $R_f$=0.25) to afford 541 mg of the compound (7) of the present invention of the formula (7)

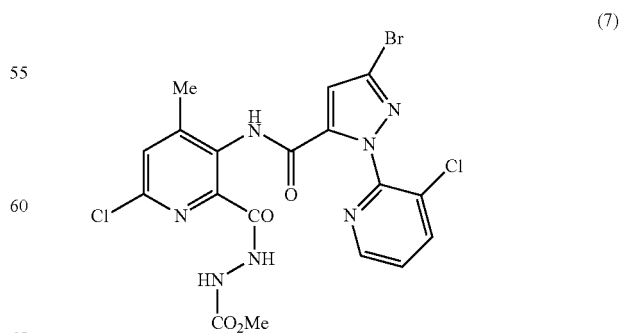

as a white solid.

$^1$H-NMR (DMSO-D$_6$) δ (ppm): 2.19 (3H, s), 3.50-3.61 (3H, br m), 7.42 (1H, s), 7.62 (1H, dd, J=8 Hz, 5 Hz), 7.73 (1H, s), 8.18 (1H, dd, J=8 Hz, 2 Hz), 8.50 (1H, dd, J=5 Hz, 2 Hz), 9.27 (1H, br s), 10.41 (1H, s), 10.56 (1H, s).

Example 8

Preparation of N'-(3-{[5-bromo-2-(3-chloro-pyridin-2-yl)-2H-pyrazole-3-carbonyl]-amino}-6-chloro-4-methyl-pyridine-2-carbonyl)-N-methyl-hydrazinecarboxylic acid methyl ester (8)

Step 1: Preparation of N-methyl-hydrazine-carboxylic acid methyl ester

Monomethylhydrazine (10.6 mL) was dissolved in methanol (50 mL) and sodium hydroxide (8.0 g) was added. The suspension was cooled with an ice bath and methyl chloroformate (15.4 mL) was added drop wise (violent reaction!), the ice bath was removed and the suspension was stirred for 1 hour at room temperature. The white precipitate was filtered off, washed with methanol and the filtrate was concentrated in vacuum. The residue was purified by distillation (50-80° C./15 mmHg) to afford 13.4 g of the title compound of the formula

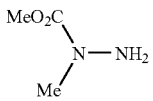

as a colorless oil.
$^1$H-NMR (CDCl$_3$, TMS) δ (ppm): 3.11 (3H, s), 3.73 (3H, s), 4.13 (2H, br s).

Step 2: Preparation of N'-(3-{[5-bromo-2-(3-chloro-pyridin-2-yl)-2H-pyrazole-3-carbonyl]-amino}-6-chloro-4-methyl-pyridine-2-carbonyl)-N-methyl-hydrazinecarboxylic acid methyl ester (8)

2-[5-Bromo-2-(3-chloro-pyridin-2-yl)-2H-pyrazol-3-yl]-6-chloro-8-methyl-pyrido[3,2-d][1,3]oxazin-4-one (140 mg) (example 7, step 4) was dissolved in DMF (10 mL) and N-methyl-hydrazinecarboxylic acid methyl ester (161 mg) was added. The solution was stirred for 3 hours at 80° C., then 12 hours at room temperature and again for 3.5 hours at 80° C. The reaction mixture was quenched was diluted with MTB-ether and washed 4× with water, washed with brine, dried over MgSO$_4$ and concentrated in vacuum. The residue was purified by column chromatography (hexane/ethyl acetate=2:1, then 1.5:1, R$_f$=0.15 in hexane/ethyl acetate=2:1) to afford 112 mg of compound 8 of the present invention of the formula (8)

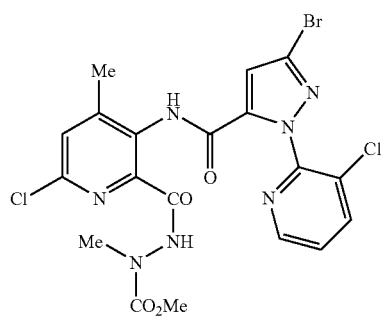

as a white solid.

$^1$H-NMR (CDCl$_3$, TMS) δ (ppm): 2.26 (3H, s), 3.28 (3H, s), 3.77 (3H, br s), 7.11 (1H, s), 7.35 (1H, s), 7.39 (1H, dd, J=8 Hz, 5 Hz), 7.86 (1H, dd, J=8 Hz, 2 Hz), 8.47 (1H, dd, J=5 Hz, 2 Hz), 9.58 (1H, s), 11.06 (1H, s).

Example 9

Preparation of N'-(3-{[5-bromo-2-(3-chloro-pyridin-2-yl)-2H-pyrazole-3-carbonyl]-amino}-6-chloro-4-methyl-pyridine-2-carbonyl)-N,N'-dimethyl-hydrazinecarboxylic acid methyl ester (9)

Step 1: Preparation of 5-bromo-2-(3-chloro-pyridin-2-yl)-2H-pyrazole-3-carboxylic acid[6-chloro-2-(N,N'-dimethyl-hydrazinocarbonyl)-4-methyl-pyridin-3-yl]-amide 1,2-Dimethylhydrazine dihydrochloride (176 mg) and potassium carbonate (366 mg) were suspended in THF (8 mL) and 10 drops of water, 2-[5-bromo-2-(3-chloro-pyridin-2-yl)-2H-pyrazol-3-yl]-6-chloro-8-methyl-pyrido[3,2-d][1,3]oxazin-4-one (example 7, step 4) (300 mg) was added and the reaction mixture was stirred for 20 h at room temperature. Water and ethyl acetate were added, the layers were separated and the aqueous layer was 2× extracted with ethyl acetate. The combined organic layer was washed with brine, dried over magnesium sulfate and concentrated in vacuum. The residue was purified by column chromatography (silica 60, chloroform/ethyl acetate=1:1, R$_f$=0.13) to afford 300 mg of the title compound of the formula

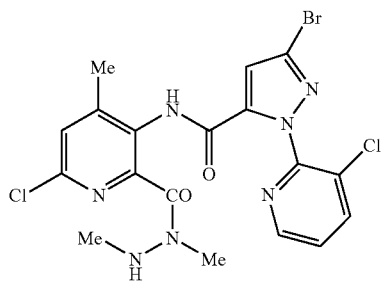

as a white solid.
$^1$H-NMR (CDCl$_3$, TMS) δ (ppm): 2.10 (1.5H, s), 2.13 (1.5H, s), 2.43 (1.5H, s), 2.66 (1.5H, s), 3.00 (1.5H, s), 3.23 (1.5H, s), 3.97 (0.5H, br s), 5.52 (0.5H, br s), 7.04 (0.5H, s), 7.11 (0.5H, s), 7.26 (0.5H, s), 7.32 (0.5H, s), 7.35-7.40 (1.0H, m), 7.82-7.87 (1.0H, m), 8.43-8.47 (1.0H, m), 10.07 (0.5H, s), 10.16 (0.5H, s).

Step 2: Preparation of N'-(3-{[5-bromo-2-(3-chloro-pyridin-2-yl)-2H-pyrazole-3-carbonyl]-amino}-6-chloro-4-methyl-pyridine-2-carbonyl)-N,N'-dimethyl-hydrazinecarboxylic acid methyl ester 5-Bromo-2-(3-chloro-pyridin-2-yl)-2H-pyrazole-3-carboxylic acid [6-chloro-2-(N,N'-dimethyl-hydrazinocarbonyl)-4-methyl-pyridin-3-yl]-amide (250 mg) was dissolved in pyridine (3 mL), methyl chloroformate (150 µL) was added and the reaction mixture was stirred at room temperature. After 30 min, 1 h and 1.5 h, methyl chloroformate (each 75 µL) was added. After 1 h stirring at room temperature, the reaction mixture was quenched with water and 3× co-evaporated with toluene. The residue was dissolved in water and ethyl acetate, the layers were separated and the aqueous layer was extracted 2× with ethyl acetate. The combined organic layer was washed with brine, dried over magnesium sulfate and concentrated in vacuum. The residue was purified by column chromatography (silica 60, hexane/ethyl acetate=1:1, $R_f$=0.20) to afford 223 mg of compound (9) of the present invention of the formula

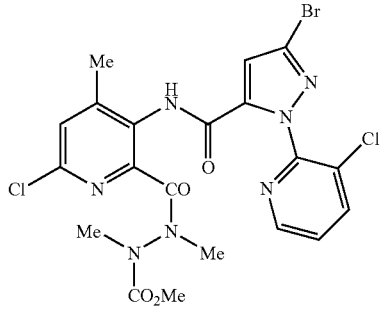

(9)

as a white solid.

$^1$H-NMR (DMSO-D$_6$) δ (ppm): 2.17 (1.5H, s), 2.24 (1.5H, s), 2.77 (1.5H, s), 2.84-2.85 (1.5H, m), 2.91-2.93 (1.5H, m), 3.09 (1.5H, s), 3.49 (2.5H, s), 3.69 (0.5H, s), 7.35-7.39 (1.0H, m), 7.61-7.68 (2.0H, m), 8.19-8.22 (1.0H, m), 8.49-8.52 (1.0H, m), 10.51-10.65 (1.0H, br m).

Example 10

Preparation of N'-(3-{[5-bromo-2-(3-chloro-pyridin-2-yl)-2H-pyrazole-3-carbonyl]-amino}-6-chloro-4-methyl-pyridine-2-carbonyl)-N-ethyl-hydrazinecarboxylic acid methyl ester (10) and N'-(3-{[5-bromo-2-(3-chloro-pyridin-2-yl)-2H-pyrazole-3-carbonyl]-amino}-6-chloro-4-methyl-pyridine-2-carbonyl)-N'-ethyl-hydrazine carboxylic acid methyl ester (11)

Step 1: Preparation of 5-bromo-2-(3-chloro-pyridin-2-yl)-2H-pyrazole-3-carboxylic acid [6-chloro-2-(N'-ethyl-hydrazine carbonyl)-4-methyl-pyridin-3-yl]-amide (10-a) and 5-bromo-2-(3-chloro-pyridin-2-yl)-2H-pyrazole-3-carboxylic acid [6-chloro-2-(N-ethyl-hydrazinocarbonyl)-4-methyl-pyridin-3-yl]-amide (11-a)

2-[5-Bromo-2-(3-chloro-pyridin-2-yl)-2H-pyrazol-3-yl]-6-chloro-8-methyl-pyrido[3,2-d][1,3]oxazin-4-one (example 7, step 4) (600 mg) was suspended in THF (16 mL), and ethyl hydrazine oxalate (398 mg) and potassium carbonate (732 mg) were added and the reaction mixture was stirred for 19 h at room temperature. Water and ethyl acetate were added and the layers were separated. The aqueous layer was 1× extracted with ethyl acetate, the combined organic layer were washed with brine, dried over magnesium sulfate and concentrated in vacuum. The residue was purified by column chromatography (silica 60, chloroform/ethyl acetate 5:1, then 3:1, then 1:1, $R_f$(10-a)=0.45, $R_f$(11-a)=0.15 in chloroform/ethyl acetate=1:1) to afford 380 mg of the title compound (10-a) of the formula

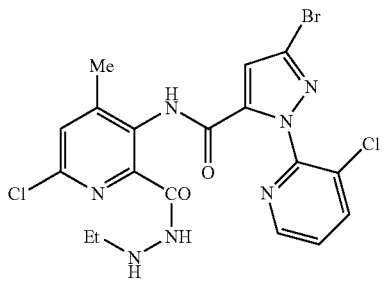

(10-a)

as a white solid, and 228 mg of the title compound (11-a) of the formula

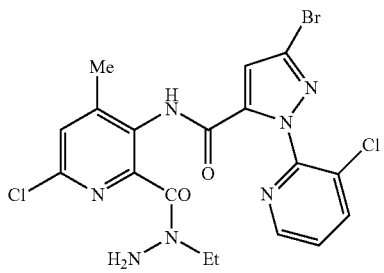

(11-a)

as a white solid.

(10-a): $^1$H-NMR (CDCl$_3$, TMS) δ (ppm): 1.18 (3H, t, J=7 Hz), 2.25 (3H, s), 2.99 (2H, q, J=7 Hz), 4.69 (1H, br s), 7.13 (1H, s), 7.29 (1H, s), 7.39 (1H, dd, J=8 Hz, 5 Hz), 7.86 (1H, dd, J=8 Hz, 2 Hz), 8.48 (1H, dd, J=5 Hz, 2 Hz), 9.18 (1H, br s), 11.45 (1H, s).

(11-a): $^1$H-NMR (CDCl$_3$, TMS) δ (ppm): 1.09-1.19 (3.0H, m), 2.08 (1.7H, s), 2.11 (1.3H, s), 3.28 (0.8H, q, J=7 Hz), 3.63 (1.2H, q, J=7 Hz), 4.16 (1.2H, s), 4.45 (0.8H, s), 7.01 (0.6H, s), 7.09 (0.4H, s), 7.31-7.33 (1.0H, m), 7.35-7.41 (1.0H, m), 7.83-7.88 (1.0H, m), 8.43-8.48 (1.0H, m), 10.24 (0.4H, s), 10.56 (0.6H, s).

Step 2: Preparation of N'-(3-{[5-bromo-2-(3-chloro-pyridin-2-yl)-2H-pyrazole-3-carbonyl]-amino}-6-chloro-4-methyl-pyridine-2-carbonyl)-N-ethyl-hydrazinecarboxylic acid methyl ester (10)

5-Bromo-2-(3-chloro-pyridin-2-yl)-2H-pyrazole-3-carboxylic acid [6-chloro-2-(N'-ethyl-hydrazinocarbonyl)-4-methyl-pyridin-3-yl]-amide (10-a) (320 mg) was dissolved in pyridine (4 mL), methyl chloroformate (190 µL) was added and the reaction mixture was stirred at room temperature. After 30 min, 1 h and 1.5 h, methyl chloroformate (each 95 µL) was added. After 1 h stirring at room temperature, the reaction mixture was quenched with water and 3× co-evaporated with toluene. The residue was dissolved in water and ethyl acetate, the layers were separated and the aqueous layer was extracted 2× with ethyl acetate. The combined organic layer was washed with brine, dried over magnesium sulfate and concentrated in vacuum. The residue was purified by column chromatography (silica 60, hexane/ethyl acetate=2:1, $R_f$=0.10) to afford 308 mg of the title compound (10) of the present invention of the formula

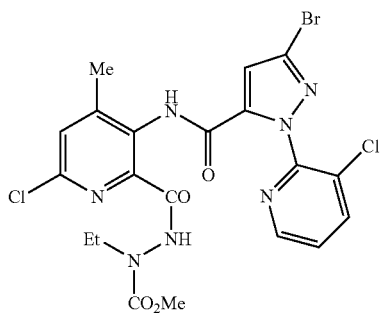

(10)

as a white solid.

¹H-NMR (CDCl₃, TMS) δ (ppm): 1.22 (3H, t, J=7 Hz), 2.26 (3H, s), 3.69 (2H, q, J=7 Hz), 3.76 (3H, s), 7.10 (1H, s), 7.35 (1H, s), 7.39 (1H, dd, J=8 Hz, 5 Hz), 7.86 (1H, dd, J=8 Hz, 2 Hz), 8.48 (1H, dd, J=5 Hz, 2 Hz), 9.52 (1H, s), 11.09 (1H, s).

Step 3: Preparation of N'-(3-{[5-bromo-2-(3-chloro-pyridin-2-yl)-2H-pyrazole-3-carbonyl]-amino}-6-chloro-4-methyl-pyridine-2-carbonyl)-N'-ethyl-hydrazine carboxylic acid methyl ester (11)

5-Bromo-2-(3-chloro-pyridin-2-yl)-2H-pyrazole-3-carboxylic acid [6-chloro-2-(N-ethyl-hydrazinocarbonyl)-4-methyl-pyridin-3-yl]-amide (11-a) (177 mg) was dissolved in pyridine (2 mL), methyl chloroformate (100 μL) was added and the reaction mixture was stirred at room temperature. After 30 min, 1 h and 1.5 h, methyl chloroformate (each 50 μL) was added. After 14 h stirring at room temperature, the reaction mixture was quenched with water and 3× co-evaporated with toluene. The residue was dissolved in water and ethyl acetate, the layers were separated and the aqueous layer was extracted 2× with ethyl acetate. The combined organic layer was washed with brine, dried over magnesium sulfate and concentrated in vacuum. The residue was purified by column chromatography (silica 60, chloroform/ethyl acetate=3:1, R_f=0.10) to afford 135 mg of the title compound (11) of the present invention of the formula

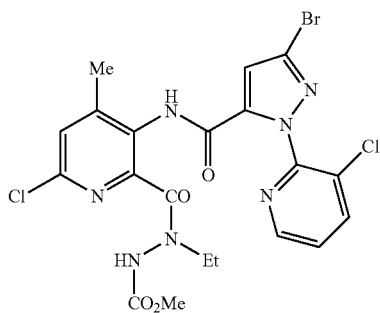

(11)

as a white solid.

¹H-NMR (CDCl₃, TMS) δ (ppm): 1.14-1.27 (3H, m), 2.17 (3H, s), 3.62-3.80 (5H, m), 7.12 (2H, s), 7.20-7.22 (1H, m), 7.39 (1H, dd, J=8 Hz, 5 Hz), 7.87 (1H, dd, J=8 Hz), 8.46 (1H, d, J=5 Hz), 9.53 (1H, br s).

Example 11

Preparation of N'-(3-{[5-bromo-2-(3-chloro-pyridin-2-yl)-2H-pyrazole-3-carbonyl]-amino}-6-chloro-4-methyl-pyridine-2-carbonyl)-N-isopropyl-hydrazine carboxylic acid methyl ester (12) and N'-(3-{[5-bromo-2-(3-chloro-pyridin-2-yl)-2H-pyrazole-3-carbonyl]-amino}-6-chloro-4-methyl-pyridine-2-carbonyl)-N'-isopropyl-hydrazinecarboxylic acid methyl ester (13)

Step 1: Preparation of 5-bromo-2-(3-chloro-pyridin-2-yl)-2H-pyrazole-3-carboxylic acid [6-chloro-2-(N'-isopropyl-hydrazinocarbonyl)-4-methyl-pyridin-3-yl]-amide (12-a) and 5-bromo-2-(3-chloro-pyridin-2-yl)-2H-pyrazole-3-carboxylic acid [6-chloro-2-(N-isopropyl-hydrazinocarbonyl)-4-methyl-pyridin-3-yl]-amide (13-a)

2-[5-Bromo-2-(3-chloro-pyridin-2-yl)-2H-pyrazol-3-yl]-6-chloro-8-methyl-pyrido[3,2-d][1,3]oxazin-4-one (example 7, step 4) (600 mg) was suspended in THF (16 mL), isopropyl hydrazine (294 mg) was added and the reaction mixture was stirred for 19 h at room temperature. Water and ethyl acetate were added and the layers were separated. The aqueous layer was 1× extracted with ethyl acetate. The combined organic layers were washed with brine, dried over magnesium sulfate and concentrated in vacuum. The residue was purified by column chromatography (silica 60, hexane/ethyl acetate 2:1, then 1:1, R_f(12-a)=0.35, R_f(13-a)=0.15 in hexane/ethyl acetate=1:1) to afford 478 mg of the title compound (12-a) of the formula

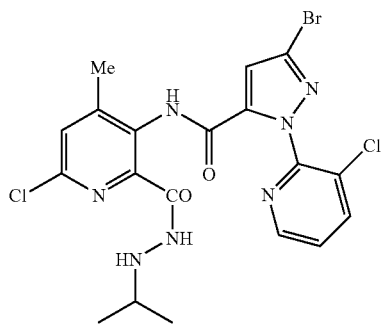

(12-a)

as a white solid, and 121 mg of the title compound (13-a) of the formula

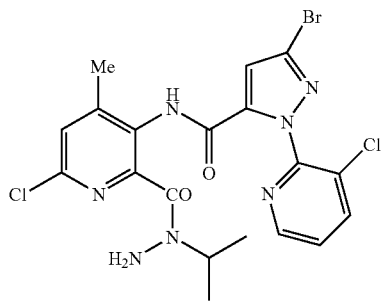

(13-a)

as a white solid.

(12-a) $^1$H-NMR (CDCl$_3$, TMS) δ (ppm): 1.14 (6H, d, J=6 Hz), 2.25 (3H, s), 3.17-3.23 (1H, m), 4.63 (1H, s), 7.12 (1H, s), 7.29 (1H, s), 7.37-7.41 (1H, m), 7.84-7.87 (1H, m), 8.46-8.48 (1H, m), 9.15 (1H, s), 11.46 (1H, s).

(13-a) $^1$H-NMR (CDCl$_3$, TMS) δ (ppm): 1.09 (3.0H, d, J=7 Hz), 1.12 (3.0H, d, J=7 Hz), 2.08 (1.5H, s), 2.11 (1.5H, s), 3.75-3.80 (0.5H, m), 3.80-4.16 (2.0H, br m), 4.69-4.75 (0.5H, m), 7.02 (0.5H, s), 7.09 (0.5H, s), 7.29 (0.5H, s), 7.31 (0.5H, s), 7.34-7.39 (1.0H, m), 7.82-7.86 (1.0H, m), 8.41-8.46 (1.0H, m), 10.12 (0.5H, s), 10.42 (0.5H, s).

Step 2: Preparation of N'-(3-{[5-bromo-2-(3-chloro-pyridin-2-yl)-2H-pyrazole-3-carbonyl]-amino}-6-chloro-4-methyl-pyridine-2-carbonyl)-N-isopropyl-hydrazine carboxylic acid methyl ester (12)

5-Bromo-2-(3-chloro-pyridin-2-yl)-2H-pyrazole-3-carboxylic acid [6-chloro-2-(N'-isopropyl-hydrazinocarbonyl)-4-methyl-pyridin-3-yl]-amide (12-a) (378 mg) was dissolved in pyridine (5 mL), methyl chloroformate (220 µL) was added and the reaction mixture was stirred at room temperature. After 30 min, 1 h and 1.5 h, methyl chloroformate (each 110 µL) was added. After 18 h stirring at room temperature, the reaction mixture was quenched with water and 3× co-evaporated with toluene. The residue was dissolved in water and ethyl acetate, the layers were separated and the aqueous layer was extracted 2× with ethyl acetate. The combined organic layer was washed with brine, dried over magnesium sulfate and concentrated in vacuum. The residue was purified by column chromatography (silica 60, chloroform/ethyl acetate=10:1, R$_f$=0.13) to afford 382 mg of the title compound (12) of the present invention of the formula

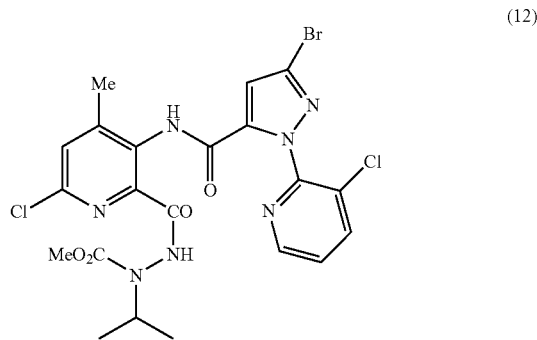

(12)

as a white solid.

$^1$H-NMR (CDCl$_3$, TMS) δ (ppm): 1.20 (6H, d, J=7 Hz), 2.26 (3H, s), 3.75 (3H, s), 4.54-4.60 (1H, m), 7.09 (1H, s), 7.36 (1H, s), 7.39 (1H, dd, J=8 Hz, 5 Hz), 7.85 (1H, dd, J=8 Hz, 2 Hz), 8.48 (1H, dd, J=5 Hz, 2 Hz), 9.28 (1H, s), 11.12 (1H, s).

Step 3: N'-(3-{[5-bromo-2-(3-chloro-pyridin-2-yl)-2H-pyrazole-3-carbonyl]-amino}-6-chloro-4-methyl-pyridine-2-carbonyl)-N'-isopropyl-hydrazinecarboxylic acid methyl ester (13)

5-Bromo-2-(3-chloro-pyridin-2-yl)-2H-pyrazole-3-carboxylic acid [6-chloro-2-(N-isopropyl-hydrazinocarbonyl)-4-methyl-pyridin-3-yl]-amide (13-a) (121 mg) was dissolved in pyridine (2 mL), methyl chloroformate (70 µL) was added and the reaction mixture was stirred at 50° C. After 1 h, methyl chloroformate (each 40 µL) was added 8× in a time interval of 30 min at 50° C. After 10 h stirring at room temperature, the reaction mixture was quenched with water and 3× co-evaporated with toluene. The residue was dissolved in water and ethyl acetate, the layers were separated and the aqueous layer was extracted 2× with ethyl acetate. The combined organic layer was washed with brine, dried over magnesium sulfate and concentrated in vacuum. The residue was purified by column chromatography (silica 60, chloroform/ethyl acetate=3:1, R$_f$=0.15) to afford 67 mg of the title compound (13) of the present invention of the formula

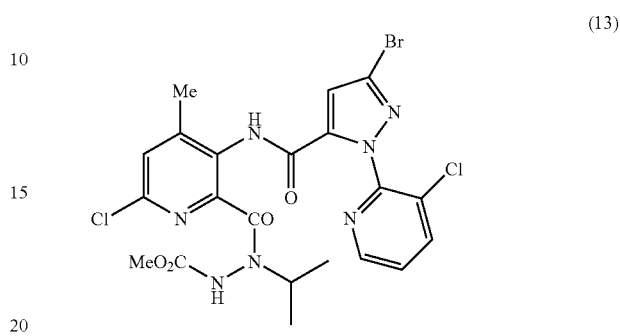

(13)

as a white solid.

$^1$H-NMR (CDCl$_3$, TMS) δ (ppm): 1.00-1.30 (6H, m), 2.14 (3H, s), 3.57-3.81 (3H, br m), 4.62-4.79 (1H, m), 6.96-7.18 (3H, m), 7.39 (1H, dd, J=8 Hz, 5 Hz), 7.86 (1H, dd, J=8 Hz), 8.45 (1H, d, J=5 Hz), 9.66-9.86 (1H, m).

Example 12

Preparation of N''-(3-{[5-bromo-2-(3-chloro-pyridin-2-yl)-2H-pyrazole-3-carbonyl]-amino}-4,6-dichloro-pyridine-2-carbonyl)-hydrazinecarboxylic acid methyl ester (14)

Step 1: Preparation of 2-chloro-pyridin-3-ylamine

3-Aminopyridine (25.0 g) was dissolved in concentrated hydrochloric acid (250 mL, 37%) at 30 to 35° C. and cooled in an ice bath after complete dissolution of the starting material. Hydrogen peroxide (28.5 mL, 30% aqueous solution) was added slowly with a dropping funnel to the solution in a rate that the temperature was kept below 10° C. over a period of 30 min. The orange solution was slowly warmed up to room temperature over a time period of 2 h and stirred at room temperature for another 2 h. The solution was cooled in an ice bath and 160 mL of an aqueous sodium hydroxide solution (50%) were added slowly. The acidic aqueous solution was washed with 30 mL toluene and the organic washing was re-extracted 1× with 5N aqueous hydrochloric acid. Aqueous sodium hydroxide solution (50%) was added to the combined acidic aqueous solution and the pH was adjusted to ~8-10. The aqueous solution was 3× extracted with 200 mL toluene, the combined organic layer was washed with brine, dried over magnesium sulfate and concentrated in vacuum. The residue was purified by column chromatography (silica 60, chloroform/ethyl acetate 20:1, R$_f$=0.25) to afford 17.6 g of the title compound of the formula

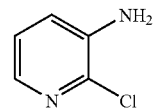

as an orange solid.

$^1$H-NMR (CDCl$_3$, TMS) δ (ppm): 4.12 (2H, br s), 7.04-7.05 (2H, m), 7.78-7.81 (1H, m).

Step 2: Preparation of 3-amino-pyridine-2-carbonitrile

2-Chloro-pyridin-3-ylamine (2.0 g) was dissolved in DMF (24 mL) and zinc cyanide (1.83 g) was added to the solution. The solution was degassed in vacuum 5×, tetrakis(triphenylphosphine) palladium(0) (901 mg) was added and the reaction mixture was stirred at 90° C. for 7 h. After the reaction mixture was cooled to room temperature, the solid was removed by filtration and the filter cake was washed with ethyl acetate. Water was added to the filtrate, the layers were separated and the aqueous layer was 2× extracted with ethyl acetate. The combined organic layer was washed 3× with water, washed with brine, dried over magnesium sulfate and concentrated in vacuum. The residue was purified by column chromatography (silica 60, chloroform/ethyl acetate 3:1, $R_f$=0.25) to afford 755 mg of the title compound of the formula

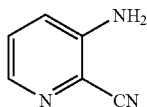

as a white solid.
$^1$H-NMR (CDCl$_3$, TMS) δ (ppm): 4.43 (2H, br s), 7.10 (1H, dd, J=9 Hz, 1 Hz), 7.25-7.29 (1H, m), 8.07 (1H, dd, J=4 Hz, 1 Hz).

Step 3: Preparation of 3-amino-4,6-dichloro-pyridine-2-carbonitrile

3-Amino-pyridine-2-carbonitrile (100 mg) was dissolved in DMF (2 mL) and N-chorosuccinimide (246 mg) was added. The solution was stirred for 20 h at room temperature before water was added. The mixture was 2× extracted with ethyl acetate, the combined organic layer was washed 3× with water, washed with brine, dried over magnesium sulfate and concentrated in vacuum. The residue was purified by column chromatography (silica 60, hexane/ethyl acetate=3:1, $R_f$=0.30) to afford 121 mg of the title compound of the formula

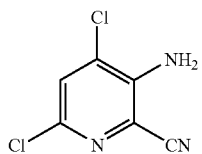

as an orange solid.
$^1$H-NMR (CDCl$_3$, TMS) δ (ppm): 4.92 (2H, br s), 7.44 (1H, s).

Step 4: Preparation of 3-amino-4,6-dichloro-pyridine-2-carboxylic acid

3-Amino-4,6-dichloro-pyridine-2-carbonitrile (121 mg) was dissolved in concentrated sulfuric acid (1 mL) and stirred for 1 h at 100° C. The reaction mixture was cooled to room temperature and water (1 mL) was slowly added. The reaction mixture was warmed again to 100° C. and stirred at this temperature for 2 h. Water was added after cooling to room temperature, the pH was adjusted to ~10 by addition of solid sodium bicarbonate and the aqueous solution was washed 2× with MTB-ether. The aqueous layer was then adjusted to pH ~2 by addition of 2 M hydrochloric acid and extracted 3× with ethyl acetate. The combined organic layer was washed with brine, dried over magnesium sulfate and concentrated in vacuum to afford 99 mg of the title compound of the formula

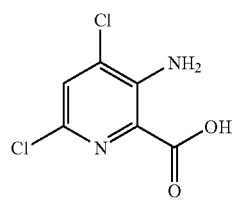

as a yellow solid.
$^1$H-NMR (CDCl$_3$, TMS) δ (ppm): 6.37 (2H, br s), 7.47 (1H, s), 10.50 (1H, br s).

Step 5: Preparation of N'-(3-{[5-bromo-2-(3-chloro-pyridin-2-yl)-2H-pyrazole-3-carbonyl]-amino}-4,6-dichloro-pyridine-2-carbonyl)-hydrazinecarboxylic acid methyl ester 5-Bromo-2-(3-chloro-pyridin-2-yl)-2H-pyrazole-3-carboxylic acid (example 1, step 5) (142 mg) was suspended in acetonitrile (1 mL) and pyridine (65 μL) and methanesulfonyl chloride (50 μL) were added. The reaction mixture was stirred for 30 min at room temperature, 3-amino-4,6-dichloro-pyridine-2-carboxylic acid (99 mg) in acetonitrile (1 mL) and pyridine (130 μL) were added and the reaction mixture was stirred 1 h at room temperature. Methanesulfonyl chloride (65 μL) was added and the reaction mixture was stirred for 20 h at room temperature. The reaction mixture was concentrated in vacuum, the residue was suspended in DMF (5 mL), carbazaic acid methyl ester (216 mg) was added and the reaction mixture was stirred for 20 h at room temperature. Water was added and the mixture was 2× extracted with MTB-ether. The combined organic layer was washed 3× with water, washed with brine, dried over magnesium sulfate and concentrated in vacuum. The residue was purified by column chromatography (silica 60, hexane/ethyl acetate=2:1, $R_f$=0.15) to afford 37 mg of the compound 14 of the present invention of the formula (14)

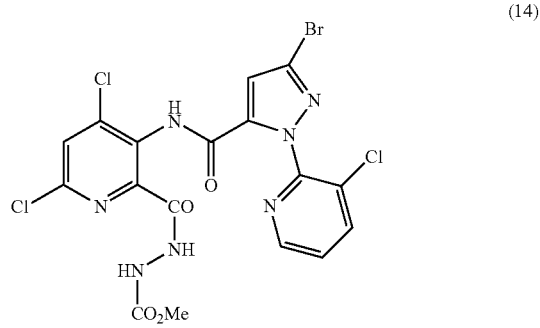

as a white solid.
$^1$H-NMR (CDCl$_3$, TMS) δ (ppm): 3.82 (3H, s), 6.66 (1H, br s), 7.08 (1H, s), 7.39 (1H, dd, J=8 Hz, 5 Hz), 7.57 (1H, s), 7.86 (1H, dd, J=8 Hz, 2 Hz), 8.47 (1H, dd, J=5 Hz, 2 Hz), 9.40 (1H, s), 10.71 (1H, s).

Example 13

Preparation of N'-(4-bromo-3-{[5-bromo-2-(3-chloro-pyridin-2-yl)-2H-pyrazole-3-carbonyl]-amino}-6-chloro-pyridine-2-carbonyl)-hydrazine carboxylic acid methyl ester (15)

Step 1: Preparation of 3-amino-6-chloro-2-iodopyridine

5-Amino-2-chloropyridine (3.0 g) was dissolved in DMF (40 mL), N-iodosuccinimide (5.25 g) was added and the reaction mixture was stirred at room temperature for 3 hours. Water and MTB-ether were added to the reaction mixture, the layers were separated and the organic layer was washed 3× with water, washed with brine, dried over $MgSO_4$ and concentrated in vacuum. The residue was purified by column chromatography (silica 60, hexane/ethyl acetate=3:1, $R_f$=0.30) to afford 4.80 g of the title compound of the formula

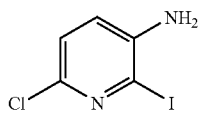

as an orange solid.
$^1$H-NMR (CDCl$_3$, TMS) δ (ppm): 4.13 (2H, br s), 6.89 (1H, d, J=8 Hz), 7.05 (1H, d, J=8 Hz).

Step 2: Preparation of 3-amino-6-chloro-2-(2-furanyl)pyridine

3-Amino-6-chloro-2-iodopyridine (1.78 g), 2-furanboronic acid (1.17 g), and sodium carbonate (1.11 g) were suspended in a solvent mixture consistent of toluene (23 mL), THF (23 mL) and water (7 mL). The mixture was degassed using subsequent evaporation and flushing with nitrogen (5×) and tetrakis(triphenylphosphine)palladium(0) (808 mg) was added. The reaction mixture was stirred at 90° C. for 7 hours and 14 hours at room temperature. After addition of 2-furanboronic acid (783 mg), the mixture was stirred again for 4 hours at 90° C., then another portion of 2-furanboronic acid (390 mg) was added and the reaction mixture was stirred for 5.5 hours at 90° C. After 15 hours stirring at room temperature, the reaction mixture was quenched with water and extracted 2× with ethyl acetate. The combined organic layer was washed with brine, dried over $MgSO_4$ and concentrated in vacuum. The residue was purified by column chromatography (silica 60, hexane/ethyl acetate=3:1, $R_f$=0.25) to afford 1.26 mg of the title compound of the formula

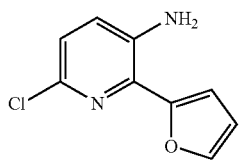

as a beige solid. The compound contained ~10% 3-amino-6-chloro-2-iodopyridine and was used without further purification in the next step.
$^1$H-NMR (CDCl$_3$, TMS) δ (ppm): 4.65 (2H, br s), 6.56 (1H, dd, J=4 Hz, 2 Hz), 6.99 (2H, s), 7.08 (1H, d, J=4 Hz), 7.54 (1H, d, J=2 Hz).

Step 3: Preparation of 3-amino-6-chloro-pyridine-2-carboxylic acid

3-Amino-6-chloro-2-(2-furanyl)pyridine (1.06 g) was dissolved in acetone (25 mL) and cooled in an ice bath to 0° C. A solution prepared of potassium permanganate (2.57 g) in water (40 mL) was added drop wise to this solution. After complete addition, the reaction mixture was allowed to warm to room temperature and stirred for hours. The mixture was cooled again to 0° C. and a second portion of potassium permanganate (858 mg) in water (15 mL) was added and the cool bath removed. After stirring for 2 hours, the reaction mixture was filtered through a pad of celite, the filter cake was washed carefully with water, methanol and ethyl acetate and concentrated to approx. 20 mL on a rotary evaporator. 2N Sodium hydroxide solution was added to adjust the pH-value to ~12 and the aqueous layer was washed 2× with MTB-ether. The aqueous layer was adjusted to pH ~2 by addition of 6N hydrochloric acid and extracted 3× with MTB-ether. The combined organic layer was washed with brine, dried over $MgSO_4$ and concentrated in vacuum to afford 636 mg of the title compound of the formula

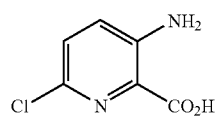

as a brown solid. The compound still contained ~30% of an unknown impurity and was used in the next step without further purification.
$^1$H-NMR (DMSO-D$_6$) δ (ppm): 7.28 (1H, d, J=9 Hz), 7.34 (1H, d, J=9 Hz).

Step 4: Preperation of 3-amino-6-chloro-pyridine-2-carboxylic acid methyl ester 3-Amino-6-chloro-pyridine-2-carboxylic acid (636 mg) was suspended in methanol (8 mL) and toluene (22 mL) was added. A solution of (trimethylsilyl)diazomethane (2.0 M in hexane, 2.4 mL) was added slowly to the reaction mixture. After 1 hour stirring at room temperature, another portion of (trimethylsilyl)diazomethane (550 µl) was added and the mixture was stirred for additional 45 minutes. The reaction mixture was quenched with water and extracted 3× with ethyl acetate. The combined organic layer was washed with 2N hydrochloric acid, saturated bicarbonate solution and brine, dried over $MgSO_4$ and concentrated in vacuum. The residue was purified by column chromatography (silica gel 60, choroform/ethyl acetate=50:1, $R_f$=0.30) to afford 365 mg of the title compound of the formula

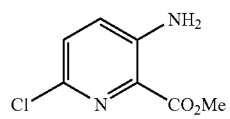

as a yellow solid. The compound still contained ~30% of an unknown impurity and was used in the next step without further purification.
$^1$H-NMR (CDCl$_3$, TMS) δ (ppm): 3.96 (3H, s), 5.82 (2H, br s), 7.05 (1H, d, J=9 Hz), 7.23 (1H, d, J=9 Hz).

Step 5: Preparation of 3-amino-4-bromo-6-chloro-pyridine-2-carboxylic acid methyl ester 3-Amino-6-chloro-pyridine-2-carboxylic acid methyl ester (365 mg) was dissolved in DMF (10 mL) and N-bomosuccinimide (418 mg) was added. The solution was stirred at 50° C. for 5 hours and diluted with MTB-ether. The organic layer was washed 4× with water, washed with brine, dried over MgSO$_4$ and concentrated in vacuum. The residue was purified by column chromatography (silica 60, hexane/ethyl acetate=5:1, R$_f$=0.25) to afford 169 mg of 3-amino-4-bromo-6-chloro-2-picolinic acid methyl ester

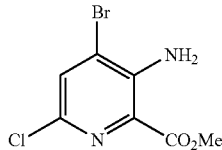

as an orange solid.

$^1$H-NMR (CDCl$_3$, TMS) δ (ppm): 3.97 (3H, s), 6.39 (2H, br s), 7.58 (1H, s).

Step 6: Preparation of 3-amino-4-bromo-6-chloro-pyridine-2-carboxylic acid

3-Amino-4-bromo-6-chloro-pyridine-2-carboxylic acid methyl ester (169 mg) was suspended in methanol (3 mL) and 2N sodium hydroxide solution (2 mL). The suspension was stirred at 50° C. for 3 hours. The precipitate was filtered off and washed carefully with diethyl ether. The precipitate was dissolved in a mixture of 2N hydrochloric acid and ethyl acetate and the layers were separated. The aqueous layer was 2× extracted with ethyl acetate, washed with brine, dried over MgSO$_4$ and concentrated in vacuum to afford 138 mg of the title compound of the formula

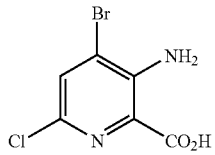

as a white solid.

$^1$H-NMR (CDCl$_3$, TMS) δ (ppm): 6.46 (2H, br s), 7.63 (1H, s), 10.59 (1H, br s).

Step 7: Preparation of 8-bromo-2-[5-bromo-2-(3-chloro-pyridin-2-yl)-2H-pyrazol-3-yl]-6-chloro-pyrido[3,2-d][1,3]oxazin-4-one A mixture of 5-bromo-2-(3-chloro-pyridin-2-yl)-2H-pyrazole-3-carboxylic acid (example 1, step 5) (183 mg) and thionyl chloride (130 μl) was stirred under reflux for 2 hours. Excess thionyl chloride was co-evaporated with dry toluene on a evaporator, the residue re-dissolved in dry acetonitrile (3 mL) and 3-amino-4-bromo-6-chloro-pyridine-2-carboxylic acid (138 mg) was added. The solution was stirred for 15 minutes at room temperature and triethylamine (85 μL) was added and stirred for 30 minutes, before a second portion of triethylamine (170 μL) was added. After the mixture was stirred for further 30 minutes at room temperature, methanesulfonyl chloride (55 μL) was added. After stirring for 21 hours at room temperature, the reaction mixture was quenched by slow addition of water. The precipitate was filtered off, washed with water/acetonitrile (1:2), acetonitrile and diethyl ether and dried in vacuum to afford 141 mg of the title compound of the formula

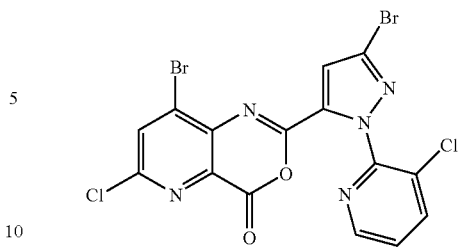

as a yellow solid.

$^1$H-NMR (CDCl$_3$, TMS) δ (ppm): 7.33 (1H, s), 7.48 (1H, dd, J=8 Hz, 5 Hz), 7.88 (1H, s), 7.98 (1H, dd, J=8 Hz, 2 Hz), 8.55 (1H, dd, J=5 Hz, 2 Hz).

Step 8: Preparation of N'-(4-bromo-3-{[5-bromo-2-(3-chloro-pyridin-2-yl)-2H-pyrazole-3-carbonyl]-amino}-6-chloro-pyridine-2-carbonyl)-hydrazine carboxylic acid methyl ester (15)

8-Bromo-2-[5-bromo-2-(3-chloro-pyridin-2-yl)-2H-pyrazol-3-yl]-6-chloro-pyrido[3,2-d][1,3]oxazin-4-one (141 mg) was dissolved in DMF (8 mL) and carbazaic acid methyl ester (243 mg) was added. The solution was stirred for 14 hours at room temperature. The reaction mixture was diluted with MTB-ether and the organic layer was washed 4× with water, brine, dried over MgSO$_4$ and concentrated in vacuum. The residue was purified by column chromatography (silica 60, chloroform/ethyl acetate=3:1, R$_f$=0.20) to afford 120 mg of compound 15 of the present invention of the formula (15)

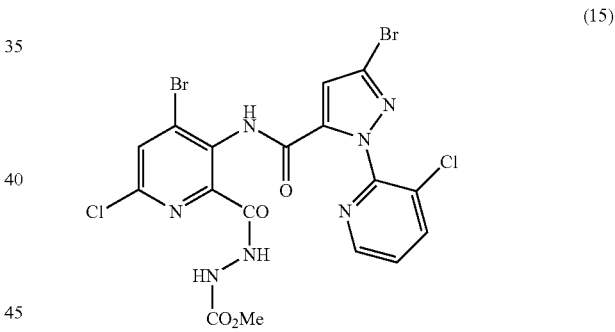

as a white solid.

$^1$H-NMR (DMSO-D$_6$) δ (ppm): 3.46-3.62 (3H, br m), 7.45 (1H, s), 7.61 (1H, dd, J=8 Hz, 5 Hz), 8.16 (1H, dd, J=8 Hz, 2 Hz), 8.28 (1H, s), 8.50 (1H, dd, J=5 Hz, 2 Hz), 9.31 (1H, br s), 10.45 (1H, s), 10.72 (1H, s).

Example 14

Preparation of N'-(4,6-dibromo-3-{[5-bromo-2-(3-chloro-pyridin-2-yl)-2H-pyrazole-3-carbonyl]-amino}-pyridine-2-carbonyl)-N'-ethyl-hydrazinecarboxylic acid methyl ester (16)

Step 1: Preparation of N'-ethylidene-hydrazinecarboxylic acid methyl ester

Carbazaic acid methyl ester (10 g) was suspended in toluene (60 mL) and warmed up to 50° C. for 10 min. The flask was equipped with a dropping funnel, filled with a solution of acetaldehyde (5.86 g) in toluene (20 mL) and the solution was slowly dropped to the suspension within 10 min. The mixture was stirred for 1 h at 50° C., and then cooled to room temperature. The product started crystallizing and cooling in an ice bath completed the crystallizing process. The white crystals were filtered off, washed with small amounts of cold toluene and dried in vacuum to give 12.07 g of the title compound of the formula

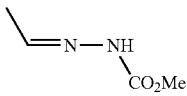

as white crystals (mainly one diastereomer).
$^1$H-NMR (CDCl$_3$, TMS) δ (ppm): 1.99 (3H, d, J=5 Hz), 3.82 (3H, br s), 7.24 (1H, q, J=5 Hz), 8.06-8.56 (1H, br m).

Step 2: Preparation of N'-ethyl-hydrazinecarboxylic acid methyl ester

N'-Ethylidene-hydrazinecarboxylic acid methyl ester (5.0 g) was dissolved in of dry THF (50 mL) and stirred at 50° C. Sodium borohydride (1.95 g) (gas evolution) and dry methanol (4.2 mL) were added. The suspension turned into a solution within 5 to 10 min and the gas evolution ceased within 30 min. The solution was stirred for 3 h at 50° C., before 50 mL dry methanol was added and the solution was stirred under reflux for 2 h. The solvent was removed on an evaporator and the residue was treated with 20 mL of chloroform and stirred for 10 min at 50° C., before it was filtered over a pad of celite and was washed 3× with 30 mL of chloroform. The filtrate was concentrated in vacuum and the residue was purified by column chromatography (silica 60, chloroform/ethyl acetate=3:1; R$_f$=0.20) to afford 3.70 g of the title compound of the formula

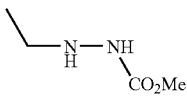

as a colorless oil.
$^1$H-NMR (DMSO-D$_6$) δ (ppm): 0.93 (3H, t, J=7 Hz), 2.66-2.73 (2H, m), 3.54 (3H, s), 4.39-4.42 (1H, m), 8.45 (1H, br s).

Step 3: Preparation of 3-amino-4,6-dibromo-pyridine-2-carbo nitrile

2-Chloro-pyridin-3-ylamine (100 mg) was dissolved in DMF (2 mL) and N-bromosuccinimide (329 mg) was added. The solution was stirred for 26 h at room temperature before water was added. The mixture was 2× extracted with ethyl acetate, the combined organic layer was washed 3× with water, washed with brine, dried over magnesium sulfate and concentrated in vacuum. The residue was purified by column chromatography (silica 60, hexane/ethyl acetate=3:1, R$_f$=0.30) to afford 158 mg of the title compound of the formula

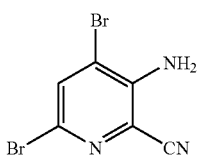

as a beige solid.
$^1$H-NMR (CDCl$_3$, TMS) δ (ppm): 4.93 (2H, s), 7.72 (1H, s).

Step 4: Preparation of 3-amino-4,6-dibromo-pyridine-2-carboxylic acid 3-amino-4,6-dibromo-pyridine-2-carbonitrile (158 mg) was dissolved in concentrated sulfuric acid (1.5 mL) and stirred for 1 h at 100° C. The reaction mixture was cooled to room temperature and water (1.5 mL) was slowly added. The reaction mixture was warmed again to 100° C. and stirred at this temperature for 2 h. Water was added after cooling to room temperature, the pH was adjusted to ~10 by addition of solid sodium bicarbonate and the aqueous solution was washed 2× with MTB-ether. The aqueous layer was then adjusted to pH ~2 by addition of 2 M hydrochloric acid and extracted 3× with ethyl acetate. The combined organic layer was washed with brine, dried over magnesium sulfate and concentrated in vacuum to afford 123 mg of the title compound of the formula

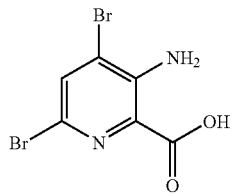

as a yellow solid.
$^1$H-NMR (CDCl$_3$, TMS) δ (ppm): 6.43 (2H, br s), 7.75 (1H, s), 10.53 (1H, br s).

Step 5: Preparation of N'-(4,6-dibromo-3-{[5-bromo-2-(3-chloro-pyridin-2-yl)-2H-pyrazole-3-carbonyl]-amino}-pyridine-2-carbonyl)-N'-ethyl-hydrazinecarboxylic acid methyl ester (16)

5-Bromo-2-(3-chloro-pyridin-2-yl)-2H-pyrazole-3-carboxylic acid (example 1, step 5) (126 mg) was suspended in acetonitrile (1 mL) and pyridine (55 µL) and methanesulfonyl chloride (40 µL) were added. The reaction mixture was stirred for 30 min at room temperature, 3-amino-4,6-dibromo-pyridine-2-carboxylic acid (123 mg) in acetonitrile (1 mL) and pyridine (115 µL) was added and the reaction mixture was stirred 1 h at room temperature. Methanesulfonyl chloride (40 µL) was added and the reaction mixture was stirred for 13 h at room temperature. The reaction mixture was concentrated in vacuum, the residue was suspended in NMP (1 mL), N'-ethyl-hydrazinecarboxylic acid methyl ester (237 mg, step 2) was added and the reaction mixture was stirred for 1 h at 80° C. Water was added after cooling to room temperature and the mixture was 2× extracted with ethyl acetate. The combined organic layer was washed 4× with water, washed with brine, dried over magnesium sulfate and concentrated in vacuum. The residue was purified by column chromatography (silica 60, chloroform/ethyl acetate=10:1, then 5:1, then 3:1, R$_f$=0.25 in chloroform/ethyl acetate=3:1) to afford 90 mg of a white solid. The compound was purified again by column chromatography (silica 60, hexane/ethyl acetate=1:1, R$_f$=0.20) to afford 60 mg of compound 16 of the present invention of the formula (16)

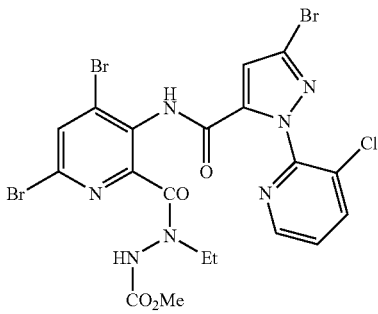

as a white solid.

¹H-NMR (CDCl₃, TMS) δ (ppm): 1.02-1.16 (3.0H, m), 3.67-3.90 (5.0H, m), 6.98 (0.5H, s), 7.18 (1.5H, s), 7.41 (1.0H, dd, J=8 Hz, 5 Hz), 7.68 (1.0H, s), 7.88 (1.0H, dd, J=8 Hz, 2 Hz), 8.47 (1.0H, dd, J=5 Hz, 2 Hz), 9.32-9.53 (1.0H, m).

Example 15

Preparation of N'-(2-{[2-(3-chloro-pyridin-2-yl)-5-trifluoromethyl-2H-pyrazole-3-carbonyl]-amino}-pyridine-3-carbonyl)-hydrazinecarboxylic acid methyl ester (17)

Step 1: Preparation of 2-[2-(3-chloro-pyridin-2-yl)-5-trifluoromethyl-2H-pyrazol-3-yl]-pyrido[2,3-d][1,3]oxazin-4-one 5-Trifluoromethyl-2-(3-chloro-pyridin-2-yl)-2H-pyrazole-3-carboxylic acid chloride (example 2, step 3) (800 mg) was added to a mixture of 2-aminonicotinic acid (356 mg) in acetonitrile (20 mL). The mixture was stirred for 10 minutes at room temperature and triethylamine (360 µL) was added and stirred for 15 minutes, before a second portion of triethylamine (720 µL) was added. After the mixture was stirred for further 15 minutes at room temperature, methanesulfonyl chloride (220 µL) was added. After stirring for 1.5 hours at room temperature, the reaction was quenched with water and extracted 2× with ethyl acetate, washed with brine, dried over MgSO₄ and concentrated in vacuum. The residue was purified by column chromatography (silica 60, chloroform/ethyl acetate=1:1, R_f=0.40) to afford 660 mg of the title compound of the formula

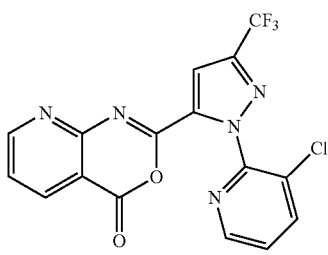

as a beige solid.

¹H-NMR (CDCl₃, TMS) δ (ppm): 7.49 (1H, dd, J=8 Hz, 5 Hz), 7.56 (1H, dd, J=8 Hz, 5 Hz), 7.62 (1H, s), 8.02 (1H, dd, J=8 Hz, 2 Hz), 8.50 (1H, dd, J=8 Hz, 2 Hz), 8.56 (1H, dd, J=5 Hz, 2 Hz), 8.94 (1H, dd, J=5 Hz, 2 Hz).

Step 2: Preparation of N'-(2-{[2-(3-chloro-pyridin-2-yl)-5-trifluoromethyl-2H-pyrazole-3-carbonyl]-amino}-pyridine-3-carbonyl)-hydrazinecarboxylic acid methyl ester (17)

2-[2-(3-Chloro-pyridin-2-yl)-5-trifluoromethyl-2H-pyrazol-3-yl]-pyrido[2,3-d][1,3]oxazin-4-one (292 mg) was dissolved in DMF (18 mL), carbazaic acid methyl ester (667 mg) was added and the solution was stirred for 16 hours at room temperature. The reaction mixture was quenched with water and extracted with MTB-ether. The organic layer was washed 3× with water, washed with brine, dried over MgSO₄ and concentrated in vacuum. The residue was purified by column chromatography (silica 60, chloroform/methanol=20:1, R_f=0.15) to afford 157 mg of compound 17 of the present invention of the formula (17)

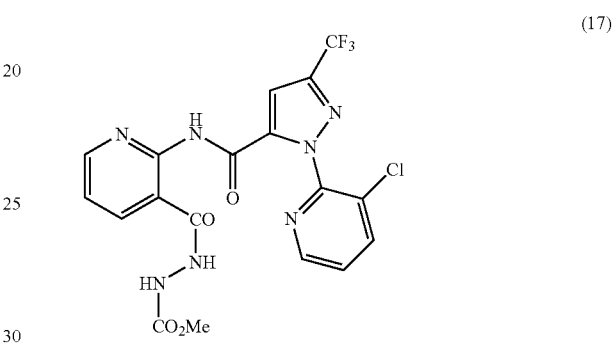

as a white solid.

¹H-NMR (DMSO-D₆) δ (ppm): 3.48-3.64 (3H, br m), 7.38 (1H, br s), 7.67-7.69 (2H, m), 8.07 (1H, br s), 8.24 (1H, dd, J=8 Hz, 1 Hz), 8.52-8.56 (2H, m), 9.31 (1H, br s), 10.43 (1H, br s), 11.48 (1H, br s).

Example 16

Preparation of N'-(3-{[5-bromo-2-(3-chloro-pyridin-2-yl)-2H-pyrazole-3-carbonyl]-amino}-4-methyl-thiophene-2-carbonyl)-hydrazinecarboxylic acid methyl ester (18)

Step 1: Preparation of 2-[5-bromo-2-(3-chloro-pyridin-2-yl)-2H-pyrazol-3-yl]-7-methyl-thieno[3,2-d][1,3]oxazin-4-one A mixture of 3-bromo-1-(3-chloro-2-pyridinyl)-1H-pyrazole-5-carboxylic acid (example 1, step 5) (600 mg) and thionyl chloride (2 ml) was heated to reflux for 2 hours. The reaction mixture was allowed to cool to room temperature and concentrated under reduced pressure. The resulting residue was dissolved in acetonitrile (10 mL) and 3-amino-4-methyl-thiophene-2-carboxylic acid (310 mg) was added. The mixture was stirred at room temperature for 30 minutes. Then, triethylamine (200 mg) was added to the mixture. After stirring the mixture at room temperature for 30 minutes, a second portion of triethylamine (400 mg) was added and the mixture was stirred at room temperature for 30 minutes. Methanesulfonyl chloride (500 mg) was added and the mixture was stirred at room temperature for 6 hours. Water was poured into the reaction mixture and the mixture was concentrated under reduced pressure. The resulting residue was washed with water and MTB-ether to afford 0.72 g of the title compound of the formula

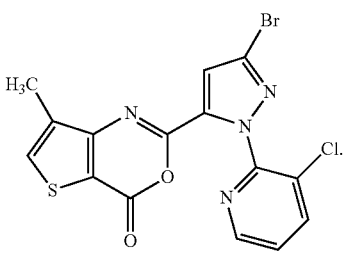

¹H-NMR (DMSO-D₆) δ (ppm): 1.74 (3H, br s), 7.52-7.57 (1H, m), 7.74-7.80 (1H, m), 8.02 (1H, br s), 8.30-8.37 (1H, m), 8.60-8.64 (1H, m).

Step 2: Preparation of N'-(3-{[5-bromo-2-(3-chloro-pyridin-2-yl)-2H-pyrazole-3-carbonyl]-amino}-4-methyl-thiophene-2-carbonyl)-hydrazinecarboxylic acid methyl ester (18)

A mixture of 2-[5-bromo-2-(3-chloro-pyridin-2-yl)-2H-pyrazol-3-yl]-7-methyl-thieno[3,2-d][1,3]oxazin-4-one (210 mg), carbazaic acid methyl ester (450 mg) and DMF (10 mL) was stirred at room temperature for 10 hours. The reaction mixture was quenched with water and the mixture was extracted with ethyl acetate. The organic layer was washed with water, dried over sodium sulfate and concentrated under reduced pressure. The resulting residue was subjected to silica gel column chromatography to afford 120 mg of compound 18 of the present invention of the formula (18)

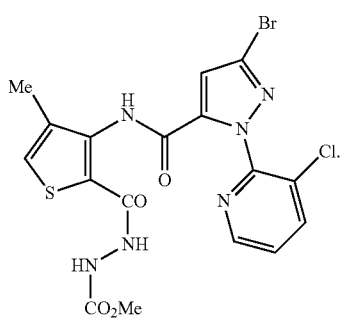

¹H-NMR (DMSO-D₆) δ (ppm): 1.96-2.01 (3H, m), 3.58-3.65 (3H, m), 7.38-7.47 (2H, m), 7.62 (1H, dd, J=8 Hz, 5 Hz), 8.16-8.23 (1H, m), 8.50 (1H, d, J=4 Hz), 9.24 (1H, br s), 9.83 (1H, br s), 10.28 (1H, br s)

Example 17

Preparation of N'-(5-{[5-bromo-2-(3-chloro-pyridin-2-yl)-2H-pyrazole-3-carbonyl]-amino}-1-methyl-1H-pyrazole-4-carbonyl)-hydrazinecarboxylic acid methyl ester (19)

Step 1: Preparation of 6-[5-bromo-2-(3-chloro-pyridin-2-yl)-2H-pyrazol-3-yl]-1-methyl-1H-pyrazolo[3,4-d][1,3]oxazin-4-one A mixture of 3-bromo-1-(3-chloro-2-pyridinyl)-1H-pyrazole-5-carboxylic acid (example 1, step 5) (1.10 g) and thionyl chloride (4 mL) was heated to reflux for 2 hours. The reaction mixture was allowed to cool to room temperature, and concentrated under reduced pressure. The resulting residue was dissolved in acetonitrile (10 mL) and of 5-amino-1-methyl-1H-pyrazole-4-carboxylic acid (520 mg) was added. The mixture was stirred at room temperature for 30 minutes. Then, triethylamine (400 mg) was added to the mixture. After stirring at room temperature for 30 minutes, a second portion of triethylamine (800 mg) was added and the mixture was stirred at room temperature for 30 minutes.

Methanesulfonyl chloride (600 mg) of was added, and the mixture was stirred at room temperature for 6 hours. Water was poured into the reaction mixture and the mixture was concentrated under reduced pressure. The resulting residue was washed with water and MTB-ether to afford 900 mg of the title compound of the formula

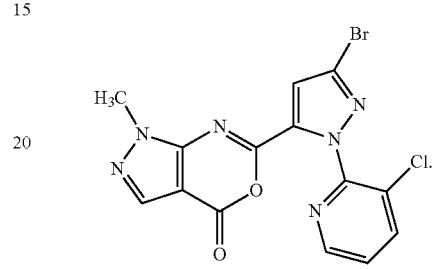

¹H-NMR (DMSO-D₆) δ (ppm): 3.46 (3H, s), 7.60 (1H, s), 7.78 (1H, dd, J=8 Hz, 5 Hz), 8.24 (1H, s), 8.35 (1H, d, J=8 Hz), 8.63 (1H, d, J=5 Hz).

Step 2: Preparation of N'-(5-{[5-bromo-2-(3-chloro-pyridin-2-yl)-2H-pyrazole-3-carbonyl]-amino}-1-methyl-1H-pyrazole-4-carbonyl)-hydrazinecarboxylic acid methyl ester (19)

A mixture of 6-[3-bromo-1-(3-chloro-2-pyridinyl)-1H-pyrazol-5-yl]-1-methyl-1H-pyrazolo[3,4-d][1,3]oxazin-4-one (300 mg), carbazaic acid methyl ester (700 mg) and DMF (10 mL) was stirred at room temperature for 10 hours. The reaction mixture was quenched with water and the mixture was extracted with ethyl acetate. The organic layer was washed with water, dried over sodium sulfate, and concentrated under reduced pressure. The resulting residue was subjected to silica gel column chromatography to afford 200 mg of compound 19 of the present invention of the formula (19)

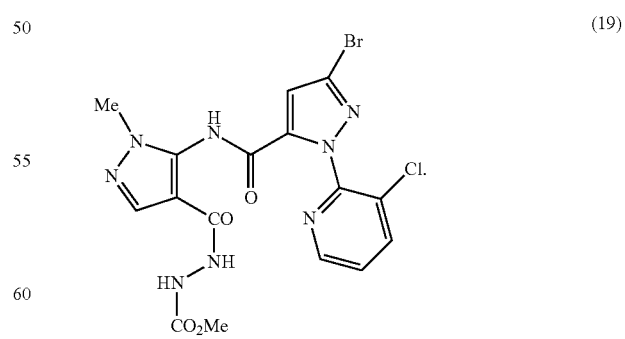

¹H-NMR (DMSO-D₆) δ (ppm): 3.55-3.60 (6H, m), 7.48 (1H, s), 7.64 (1H, dd, J=8 Hz, 5 Hz), 7.96 (1H, s), 8.20 (1H, d, J=8 Hz), 8.52 (1H, d, J=5 Hz), 9.08 (1H, br s), 9.86 (1H, br s), 10.79 (1H, br s).

Example 18

Preparation of N'-(6-{[2-(3-chloro-pyridin-2-yl)-5-trifluoromethyl-2H-pyrazole-3-carbonyl]-amino}-5-methyl-2-trifluoromethyl-quinoline-7-carbonyl)-hydrazinecarboxylic acid methyl ester (20)

Step 1: Preparation of 5-oxo-2-trifluoromethyl-5,6,7,8-tetra hydro-quinoline-7-carboxylic acid methyl ester A solution of 3,5-dioxo-cyclohexanecarboxylic acid methyl ester (3.6 g, preparation as described in *J. Chem. Soc., Perkin Trans.* 1 (1976), (13), 1382-4), (Z)-amino-1,1,1-trifluoro-but-3-en-2-one (2.94 g, prepared as described in EP 744400 (1996)), trifluoroacetic acid (1.21 g) and ammonium trifluoroacetate (1.39 g) in toluene (50 mL) are heated at reflux temperature in a Dean-Stark apparatus. After reaction completion, the reaction mixture is cooled, diluted with ethyl acetate and washed successively with saturated aqueous sodium bicarbonate and water. The organic phase is dried over anhydrous sodium sulfate, filtered and concentrated in vacuum. The residue is purified by column chromatography (eluting with hexane/ethyl acetate=4:1) to give 1.5 g of the title compound of the formula

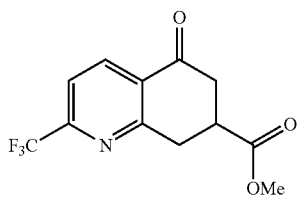

as white crystals.

Step 2: Preparation of 5-hydroxy-2-trifluoromethyl-quinoline-7-carboxylic acid methyl ester A solution of 5-oxo-2-trifluoromethyl-5,6,7,8-tetrahydro-quinoline-7-carboxylic acid methyl ester (50.0 g) is dissolved in methylene chloride (500 mL) and treated drop wise with a solution of bromotrichloromethane (54.43 g) and 1,8-diazabicylo[5.4.0]undec-7-en (55.72 g) in methylene chloride (100 mL) at 0-5° C. After the addition is complete, the reaction mixture is allowed to warm to room temperature, and stirred for 1 h. The reaction mixture is diluted with ethyl acetate and then washed successively with diluted aqueous hydrochloric acid and brine. The ethyl acetate phase is dried over anhydrous sodium sulfate, filtered and concentrated in vacuum. The residue is purified by recrystallization from hexane/ethyl acetate to give 47.13 g of the title compound of the formula

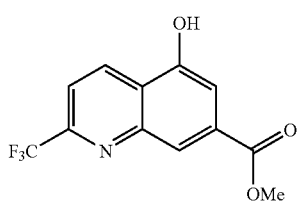

as pale yellow crystals.

Step 3: Preparation of 5-hydroxy-6-nitro-2-trifluoromethyl-quinoline-7-carboxylic acid methyl ester 5-Hydroxy-2-trifluoromethyl-quinoline-7-carboxylic acid methyl ester (46.0 g) is dissolved in concentrated sulfuric acid (200 mL, 97%) at 0-5° C. To this cooled solution is added drop wise fuming nitric acid (7 mL, 100%). After the addition is complete, the reaction mixture is allowed to warm to room temperature. TLC analysis (hexane/ethyl acetate=4:1) after 30 min shows reaction completion. The reaction mixture is slowly poured onto an ice/water mixture (ca. 2 mL) and the crystals were filtered off, washed thoroughly with water and dried in vacuum to afford 47.0 g of the title compound of the formula

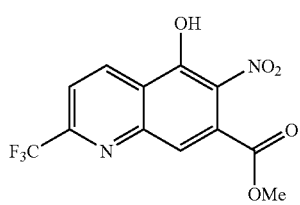

as pale yellow crystals.

Step 4: Preparation of 6-nitro-5-trifluoromethanesulfonyloxy-2-trifluoromethyl-quinoline-7-carboxylic acid methyl ester A solution of 5-hydroxy-6-nitro-2-trifluoromethyl-quinoline-7-carboxylic acid methyl ester (6.82 g) in methylene chloride (50 mL) is treated with triethylamne (6.69 g) and a catalytic amount of 4-dimethylamino pyridine (0.26 g). To this solution is added trifluoromethanesulfonic anhydride (9.1 g), maintaining the temperature at 25° C. for 1 h. The reaction mixture is diluted with methylene chloride and then washed successively with diluted aqueous hydrochloric acid, water, saturated aqueous sodium bicarbonate and water. The methylene chloride phase is dried over anhydrous sodium sulfate, filtered and concentrated in vacuum. The residue is purified by column chromatography (hexane/ethyl acetate=9:1) to give 6.6 g of the title compound of the formula

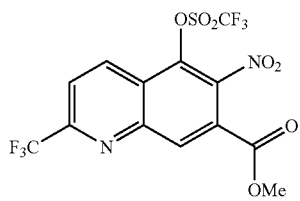

as pale yellow crystals.

Step 5: Preparation of 5-methyl-6-nitro-2-trifluoromethyl-quinoline-7-carboxylic acid methyl ester A suspension of indium trichloride (2.0 g) in dry THF (5 mL) under an argon atmosphere is cooled to −78° C. and then treated drop wise with methyl magnesium chloride (9.1 mL, 3 M in THF). The milky suspension is allowed to warm to room temperature and then added drop wise to a refluxing solution of bis(triphenylphosphine)palladium(II)chloride (0.19 g) and 6-nitro-5-trifluoromethanesulfonyloxy-2-trifluoromethyl-quinoline-7-carboxylic acid methyl ester (4.05 g) in dry THF (35 mL). The mixture is refluxed under an argon atmosphere, monitoring by TLC. After reaction completion, the reaction mixture is concentrated in vacuum. The residue is taken up in diethyl ether and washed successively with diluted hydrochloric acid and brine. The diethyl ether phase is dried over anhydrous sodium sulfate, filtered and concentrated in vacuum. The residue is purified by column chromatography (hexane/ethyl acetate=4:1) to give 2.0 g of the title compound of the formula

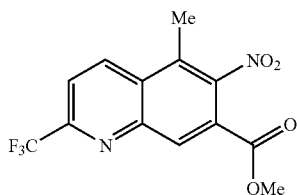

as yellow crystals.

Step 6: Preparation of 5-methyl-6-nitro-2-trifluoromethyl-quinoline-7-carboxylic acid 5-Methyl-6-nitro-2-trifluoromethyl-quinoline-7-carboxylic acid methyl ester (3.78 g) is dissolved in 200 mL of methanol/water (3:1 mixture) and treated with lithium hydroxide hydrate (1.06 g) at room temperature. After reaction completion, the mixture is poured into ethyl acetate and 2N hydrochloric acid, the organic phase is washed 3× with water, dried over sodium sulfate, filtered and concentrated in vacuum. The residue is triturated with a small amount of hexane. Filtration gives 3.50 g of the title compound of the formula

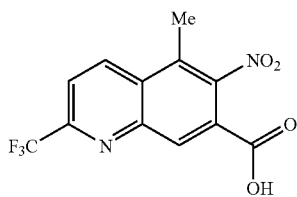

as white crystals.

Step 7: Preparation of 6-amino-5-methyl-2-trifluoromethyl-quinoline-7-carboxylic acid A solution of 5-methyl-6-nitro-2-trifluoromethyl-quinoline-7-carboxylic acid (1.40 g) in ethanol (100 mL) is hydrogenated at atmosphere pressure and ambient temperature in the presence of Raney-nickel catalyst. TLC analysis after 12 h shows reaction completion. The mixture is filtered over hyflo and the filtrate concentrated in vacuum. The residue is recrystallized from hexane/ethyl acetate to give 0.90 g of the title compound of the formula

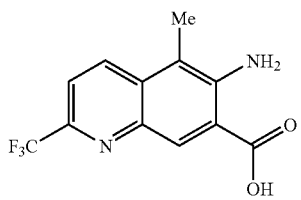

as yellow crystals.

Step 8: Preparation of 2-[2-(3-chloro-pyridin-2-yl)-5-trifluoromethyl-2H-pyrazol-3-yl]-9-methyl-6-trifluoromethyl-3-oxa-1,5-diaza-anthracen-4-one A solution of 6-amino-5-methyl-2-trifluoromethyl-quinoline-7-carboxylic acid (0.60 g), 2-(3-chloro-pyridin-2-yl)-5-trifluoromethyl-2H-pyrazole-3-carboxylic acid (0.65 g, example 2, step 2) and pyridine (0.79 g) in acetonitrile (30 mL) is cooled to 0-5° C. and treated drop wise with methane sulfonyl chloride (0.89 g) dissolved in 2 mL acetonitrile. TLC analysis (hexane/ethyl acetate 4:1) after 2 h shows reaction completion. The reaction mixture is concentrated to ⅔ of the original volume in vacuum and poured onto 75 mL of ice/water. The resultant crystals are filtered off, washed with water and dried in vacuum to give 1.0 g of the title compound of the formula

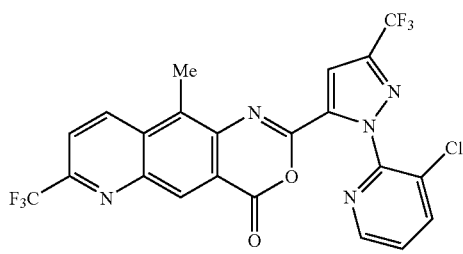

as orange crystals.

Step 9: Preparation of N'-(6-{[2-(3-chloro-pyridin-2-yl)-5-trifluoromethyl-2H-pyrazole-3-carbonyl]-amino}-5-methyl-2-trifluoromethyl-quinoline-7-carbonyl)-hydrazinecarboxylic acid methyl ester (20)

2-[2-(3-Chloro-pyridin-2-yl)-5-trifluoromethyl-2H-pyrazol-3-yl]-9-methyl-6-trifluoromethyl-3-oxa-1,5-diaza-anthracen-4-one (600 mg, can be prepared as in WO 2007/020050) is suspended in DMF and carbazaic acid methyl ester (1.18 g) is added. The solution is stirred for 15 h at 50° C. before it is quenched with water. The mixture is 2× extracted with ethyl acetate, the combined organic layer is 3× washed with water, washed with brine, dried over magnesium sulfate and concentrated in vacuum. The residue is purified by column chromatography to afford the title compound of the formula

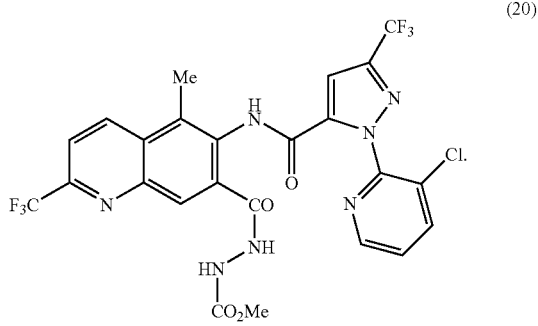

(20)

Then, Formulation Examples will be shown. All parts are by weight.

Formulation Example 1

Into a mixture of 35 parts of xylene and 35 parts of N,N-dimethylformamide, 10 parts of any one of the present compounds (1) to (19) is dissolved, and then 14 parts of polyoxyethylene styrylphenyl ether and 6 parts of calcium dodecylbenzenesulfonate are added. The mixture is stirred thoroughly to obtain a 10% emulsion.

Formulation Example 2

To a mixture of 4 parts of sodium laurylsulfate, 2 parts of calcium ligninsulfonate, 20 parts of synthetic hydrous silicon oxide fine powder and 54 parts of diatomaceous earth, 20 parts of any one of the present compounds (1) to (19) is added. The mixture is stirred thoroughly to obtain a 20% wettable agent.

Formulation Example 3

To 2 parts of any one of the present compounds (1) to (19), 1 part of synthetic hydrous silicon oxide fine powder, 2 parts of calcium ligninsulfonate, 30 parts of bentonite and 65 parts of kaolin clay are added, and then stirred thoroughly. Then, an appropriate amount of water is added to the mixture. The mixture is further stirred, granulated with a granulator, and forced-air dried to obtain a 2% granule.

Formulation Example 4

Into an appropriate amount of acetone, 1 part of any one of the present compounds (1) to (19) is dissolved, and then 5 parts of synthetic hydrous silicon oxide fine powder, 0.3 part of PAP and 93.7 parts of fubasami clay are added. The mixture is stirred thoroughly. Then, acetone is removed from the mixture by evaporation to obtain a 1% powder.

Formulation Example 5

A mixture of 10 parts of any one of the present compounds (1) to (19); 35 parts of white carbon containing parts of polyoxyethylene alkyl ether sulfate ammonium salt; and 55 parts of water is finely ground by a wet grinding method to obtain a 10% flowable agent.

Formulation Example 6

In 5 parts of xylene and 5 parts of trichloroethane, 0.1 part of any one of the present compounds (1) to (19) is dissolved. The solution is mixed with 89.9 parts of deodorized kerosene to obtain a 0.1% oil.

Formulation Example 7

In 0.5 ml of acetone, 10 mg of any one of the present compounds (1) to (19) is dissolved. The solution is mixed uniformly with 5 g of a solid feed powder for an animal (solid feed powder for rearing and breeding CE-2, manufactured by CLEA Japan, Inc.), and then dried by evaporation of acetone to obtain poison bait.

Then, it will be shown by Test Examples that the present compound is effective in controlling harmful arthropods. In the Test Example, controlling values were calculated by the following equation:

Controlling value(%)={1−(Cb×Tai)/(Cai×Tb)}×100 wherein
Cb: the number of worms in a non-treated section before treatment
Cai: the number of worms in a non-treated section on observation
Tb: the number of worms in a treated-section before treatment
Tai: the number of worms in a treated-section on observation.

Test Example 1

Preparations of the test compounds obtained in Formulation Example 5 were diluted with water so that the active ingredient concentration became 500 ppm, to prepare test spray solutions.

At the same time, cabbage was planted in a polyethylene cup, and grown until the third true leaf or the fourth true leaf was developed. The test spray solution as described above was sprayed in an amount of 20 ml/cup on the cabbage.

After the spray solution on the cabbage was dried, 10 third-instar larvae of diamondback moths (*Plutella xylostella*) were put on the cabbage. After 5 days, the number of diamondback moths was counted, and the controlling value was calculated by the above equation.

As a result, the test spray solutions of the present compounds (1), (2), (3), (4), (5), (7), (8), (9), (10), (11), (14), (15), (16), (17) and (19) each exhibited a controlling value of 90% or more.

Furthermore, preparations of the test compound (7) and a comparative compound of the formula

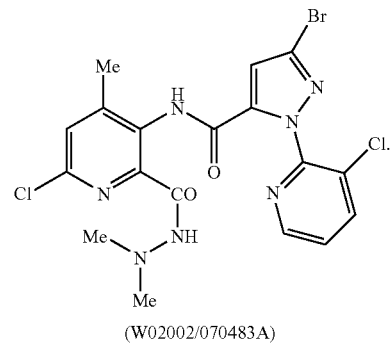

(WO2002/070483A)

obtained in a formulation according to Formulation Example 5 were diluted with water so that the active ingredient concentration became 0.2 ppm, to prepare test spray solution.

At the same time, cabbage was planted in a polyethylene cup, and grown until the third true leaf or the fourth true leaf was developed. The test spray solution as described above was sprayed in an amount of 20 ml/cup on the cabbage.

After the spray solution on the cabbage was dried, 10 third-instar larvae of diamondback moths (*Plutella xylostella*) were put on the cabbage. After 5 days, the number of diamondback moths was counted, and the controlling value was calculated by the above equation.

Compound (7) exhibited a control value of more than 80%, whereas the comparison compound of the above formula exhibited less than 80% control.

Test Example 2

Preparations of the test compounds obtained in Formulation Example 5 were diluted with water so that the active ingredient concentration became 500 ppm to prepare test spray solutions.

At the same time, cucumber was planted in a polyethylene cup, and was grown until the first true leaf was developed. About 30 cotton aphids were put on the cucumber. One day after, the test spray solution as described above was sprayed in an amount of 20 ml/cup on the cucumber. Six days after spraying, the number of cotton aphids (*Aphis gossypii*) was counted, and a controlling value was calculated by the above equation.

As a result, the test spray solutions of the present compounds (1), (2), (3), (4), (5), (7), (8), (9), (10), (11), (14), (15), (16), (18) and (19) each exhibited a controlling value of 90% or more.

Test Example 3

Preparations of the test compounds obtained in Formulation Example 5 were diluted with water so that the active ingredient concentration became 500 ppm to prepare test spray solutions.

At the same time, cabbage was planted in a polyethylene cup, and grown until the third true leaf or the fourth true leaf was developed. The test spray solution as described above was sprayed in an amount of 20 ml/cup on the cabbage. After the spray solution sprayed on the cabbage was dried, 10 fourth-instar larvae of Spodoptera litura were put on the cabbage. After 5 days, the number of Spodoptera litura surviving on the cabbage leaves was counted, and a controlling value was calculated by the above equation.

As a result, the test spray solutions of the present compounds (1), (3), (4), (5), (7), (8), (9), (10), (11), (14), (15), (16) and (17) each exhibited a controlling value of 80% or more.

Test Example 4

Preparations of the test compounds obtained in Formulation Example 5 were diluted with water so that the active ingredient concentration became 500 ppm to prepare test spray solutions.

At the same time, 20 ml of the test spray solution as described above was sprayed to an apple seedling (28 day-old seeding, tree height: about 15 cm) planted in a plastic cup. The apple seedling was air-dried to such an extent that the spray solution sprayed on the apple seedling was dried. About 30 first-instar larvae of Adoxophyes orana fasciata were released. Seven days after spraying, the number of worms surviving on the apple seedling was counted, and a controlling value was calculated by the above equation.

As a result, the test spray solutions of the present compounds (1), (2), (3), (4), (5), (7), (8), (14), (15) and (19) each exhibited a controlling value of 90% or more.

Test Example 5

Preparations of the test compounds obtained in Formulation Example 5 were diluted with water so that the active ingredient concentration became 500 ppm to prepare test spray solutions.

At the same time, cucumber was planted in a polyethylene cup, and was grown until the first true leaf was developed. The test spray solution as described above was sprayed in an amount of 20 ml/cup on the cucumber. After the spray solution on the cucumber was dried, the first true leaf was cut and then placed on a filter paper (diameter: 70 mm) containing water in a polyethylene cup (diameter: 110 mm). On the cucumber leaf, 20 larvae of Franklinella occidentalis were released, and the polyethylene cup was capped. Seven days after spraying, the percentage of leaf area damaged by the insect was examined.

As a result, the test spray solutions of the present compounds (1), (2), (3), (4), (7), (8), (9), (10), (11), (14), (15) and (16) each suppressed the feeding damage to the level of damaged area of 5% or less.

Test Example 6

Preparations of the test compounds obtained in Formulation Example 5 were diluted with water so that the active ingredient concentration became 500 ppm to prepare test spray solutions.

At the same time, cabbage was planted in a polyethylene cup, and grown until the first true leaf was developed. All leaves excluding the first true leaf were cut off. On the first true leaf, adults of silver leaf whitefly, Bemisia argentifolii (or biotype B of tobacco whitefly, Bemisia tabaci) were released and allowed to lay eggs for about 24 hours. The cabbage was retained in a greenhouse for 8 days. When larvae hatched from the laid eggs, the test spray solution as described above was sprayed in an amount of 20 ml/cup to the cabbage. Seven days after spraying, the number of larvae surviving on the cabbage was counted, and a controlling value was calculated by the above equation.

As a result, the test spray solutions of the present compounds (7), (8), (9), (10), (11), (14) and (15) each exhibited a controlling value of 90% or more.

INDUSTRIAL APPLICABILITY

According to the present invention, since the hydrazide compound of the present invention has excellent efficacy of controlling pests, it is useful as an active ingredient of a pesticide.

The invention claimed is:

1. A hydrazide compound represented by the formula (1), an N-oxide thereof or suitable salt thereof:

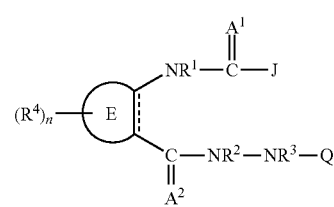

wherein
A$^1$ and A$^2$ independently represent an oxygen atom or a sulfur atom;
E represents, together with the two contiguous linking carbon atoms, a 5- or 6-membered heteroaromatic ring system or an 8-, 9- or 10-membered fused heterobicyclic ring system;
R$^1$ represents a hydrogen atom, C1-C6 alkyl optionally substituted with one or more halogen atoms, C2-C6 cyanoalkyl, C1-C6 hydroxyalkyl, C2-C6 alkoxyalkyl optionally substituted with one or more halogen atoms, C2-C6 alkenyl optionally substituted with one or more halogen atoms, C2-C6 alkynyl optionally substituted with one or more halogen atoms, C3-C6 cycloalkyl optionally substituted with one or more halogen atoms, C1-C6 alkylthio optionally substituted with one or more halogen atoms, C1-C6 alkylsulfinyl optionally substituted with one or more halogen atoms, C1-C6 alkylsulfonyl optionally substituted with one or more halogen atoms, C2-C6 alkylcarbonyl optionally substituted with one or more halogen atoms, C2-C6 alkoxycarbonyl, C2-C6 alkylaminocarbonyl, C3-C8 dialkylaminocarbonyl, C4-C6 cycloalkylaminocarbonyl, or C3-C6 trialkylsilyl;
or represents phenyl, C7-C9 phenylalkyl or phenylcarbonyl: each said phenyl ring optionally substituted with one or more independent substituents selected from the group consisting of (1) a halogen atom, (2) cyano, (3) nitro, (4) hydroxyl, (5) carboxyl, (6) C1-C6 alkyl optionally substituted with one or more halogen atoms, (7) C1-C6 hydroxyalkyl, (8) C1-C6 alkoxy optionally substituted with one or more halogen atoms, (9) C2-C6 cyanoalkyl, (10) C2-C6 alkoxyalkyl optionally substituted with one or more halogen atoms, (11) C2-C6 alkenyl optionally substituted with one or more halogen atoms, (12) C2-C6 alkynyl optionally substituted with one or more halogen atoms, (13) C3-C6 cycloalkyl optionally substituted with one or more halogen atoms, (14) C1-C6 alkylthio optionally substituted with one or more halogen atoms, (15) C1-C6 alkylsulfinyl optionally substituted with one or more halogen atoms, (16) C1-C6 alkylsulfonyl optionally substituted with one or more halogen atoms, (17) C1-C6 alkylamino, (18) C2-C8 dialkylamino, (19) C3-C6 cycloalkylamino, (20) C2-C6 alkylcarbonyl, (21) C2-C6 alkoxycarbonyl, (22) C2-C6 alkylaminocarbonyl, (23) C3-C8 dialkylaminocarbonyl, (24) C4-C6 cycloalkylaminocarbonyl and (25) C3-C6 trialkylsilyl;

$R^2$ and $R^3$ independently represent a hydrogen atom, C1-C6 alkyl optionally substituted with one or more halogen atoms, C2-C6 cyanoalkyl, C1-C6 hydroxyalkyl, C2-C6 alkoxyalkyl optionally substituted with one or more halogen atoms, C2-C6 alkenyl optionally substituted with one or more halogen atoms, C2-C6 alkynyl optionally substituted with one or more halogen atoms, C3-C6 cycloalkyl optionally substituted with one or more halogen atoms, C1-C6 alkylthio optionally substituted with one or more halogen atoms, C1-C6 alkylsulfinyl optionally substituted with one or more halogen atoms, C1-C6 alkylsulfonyl optionally substituted with one or more halogen atoms, C2-C6 alkylcarbonyl optionally substituted with one or more halogen atoms, C2-C6 alkoxycarbonyl, C2-C6 alkylaminocarbonyl, C3-C8 dialkylaminocarbonyl, C4-C6 cycloalkylaminocarbonyl, or C3-C6 trialkylsilyl;

or represents phenyl, C7-C9 phenylalkyl or phenylcarbonyl: each said phenyl ring optionally substituted with one or more independent substituents selected from the group consisting of (1) a halogen atom, (2) cyano, (3) nitro, (4) hydroxyl, (5) carboxyl, (6) C1-C6 alkyl optionally substituted with one or more halogen atoms, (7) C1-C6 hydroxyalkyl, (8) C1-C6 alkoxy optionally substituted with one or more halogen atoms, (9) C2-C6 cyanoalkyl, (10) C2-C6 alkoxyalkyl optionally substituted with one or more halogen atoms, (11) C2-C6 alkenyl optionally substituted with one or more halogen atoms, (12) C2-C6 alkynyl optionally substituted with one or more halogen atoms, (13) C3-C6 cycloalkyl optionally substituted with one or more halogen atoms, (14) C1-C6 alkylthio optionally substituted with one or more halogen atoms, (15) C1-C6 alkylsulfinyl optionally substituted with one or more halogen atoms, (16) C1-C6 alkylsulfonyl optionally substituted with one or more halogen atoms, (17) C1-C6 alkylamino, (18) C2-C8 dialkylamino, (19) C3-C6 cycloalkylamino, (20) C2-C6 alkylcarbonyl, (21) C2-C6 alkoxycarbonyl, (22) C2-C6 alkylaminocarbonyl, (23) C3-C8 dialkylaminocarbonyl, (24) C4-C6 cycloalkylaminocarbonyl and (25) C3-C6 trialkylsilyl; or $R^2$ and $R^3$ are taken together with the two nitrogen atoms to which they are attached to form a 5- to 8-membered ring containing two nitrogen atoms, one or more $CH_2$ or $C(=O)$, and optionally one or two ring members selected from the group consisting of (1) an oxygen atom, (2) a sulfur atom, (3) $S(=O)$, (4) $S(=O)_2$ and (4) $NR^a$ (wherein $R^a$ represents C1-C6 alkyl optionally substituted with one or more halogen atoms, C2-C6 alkoxycarbonyl optionally substituted with one or more halogen atoms, or a phenyl optionally substituted with one or more independent substituents from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms); and wherein the ring at the carbon atoms is optionally substituted with one or more independent substituents selected from the group consisting of (1) a halogen atom, (2) C1-C6 alkyl optionally substituted with one or more halogen atoms, and (3) C2-C6 alkoxycarbonyl optionally substituted with one or more halogen atoms;

$R^4$ represents a halogen atom, cyano, nitro, hydroxyl, carboxyl, C1-C6 alkyl optionally substituted with one or more halogen atoms, C1-C6 alkoxy optionally substituted with one or more halogen atoms, C2-C6 cyanoalkyl, C2-C6 alkoxyalkyl optionally substituted with one or more halogen atoms, C2-C6 alkenyl optionally substituted with one or more halogen atoms, C2-C6 alkynyl optionally substituted with one or more halogen atoms, C3-C6 cycloalkyl optionally substituted with one or more halogen atoms, C1-C6 alkylthio optionally substituted with one or more halogen atoms, C1-C6 alkylsulfinyl optionally substituted with one or more halogen atoms, C1-C6 alkylsulfonyl optionally substituted with one or more halogen atoms, C1-C6 alkylamino, C2-C8 dialkylamino, C3-C6 cycloalkylamino, C2-C6 alkylcarbonyl optionally substituted with one or more halogen atoms, C2-C6 alkoxycarbonyl, C2-C6 alkylaminocarbonyl, C3-C8 dialkylaminocarbonyl, or C3-C6 trialkylsilyl;

or represents a phenyl, benzyl, phenoxy, or a 5- or 6-membered heteroaromatic ring, each ring optionally substituted with one or more substituents selected from the group consisting of (1) a halogen atom, (2) cyano, (3) nitro, (4) hydroxyl, (5) carboxyl, (6) C1-C6 alkyl optionally substituted with one or more halogen atoms, (7) C1-C6 hydroxyalkyl, (8) C1-C6 alkoxy optionally substituted with one or more halogen atoms, (9) C2-C6 cyanoalkyl, (10) C2-C6 alkoxyalkyl optionally substituted with one or more halogen atoms, (11) C2-C6 alkenyl optionally substituted with one or more halogen atoms, (12) C2-C6 alkynyl optionally substituted with one or more halogen atoms, (13) C3-C6 cycloalkyl optionally substituted with one or more halogen atoms, (14) C1-C6 alkylthio optionally substituted with one or more halogen atoms. (15) C1-C6 alkylsulfinyl optionally substituted with one or more halogen atoms, (16) C1-C6 alkylsulfonyl optionally substituted with one or more halogen atoms, (17) C1-C6 alkylamino, (18) C2-C8 dialkylamino, (19) C3-C6 cycloalkylamino, (20) C2-C6 alkylcarbonyl, (21) C2-C6 alkoxycarbonyl, (22) C2-C6 alkylaminocarbonyl, (23) C3-C8 dialkylaminocarbonyl, (24) C4-C6 cycloalkylaminocarbonyl and (25) C3-C6 trialkylsilyl;

n represents an integer of 0 to 3 (provided that, when n is an integer of 2 or more, $R^4$'s may be the same or different);

Q represents Q1, Q2, Q3, Q4, Q5 or Q6:
 $Q^1$: —$C(=A^{31})$—$R^6$
 $Q^2$: —$C(=A^{32})$—$OR^7$
 $Q^3$: —$C(=A^{33})$—$SR^8$
 $Q^4$: —$C(=A^{34})$—$NR^9R^{10}$
 $Q^5$: —$S(O)_m$—$R^{11}$
 $Q^6$: —$S(O)_m$—$NR^{12}R^{13}$, $A^{31}$, $A^{32}$, $A^{33}$ and $A^{34}$ represent an oxygen atom, or a sulfur atom;

m represents an integer of 0 to 2;

R⁶ represents a hydrogen atom; C2-C6 alkenyl optionally substituted with one or more halogen atoms; C2-C6 alkynyl optionally substituted with one or more halogen atoms; C1-C6 alkyl optionally substituted with one or more independent substituents selected from the group consisting of (1) a halogen atom, (2) C1-C6 alkoxy optionally substituted with one or more halogen atoms, (3) C1-C6 alkylthio optionally substituted with one or more halogen atoms, (4) C1-C6 alkylsulfinyl optionally substituted, with one or more halogen atoms, (5) C1-C6 alkylsulfonyl optionally substituted with one or more halogen atoms, (6) C2-C6 dialkylamino optionally substituted with one or more halogen atoms, and (7) C3-C6 cycloalkyl optionally substituted with one or more halogen atoms; C3-C6 cycloalkyl optionally substituted with one or more independent substituents selected from the group consisting of (1) a halogen atom, and (2) C1-C6 alkyl optionally substituted with one or more halogen atoms; phenyl optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarhonyl optionally substituted with one or more halogen atoms and (14) C3-C6 dialkylaminocarbonyl optionally substituted with one or more halogen atoms; naphthyl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms; 5- to 6-membered heteroaryl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms; 3- to 8-membered non-aromatic heterocyclic ring optionally substituted with one or more independent substituents selected from the group consisting of (1) a halogen atom, and (2) C1-C6 alkyl optionally substituted with one or more halogen atoms; C7-C9 phenylalkyl or C7-C9 phenoxyalkyl: each said phenyl ring optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms;

R⁷ and R⁸ represent C1-C6 alkyl optionally substituted with one or more halogen atoms; C2-C6 alkoxyalkyl optionally substituted with one or more halogen atoms; C2-C6 alkenyl optionally substituted with one or more halogen atoms; C2-C6 alkynyl optionally substituted with one or more halogen atoms; C3-C6 cycloalkyl optionally substituted with one or more independent substituents selected from the group consisting of (1) a halogen atom, and (2) C1-C6 alkyl optionally substituted with one or more halogen atoms; phenyl optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms; 5- to 6-membered heteroaryl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms; or C7-C9 phenylalkyl whose phenyl ring moiety optionally is substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms;

R⁹ and R¹⁰ independently represent a hydrogen atom; C1-C6 alkyl optionally substituted with one or more halogen atoms; C2-C6 alkoxyalkyl optionally substituted with one or more halogen atoms; C2-C6 alkenyl optionally substituted with one or more halogen atoms; C2-C6 alkynyl optionally substituted with one or more halogen atoms; C3-C6 cycloalkyl optionally substituted with one or more independent substituents selected from the group consisting of (1) a halogen atom, and (2) C1-C6 alkyl optionally substituted with one or more halogen atoms; phenyl optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms; 5- to 6-membered heteroaryl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms; or C7-C9 phenylalkyl whose phenyl ring moiety optionally is substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms;

$R^{11}$ represents C1-C6 alkyl optionally substituted with one or more halogen atoms; C3-C6 cycloalkyl optionally substituted with one or more independent substituents selected from the group consisting of (1) a halogen atom, and (2) C1-C6 alkyl optionally substituted with one or more halogen atoms; or a phenyl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms; 5- to 6-membered heteroaryl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms; or 3- to 8-membered non-aromatic heterocyclic ring optionally substituted with one or more independent substituents selected from the group consisting of (1) a halogen atom, and (2) C1-C6 alkyl optionally substituted with one or more halogen atoms;

$R^{12}$ and $R^{13}$ independently represent C1-C6 alkyl optionally substituted with one or more halogen atoms; C3-C6 cycloalkyl optionally substituted with one or more independent substituents selected from the group consisting of (1) a halogen atom, and (2) C1-C6 alkyl optionally substituted with one or more halogen atoms; or phenyl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms;

J represents J1 or J2:

J1:

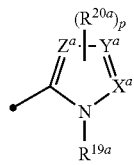

J2:

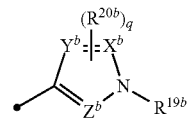

wherein
$X^a, Y^a, Z^a, X^b, Y^b$ and $Z^b$ independently represent CH or a nitrogen atom;
$R^{19a}$ and $R^{19b}$ represent a hydrogen atom; C1-C6 alkyl optionally substituted with one or more halogen atoms; C2-C6 cyanoalkyl, C2-C6 alkoxyalkyl optionally substituted with one or more halogen atoms; C2-C6 alkenyl optionally substituted with one or more halogen atoms; C2-C6 alkynyl optionally substituted with one or more halogen atoms; C3-C6 cycloalkyl optionally substituted with one or more independent substituents selected from the group consisting of (1) a halogen atom, and (2) C1-C6 alkyl optionally substituted with one or more halogen atoms; phenyl optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms; 5- to 6-membered heteroaryl optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms. (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms; C7-C9 phenylalkyl whose phenyl ring is optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms; or C7-C9 pyridinylalkyl whose pyridine ring is optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14)

C3-C6 dialkylaminocarbonyl optionally substituted with one or more halogen atoms;

$R^{20a}$ and $R^{20b}$ represent a halogen atom; cyano; nitro; thiocyanato; C1-C6 alkyl optionally substituted with one or more halogen atoms; C1-C6 alkoxy optionally substituted with one or more halogen atoms; C2-C6 cyanoalkyloxy; C2-C6 alkoxyalkyloxy optionally substituted with one or more halogen atoms; C2-C6 alkenyloxy optionally substituted with one or more halogen atoms; C2-C6 alkynyloxy optionally substituted with one or more halogen atoms; C1-C6 alkylthio optionally substituted with one or more halogen atoms; C1-C6 alkylsulfinyl optionally substituted with one or more halogen atoms; C1-C6 alkylsulfonyl optionally substituted with one or more halogen atoms; phenyl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms; 5- to 6-membered heteroaryl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms; or phenoxy optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms;

p represents an integer of 0 to 3 (provided that, when p is an integer of 2 or 3, two or more $R^{20a}$'s may be the same or different); and q represents an integer of 0 to 3 (provided that, when q is an integer of 2 or 3, two or more $R^{20b}$'s may be the same or different).

2. The compound according to claim 1, wherein E is a 5- or 6-membered heteroaromatic ring.

3. The compound according to claim 1 or 2, wherein $A^1$ and $A^2$ are oxygen atoms; and
$R^1$ is a hydrogen atom or alkyl optionally substituted with one or more halogen atoms.

4. The compound according to claim 1, wherein J is J-1.1, J-1.2, J-2.1, J-2.2 or J-2.3:

J-1.1:

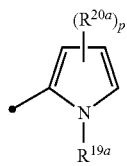

J-1.2:

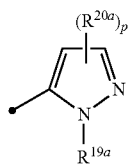

J-2.1:

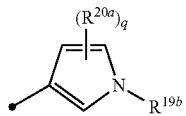

J-2.2:

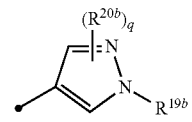

J-2.3:

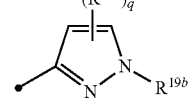

wherein $R^{19a}$ and $R^{19b}$ represent a hydrogen atom; C1-C6 alkyl optionally substituted with one or more halogen atoms; C3-C6 cycloalkyl optionally substituted with one or more independent substituents selected from the group consisting of (1) a halogen atom and (2) C1-C6 alkyl optionally substituted with one or more halogen atoms; phenyl, optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms; 5- to 6-membered heteroaryl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms;

$R^{20a}$ and $R^{20b}$ represent a halogen atom, cyano, C1-C6 alkyl optionally substituted with one or more halogen atoms, C1-C6 alkoxy optionally substituted with one or more halogen atoms, C2-C6 cyanoalkyloxy, C2-C6 alkoxyalkyloxy optionally substituted with one or more halogen atoms, C2-C6 alkenyloxy optionally substituted with one or more halogen atoms, C1-C6 alkylthio optionally substituted with one or more halogen atoms, C1-C6 alkylsulfinyl optionally substituted with one or more halogen atoms, C1-C6 alkylsulfonyl optionally substituted with one or more halogen atoms;

or phenyl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms;

5- to 6-membered heteroaryl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms or phenoxy optionally substituted with one or more independent substituents selected from the group consisting of (1) a halogen atom; (2) cyano, (3) nitro, (4) C1-C6 alkyl optionally substituted with one or more halogen atoms and (5) C1-C6 alkoxy optionally substituted with one or more halogen atoms;

p represents an integer of 0 to 3; and q represents an integer of 0 to 3 (provided that, when p is an integer of 2 or 3, two or more $R^{20a}$'s may be the same or different and, when q is an integer of 2 or 3, two or more $R^{20b}$'s may be the same or different).

5. The compound according to claim 1, an N-oxide thereof or suitable salt thereof, wherein Q is Q1;

$A^{31}$ is oxygen; and $R^6$ represents a hydrogen atom; C1-C6 alkyl optionally substituted with one or more independent substituents selected from the group consisting of (1) a halogen atom, (2) C1-C6 alkoxy optionally substituted with one or more halogen atoms, (3) C1-C6 alkylthio optionally substituted with one or more halogen atoms, (4) C1-C6 alkylsulfinyl optionally substituted with one or more halogen atoms, (5) C1-C6 alkylsulfonyl optionally substituted with one or more halogen atoms, (6) C2-C6 dialkylamino optionally substituted with one or more halogen atoms, and (7) C3-C6 cycloalkyl optionally substituted with one or more halogen atoms;

C3-C6 cycloalkyl optionally substituted with one or more independent substituents selected from the group consisting of (1) a halogen atom, and (2) C1-C6 alkyl optionally substituted with one or more halogen atoms;

phenyl optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms;

5- to 6-membered heteroaryl optionally substituted with one or more independent substituents selected from the group consisting of (1) a halogen atom; (2) cyano, (3) nitro, (4) C1-C6 alkyl optionally substituted with one or more halogen atoms and (5) C1-C6 alkoxy optionally substituted with one or more halogen atoms;

3- to 8-membered non-aromatic heterocyclic optionally substituted with one or more independent substituents selected from the grOup consisting of (1) a halogen atom, and (2) C1-C6 alkyl optionally substituted with one or more halogen atoms or C7-C9 phenylalkyl or C7-C9 phenoxyalkyl: each said phenyl ring optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms.

6. The compound according to claim 5, wherein $A^1$ and $A^2$ are oxygen atoms.

7. The compound according to claim 1, an N-oxide thereof or suitable salt thereof, wherein Q is Q2;

$A^{32}$ is oxygen; and $R^7$ is C1-C6 alkyl optionally substituted with one or more halogen atoms; C2-C6 alkenyl optionally substituted with one or more halogen atoms; C3-C6 cycloalkyl optionally substituted with one or more independent substituents selected from the group consisting of (1) a halogen atom, and (2) C1-C6 alkyl optionally substituted with one or more halogen atoms;

phenyl optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms;

5- to 6-membered heteroaryl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms or C7-C9 phenylalkyl whose ring moiety is optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms.

8. The compound according to claim 7, wherein $A^1$ and $A^2$ are oxygen atoms.

9. The compound according to claim 1, an N-oxide thereof or suitable salt thereof, wherein Q is $Q^4$;

$A^{34}$ is oxygen; and $R^9$ and $R^{10}$ independently represent a hydrogen atom; C1-C6 alkyl optionally substituted with one or more halogen atoms; C3-C6 cycloalkyl optionally substituted with one or more independent substituents selected from the group consisting of (1) a halogen atom, and (2) C1-C6 alkyl optionally substituted with one or more halogen atoms;

phenyl optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms;

5- to 6-membered heteroaryl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms or C7-C9 phenylalkyl whose ring moiety is optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms.

10. The compound according to claim 9, wherein $A^1$ and $A^2$ are oxygen atoms.

11. A hydrazide compound represented by the formula (II-1) or (II-2);

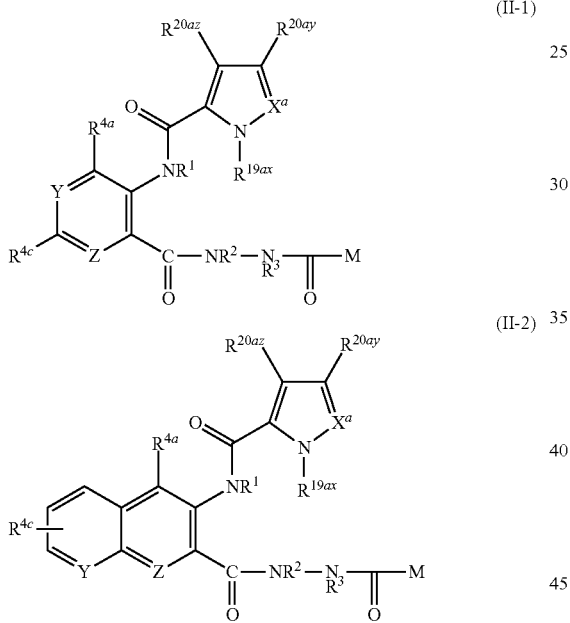

wherein
X$^a$ represents a nitrogen atom or CR$^{20ax}$;
Y and Z represent independently a nitrogen atom or CR$^{4b}$, but not Y and Z are CR$^{4b}$ at the same time;
R$^1$ represents a hydrogen atom or C1-C6 alkyl optionally substituted with one or more halogen atoms;
R$^2$ and R$^3$ independently represent a hydrogen atom, C1-C6 alkyl optionally substituted with one or more halogen atoms, C2-C6 cyanoalkyl, C1-C6 hydroxyalkyl, C2-C6 alkoxyalkyl optionally substituted with one or more halogen atoms, C2-C6 alkenyl optionally substituted with one or more halogen atoms, C2-C6 alkynyl optionally substituted with one or more halogen atoms, C3-C6 cycloalkyl optionally substituted with one or more halogen atoms, C1-C6 alkylthio optionally substituted with one or more halogen atoms, C1-C6 alkylsulfinyl optionally substituted with one or more halogen atoms, C1-C6 alkylsulfonyl optionally substituted with one or more halogen atoms, C2-C6 alkylcarbonyl optionally substituted with one or more halogen atoms, C2-C6 alkoxycarbonyl, C2-C6 alkylaminocarbonyl, C3-C8 dialkylaminocarbonyl, C4-C6 cycloalkylaminocarbonyl, or C3-C6 trialkylsilyl;

or represents phenyl, C7-C9 phenylalkyl or phenylcarbonyl: each said phenyl ring optionally substituted with one or more independent substituents selected from the group consisting of (1) a halogen atom, (2) cyano, (3) nitro, (4) hydroxyl, (5) carboxyl, (6) C1-C6 alkyl optionally substituted with one or more halogen atoms, (7) C1-C6 hydroxyalkyl, (8) C1-C6 alkoxy optionally substituted with one or more halogen atoms, (9) C2-C6 cyanoalkyl, (10) C2-C6 alkoxyalkyl optionally substituted with one or more halogen atoms, (11) C2-C6 alkenyl optionally substituted with one or more halogen atoms, (12) C2-C6 alkynyl optionally substituted with one or more halogen atoms, (13) C3-C6 cycloalkyl optionally substituted with one or more halogen atoms, (14) C1-C6 alkylthio optionally substituted with one or more halogen atoms, (15) C1-C6 alkylsulfinyl optionally substituted with one or more halogen atoms, (16) C1-C6 alkylsulfonyl optionally substituted with one or more halogen atoms, (17) C1-C6 alkylamino, (18) C2-C8 dialkylamino, (19) C3-C6 cycloalkylamino, (20) C2-C6 alkylcarbonyl, (21) C2-C6 alkoxycarbonyl, (22) C2-C6 alkylaminocarbonyl, (23) C3-C8 dialkylaminocarbonyl, (24) C4-C6 cycloalkylaminocarbonyl and (25) C3-C6 trialkylsilyl; or R$^2$ and R$^3$ are taken together with the two nitrogen atoms to which they are attached to form a 5- to 8-membered ring containing two nitrogen atoms, one or more CH$_2$ or C(=O), and optionally one or two ring members selected from the group consisting of (1) an oxygen atom, (2) a sulfur atom, (3) S(=O), (4) S(=O)$_2$ and (4) NR$^a$ (wherein R$^a$ represents C1-C6 alkyl optionally substituted with one or more halogen atoms, C2-C6 alkoxycarbonyl optionally substituted with one or more halogen atoms, or a phenyl optionally substituted with one or more independent substituents from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms); and wherein the ring at the carbon atoms is optionally substituted with one or more independent substituents selected from the group consisting of (1) a halogen atom, (2) C1-C6 alkyl optionally substituted with one or more halogen atoms, and (3) C2-C6 alkoxycarbonyl optionally substituted with one or more halogen atoms;

R$^{4a}$, R$^{4b}$ and R$^{4c}$ independently represent a halogen atom, cyano, nitro, hydroxyl, carboxyl, C1-C6 alkyl optionally substituted with one or more halogen atoms, C2-C6 alkoxy optionally substituted with one or more halogen atoms, C2-C6 cyanoalkyl C2-C6 alkoxyalkyl optionally substituted with one or more halogen atoms, C2-C6 alkenyl optionally substituted with one or more halogen atoms, C2-C6 alkynyl optionally substituted with one or more halogen atoms, C3-C6 cycloalkyl optionally substituted with one or more halogen atoms, C1-C6 alkylthio optionally substituted with one or more halogen atoms, C1-C6 alkylsulfinyl optionally substituted with one or more halogen atoms, C1-C6 alkylsulfonyl optionally substituted with one or more halogen atoms, C1-C6 alkylamino, C2-C8 dialkylamino, C3-C6 cycloalkylamino, C2-C6 alkylcarbonyl optionally substituted with one or more halogen atoms, C2-C6 alkoxycarbonyl, C2-C6 alkylaminocarbonyl, C3-C8 dialkylaminocarbonyl, C3-C6 trialkylsilyl;

or represents independently phenyl, benzyl, phenoxy, or 5- or 6-membered heteroaromatic ring, each ring optionally substituted with one or more substituents selected from the group consisting of (1) a halogen atom, (2) cyano, (3) nitro, (4) hydroxyl, (5) carboxyl, (6) C1-C6 alkyl optionally substituted with one or more halogen atoms, (7) C1-C6 hydroxyalkyl, (8) C1-C6 alkoxy optionally substituted with one or more halogen atoms, (9) C2-C6 cyanoalkyl, (10) C2-C6 alkoxyalkyl optionally substituted with one or more halogen atoms, (11) C2-C6 alkenyl optionally substituted with one or more halogen atoms, (12) C2-C6 alkynyl optionally substituted with one or more halogen atoms, (13) C3-C6 cycloalkyl optionally substituted with one or more halogen atoms, (14) C1-C6 alkylthio optionally substituted with one or more halogen atoms, (15) C1-C6 alkylsulfinyl optionally substituted with one or more halogen atoms, (16) C1-C6 alkylsulfonyl optionally substituted with one or more halogen atoms, (17) C1-C6 alkylamino, (18) C2-C8 dialkylamino, (19) C3-C6 cycloalkylamino, (20) C2-C6 alkylcarbonyl, (21) C2-C6 alkoxycarbonyl, (22) C2-C6 alkylaminocarbonyl, (23) C3-C8 dialkylaminocarbonyl, (24) C4-C6 cycloalkylaminocarbonyl and (25) C3-C6 trialkylsilyl;

M is a hydrogen atom; C1-C6 alkyl optionally substituted with one or more independent substituents selected from the group consisting of (1) a halogen atom, (2) C1-C6 alkoxy optionally substituted with one or more halogen atoms, (3) C1-C6 alkylthio optionally substituted with one or more halogen atoms, (4) C1-C6 alkylsulfinyl optionally substituted with one or more halogen atoms, (5) C1-C6 alkylsulfonyl optionally substituted with one or more halogen atoms, (6) C2-C6 dialkylamino optionally substituted with one or more halogen atoms, and (7) C3-C6 cycloalkyl optionally substituted with one or more halogen atoms; C1-C6 alkoxy optionally substituted with one or more halogen atoms; C1-C6 alkylthio optionally substituted with one or more halogen atoms; C1-C6 alkylamino; C2-C8 dialkylamino;

phenyl, C7-C9 phenylalkyl or C7-C9 phenoxyalkyl: each said phenyl ring optionally substituted with one or more independent substituents selected from the group consisting of (1) a halogen atom, (2) cyano, (3) nitro, (4) C1-C6 alkyl optionally substituted with one or more halogen atoms, and (5) C1-C6 alkoxy optionally substituted with one or more halogen atoms;

5- to 6-membered heteroaryl optionally substituted with one or more independent substituents selected from the group consisting of (1) a halogen atom, (2) cyano, (3) nitro, (4) C1-C6 alkyl optionally substituted with one or more halogen atoms, and (5) C1-C6 alkoxy optionally substituted with one or more halogen atoms;

or 3- to 8-membered non-aromatic heterocyclic ring optionally substituted with one or more independent substituents selected from the group consisting of (1) a halogen atom, and (2) C1-C6 alkyl optionally substituted with one or more halogen atoms;

$R^{19ax}$ represents a hydrogen atom; C1-C6 alkyl optionally substituted with one or more halogen atoms; C2-C6 cyanoalkyl; C2-C6 alkoxyalkyl optionally substituted with one or more halogen atoms; C2-C6 alkenyl optionally substituted with one or more halogen atoms; C2-C6 alkenyl optionally substituted with one or more halogen atoms; C3-C6 cycloalkyl optionally substituted with one or more independent substituents selected from the group consisting of (1) a halogen atom, and (2) C1-C6 alkyl optionally substituted with one or more halogen atoms; phenyl optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms; 5- to 6-membered heteroaryl optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms; C7-C9 phenylalkyl whose phenyl ring is optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms; or C7-C9 pyridinylalkyl whose pyridine ring is optionally substituted with one or more independent substituents selected from the group consisting of (1) a halogen atom, (2) cyano, (3) nitro, (4) C1-C6 alkyl optionally substituted with one or more halogen atoms, (5) C1-C6 alkoxy optionally substituted with one or more halogen atoms, (6) C1-C6 alkylthio optionally substituted with one or more halogen atoms, (7) C1-C6 alkylsulfinyl optionally substituted with one or more halogen atoms, (8) C1-C6 alkylsulfonyl optionally substituted with one or more halogen atoms, (9) C1-C6 alkylamino optionally substituted with one or more halogen atoms, (10) C2-C6 dialkylamino optionally substituted with one or more halogen atoms, (11) C2-C6 alkylcarbonyl optionally substituted with one or more halogen atoms, (12) C2-C6 alkoxycarbonyl optionally substituted with one or more halogen atoms, (13) C2-C6 alkylaminocarbonyl optionally substituted with one or more halogen atoms and (14) C3-C6 dialkylaminocarbonyl optionally substituted with one or more halogen atoms;

$R^{20ax}$, $R^{20ay}$ and $R^{20az}$ represent a halogen atom; cyano; nitro; thiocyanato; C1-C6 alkyl optionally substituted with one or more halogen atoms; C1-C6 alkoxy optionally substituted with one or more halogen atoms; C2-C6 cyanoalkyloxy; C2-C6 alkoxyalkyloxy optionally substituted with one or more halogen atoms; C2-C6 alkenyloxy optionally substituted with one or more halogen atoms; C2-C6 alkynyloxy optionally substituted with one or more halogen atoms; C1-C6 alkylthio optionally substituted with one or more halogen atoms; C1-C6 alkylsulfinyl optionally substituted with one or more halogen atoms; C1-C6 alkylsulfonyl optionally substituted with one or more halogen atoms; phenyl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms; 5- to 6-membered heteroaryl optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms; or phenoxy optionally substituted with one or more independent substituents selected from the group consisting of (1) a halogen atom, (2) cyano, (3) nitro, (4) C1-C6 alkyl optionally substituted with one or more halogen atoms and (5) C1-C6 alkoxy optionally substituted with one or more halogen atoms.

12. The compound according to claim 11, wherein $R^1$ is a hydrogen atom;

$R^2$ is a hydrogen atom or C1-C6 alkyl optionally substituted with one or more halogen atoms;

$R^3$ is a hydrogen atom, C1-C6 alkyl optionally substituted with one or more halogen atoms or C2-C6 alkoxycarbonyl;

$R^{4a}$ is a halogen atom or C1-C6 alkyl optionally substituted with one or more halogen atoms;

$R^{4c}$ is a hydrogen atom, a halogen atom, cyano or C1-C6 alkyl optionally substituted with one or more halogen atoms;

$R^{19a}$ is

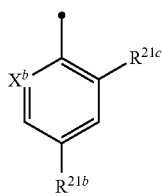

wherein $X^b$ is a nitrogen atom or $CR^{21a}$;

$R^{20ax}$ and $R^{20ay}$ are independently a hydrogen atom, a halogen atom, C1-C6 alkyl optionally substituted with one or more halogen atoms, C1-C6 alkoxy optionally substituted with one or more halogen atoms or C1-C6 alkylthio optionally substituted with one or more halogen atoms;

$R^{20az}$ is a hydrogen atom; and $R^{21a}$, $R^{21b}$ and $R^{21c}$ are independently selected from the group consisting of a hydrogen atom, a halogen atom or C1-C6 alkyl optionally substituted with one or more halogen atoms.

13. The compound according to claim 12, wherein $X^a$ and $X^b$ are nitrogen atoms;

Y is CH: and

Z is a nitrogen atom.

14. The compound according to claim 12, wherein $X^a$ and $X^b$ are nitrogen atoms;

Y is a nitrogen atom; and

Z is CH.

15. The compound according to claim 12, wherein $R^{4b}$ is a hydrogen atom.

16. The compound according to claim 15, wherein M is a hydrogen atom, C1-C6 alkyl, C1-C6 alkoxy, amino, C1-C6 alkylamino or C2-C8 dialkylamino.

17. The compound according to claim 16, wherein $R^2$ is a hydrogen atom, methyl or ethyl;

$R^3$ is a hydrogen atom, methyl, ethyl or methoxycarbonyl;

$R^{4a}$ is methyl, chloro, bromo or iodo;

$R^{4c}$ is hydrogen, fluoro, chloro, bromo, iodo or cyano;

$R^{20ay}$ is cchloro, bromo, iodo, trifluoromethyl or pentafluoroethoxy;

$R^{21b}$ is a hydrogen atom;

$R^{21c}$ is chloro or bromo; and

M is hydrogen, methoxy, ethoxy, methylamino or dimethylamino.

18. The compound of claim 17, wherein $R^2$ is a hydrogen atom;

$R^3$ is methyl or ethyl; and

M is a hydrogen atom.

19. The compound of claim 17, wherein $R^2$ and $R^3$ are independently hydrogen, methyl or ethyl; and M is methoxy or ethoxy.

20. A pesticide comprising the compound according to claim 1 as an active ingredient.

21. A method of controlling a pest which comprises applying the compound according to claim 1 directly to a pest, or to a place where a pest inhabits.

* * * * *